US011795460B2

(12) United States Patent
Kanjolia et al.

(10) Patent No.: US 11,795,460 B2
(45) Date of Patent: Oct. 24, 2023

(54) COMPOSITIONS AND METHODS FOR TTR GENE EDITING AND TREATING ATTR AMYLOIDOSIS

(71) Applicant: Intellia Therapeutics, Inc., Cambridge, MA (US)

(72) Inventors: Arti Mahendra Prakash Kanjolia, Malden, MA (US); Shobu Odate, Arlington, MA (US); Jessica Lynn Seitzer, Windham, NH (US); Reynald Michael Lescarbeau, Medford, MA (US); Walter Strapps, Dedham, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 18/064,086

(22) Filed: Dec. 9, 2022

(65) Prior Publication Data
US 2023/0118592 A1   Apr. 20, 2023

Related U.S. Application Data

(60) Division of application No. 16/828,573, filed on Mar. 24, 2020, which is a continuation of application No. PCT/US2018/053382, filed on Sep. 28, 2018.

(60) Provisional application No. 62/671,902, filed on May 15, 2018, provisional application No. 62/566,236, filed on Sep. 29, 2017.

(51) Int. Cl.
*C12N 15/113*   (2010.01)
*C12N 9/22*   (2006.01)
*A61P 25/28*   (2006.01)
*C12N 15/10*   (2006.01)
(Continued)

(52) U.S. Cl.
CPC ............ *C12N 15/113* (2013.01); *A61P 25/28* (2018.01); *C12N 9/22* (2013.01); *C12N 15/102* (2013.01); *A61K 48/00* (2013.01); *A61K 48/0091* (2013.01); *C12N 15/111* (2013.01);
(Continued)

(58) Field of Classification Search
CPC .................. A61K 48/005; C12N 15/113; C12N 2310/20; C12N 2310/321; C12N 15/88
See application file for complete search history.

(56) References Cited

U.S. PATENT DOCUMENTS 5,378,825 A   1/1995   Cook et al.
5,585,481 A   12/1996   Arnold, Jr. et al.
(Continued)

FOREIGN PATENT DOCUMENTS

JP   2016515401 A   5/2016
WO   1993013121 A1   7/1993
(Continued)

OTHER PUBLICATIONS

GenBank Accession No. EZM83080, by Cuomo et al. Submitted (Mar. 25, 2014) Broad Institute of MIT and Harvard, 7 Cambridge Center, Cambridge, MA 02142, USA.*
(Continued)

*Primary Examiner* — Terra C Gibbs
(74) *Attorney, Agent, or Firm* — McNeill Baur PLLC

(57) ABSTRACT

Compositions and methods for editing, e.g., introducing double-stranded breaks, within the TTR gene are provided. Compositions and methods for treating subjects having amyloidosis associated with transthyretin (ATTR), are provided.

24 Claims, 47 Drawing Sheets
Specification includes a Sequence Listing.

(51) Int. Cl.
  *A61K 48/00* (2006.01)
  *C12N 15/11* (2006.01)
(52) U.S. Cl.
  CPC .... *C12N 2310/20* (2017.05); *C12N 2310/321* (2013.01); *C12N 2800/80* (2013.01)

(56) References Cited

U.S. PATENT DOCUMENTS

| | | |
|---|---|---|
| 8,889,356 B2 | 11/2014 | Zhang |
| 9,023,649 B2 | 5/2015 | Mali et al. |
| 2005/0038117 A1 | 2/2005 | Kong et al. |
| 2012/0294905 A1 | 11/2012 | Sah |
| 2014/0186958 A1 | 7/2014 | Zhang et al. |
| 2015/0166980 A1 | 6/2015 | Liu et al. |
| 2016/0046960 A1 | 2/2016 | Frendewey et al. |
| 2016/0312198 A1 | 10/2016 | Joung et al. |
| 2016/0312199 A1 | 10/2016 | Joung et al. |
| 2019/0136231 A1* | 5/2019 | Morrissey ............ C12N 5/0602 |

FOREIGN PATENT DOCUMENTS

| | | |
|---|---|---|
| WO | 1995032305 | 11/1995 |
| WO | 2002029103 A2 | 4/2002 |
| WO | 2006007712 | 1/2006 |
| WO | 2010017509 A1 | 2/2010 |
| WO | 2010048228 A2 | 4/2010 |
| WO | 2011056883 A1 | 5/2011 |
| WO | 2011139917 A1 | 11/2011 |
| WO | 2013075035 A1 | 5/2013 |
| WO | 2014093622 A2 | 6/2014 |
| WO | 2014136086 | 9/2014 |
| WO | 2014172489 A2 | 10/2014 |
| WO | 2014179627 A2 | 11/2014 |
| WO | 2014204728 A1 | 12/2014 |
| WO | 2015095340 | 6/2015 |
| WO | 2015183026 A1 | 12/2015 |
| WO | 2016010840 | 1/2016 |
| WO | 2017053297 | 3/2017 |
| WO | 2017053431 A2 | 3/2017 |
| WO | 2017077386 A1 | 5/2017 |
| WO | 2017093804 A2 | 6/2017 |
| WO | 2017158422 A1 | 9/2017 |
| WO | 2017173054 | 10/2017 |
| WO | 2018007871 A1 | 1/2018 |
| WO | 2018107028 A1 | 6/2018 |

OTHER PUBLICATIONS

Kudla et al. (PLoS Biol. 2006;4:e180).*
Anders, C., et al., "In Vitro Enzymology of Cas9," Methods in Enzymology, vol. 546, pp. 1-20 (2014).
Morrissey, D., "Robust In Vivo Editing of Hepatocyte Target DNA Mediated by Lipid Nanoparticle Delivery of CRISPR/Cas9 Components," ASGCT 20th Annual Meeting, 30 pages (May 13, 2017).
Abbas et al. (2017) "Structure of human IFIT1 with capped RNA reveals adaptable mRNA binding and mechanisms for sensing N1 and N2 ribose 2'-O methylations" Proc Natl Acad Sci USA 114(11):E2106-E2115.
Anonymous: , "Intellia Therapeutics Company Overview" Jefferies Healthcare Conference, Jun. 6, 2017, XP55527492, New York, Retrieved from the Internet: URL:http://www.jefferies.com/CMSFiles/Jeff eries.com/files/Intellia%20Therapeutics%20 Inc(3).pdf.
Beaudet, A.L. et al: "Gene-targeting pharmaceuticals, for single-gene disorders" Human Molecular Genetics, vol. 25, No. R1, Nov. 30, 2015, pp. R18-R26.
Butler et al., "Preclinical evaluation of RNAi as a treatment for transthyretin-mediated amyloidosis" Amyloid. Jun. 2016;23(2):109-18.
Chang, Y., "Delivering on the therapeutic potential of CRISPR/Cas9: Development of an LNP-mediated genome editing therapeutic for the treatment of ATTR" 26th Annual Congress of the European Society of Gene and Cell Therapy, Oct. 18, 2018.

Doench, et al. (2016), "Optimized sgRNA design to maximize activity and minimize off-target effects of CRISPR-Cas9", Nature Biotechnology, 34(2), pp. 184-191 & supplementary information.
Finn, J.D. et al: "A Single Administration of CRISPR/Cas9 Lipid Nanoparticles Achieves Robust and Persistent In Vivo Genome Editing", Cell Reports, vol. 22, No. 9, Feb. 27, 2018, pp. 2227-2235.
Galant, N. J., et al: "Transthyretin amyloidosis: an under-recognized neuropathy and cardiomyopathy", Clinical Science., vol. 131, No. 5, Feb. 17, 2017, pp. 395-409.
Gilbert, Luke A et al. "CRISPR-mediated modular RNA-guided regulation of transcription in eukaryotes." Cell vol. 154,2 (2013): 442-51.
Gonçalves et al., "Interleukin-1 signaling pathway as a therapeutic target in transthyretin amyloidosis" Amyloid. Sep. 2014; 21(3): 175-184.
Guo, P. and Moss, B. (1990) "Interaction and mutual stabilization of the two subunits of vaccinia virus mRNA capping enzyme coexpressed in *Escherichia coli*" Proc. Natl. Acad. Sci. USA 87, 4023-4027.
Ishikawa et al., "Preparation of eukaryotic mRNA having differently methylated adenosine at the 5'-terminus and the effect of the methyl group in translation" Nucl. Acids. Symp. Ser. (2009) No. 53, 129-130.
Kariko, et al. "Generating the optimal mRNA for therapy: HPLC purification eliminates immune activation and improves translation of nucleoside-modified, protein-encoding mRNA" Nucleic Acids Research, 2011, vol. 39, No. 21 e142.
Katibah et al. (2014) "Broad and adaptable RNA structure recognition by the human interferon-induced tetratricopeptide repeat protein IFIT5" Proc Natl Acad Sci USA 111(33):12025-30.
Kerschen, P. et al: "Current and Future Treatment Approaches in Transthyretin Familial Amyloid Polyneuropathy", Current Treatment Options in Neurology, Springer US, Boston, vol. 18, No. 12, Nov. 21, 2016 (Nov. 21, 2016), pp. 1-13.
Maier, Martin A et al. "Biodegradable lipids enabling rapidly eliminated lipid nanoparticles for systemic delivery of RNAi therapeutics." Molecular therapy : the journal of the American Society of Gene Therapy vol. 21,8 (2013): 1570-8.
Makarova et al., "An updated evolutionary classification of CRISPR-Cas systems" Nat Rev Microbiol, 13(11): 722-36 (2015).
Makarova et al., "Evolution and classification of the CRISPR-Cas systems" Nat. Rev. Microbiol. 9:467-477 (2011).
Mali, Prashant et al. "CAS9 transcriptional activators for target specificity screening and paired nickases for cooperative genome engineering." Nature biotechnology vol. 31,9 (2013): 833-8.
Mao, X. and Shuman, S. (1994) "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer" J. Biol. Chem. 269, 24472-24479.
Mefferd et al., "Expression of CRISPR/Cas single guide RNAs using small tRNA promoters" RNA. 2015 21:1683-9.
Perez-Pinera, Pablo et al. "RNA-guided gene activation by CRISPR-Cas9-based transcription factors." Nature methods vol. 10,10 (2013): 973-6.
Qi, Lei S et al. "Repurposing CRISPR as an RNA-guided platform for sequence-specific control of gene expression." Cell vol. 152,5 (2013): 1173-83.
Rejman et al., "Characterization and transfection properties of lipoplexes stabilized with novel exchangeable polyethylene glycol-lipid conjugates" Biochimica et Biophysica Acta 1660 (2004) 41-52.
Romberg et al., "Sheddable coatings for long-circulating nanoparticles" Pharmaceutical Research, vol. 25, No. 1, 2008, p. 55-71.
Santos et al., "The heat shock response modulates transthyretin deposition in the peripheral and autonomic nervous systems" Neurobiol Aging. Feb. 2010;31(2):280-9.
Saraiva, M. et al. "Rescue of Amyloid Deposition Phenotype after Single-Treatment CRISPR/Cas9 Gene Editing in a Humanized Mouse Model of TTR Amyloidosis" ASGCT 2018, May 14, 2018, abstract No. 276.
Scherer et al., "Optimization and characterization of tRNA-shRNA expression constructs" Nucleic Acids Res. 2007 35: 2620-2628.

(56) References Cited

OTHER PUBLICATIONS

Sekijima et al: "Recent progress in the understanding and treatment of transthyretin amyloidosis" Journal of Clinical Pharmacy and Therapeutics, Blackwell Scientific Publication, Oxford, GB, vol. 39, No. 3, Apr. 18, 2014, pp. 225-233.
Shmakov et al., "Discovery and Functional Characterization of Diverse Class 2 CRISPR-Cas Systems" Molecular Cell, 60:385-397 (2015).
Stepinski et al., "Synthesis and Properties of mRNAs Containing the Novel (anti-reverse) Cap Analogs 7-methyl(3'-O-methyl)GpppG and 7-methyl(3'-deoxy)GpppG", RNA, (2001) 7:1486-1495.
The Biochemistry of the Nucleic Acids, Adams et al., ed., 11th ed., 1992, pp. 5-36.
Tsai et al., "GUIDE-seq enables genome-wide profiling of off-target cleavage by CRISPR-Cas nucleases" Nature Biotechnology 33, 187-197; 2015.
Vester and Wengel, 2004, "LNA (locked nucleic acid): high-affinity targeting of complementary RNA and DNA" Biochemistry 43(42):13233-41.
Zetsche et al. (2015) "Cpf1 is a single RNA-guided endonuclease of a class 2 CRISPR-Cas system" Cell Oct. 22:163 (3): 759-771.
Coelho, T., et al., "Safety and Efficacy of RNAi Therapy for Transthyretin Amyloidosis," The New England Journal of Medicine, vol. 369:9, pp. 819-829 plus supplemental information (2013).

\* cited by examiner

COMPOSITIONS AND METHODS FOR TTR GENE EDITING AND TREATING ATTR AMYLOIDOSIS

This application is a Divisional of U.S. application Ser. No. 16/828,573, which was filed on Mar. 24, 2020, which is a Continuation of International Application No. PCT/US2018/053382, which was filed on Sep. 28, 2018, which claims the benefit of priority to U.S. Provisional Application No. 62/556,236, which was filed on Sep. 29, 2017, and U.S. Provisional Application No. 62/671,902, which was filed on May 15, 2018, the contents of each of which are incorporated by reference in their entirety.

The patent application is filed with a sequence listing in electronic format. The Sequence Listing is provided as a file entitled "01155-0013-02US-T1_ST26.xml," which was created on Nov. 30, 2022, and which is 567,665 bytes in size. The information in the electronic format of the sequence listing is incorporated herein by reference in its entirety.

Transthyretin (TTR) is a protein produced by the TTR gene that normally functions to transport retinol and thyroxine throughout the body. TTR is predominantly synthesized in the liver, with small fractions being produced in the choroid plexus and retina. TTR normally circulates as a soluble tetrameric protein in the blood.

Pathogenic variants of TTR, which may disrupt tetramer stability, can be encoded by mutant alleles of the TTR gene. Mutant TTR may result in misfolded TTR, which may generate amyloids (i.e., aggregates of misfolded TTR protein). In some cases, pathogenic variants of TTR can lead to amyloidosis, or disease resulting from build-up of amyloids. For example, misfolded TTR monomers can polymerize into amyloid fibrils within tissues, such as the peripheral nerves, heart, and gastrointestinal tract. Amyloid plaques can also comprise wild-type TTR that has deposited on misfolded TTR.

Misfolding and deposition of wild-type TTR has also been observed in males aged 60 or more and is associated with heart rhythm problems, heart failure, and carpal tunnel.

Amyloidosis characterized by deposition of TTR may be referred to as "ATTR," "TTR-related amyloidosis," "TTR amyloidosis," or "ATTR amyloidosis," "ATTR familial amyloidosis" (when associated with a genetic mutation in a family), or "ATTRwt" or "wild-type ATTR" (when arising from misfolding and deposition of wild-type TTR).

ATTR can present with a wide spectrum of symptoms, and patients with different classes of ATTR may have different characteristics and prognoses. Some classes of ATTR include familial amyloid polyneuropathy (FAP), familial amyloid cardiomyopathy (FAC), and wild-type TTR amyloidosis (wt-TTR amyloidosis). FAP commonly presents with sensorimotor neuropathy, while FAC and wt-TTR amyloidosis commonly present with congestive heart failure. FAP and FAC are usually associated with a genetic mutation in the FIR gene, and more than 100 different mutations in the TTR gene have been associated with ATTR. In contrast, wt-TTR amyloidosis is associated with aging and not with a genetic mutation in TTR. It is estimated that approximately 50,000 patients worldwide may be affected by FAP and FAC.

While more than 100 mutations in TTR are associated with ATTR, certain mutations have been more closely associated with neuropathy and/or cardiomyopathy. For example, mutations at T60 of TTR are associated with both cardiomyopathy and neuropathy; mutations at V30 are more associated with neuropathy; and mutations at V122 are more associated with cardiomyopathy.

A range of treatment approaches have been studied for treatment of ATTR, but there are no approved drugs that stop disease progression and improve quality of life. While liver transplant has been studied for treatment of ATTR, its use is declining as it involves significant risk and disease progression sometimes continues after transplantation. Small molecule stabilizers, such as diflunisal and tafamidis, appear to slow ATTR progression, but these agents do not halt disease progression.

Approaches using small interfering RNA (siRNA) knockdown, antisense knockdown, or a monoclonal antibody targeting amyloid fibrils for destruction are also currently being investigated, but while results on short-term suppression of TTR expression show encouraging preliminary data, a need exists for treatments that can produce long-lasting suppression of TTR.

Accordingly, the following embodiments are provided. In some embodiments, the present invention provides compositions and methods using a guide RNA with an RNA-guided DNA binding agent such as the CRISPR/Cas system to substantially reduce or knockout expression of the TTR gene, thereby substantially reducing or eliminating the production of TTR protein associated with ATTR. The substantial reduction or elimination of the production of TTR protein associated with ATTR through alteration of the TTR gene can be a long-term reduction or elimination.

SUMMARY

Embodiment 1 is a method of inducing a double-stranded break (DSB) within the TTR gene, comprising delivering a composition to a cell, wherein the composition comprises
  a. a guide RNA comprising a guide sequence selected from SEQ ID NOs: 5-82;
  b. a guide RNA comprising at least 17, 18, 19, or 20 contiguous nucleotides of a sequence selected from SEQ ID NOs: 5-82; or
  c. a guide RNA comprising a guide sequence that is at least 99%, 98%, 97%, 96%, 95%, 94%, 93%, 92%, 91%, or 90% identical to a sequence selected from SEQ ID NOs: 5-82.

Embodiment 2 is a method of modifying the TTR gene comprising delivering a composition to a cell, wherein the composition comprises (i) an RNA-guided DNA binding agent or a nucleic acid encoding an RNA-guided DNA binding agent and (ii) a guide RNA comprising:
  a. a guide sequence selected from SEQ ID NOs: 5-82;
  b. at least 17, 18, 19, or 20 contiguous nucleotides of a sequence selected from SEQ ID NOs: 5-82; or
  c. a guide sequence that is at least 99%, 98%, 97%, 96%, 95%, 94%, 93%, 92%, 91%, or 90% identical to a sequence selected from SEQ ID NOs: 5-82.

Embodiment 3 is a method of treating amyloidosis associated with TTR (ATTR), comprising administering a composition to a subject in need thereof, wherein the composition comprises (i) an RNA-guided DNA binding agent or a nucleic acid encoding an RNA-guided DNA binding agent and (ii) a guide RNA comprising:
  a. a guide sequence selected from SEQ ID NOs: 5-82;
  b. at least 17, 18, 19, or 20 contiguous nucleotides of a sequence selected from SEQ ID NOs: 5-82; or
  c. a guide sequence that is at least 99%, 98%, 97%, 96%, 95%, 94%, 93%, 92%, 91%, or 90% identical to a sequence selected from SEQ ID NOs: 5-82, thereby treating ATTR.

Embodiment 4 is a method of reducing TTR serum concentration, comprising administering a composition to a subject in need thereof, wherein the composition comprises (i) an RNA-guided DNA binding agent or a nucleic acid encoding an RNA-guided DNA binding agent and (ii) a guide RNA comprising:
  a. a guide sequence selected from SEQ ID NOs: 5-82;
  b. at least 17, 18, 19, or 20 contiguous nucleotides of a sequence selected from SEQ ID NOs: 5-82; or
  c. a guide sequence that is at least 99%, 98%, 97%, 96%, 95%, 94%, 93%, 92%, 91%, or 90% identical to a sequence selected from SEQ ID NOs: 5-82, thereby reducing TTR serum concentration.

Embodiment 5 is a method for reducing or preventing the accumulation of amyloids or amyloid fibrils comprising TTR in a subject, comprising administering a composition to a subject in need thereof, wherein the composition comprises (i) an RNA-guided DNA binding agent or a nucleic acid encoding an RNA-guided DNA binding agent and (ii) a guide RNA comprising:
  a. a guide sequence selected from SEQ ID NOs: 5-82;
  b. at least 17, 18, 19, or 20 contiguous nucleotides of a sequence selected from SEQ ID NOs: 5-82; or
  c. a guide sequence that is at least 99%, 98%, 97%, 96%, 95%, 94%, 93%, 92%, 91%, or 90% identical to a sequence selected from SEQ ID NOs: 5-82, thereby reducing accumulation of amyloids or amyloid fibrils.

Embodiment 6 is a composition comprising a guide RNA comprising:
  a. a guide sequence selected from SEQ ID NOs: 5-82;
  b. at least 17, 18, 19, or 20 contiguous nucleotides of a sequence selected from SEQ ID NOs: 5-82; or
  c. a guide sequence that is at least 99%, 98%, 97%, 96%, 95%, 94%, 93%, 92%, 91%, or 90% identical to a sequence selected from SEQ ID NOs: 5-82.

Embodiment 7 is a composition comprising a vector encoding a guide RNA, wherein the guide RNA comprises:
  a. a guide sequence selected from SEQ ID NOs: 5-82;
  b. at least 17, 18, 19, or 20 contiguous nucleotides of a sequence selected from SEQ ID NOs: 5-82; or
  c. a guide sequence that is at least 99%, 98%, 97%, 96%, 95%, 94%, 93%, 92%, 91%, or 90% identical to a sequence selected from SEQ ID NOs: 5-82.

Embodiment 8 is the composition of embodiment 6 or 7, for use in inducing a double-stranded break (DSB) within the TTR gene in a cell or subject.

Embodiment 9 is the composition of embodiment 6 or 7, for use in modifying the TTR gene in a cell or subject.

Embodiment 10 is the composition of embodiment 6 or 7, for use in treating amyloidosis associated with TTR (ATTR) in a subject.

Embodiment 11 is the composition of embodiment 6 or 7, for use in reducing TTR serum concentration in a subject.

Embodiment 12 is the composition of embodiment 6 or 7, for use in reducing or preventing the accumulation of amyloids or amyloid fibrils in a subject.

Embodiment 13 is the method of any one of embodiments 1-5 or the composition for use of any one of embodiments 8-12, wherein the composition reduces serum TTR levels.

Embodiment 14 is the method or composition for use of embodiment 13, wherein the serum TTR levels are reduced by at least 50% as compared to serum TTR levels before administration of the composition.

Embodiment 15 is the method or composition for use of embodiment 13, wherein the serum TTR levels are reduced by 50-60%, 60-70%, 70-80%, 80-90%, 90-95%, 95-98%, 98-99%, or 99-100% as compared to serum TTR levels before administration of the composition.

Embodiment 16 is the method or composition for use of any one of embodiments 1-5 or 8-15, wherein the composition results in editing of the TTR gene.

Embodiment 17 is the method or composition for use of embodiment 16, wherein the editing is calculated as a percentage of the population that is edited (percent editing).

Embodiment 18 is the method or composition for use of embodiment 17, wherein the percent editing is between 30 and 99% of the population.

Embodiment 19 is the method or composition for use of embodiment 17, wherein the percent editing is between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the population.

Embodiment 20 is the method of any one of embodiments 1-5 or the composition for use of any one of embodiments 8-19, wherein the composition reduces amyloid deposition in at least one tissue.

Embodiment 21 is the method or composition for use of embodiment 20, wherein the at least one tissue comprises one or more of stomach, colon, sciatic nerve, or dorsal root ganglion.

Embodiment 22 is the method or composition for use of embodiment 20 or 21, wherein amyloid deposition is measured 8 weeks after administration of the composition.

Embodiment 23 is the method or composition for use of any one of embodiments 20-22, wherein amyloid deposition is compared to a negative control or a level measured before administration of the composition.

Embodiment 24 is the method or composition for use of any one of embodiments 20-23, wherein amyloid deposition is measured in a biopsy sample and/or by immunostaining.

Embodiment 25 is the method or composition for use of any one of embodiments 20-24, wherein amyloid deposition is reduced by between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the amyloid deposition seen in a negative control.

Embodiment 26 is the method or composition for use of any one of embodiments 20-25, wherein amyloid deposition is reduced by between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the amyloid deposition seen before administration of the composition.

Embodiment 27 is the method or composition for use of any one of embodiments 1-5 or 8-26, wherein the composition is administered or delivered at least two times.

Embodiment 28 is the method or composition for use of embodiment 27, wherein the composition is administered or delivered at least three times.

Embodiment 29 is the method or composition for use of embodiment 27, wherein the composition is administered or delivered at least four times.

Embodiment 30 is the method or composition for use of embodiment 27, wherein the composition is administered or delivered up to five, six, seven, eight, nine, or ten times.

Embodiment 31 is the method or composition for use of any one of embodiments 27-30, wherein the administration or delivery occurs at an interval of 1, 2, 3, 4, 5, 6, 7, 8, 9, 10, 11, 12, 13, 14, or 15 days.

Embodiment 32 is the method or composition for use of any one of embodiments 27-30, wherein the administration or delivery occurs at an interval of 1, 2, 3, 4, 5, 6, 7, 8, 9, 10, 11, 12, 13, 14, or 15 weeks.

Embodiment 33 is the method or composition for use of any one of embodiments 27-30, wherein the administration or delivery occurs at an interval of 1, 2, 3, 4, 5, 6, 7, 8, 9, 10, 11, 12, 13, 14, or 15 months.

Embodiment 34 is the method or composition of any one of the preceding embodiments, wherein the guide sequence is selected from SEQ ID NOs: 5-82.

Embodiment 35 is the method or composition of any one of the preceding embodiments, wherein the guide RNA is at least partially complementary to a target sequence present in the human TTR gene.

Embodiment 36 is the method or composition of embodiment 35, wherein the target sequence is in exon 1, 2, 3, or 4 of the human TTR gene.

Embodiment 37 is the method or composition of embodiment 35, wherein the target sequence is in exon 1 of the human TTR gene.

Embodiment 38 is the method or composition of embodiment 35, wherein the target sequence is in exon 2 of the human TTR gene.

Embodiment 39 is the method or composition of embodiment 35, wherein the target sequence is in exon 3 of the human TTR gene.

Embodiment 40 is the method or composition of embodiment 35, wherein the target sequence is in exon 4 of the human TTR gene.

Embodiment 41 is the method or composition of any one of embodiments 1-40, wherein the guide sequence is complementary to a target sequence in the positive strand of TTR.

Embodiment 42 is the method or composition of any one of embodiments 1-40, wherein the guide sequence is complementary to a target sequence in the negative strand of TTR.

Embodiment 43 is the method or composition of any one of embodiments 1-40, wherein the first guide sequence is complementary to a first target sequence in the positive strand of the TTR gene, and wherein the composition further comprises a second guide sequence that is complementary to a second target sequence in the negative strand of the TTR gene.

Embodiment 44 is the method or composition of any one of the preceding embodiments, wherein the guide RNA comprises a crRNA that comprises the guide sequence and further comprises a nucleotide sequence of SEQ ID NO: 126, wherein the nucleotides of SEQ ID NO: 126 follow the guide sequence at its 3' end.

Embodiment 45 is the method or composition of any one of the preceding embodiments, wherein the guide RNA is a dual guide (dgRNA).

Embodiment 46 is the method or composition of embodiment 45, wherein the dual guide RNA comprises a crRNA comprising a nucleotide sequence of SEQ ID NO: 126, wherein the nucleotides of SEQ ID NO: 126 follow the guide sequence at its 3' end, and a trRNA.

Embodiment 47 is the method or composition of any one of embodiments 1-43, wherein the guide RNA is a single guide (sgRNA).

Embodiment 48 is the method or composition of embodiment 47, wherein the sgRNA comprises a guide sequence that has the pattern of SEQ ID NO: 3.

Embodiment 49 is the method or composition of embodiment 47, wherein the sgRNA comprises the sequence of SEQ ID NO: 3.

Embodiment 50 is the method or composition of embodiment 48 or 49, wherein each N in SEQ ID NO: 3 is any natural or non-natural nucleotide, wherein the N's form the guide sequence, and the guide sequence targets Cas9 to the TTR gene.

Embodiment 51 is the method or composition of any one of embodiments 47-50, wherein the sgRNA comprises any one of the guide sequences of SEQ ID NOs: 5-82 and the nucleotides of SEQ ID NO: 126.

Embodiment 52 is the method or composition of any one of embodiments 47-51, wherein the sgRNA comprises a guide sequence that is at least 99%, 98%, 97%, 96%, 95%, 94%, 93%, 92%, 91%, or 90% identical to a sequence selected from SEQ ID Nos: 87-124.

Embodiment 53 is the method or composition of embodiment 47, wherein the sgRNA comprises a sequence selected from SEQ ID Nos: 87-124.

Embodiment 54 is the method or composition of any one of the preceding embodiments, wherein the guide RNA comprises at least one modification.

Embodiment 55 is the method or composition of embodiment 54, wherein the at least one modification includes a 2'-O-methyl (2'-O-Me) modified nucleotide.

Embodiment 56 is the method or composition of embodiment 54 or 55, wherein the at least one modification includes a phosphorothioate (PS) bond between nucleotides.

Embodiment 57 is the method or composition of any one of embodiments 54-56, wherein the at least one modification includes a 2'-fluoro (2'-F) modified nucleotide.

Embodiment 58 is the method or composition of any one of embodiments 54-57, wherein the at least one modification includes a modification at one or more of the first five nucleotides at the 5' end.

Embodiment 59 is the method or composition of any one of embodiments 54-58, wherein the at least one modification includes a modification at one or more of the last five nucleotides at the 3' end.

Embodiment 60 is the method or composition of any one of embodiments 54-59, wherein the at least one modification includes PS bonds between the first four nucleotides.

Embodiment 61 is the method or composition of any one of embodiments 54-60, wherein the at least one modification includes PS bonds between the last four nucleotides.

Embodiment 62 is the method or composition of any one of embodiments 54-61, wherein the at least one modification includes 2'-O-Me modified nucleotides at the first three nucleotides at the 5' end.

Embodiment 63 is the method or composition of any one of embodiments 54-62, wherein the at least one modification includes 2'-O-Me modified nucleotides at the last three nucleotides at the 3' end.

Embodiment 64 is the method or composition of any one of embodiments 54-63, wherein the guide RNA comprises the modified nucleotides of SEQ ID NO: 3.

Embodiment 65 is the method or composition of any one of embodiments 1-64, wherein the composition further comprises a pharmaceutically acceptable excipient.

Embodiment 66 is the method or composition of any one of embodiments 1-65, wherein the guide RNA is associated with a lipid nanoparticle (LNP).

Embodiment 67 is the method or composition of embodiment 66, wherein the LNP comprises a CCD lipid.

Embodiment 68 is the method or composition of embodiment 67, wherein the CCD lipid is Lipid a or Lipid B.

Embodiment 69 is the method or composition of embodiment 66-68, wherein the LNP comprises a neutral lipid.

Embodiment 70 is the method or composition of embodiment 69, wherein the neutral lipid is DSPC Embodiment 71 is the method or composition of any one of embodiments 66-70, wherein the LNP comprises a helper lipid.

Embodiment 72 is the method or composition of embodiment 71, wherein the helper lipid is cholesterol.

Embodiment 73 is the method or composition of any one of embodiments 66-72, wherein the LNP comprises a stealth lipid.

Embodiment 74 is the method or composition of embodiment 73, wherein the stealth lipid is PEG2k-DMG.

Embodiment 75 is the method or composition of any one of the preceding embodiments, wherein the composition further comprises an RNA-guided DNA binding agent.

Embodiment 76 is the method or composition of any one of the preceding embodiments, wherein the composition further comprises an mRNA that encodes an RNA-guided DNA binding agent.

Embodiment 77 is the method or composition of embodiment 75 or 76, wherein the RNA-guided DNA binding agent is a Cas cleavase.

Embodiment 78 is the method or composition of embodiment 77, wherein the RNA-guided DNA binding agent is Cas9.

Embodiment 79 is the method or composition of any one of embodiments 75-78, wherein the RNA-guided DNA binding agent is modified.

Embodiment 80 is the method or composition of any one of embodiments 75-79, wherein the RNA-guided DNA binding agent is a nickase.

Embodiment 81 is the method or composition of embodiment 79 or 80, wherein the modified RNA-guided DNA binding agent comprises a nuclear localization signal (NLS).

Embodiment 82 is the method or composition of any one of embodiments 75-81, wherein the RNA-guided DNA binding agent is a Cas from a Type-II CRISPR/Cas system.

Embodiment 83 is the method or composition of any one of the preceding embodiments, wherein the composition is a pharmaceutical formulation and further comprises a pharmaceutically acceptable carrier.

Embodiment 84 is the method or composition for use of any one of embodiments 1-5 or 8-83, wherein the composition reduces or prevents amyloids or amyloid fibrils comprising TTR.

Embodiment 85 is the method or composition for use of embodiment 84, wherein the amyloids or amyloid fibrils are in the nerves, heart, or gastrointestinal track.

Embodiment 86 is the method or composition for use of any one of embodiments 1-5 or 8-83, wherein non-homologous ending joining (NHEJ) leads to a mutation during repair of a DSB in the TTR gene.

Embodiment 87 is the method or composition for use of embodiment 86, wherein NHEJ leads to a deletion or insertion of a nucleotide(s) during repair of a DSB in the TTR gene.

Embodiment 88 is the method or composition for use of embodiment 87, wherein the deletion or insertion of a nucleotide(s) induces a frame shift or nonsense mutation in the TTR gene.

Embodiment 89 is the method or composition for use of embodiment 87, wherein a frame shift or nonsense mutation is induced in the TTR gene of at least 50% of liver cells.

Embodiment 90 is the method or composition for use of embodiment 89, wherein a frame shift or nonsense mutation is induced in the TTR gene of 50%-60%, 60%-70%, 70% or 80%, 80%-90%, 90-95%, 95%-99%, or 99%-100% of liver cells.

Embodiment 91 is the method or composition for use of any one of embodiments 87-90, wherein a deletion or insertion of a nucleotide(s) occurs in the TTR gene at least 50-fold or more than in off-target sites.

Embodiment 92 is the method or composition for use of embodiment 91, wherein the deletion or insertion of a nucleotide(s) occurs in the TTR gene 50-fold to 150-fold, 150-fold to 500-fold, 500-fold to 1500-fold, 1500-fold to 5000-fold, 5000-fold to 15000-fold, 15000-fold to 30000-fold, or 30000-fold to 60000-fold more than in off-target sites.

Embodiment 93 is the method or composition for use of any one of embodiments 87-92, wherein the deletion or insertion of a nucleotide(s) occurs at less than or equal to 3, 2, 1, or 0 off-target site(s) in primary human hepatocytes, optionally wherein the off-target site(s) does (do) not occur in a protein coding region in the genome of the primary human hepatocytes.

Embodiment 94 is the method or composition for use of embodiment 93, wherein the deletion or insertion of a nucleotide(s) occurs at a number of off-target sites in primary human hepatocytes that is less than the number of off-target sites at which a deletion or insertion of a nucleotide(s) occurs in Cas9-overexpressing cells, optionally wherein the off-target site(s) does (do) not occur in a protein coding region in the genome of the primary human hepatocytes.

Embodiment 95 is the method or composition for use of embodiment 94, wherein the Cas9-overexpressing cells are HEK293 cells stably expressing Cas9.

Embodiment 96 is the method or composition for use of any one of embodiments 93-95, wherein the number of off-target sites in primary human hepatocytes is determined by analyzing genomic DNA from primary human hepatocytes transfected in vitro with Cas9 mRNA and the guide RNA, optionally wherein the off-target site(s) does (do) not occur in a protein coding region in the genome of the primary human hepatocytes.

Embodiment 97 is the method or composition for use of any one of embodiments 93-95, wherein the number of off-target sites in primary human hepatocytes is determined by an oligonucleotide insertion assay comprising analyzing genomic DNA from primary human hepatocytes transfected in vitro with Cas9 mRNA, the guide RNA, and a donor oligonucleotide, optionally wherein the off-target site(s) does (do) not occur in a protein coding region in the genome of the primary human hepatocytes.

Embodiment 98 is the method or composition of any one of embodiments 1-43 or 47-97, wherein the sequence of the guide RNA is:
  a) SEQ ID NO: 92 or 104;
  b) SEQ ID NO: 87, 89, 96, or 113;
  c) SEQ ID NO: 100, 102, 106, 111, or 112; or
  d) SEQ ID NO: 88, 90, 91, 93, 94, 95, 97, 101, 103, 108, or 109,
optionally wherein the guide RNA does not produce indels at off-target site(s) that occur in a protein coding region in the genome of primary human hepatocytes.

Embodiment 99 is the method or composition for use of any one of embodiments 1-5 or 8-98, wherein administering the composition reduces levels of TTR in the subject.

Embodiment 100 is the method or composition for use of embodiment 99, wherein the levels of TTR are reduced by at least 50%.

Embodiment 101 is the method or composition for use of embodiment 100, wherein the levels of TTR are reduced by 50%-60%, 60%-70%, 70% or 80%, 80%-90%, 90-95%, 95%-99%, or 99%-100%.

Embodiment 102 is the method or composition for use of embodiment 100 or 101, wherein the levels of TTR are measured in serum, plasma, blood, cerebral spinal fluid, or sputum.

Embodiment 103 is the method or composition for use of embodiment 100 or 101, wherein the levels of TTR are measured in liver, choroid plexus, and/or retina.

Embodiment 104 is the method or composition for use of any one of embodiments 99-103, wherein the levels of TTR are measured via enzyme-linked immunosorbent assay (ELISA).

Embodiment 105 is the method or composition for use of any one of embodiments 1-5 or 8-104, wherein the subject has ATTR.

Embodiment 106 is the method or composition for use of any one of embodiments 1-5 or 8-105, wherein the subject is human.

Embodiment 107 is the method or composition for use of embodiment 105 or 106, wherein the subject has ATTRwt.

Embodiment 108 is the method or composition for use of embodiment 105 or 106, wherein the subject has hereditary ATTR.

Embodiment 109 is the method or composition for use of any one of embodiments 1-5, 8-106, or 108, wherein the subject has a family history of ATTR.

Embodiment 110 is the method or composition for use of any one of embodiments 1-5, 8-106, or 108-109, wherein the subject has familial amyloid polyneuropathy.

Embodiment 111 is the method or composition for use of any one of embodiments 1-5 or 8-110, wherein the subject has only or predominantly nerve symptoms of ATTR.

Embodiment 112 is the method or composition for use of any one of embodiments 1-5 or 8-110, wherein the subject has familial amyloid cardiomyopathy.

Embodiment 113 is the method or composition for use of any one of embodiments 1-5, 8-109, or 112, wherein the subject has only or predominantly cardiac symptoms of ATTR.

Embodiment 114 is the method or composition for use of any one of embodiments 1-5 or 8-113, wherein the subject expresses TTR having a V30 mutation.

Embodiment 115 is the method or composition for use of embodiment 114, wherein the V30 mutation is V30A, V30G, V30L, or V30M.

Embodiment 116 is the method or composition for use of embodiment any one of embodiments 1-5 or 8-113, wherein the subject expresses TTR having a T60 mutation.

Embodiment 117 is the method or composition for use of embodiment 116, wherein the T60 mutation is T60A.

Embodiment 118 is the method or composition for use of embodiment any one of embodiments 1-5 or 8-113, wherein the subject expresses TTR having a V122 mutation.

Embodiment 119 is the method or composition for use of embodiment 118, wherein the V122 mutation is V122A, V122I, or V122(-).

Embodiment 120 is the method or composition for use of any one of embodiments 1-5 or 8-119, wherein the subject expresses wild-type TTR.

Embodiment 121 is the method or composition for use of any one of embodiments 1-5, 8-107, or 120, wherein the subject does not express TTR having a V30, T60, or V122 mutation.

Embodiment 122 is the method or composition for use of any one of embodiments 1-5, 8-107, or 120-121, wherein the subject does not express TTR having a pathological mutation.

Embodiment 123 is the method or composition for use of embodiment 121, wherein the subject is homozygous for wild-type TTR.

Embodiment 124 is the method or composition for use of any one of embodiments 1-5 or 8-123, wherein after administration the subject has an improvement, stabilization, or slowing of change in symptoms of sensorimotor neuropathy.

Embodiment 125 is the method or composition for use of embodiment 124, wherein the improvement, stabilization, or slowing of change in sensory neuropathy is measured using electromyogram, nerve conduction tests, or patient-reported outcomes.

Embodiment 126 is the method or composition for use of any one of embodiments 1-5 or 8-125, wherein the subject has an improvement, stabilization, or slowing of change in symptoms of congestive heart failure.

Embodiment 127 is the method or composition for use of embodiment 126, wherein the improvement, stabilization, or slowing of change in congestive heart failure is measured using cardiac biomarker tests, lung function tests, chest x-rays, or electrocardiography.

Embodiment 128 is the method or composition for use of any one of embodiments 1-5 or 8-127, wherein the composition or pharmaceutical formulation is administered via a viral vector.

Embodiment 129 is the method or composition for use of any one of embodiments 1-5 or 8-127, wherein the composition or pharmaceutical formulation is administered via lipid nanoparticles.

Embodiment 130 is the method or composition for use of any one of embodiments 1-5 or 8-129, wherein the subject is tested for specific mutations in the TTR gene before administering the composition or formulation.

Embodiment 131 is the method or composition of any one of embodiments 1-130, wherein the sequence selected from SEQ ID NOs: 5-82 is SEQ ID NO: 5.

Embodiment 132 is the method or composition of any one of embodiments 1-130, wherein the sequence selected from SEQ ID NOs: 5-82 is SEQ ID NO: 6.

Embodiment 133 is the method or composition of any one of embodiments 1-130, wherein the sequence selected from SEQ ID NOs: 5-82 is SEQ ID NO: 7.

Embodiment 134 is the method or composition of any one of embodiments 1-130, wherein the sequence selected from SEQ ID NOs: 5-82 is SEQ ID NO: 8.

Embodiment 135 is the method or composition of any one of embodiments 1-130, wherein the sequence selected from SEQ ID NOs: 5-82 is SEQ ID NO: 9.

Embodiment 136 is the method or composition of any one of embodiments 1-130, wherein the sequence selected from SEQ ID NOs: 5-82 is SEQ ID NO: 10.

Embodiment 137 is the method or composition of any one of embodiments 1-130, wherein the sequence selected from SEQ ID NOs: 5-82 is SEQ ID NO: 11.

Embodiment 138 is the method or composition of any one of embodiments 1-130, wherein the sequence selected from SEQ ID NOs: 5-82 is SEQ ID NO: 12.

Embodiment 139 is the method or composition of any one of embodiments 1-130, wherein the sequence selected from SEQ ID NOs: 5-82 is SEQ ID NO: 13.

Embodiment 140 is the method or composition of any one of embodiments 1-130, wherein the sequence selected from SEQ ID NOs: 5-82 is SEQ ID NO: 14.

Embodiment 141 is the method or composition of any one of embodiments 1-130, wherein the sequence selected from SEQ ID NOs: 5-82 is SEQ ID NO: 15.

Embodiment 142 is the method or composition of any one of embodiments 1-130, wherein the sequence selected from SEQ ID NOs: 5-82 is SEQ ID NO: 16.

Embodiment 143 is the method or composition of any one of embodiments 1-130, wherein the sequence selected from SEQ ID NOs: 5-82 is SEQ ID NO: 17.

Embodiment 144 is the method or composition of any one of embodiments 1-130, wherein the sequence selected from SEQ ID NOs: 5-82 is SEQ ID NO: 18.

Embodiment 145 is the method or composition of any one of embodiments 1-130, wherein the sequence selected from SEQ ID NOs: 5-82 is SEQ ID NO: 19.

Embodiment 146 is the method or composition of any one of embodiments 1-130, wherein the sequence selected from SEQ ID NOs: 5-82 is SEQ ID NO: 20.

Embodiment 147 is the method or composition of any one of embodiments 1-130, wherein the sequence selected from SEQ ID NOs: 5-82 is SEQ ID NO: 21.

Embodiment 148 is the method or composition of any one of embodiments 1-130, wherein the sequence selected from SEQ ID NOs: 5-82 is SEQ ID NO: 22.

Embodiment 149 is the method or composition of any one of embodiments 1-130, wherein the sequence selected from SEQ ID NOs: 5-82 is SEQ ID NO: 23.

Embodiment 150 is the method or composition of any one of embodiments 1-130, wherein the sequence selected from SEQ ID NOs: 5-82 is SEQ ID NO: 24.

Embodiment 151 is the method or composition of any one of embodiments 1-130, wherein the sequence selected from SEQ ID NOs: 5-82 is SEQ ID NO: 25.

Embodiment 152 is the method or composition of any one of embodiments 1-130, wherein the sequence selected from SEQ ID NOs: 5-82 is SEQ ID NO: 26.

Embodiment 153 is the method or composition of any one of embodiments 1-130, wherein the sequence selected from SEQ ID NOs: 5-82 is SEQ ID NO: 27.

Embodiment 154 is the method or composition of any one of embodiments 1-130, wherein the sequence selected from SEQ ID NOs: 5-82 is SEQ ID NO: 28.

Embodiment 155 is the method or composition of any one of embodiments 1-130, wherein the sequence selected from SEQ ID NOs: 5-82 is SEQ ID NO: 29.

Embodiment 156 is the method or composition of any one of embodiments 1-130, wherein the sequence selected from SEQ ID NOs: 5-82 is SEQ ID NO: 30.

Embodiment 157 is the method or composition of any one of embodiments 1-130, wherein the sequence selected from SEQ ID NOs: 5-82 is SEQ ID NO: 31.

Embodiment 158 is the method or composition of any one of embodiments 1-130, wherein the sequence selected from SEQ ID NOs: 5-82 is SEQ ID NO: 32.

Embodiment 159 is the method or composition of any one of embodiments 1-130, wherein the sequence selected from SEQ ID NOs: 5-82 is SEQ ID NO: 33.

Embodiment 160 is the method or composition of any one of embodiments 1-130, wherein the sequence selected from SEQ ID NOs: 5-82 is SEQ ID NO: 34.

Embodiment 161 is the method or composition of any one of embodiments 1-130, wherein the sequence selected from SEQ ID NOs: 5-82 is SEQ ID NO: 35.

Embodiment 162 is the method or composition of any one of embodiments 1-130, wherein the sequence selected from SEQ ID NOs: 5-82 is SEQ ID NO: 36.

Embodiment 163 is the method or composition of any one of embodiments 1-130, wherein the sequence selected from SEQ ID NOs: 5-82 is SEQ ID NO: 37.

Embodiment 164 is the method or composition of any one of embodiments 1-130, wherein the sequence selected from SEQ ID NOs: 5-82 is SEQ ID NO: 38.

Embodiment 165 is the method or composition of any one of embodiments 1-130, wherein the sequence selected from SEQ ID NOs: 5-82 is SEQ ID NO: 39.

Embodiment 166 is the method or composition of any one of embodiments 1-130, wherein the sequence selected from SEQ ID NOs: 5-82 is SEQ ID NO: 40.

Embodiment 167 is the method or composition of any one of embodiments 1-130, wherein the sequence selected from SEQ ID NOs: 5-82 is SEQ ID NO: 41.

Embodiment 168 is the method or composition of any one of embodiments 1-130, wherein the sequence selected from SEQ ID NOs: 5-82 is SEQ ID NO: 42.

Embodiment 169 is the method or composition of any one of embodiments 1-130, wherein the sequence selected from SEQ ID NOs: 5-82 is SEQ ID NO: 43.

Embodiment 170 is the method or composition of any one of embodiments 1-130, wherein the sequence selected from SEQ ID NOs: 5-82 is SEQ ID NO: 44.

Embodiment 171 is the method or composition of any one of embodiments 1-130, wherein the sequence selected from SEQ ID NOs: 5-82 is SEQ ID NO: 45.

Embodiment 172 is the method or composition of any one of embodiments 1-130, wherein the sequence selected from SEQ ID NOs: 5-82 is SEQ ID NO: 46.

Embodiment 173 is the method or composition of any one of embodiments 1-130, wherein the sequence selected from SEQ ID NOs: 5-82 is SEQ ID NO: 47.

Embodiment 174 is the method or composition of any one of embodiments 1-130, wherein the sequence selected from SEQ ID NOs: 5-82 is SEQ ID NO: 48.

Embodiment 175 is the method or composition of any one of embodiments 1-130, wherein the sequence selected from SEQ ID NOs: 5-82 is SEQ ID NO: 49.

Embodiment 176 is the method or composition of any one of embodiments 1-130, wherein the sequence selected from SEQ ID NOs: 5-82 is SEQ ID NO: 50.

Embodiment 177 is the method or composition of any one of embodiments 1-130, wherein the sequence selected from SEQ ID NOs: 5-82 is SEQ ID NO: 51.

Embodiment 178 is the method or composition of any one of embodiments 1-130, wherein the sequence selected from SEQ ID NOs: 5-82 is SEQ ID NO: 52.

Embodiment 179 is the method or composition of any one of embodiments 1-130, wherein the sequence selected from SEQ ID NOs: 5-82 is SEQ ID NO: 53.

Embodiment 180 is the method or composition of any one of embodiments 1-130, wherein the sequence selected from SEQ ID NOs: 5-82 is SEQ ID NO: 54.

Embodiment 181 is the method or composition of any one of embodiments 1-130, wherein the sequence selected from SEQ ID NOs: 5-82 is SEQ ID NO: 55.

Embodiment 182 is the method or composition of any one of embodiments 1-130, wherein the sequence selected from SEQ ID NOs: 5-82 is SEQ ID NO: 56.

Embodiment 183 is the method or composition of any one of embodiments 1-130, wherein the sequence selected from SEQ ID NOs: 5-82 is SEQ ID NO: 57.

Embodiment 184 is the method or composition of any one of embodiments 1-130, wherein the sequence selected from SEQ ID NOs: 5-82 is SEQ ID NO: 58.

Embodiment 185 is the method or composition of any one of embodiments 1-130, wherein the sequence selected from SEQ ID NOs: 5-82 is SEQ ID NO: 59.

Embodiment 186 is the method or composition of any one of embodiments 1-130, wherein the sequence selected from SEQ ID NOs: 5-82 is SEQ ID NO: 60.

Embodiment 187 is the method or composition of any one of embodiments 1-130, wherein the sequence selected from SEQ ID NOs: 5-82 is SEQ ID NO: 61.

Embodiment 188 is the method or composition of any one of embodiments 1-130, wherein the sequence selected from SEQ ID NOs: 5-82 is SEQ ID NO: 62.

Embodiment 189 is the method or composition of any one of embodiments 1-130, wherein the sequence selected from SEQ ID NOs: 5-82 is SEQ ID NO: 63.

Embodiment 190 is the method or composition of any one of embodiments 1-130, wherein the sequence selected from SEQ ID NOs: 5-82 is SEQ ID NO: 64.

Embodiment 191 is the method or composition of any one of embodiments 1-130, wherein the sequence selected from SEQ ID NOs: 5-82 is SEQ ID NO: 65.

Embodiment 192 is the method or composition of any one of embodiments 1-130, wherein the sequence selected from SEQ ID NOs: 5-82 is SEQ ID NO: 66.

Embodiment 193 is the method or composition of any one of embodiments 1-130, wherein the sequence selected from SEQ ID NOs: 5-82 is SEQ ID NO: 67.

Embodiment 194 is the method or composition of any one of embodiments 1-130, wherein the sequence selected from SEQ ID NOs: 5-82 is SEQ ID NO: 68.

Embodiment 195 is the method or composition of any one of embodiments 1-130, wherein the sequence selected from SEQ ID NOs: 5-82 is SEQ ID NO: 69.

Embodiment 196 is the method or composition of any one of embodiments 1-130, wherein the sequence selected from SEQ ID NOs: 5-82 is SEQ ID NO: 70.

Embodiment 197 is the method or composition of any one of embodiments 1-130, wherein the sequence selected from SEQ ID NOs: 5-82 is SEQ ID NO: 71.

Embodiment 198 is the method or composition of any one of embodiments 1-130, wherein the sequence selected from SEQ ID NOs: 5-82 is SEQ ID NO: 72.

Embodiment 199 is the method or composition of any one of embodiments 1-130, wherein the sequence selected from SEQ ID NOs: 5-82 is SEQ ID NO: 73.

Embodiment 200 is the method or composition of any one of embodiments 1-130, wherein the sequence selected from SEQ ID NOs: 5-82 is SEQ ID NO: 74.

Embodiment 201 is the method or composition of any one of embodiments 1-130, wherein the sequence selected from SEQ ID NOs: 5-82 is SEQ ID NO: 75.

Embodiment 202 is the method or composition of any one of embodiments 1-130, wherein the sequence selected from SEQ ID NOs: 5-82 is SEQ ID NO: 76.

Embodiment 203 is the method or composition of any one of embodiments 1-130, wherein the sequence selected from SEQ ID NOs: 5-82 is SEQ ID NO: 77.

Embodiment 204 is the method or composition of any one of embodiments 1-130, wherein the sequence selected from SEQ ID NOs: 5-82 is SEQ ID NO: 78.

Embodiment 205 is the method or composition of any one of embodiments 1-130, wherein the sequence selected from SEQ ID NOs: 5-82 is SEQ ID NO: 79.

Embodiment 206 is the method or composition of any one of embodiments 1-130, wherein the sequence selected from SEQ ID NOs: 5-82 is SEQ ID NO: 80.

Embodiment 207 is the method or composition of any one of embodiments 1-130, wherein the sequence selected from SEQ ID NOs: 5-82 is SEQ ID NO: 81.

Embodiment 208 is the method or composition of any one of embodiments 1-130, wherein the sequence selected from SEQ ID NOs: 5-82 is SEQ ID NO: 82.

Embodiment 209 is a use of a composition or formulation of any of embodiments 6-208 for the preparation of a medicament for treating a human subject having ATTR.

Also disclosed is the use of a composition or formulation of any of the foregoing embodiments for the preparation of a medicament for treating a human subject having ATTR. Also disclosed are any of the foregoing compositions or formulations for use in treating ATTR or for use in modifying (e.g., forming an indel in, or forming a frameshift or nonsense mutation in) a TTR gene.

BRIEF DESCRIPTION OF THE DRAWINGS

FIGS. 19A and 19C) and editing results following dosing of LNP formulations at the indicated ratios and amounts (FIGS. 19B and 19D).

FIG. 21B is a re-scaled version of the OT2, OT4, and negative control (Neg Cont) data in FIG. 21A.

FIG. 22B is a re-scaled version of the OT4 and negative control (Neg Cont) data in FIG. 22A.

FIG. 23A shows percent editing at the TTR locus in control and treatment (dosed with lipid nanoparticle formulated TTR specific sgRNA) groups. FIG. 23B shows the number of insertion and deletion events at the TTR locus when editing was observed in the treatment group of FIG. 23A.

DETAILED DESCRIPTION

Figure 1:
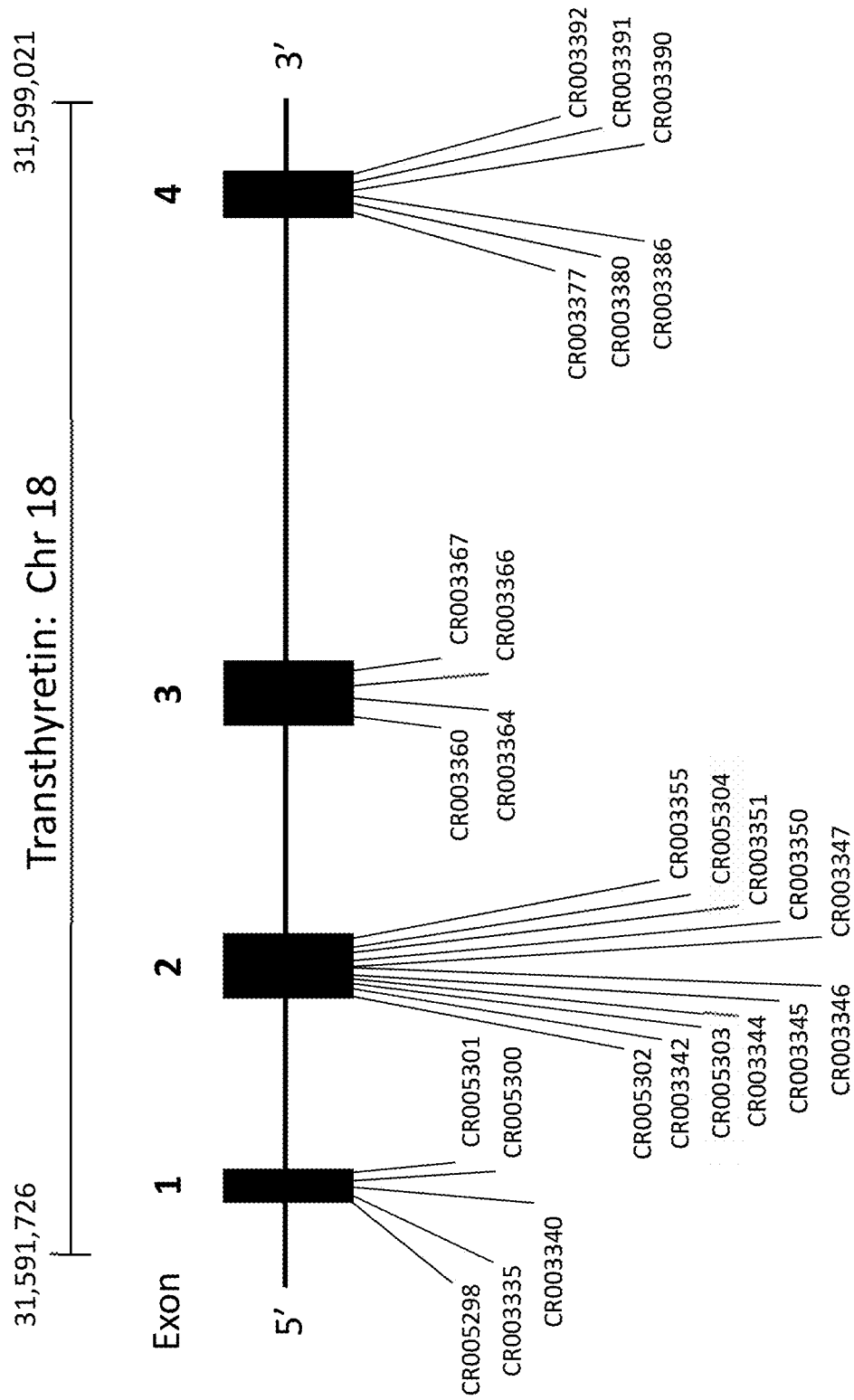
FIG. 1 shows a schematic of chromosome 18 with the regions of the TTR gene that are targeted by the guide sequences provided in Table 1.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measureable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). The term "or" is used in an inclusive sense, i.e., equivalent to "and/or," unless the context clearly indicates otherwise.

The section headings used herein are for organizational purposes only and are not to be construed as limiting the desired subject matter in any way. In the event that any material incorporated by reference contradicts any term defined in this specification or any other express content of this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

I. Definitions

Unless stated otherwise, the following terms and phrases as used herein are intended to have the following meanings:

"Polynucleotide" and "nucleic acid" are used herein to refer to a multimeric compound comprising nucleosides or nucleoside analogs which have nitrogenous heterocyclic bases or base analogs linked together along a backbone, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., modified uridines such as 5-methoxyuridine, pseudouridine, or N1-methylpseudouridine, or others); inosine; derivatives of purines or pyrimidines (e.g., $N^4$-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). For general discussion see The Biochemistry of the Nucleic Acids 5-36, Adams et al., ed., $11^{th}$ ed., 1992). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, Biochemistry 43(42): 13233-41). RNA and DNA have different sugar moieties and can differ by the presence of uracil or analogs thereof in RNA and thymine or analogs thereof in DNA.

"Guide RNA", "gRNA", and "guide" are used herein interchangeably to refer to either a crRNA (also known as CRISPR RNA), or the combination of a crRNA and a trRNA (also known as tracrRNA). The crRNA and trRNA may be associated as a single RNA molecule (single guide RNA, sgRNA) or in two separate RNA molecules (dual guide RNA, dgRNA). "Guide RNA" or "gRNA" refers to each type. The trRNA may be a naturally-occurring sequence, or a trRNA sequence with modifications or variations compared to naturally-occurring sequences.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of Streptococcus pyogenes (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. For example, in some embodiments, the guide sequence comprises at least 17, 18, 19, or 20 contiguous nucleotides of a sequence selected from SEQ ID NOs: 5-82. In some embodiments, the target sequence is in a gene or on a chromosome, for example, and is complementary to the guide sequence. In some embodiments, the degree of complementarity or identity between a guide sequence and its corresponding target sequence may be about 75%, 80%, 85%, 88%, 90%, 95%, 96%, 97%, 98%, 99%, or 100%. For example, in some embodiments, the guide sequence comprises a sequence with about 75%, 80%, 85%, 88%, 90%, 95%, 96%, 97%, 98%, 99%, or 100% identity to at least 17, 18, 19, or 20 contiguous nucleotides of a sequence selected from SEQ ID NOs: 5-82. In some embodiments, the guide sequence and the target region may be 100% complementary or identical. In other embodiments, the guide sequence and the target region may contain at least one mismatch. For example, the guide sequence and the target sequence may contain 1, 2, 3, or 4 mismatches, where the total length of the target sequence is at least 17, 18, 19, 20 or more base pairs. In some embodiments, the guide sequence and the target region may contain 1-4 mismatches where the guide sequence comprises at least 17, 18, 19, 20 or more nucleotides. In some embodiments, the guide sequence and the target region may contain 1, 2, 3, or 4 mismatches where the guide sequence comprises 20 nucleotides.

Target sequences for Cas proteins include both the positive and negative strands of genomic DNA (i.e., the sequence given and the sequence's reverse compliment), as a nucleic acid substrate for a Cas protein is a double stranded nucleic acid. Accordingly, where a guide sequence is said to be "complementary to a target sequence", it is to be understood that the guide sequence may direct a guide RNA to bind to the reverse complement of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

As used herein, an "RNA-guided DNA binding agent" means a polypeptide or complex of polypeptides having RNA and DNA binding activity, or a DNA-binding subunit of such a complex, wherein the DNA binding activity is sequence-specific and depends on the sequence of the RNA. Exemplary RNA-guided DNA binding agents include Cas cleavases/nickases and inactivated forms thereof ("dCas DNA binding agents"). "Cas nuclease", also called "Cas protein", as used herein, encompasses Cas cleavases, Cas nickases, and dCas DNA binding agents. Cas cleavases/nickases and dCas DNA binding agents include a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single-chain polypeptide with RNA-guided DNA binding activity, such as a Cas9 nuclease or a Cpf1 nuclease. Class 2 Cas nucleases include Class 2 Cas cleavases and Class 2 Cas nickases (e.g., H840A, D10A, or N863A variants), which further have RNA-guided DNA cleavases or nickase activity, and Class 2 dCas DNA binding agents, in which cleavase/nickase activity is inactivated. Class 2 Cas nucleases include, for example, Cas9, Cpf1, C2c1, C2c2, C2c3, HF Cas9 (e.g., N497A, R661A, Q695A, Q926A variants), HypaCas9 (e.g., N692A, M694A, Q695A, H698A variants), eSPCas9(1.0) (e.g, K810A, K1003A, R1060A variants), and eSPCas9(1.1) (e.g., K848A, K1003A, R1060A variants) proteins and modifications thereof. Cpf1 protein, Zetsche et al., *Cell*, 163: 1-13 (2015), is homologous to Cas9, and contains a RuvC-like nuclease domain. Cpf1 sequences of Zetsche are incorporated by reference in their entirety. See, e.g., Zetsche, Tables S1 and S3. "Cas9" encompasses Spy Cas9, the variants of Cas9 listed herein, and equivalents thereof. See, e.g., Makarova et al., *Nat Rev Microbiol*, 13(11): 722-36 (2015); Shmakov et al., *Molecular Cell*, 60:385-397 (2015).

"Modified uridine" is used herein to refer to a nucleoside other than thymidine with the same hydrogen bond acceptors as uridine and one or more structural differences from uridine. In some embodiments, a modified uridine is a substituted uridine, i.e., a uridine in which one or more non-proton substituents (e.g., alkoxy, such as methoxy) takes the place of a proton. In some embodiments, a modified uridine is pseudouridine. In some embodiments, a modified uridine is a substituted pseudouridine, i.e., a pseudouridine in which one or more non-proton substituents (e.g., alkyl, such as methyl) takes the place of a proton. In some embodiments, a modified uridine is any of a substituted uridine, pseudouridine, or a substituted pseudouridine.

"Uridine position" as used herein refers to a position in a polynucleotide occupied by a uridine or a modified uridine. Thus, for example, a polynucleotide in which "100% of the uridine positions are modified uridines" contains a modified uridine at every position that would be a uridine in a conventional RNA (where all bases are standard A, U, C, or G bases) of the same sequence. Unless otherwise indicated, a U in a polynucleotide sequence of a sequence table or sequence listing in, or accompanying, this disclosure can be a uridine or a modified uridine.

As used herein, a first sequence is considered to "comprise a sequence with at least X % identity to" a second sequence if an alignment of the first sequence to the second sequence shows that X % or more of the positions of the second sequence in its entirety are matched by the first sequence. For example, the sequence AAGA comprises a sequence with 100% identity to the sequence AAG because an alignment would give 100% identity in that there are matches to all three positions of the second sequence. The differences between RNA and DNA (generally the exchange of uridine for thymidine or vice versa) and the presence of nucleoside analogs such as modified uridines do not contribute to differences in identity or complementarity among polynucleotides as long as the relevant nucleotides (such as thymidine, uridine, or modified uridine) have the same complement (e.g., adenosine for all of thymidine, uridine, or modified uridine; another example is cytosine and 5-methylcytosine, both of which have guanosine or modified guanosine as a complement). Thus, for example, the sequence 5'-AXG where X is any modified uridine, such as pseudouridine, N1-methyl pseudouridine, or 5-methoxyuridine, is considered 100% identical to AUG in that both are perfectly complementary to the same sequence (5'-CAU). Exemplary alignment algorithms are the Smith-Waterman and Needleman-Wunsch algorithms, which are well-known in the art. One skilled in the art will understand what choice of algorithm and parameter settings are appropriate for a given pair of sequences to be aligned; for sequences of generally similar length and expected identity >50% for amino acids or >75% for nucleotides, the Needleman-Wunsch algorithm with default settings of the Needleman-Wunsch algorithm interface provided by the EBI at the www.ebi.ac.uk web server is generally appropriate.

"mRNA" is used herein to refer to a polynucleotide that is not DNA and comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of an mRNA phosphate-sugar backbone consist essentially of ribose residues, 2'-methoxy ribose residues, or a combination thereof. In general, mRNAs do not contain a substantial quantity of thymidine residues (e.g., 0 residues or fewer than 30, 20, 10, 5, 4, 3, or 2 thymidine residues; or less than 10%, 9%, 8%, 7%, 6%, 5%, 4%, 4%, 3%, 2%, 1%, 0.5%, 0.2%, or 0.1% thymidine content). An mRNA can contain modified uridines at some or all of its uridine positions.

As used herein, the "minimum uridine content" of a given open reading frame (ORF) is the uridine content of an ORF that (a) uses a minimal uridine codon at every position and (b) encodes the same amino acid sequence as the given ORF. The minimal uridine codon(s) for a given amino acid is the codon(s) with the fewest uridines (usually 0 or 1 except for a codon for phenylalanine, where the minimal uridine codon has 2 uridines). Modified uridine residues are considered equivalent to uridines for the purpose of evaluating minimum uridine content.

As used herein, the "minimum uridine dinucleotide content" of a given open reading frame (ORF) is the lowest possible uridine dinucleotide (UU) content of an ORF that (a) uses a minimal uridine codon (as discussed above) at every position and (b) encodes the same amino acid sequence as the given ORF. The uridine dinucleotide (UU) content can be expressed in absolute terms as the enumeration of UU dinucleotides in an ORF or on a rate basis as the percentage of positions occupied by the uridines of uridine dinucleotides (for example, AUUAU would have a uridine dinucleotide content of 40% because 2 of 5 positions are occupied by the uridines of a uridine dinucleotide). Modified uridine residues are considered equivalent to uridines for the purpose of evaluating minimum uridine dinucleotide content.

As used herein, "TTR" refers to transthyretin, which is the gene product of a TTR gene.

As used herein, "amyloid" refers to abnormal aggregates of proteins or peptides that are normally soluble. Amyloids are insoluble, and amyloids can create proteinaceous deposits in organs and tissues. Proteins or peptides in amyloids may be misfolded into a form that allows many copies of the protein to stick together to form fibrils. While some forms of amyloid may have normal functions in the human body, "amyloids" as used herein refers to abnormal or pathologic aggregates of protein. Amyloids may comprise a single protein or peptide, such as TTR, or they may comprise multiple proteins or peptides, such as TTR and additional proteins.

As used herein, "amyloid fibrils" refers to insoluble fibers of amyloid that are resistant to degradation. Amyloid fibrils can produce symptoms based on the specific protein or peptide and the tissue and cell type in which it has aggregated.

As used herein, "amyloidosis" refers to a disease characterized by symptoms caused by deposition of amyloid or amyloid fibrils. Amyloidosis can affect numerous organs including the heart, kidney, liver, spleen, nervous system, and digestive track.

As used herein, "ATTR," "TTR-related amyloidosis," "TTR amyloidosis," "ATTR amyloidosis," or "amyloidosis associated with TTR" refers to amyloidosis associated with deposition of TTR.

As used herein, "familial amyloid cardiomyopathy" or "FAC" refers to a hereditary transthyretin amyloidosis (ATTR) characterized primarily by restrictive cardiomyopathy. Congestive heart failure is common in FAC. Average age of onset is approximately 60-70 years of age, with an estimated life expectancy of 4-5 years after diagnosis.

As used herein, "familial amyloid polyneuropathy" or "FAP" refers to a hereditary transthyretin amyloidosis (ATTR) characterized primarily by sensorimotor neuropathy. Autonomic neuropathy is common in FAP. While neuropathy is a primary feature, symptoms of FAP may also include cachexia, renal failure, and cardiac disease. Average age of onset of FAP is approximately 30-50 years of age, with an estimated life expectancy of 5-15 after diagnosis.

As used herein, "wild-type ATTR" and "ATTRwt" refer to ATTR not associated with a pathological TTR mutation such as T60A, V30M, V30A, V30G, V30L, V122I, V122A, or V122(-). ATTRwt has also been referred to as senile systemic amyloidosis. Onset typically occurs in men aged 60 or higher with the most common symptoms being congestive heart failure and abnormal heart rhythm such as atrial fibrillation. Additional symptoms include consequences of poor heart function such as shortness of breath, fatigue, dizziness, swelling (especially in the legs), nausea, angina, disrupted sleep, and weight loss. A history of carpal tunnel syndrome indicates increased risk for ATTRwt and may in some cases be indicative of early-stage disease. ATTRwt generally leads to decreasing heart function over time but can have a better prognosis than hereditary ATTR because wild-type TTR deposits accumulate more slowly. Existing treatments are similar to other forms of ATTR (other than liver transplantation) and are generally directed to supporting or improving heart function, ranging from diuretics and limited fluid and salt intake to anticoagulants, and in severe cases, heart transplants. Nonetheless, like FAC, ATTRwt can result in death from heart failure, sometimes within 3-5 years of diagnosis.

Guide sequences useful in the guide RNA compositions and methods described herein are shown in Table 1 and throughout the application.

As used herein, "hereditary ATTR" refers to ATTR that is associated with a mutation in the sequence of the TTR gene. Known mutations in the TTR gene associated with ATTR include those resulting in TTR with substitutions of T60A, V30M, V30A, V30G, V30L, V122I, V122A, or V122(-).

As used herein, "indels" refer to insertion/deletion mutations consisting of a number of nucleotides that are either inserted or deleted at the site of double-stranded breaks (DSBs) in a target nucleic acid.

As used herein, "knockdown" refers to a decrease in expression of a particular gene product (e.g., protein, mRNA, or both). Knockdown of a protein can be measured either by detecting protein secreted by tissue or population of cells (e.g., in serum or cell media) or by detecting total cellular amount of the protein from a tissue or cell population of interest. Methods for measuring knockdown of mRNA are known, and include sequencing of mRNA isolated from a tissue or cell population of interest. In some embodiments, "knockdown" may refer to some loss of expression of a particular gene product, for example a decrease in the amount of mRNA transcribed or a decrease in the amount of protein expressed or secreted by a population of cells (including in vivo populations such as those found in tissues).

As used herein, "knockout" refers to a loss of expression of a particular protein in a cell. Knockout can be measured either by detecting the amount of protein secretion from a tissue or population of cells (e.g., in serum or cell media) or by detecting total cellular amount of a protein a tissue or a population of cells. In some embodiments, the methods of the disclosure "knockout" TTR in one or more cells (e.g., in a population of cells including in vivo populations such as those found in tissues). In some embodiments, a knockout is not the formation of mutant TTR protein, for example, created by indels, but rather the complete loss of expression of TTR protein in a cell.

As used herein, "mutant TTR" refers to a gene product of TTR (i.e., the TTR protein) having a change in the amino acid sequence of TTR compared to the wildtype amino acid sequence of TTR. The human wild-type TTR sequence is available at NCBI Gene ID: 7276; Ensembl: Ensembl: ENSG00000118271. Mutants forms of TTR associated with ATTR, e.g., in humans, include T60A, V30M, V30A, V30G, V30L, V122I, V122A, or V122(-).

As used herein, "mutant TTR" or "mutant TTR allele" refers to a TTR sequence having a change in the nucleotide sequence of TTR compared to the wildtype sequence (NCBI Gene ID: 7276; Ensembl: ENSG00000118271).

As used herein, "ribonucleoprotein" (RNP) or "RNP complex" refers to a guide RNA together with an RNA-guided DNA binding agent, such as a Cas nuclease, e.g., a Cas cleavase, Cas nickase, or dCas DNA binding agent (e.g., Cas9). In some embodiments, the guide RNA guides the RNA-guided DNA binding agent such as Cas9 to a target sequence, and the guide RNA hybridizes with and the agent binds to the target sequence; in cases where the agent is a cleavase or nickase, binding can be followed by cleaving or nicking.

As used herein, a "target sequence" refers to a sequence of nucleic acid in a target gene that has complementarity to the guide sequence of the gRNA. The interaction of the target sequence and the guide sequence directs an RNA-guided DNA binding agent to bind, and potentially nick or cleave (depending on the activity of the agent), within the target sequence.

As used herein, "treatment" refers to any administration or application of a therapeutic for disease or disorder in a subject, and includes inhibiting the disease, arresting its development, relieving one or more symptoms of the disease, curing the disease, or preventing reoccurrence of one or more symptoms of the disease. For example, treatment of ATTR may comprise alleviating symptoms of ATTR.

"Modified uridine" is used herein to refer to a nucleoside other than thymidine with the same hydrogen bond acceptors as uridine and one or more structural differences from uridine. In some embodiments, a modified uridine is a substituted uridine, i.e., a uridine in which one or more non-proton substituents (e.g., alkoxy, such as methoxy) takes the place of a proton. In some embodiments, a modified uridine is pseudouridine. In some embodiments, a modified uridine is a substituted pseudouridine, i.e., a pseudouridine in which one or more non-proton substituents (e.g., alkyl, such as methyl) takes the place of a proton, e.g., N1-methyl pseudouridine. In some embodiments, a modified uridine is any of a substituted uridine, pseudouridine, or a substituted pseudouridine.

As used herein, a first sequence is considered to "comprise a sequence with at least X % identity to" a second sequence if an alignment of the first sequence to the second sequence shows that X % or more of the positions of the second sequence in its entirety are matched by the first sequence. For example, the sequence AAGA comprises a sequence with 100% identity to the sequence AAG because an alignment would give 100% identity in that there are matches to all three positions of the second sequence. The differences between RNA and DNA (generally the exchange of uridine for thymidine or vice versa) and the presence of nucleoside analogs such as modified uridines do not contribute to differences in identity or complementarity among polynucleotides as long as the relevant nucleotides (such as thymidine, uridine, or modified uridine) have the same complement (e.g., adenosine for all of thymidine, uridine, or modified uridine; another example is cytosine and 5-methylcytosine, both of which have guanosine as a complement). Thus, for example, the sequence 5'-AXG where X is any modified uridine, such as pseudouridine, N1-methyl pseudouridine, or 5-methoxyuridine, is considered 100% identical to AUG in that both are perfectly complementary to the same sequence (5'-CAU). Exemplary alignment algorithms are the Smith-Waterman and Needleman-Wunsch algorithms, which are well-known in the art. One skilled in the art will understand what choice of algorithm and parameter settings are appropriate for a given pair of sequences to be aligned; for sequences of generally similar length and expected identity >50% for amino acids or >75% for nucleotides, the Needleman-Wunsch algorithm with default settings of the Needleman-Wunsch algorithm interface provided by the EBI at the www.ebi.ac.uk web server are generally appropriate.

The term "about" or "approximately" means an acceptable error for a particular value as determined by one of ordinary skill in the art, which depends in part on how the value is measured or determined.

II. Compositions

A. Compositions Comprising Guide RNA (gRNAs)

Provided herein are compositions useful for editing the TTR gene, e.g., using a guide RNA with an RNA-guided DNA binding agent (e.g., a CRISPR/Cas system). The compositions may be administered to subjects having wild-type or non-wild type TTR gene sequences, such as, for example, subjects with ATTR, which may be ATTR wt or a hereditary or familial form of ATTR. Guide sequences targeting the TTR gene are shown in Table 1 at SEQ ID Nos: 5-82.

TABLE 1

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 5 | CR003335 | TTR (Exon 1) | Human | chr18:31591917-31591937 | CUGCUCCUCCUCUGCCUUGC |
| 6 | CR003336 | TTR (Exon 1) | Human | chr18:31591922-31591942 | CCUCCUCUGCCUUGCUGGAC |
| 7 | CR003337 | TTR (Exon 1) | Human | chr18:31591925-31591945 | CCAGUCCAGCAAGGCAGAGG |
| 8 | CR003338 | TTR (Exon 1) | Human | chr18:31591928-31591948 | AUACCAGUCCAGCAAGGCAG |
| 9 | CR003339 | TTR (Exon 1) | Human | chr18:31591934-31591954 | ACACAAAUACCAGUCCAGCA |
| 10 | CR003340 | TTR (Exon 1) | Human | chr18:31591937-31591957 | UGGACUGGUAUUUGUGUCUG |
| 11 | CR003341 | TTR (Exon 1) | Human | chr18:31591941-31591961 | CUGGUAUUUGUGUCUGAGGC |
| 12 | CR003342 | TTR (Exon 2) | Human | chr18:31592880-31592900 | CUUCUCUACACCCAGGGCAC |
| 13 | CR003343 | TTR (Exon 2) | Human | chr18:31592902-31592922 | CAGAGGACACUUGGAUUCAC |
| 14 | CR003344 | TTR (Exon 2) | Human | chr18:31592911-31592931 | UUUGACCAUCAGAGGACACU |
| 15 | CR003345 | TTR (Exon 2) | Human | chr18:31592919-31592939 | UCUAGAACUUUGACCAUCAG |

TABLE 1-continued

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 16 | CR003346 | TTR (Exon 2) | Human | chr18:31592928-31592948 | AAAGUUCUAGAUGCUGUCCG |
| 17 | CR003347 | TTR (Exon 2) | Human | chr18:31592948-31592968 | CAUUGAUGGCAGGACUGCCU |
| 18 | CR003348 | TTR (Exon 2) | Human | chr18:31592948-31592968 | AGGCAGUCCUGCCAUCAAUG |
| 19 | CR003349 | TTR (Exon 2) | Human | chr18:31592958-31592978 | UGCACGGCCACAUUGAUGGC |
| 20 | CR003350 | TTR (Exon 2) | Human | chr18:31592962-31592982 | CACAUGCACGGCCACAUUGA |
| 21 | CR003351 | TTR (Exon 2) | Human | chr18:31592974-31592994 | AGCCUUUCUGAACACAUGCA |
| 22 | CR003352 | TTR (Exon 2) | Human | chr18:31592986-31593006 | GAAAGGCUGCUGAUGACACC |
| 23 | CR003353 | TTR (Exon 2) | Human | chr18:31592987-31593007 | AAAGGCUGCUGAUGACACCU |
| 24 | CR003354 | TTR (Exon 2) | Human | chr18:31593003-31593023 | ACCUGGGAGCCAUUUGCCUC |
| 25 | CR003355 | TTR (Exon 2) | Human | chr18:31593007-31593027 | CCCAGAGGCAAAUGGCUCCC |
| 26 | CR003356 | TTR (Exon 2) | Human | chr18:31593015-31593035 | GCAACUUACCCAGAGGCAAA |
| 27 | CR003357 | TTR (Exon 2) | Human | chr18:31593022-31593042 | UUCUUUGGCAACUUACCCAG |
| 28 | CR003358 | TTR (Exon 3) | Human | chr18:31595127-31595147 | AUGCAGCUCUCCAGACUCAC |
| 29 | CR003359 | TTR (Exon 3) | Human | chr18:31595126-31595146 | AGUGAGUCUGGAGAGCUGCA |
| 30 | CR003360 | TTR (Exon 3) | Human | chr18:31595127-31595147 | GUGAGUCUGGAGAGCUGCAU |
| 31 | CR003361 | TTR (Exon 3) | Human | chr18:31595140-31595160 | GCUGCAUGGGCUCACAACUG |
| 32 | CR003362 | TTR (Exon 3) | Human | chr18:31595143-31595163 | GCAUGGGCUCACAACUGAGG |
| 33 | CR003363 | TTR (Exon 3) | Human | chr18:31595156-31595176 | ACUGAGGAGGAAUUUGUAGA |
| 34 | CR003364 | TTR (Exon 3) | Human | chr18:31595157-31595177 | CUGAGGAGGAAUUUGUAGAA |
| 35 | CR003365 | TTR (Exon 3) | Human | chr18:31595170-31595190 | UGUAGAAGGGAUAUACAAAG |
| 36 | CR003366 | TTR (Exon 3) | Human | chr18:31595193-31595213 | AAAUAGACACCAAAUCUUAC |
| 37 | CR003367 | TTR (Exon 3) | Human | chr18:31595197-31595217 | AGACACCAAAUCUUACUGGA |
| 38 | CR003368 | TTR (Exon 3) | Human | chr18:31595205-31595225 | AAGUGCCUUCCAGUAAGAUU |
| 39 | CR003369 | TTR (Exon 3) | Human | chr18:31595235-31595255 | CUCUGCAUGCUCAUGGAAUG |

TABLE 1-continued

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 40 | CR003370 | TTR (Exon 3) | Human | chr18:31595236-31595256 | CCUCUGCAUGCUCAUGGAAU |
| 41 | CR003371 | TTR (Exon 3) | Human | chr18:31595237-31595257 | ACCUCUGCAUGCUCAUGGAA |
| 42 | CR003372 | TTR (Exon 3) | Human | chr18:31595242-31595262 | UACUCACCUCUGCAUGCUCA |
| 43 | CR003373 | TTR (Exon 4) | Human | chr18:31598570-31598590 | GUAUUCACAGCCAACGACUC |
| 44 | CR003374 | TTR (Exon 4) | Human | chr18:31598583-31598603 | GCGGCGGGGGCCGGAGUCGU |
| 45 | CR003375 | TTR (Exon 4) | Human | chr18:31598592-31598612 | AAUGGUGUAGCGGCGGGGGC |
| 46 | CR003376 | TTR (Exon 4) | Human | chr18:31598596-31598616 | CGGCAAUGGUGUAGCGGCGG |
| 47 | CR003377 | TTR (Exon 4) | Human | chr18:31598597-31598617 | GCGGCAAUGGUGUAGCGGCG |
| 48 | CR003378 | TTR (Exon 4) | Human | chr18:31598598-31598618 | GGCGGCAAUGGUGUAGCGGC |
| 49 | CR003379 | TTR (Exon 4) | Human | chr18:31598599-31598619 | GGGCGGCAAUGGUGUAGCGG |
| 50 | CR003380 | TTR (Exon 4) | Human | chr18:31598602-31598622 | GCAGGGCGGCAAUGGUGUAG |
| 51 | CR003381 | TTR (Exon 4) | Human | chr18:31598610-31598630 | GGGGCUCAGCAGGGCGGCAA |
| 52 | CR003382 | TTR (Exon 4) | Human | chr18:31598616-31598636 | GGAGUAGGGGCUCAGCAGGG |
| 53 | CR003383 | TTR (Exon 4) | Human | chr18:31598619-31598639 | AUAGGAGUAGGGGCUCAGCA |
| 54 | CR003384 | TTR (Exon 4) | Human | chr18:31598620-31598640 | AAUAGGAGUAGGGGCUCAGC |
| 55 | CR003385 | TTR (Exon 4) | Human | chr18:31598626-31598646 | CCCCUACUCCUAUUCCACCA |
| 56 | CR003386 | TTR (Exon 4) | Human | chr18:31598629-31598649 | CCGUGGUGGAAUAGGAGUAG |
| 57 | CR003387 | TTR (Exon 4) | Human | chr18:31598630-31598650 | GCCGUGGUGGAAUAGGAGUA |
| 58 | CR003388 | TTR (Exon 4) | Human | chr18:31598637-31598657 | GACGACAGCCGUGGUGGAAU |
| 59 | CR003389 | TTR (Exon 4) | Human | chr18:31598643-31598663 | AUUGGUGACGACAGCCGUGG |
| 60 | CR003390 | TTR (Exon 4) | Human | chr18:31598646-31598666 | GGGAUUGGUGACGACAGCCG |
| 61 | CR003391 | TTR (Exon 4) | Human | chr18:31598647-31598667 | GGCUGUCGUCACCAAUCCCA |
| 62 | CR003392 | TTR (Exon 4) | Human | chr18:31598661-31598681 | AGUCCCUCAUUCCUUGGGAU |
| 63 | CR005298 | TTR (Exon 1) | Human | chr18:31591883-31591903 | UCCACUCAUUCUUGGCAGGA |

TABLE 1-continued

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 64 | CR005299 | TTR (Exon 4) | Human | chr18:31598631-31598651 | AGCCGUGGUGGAAUAGGAGU |
| 65 | CR005300 | TTR (Exon 1) | Human | chr18:31591967-31591987 | UCACAGAAACACUCACCGUA |
| 66 | CR005301 | TTR (Exon 1) | Human | chr18:31591968-31591988 | GUCACAGAAACACUCACCGU |
| 67 | CR005302 | TTR (Exon 2) | Human | chr18:31592874-31592894 | ACGUGUCUUCUCUACACCCA |
| 68 | CR005303 | TTR (Exon 2) | Human | chr18:31592903-31592923 | UGAAUCCAAGUGUCCUCUGA |
| 69 | CR005304 | TTR (Exon 2) | Human | chr18:31592969-31592989 | GGCCGUGCAUGUGUUCAGAA |
| 70 | CR005305 | TTR (Exon 3) | Human | chr18:31595114-31595134 | UAUAGGAAAACCAGUGAGUC |
| 71 | CR005306 | TTR (Exon 3) | Human | chr18:31595204-31595224 | AAAUCUUACUGGAAGGCACU |
| 72 | CR005307 | TTR (Exon 4) | Human | chr18:31598548-31598568 | UGUCUGUCUUCUCUCAUAGG |
| 73 | CR000689 | TTR | Cyno | chr18:50681533-50681553 | ACACAAAUACCAGUCCAGCG |
| 74 | CR005364 | TTR | Cyno | chr18:50680481-50680501 | AAAGGCUGCUGAUGAGACCU |
| 75 | CR005365 | TTR | Cyno | chr18:50680520-50680540 | CAUUGACAGCAGGACUGCCU |
| 76 | CR005366 | TTR | Cyno | chr18:50681539-50681559 | AUACCAGUCCAGCGAGGCAG |
| 77 | CR005367 | TTR | Cyno | chr18:50681542-50681562 | CCAGUCCAGCGAGGCAGAGG |
| 78 | CR005368 | TTR | Cyno | chr18:50681545-50681565 | CCUCCUCUGCCUCGCUGGAC |
| 79 | CR005369 | TTR | Cyno | chr18:50680540-50680560 | AAAGUUCUAGAUGCCGUCCG |
| 80 | CR005370 | TTR | Cyno | chr18:50680594-50680614 | ACUUGUCUUCUCUAUACCCA |
| 81 | CR005371 | TTR | Cyno | chr18:50678216-50678236 | AAGUGACUUCCAGUAAGAUU |
| 82 | CR005372 | TTR | Cyno | chr18:50680482-50680502 | AAAAGGCUGCUGAUGAGACC |

Each of the Guide Sequences above may further comprise additional nucleotides to form a crRNA, e.g., with the following exemplary nucleotide sequence following the Guide Sequence at its 3' end: GUUUUAGAGCUAUGCU-GUUUUG (SEQ ID NO: 126). In the case of a sgRNA, the above Guide Sequences may further comprise additional nucleotides to form a sgRNA, e.g., with the following exemplary nucleotide sequence following the 3' end of the Guide Sequence: GUUUUAGAGCUA-GAAAUAGCAAGUUAAAAUAAGGCUAGU-CCGUUAUCAACUU GAAAAAGUGGCACCGAGUCG-GUGCUUUU (SEQ ID NO: 125) in 5' to 3' orientation.

In some embodiments, the sgRNA is modified. In some embodiments, the sgRNA comprises the modification pattern shown below in SEQ ID NO: 3, where N is any natural or non-natural nucleotide, and where the totality of the N's comprise a guide sequence as described herein and the modified sgRNA comprises the following sequence: mN*mN*mN*NNGUUUUAGAmGmCmUmAmGmAm-AmAmU mAmGmCAAGUUAAAAUAAGGCUAGU-CCGUUAUCAmAmCmUmUmGmAmAmAm AmAmG-mUmGmGmCmAmCmCmGmAmGmUmCm-GmGmUmGmCmU*mU*mU*mU (SEQ ID NO: 3), where "N" may be any natural or non-natural nucleotide. For example, encompassed herein is SEQ ID NO: 3, where the N's are replaced with any of the guide sequences disclosed herein. The modifications remain as shown in SEQ ID NO: 3 despite the substitution of N's for the nucleotides of a guide. That is, although the nucleotides of the guide replace the "N's", the first three nucleotides are 2'OMe modified and there are phosphorothioate linkages between the first and second nucleotides, the second and third nucleotides and the third and fourth nucleotides.

In some embodiments, any one of the sequences recited in Table 2 is encompassed.

TABLE 2

TTR targeted sgRNA sequences

| SEQ ID No. | Guide ID | Target and Description | Species | Sequence |
|---|---|---|---|---|
| 87 | G000480 | TTR sgRNA modified sequence | Human | mA*mA*mA*GGCUGCUGAUGACACCUGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 88 | G000481 | TTR sgRNA modified sequence | Human | mU*mC*mU*AGAACUUUGACCAUCAGGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 89 | G000482 | TTR sgRNA modified sequence | Human | mU*mG*mU*AGAAGGGAUAUACAAAGGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU |
| 90 | G000483 | TTR sgRNA modified sequence | Human | mU*mC*mC*ACUCAUUCUUGGCAGGAGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 91 | G000484 | TTR sgRNA modified sequence | Human | mA*mG*mA*CACCAAAUCUUACUGGAGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 92 | G000485 | TTR sgRNA modified sequence | Human | mC*mC*mU*CCUCUGCCUUGCUGGACGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 93 | G000486 | TTR sgRNA modified sequence | Human | mA*mC*mA*CAAAUACCAGUCCAGCAGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 94 | G000487 | TTR sgRNA modified sequence | Human | mU*mU*mC*UUUGGCAACUUACCCAGGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |
| 95 | G000488 | TTR sgRNA modified sequence | Human | mA*mA*mA*GUUCUAGAUGCUGUCCGGUUUUAGAmGmCmUmAmGmAmAmAmUmAmGmCAAGUUAAAAUAAGGCUAGUCCGUUAUCAmAmCmUmUmGmAmAmAmAmGmGmGmCmAmCmCmGmAmGmUmCmGmGmUmGmCmU*mU*mU*mU |

TABLE 2-continued

TTR targeted sgRNA sequences

| SEQ ID No. | Guide ID | Target and Description | Species | Sequence |
|---|---|---|---|---|
| 96 | G000489 | TTR sgRNA modified sequence | Human | mU*mU*mU*GACCAUCAGAGGACACUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 97 | G000490 | TTR sgRNA modified sequence | Human | mA*mA*mA*UAGACACCAAAUCUUACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 98 | G000491 | TTR sgRNA modified sequence | Human | mA*mU*mA*CCAGUCCAGCAAGGCAGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 99 | G000492 | TTR sgRNA modified sequence | Human | mC*mU*mU*CUCUACACCCAGGGCACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 100 | G000493 | TTR sgRNA modified sequence | Human | mA*mA*mG*UGCCUUCCAGUAAGAUUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 101 | G000494 | TTR sgRNA modified sequence | Human | mG*mU*mG*AGUCUGGAGAGCUGCAUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 102 | G000495 | TTR sgRNA modified sequence | Human | mC*mA*mG*AGGACACUUGGAUUCACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 103 | G000496 | TTR sgRNA modified sequence | Human | mG*mG*mC*CGUGCAUGUGUUCAGAAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 104 | G000497 | TTR sgRNA modified sequence | Human | mC*mU*mG*CUCCUCCUCUGCCUUGCGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 105 | G000498 | TTR sgRNA modified sequence | Human | mA*mG*mU*GAGUCUGGAGAGCUGCAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |

TABLE 2-continued

TTR targeted sgRNA sequences

| SEQ ID No. | Guide ID | Target and Description | Species | Sequence |
|---|---|---|---|---|
| 106 | G000499 | TTR sgRNA modified sequence | Human | mU*mG*mA*AUCCAAGUGUCCUCUGAGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 107 | G000500 | TTR sgRNA modified sequence | Human | mC*mC*mA*GUCCAGCAAGGCAGAGGGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 108 | G000501 | TTR sgRNA modified sequence | Human | mU*mC*mA*CAGAAACACUCACCGUAGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 109 | G000567 | TTR sgRNA modified sequence | Human | mG*mA*mA*AGGCUGCUGAUGACACCGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 110 | G000568 | TTR sgRNA modified sequence | Human | mG*mG*mC*UGUCGUCACCAAUCCCAGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 111 | G000570 | TTR sgRNA modified sequence | Human | mC*mA*mU*UGAUGGCAGGACUGCCUGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 112 | G000571 | TTR sgRNA modified sequence | Human | mG*mU*mC*ACAGAAACACUCACCGUGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 113 | G000572 | TTR sgRNA modified sequence | Human | mC*mC*mC*CUACUCCUAUUCCACCAGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 114 | G000502 | TTR Cyno specific sgRNA modified sequence | Cyno | mA*mC*mA*CAAAUACCAGUCCAGCGGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 115 | G000503 | TTR Cyno specific sgRNA modified sequence | Cyno | mA*mA*mA*AGGCUGCUGAUGAGACCGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |

TABLE 2-continued

TTR targeted sgRNA sequences

| SEQ ID No. | Guide ID | Target and Description | Species | Sequence |
|---|---|---|---|---|
| 116 | G000504 | TTR Cyno specific sgRNA modified sequence | Cyno | mA*mA*mA*GGCUGCUGAUGAGACCUGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 117 | G000505 | TTR Cyno specific sgRNA modified sequence | Cyno | mC*mA*mU*UGACAGCAGGACUGCCUGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 118 | G000506 | TTR Cyno specific sgRNA modified sequence | Cyno | mA*mU*mA*CCAGUCCAGCGAGGCAGGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 119 | G000507 | TTR Cyno specific sgRNA modified sequence | Cyno | mC*mC*mA*GUCCAGCGAGGCAGAGGGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 120 | G000508 | TTR Cyno specific sgRNA modified sequence | Cyno | mC*mC*mU*CCUCUGCCUCGCUGGACGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 121 | G000509 | TTR Cyno specific sgRNA modified sequence | Cyno | mA*mA*mA*GUUCUAGAUGCCGUCCGGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 122 | G000510 | TTR Cyno specific sgRNA modified sequence | Cyno | mA*mC*mU*UGUCUUCUCUAUACCCAGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 123 | G000511 | TTR Cyno specific sgRNA modified sequence | Cyno | mA*mA*mG*UGACUUCCAGUAAGAUUGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |
| 124 | G000282 | TTR | Mouse | mU*mU*mA*CAGCCACGUCUACAGCAGU UUUAGAmGmCmUmAmGmAmAmAmUmA mGmCAAGUUAAAAUAAGGCUAGUCCGU UAUCAmAmCmUmUmGmAmAmAmAmAm GmUmGmCmAmCmCmGmAmGmUmCm GmGmUmGmCmU*mU*mU*mU |

* = PS linkage; 'm' = 2'-O-Me nucleotide

An alignment mapping of the Guide IDs with the corresponding sgRNA IDs as well as homology to the cyno genome and cyno matched guide IDs are provided in Table 3.

TABLE 3

TTR targeted guide sequence ID mapping and Cyno Homology

| Description | Human Dual Guide ID | Human Single Guide ID | Number Mismatches to Cyno Genome | Cyno Matched dgRNA ID | Cyno Matched sgRNA ID |
|---|---|---|---|---|---|
| TTR | CR003335 | G000497 | 1 | | |
| TTR | CR003336 | G000485 | 1 | CR005368 | G000508 |
| TTR | CR003337 | G000500 | 1 | CR005367 | G000507 |
| TTR | CR003338 | G000491 | 1 | CR005366 | G000506 |
| TTR | CR003339 | G000486 | 1 | CR000689 | G000502 |
| TTR | CR003340 | | 0 | | |
| TTR | CR003341 | | 0 | | |
| TTR | CR003342 | G000492 | no PAM in cyno | | |
| TTR | CR003343 | G000495 | no PAM in cyno | | |
| TTR | CR003344 | G000489 | 0 | | |
| TTR | CR003345 | G000481 | 0 | | |
| TTR | CR003346 | G000488 | 1 | CR005369 | G000509 |
| TTR | CR003347 | G000570 | 2 | CR005365 | G000505 |
| TTR | CR003348 | | 2 | | |
| TTR | CR003349 | | >3 | | |
| TTR | CR003350 | | no PAM in cyno | | |
| TTR | CR003351 | | no PAM in cyno | | |
| TTR | CR003352 | G000567 | 2 | CR005372 | G000503 |
| TTR | CR003353 | G000480 | 1 | CR005364 | G000504 |
| TTR | CR003354 | | 1 | | |
| TTR | CR003355 | | 1 | | |
| TTR | CR003356 | | 3 | | |
| TTR | CR003357 | G000487 | >3 | | |
| TTR | CR003358 | | 0 | | |
| TTR | CR003359 | G000498 | 0 | | |
| TTR | CR003360 | G000494 | 0 | | |
| TTR | CR003361 | | 0 | | |
| TTR | CR003362 | | 0 | | |
| TTR | CR003363 | | 0 | | |
| TTR | CR003364 | | 0 | | |
| TTR | CR003365 | G000482 | 0 | | |
| TTR | CR003366 | G000490 | 0 | | |
| TTR | CR003367 | G000484 | no PAM in cyno | | |
| TTR | CR003368 | G000493 | 1 | CR005371 | G000511 |
| TTR | CR003369 | | 0 | | |
| TTR | CR003370 | | 0 | | |
| TTR | CR003371 | | 0 | | |
| TTR | CR003372 | | 0 | | |
| TTR | CR003373 | | 1 | | |
| TTR | CR003374 | | 2 | | |
| TTR | CR003375 | | 2 | | |
| TTR | CR003376 | | 2 | | |
| TTR | CR003377 | | 2 | | |
| TTR | CR003378 | | 2 | | |
| TTR | CR003379 | | 2 | | |
| TTR | CR003380 | | 1 | | |
| TTR | CR003381 | | 1 | | |
| TTR | CR003382 | | 0 | | |
| TTR | CR003383 | | 0 | | |
| TTR | CR003384 | | 0 | | |
| TTR | CR003385 | G000572 | 0 | | |
| TTR | CR003386 | | 0 | | |
| TTR | CR003387 | | 0 | | |
| TTR | CR003388 | | 0 | | |
| TTR | CR003389 | G000569 | 0 | | |
| TTR | CR003390 | | 0 | | |
| TTR | CR003391 | G000568 | 0 | | |
| TTR | CR003392 | | 0 | | |
| TTR | CR005298 | G000483 | 1 | | |
| TTR | CR005299 | | 0 | | |
| TTR | CR005300 | G000501 | no PAM in cyno | | |
| TTR | CR005301 | G000571 | 0 | | |
| TTR | CR005302 | | 2 | CR005370 | G000510 |
| TTR | CR005303 | G000499 | 0 | | |
| TTR | CR005304 | G000496 | >3 | | |
| TTR | CR005305 | | 0 | | |
| TTR | CR005306 | | 1 | | |
| TTR | CR005307 | | 0 | | |

In some embodiments, the invention provides a composition comprising one or more guide RNA (gRNA) comprising guide sequences that direct an RNA-guided DNA binding agent, which can be a nuclease (e.g., a Cas nuclease such as Cas9), to a target DNA sequence in TTR. The gRNA may comprise a crRNA comprising a guide sequence shown in Table 1. The gRNA may comprise a crRNA comprising 17, 18, 19, or 20 contiguous nucleotides of a guide sequence shown in Table 1. In some embodiments, the gRNA comprises a crRNA comprising a sequence with about 75%, 80%, 85%, 90%, 95%, 96%, 97%, 98%, 99%, or 100% identity to at least 17, 18, 19, or 20 contiguous nucleotides of a guide sequence shown in Table 1. In some embodiments, the gRNA comprises a crRNA comprising a sequence with about 75%, 80%, 85%, 90%, 95%, 96%, 97%, 98%, 99%, or 100% identity to a guide sequence shown in Table 1. The gRNA may further comprise a trRNA. In each composition and method embodiment described herein, the crRNA and trRNA may be associated as a single RNA (sgRNA), or may be on separate RNAs (dgRNA). In the context of sgRNAs, the crRNA and trRNA components may be covalently linked, e.g., via a phosphodiester bond or other covalent bond.

In each of the composition, use, and method embodiments described herein, the guide RNA may comprise two RNA molecules as a "dual guide RNA" or "dgRNA". The dgRNA comprises a first RNA molecule comprising a crRNA comprising, e.g., a guide sequence shown in Table 1, and a second RNA molecule comprising a trRNA. The first and second RNA molecules may not be covalently linked, but may form a RNA duplex via the base pairing between portions of the crRNA and the trRNA.

In each of the composition, use, and method embodiments described herein, the guide RNA may comprise a single RNA molecule as a "single guide RNA" or "sgRNA". The sgRNA may comprise a crRNA (or a portion thereof) comprising a guide sequence shown in Table 1 covalently linked to a trRNA. The sgRNA may comprise 17, 18, 19, or 20 contiguous nucleotides of a guide sequence shown in Table 1. In some embodiments, the crRNA and the trRNA are covalently linked via a linker. In some embodiments, the sgRNA forms a stem-loop structure via the base pairing between portions of the crRNA and the trRNA. In some embodiments, the crRNA and the trRNA are covalently linked via one or more bonds that are not a phosphodiester bond.

In some embodiments, the trRNA may comprise all or a portion of a trRNA sequence derived from a naturally-occurring CRISPR/Cas system. In some embodiments, the trRNA comprises a truncated or modified wild type trRNA. The length of the trRNA depends on the CRISPR/Cas system used. In some embodiments, the trRNA comprises or consists of 5, 6, 7, 8, 9, 10, 11, 12, 13, 14, 15, 16, 17, 18, 19, 20, 25, 30, 40, 50, 60, 70, 80, 90, 100, or more than 100 nucleotides. In some embodiments, the trRNA may comprise certain secondary structures, such as, for example, one or more hairpin or stem-loop structures, or one or more bulge structures.

In some embodiments, the invention provides a composition comprising one or more guide RNAs comprising a guide sequence of any one of SEQ ID NOs: 5-82.

In one aspect, the invention provides a composition comprising a gRNA that comprises a guide sequence that is at least 99%, 98%, 97%, 96%, 95%, 94%, 93%, 92%, 91%, or 90% identical to any of the nucleic acids of SEQ ID NOs: 5-82.

In other embodiments, the composition comprises at least one, e.g., at least two gRNA's comprising guide sequences selected from any two or more of the guide sequences of SEQ ID NOs: 5-82. In some embodiments, the composition comprises at least two gRNA's that each comprise a guide sequence at least 99%, 98%, 97%, 96%, 95%, 94%, 93%, 92%, 91%, or 90% identical to any of the nucleic acids of SEQ ID NOs: 5-82.

In some embodiments, the gRNA is a sgRNA comprising any one of the sequences shown in Table 2 (SEQ ID Nos. 87-124). In some embodiments, the gRNA is a sgRNA comprising any one of the sequences shown in Table 2 (SEQ ID Nos. 87-124, but without the modifications as shown (i.e., unmodified SEQ ID Nos. 87-124). In some embodiments, the sgRNA comprises a sequence that is at least 99%, 98%, 97%, 96%, 95%, 94%, 93%, 92%, 91%, or 90% identical to any of the nucleic acids of SEQ ID Nos. 87-124. In some embodiments, the sgRNA comprises a sequence that is at least 99%, 98%, 97%, 96%, 95%, 94%, 93%, 92%, 91%, or 90% identical to any of the nucleic acids of SEQ ID Nos. 87-124, but without the modifications as shown (i.e., unmodified SEQ ID Nos. 87-124). In some embodiments, the sgRNA comprises any one of the guide sequences shown in Table 1 in place of the guide sequences shown in the sgRNA sequences of Table 2 at SEQ ID Nos: 87-124, with or without the modifications.

The guide RNA compositions of the present invention are designed to recognize (e.g., hybridize to) a target sequence in the TTR gene. For example, the TTR target sequence may be recognized and cleaved by a provided Cas cleavase comprising a guide RNA. In some embodiments, an RNA-guided DNA binding agent, such as a Cas cleavase, may be directed by a guide RNA to a target sequence of the TTR gene, where the guide sequence of the guide RNA hybridizes with the target sequence and the RNA-guided DNA binding agent, such as a Cas cleavase, cleaves the target sequence.

In some embodiments, the selection of the one or more guide RNAs is determined based on target sequences within the TTR gene.

Without being bound by any particular theory, mutations (e.g., frameshift mutations resulting from indels occurring as a result of a nuclease-mediated DSB) in certain regions of the gene may be less tolerable than mutations in other regions of the gene, thus the location of a DSB is an important factor in the amount or type of protein knockdown that may result. In some embodiments, a gRNA complementary or having complementarity to a target sequence within TTR is used to direct the RNA-guided DNA binding agent to a particular location in the TTR gene. In some embodiments, gRNAs are designed to have guide sequences that are complementary or have complementarity to target sequences in exon 1, exon 2, exon 3, or exon 4 of TTR.

In some embodiments, the guide sequence is at least 99%, 98%, 97%, 96%, 95%, 94%, 93%, 92%, 91%, or 90% identical to a target sequence present in the human TTR gene. In some embodiments, the target sequence may be complementary to the guide sequence of the guide RNA. In some embodiments, the degree of complementarity or identity between a guide sequence of a guide RNA and its corresponding target sequence may be at least 80%, 85%, 90%, 95%, 96%, 97%, 98%, 99%, or 100%. In some embodiments, the target sequence and the guide sequence of the gRNA may be 100% complementary or identical. In other embodiments, the target sequence and the guide sequence of the gRNA may contain at least one mismatch. For example, the target sequence and the guide sequence of the gRNA may contain 1, 2, 3, or 4 mismatches, where the total length of the guide sequence is 20. In some embodiments, the target sequence and the guide sequence of the gRNA may contain 1-4 mismatches where the guide sequence is 20 nucleotides.

In some embodiments, a composition or formulation disclosed herein comprises an mRNA comprising an open reading frame (ORF) encoding an RNA-guided DNA binding agent, such as a Cas nuclease as described herein. In some embodiments, an mRNA comprising an ORF encoding an RNA-guided DNA binding agent, such as a Cas nuclease, is provided, used, or administered.

In some embodiments, the RNA-guided DNA-binding agent is a Class 2 Cas nuclease. In some embodiments, the RNA-guided DNA-binding agent has cleavase activity, which can also be referred to as double-strand endonuclease activity. In some embodiments, the RNA-guided DNA-binding agent comprises a Cas nuclease, such as a Class 2 Cas nuclease (which may be, e.g., a Cas nuclease of Type II, V, or VI). Class 2 Cas nucleases include, for example, Cas9, Cpf1, C2c1, C2c2, and C2c3 proteins and modifications thereof. Examples of Cas9 nucleases include those of the type II CRISPR systems of *S. pyogenes*, *S. aureus*, and other prokaryotes (see, e.g., the list in the next paragraph), and modified (e.g., engineered or mutant) versions thereof. See, e.g., US2016/0312198 A1; US 2016/0312199 A1. Other examples of Cas nucleases include a Csm or Cmr complex of a type III CRISPR system or the Cas10, Csm1, or Cmr2 subunit thereof and a Cascade complex of a type I CRISPR system, or the Cas3 subunit thereof. In some embodiments, the Cas nuclease may be from a Type-IIA, Type-IIB, or Type-IIC system. For discussion of various CRISPR systems and Cas nucleases see, e.g., Makarova et al., NAT. REV. MICROBIOL. 9:467-477 (2011); Makarova et al., NAT. REV. MICROBIOL, 13: 722-36 (2015); Shmakov et al., MOLECULAR CELL, 60:385-397 (2015).

Non-limiting exemplary species that the Cas nuclease can be derived from include *Streptococcus pyogenes, Streptococcus thermophilus, Streptococcus sp., Staphylococcus aureus, Listeria innocua, Lactobacillus gasseri, Francisella novicida, Wolinella succinogenes, Sutterella wadsworthensis,* Gammaproteobacterium, *Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina,* Burkholderiales *bacterium, Polaromonas naphthalenivorans, Polaromonas sp., Crocosphaera watsonii,* Cyanothece sp., *Microcystis aeruginosa, Synechococcus* sp., *Acetohalobium arabaticum, Ammonifex degensii,*

Caldicelulosiruptor becscii, *Candidatus* Desulforudis, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, *Streptococcus pasteurianus*, *Neisseria cinerea*, *Campylobacter lari*, *Parvibaculum lavamentivorans*, *Corynebacterium diphtheria*, *Acidaminococcus* sp., Lachnospiraceae *bacterium* ND2006, and Acaryochloris *marina*.

In some embodiments, the Cas nuclease is the Cas9 nuclease from *Streptococcus pyogenes*. In some embodiments, the Cas nuclease is the Cas9 nuclease from *Streptococcus thermophilus*. In some embodiments, the Cas nuclease is the Cas9 nuclease from *Neisseria meningitidis*. In some embodiments, the Cas nuclease is the Cas9 nuclease is from *Staphylococcus aureus*. In some embodiments, the Cas nuclease is the Cpf1 nuclease from *Francisella novicida*. In some embodiments, the Cas nuclease is the Cpf1 nuclease from *Acidaminococcus* sp. In some embodiments, the Cas nuclease is the Cpf1 nuclease from Lachnospiraceae *bacterium* ND2006. In further embodiments, the Cas nuclease is the Cpf1 nuclease from *Francisella tularensis*, Lachnospiraceae *bacterium*, *Butyrivibrio proteoclasticus*, Peregrinibacteria *bacterium*, Parcubacteria *bacterium*, *Smithella*, *Acidaminococcus*, *Candidatus* Methanoplasma *termitum*, *Eubacterium eligens*, *Moraxella bovoculi*, *Leptospira inadai*, *Porphyromonas crevioricanis*, *Prevotella disiens*, or *Porphyromonas macacae*. In certain embodiments, the Cas nuclease is a Cpf1 nuclease from an *Acidaminococcus* or Lachnospiraceae.

Wild type Cas9 has two nuclease domains: RuvC and HNH. The RuvC domain cleaves the non-target DNA strand, and the HNH domain cleaves the target strand of DNA. In some embodiments, the Cas9 nuclease comprises more than one RuvC domain and/or more than one HNH domain. In some embodiments, the Cas9 nuclease is a wild type Cas9. In some embodiments, the Cas9 is capable of inducing a double strand break in target DNA. In certain embodiments, the Cas nuclease may cleave dsDNA, it may cleave one strand of dsDNA, or it may not have DNA cleavase or nickase activity. An exemplary Cas9 amino acid sequence is provided as SEQ ID NO: 203. An exemplary Cas9 mRNA ORF sequence, which includes start and stop codons, is provided as SEQ ID NO: 204. An exemplary Cas9 mRNA coding sequence, suitable for inclusion in a fusion protein, is provided as SEQ ID NO: 210.

In some embodiments, chimeric Cas nucleases are used, where one domain or region of the protein is replaced by a portion of a different protein. In some embodiments, a Cas nuclease domain may be replaced with a domain from a different nuclease such as Fok1. In some embodiments, a Cas nuclease may be a modified nuclease.

In other embodiments, the Cas nuclease may be from a Type-I CRISPR/Cas system. In some embodiments, the Cas nuclease may be a component of the Cascade complex of a Type-I CRISPR/Cas system. In some embodiments, the Cas nuclease may be a Cas3 protein. In some embodiments, the Cas nuclease may be from a Type-III CRISPR/Cas system. In some embodiments, the Cas nuclease may have an RNA cleavage activity.

In some embodiments, the RNA-guided DNA-binding agent has single-strand nickase activity, i.e., can cut one DNA strand to produce a single-strand break, also known as a "nick." In some embodiments, the RNA-guided DNA-binding agent comprises a Cas nickase. A nickase is an enzyme that creates a nick in dsDNA, i.e., cuts one strand but not the other of the DNA double helix. In some embodiments, a Cas nickase is a version of a Cas nuclease (e.g., a Cas nuclease discussed above) in which an endonucleolytic active site is inactivated, e.g., by one or more alterations (e.g., point mutations) in a catalytic domain. See, e.g., U.S. Pat. No. 8,889,356 for discussion of Cas nickases and exemplary catalytic domain alterations. In some embodiments, a Cas nickase such as a Cas9 nickase has an inactivated RuvC or HNH domain. An exemplary Cas9 nickase amino acid sequence is provided as SEQ ID NO: 206. An exemplary Cas9 nickase mRNA ORF sequence, which includes start and stop codons, is provided as SEQ ID NO: 207. An exemplary Cas9 nickase mRNA coding sequence, suitable for inclusion in a fusion protein, is provided as SEQ ID NO: 211.

In some embodiments, the RNA-guided DNA-binding agent is modified to contain only one functional nuclease domain. For example, the agent protein may be modified such that one of the nuclease domains is mutated or fully or partially deleted to reduce its nucleic acid cleavage activity. In some embodiments, a nickase is used having a RuvC domain with reduced activity. In some embodiments, a nickase is used having an inactive RuvC domain. In some embodiments, a nickase is used having an HNH domain with reduced activity. In some embodiments, a nickase is used having an inactive HNH domain.

In some embodiments, a conserved amino acid within a Cas protein nuclease domain is substituted to reduce or alter nuclease activity. In some embodiments, a Cas nuclease may comprise an amino acid substitution in the RuvC or RuvC-like nuclease domain. Exemplary amino acid substitutions in the RuvC or RuvC-like nuclease domain include D10A (based on the *S. pyogenes* Cas9 protein). See, e.g., Zetsche et al. (2015) *Cell* October 22:163(3): 759-771. In some embodiments, the Cas nuclease may comprise an amino acid substitution in the HNH or HNH-like nuclease domain. Exemplary amino acid substitutions in the HNH or HNH-like nuclease domain include E762A, H840A, N863A, H983A, and D986A (based on the *S. pyogenes* Cas9 protein). See, e.g., Zetsche et al. (2015). Further exemplary amino acid substitutions include D917A, E1006A, and D1255A (based on the *Francisella novicida* U112 Cpf1 (FnCpf1) sequence (UniProtKB-AOQ7Q2 (CPF1_FRATN)).

In some embodiments, an mRNA encoding a nickase is provided in combination with a pair of guide RNAs that are complementary to the sense and antisense strands of the target sequence, respectively. In this embodiment, the guide RNAs direct the nickase to a target sequence and introduce a DSB by generating a nick on opposite strands of the target sequence (i.e., double nicking). In some embodiments, use of double nicking may improve specificity and reduce off-target effects. In some embodiments, a nickase is used together with two separate guide RNAs targeting opposite strands of DNA to produce a double nick in the target DNA. In some embodiments, a nickase is used together with two separate guide RNAs that are selected to be in close proximity to produce a double nick in the target DNA.

In some embodiments, the RNA-guided DNA-binding agent lacks cleavase and nickase activity. In some embodiments, the RNA-guided DNA-binding agent comprises a dCas DNA-binding polypeptide. A dCas polypeptide has DNA-binding activity while essentially lacking catalytic (cleavase/nickase) activity. In some embodiments, the dCas polypeptide is a dCas9 polypeptide. In some embodiments, the RNA-guided DNA-binding agent lacking cleavase and nickase activity or the dCas DNA-binding polypeptide is a version of a Cas nuclease (e.g., a Cas nuclease discussed above) in which its endonucleolytic active sites are inactivated, e.g., by one or more alterations (e.g., point mutations) in its catalytic domains. See, e.g., US 2014/0186958 A1; US 2015/0166980 A1. An exemplary dCas9 amino acid sequence is provided as SEQ ID NO: 208. An exemplary dCas9 mRNA ORF sequence, which includes start and stop codons, is provided as SEQ ID NO: 209. An exemplary dCas9 mRNA coding sequence, suitable for inclusion in a fusion protein, is provided as SEQ ID NO: 212.

In some embodiments, the RNA-guided DNA-binding agent comprises one or more heterologous functional domains (e.g., is or comprises a fusion polypeptide).

In some embodiments, the heterologous functional domain may facilitate transport of the RNA-guided DNA-binding agent into the nucleus of a cell. For example, the heterologous functional domain may be a nuclear localization signal (NLS). In some embodiments, the RNA-guided DNA-binding agent may be fused with 1-10 NLS(s). In some embodiments, the RNA-guided DNA-binding agent may be fused with 1-5 NLS(s). In some embodiments, the RNA-guided DNA-binding agent may be fused with one NLS. Where one NLS is used, the NLS may be linked at the N-terminus or the C-terminus of the RNA-guided DNA-binding agent sequence. It may also be inserted within the RNA-guided DNA binding agent sequence. In other embodiments, the RNA-guided DNA-binding agent may be fused with more than one NLS. In some embodiments, the RNA-guided DNA-binding agent may be fused with 2, 3, 4, or 5 NLSs. In some embodiments, the RNA-guided DNA-binding agent may be fused with two NLSs. In certain circumstances, the two NLSs may be the same (e.g., two SV40 NLSs) or different. In some embodiments, the RNA-guided DNA-binding agent is fused to two SV40 NLS sequences linked at the carboxy terminus. In some embodiments, the RNA-guided DNA-binding agent may be fused with two NLSs, one linked at the N-terminus and one at the C-terminus. In some embodiments, the RNA-guided DNA-binding agent may be fused with 3 NLSs. In some embodiments, the RNA-guided DNA-binding agent may be fused with no NLS. In some embodiments, the NLS may be a monopartite sequence, such as, e.g., the SV40 NLS, PKKKRKV (SEQ ID NO: 274) or PKKKRRV (SEQ ID NO: 275). In some embodiments, the NLS may be a bipartite sequence, such as the NLS of nucleoplasmin, KRPAATK-KAGQAKKKK (SEQ ID NO: 276). In a specific embodiment, a single PKKKRKV (SEQ ID NO: 274) NLS may be linked at the C-terminus of the RNA-guided DNA-binding agent. One or more linkers are optionally included at the fusion site.

In some embodiments, the heterologous functional domain may be capable of modifying the intracellular half-life of the RNA-guided DNA binding agent. In some embodiments, the half-life of the RNA-guided DNA binding agent may be increased. In some embodiments, the half-life of the RNA-guided DNA-binding agent may be reduced. In some embodiments, the heterologous functional domain may be capable of increasing the stability of the RNA-guided DNA-binding agent. In some embodiments, the heterologous functional domain may be capable of reducing the stability of the RNA-guided DNA-binding agent. In some embodiments, the heterologous functional domain may act as a signal peptide for protein degradation. In some embodiments, the protein degradation may be mediated by proteolytic enzymes, such as, for example, proteasomes, lysosomal proteases, or calpain proteases. In some embodiments, the heterologous functional domain may comprise a PEST sequence. In some embodiments, the RNA-guided DNA-binding agent may be modified by addition of ubiquitin or a polyubiquitin chain. In some embodiments, the ubiquitin may be a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally downregulated protein-8 (NEDD8, also called Rub1 in *S. cerevisiae*), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBL5).

In some embodiments, the heterologous functional domain may be a marker domain. Non-limiting examples of marker domains include fluorescent proteins, purification tags, epitope tags, and reporter gene sequences. In some embodiments, the marker domain may be a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalamal, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain may be a purification tag and/or an epitope tag. Non-limiting exemplary tags include glutathione-S-transferase (GST), chitin binding protein (CBP), maltose binding protein (MBP), thioredoxin (TRX), poly(NANP), tandem affinity purification (TAP) tag, myc, AcV5, AU1, AUS, E, ECS, E2, FLAG, HA, nus, Softag 1, Softag 3, Strep, SBP, Glu-Glu, HSV, KT3, S, 51, T7, V5, VSV-G, 6×His, 8×His, biotin carboxyl carrier protein (BCCP), poly-His, and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the heterologous functional domain may target the RNA-guided DNA-binding agent to a specific organelle, cell type, tissue, or organ. In some embodiments, the heterologous functional domain may target the RNA-guided DNA-binding agent to mitochondria.

In further embodiments, the heterologous functional domain may be an effector domain. When the RNA-guided DNA-binding agent is directed to its target sequence, e.g., when a Cas nuclease is directed to a target sequence by a gRNA, the effector domain may modify or affect the target sequence. In some embodiments, the effector domain may be chosen from a nucleic acid binding domain, a nuclease domain (e.g., a non-Cas nuclease domain), an epigenetic modification domain, a transcriptional activation domain, or a transcriptional repressor domain. In some embodiments, the heterologous functional domain is a nuclease, such as a Fok1 nuclease. See, e.g., U.S. Pat. No. 9,023,649. In some embodiments, the heterologous functional domain is a transcriptional activator or repressor. See, e.g., Qi et al., "Repurposing CRISPR as an RNA-guided platform for sequence-specific control of gene expression," *Cell* 152:1173-83 (2013); Perez-Pinera et al., "RNA-guided gene activation by CRISPR-Cas9-based transcription factors," *Nat. Methods* 10:973-6 (2013); Mali et al., "CAS9 transcriptional activators for target specificity screening and paired nickases for cooperative genome engineering," *Nat. Biotechnol.* 31:833-8 (2013); Gilbert et al., "CRISPR-mediated modular RNA-guided regulation of transcription in eukaryotes," *Cell* 154:442-51 (2013). As such, the RNA-guided DNA-binding agent essentially becomes a transcription factor that can be directed to bind a desired target sequence using a guide RNA.

B. Modified gRNAs and mRNAs

In some embodiments, the gRNA is chemically modified. A gRNA comprising one or more modified nucleosides or nucleotides is called a "modified" gRNA or "chemically modified" gRNA, to describe the presence of one or more non-naturally and/or naturally occurring components or configurations that are used instead of or in addition to the canonical A, G, C, and U residues. In some embodiments, a modified gRNA is synthesized with a non-canonical nucleoside or nucleotide, is here called "modified." Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification).

As noted above, in some embodiments, a composition or formulation disclosed herein comprises an mRNA comprising an open reading frame (ORF) encoding an RNA-guided DNA binding agent, such as a Cas nuclease as described herein. In some embodiments, an mRNA comprising an ORF encoding an RNA-guided DNA binding agent, such as a Cas nuclease, is provided, used, or administered. In some embodiments, the ORF encoding an RNA-guided DNA nuclease is a "modified RNA-guided DNA binding agent ORF" or simply a "modified ORF," which is used as shorthand to indicate that the ORF is modified in one or more of the following ways: (1) the modified ORF has a uridine content ranging from its minimum uridine content to 150% of the minimum uridine content; (2) the modified ORF has a uridine dinucleotide content ranging from its minimum uridine dinucleotide content to 150% of the minimum uridine dinucleotide content; (3) the modified ORF has at least 90% identity to any one of SEQ ID NOs: 201, 204, 210, 214, 215, 223, 224, 250, 252, 254, 265, or 266; (4) the modified ORF consists of a set of codons of which at least 75% of the codons are codons listed in the Table 3A of Minimal Uridine Codons; or (5) the modified ORF comprises at least one modified uridine. In some embodiments, the modified ORF is modified in at least two, three, or four of the foregoing ways. In some embodiments, the modified ORF comprises at least one modified uridine and is modified in at least one, two, three, or all of (1)-(4) above.

TABLE 3A of Minimal Uridine Codons

| Amino Acid | | Minimal uridine codon |
|---|---|---|
| A | Alanine | GCA or GCC or GCG |
| G | Glycine | GGA or GGC or GGG |
| V | Valine | GUC or GUA or GUG |
| D | Aspartic acid | GAC |
| E | Glutamic acid | GAA or GAG |
| I | Isoleucine | AUC or AUA |
| T | Threonine | ACA or ACC or ACG |
| N | Asparagine | AAC |
| K | Lysine | AAG or AAA |
| S | Serine | AGC |
| R | Arginine | AGA or AGG |
| L | Leucine | CUG or CUA or CUC |
| P | Proline | CCG or CCA or CCC |
| H | Histidine | CAC |
| Q | Glutamine | CAG or CAA |
| F | Phenylalanine | UUC |
| Y | Tyrosine | UAC |
| C | Cysteine | UGC |
| W | Tryptophan | UGG |
| M | Methionine | AUG |

In any of the foregoing embodiments, the modified ORF may consist of a set of codons of which at least 75%, 80%, 85%, 90%, 95%, 98%, 99%, or 100% of the codons are codons listed in Table 3A showing Minimal Uridine Codons.

In any of the foregoing embodiments, the modified ORF may comprise a sequence with at least 90%, 95%, 98%, 99%, or 100% identity to any one of SEQ ID NO: 201, 204, 210, 214, 215, 223, 224, 250, 252, 254, 265, or 266.

In any of the foregoing embodiments, the modified ORF may have a uridine content ranging from its minimum uridine content to 150%, 145%, 140%, 135%, 130%, 125%, 120%, 115%, 110%, 105%, 104%, 103%, 102%, or 101% of the minimum uridine content.

In any of the foregoing embodiments, the modified ORF may have a uridine dinucleotide content ranging from its minimum uridine dinucleotide content to 150%, 145%, 140%, 135%, 130%, 125%, 120%, 115%, 110%, 105%, 104%, 103%, 102%, or 101% of the minimum uridine dinucleotide content.

In any of the foregoing embodiments, the modified ORF may comprise a modified uridine at least at one, a plurality of, or all uridine positions. In some embodiments, the modified uridine is a uridine modified at the 5 position, e.g., with a halogen, methyl, or ethyl. In some embodiments, the modified uridine is a pseudouridine modified at the 1 position, e.g., with a halogen, methyl, or ethyl. The modified uridine can be, for example, pseudouridine, N1-methyl-pseudouridine, 5-methoxyuridine, 5-iodouridine, or a combination thereof. In some embodiments, the modified uridine is 5-methoxyuridine. In some embodiments, the modified uridine is 5-iodouridine. In some embodiments, the modified uridine is pseudouridine. In some embodiments, the modified uridine is N1-methyl-pseudouridine. In some embodiments, the modified uridine is a combination of pseudouridine and N1-methyl-pseudouridine. In some embodiments, the modified uridine is a combination of pseudouridine and 5-methoxyuridine. In some embodiments, the modified uridine is a combination of N1-methyl pseudouridine and 5-methoxyuridine. In some embodiments, the modified uridine is a combination of 5-iodouridine and N1-methyl-pseudouridine. In some embodiments, the modified uridine is a combination of pseudouridine and 5-iodouridine. In some embodiments, the modified uridine is a combination of 5-iodouridine and 5-methoxyuridine.

In some embodiments, at least 10%, 15%, 20%, 25%, 30%, 35%, 40%, 45%, 50%, 55%, 60%, 65%, 70%, 75%, 80%, 85%, 90%, 95%, 98%, 99%, or 100% of the uridine positions in an mRNA according to the disclosure are modified uridines. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are modified uridines, e.g., 5-methoxyuridine, 5-iodouridine, N1-methyl pseudouridine, pseudouridine, or a combination thereof. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are 5-methoxyuridine. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are pseudouridine. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are N1-methyl pseudouridine. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are 5-iodouridine. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are 5-methoxyuridine, and the remainder are N1-methyl pseudouridine. In some embodiments, 10%-25%, 15-25%, 25-35%, 35-45%, 45-55%, 55-65%, 65-75%, 75-85%, 85-95%, or 90-100% of the uridine positions in an mRNA according to the disclosure are 5-iodouridine, and the remainder are N1-methyl pseudouridine.

In some embodiments, the mRNA comprises at least one UTR from an expressed mammalian mRNA, such as a constitutively expressed mRNA. An mRNA is considered constitutively expressed in a mammal if it is continually transcribed in at least one tissue of a healthy adult mammal. In some embodiments, the mRNA comprises a 5' UTR, 3' UTR, or 5' and 3' UTRs from an expressed mammalian RNA, such as a constitutively expressed mammalian mRNA. Actin mRNA is an example of a constitutively expressed mRNA.

In some embodiments, the mRNA comprises at least one UTR from Hydroxysteroid 17-Beta Dehydrogenase 4 (HSD17B4 or HSD), e.g., a 5' UTR from HSD. In some embodiments, the mRNA comprises at least one UTR from a globin mRNA, for example, human alpha globin (HBA) mRNA, human beta globin (HBB) mRNA, or Xenopus laevis beta globin (XBG) mRNA. In some embodiments, the mRNA comprises a 5' UTR, 3' UTR, or 5' and 3' UTRs from a globin mRNA, such as HBA, HBB, or XBG. In some embodiments, the mRNA comprises a 5' UTR from bovine growth hormone, cytomegalovirus (CMV), mouse Hba-a1, HSD, an albumin gene, HBA, HBB, or XBG. In some embodiments, the mRNA comprises a 3' UTR from bovine growth hormone, cytomegalovirus, mouse Hba-a1, HSD, an albumin gene, HBA, HBB, or XBG. In some embodiments, the mRNA comprises 5' and 3' UTRs from bovine growth hormone, cytomegalovirus, mouse Hba-a1, HSD, an albumin gene, HBA, HBB, XBG, heat shock protein 90 (Hsp90), glyceraldehyde 3-phosphate dehydrogenase (GAPDH), beta-actin, alpha-tubulin, tumor protein (p53), or epidermal growth factor receptor (EGFR).

In some embodiments, the mRNA comprises 5' and 3' UTRs that are from the same source, e.g., a constitutively expressed mRNA such as actin, albumin, or a globin such as HBA, HBB, or XBG.

In some embodiments, the mRNA does not comprise a 5' UTR, e.g., there are no additional nucleotides between the 5' cap and the start codon. In some embodiments, the mRNA comprises a Kozak sequence (described below) between the 5' cap and the start codon, but does not have any additional 5' UTR. In some embodiments, the mRNA does not comprise a 3' UTR, e.g., there are no additional nucleotides between the stop codon and the poly-A tail.

In some embodiments, the mRNA comprises a Kozak sequence. The Kozak sequence can affect translation initiation and the overall yield of a polypeptide translated from an mRNA. A Kozak sequence includes a methionine codon that can function as the start codon. A minimal Kozak sequence is NNNRUGN wherein at least one of the following is true: the first N is A or G and the second N is G. In the context of a nucleotide sequence, R means a purine (A or G). In some embodiments, the Kozak sequence is RNNRUGN, NNNRUGG, RNNRUGG, RNNAUGN, NNNAUGG, or RNNAUGG. In some embodiments, the Kozak sequence is rccRUGg with zero mismatches or with up to one or two mismatches to positions in lowercase. In some embodiments, the Kozak sequence is rccAUGg with zero mismatches or with up to one or two mismatches to positions in lowercase. In some embodiments, the Kozak sequence is gccRccAUGG (SEQ ID NO: 277) with zero mismatches or with up to one, two, or three mismatches to positions in lowercase. In some embodiments, the Kozak sequence is gccAccAUG with zero mismatches or with up to one, two, three, or four mismatches to positions in lowercase. In some embodiments, the Kozak sequence is GCCACCAUG. In some embodiments, the Kozak sequence is gccgccRccAUGG (SEQ ID NO: 278) with zero mismatches or with up to one, two, three, or four mismatches to positions in lowercase.

In some embodiments, the mRNA comprising an ORF encoding an RNA-guided DNA binding agent comprises a sequence having at least 90% identity to SEQ ID NO: 1, optionally wherein the ORF of SEQ ID NO: 1 (i.e., SEQ ID NO: 204) is substituted with an alternative ORF of any one of SEQ ID NO: 210, 214, 215, 223, 224, 250, 252, 254, 265, or 266.

In some embodiments, the mRNA comprising an ORF encoding an RNA-guided DNA binding agent comprises a sequence having at least 90% identity to SEQ ID NO: 244, optionally wherein the ORF of SEQ ID NO: 244 (i.e., SEQ ID NO: 204) is substituted with an alternative ORF of any one of SEQ ID NO: 210, 214, 215, 223, 224, 250, 252, 254, 265, or 266.

In some embodiments, the mRNA comprising an ORF encoding an RNA-guided DNA binding agent comprises a sequence having at least 90% identity to SEQ ID NO: 256, optionally wherein the ORF of SEQ ID NO: 256 (i.e., SEQ ID NO: 204) is substituted with an alternative ORF of any one of SEQ ID NO: 210, 214, 215, 223, 224, 250, 252, 254, 265, or 266.

In some embodiments, the mRNA comprising an ORF encoding an RNA-guided DNA binding agent comprises a sequence having at least 90% identity to SEQ ID NO: 257, optionally wherein the ORF of SEQ ID NO: 257 (i.e., SEQ ID NO: 204) is substituted with an alternative ORF of any one of SEQ ID NO: 210, 214, 215, 223, 224, 250, 252, 254, 265, or 266.

In some embodiments, the mRNA comprising an ORF encoding an RNA-guided DNA binding agent comprises a sequence having at least 90% identity to SEQ ID NO: 257, optionally wherein the ORF of SEQ ID NO: 258 (i.e., SEQ ID NO: 204) is substituted with an alternative ORF of any one of SEQ ID NO: 210, 214, 215, 223, 224, 250, 252, 254, 265, or 266.

In some embodiments, the mRNA comprising an ORF encoding an RNA-guided DNA binding agent comprises a sequence having at least 90% identity to SEQ ID NO: 259, optionally wherein the ORF of SEQ ID NO: 259 (i.e., SEQ ID NO: 204) is substituted with an alternative ORF of any one of SEQ ID NO: 210, 214, 215, 223, 224, 250, 252, 254, 265, or 266.

In some embodiments, the mRNA comprising an ORF encoding an RNA-guided DNA binding agent comprises a sequence having at least 90% identity to SEQ ID NO: 260, optionally wherein the ORF of SEQ ID NO: 260 (i.e., SEQ ID NO: 204) is substituted with an alternative ORF of any one of SEQ ID NO: 210, 214, 215, 223, 224, 250, 252, 254, 265, or 266.

2'-methoxy and a 2'-hydroxyl, respectively. In Cap2, the riboses of the first and second cap-proximal nucleotides of the mRNA both comprise a 2'-methoxy. See, e.g., Katibah et al. (2014) *Proc Natl Acad Sci USA* 111(33):12025-30; Abbas et al. (2017) *Proc Natl Acad Sci USA* 114(11):E2106-E2115. Most endogenous higher eukaryotic mRNAs, including mammalian mRNAs such as human mRNAs, comprise Cap1 or Cap2. Cap0 and other cap structures differing from Cap1 and Cap2 may be immunogenic in mammals, such as humans, due to recognition as "non-self" by components of the innate immune system such as IFIT-1 and IFIT-5, which can result in elevated cytokine levels including type I interferon. Components of the innate immune system such as IFIT-1 and IFIT-5 may also compete with eIF4E for binding of an mRNA with a cap other than Cap1 or Cap2, potentially inhibiting translation of the mRNA.

A cap can be included co-transcriptionally. For example, ARCA (anti-reverse cap analog; Thermo Fisher Scientific Cat. No. AM8045) is a cap analog comprising a 7-methyl-guanine 3'-methoxy-5'-triphosphate linked to the 5' position of a guanine ribonucleotide which can be incorporated in vitro into a transcript at initiation. ARCA results in a Cap0 cap in which the 2' position of the first cap-proximal nucleotide is hydroxyl. See, e.g., Stepinski et al., (2001) "Synthesis and properties of mRNAs containing the novel 'anti-reverse' cap analogs 7-methyl(3'-O-methyl)GpppG and 7-methyl(3' deoxy)GpppG," *RNA* 7: 1486-1495. The ARCA structure is shown below.

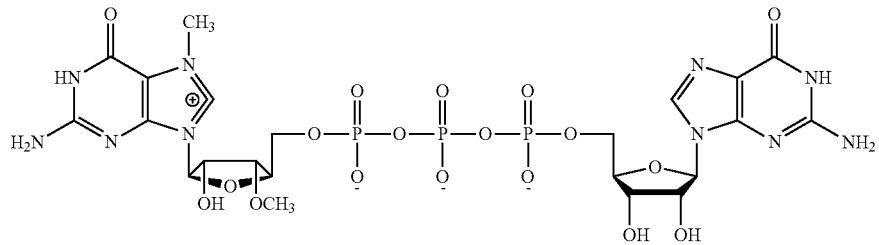

In some embodiments, the mRNA comprising an ORF encoding an RNA-guided DNA binding agent comprises a sequence having at least 90% identity to SEQ ID NO: 261, optionally wherein the ORF of SEQ ID NO: 261 (i.e., SEQ ID NO: 204) is substituted with an alternative ORF of any one of SEQ ID NO: 210, 214, 215, 223, 224, 250, 252, 254, 265, or 266.

In some embodiments, the degree of identity to the optionally substituted sequences of SEQ ID NOs 243, 244, or 256-261 is 95%. In some embodiments, the degree of identity to the optionally substituted sequences of SEQ ID NOs 243, 244, or 256-261 is 98%. In some embodiments, the degree of identity to the optionally substituted sequences of SEQ ID NOs 243, 244, or 256-261 is 99%. In some embodiments, the degree of identity to the optionally substituted sequences of SEQ ID NOs 243, 244, or 256-261 is 100%.

In some embodiments, an mRNA disclosed herein comprises a 5' cap, such as a Cap0, Cap1, or Cap2. A 5' cap is generally a 7-methylguanine ribonucleotide (which may be further modified, as discussed below e.g. with respect to ARCA) linked through a 5'-triphosphate to the 5' position of the first nucleotide of the 5'-to-3' chain of the mRNA, i.e., the first cap-proximal nucleotide. In Cap0, the riboses of the first and second cap-proximal nucleotides of the mRNA both comprise a 2'-hydroxyl. In Cap1, the riboses of the first and second transcribed nucleotides of the mRNA comprise a CleanCap™ AG (m7G(5')ppp(5')(2'OMeA)pG; TriLink Biotechnologies Cat. No. N-7113) or CleanCap™ GG (m7G (5')ppp(5')(2'OMeG)pG; TriLink Biotechnologies Cat. No. N-7133) can be used to provide a Cap1 structure co-transcriptionally. 3'-O-methylated versions of CleanCap™ AG and CleanCap™ GG are also available from TriLink Biotechnologies as Cat. Nos. N-7413 and N-7433, respectively. The CleanCap™ AG structure is shown below.

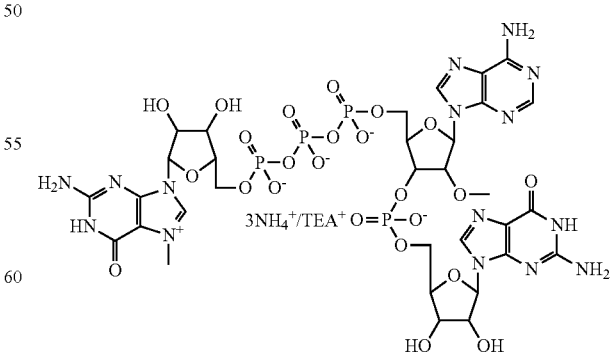

Alternatively, a cap can be added to an RNA post-transcriptionally. For example, Vaccinia capping enzyme is commercially available (New England Biolabs Cat. No.

M2080S) and has RNA triphosphatase and guanylyltransferase activities, provided by its D1 subunit, and guanine methyltransferase, provided by its D12 subunit. As such, it can add a 7-methylguanine to an RNA, so as to give Cap0, in the presence of S-adenosyl methionine and GTP. See, e.g., Guo, P. and Moss, B. (1990) *Proc. Natl. Acad. Sci. USA* 87, 4023-4027; Mao, X. and Shuman, S. (1994) *J. Biol. Chem.* 269, 24472-24479. For additional discussion of caps and capping approaches, see, e.g., WO2017/053297 and Ishikawa et al., *Nucl. Acids. Symp. Ser.* (2009) No. 53, 129-130.

In some embodiments, the mRNA further comprises a poly-adenylated (poly-A) tail. In some embodiments, the poly-A tail comprises at least 20, 30, 40, 50, 60, 70, 80, 90, or 100 adenines, optionally up to 300 adenines. In some embodiments, the poly-A tail comprises 95, 96, 97, 98, 99, or 100 adenine nucleotides. In some instances, the poly-A tail is "interrupted" with one or more non-adenine nucleotide "anchors" at one or more locations within the poly-A tail. The poly-A tails may comprise at least 8 consecutive adenine nucleotides, but also comprise one or more non-adenine nucleotide. As used herein, "non-adenine nucleotides" refer to any natural or non-natural nucleotides that do not comprise adenine. Guanine, thymine, and cytosine nucleotides are exemplary non-adenine nucleotides. Thus, the poly-A tails on the mRNA described herein may comprise consecutive adenine nucleotides located 3' to nucleotides encoding an RNA-guided DNA binding agent or a sequence of interest. In some instances, the poly-A tails on mRNA comprise non-consecutive adenine nucleotides located 3' to nucleotides encoding an RNA-guided DNA binding agent or a sequence of interest, wherein non-adenine nucleotides interrupt the adenine nucleotides at regular or irregularly spaced intervals.

In some embodiments, the one or more non-adenine nucleotides are positioned to interrupt the consecutive adenine nucleotides so that a poly(A) binding protein can bind to a stretch of consecutive adenine nucleotides. In some embodiments, one or more non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8-100 consecutive adenine nucleotides. In some embodiments, the non-adenine nucleotide is after one, two, three, four, five, six, or seven adenine nucleotides and is followed by at least 8 consecutive adenine nucleotides.

The poly-A tail may comprise one sequence of consecutive adenine nucleotides followed by one or more non-adenine nucleotides, optionally followed by additional adenine nucleotides.

In some embodiments, the poly-A tail comprises or contains one non-adenine nucleotide or one consecutive stretch of 2-10 non-adenine nucleotides. In some embodiments, the non-adenine nucleotide(s) is located after at least 8, 9, 10, 11, or 12 consecutive adenine nucleotides. In some instances, the one or more non-adenine nucleotides are located after at least 8-50 consecutive adenine nucleotides. In some embodiments, the one or more non-adenine nucleotides are located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the non-adenine nucleotide is guanine, cytosine, or thymine. In some instances, the non-adenine nucleotide is a guanine nucleotide. In some embodiments, the non-adenine nucleotide is a cytosine nucleotide. In some embodiments, the non-adenine nucleotide is a thymine nucleotide. In some instances, where more than one non-adenine nucleotide is present, the non-adenine nucleotide may be selected from: a) guanine and thymine nucleotides; b) guanine and cytosine nucleotides; c) thymine and cytosine nucleotides; or d) guanine, thymine and cytosine nucleotides. An exemplary poly-A tail comprising non-adenine nucleotides is provided as SEQ ID NO: 4.

In some embodiments, the mRNA further comprises a poly-adenylated (poly-A) tail. In some instances, the poly-A tail is "interrupted" with one or more non-adenine nucleotide "anchors" at one or more locations within the poly-A tail. The poly-A tails may comprise at least 8 consecutive adenine nucleotides, but also comprise one or more non-adenine nucleotide. As used herein, "non-adenine nucleotides" refer to any natural or non-natural nucleotides that do not comprise adenine. Guanine, thymine, and cytosine nucleotides are exemplary non-adenine nucleotides. Thus, the poly-A tails on the mRNA described herein may comprise consecutive adenine nucleotides located 3' to nucleotides encoding an RNA-guided DNA-binding agent or a sequence of interest. In some instances, the poly-A tails on mRNA comprise non-consecutive adenine nucleotides located 3' to nucleotides encoding an RNA-guided DNA-binding agent or a sequence of interest, wherein non-adenine nucleotides interrupt the adenine nucleotides at regular or irregularly spaced intervals.

In some embodiments, the one or more non-adenine nucleotides are positioned to interrupt the consecutive adenine nucleotides so that a poly(A) binding protein can bind to a stretch of consecutive adenine nucleotides. In some embodiments, one or more non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8-100 consecutive adenine nucleotides. In some embodiments, the non-adenine nucleotide is after one, two, three, four, five, six, or seven adenine nucleotides and is followed by at least 8 consecutive adenine nucleotides.

The poly-A tail of the present invention may comprise one sequence of consecutive adenine nucleotides followed by one or more non-adenine nucleotides, optionally followed by additional adenine nucleotides.

In some embodiments, the poly-A tail comprises or contains one non-adenine nucleotide or one consecutive stretch of 2-10 non-adenine nucleotides. In some embodiments, the non-adenine nucleotide(s) is located after at least 8, 9, 10, 11, or 12 consecutive adenine nucleotides. In some instances, the one or more non-adenine nucleotides are located after at least 8-50 consecutive adenine nucleotides. In some embodiments, the one or more non-adenine nucleotides are located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the non-adenine nucleotide is guanine, cytosine, or thymine. In some instances, the non-adenine nucleotide is a guanine nucleotide. In some embodiments, the non-adenine nucleotide is a cytosine nucleotide. In some embodiments, the non-adenine nucleotide is a thymine nucleotide. In some instances, where more than one non-adenine nucleotide is present, the non-adenine nucleotide may be selected from: a) guanine and thymine nucleotides; b) guanine and cytosine nucleotides; c) thymine and cytosine nucleotides; or d) guanine, thymine and cytosine nucleotides. An exemplary poly-A tail comprising non-adenine nucleotides is provided as SEQ ID NO: 4:

AAAAAAAAAAAAAAAAAAAAAAAAAAAAAAGCGAAAAAAAAAAAAAAA
AAAAAAAAAAAAAACCGAAAAAAAAAAAAAAAAAAAAAAAAAAAAAA
AAAAAAA.

Chemical modifications such as those listed above can be combined to provide modified gRNAs and/or mRNAs comprising nucleosides and nucleotides (collectively "residues") that can have two, three, four, or more modifications. For example, a modified residue can have a modified sugar and a modified nucleobase. In some embodiments, every base of a gRNA is modified, e.g., all bases have a modified phosphate group, such as a phosphorothioate group. In certain embodiments, all, or substantially all, of the phosphate groups of an gRNA molecule are replaced with phosphorothioate groups. In some embodiments, modified gRNAs comprise at least one modified residue at or near the 5' end of the RNA. In some embodiments, modified gRNAs comprise at least one modified residue at or near the 3' end of the RNA.

In some embodiments, the gRNA comprises one, two, three or more modified residues. In some embodiments, at least 5% (e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%) of the positions in a modified gRNA are modified nucleosides or nucleotides.

Unmodified nucleic acids can be prone to degradation by, e.g., intracellular nucleases or those found in serum. For example, nucleases can hydrolyze nucleic acid phosphodiester bonds. Accordingly, in one aspect the gRNAs described herein can contain one or more modified nucleosides or nucleotides, e.g., to introduce stability toward intracellular or serum-based nucleases. In some embodiments, the modified gRNA molecules described herein can exhibit a reduced innate immune response when introduced into a population of cells, both in vivo and ex vivo. The term "innate immune response" includes a cellular response to exogenous nucleic acids, including single stranded nucleic acids, which involves the induction of cytokine expression and release, particularly the interferons, and cell death.

In some embodiments of a backbone modification, the phosphate group of a modified residue can be modified by replacing one or more of the oxygens with a different substituent. Further, the modified residue, e.g., modified residue present in a modified nucleic acid, can include the wholesale replacement of an unmodified phosphate moiety with a modified phosphate group as described herein. In some embodiments, the backbone modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom in an unmodified phosphate group is achiral. However, replacement of one of the nonbridging oxygens with one of the above atoms or groups of atoms can render the phosphorous atom chiral. The stereogenic phosphorous atom can possess either the "R" configuration (herein Rp) or the "S" configuration (herein Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Scaffolds that can mimic nucleic acids can also be constructed wherein the phosphate linker and ribose sugar are replaced by nuclease resistant nucleoside or nucleotide surrogates. Such modifications may comprise backbone and sugar modifications. In some embodiments, the nucleobases can be tethered by a surrogate backbone. Examples can include, without limitation, the morpholino, cyclobutyl, pyrrolidine and peptide nucleic acid (PNA) nucleoside surrogates.

The modified nucleosides and modified nucleotides can include one or more modifications to the sugar group, i.e. at sugar modification. For example, the 2' hydroxyl group (OH) can be modified, e.g. replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion.

Examples of 2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In some embodiments, the 2' hydroxyl group modification can be 2'-O-Me. In some embodiments, the 2' hydroxyl group modification can be a 2'-fluoro modification, which replaces the 2' hydroxyl group with a fluoride. In some embodiments, the 2' hydroxyl group modification can include "locked" nucleic acids (LNA) in which the 2' hydroxyl can be connected, e.g., by a C1-6 alkylene or C1-6 heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the 2' hydroxyl group modification can included "unlocked" nucleic acids (UNA) in which the ribose ring lacks the C2'-C3' bond. In some embodiments, the 2' hydroxyl group modification can include the methoxyethyl group (MOE), ($OCH_2CH_2OCH_3$, e.g., a PEG derivative).

"Deoxy" 2' modifications can include hydrogen (i.e. deoxyribose sugars, e.g., at the overhang portions of partially dsRNA); halo (e.g., bromo, chloro, fluoro, or iodo); amino (wherein amino can be, e.g., NH$_2$; alkylamino, dialkylamino, heterocyclyl, arylamino, diarylamino, heteroarylamino, diheteroarylamino, or amino acid); NH(CH$_2$CH$_2$NH)$_n$CH$_2$CH$_2$— amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar modification can comprise a sugar group which may also contain one or more carbons that possess the opposite stereochemical configuration than that of the corresponding carbon in ribose. Thus, a modified nucleic acid can include nucleotides containing e.g., arabinose, as the sugar. The modified nucleic acids can also include abasic sugars. These abasic sugars can also be further modified at one or more of the constituent sugar atoms. The modified nucleic acids can also include one or more sugars that are in the L form, e.g. L-nucleosides.

The modified nucleosides and modified nucleotides described herein, which can be incorporated into a modified nucleic acid, can include a modified base, also called a nucleobase. Examples of nucleobases include, but are not limited to, adenine (A), guanine (G), cytosine (C), and uracil (U). These nucleobases can be modified or wholly replaced to provide modified residues that can be incorporated into modified nucleic acids. The nucleobase of the nucleotide can be independently selected from a purine, a pyrimidine, a purine analog, or pyrimidine analog. In some embodiments, the nucleobase can include, for example, naturally-occurring and synthetic derivatives of a base.

In embodiments employing a dual guide RNA, each of the crRNA and the tracr RNA can contain modifications. Such modifications may be at one or both ends of the crRNA and/or tracr RNA. In embodiments comprising an sgRNA, one or more residues at one or both ends of the sgRNA may be chemically modified, or the entire sgRNA may be chemically modified. Certain embodiments comprise a 5' end modification. Certain embodiments comprise a 3' end modification. In certain embodiments, one or more or all of the nucleotides in single stranded overhang of a guide RNA molecule are deoxynucleotides.

In some embodiments, the guide RNAs disclosed herein comprise one of the modification patterns disclosed in U.S. 62/431,756, filed Dec. 8, 2016, titled "Chemically Modified Guide RNAs," the contents of which are hereby incorporated by reference in their entirety.

In some embodiments, the invention comprises a gRNA comprising one or more modifications. In some embodiments, the modification comprises a 2'-O-methyl (2'-O-Me) modified nucleotide. In some embodiments, the modification comprises a phosphorothioate (PS) bond between nucleotides.

The terms "mA," "mC," "mU," or "mG" may be used to denote a nucleotide that has been modified with 2'-O-Me.

Modification of 2'-O-methyl can be depicted as follows:

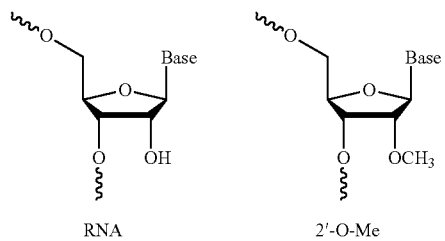

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fU," or "fG" may be used to denote a nucleotide that has been substituted with 2'-F.

Substitution of 2'-F can be depicted as follows:

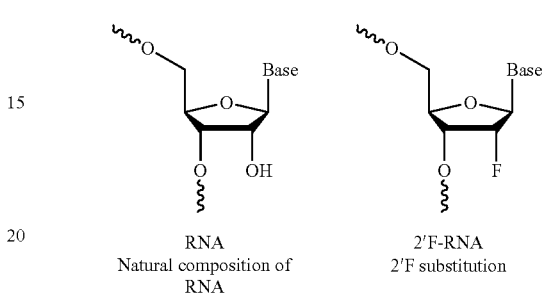

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

The diagram below shows the substitution of S— into a nonbridging phosphate oxygen, generating a PS bond in lieu of a phosphodiester bond:

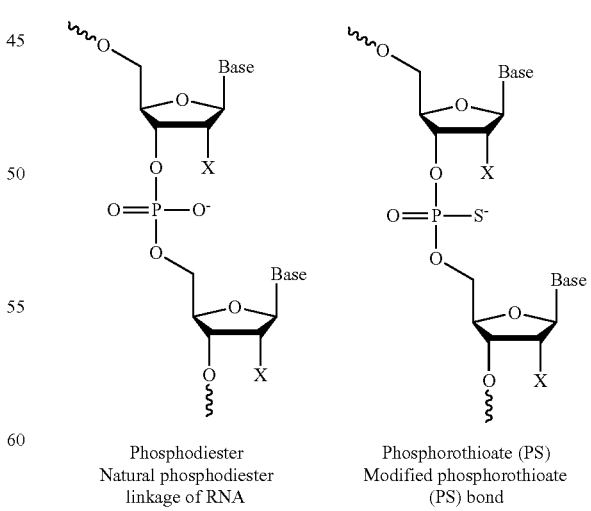

Abasic nucleotides refer to those which lack nitrogenous bases. The figure below depicts an oligonucleotide with an abasic (also known as apurinic) site that lacks a base:

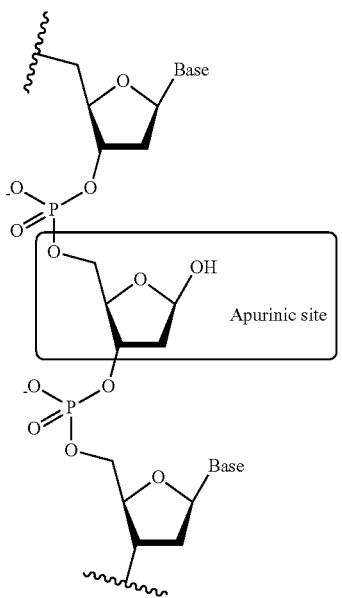

Apurinic site

Inverted bases refer to those with linkages that are inverted from the normal 5' to 3' linkage (i.e., either a 5' to 5' linkage or a 3' to 3' linkage). For example:

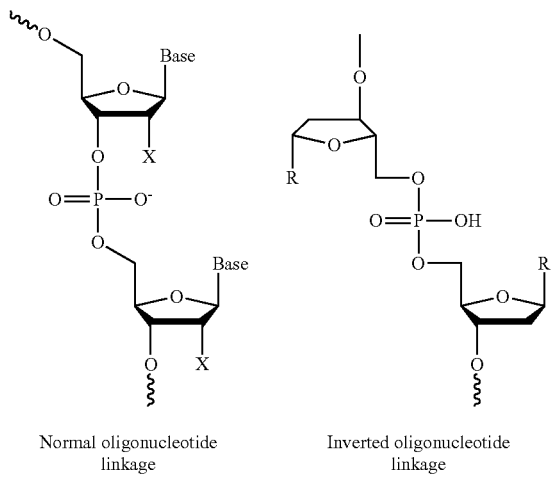

Normal oligonucleotide linkage

Inverted oligonucleotide linkage

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap.

In some embodiments, one or more of the first three, four, or five nucleotides at the 5' terminus, and one or more of the last three, four, or five nucleotides at the 3' terminus are modified. In some embodiments, the modification is a 2'-O-Me, 2'-F, inverted abasic nucleotide, PS bond, or other nucleotide modification well known in the art to increase stability and/or performance.

In some embodiments, the first four nucleotides at the 5' terminus, and the last four nucleotides at the 3' terminus are linked with phosphorothioate (PS) bonds.

In some embodiments, the first three nucleotides at the 5' terminus, and the last three nucleotides at the 3' terminus comprise a 2'-O-methyl (2'-O-Me) modified nucleotide. In some embodiments, the first three nucleotides at the 5' terminus, and the last three nucleotides at the 3' terminus comprise a 2'-fluoro (2'-F) modified nucleotide. In some embodiments, the first three nucleotides at the 5' terminus, and the last three nucleotides at the 3' terminus comprise an inverted abasic nucleotide.

In some embodiments, the guide RNA comprises a modified sgRNA. In some embodiments, the sgRNA comprises the modification pattern shown in SEQ ID No: 3, where N is any natural or non-natural nucleotide, and where the totality of the N's comprise a guide sequence that directs a nuclease to a target sequence.

In some embodiments, the guide RNA comprises a sgRNA shown in any one of SEQ ID No: 87-124. In some embodiments, the guide RNA comprises a sgRNA comprising any one of the guide sequences of SEQ ID No: 5-82 and the nucleotides of SEQ ID No: 125, wherein the nucleotides of SEQ ID No: 125 are on the 3' end of the guide sequence, and wherein the guide sequence may be modified as shown in SEQ ID No: 3.

C. Ribonucleoprotein Complex

In some embodiments, a composition is encompassed comprising one or more gRNAs comprising one or more guide sequences from Table 1 or one or more sgRNAs from Table 2 and an RNA-guided DNA binding agent, e.g., a nuclease, such as a Cas nuclease, such as Cas9. In some embodiments, the encoded RNA-guided DNA-binding agent has cleavase activity, which can also be referred to as double-strand endonuclease activity. In some embodiments, the RNA-guided DNA-binding agent comprises a Cas nuclease. Examples of Cas9 nucleases include those of the type II CRISPR systems of *S. pyogenes*, *S. aureus*, and other prokaryotes (see, e.g., the list in the next paragraph), and modified (e.g., engineered or mutant) versions thereof. See, e.g., US2016/0312198 A1; US 2016/0312199 A1. Other examples of Cas nucleases include a Csm or Cmr complex of a type III CRISPR system or the Cas10, Csm1, or Cmr2 subunit thereof and a Cascade complex of a type I CRISPR system, or the Cas3 subunit thereof. In some embodiments, the Cas nuclease may be from a Type-IIA, Type-IIB, or Type-IIC system. For discussion of various CRISPR systems and Cas nucleases see, e.g., Makarova et al., NAT. REV. MICROBIOL. 9:467-477 (2011); Makarova et al., NAT. REV. MICROBIOL, 13: 722-36 (2015); Shmakov et al., MOLECULAR CELL, 60:385-397 (2015).

Non-limiting exemplary species that the Cas nuclease can be derived from include *Streptococcus pyogenes*, *Streptococcus thermophilus*, *Streptococcus* sp., *Staphylococcus aureus*, *Listeria innocua*, *Lactobacillus gasseri*, *Francisella novicida*, *Wolinella succinogenes*, *Sutterella wadsworthensis*, Gammaproteobacterium, *Neisseria meningitidis*, *Campylobacter jejuni*, *Pasteurella multocida*, *Fibrobacter succinogene*, *Rhodospirillum rubrum*, *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Lactobacillus buchneri*, *Treponema denticola*, *Microscilla marina*, Burkholderiales *bacterium*, *Polaromonas naphthalenivorans*, *Polaromonas* sp., *Crocosphaera watsonii*, Cyanothece sp., *Microcystis aeruginosa*, *Synechococcus* sp., *Acetohalobium arabaticum*, *Ammonifex degensii*, Caldicelulosiruptor becscii, *Candidatus* Desulforudis, *Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria, Acidaminococcus* sp., Lachnospiraceae *bacterium* ND2006, and Acaryochloris *marina*.

In some embodiments, the Cas nuclease is the Cas9 nuclease from *Streptococcus pyogenes*. In some embodiments, the Cas nuclease is the Cas9 nuclease from *Streptococcus thermophilus*. In some embodiments, the Cas nuclease is the Cas9 nuclease from *Neisseria meningitidis*. In some embodiments, the Cas nuclease is the Cas9 nuclease is from *Staphylococcus aureus*. In some embodiments, the Cas nuclease is the Cpf1 nuclease from *Francisella novicida*. In some embodiments, the Cas nuclease is the Cpf1 nuclease from *Acidaminococcus* sp. In some embodiments, the Cas nuclease is the Cpf1 nuclease from Lachnospiraceae *bacterium* ND2006. In further embodiments, the Cas nuclease is the Cpf1 nuclease from *Francisella tularensis*, Lachnospiraceae *bacterium, Butyrivibrio proteoclasticus*, Peregrinibacteria *bacterium*, Parcubacteria *bacterium, Smithella, Acidaminococcus, Candidatus* Methanoplasma *termitum, Eubacterium eligens, Moraxella bovoculi, Leptospira inadai, Porphyromonas crevioricanis, Prevotella disiens*, or *Porphyromonas macacae*. In certain embodiments, the Cas nuclease is a Cpf1 nuclease from an *Acidaminococcus* or Lachnospiraceae.

In some embodiments, the gRNA together with an RNA-guided DNA binding agent is called a ribonucleoprotein complex (RNP). In some embodiments, the RNA-guided DNA binding agent is a Cas nuclease. In some embodiments, the gRNA together with a Cas nuclease is called a Cas RNP. In some embodiments, the RNP comprises Type-I, Type-II, or Type-III components. In some embodiments, the Cas nuclease is the Cas9 protein from the Type-II CRISPR/Cas system. In some embodiment, the gRNA together with Cas9 is called a Cas9 RNP.

Wild type Cas9 has two nuclease domains: RuvC and HNH. The RuvC domain cleaves the non-target DNA strand, and the HNH domain cleaves the target strand of DNA. In some embodiments, the Cas9 protein comprises more than one RuvC domain and/or more than one HNH domain. In some embodiments, the Cas9 protein is a wild type Cas9. In each of the composition, use, and method embodiments, the Cas induces a double strand break in target DNA.

Wild type Cas9 has two nuclease domains: RuvC and HNH. The RuvC domain cleaves the non-target DNA strand, and the HNH domain cleaves the target strand of DNA. In some embodiments, the Cas9 nuclease comprises more than one RuvC domain and/or more than one HNH domain. In some embodiments, the Cas9 nuclease is a wild type Cas9. In some embodiments, the Cas9 is capable of inducing a double strand break in target DNA. In certain embodiments, the Cas nuclease may cleave dsDNA, it may cleave one strand of dsDNA, or it may not have DNA cleavage or nickase activity. An exemplary Cas9 amino acid sequence is provided as SEQ ID NO: 203. An exemplary Cas9 mRNA ORF sequence, which includes start and stop codons, is provided as SEQ ID NO: 204. An exemplary Cas9 mRNA coding sequence, suitable for inclusion in a fusion protein, is provided as SEQ ID NO: 210.

In some embodiments, chimeric Cas nucleases are used, where one domain or region of the protein is replaced by a portion of a different protein. In some embodiments, a Cas nuclease domain may be replaced with a domain from a different nuclease such as Fok1. In some embodiments, a Cas nuclease may be a modified nuclease.

In other embodiments, the Cas nuclease may be from a Type-I CRISPR/Cas system. In some embodiments, the Cas nuclease may be a component of the Cascade complex of a Type-I CRISPR/Cas system. In some embodiments, the Cas nuclease may be a Cas3 protein. In some embodiments, the Cas nuclease may be from a Type-III CRISPR/Cas system. In some embodiments, the Cas nuclease may have an RNA cleavage activity.

In some embodiments, the RNA-guided DNA-binding agent has single-strand nickase activity, i.e., can cut one DNA strand to produce a single-strand break, also known as a "nick." In some embodiments, the RNA-guided DNA-binding agent comprises a Cas nickase. A nickase is an enzyme that creates a nick in dsDNA, i.e., cuts one strand but not the other of the DNA double helix. In some embodiments, a Cas nickase is a version of a Cas nuclease (e.g., a Cas nuclease discussed above) in which an endonucleolytic active site is inactivated, e.g., by one or more alterations (e.g., point mutations) in a catalytic domain. See, e.g., U.S. Pat. No. 8,889,356 for discussion of Cas nickases and exemplary catalytic domain alterations. In some embodiments, a Cas nickase such as a Cas9 nickase has an inactivated RuvC or HNH domain. An exemplary Cas9 nickase amino acid sequence is provided as SEQ ID NO: 206. An exemplary Cas9 nickase mRNA ORF sequence, which includes start and stop codons, is provided as SEQ ID NO: 207. An exemplary Cas9 nickase mRNA coding sequence, suitable for inclusion in a fusion protein, is provided as SEQ ID NO: 211.

In some embodiments, the RNA-guided DNA-binding agent is modified to contain only one functional nuclease domain. For example, the agent protein may be modified such that one of the nuclease domains is mutated or fully or partially deleted to reduce its nucleic acid cleavage activity. In some embodiments, a nickase is used having a RuvC domain with reduced activity. In some embodiments, a nickase is used having an inactive RuvC domain. In some embodiments, a nickase is used having an HNH domain with reduced activity. In some embodiments, a nickase is used having an inactive HNH domain.

In some embodiments, a conserved amino acid within a Cas protein nuclease domain is substituted to reduce or alter nuclease activity. In some embodiments, a Cas nuclease may comprise an amino acid substitution in the RuvC or RuvC-like nuclease domain. Exemplary amino acid substitutions in the RuvC or RuvC-like nuclease domain include D10A (based on the *S. pyogenes* Cas9 protein). See, e.g., Zetsche et al. (2015) *Cell* October 22:163(3): 759-771. In some embodiments, the Cas nuclease may comprise an amino acid substitution in the HNH or HNH-like nuclease domain. Exemplary amino acid substitutions in the HNH or HNH-like nuclease domain include E762A, H840A, N863A, H983A, and D986A (based on the *S. pyogenes* Cas9 protein). See, e.g., Zetsche et al. (2015). Further exemplary amino acid substitutions include D917A, E1006A, and D1255A (based on the *Francisella novicida* U112 Cpf1 (FnCpf1) sequence (UniProtKB-A0Q7Q2 (CPF1_FRATN)).

In some embodiments, an mRNA encoding a nickase is provided in combination with a pair of guide RNAs that are complementary to the sense and antisense strands of the target sequence, respectively. In this embodiment, the guide RNAs direct the nickase to a target sequence and introduce a DSB by generating a nick on opposite strands of the target sequence (i.e., double nicking). In some embodiments, use of double nicking may improve specificity and reduce off-target effects. In some embodiments, a nickase is used together with two separate guide RNAs targeting opposite strands of DNA to produce a double nick in the target DNA. In some embodiments, a nickase is used together with two separate guide RNAs that are selected to be in close proximity to produce a double nick in the target DNA.

In some embodiments, the RNA-guided DNA-binding agent lacks cleavase and nickase activity. In some embodiments, the RNA-guided DNA-binding agent comprises a dCas DNA-binding polypeptide. A dCas polypeptide has DNA-binding activity while essentially lacking catalytic (cleavase/nickase) activity. In some embodiments, the dCas polypeptide is a dCas9 polypeptide. In some embodiments, the RNA-guided DNA-binding agent lacking cleavase and nickase activity or the dCas DNA-binding polypeptide is a version of a Cas nuclease (e.g., a Cas nuclease discussed above) in which its endonucleolytic active sites are inactivated, e.g., by one or more alterations (e.g., point mutations) in its catalytic domains. See, e.g., US 2014/0186958 A1; US 2015/0166980 A1. An exemplary dCas9 amino acid sequence is provided as SEQ ID NO: 208. An exemplary Cas9 mRNA ORF sequence, which includes start and stop codons, is provided as SEQ ID NO: 209. An exemplary Cas9 mRNA coding sequence, suitable for inclusion in a fusion protein, is provided as SEQ ID NO: 212.

In some embodiments, the RNA-guided DNA-binding agent comprises one or more heterologous functional domains (e.g., is or comprises a fusion polypeptide).

In some embodiments, the heterologous functional domain may facilitate transport of the RNA-guided DNA-binding agent into the nucleus of a cell. For example, the heterologous functional domain may be a nuclear localization signal (NLS). In some embodiments, the RNA-guided DNA-binding agent may be fused with 1-10 NLS(s). In some embodiments, the RNA-guided DNA-binding agent may be fused with 1-5 NLS(s). In some embodiments, the RNA-guided DNA-binding agent may be fused with one NLS. Where one NLS is used, the NLS may be linked at the N-terminus or the C-terminus of the RNA-guided DNA-binding agent sequence. In some embodiments, the RNA-guided DNA-binding agent may be fused C-terminally to at least one NLS. An NLS may also be inserted within the RNA-guided DNA binding agent sequence. In other embodiments, the RNA-guided DNA-binding agent may be fused with more than one NLS. In some embodiments, the RNA-guided DNA-binding agent may be fused with 2, 3, 4, or 5 NLSs. In some embodiments, the RNA-guided DNA-binding agent may be fused with two NLSs. In certain circumstances, the two NLSs may be the same (e.g., two SV40 NLSs) or different. In some embodiments, the RNA-guided DNA-binding agent is fused to two SV40 NLS sequences linked at the carboxy terminus. In some embodiments, the RNA-guided DNA-binding agent may be fused with two NLSs, one linked at the N-terminus and one at the C-terminus. In some embodiments, the RNA-guided DNA-binding agent may be fused with 3 NLSs. In some embodiments, the RNA-guided DNA-binding agent may be fused with no NLS. In some embodiments, the NLS may be a monopartite sequence, such as, e.g., the SV40 NLS, PKKKRKV (SEQ ID NO: 274) or PKKKRRV (SEQ ID NO: 275). In some embodiments, the NLS may be a bipartite sequence, such as the NLS of nucleoplasmin, KRPAATKKAGQAKKKK (SEQ ID NO: 276). In a specific embodiment, a single PKKKRKV (SEQ ID NO: 274) NLS may be linked at the C-terminus of the RNA-guided DNA-binding agent. One or more linkers are optionally included at the fusion site. In some embodiments, one or more NLS(s) according to any of the foregoing embodiments are present in the RNA-guided DNA-binding agent in combination with one or more additional heterologous functional domains, such as any of the heterologous functional domains described below.

In some embodiments, the heterologous functional domain may be capable of modifying the intracellular half-life of the RNA-guided DNA binding agent. In some embodiments, the half-life of the RNA-guided DNA binding agent may be increased. In some embodiments, the half-life of the RNA-guided DNA-binding agent may be reduced. In some embodiments, the heterologous functional domain may be capable of increasing the stability of the RNA-guided DNA-binding agent. In some embodiments, the heterologous functional domain may be capable of reducing the stability of the RNA-guided DNA-binding agent. In some embodiments, the heterologous functional domain may act as a signal peptide for protein degradation. In some embodiments, the protein degradation may be mediated by proteolytic enzymes, such as, for example, proteasomes, lysosomal proteases, or calpain proteases. In some embodiments, the heterologous functional domain may comprise a PEST sequence. In some embodiments, the RNA-guided DNA-binding agent may be modified by addition of ubiquitin or a polyubiquitin chain. In some embodiments, the ubiquitin may be a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally downregulated protein-8 (NEDD8, also called Rub1 in *S. cerevisiae*), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBL5).

In some embodiments, the heterologous functional domain may be a marker domain. Non-limiting examples of marker domains include fluorescent proteins, purification tags, epitope tags, and reporter gene sequences. In some embodiments, the marker domain may be a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalamal, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain may be a purification tag and/or an epitope tag. Non-limiting exemplary tags include glutathione-S-transferase (GST), chitin binding protein (CBP), maltose binding protein (MBP), thioredoxin (TRX), poly(NANP), tandem affinity purification (TAP) tag, myc, AcV5, AU1, AUS, E, ECS, E2, FLAG, HA, nus, Softag 1, Softag 3, Strep, SBP, Glu-Glu, HSV, KT3, S, 51, T7, V5, VSV-G, 6×His, 8×His, biotin carboxyl carrier protein (BCCP), poly-His, and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the heterologous functional domain may target the RNA-guided DNA-binding agent to a specific organelle, cell type, tissue, or organ. In some embodiments, the heterologous functional domain may target the RNA-guided DNA-binding agent to mitochondria.

In further embodiments, the heterologous functional domain may be an effector domain. When the RNA-guided DNA-binding agent is directed to its target sequence, e.g., when a Cas nuclease is directed to a target sequence by a gRNA, the effector domain may modify or affect the target sequence. In some embodiments, the effector domain may be chosen from a nucleic acid binding domain, a nuclease domain (e.g., a non-Cas nuclease domain), an epigenetic modification domain, a transcriptional activation domain, or a transcriptional repressor domain. In some embodiments, the heterologous functional domain is a nuclease, such as a FokI nuclease. See, e.g., U.S. Pat. No. 9,023,649. In some embodiments, the heterologous functional domain is a transcriptional activator or repressor. See, e.g., Qi et al., "Repurposing CRISPR as an RNA-guided platform for sequence-specific control of gene expression," *Cell* 152:1173-83 (2013); Perez-Pinera et al., "RNA-guided gene activation by CRISPR-Cas9-based transcription factors," *Nat. Methods* 10:973-6 (2013); Mali et al., "CAS9 transcriptional activators for target specificity screening and paired nickases for cooperative genome engineering," *Nat. Biotechnol.* 31:833-8 (2013); Gilbert et al., "CRISPR-mediated modular RNA-guided regulation of transcription in eukaryotes," *Cell* 154:442-51 (2013). As such, the RNA-guided DNA-binding agent essentially becomes a transcription factor that can be directed to bind a desired target sequence using a guide RNA.

D. Determination of Efficacy of gRNAs

In some embodiments, the efficacy of a gRNA is determined when delivered or expressed together with other components forming an RNP. In some embodiments, the gRNA is expressed together with an RNA-guided DNA nuclease, such as a Cas protein. In some embodiments, the gRNA is delivered to or expressed in a cell line that already stably expresses an RNA-guided DNA nuclease, such as a Cas protein. In some embodiments the gRNA is delivered to a cell as part of a RNP. In some embodiments, the gRNA is delivered to a cell along with a mRNA encoding an RNA-guided DNA nuclease, such as a Cas nuclease.

As described herein, use of an RNA-guided DNA nuclease and a guide RNA disclosed herein can lead to double-stranded breaks in the DNA which can produce errors in the form of insertion/deletion (indel) mutations upon repair by cellular machinery. Many mutations due to indels alter the reading frame or introduce premature stop codons and, therefore, produce a non-functional protein.

In some embodiments, the efficacy of particular gRNAs is determined based on in vitro models. In some embodiments, the in vitro model is HEK293 cells stably expressing Cas9 (HEK293 Cas9). In some embodiments, the in vitro model is HUH7 human hepatocarcinoma cells. In some embodiments, the in vitro model is HepG2 cells. In some embodiments, the in vitro model is primary human hepatocytes. In some embodiments, the in vitro model is primary cynomolgus hepatocytes. With respect to using primary human hepatocytes, commercially available primary human hepatocytes can be used to provide greater consistency between experiments. In some embodiments, the number of off-target sites at which a deletion or insertion occurs in an in vitro model (e.g., in primary human hepatocytes) is determined, e.g., by analyzing genomic DNA from primary human hepatocytes transfected in vitro with Cas9 mRNA and the guide RNA. In some embodiments, such a determination comprises analyzing genomic DNA from primary human hepatocytes transfected in vitro with Cas9 mRNA, the guide RNA, and a donor oligonucleotide. Exemplary procedures for such determinations are provided in the working examples below.

In some embodiments, the efficacy of particular gRNAs is determined across multiple in vitro cell models for a gRNA selection process. In some embodiments, a cell line comparison of data with selected gRNAs is performed. In some embodiments, cross screening in multiple cell models is performed.

In some embodiments, the efficacy of particular gRNAs is determined based on in vivo models. In some embodiments, the in vivo model is a rodent model. In some embodiments, the rodent model is a mouse which expresses a human TTR gene, which may be a mutant human TTR gene. In some embodiments, the in vivo model is a non-human primate, for example cynomolgus monkey.

In some embodiments, the efficacy of a guide RNA is measured by percent editing of TTR. In some embodiments, the percent editing of TTR is compared to the percent editing necessary to achieve knockdown of TTR protein, e.g., in the cell culture media in the case of an in vitro model or in serum or tissue in the case of an in vivo model.

In some embodiments, the efficacy of a guide RNA is measured by the number and/or frequency of indels at off-target sequences within the genome of the target cell type. In some embodiments, efficacious guide RNAs are provided which produce indels at off target sites at very low frequencies (e.g., <5%) in a cell population and/or relative to the frequency of indel creation at the target site. Thus, the disclosure provides for guide RNAs which do not exhibit off-target indel formation in the target cell type (e.g., a hepatocyte), or which produce a frequency of off-target indel formation of <5% in a cell population and/or relative to the frequency of indel creation at the target site. In some embodiments, the disclosure provides guide RNAs which do not exhibit any off target indel formation in the target cell type (e.g., hepatocyte). In some embodiments, guide RNAs are provided which produce indels at less than 5 off-target sites, e.g., as evaluated by one or more methods described herein. In some embodiments, guide RNAs are provided which produce indels at less than or equal to 4, 3, 2, or 1 off-target site(s) e.g., as evaluated by one or more methods described herein. In some embodiments, the off-target site(s) does not occur in a protein coding region in the target cell (e.g., hepatocyte) genome.

In some embodiments, detecting gene editing events, such as the formation of insertion/deletion ("indel") mutations and homology directed repair (HDR) events in target DNA utilize linear amplification with a tagged primer and isolating the tagged amplification products (herein after referred to as "LAM-PCR," or "Linear Amplification (LA)" method).

In some embodiments, the method comprises isolating cellular DNA from a cell that has been induced to have a double strand break (DSB) and optionally that has been provided with an HDR template to repair the DSB; performing at least one cycle of linear amplification of the DNA with a tagged primer; isolating the linear amplification products that comprise tag, thereby discarding any amplification product that was amplified with a non-tagged primer; optionally further amplifying the isolated products; and analyzing the linear amplification products, or the further amplified products, to determine the presence or absence of an editing event such as, for example, a double strand break, an insertion, deletion, or HDR template sequence in the target DNA. In some instances, the editing event can be quantified. Quantification and the like as used herein (including in the context of HDR and non-HDR editing events such as indels) includes detecting the frequency and/or type(s) of editing events in a population.

In some embodiments, only one cycle of linear amplification is conducted.

In some instances, the tagged primer comprises a molecular barcode. In some embodiments, the tagged primer comprises a molecular barcode, and only one cycle of linear amplification is conducted.

In some embodiments, the analyzing step comprises sequencing the linear amplified products or the further amplified products. Sequencing may comprise any method known to those of skill in the art, including, next generation sequencing, and cloning the linear amplification products or further amplified products into a plasmid and sequencing the plasmid or a portion of the plasmid. In other aspects, the analyzing step comprises performing digital PCR (dPCR) or droplet digital PCR (ddPCR) on the linear amplified products or the further amplified products. In other instances, the analyzing step comprises contacting the linear amplified products or the further amplified products with a nucleic acid probe designed to identify DNA comprising HDR template sequence and detecting the probes that have bound to the linear amplified product(s) or further amplified product(s). In some embodiments, the method further comprises determining the location of the HDR template in the target DNA.

In certain embodiments, the method further comprises determining the sequence of an insertion site in the target DNA, wherein the insertion site is the location where the HDR template incorporates into the target DNA, and wherein the insertion site may include some target DNA sequence and some HDR template sequence.

In some embodiments, the linear amplification of the target DNA with a tagged primer is performed for 1-50 cycles, 1-60 cycles, 1-70 cycles, 1-80 cycles, 1-90 cycles, or 1-100 cycles.

In some embodiments, the linear amplification of the target DNA with a tagged primer comprises a denaturation step to separate DNA duplexes, an annealing step to allow primer binding, and an elongation step. In some embodiments, the linear amplification is isothermal (does not require a change in temperature). In some embodiments, the isothermal linear amplification is a loop-mediated isothermal amplification (LAMP), a strand displacement amplification (SDA), a helicase-dependent amplification, or a nicking enzyme amplification reaction.

In some embodiments, the tagged primer anneals to the target DNA at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 1,000, at least 5,000, or at least 10,000 nucleotides away from of the expected editing event location, e.g., the insertion, deletion, or template insertion site.

In some embodiments, the tagged primer comprises a molecular barcode. In some embodiments, the molecular barcode comprises a sequence that is not complementary to the target DNA. In some embodiments, the molecular barcode comprises 6, 8, 10, or 12 nucleotides.

In some embodiments, the tag on the primer is biotin, streptavidin, digoxigenin, a DNA sequence, or fluorescein isothiocyanate (FITC).

In some embodiments, the linear amplification product(s) are isolated using a capture reagent specific for the tag on the primer. In some embodiments, the capture reagent is on a bead, solid support, matrix, or column. In some embodiments, the isolation step comprises contacting the linear amplification product(s) with a capture reagent specific for the tag on the primer. In some embodiments, the capture reagent is biotin, streptavidin, digoxigenin, a DNA sequence, or fluorescein isothiocyanate (FITC).

In some embodiments, the tag is biotin and capture reagent is streptavidin. In some embodiments, the tag is streptavidin and the capture reagent is biotin. In some embodiments, the tag is on the 5' terminus of the primer, the 3' terminus of the primer, or internal to the primer. In some embodiments, the tag and/or the capture reagent is removed after the isolation step. In some embodiments, the tag and/or the capture reagent is not removed, and the further amplifying and analyzing steps are performed in the presence of tag and/or capture.

In some embodiments, the further amplification is non-linear. In some embodiments, the further amplification is digital PCR, qPCR, or RT-PCR. In some embodiments, the sequencing is next generation sequencing (NGS).

In some embodiments, the target DNA is genomic or mitochondrial. In some embodiments, the target DNA is genomic DNA of a prokaryotic or eukaryotic cell. In some embodiments, the target DNA is mammalian. The target DNA may be from a non-dividing cell or a dividing cell. In some embodiments, the target DNA may be from a primary cell. In some embodiments, the target DNA is from a replicating cell.

In some instances, the cellular DNA is sheared prior to linear amplification. In some embodiments, the sheared DNA has an average size between 0.5 kb and 20 kb. In some instances, the cellular DNA is sheared to an average size of 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.5, 16.75, 17.0, 17.25, 17.5, 17.75, 18.0, 18.25, 18.5, 18.75, 19.0, 19.25, 19.5, 19.75, or 20.0 kb. In some instances, the cellular DNA is sheared to an average size of about 1.5 kb.

In some embodiments, the efficacy of a guide RNA is measured by secretion of TTR. In some embodiments, secretion of TTR is measured using an enzyme-linked immunosorbent assay (ELISA) assay with cell culture media or serum. In some embodiments, secretion of TTR is measured in the same in vitro or in vivo systems or models used to measure editing. In some embodiments, secretion of TTR is measured in primary human hepatocytes. In some embodiments, secretion of TTR is measured in HUH7 cells. In some embodiments, secretion of TTR is measured in HepG2 cells.

ELISA assays are generally known to the skilled artisan and can be designed to determine serum TTR levels. In one exemplary embodiment, blood is collected and the serum is isolated. The total TTR serum levels may be determined using a Mouse Prealbumin (Transthyretin) ELISA Kit (Aviva Systems Biology, Cat. OKIA00111) or similar kit for measuring human TTR. If no kit is available, an ELISA can be developed using plates that are pre-coated with capture antibody specific for the TTR one is measuring. The plate is next incubated at room temperature for a period of time before washing. Enzyme-anti-TTR antibody conjugate is added and incubated. Unbound antibody conjugate is removed and the plate washed before the addition of the chromogenic substrate solution that reacts with the enzyme. The plate is read on an appropriate plate reader at an absorbance specific for the enzyme and substrate used.

In some embodiments, the amount of TTR in cells (including those from tissue) measures efficacy of a gRNA. In some embodiments, the amount of TTR in cells is measured using western blot. In some embodiments, the cell used is HUH7 cells. In some embodiments, the cell used is a primary human hepatocyte. In some embodiments, the cell used is a primar cell obtained from an animal. In some embodiments, the amount of TTR is compared to the amount of glyceraldehyde 3-phosphate dehydrogenase GAPDH (a housekeeping gene) to control for changes in cell number.

III. LNP Formulations and Treatment of ATTR

In some embodiments, a method of inducing a double-stranded break (DSB) within the TTR gene is provided comprising administering a composition comprising a guide RNA comprising any one or more guide sequences of SEQ ID Nos: 5-82, or any one or more of the sgRNAs of SEQ ID Nos: 87-124. In some embodiments, gRNAs comprising any one or more of the guide sequences of SEQ ID Nos: 5-82 are administered to induce a DSB in the IR gene. The guide RNAs may be administered together with an RNA-guided DNA nuclease such as a Cas nuclease (e.g., Cas9) or an mRNA or vector encoding an RNA-guided DNA nuclease such as a Cas nuclease (e.g., Cas9).

In some embodiments, a method of modifying the TTR gene is provided comprising administering a composition comprising a guide RNA comprising any one or more of the guide sequences of SEQ ID Nos: 5-82, or any one or more of the sgRNAs of SEQ ID Nos: 87-124. In some embodiments, gRNAs comprising any one or more of the guide sequences of SEQ ID Nos: 5-82, or any one or more of the sgRNAs of SEQ ID Nos: 87-124, are administered to modify the TTR gene. The guide RNAs may be administered together with an RNA-guided DNA nuclease such as a Cas nuclease (e.g., Cas9) or an mRNA or vector encoding an RNA-guided DNA nuclease such as a Cas nuclease (e.g., Cas9).

In some embodiments, a method of treating ATTR is provided comprising administering a composition comprising a guide RNA comprising any one or more of the guide sequences of SEQ ID NOs: 5-82, or any one or more of the sgRNAs of SEQ ID Nos: 87-124. In some embodiments, gRNAs comprising any one or more of the guide sequences of SEQ ID NOs: 5-82, or any one or more of the sgRNAs of SEQ ID Nos: 87-124 are administered to treat ATTR. The guide RNAs may be administered together with an RNA-guided DNA nuclease such as a Cas nuclease (e.g., Cas9) or an mRNA or vector encoding an RNA-guided DNA nuclease such as a Cas nuclease (e.g., Cas9).

In some embodiments, a method of reducing TTR serum concentration is provided comprising administering a guide RNA comprising any one or more of the guide sequences of SEQ ID NOs: 5-82, or any one or more of the sgRNAs of SEQ ID Nos: 87-124. In some embodiments, gRNAs comprising any one or more of the guide sequences of SEQ ID NOs: 5-82 or any one or more of the sgRNAs of SEQ ID Nos: 87-124 are administered to reduce or prevent the accumulation of TTR in amyloids or amyloid fibrils. The gRNAs may be administered together with an RNA-guided DNA nuclease such as a Cas nuclease (e.g., Cas9) or an mRNA or vector encoding an RNA-guided DNA nuclease such as a Cas nuclease (e.g., Cas9).

In some embodiments, a method of reducing or preventing the accumulation of TTR in amyloids or amyloid fibrils of a subject is provided comprising administering a composition comprising a guide RNA comprising any one or more of the guide sequences of SEQ ID NOs: 5-82, or any one or more of the sgRNAs of SEQ ID Nos: 87-124. In some embodiments, a method of reducing or preventing the accumulation of TTR in amyloids or amyloid fibrils of a subject is provided comprising administering a composition comprising any one or more of the sgRNAs of SEQ ID Nos: 87-113. In some embodiments, gRNAs comprising any one or more of the guide sequences of SEQ ID NOs: 5-82 or any one or more of the sgRNAs of SEQ ID Nos: 87-124 are administered to reduce or prevent the accumulation of TTR in amyloids or amyloid fibrils. The gRNAs may be administered together with an RNA-guided DNA nuclease such as a Cas nuclease (e.g., Cas9) or an mRNA or vector encoding an RNA-guided DNA nuclease such as a Cas nuclease (e.g., Cas9).

In some embodiments, the gRNAs comprising the guide sequences of Table 1 or one or more sgRNAs from Table 2 together with an RNA-guided DNA nuclease such as a Cas nuclease induce DSBs, and non-homologous ending joining (NHEJ) during repair leads to a mutation in the TTR gene. In some embodiments, NHEJ leads to a deletion or insertion of a nucleotide(s), which induces a frame shift or nonsense mutation in the TTR gene.

In some embodiments, administering the guide RNAs of the invention (e.g., in a composition provided herein) reduces levels (e.g., serum levels) of TTR in the subject, and therefore prevents accumulation and aggregation of TTR in amyloids or amyloid fibrils.

In some embodiments, reducing or preventing the accumulation of TTR in amyloids or amyloid fibrils of a subject comprises reducing or preventing TTR deposition in one or more tissues of the subject, such as stomach, colon, or nervous tissue. In some embodiments, the nervous tissue comprises sciatic nerve or dorsal root ganglion. In some embodiments, TTR deposition is reduced in two, three, or four of the stomach, colon, dorsal root ganglion, and sciatic nerve. The level of deposition in a given tissue can be determined using a biopsy sample, e.g., using immunostaining. In some embodiments, reducing or preventing the accumulation of TTR in amyloids or amyloid fibrils of a subject and/or reducing or preventing TTR deposition is inferred based on reducing serum TTR levels for a period of time. As discussed in the examples, it has been found that reducing serum TTR levels in accordance with methods and uses provided herein can result in clearance of deposited TTR from tissues such as those discussed above and in the examples, e.g., as measured 8 weeks after administration of the composition.

In some embodiments, the subject is mammalian. In some embodiments, the subject is human. In some embodiments, the subject is cow, pig, monkey, sheep, dog, cat, fish, or poultry.

In some embodiments, the use of a guide RNAs comprising any one or more of the guide sequences in Table 1 or one or more sgRNAs from Table 2 (e.g., in a composition provided herein) is provided for the preparation of a medicament for treating a human subject having ATTR.

In some embodiments, the guide RNAs, compositions, and formulations are administered intravenously. In some embodiments, the guide RNAs, compositions, and formulations are administered into the hepatic circulation.

In some embodiments, a single administration of a composition comprising a guide RNA provided herein is sufficient to knock down expression of the mutant protein. In some embodiments, a single administration of a composition comprising a guide RNA provided herein is sufficient to knock out expression of the mutant protein in a population of cells. In other embodiments, more than one administration of a composition comprising a guide RNA provided herein may be beneficial to maximize editing via cumulative effects. For example, a composition provided herein can be administered 2, 3, 4, 5, or more times, such as 2 times. Administrations can be separated by a period of time ranging from, e.g., 1 day to 2 years, such as 1 to 7 days, 7 to 14 days, 14 days to 30 days, 30 days to 60 days, 60 days to 120 days, 120 days to 183 days, 183 days to 274 days, 274 days to 366 days, or 366 days to 2 years.

In some embodiments, a composition is administered in an effective amount in the range of 0.01 to 10 mg/kg (mpk), e.g., 0.01 to 0.1 mpk, 0.1 to 0.3 mpk, 0.3 to 0.5 mpk, 0.5 to 1 mpk, 1 to 2 mpk, 2 to 3 mpk, 3 to 5 mpk, 5 to 10 mpk, or 0.1, 0.2, 0.3, 0.5, 1, 2, 3, 5, or 10 mpk.

In some embodiments, the efficacy of treatment with the compositions of the invention is seen at 1 year, 2 years, 3 years, 4 years, 5 years, or 10 years after delivery. In some embodiments, efficacy of treatment with the compositions of the invention is assessed by measuring serum levels of TTR before and after treatment. In some embodiments, efficacy of treatment with the compositions assessed via a reduction of serum levels of TTR is seen at 1 week, 2 weeks, 3 weeks, 4 weeks, 2 months, 3 months, 4 months, 5 months, 6 months, 7 months, 8 months, 9 months, 10 months, or at 11 months.

In some embodiments, treatment slows or halts disease progression.

In some embodiments, treatment slows or halts progression of FAP. In some embodiments, treatment results in improvement, stabilization, or slowing of change in symptoms of sensorimotor neuropathy or autonomic neuropathy. In some embodiments, treatment results in improvement, stabilization, or slowing of change in symptoms of FAC. In some embodiments, treatment results in improvement, stabilization, or slowing of change symptoms of restrictive cardiomyopathy or congestive heart failure.

In some embodiments, efficacy of treatment is measured by increased survival time of the subject.

In some embodiments, efficacy of treatment is measured by improvement or slowing of progression in symptoms of sensorimotor or autonomic neuropathy. In some embodiments, efficacy of treatment is measured by an increase or a a slowing of decrease in ability to move an area of the body or to feel in any area of the body. In some embodiments, efficacy of treatment is measured by improvement or a slowing of decrease in the ability to swallow; breath; use arms, hands, legs, or feet; or walk. In some embodiments, efficacy of treatment is measured by improvement or a slowing of progression of neuralgia. In some embodiments, the neuralgia is characterized by pain, burning, tingling, or abnormal feeling.

In some embodiments, efficacy of treatment is measured by improvement or a slowing of increase in postural hypotension, dizziness, gastrointestinal dysmotility, bladder dysfunction, or sexual dysfunction. In some embodiments, efficacy of treatment is measured by improvement or a slowing of progression of weakness. In some embodiments, efficacy of treatment is measured using electromyogram, nerve conduction tests, or patient-reported outcomes.

In some embodiments, efficacy of treatment is measured by improvement or slowing of progression of symptoms of congestive heart failure or CHF. In some embodiments, efficacy of treatment is measured by an decrease or a slowing of increase in shortness of breath, trouble breathing, fatigue, or swelling in the ankles, feet, legs, abdomen, or veins in the neck. In some embodiments, efficacy of treatment is measured by improvement or a slowing of progression of fluid buildup in the body, which may be assessed by measures such as weight gain, frequent urination, or nighttime cough. In some embodiments, efficacy of treatment is measured using cardiac biomarker tests (such as B-type natriuretic peptide [BNP] or N-terminal pro b-type natriuretic peptide [NT-proBNP]), lung function tests, chest x-rays, or electrocardiography.

A. Combination Therapy

In some embodiments, the invention comprises combination therapies comprising any one of the gRNAs comprising any one or more of the guide sequences disclosed in Table 1 or any one or more of the sgRNAs in Table 2 (e.g., in a composition provided herein) together with an additional therapy suitable for alleviating symptoms of ATTR.

In some embodiments, the additional therapy for ATTR is a treatment for sensorimotor or autonomic neuropathy. In some embodiments, the treatment for sensorimotor or autonomic neuropathy is a nonsteroidal anti-inflammatory drug, antidepressant, anticonvulsant medication, antiarrythmic medication, or narcotic agent. In some embodiments, the antidepressant is a tricylic agent or a serotonin-norepinephrine reuptake inhibitor. In some embodiments, the antidepressant is amitriptyline, duloxetine, or venlafaxine. In some embodiments, the anticonvulsant agent is gabapentin, pregabalin, topiramate, or carbamazepine. In some embodiments, the additional therapy for sensorimotor neuropathy is transcutaneous electrical nerve stimulation.

In some embodiments, the additional therapy for ATTR is a treatment for restrictive cardiomyopathy or congestive heart failure (CHF). In some embodiments, the treatment for CHF is a ACE inhibitor, aldosterone antagonist, angiotensin receptor blocker, beta blocker, digoxin, diuretic, or isosorbide dinitrate/hydralazine hydrochloride. In some embodiments, the ACE inhibitor is enalapril, captopril, ramipril, perindopril, imidapril, or quinapril. In some embodiments, the aldosterone antagonist is eplerenone or spironolactone. In some embodiments, the angiotensin receptor blocker is azilsartan, cadesartan, eprosartan, irbesartan, losartan, olmesartan, telmisartan, or valsartan. In some embodiments, the beta blocker is acebutolol, atenolol, bisoprolol, metoprolol, nadolol, nebivolol, or propranolol. In some embodiments, the diuretic is chlorothiazide, chlorthalidone, hydrochlorothiazide, indapamide, metolazone, bumetanide, furosemide, torsemide, amiloride, or triameterene.

In some embodiments, the combination therapy comprises any one of the gRNAs comprising any one or more of the guide sequences disclosed in Table 1 or any one or more of the sgRNAs in Table 2 (e.g., in a composition provided herein) together with a siRNA that targets TTR or mutant TTR. In some embodiments, the siRNA is any siRNA capable of further reducing or eliminating the expression of wild type or mutant TTR. In some embodiments, the siRNA is the drug Patisiran (ALN-TTR02) or ALN-TTRsc02. In some embodiments, the siRNA is administered after any one of the gRNAs comprising any one or more of the guide sequences disclosed in Table 1 or any one or more of the sgRNAs in Table 2 (e.g., in a composition provided herein). In some embodiments, the siRNA is administered on a regular basis following treatment with any of the gRNA compositions provided herein.

In some embodiments, the combination therapy comprises any one of the gRNAs comprising any one or more of the guide sequences disclosed in Table 1 or any one or more of the sgRNAs in Table 2 (e.g., in a composition provided herein) together with antisense nucleotide that targets TTR or mutant TTR. In some embodiments, the antisense nucleotide is any antisense nucleotide capable of further reducing or eliminating the expression of wild type or mutant TTR. In some embodiments, the antisense nucleotide is the drug Inotersen (IONS-TTR$_{Rx}$). In some embodiments, the antisense nucleotide is administered after any one of the gRNAs comprising any one or more of the guide sequences disclosed in Table 1 or any one or more of the sgRNAs in Table 2 (e.g., in a composition provided herein). In some embodiments, the antisense nucleotide is administered on a regular basis following treatment with any of the gRNA compositions provided herein.

In some embodiments, the combination therapy comprises any one of the gRNAs comprising any one or more of the guide sequences disclosed in Table 1 or any one or more of the sgRNAs in Table 2 (e.g., in a composition provided herein) together with a small molecule stabilizer that promotes kinetic stabilization of the correctly folded tetrameric form of TTR. In some embodiments, the small molecule stabilizer is the drug tafamidis (Vyndaqel®) or diflunisal. In some embodiments, the small molecule stabilizer is administered after any one of the gRNAs comprising any one or more of the guide sequences disclosed in Table 1 or any one or more of the sgRNAs in Table 2 (e.g., in a composition provided herein). In some embodiments, the small molecule stabilizer is administered on a regular basis following treatment with any of the gRNA compositions provided herein.

B. Delivery of gRNA Compositions

In some embodiments, the guide RNA compositions described herein, alone or encoded on one or more vectors, are formulated in or administered via a lipid nanoparticle; see e.g., PCT/US2017/024973, filed Mar. 30, 2017 entitled "LIPID NANOPARTICLE FORMULATIONS FOR CRISPR/CAS COMPONENTS," the contents of which are hereby incorporated by reference in their entirety. Any lipid nanoparticle (LNP) known to those of skill in the art to be capable of delivering nucleotides to subjects may be utilized with the guide RNAs described herein, as well as either mRNA encoding an RNA-guided DNA nuclease such as Cas or Cas9, or an RNA-guided DNA nuclease such as Cas or Cas9 protein itself.

Disclosed herein are various embodiments of LNP formulations for RNAs, including CRISPR/Cas cargoes. Such LNP formulations may include (i) a CCD lipid, such as an amine lipid, (ii) a neutral lipid, (iii) a helper lipid, and (iv) a stealth lipid, such as a PEG lipid. Some embodiments of the LNP formulations include an "amine lipid", along with a helper lipid, a neutral lipid, and a stealth lipid such as a PEG lipid. By "lipid nanoparticle" is meant a particle that comprises a plurality of (i.e. more than one) lipid molecules physically associated with each other by intermolecular forces.

CCD Lipids

Lipid compositions for delivery of CRISPR/Cas mRNA and guide RNA components to a liver cell comprise a CCD Lipid.

In some embodiments, the CCD lipid is Lipid A, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. Lipid A can be depicted as:

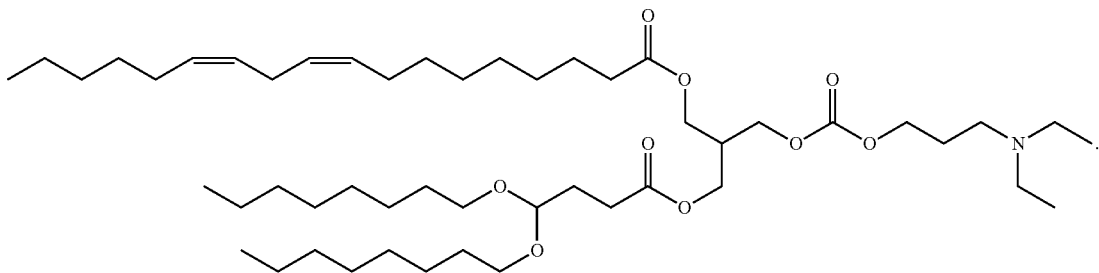 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid A may be synthesized according to WO2015/095340 (e.g., pp. 84-86).

In some embodiments, the CCD lipid is Lipid B, which is ((5-((dimethylamino)methyl)-1,3-phenylene)bis(oxy))bis (octane-8,1-diyl)bis(decanoate), also called ((5-((dimethylamino)methyl)-1,3-phenylene)bis(oxy))bis(octane-8,1-diyl) bis(decanoate). Lipid B can be depicted as:

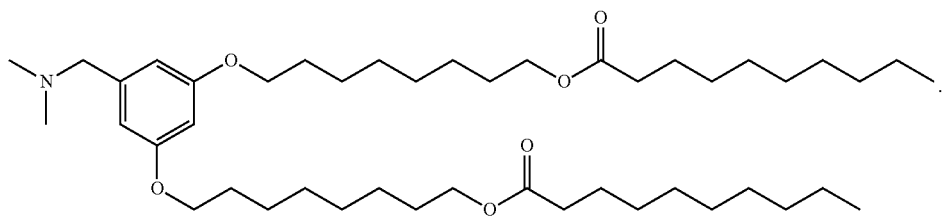 [SMILES: CCCCCCCCCC(=O)OCCCCCCCCOc1cc(CN(C)C)cc(OCCCCCCCCOC(=O)CCCCCCCCC)c1]

Lipid B may be synthesized according to WO2014/136086 (e.g., pp. 107-09).

In some embodiments, the CCD lipid is Lipid C, which is 2-((4-(((3-(dimethylamino)propoxy)carbonyl)oxy)hexadecanoyl)oxy)propane-1,3-diyl (9Z,9'Z,12Z,12'Z)-bis(octadeca-9,12-dienoate). Lipid C can be depicted as:

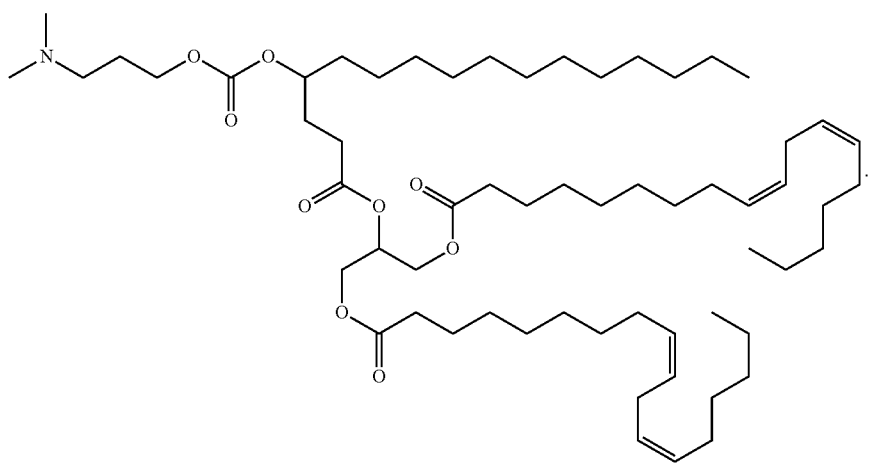 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

In some embodiments, the CCD lipid is Lipid D, which is 3-(((3-(dimethylamino)propoxy)carbonyl)oxy)-13-(octanoyloxy)tridecyl 3-octylundecanoate.

Lipid D can be depicted as:

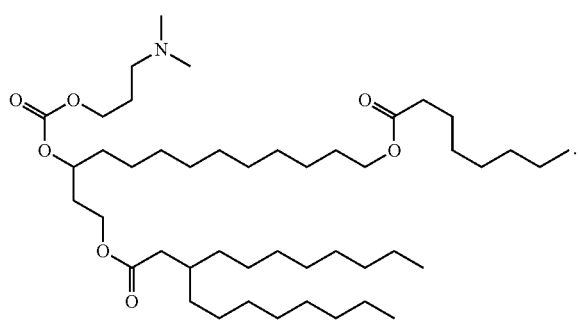 [SMILES: CCCCCCCCC(CCCCCCCC)CC(=O)OCCC(CCCCCCCCCCOC(=O)CCCCCCC)OC(=O)OCCCN(C)C]

Lipid C and Lipid D may be synthesized according to WO2015/095340.

The CCD lipid can also be an equivalent to Lipid A, Lipid B, Lipid C, or Lipid D. In certain embodiments, the CCD lipid is an equivalent to Lipid A, an equivalent to Lipid B, an equivalent to Lipid C, or an equivalent to Lipid D.

Amine Lipids

In some embodiments, the LNP compositions for the delivery of biologically active agents comprise an "amine lipid", which is defined as Lipid A, Lipid B, Lipid C, Lipid D or equivalents of Lipid A (including acetal analogs of Lipid A), equivalents of Lipid B, equivalents of Lipid C, and equivalents of Lipid D.

In some embodiments, the amine lipid is Lipid A, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. Lipid A can be depicted as:

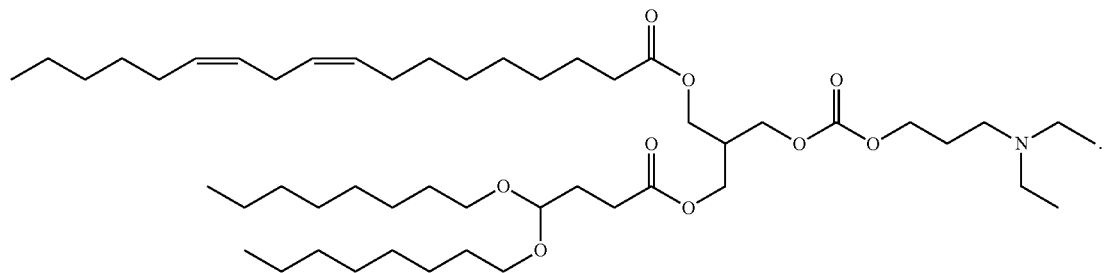 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid A may be synthesized according to WO2015/095340 (e.g., pp. 84-86). In certain embodiments, the amine lipid is an equivalent to Lipid A.

In certain embodiments, an amine lipid is an analog of Lipid A. In certain embodiments, a Lipid A analog is an acetal analog of Lipid A. In particular LNP compositions, the acetal analog is a C4-C12 acetal analog. In some embodiments, the acetal analog is a C5-C12 acetal analog. In additional embodiments, the acetal analog is a C5-C10 acetal analog. In further embodiments, the acetal analog is chosen from a C4, C5, C6, C7, C9, C10, C11, and C12 acetal analog.

Amine lipids suitable for use in the LNPs described herein are biodegradable in vivo. The amine lipids have low toxicity (e.g., are tolerated in animal models without adverse effect in amounts of greater than or equal to 10 mg/kg). In certain embodiments, LNPs comprising an amine lipid include those where at least 75% of the amine lipid is cleared from the plasma within 8, 10, 12, 24, or 48 hours, or 3, 4, 5, 6, 7, or 10 days. In certain embodiments, LNPs comprising an amine lipid include those where at least 50% of the mRNA or gRNA is cleared from the plasma within 8, 10, 12, 24, or 48 hours, or 3, 4, 5, 6, 7, or 10 days. In certain embodiments, LNPs comprising an amine lipid include those where at least 50% of the LNP is cleared from the plasma within 8, 10, 12, 24, or 48 hours, or 3, 4, 5, 6, 7, or 10 days, for example by measuring a lipid (e.g. an amine lipid), RNA (e.g. mRNA), or other component. In certain embodiments, lipid-encapsulated versus free lipid, RNA, or nucleic acid component of the LNP is measured.

Lipid clearance may be measured as described in literature. See Maier, M. A., et al. Biodegradable Lipids Enabling Rapidly Eliminated Lipid Nanoparticles for Systemic Delivery of RNAi Therapeutics. Mol. Ther. 2013, 21(8), 1570-78 ("Maier"). For example, in Maier, LNP-siRNA systems containing luciferases-targeting siRNA were administered to six- to eight-week old male C57Bl/6 mice at 0.3 mg/kg by intravenous bolus injection via the lateral tail vein. Blood, liver, and spleen samples were collected at 0.083, 0.25, 0.5, 1, 2, 4, 8, 24, 48, 96, and 168 hours post-dose. Mice were perfused with saline before tissue collection and blood samples were processed to obtain plasma. All samples were processed and analyzed by LC-MS. Further, Maier describes a procedure for assessing toxicity after administration of LNP-siRNA formulations. For example, a luciferase-targeting siRNA was administered at 0, 1, 3, 5, and 10 mg/kg (5 animals/group) via single intravenous bolus injection at a dose volume of 5 mL/kg to male Sprague-Dawley rats. After 24 hours, about 1 mL of blood was obtained from the jugular vein of conscious animals and the serum was isolated. At 72 hours post-dose, all animals were euthanized for necropsy. Assessment of clinical signs, body weight, serum chemistry, organ weights and histopathology was performed. Although Maier describes methods for assessing siRNA-LNP formulations, these methods may be applied to assess clearance, pharmacokinetics, and toxicity of administration of LNP compositions of the present disclosure.

The amine lipids lead to an increased clearance rate. In some embodiments, the clearance rate is a lipid clearance rate, for example the rate at which an amine lipid is cleared from the blood, serum, or plasma. In some embodiments, the clearance rate is an RNA clearance rate, for example the rate at which an mRNA or a gRNA is cleared from the blood, serum, or plasma. In some embodiments, the clearance rate is the rate at which LNP is cleared from the blood, serum, or plasma. In some embodiments, the clearance rate is the rate at which LNP is cleared from a tissue, such as liver tissue or spleen tissue. In certain embodiments, a high rate of clearance rate leads to a safety profile with no substantial adverse effects. The amine lipids reduce LNP accumulation in circulation and in tissues. In some embodiments, a reduction in LNP accumulation in circulation and in tissues leads to a safety profile with no substantial adverse effects.

The amine lipids of the present disclosure may be ionizable depending upon the pH of the medium they are in. For example, in a slightly acidic medium, the amine lipids may be protonated and thus bear a positive charge. Conversely, in a slightly basic medium, such as, for example, blood where pH is approximately 7.35, the amine lipids may not be protonated and thus bear no charge. In some embodiments, the amine lipids of the present disclosure may be protonated at a pH of at least about 9. In some embodiments, the amine lipids of the present disclosure may be protonated at a pH of at least about 9. In some embodiments, the amine lipids of the present disclosure may be protonated at a pH of at least about 10.

The ability of an amine lipid to bear a charge is related to its intrinsic pKa. For example, the amine lipids of the present disclosure may each, independently, have a pKa in the range of from about 5.8 to about 6.2. For example, the amine lipids of the present disclosure may each, independently, have a pKa in the range of from about 5.8 to about 6.5. This may be advantageous as it has been found that cationic lipids with a pKa ranging from about 5.1 to about 7.4 are effective for delivery of cargo in vivo, e.g. to the liver. Further, it has been found that cationic lipids with a pKa ranging from about 5.3 to about 6.4 are effective for delivery in vivo, e.g. to tumors. See, e.g., WO2014/136086.

Additional Lipids

"Neutral lipids" suitable for use in a lipid composition of the disclosure include, for example, a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid may be selected from the group consisting of distearoylphosphatidylcholine (DSPC) and dimyristoyl phosphatidyl ethanolamine (DMPE). In another embodiment, the neutral phospholipid may be distearoylphosphatidylcholine (DSPC).

"Helper lipids" include steroids, sterols, and alkyl resorcinols. Helper lipids suitable for use in the present disclosure include, but are not limited to, cholesterol, 5-heptadecylresorcinol, and cholesterol hemisuccinate. In one embodiment, the helper lipid may be cholesterol. In one embodiment, the helper lipid may be cholesterol hemisuccinate.

"Stealth lipids" are lipids that alter the length of time the nanoparticles can exist in vivo (e.g., in the blood). Stealth lipids may assist in the formulation process by, for example, reducing particle aggregation and controlling particle size. Stealth lipids used herein may modulate pharmacokinetic properties of the LNP. Stealth lipids suitable for use in a lipid composition of the disclosure include, but are not limited to, stealth lipids having a hydrophilic head group linked to a lipid moiety. Stealth lipids suitable for use in a lipid composition of the present disclosure and information about the biochemistry of such lipids can be found in Romberg et al., Pharmaceutical Research, Vol. 25, No. 1, 2008, pg. 55-71 and Hoekstra et al., Biochimica et Biophysica Acta 1660 (2004) 41-52. Additional suitable PEG lipids are disclosed, e.g., in WO 2006/007712.

In one embodiment, the hydrophilic head group of stealth lipid comprises a polymer moiety selected from polymers based on PEG. Stealth lipids may comprise a lipid moiety. In some embodiments, the stealth lipid is a PEG lipid.

In one embodiment, a stealth lipid comprises a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids and poly[N-(2-hydroxypropyl)methacrylamide].

In one embodiment, the PEG lipid comprises a polymer moiety based on PEG (sometimes referred to as poly(ethylene oxide)).

The PEG lipid further comprises a lipid moiety. In some embodiments, the lipid moiety may be derived from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. In some embodiments, the alkyl chail length comprises about C10 to C20. The dialkylglycerol or dialkylglycamide group can further comprise one or more substituted alkyl groups. The chain lengths may be symmetrical or assymetric.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment, PEG is unsubstituted. In one embodiment, the PEG is substituted, e.g., by one or more alkyl, alkoxy, acyl, hydroxy, or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment, about 150 to about 30,000, in a sub-embodiment, about 150 to about 20,000, in a sub-embodiment about 150 to about 15,000, in a sub-embodiment, about 150 to about 10,000, in a sub-embodiment, about 150 to about 6,000, in a sub-embodiment, about 150 to about 5,000, in a sub-embodiment, about 150 to about 4,000, in a sub-embodiment, about 150 to about 3,000, in a sub-embodiment, about 300 to about 3,000, in a sub-embodiment, about 1,000 to about 3,000, and in a sub-embodiment, about 1,500 to about 2,500.

In certain embodiments, the PEG (e.g., conjugated to a lipid moiety or lipid, such as a stealth lipid), is a "PEG-2K," also termed "PEG 2000," which has an average molecular weight of about 2,000 daltons. PEG-2K is represented herein by the following formula (I), wherein n is 45, meaning that the number averaged degree of polymerization comprises about 45 subunits. However, other PEG embodiments known in the art may be used, including, e.g., those where the number-averaged degree of polymerization comprises about 23 subunits (n=23), and/or 68 subunits (n=68). In some embodiments, n may range from about 30 to about 60. In some embodiments, n may range from about 35 to about 55. In some embodiments, n may range from about 40 to about 50. In some embodiments, n may range from about 42 to about 48. In some embodiments, n may be 45. In some embodiments, R may be selected from H, substituted alkyl, and unsubstituted alkyl. In some embodiments, R may be unsubstituted alkyl. In some embodiments, R may be methyl.

In any of the embodiments described herein, the PEG lipid may be selected from PEG-dilauroylglycerol, PEG-dimyristoylglycerol (PEG-DMG) (catalog #GM-020 from NOF, Tokyo, Japan), PEG-dipalmitoylglycerol, PEG-distearoylglycerol (PEG-DSPE) (catalog #DSPE-020CN, NOF, Tokyo, Japan), PEG-dilaurylglycamide, PEG-dimyristylglycamide, PEG-dipalmitoylglycamide, and PEG-distearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG) (cat. #880150P from Avanti Polar Lipids, Alabaster, Alabama, USA), 1,2-distearoyl-sn-glycero-3-phosphoethanolamine-N-[methoxy(polyethylene glycol)-2000] (PEG2k-DSPE) (cat. #880120C from Avanti Polar Lipids, Alabaster, Alabama, USA), 1,2-distearoyl-sn-glycerol, methoxypolyethylene glycol (PEG2k-DSG; GS-020, NOF Tokyo, Japan), poly(ethylene glycol)-2000-dimethacrylate (PEG2k-DMA), and 1,2-distearyloxypropyl-3-amine-N-[methoxy(polyethylene glycol)-2000](PEG2k-DSA). In one embodiment, the PEG lipid may be PEG2k-DMG. In some embodiments, the PEG lipid may be PEG2k-DSG. In one embodiment, the PEG lipid may be PEG2k-DSPE. In one embodiment, the PEG lipid may be PEG2k-DMA. In one embodiment, the PEG lipid may be PEG2k-C-DMA. In one embodiment, the PEG lipid may be compound 5027, disclosed in WO2016/010840 (paragraphs [00240] to [00244]). In one embodiment, the PEG lipid may be PEG2k-DSA. In one embodiment, the PEG lipid may be PEG2k-C11. In some embodiments, the PEG lipid may be PEG2k-C14. In some embodiments, the PEG lipid may be PEG2k-C16. In some embodiments, the PEG lipid may be PEG2k-C18.

LNP Formulations

The LNP may contain (i) an amine lipid for encapsulation and for endosomal escape, (ii) a neutral lipid for stabilization, (iii) a helper lipid, also for stabilization, and (iv) a stealth lipid, such as a PEG lipid.

In some embodiments, an LNP composition may comprise an RNA component that includes one or more of an RNA-guided DNA-binding agent, a Cas nuclease mRNA, a Class 2 Cas nuclease mRNA, a Cas9 mRNA, and a gRNA. In some embodiments, an LNP composition may include a Class 2 Cas nuclease and a gRNA as the RNA component. In certain embodiments, an LNP composition may comprise the RNA component, an amine lipid, a helper lipid, a neutral lipid, and a stealth lipid. In certain LNP compositions, the helper lipid is cholesterol. In other compositions, the neutral lipid is DSPC. In additional embodiments, the stealth lipid is PEG2k-DMG or PEG2k-C11. In certain embodiments, the LNP composition comprises Lipid A or an equivalent of Lipid A; a helper lipid; a neutral lipid; a stealth lipid; and a guide RNA. In certain compositions, the amine lipid is Lipid A. In certain compositions, the amine lipid is Lipid A or an acetal analog thereof; the helper lipid is cholesterol; the neutral lipid is DSPC; and the stealth lipid is PEG2k-DMG.

In certain embodiments, lipid compositions are described according to the respective molar ratios of the component lipids in the formulation. Embodiments of the present disclosure provide lipid compositions described according to the respective molar ratios of the component lipids in the formulation. In one embodiment, the mol-% of the amine lipid may be from about 30 mol-% to about 60 mol-%. In one embodiment, the mol-% of the amine lipid may be from about 40 mol-% to about 60 mol-%. In one embodiment, the mol-% of the amine lipid may be from about 45 mol-% to about 60 mol-%. In one embodiment, the mol-% of the amine lipid may be from about 50 mol-% to about 60 mol-%. In one embodiment, the mol-% of the amine lipid may be from about 55 mol-% to about 60 mol-%. In one embodiment, the mol-% of the amine lipid may be from about 50 mol-% to about 55 mol-%. In one embodiment, the mol-% of the amine lipid may be about 50 mol-%. In one embodiment, the mol-% of the amine lipid may be about 55 mol-%. In some embodiments, the amine lipid mol-% of the LNP batch will be ±30%, ±25%, ±20%, ±15%, ±10%, ±5%, or ±2.5% of the target mol-%. In some embodiments, the amine lipid mol-% of the LNP batch will be ±4 mol-%, ±3 mol-%, ±2 mol-%, ±1.5 mol-%, ±1 mol-%, ±0.5 mol-%, or ±0.25 mol-% of the target mol-%. All mol-% numbers are given as a fraction of the lipid component of the LNP compositions. In certain embodiments, LNP inter-lot variability of the amine lipid mol-% will be less than 15%, less than 10% or less than 5%.

In one embodiment, the mol-% of the neutral lipid may be from about 5 mol-% to about 15 mol-%. In one embodiment, the mol-% of the neutral lipid may be from about 7 mol-% to about 12 mol-%. In one embodiment, the mol-% of the neutral lipid may be about 9 mol-%. In some embodiments, the neutral lipid mol-% of the LNP batch will be ±30%, ±25%, ±20%, ±15%, ±10%, ±5%, or ±2.5% of the target neutral lipid mol-%. In certain embodiments, LNP inter-lot variability will be less than 15%, less than 10% or less than 5%.

In one embodiment, the mol-% of the helper lipid may be from about 20 mol-% to about 60 mol-%. In one embodiment, the mol-% of the helper lipid may be from about 25 mol-% to about 55 mol-%. In one embodiment, the mol-% of the helper lipid may be from about 25 mol-% to about 50 mol-%. In one embodiment, the mol-% of the helper lipid may be from about 25 mol-% to about 40 mol-%. In one embodiment, the mol-% of the helper lipid may be from about 30 mol-% to about 50 mol-%. In one embodiment, the mol-% of the helper lipid may be from about 30 mol-% to about 40 mol-%. In one embodiment, the mol-% of the helper lipid is adjusted based on amine lipid, neutral lipid, and PEG lipid concentrations to bring the lipid component to 100 mol-%. In some embodiments, the helper mol-% of the LNP batch will be ±30%, ±25%, ±20%, ±15%, ±10%, ±5%, or ±2.5% of the target mol-%. In certain embodiments, LNP inter-lot variability will be less than 15%, less than 10% or less than 5%.

In one embodiment, the mol-% of the PEG lipid may be from about 1 mol-% to about 10 mol-%. In one embodiment, the mol-% of the PEG lipid may be from about 2 mol-% to about 10 mol-%. In one embodiment, the mol-% of the PEG lipid may be from about 2 mol-% to about 8 mol-%. In one embodiment, the mol-% of the PEG lipid may be from about 2 mol-% to about 4 mol-%. In one embodiment, the mol-% of the PEG lipid may be from about 2.5 mol-% to about 4 mol-%. In one embodiment, the mol-% of the PEG lipid may be about 3 mol-%. In one embodiment, the mol-% of the PEG lipid may be about 2.5 mol-%. In some embodiments, the PEG lipid mol-% of the LNP batch will be ±30%, ±25%, ±20%, ±15%, ±10%, ±5%, or ±2.5% of the target PEG lipid mol-%. In certain embodiments, LNP inter-lot variability will be less than 15%, less than 10% or less than 5%.

In certain embodiments, the cargo includes an mRNA encoding an RNA-guided DNA-binding agent (e.g. a Cas nuclease, a Class 2 Cas nuclease, or Cas9), and a gRNA or a nucleic acid encoding a gRNA, or a combination of mRNA and gRNA. In one embodiment, an LNP composition may comprise a Lipid A or its equivalents. In some aspects, the amine lipid is Lipid A. In some aspects, the amine lipid is a Lipid A equivalent, e.g. an analog of Lipid A. In certain aspects, the amine lipid is an acetal analog of Lipid A. In various embodiments, an LNP composition comprises an amine lipid, a neutral lipid, a helper lipid, and a PEG lipid. In certain embodiments, the helper lipid is cholesterol. In certain embodiments, the neutral lipid is DSPC. In specific embodiments, PEG lipid is PEG2k-DMG. In some embodiments, an LNP composition may comprise a Lipid A, a helper lipid, a neutral lipid, and a PEG lipid. In some embodiments, an LNP composition comprises an amine lipid, DSPC, cholesterol, and a PEG lipid. In some embodiments, the LNP composition comprises a PEG lipid comprising DMG. In certain embodiments, the amine lipid is selected from Lipid A, and an equivalent of Lipid A, including an acetal analog of Lipid A. In additional embodiments, an LNP composition comprises Lipid A, cholesterol, DSPC, and PEG2k-DMG.

Embodiments of the present disclosure also provide lipid compositions described according to the molar ratio between the positively charged amine groups of the amine lipid (N) and the negatively charged phosphate groups (P) of the nucleic acid to be encapsulated. This may be mathematically represented by the equation N/P. In some embodiments, an LNP composition may comprise a lipid component that comprises an amine lipid, a helper lipid, a neutral lipid, and a helper lipid; and a nucleic acid component, wherein the N/P ratio is about 3 to 10. In some embodiments, an LNP composition may comprise a lipid component that comprises an amine lipid, a helper lipid, a neutral lipid, and a helper lipid; and an RNA component, wherein the N/P ratio is about 3 to 10. In one embodiment, the N/P ratio may about 5-7. In one embodiment, the N/P ratio may about 4.5-8. In one embodiment, the N/P ratio may about 6. In one embodiment, the N/P ratio may be 6±1. In one embodiment, the N/P ratio may about 6±0.5. In some embodiments, the N/P ratio will be ±30%, ±25%, ±20%, ±15%, ±10%, ±5%, or ±2.5% of the target N/P ratio. In certain embodiments, LNP inter-lot variability will be less than 15%, less than 10% or less than 5%.

In some embodiments, the RNA component may comprise an mRNA, such as an mRNA disclosed herein, e.g., encoding a Cas nuclease. In one embodiment, RNA component may comprise a Cas9 mRNA. In some compositions comprising an mRNA encoding a Cas nuclease, the LNP further comprises a gRNA nucleic acid, such as a gRNA. In some embodiments, the RNA component comprises a Cas nuclease mRNA and a gRNA. In some embodiments, the RNA component comprises a Class 2 Cas nuclease mRNA and a gRNA.

In certain embodiments, an LNP composition may comprise an mRNA disclosed herein, e.g., encoding a Cas nuclease, such as a Class 2 Cas nuclease, an amine lipid, a helper lipid, a neutral lipid, and a PEG lipid. In certain LNP compositions comprising an mRNA encoding a Cas nuclease such as a Class 2 Cas nuclease, the helper lipid is cholesterol. In other compositions comprising an mRNA encoding a Cas nuclease such as a Class 2 Cas nuclease, the neutral lipid is DSPC. In additional embodiments comprising an mRNA encoding a Cas nuclease such as a Class 2 Cas nuclease, the PEG lipid is PEG2k-DMG or PEG2k-C11. In specific compositions comprising an mRNA encoding a Cas nuclease such as a Class 2 Cas nuclease, the amine lipid is selected from Lipid A and its equivalents, such as an acetal analog of Lipid A.

In some embodiments, an LNP composition may comprise a gRNA. In certain embodiments, an LNP composition may comprise an amine lipid, a gRNA, a helper lipid, a neutral lipid, and a PEG lipid. In certain LNP compositions comprising a gRNA, the helper lipid is cholesterol. In some compositions comprising a gRNA, the neutral lipid is DSPC. In additional embodiments comprising a gRNA, the PEG lipid is PEG2k-DMG or PEG2k-C11. In certain embodiments, the amine lipid is selected from Lipid A and its equivalents, such as an acetal analog of Lipid A.

In one embodiment, an LNP composition may comprise an sgRNA. In one embodiment, an LNP composition may comprise a Cas9 sgRNA. In one embodiment, an LNP composition may comprise a Cpf1 sgRNA. In some compositions comprising an sgRNA, the LNP includes an amine lipid, a helper lipid, a neutral lipid, and a PEG lipid. In certain compositions comprising an sgRNA, the helper lipid is cholesterol. In other compositions comprising an sgRNA, the neutral lipid is DSPC. In additional embodiments comprising an sgRNA, the PEG lipid is PEG2k-DMG or PEG2k-C11. In certain embodiments, the amine lipid is selected from Lipid A and its equivalents, such as acetal analogs of Lipid A.

In certain embodiments, an LNP composition comprises an mRNA encoding a Cas nuclease and a gRNA, which may be an sgRNA. In one embodiment, an LNP composition may comprise an amine lipid, an mRNA encoding a Cas nuclease, a gRNA, a helper lipid, a neutral lipid, and a PEG lipid. In certain compositions comprising an mRNA encoding a Cas nuclease and a gRNA, the helper lipid is cholesterol. In some compositions comprising an mRNA encoding a Cas nuclease and a gRNA, the neutral lipid is DSPC. In additional embodiments comprising an mRNA encoding a Cas nuclease and a gRNA, the PEG lipid is PEG2k-DMG or PEG2k-C11. In certain embodiments, the amine lipid is selected from Lipid A and its equivalents, such as acetal analogs of Lipid A.

In certain embodiments, the LNP compositions include a Cas nuclease mRNA, such as a Class 2 Cas mRNA and at least one gRNA. In certain embodiments, the LNP composition includes a ratio of gRNA to Cas nuclease mRNA, such as Class 2 Cas nuclease mRNA from about 25:1 to about 1:25. In certain embodiments, the LNP formulation includes a ratio of gRNA to Cas nuclease mRNA, such as Class 2 Cas nuclease mRNA from about 10:1 to about 1:10. In certain embodiments, the LNP formulation includes a ratio of gRNA to Cas nuclease mRNA, such as Class 2 Cas nuclease mRNA from about 8:1 to about 1:8. As measured herein, the ratios are by weight. In some embodiments, the LNP formulation includes a ratio of gRNA to Cas nuclease mRNA, such as Class 2 Cas mRNA from about 5:1 to about 1:5. In some embodiments, ratio range is about 3:1 to 1:3, about 2:1 to 1:2, about 5:1 to 1:2, about 5:1 to 1:1, about 3:1 to 1:2, about 3:1 to 1:1, about 3:1, about 2:1 to 1:1. In some embodiments, the gRNA to mRNA ratio is about 3:1 or about 2:1 In some embodiments the ratio of gRNA to Cas nuclease mRNA, such as Class 2 Cas nuclease is about 1:1. The ratio may be about 25:1, 10:1, 5:1, 3:1, 1:1, 1:3, 1:5, 1:10, or 1:25.

The LNP compositions disclosed herein may include a template nucleic acid. The template nucleic acid may be co-formulated with an mRNA encoding a Cas nuclease, such as a Class 2 Cas nuclease mRNA. In some embodiments, the template nucleic acid may be co-formulated with a guide RNA. In some embodiments, the template nucleic acid may be co-formulated with both an mRNA encoding a Cas nuclease and a guide RNA. In some embodiments, the template nucleic acid may be formulated separately from an mRNA encoding a Cas nuclease or a guide RNA. The template nucleic acid may be delivered with, or separately from the LNP compositions. In some embodiments, the template nucleic acid may be single- or double-stranded, depending on the desired repair mechanism. The template may have regions of homology to the target DNA, or to sequences adjacent to the target DNA.

In some embodiments, LNPs are formed by mixing an aqueous RNA solution with an organic solvent-based lipid solution, e.g., 100% ethanol. Suitable solutions or solvents include or may contain: water, PBS, Tris buffer, NaCl, citrate buffer, ethanol, chloroform, diethylether, cyclohexane, tetrahydrofuran, methanol, isopropanol. A pharmaceutically acceptable buffer, e.g., for in vivo administration of LNPs, may be used. In certain embodiments, a buffer is used to maintain the pH of the composition comprising LNPs at or above pH 6.5. In certain embodiments, a buffer is used to maintain the pH of the composition comprising LNPs at or above pH 7.0. In certain embodiments, the composition has a pH ranging from about 7.2 to about 7.7. In additional embodiments, the composition has a pH ranging from about 7.3 to about 7.7 or ranging from about 7.4 to about 7.6. In further embodiments, the composition has a pH of about 7.2, 7.3, 7.4, 7.5, 7.6, or 7.7. The pH of a composition may be measured with a micro pH probe. In certain embodiments, a cryoprotectant is included in the composition. Non-limiting examples of cryoprotectants include sucrose, trehalose, glycerol, DMSO, and ethylene glycol. Exemplary compositions may include up to 10% cryoprotectant, such as, for example, sucrose. In certain embodiments, the LNP composition may include about 1, 2, 3, 4, 5, 6, 7, 8, 9, or 10% cryoprotectant. In certain embodiments, the LNP composition may include about 1, 2, 3, 4, 5, 6, 7, 8, 9, or 10% sucrose. In some embodiments, the LNP composition may include a buffer. In some embodiments, the buffer may comprise a phosphate buffer (PBS), a Tris buffer, a citrate buffer, and mixtures thereof. In certain exemplary embodiments, the buffer comprises NaCl. In certain embodiments, NaCl is omitted. Exemplary amounts of NaCl may range from about 20 mM to about 45 mM. Exemplary amounts of NaCl may range from about 40 mM to about 50 mM. In some embodiments, the amount of NaCl is about 45 mM. In some embodiments, the buffer is a Tris buffer. Exemplary amounts of Tris may range from about 20 mM to about 60 mM. Exemplary amounts of Tris may range from about 40 mM to about 60 mM. In some embodiments, the amount of Tris is about 50 mM. In some embodiments, the buffer comprises NaCl and Tris. Certain exemplary embodiments of the LNP compositions contain 5% sucrose and 45 mM NaCl in Tris buffer. In other exemplary embodiments, compositions contain sucrose in an amount of about 5% w/v, about 45 mM NaCl, and about 50 mM Tris at pH 7.5. The salt, buffer, and cryoprotectant amounts may be varied such that the osmolality of the overall formulation is maintained. For example, the final osmolality may be maintained at less than 450 mOsm/L. In further embodiments, the osmolality is between 350 and 250 mOsm/L. Certain embodiments have a final osmolality of 300+/−20 mOsm/L.

In some embodiments, microfluidic mixing, T-mixing, or cross-mixing is used. In certain aspects, flow rates, junction size, junction geometry, junction shape, tube diameter, solutions, and/or RNA and lipid concentrations may be varied. LNPs or LNP compositions may be concentrated or purified, e.g., via dialysis, tangential flow filtration, or chromatography. The LNPs may be stored as a suspension, an emulsion, or a lyophilized powder, for example. In some embodiments, an LNP composition is stored at 2-8° C., in certain aspects, the LNP compositions are stored at room temperature. In additional embodiments, an LNP composition is stored frozen, for example at −20° C. or −80° C. In other embodiments, an LNP composition is stored at a temperature ranging from about 0° C. to about −80° C. Frozen LNP compositions may be thawed before use, for example on ice, at 4° C., at room temperature, or at 25° C. Frozen LNP compositions may be maintained at various temperatures, for example on ice, at 4° C., at room temperature, at 25° C., or at 37° C.

In some embodiments, an LNP composition has greater than about 80% encapsulation. In some embodiments, an LNP composition has a particle size less than about 120 nm. In some embodiments, an LNP composition has a pdi less than about 0.2. In some embodiments, at least two of these features are present. In some embodiments, each of these three features is present. Analytical methods for determining these parameters are discussed below in the general reagents and methods section.

In some embodiments, microfluidic mixing, T-mixing, or cross-mixing is used. In certain aspects, flow rates, junction size, junction geometry, junction shape, tube diameter, solutions, and/or RNA and lipid concentrations may be varied. LNPs or LNP compositions may be concentrated or purified, e.g., via dialysis or chromatography. The LNPs may be stored as a suspension, an emulsion, or a lyophilized powder, for example. In some embodiments, the LNP compositions are stored at 2-8° C., in certain aspects, the LNP compositions are stored at room temperature. In additional embodiments, the LNP composition is stored frozen, for example at −20° C. or −80° C. In other embodiments, the LNP composition is stored at a temperature ranging from 0° C. to −80° C. Frozen LNP compositions may be thawed before use, for example on ice, at room temperature, or at 25° C.

Dynamic Light Scattering ("DLS") can be used to characterize the polydispersity index ("pdi") and size of the LNPs of the present disclosure. DLS measures the scattering of light that results from subjecting a sample to a light source. PDI, as determined from DLS measurements, represents the distribution of particle size (around the mean particle size) in a population, with a perfectly uniform population having a PDI of zero. In some embodiments, the pdi may range from 0.005 to 0.75. In some embodiments, the pdi may range from 0.01 to 0.5. In some embodiments, the pdi may range from 0.02 to 0.4. In some embodiments, the pdi may range from 0.03 to 0.35. In some embodiments, the pdi may range from 0.1 to 0.35.

In some embodiments, LNPs disclosed herein have a size of 1 to 250 nm. In some embodiments, the LNPs have a size of 10 to 200 nm. In further embodiments, the LNPs have a size of 20 to 150 nm. In some embodiments, the LNPs have a size of 50 to 150 nm. In some embodiments, the LNPs have a size of 50 to 100 nm. In some embodiments, the LNPs have a size of 50 to 120 nm. In some embodiments, the LNPs have a size of 75 to 150 nm. In some embodiments, the LNPs have a size of 30 to 200 nm. Unless indicated otherwise, all sizes referred to herein are the average sizes (diameters) of the fully formed nanoparticles, as measured by dynamic light scattering on a Malvern Zetasizer. The nanoparticle sample is diluted in phosphate buffered saline (PBS) so that the count rate is approximately 200-400 kcts. The data is presented as a weighted-average of the intensity measure. In some embodiments, the LNPs are formed with an average encapsulation efficiency ranging from 50% to 100%. In some embodiments, the LNPs are formed with an average encapsulation efficiency ranging from 50% to 70%. In some embodiments, the LNPs are formed with an average encapsulation efficiency ranging from 70% to 90%. In some embodiments, the LNPs are formed with an average encapsulation efficiency ranging from 90% to 100%. In some embodiments, the LNPs are formed with an average encapsulation efficiency ranging from 75% to 95%.

In some embodiments, LNPs associated with the gRNAs disclosed herein are for use in preparing a medicament for treating ATTR. In some embodiments, LNPs associated with the gRNAs disclosed herein are for use in preparing a medicament for reducing or preventing accumulation and aggregation of TTR in amyloids or amyloid fibrils in subjects having ATTR. In some embodiments, LNPs associated with the gRNAs disclosed herein are for use in preparing a medicament for reducing serum TTR concentration. In some embodiments, LNPs associated with the gRNAs disclosed herein are for use in treating ATTR in a subject, such as a mammal, e.g., a primate such as a human. In some embodiments, LNPs associated with the gRNAs disclosed herein are for use in reducing or preventing accumulation and aggregation of TTR in amyloids or amyloid fibrils in subjects having ATTR, such as a mammal, e.g., a primate such as a human. In some embodiments, LNPs associated with the gRNAs disclosed herein are for use in reducing serum TTR concentration in a subject, such as a mammal, e.g., a primate such as a human.

Electroporation is also a well-known means for delivery of cargo, and any electroporation methodology may be used for delivery of any one of the gRNAs disclosed herein. In some embodiments, electroporation may be used to deliver any one of the gRNAs disclosed herein and an RNA-guided DNA nuclease such as Cas9 or an mRNA encoding an RNA-guided DNA nuclease such as Cas9.

In some embodiments, the invention comprises a method for delivering any one of the gRNAs disclosed herein to an ex vivo cell, wherein the gRNA is associated with an LNP or not associated with an LNP. In some embodiments, the gRNA/LNP or gRNA is also associated with an RNA-guided DNA nuclease such as Cas9 or an mRNA encoding an RNA-guided DNA nuclease such as Cas9.

In certain embodiments, the invention comprises DNA or RNA vectors encoding any of the guide RNAs comprising any one or more of the guide sequences described herein. In some embodiments, in addition to guide RNA sequences, the vectors further comprise nucleic acids that do not encode guide RNAs. Nucleic acids that do not encode guide RNA include, but are not limited to, promoters, enhancers, regulatory sequences, and nucleic acids encoding an RNA-guided DNA nuclease, which can be a nuclease such as Cas9. In some embodiments, the vector comprises one or more nucleotide sequence(s) encoding a crRNA, a trRNA, or a crRNA and trRNA. In some embodiments, the vector comprises one or more nucleotide sequence(s) encoding a sgRNA and an mRNA encoding an RNA-guided DNA nuclease, which can be a Cas nuclease, such as Cas9 or Cpf1. In some embodiments, the vector comprises one or more nucleotide sequence(s) encoding a crRNA, a trRNA, and an mRNA encoding an RNA-guided DNA nuclease, which can be a Cas protein, such as, Cas9. In one embodiment, the Cas9 is from *Streptococcus pyogenes* (i.e., Spy Cas9). In some embodiments, the nucleotide sequence encoding the crRNA, trRNA, or crRNA and trRNA (which may be a sgRNA) comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the crRNA and the trRNA are encoded by non-contiguous nucleic acids within one vector. In other embodiments, the crRNA and the trRNA may be encoded by a contiguous nucleic acid. In some embodiments, the crRNA and the trRNA are encoded by opposite strands of a single nucleic acid. In other embodiments, the crRNA and the trRNA are encoded by the same strand of a single nucleic acid.

In some embodiments, the vector may be circular. In other embodiments, the vector may be linear. In some embodiments, the vector may be enclosed in a lipid nanoparticle, liposome, non-lipid nanoparticle, or viral capsid. Non-limiting exemplary vectors include plasmids, phagemids, cosmids, artificial chromosomes, minichromosomes, transposons, viral vectors, and expression vectors.

In some embodiments, the vector may be a viral vector. In some embodiments, the viral vector may be genetically modified from its wild type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, helper dependent adenoviral vectors (HDAd), herpes simplex virus (HSV-1) vectors, bacteriophage T4, baculovirus vectors, and retrovirus vectors. In some embodiments, the viral vector may be an AAV vector. In some embodiments, the viral vector is AAV2, AAV3, AAV3B, AAV5, AAV6, AAV6.2, AAV7, AAVrh.64R1, AAVhu.37, AAVrh.8, AAVrh.32.33, AAV8, AAV9, AAVrh10, or AAVLK03. In other embodiments, the viral vector may a lentivirus vector.

In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal ('I') are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding an RNA-guided DNA nuclease such as a Cas nuclease, while a second AAV vector may contain one or more guide sequences.

In some embodiments, the vector may be capable of driving expression of one or more coding sequences in a cell. In some embodiments, the cell may be a prokaryotic cell, such as, e.g., a bacterial cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding an RNA-guided DNA nuclease such as a nuclease described herein. In some embodiments, the nuclease encoded by the vector may be a Cas protein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1a) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1a promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In some embodiments, the promoter may be a tissue-specific promoter, e.g., a promoter specific for expression in the liver.

The vector may further comprise a nucleotide sequence encoding the guide RNA described herein. In some embodiments, the vector comprises one copy of the guide RNA. In other embodiments, the vector comprises more than one copy of the guide RNA. In embodiments with more than one guide RNA, the guide RNAs may be non-identical such that they target different target sequences, or may be identical in that they target the same target sequence. In some embodiments where the vectors comprise more than one guide RNA, each guide RNA may have other different properties, such as activity or stability within a complex with an RNA-guided DNA nuclease, such as a Cas RNP complex. In some embodiments, the nucleotide sequence encoding the guide RNA may be operably linked to at least one transcriptional or translational control sequence, such as a promoter, a 3' UTR, or a 5' UTR. In one embodiment, the promoter may be a tRNA promoter, e.g., tRNA$^{Lys3}$, or a tRNA chimera. See Mefferd et al., *RNA*. 2015 21:1683-9; Scherer et al., *Nucleic Acids Res.* 2007 35: 2620-2628. In some embodiments, the promoter may be recognized by RNA polymerase III (Pol III). Non-limiting examples of Pol III promoters include U6 and H1 promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In embodiments with more than one guide RNA, the promoters used to drive expression may be the same or different. In some embodiments, the nucleotide encoding the crRNA of the guide RNA and the nucleotide encoding the trRNA of the guide RNA may be provided on the same vector. In some embodiments, the nucleotide encoding the crRNA and the nucleotide encoding the trRNA may be driven by the same promoter. In some embodiments, the crRNA and trRNA may be transcribed into a single transcript. For example, the crRNA and trRNA may be processed from the single transcript to form a double-molecule guide RNA. Alternatively, the crRNA and trRNA may be transcribed into a single-molecule guide RNA (sgRNA). In other embodiments, the crRNA and the trRNA may be driven by their corresponding promoters on the same vector. In yet other embodiments, the crRNA and the trRNA may be encoded by different vectors.

In some embodiments, the nucleotide sequence encoding the guide RNA may be located on the same vector comprising the nucleotide sequence encoding an RNA-guided DNA nuclease such as a Cas nuclease. In some embodiments, expression of the guide RNA and of the RNA-guided DNA nuclease such as a Cas protein may be driven by their own corresponding promoters. In some embodiments, expression of the guide RNA may be driven by the same promoter that drives expression of the RNA-guided DNA nuclease such as a Cas protein. In some embodiments, the guide RNA and the RNA-guided DNA nuclease such as a Cas protein transcript may be contained within a single transcript. For example, the guide RNA may be within an untranslated region (UTR) of the RNA-guided DNA nuclease such as a Cas protein transcript. In some embodiments, the guide RNA may be within the 5' UTR of the transcript. In other embodiments, the guide RNA may be within the 3' UTR of the transcript. In some embodiments, the intracellular half-life of the transcript may be reduced by containing the guide RNA within its 3' UTR and thereby shortening the length of its 3' UTR. In additional embodiments, the guide RNA may be within an intron of the transcript. In some embodiments, suitable splice sites may be added at the intron within which the guide RNA is located such that the guide RNA is properly spliced out of the transcript. In some embodiments, expression of the RNA-guided DNA nuclease such as a Cas protein and the guide RNA from the same vector in close temporal proximity may facilitate more efficient formation of the CRISPR RNP complex.

In some embodiments, the compositions comprise a vector system. In some embodiments, the vector system may comprise one single vector. In other embodiments, the vector system may comprise two vectors. In additional embodiments, the vector system may comprise three vectors. When different guide RNAs are used for multiplexing, or when multiple copies of the guide RNA are used, the vector system may comprise more than three vectors.

In some embodiments, the vector system may comprise inducible promoters to start expression only after it is delivered to a target cell. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In additional embodiments, the vector system may comprise tissue-specific promoters to start expression only after it is delivered into a specific tissue.

The vector may be delivered by liposome, a nanoparticle, an exosome, or a microvesicle. The vector may also be delivered by a lipid nanoparticle (LNP); see e.g., U.S. Ser. No. 62/433,228, filed Dec. 12, 2016 and entitled "LIPID NANOPARTICLE FORMULATIONS FOR CRISPR/CAS COMPONENTS," the contents of which are hereby incorporated by reference in their entirety. Any of the LNPs and LNP formulations described herein are suitable for delivery of the guides alone or together a cas nuclease or an mRNA encoding a cas nuclease. In some embodiments, an LNP composition is encompassed comprising: an RNA component and a lipid component, wherein the lipid component comprises an amine lipid, a neutral lipid, a helper lipid, and a stealth lipid; and wherein the N/P ratio is about 1-10.

In some instances, the lipid component comprises Lipid A or its acetal analog, cholesterol, DSPC, and PEG-DMG; and wherein the N/P ratio is about 1-10. In some embodiments, the lipid component comprises: about 40-60 mol-% amine lipid; about 5-15 mol-% neutral lipid; and about 1.5-10 mol-% PEG lipid, wherein the remainder of the lipid component is helper lipid, and wherein the N/P ratio of the LNP composition is about 3-10. In some embodiments, the lipid component comprises about 50-60 mol-% amine lipid; about 8-10 mol-% neutral lipid; and about 2.5-4 mol-% PEG lipid, wherein the remainder of the lipid component is helper lipid, and wherein the N/P ratio of the LNP composition is about 3-8. In some instances, the lipid component comprises: about 50-60 mol-% amine lipid; about 5-15 mol-% DSPC; and about 2.5-4 mol-% PEG lipid, wherein the remainder of the lipid component is cholesterol, and wherein the N/P ratio of the LNP composition is about 3-8. In some instances, the lipid component comprises: 48-53 mol-% Lipid A; about 8-10 mol-% DSPC; and 1.5-10 mol-% PEG lipid, wherein the remainder of the lipid component is cholesterol, and wherein the N/P ratio of the LNP composition is 3-8±0.2.

In some embodiments, the vector may be delivered systemically. In some embodiments, the vector may be delivered into the hepatic circulation.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1. Materials and Methods

In Vitro Transcription ("IVT") of Nuclease mRNA

Capped and polyadenylated *Streptococcus pyogenes* ("Spy") Cas9 mRNA containing N1-methyl pseudo-U was generated by in vitro transcription using a linearized plasmid DNA template and T7 RNA polymerase. Plasmid DNA containing a T7 promoter, a sequence for transcription according to SEQ ID NO: 1 or 2, and a 100 nt poly (A/T) region was linearized by incubating at 37° C. for 2 hours with XbaI with the following conditions: 200 ng/µL plasmid, 2 U/µL XbaI (NEB), and 1× reaction buffer. The XbaI was inactivated by heating the reaction at 65° C. for 20 min. The linearized plasmid was purified from enzyme and buffer salts using a silica maxi spin column (Epoch Life Sciences) and analyzed by agarose gel to confirm linearization. The IVT reaction to generate Cas9 modified mRNA was incubated at 37° C. for 4 hours in the following conditions: 50 ng/µL linearized plasmid; 2 mM each of GTP, ATP, CTP, and N1-methyl pseudo-UTP (Trilink); 10 mM ARCA (Trilink); 5 U/µL T7 RNA polymerase (NEB); 1 U/µL Murine RNase inhibitor (NEB); 0.004 U/µL Inorganic *E. coli* pyrophosphatase (NEB); and 1× reaction buffer. After the 4-hour incubation, TURBO DNase (ThermoFisher) was added to a final concentration of 0.01 U/µL, and the reaction was incubated for an additional 30 minutes to remove the DNA template. The Cas9 mRNA was purified from enzyme and nucleotides using a MegaClear Transcription Clean-up kit per the manufacturer's protocol (ThermoFisher). Alternatively, the mRNA was purified through a precipitation protocol, which in some cases was followed by HPLC-based purification. Briefly, after the DNase digestion, the mRNA was precipitated by adding 0.21×vol of a 7.5 M LiCl solution and mixing, and the precipitated mRNA was pelleted by centrifugation. Once the supernatant was removed, the mRNA was reconstituted in water. The mRNA was precipitated again using ammonium acetate and ethanol. 5M Ammonium acetate was added to the mRNA solution for a final concentration of 2M along with 2×volume of 100% EtOH. The solution was mixed and incubated at −20° C. for 15 min. The precipitated mRNA was again pelleted by centrifugation, the supernatant was removed, and the mRNA was reconstituted in water. As a final step, the mRNA was precipitated using sodium acetate and ethanol. ⅒ volume of 3 M sodium acetate (pH 5.5) was added to the solution along with 2×volume of 100% EtOH. The solution was mixed and incubated at −20° C. for 15 min. The precipitated mRNA was again pelleted by centrifugation, the supernatant was removed, the pellet was washed with 70% cold ethanol and allowed to air dry. The mRNA was reconstituted in water.

For HPLC purified mRNA, after the LiCl precipitation and reconstitution, the mRNA was purified by RP-IP HPLC (see, e.g., Kariko, et al. *Nucleic Acids Research,* 2011, Vol. 39, No. 21 e142). The fractions chosen for pooling were combined and desalted by sodium acetate/ethanol precipitation as described above. The transcript concentration was determined by measuring the light absorbance at 260 nm (Nanodrop), and the transcript was analyzed by capillary electrophoresis by Bioanlayzer (Agilent).

When SEQ ID NOs: 1 and 2 are referred to below with respect to RNAs, it is understood that Ts should be replaced with Us (which were N1-methyl pseudouridines as described above). Cas9 mRNAs used in the Examples include a 5' cap and a 3' poly-A tail, e.g., up to 100 nts, and are identified by SEQ ID NO.

```
SEQ ID NO: 1: Cas9 sequence 1 for transcription
GGGTCCCGCAGTCGGCGTCCAGCGGCTCTGCTTGTTCGTGTGTGTGTCGTTGCAGGCCTTAT

TCGGATCCGCCACCATGGACAAGAAGTACAGCATCGGACTGGACATCGGAACAAACAGCGTC

GGATGGGCAGTCATCACAGACGAATACAAGGTCCCGAGCAAGAAGTTCAAGGTCCTGGGAAA

CACAGACAGACACAGCATCAAGAAGAACCTGATCGGAGCACTGCTGTTCGACAGCGGAGAAA

CAGCAGAAGCAACAAGACTGAAGAGAACAGCAAGAAGAAGATACACAAGAAGAAAGAACAGA

ATCTGCTACCTGCAGGAAATCTTCAGCAACGAAATGGCAAAGGTCGACGACAGCTTCTTCCA

CAGACTGGAAGAAAGCTTCCTGGTCGAAGAAGACAAGAAGCACGAAAGACACCCGATCTTCG

GAAACATCGTCGACGAAGTCGCATACCACGAAAAGTACCCGACAATCTACCACCTGAGAAAG

AAGCTGGTCGACAGCACAGACAAGGCAGACCTGAGACTGATCTACCTGGCACTGGCACACAT

GATCAAGTTCAGAGGACACTTCCTGATCGAAGGAGACCTGAACCCGGACAACAGCGACGTCG

ACAAGCTGTTCATCCAGCTGGTCCAGACATACAACCAGCTGTTCGAAGAAAACCCGATCAAC

GCAAGCGGAGTCGACGCAAAGGCAATCCTGAGCGCAAGACTGAGCAAGAGCAGAAGACTGGA

AAACCTGATCGCACAGCTGCCGGGAGAAAAGAAGAACGGACTGTTCGGAAACCTGATCGCAC

TGAGCCTGGGACTGACACCGAACTTCAAGAGCAACTTCGACCTGGCAGAAGACGCAAAGCTG

CAGCTGAGCAAGGACACATACGACGACGACCTGGACAACCTGCTGGCACAGATCGGAGACCA

GTACGCAGACCTGTTCCTGGCAGCAAAGAACCTGAGCGACGCAATCCTGCTGAGCGACATCC

TGAGAGTCAACACAGAAATCACAAAGGCACCGCTGAGCGCAAGCATGATCAAGAGATACGAC

GAACACCACCAGGACCTGACACTGCTGAAGGCACTGGTCAGACAGCAGCTGCCGGAAAAGTA

CAAGGAAATCTTCTTCGACCAGAGCAAGAACGGATACGCAGGATACATCGACGGAGGAGCAA

GCCAGGAAGAATTCTACAAGTTCATCAAGCCGATCCTGGAAAAGATGGACGGAACAGAAGAA

CTGCTGGTCAAGCTGAACAGAGAAGACCTGCTGAGAAAGCAGAGAACATTCGACAACGGAAG

CATCCCGCACCAGATCCACCTGGGAGAACTGCACGCAATCCTGAGAAGACAGGAAGACTTCT

ACCCGTTCCTGAAGGACAACAGAGAAAAGATCGAAAAGATCCTGACATTCAGAATCCCGTAC

TACGTCGGACCGCTGGCAAGAGGAAACAGCAGATTCGCATGGATGACAAGAAAGAGCGAAGA

AACAATCACACCGTGGAACTTCGAAGAAGTCGTCGACAAGGGAGCAAGCGCACAGAGCTTCA

TCGAAAGAATGACAAACTTCGACAAGAACCTGCCGAACGAAAAGGTCCTGCCGAAGCACAGC

CTGCTGTACGAATACTTCACAGTCTACAACGAACTGACAAAGGTCAAGTACGTCACAGAAGG

AATGAGAAAGCCGGCATTCCTGAGCGGAGAACAGAAGAAGGCAATCGTCGACCTGCTGTTCA

AGACAAACAGAAAGGTCACAGTCAAGCAGCTGAAGGAAGACTACTTCAAGAAGATCGAATGC

TTCGACAGCGTCGAAATCAGCGGAGTCGAAGACAGATTCAACGCAAGCCTGGGAACATACCA

CGACCTGCTGAAGATCATCAAGGACAAGGACTTCCTGGACAACGAAGAAAACGAAGACATCC

TGGAAGACATCGTCCTGACACTGACACTGTTCGAAGACAGAGAAATGATCGAAGAAAGACTG

AAGACATACGCACACCTGTTCGACGACAAGGTCATGAAGCAGCTGAAGAGAAGAAGATACAC

AGGATGGGGAAGACTGAGCAGAAAGCTGATCAACGGAATCAGAGACAAGCAGAGCGGAAAGA
```

-continued

```
CAATCCTGGACTTCCTGAAGAGCGACGGATTCGCAAACAGAAACTTCATGCAGCTGATCCAC

GACGACAGCCTGACATTCAAGGAAGACATCCAGAAGGCACAGGTCAGCGGACAGGGAGACAG

CCTGCACGAACACATCGCAAACCTGGCAGGAAGCCCGGCAATCAAGAAGGGAATCCTGCAGA

CAGTCAAGGTCGTCGACGAACTGGTCAAGGTCATGGGAAGACACAAGCCGGAAAACATCGTC

ATCGAAATGGCAAGAGAAAACCAGACAACACAGAAGGGACAGAAGAACAGCAGAGAAAGAAT

GAAGAGAATCGAAGAAGGAATCAAGGAACTGGGAAGCCAGATCCTGAAGGAACACCCGGTCG

AAAACACACAGCTGCAGAACGAAAAGCTGTACCTGTACTACCTGCAGAACGGAAGAGACATG

TACGTCGACCAGGAACTGGACATCAACAGACTGAGCGACTACGACGTCGACCACATCGTCCC

GCAGAGCTTCCTGAAGGACGACAGCATCGACAACAAGGTCCTGACAAGAAGCGACAAGAACA

GAGGAAAGAGCGACAACGTCCCGAGCGAAGAAGTCGTCAAGAAGATGAAGAACTACTGGAGA

CAGCTGCTGAACGCAAAGCTGATCACACAGAGAAAGTTCGACAACCTGACAAAGGCAGAGAG

AGGAGGACTGAGCGAACTGGACAAGGCAGGATTCATCAAGAGACAGCTGGTCGAAACAAGAC

AGATCACAAAGCACGTCGCACAGATCCTGGACAGCAGAATGAACACAAAGTACGACGAAAAC

GACAAGCTGATCAGAGAAGTCAAGGTCATCACACTGAAGAGCAAGCTGGTCAGCGACTTCAG

AAAGGACTTCCAGTTCTACAAGGTCAGAGAAATCAACAACTACCACCACGCACACGACGCAT

ACCTGAACGCAGTCGTCGGAACAGCACTGATCAAGAAGTACCCGAAGCTGGAAAGCGAATTC

GTCTACGGAGACTACAAGGTCTACGACGTCAGAAAGATGATCGCAAAGAGCGAACAGGAAAT

CGGAAAGGCAACAGCAAAGTACTTCTTCTACAGCAACATCATGAACTTCTTCAAGACAGAAA

TCACACTGGCAAACGGAGAAATCAGAAAGAGACCGCTGATCGAAACAAACGGAGAAACAGGA

GAAATCGTCTGGGACAAGGGAAGAGACTTCGCAACAGTCAGAAAGGTCCTGAGCATGCCGCA

GGTCAACATCGTCAAGAAGACAGAAGTCCAGACAGGAGGATTCAGCAAGGAAAGCATCCTGC

CGAAGAGAAACAGCGACAAGCTGATCGCAAGAAAGAAGGACTGGGACCCGAAGAAGTACGGA

GGATTCGACAGCCCGACAGTCGCATACAGCGTCCTGGTCGTCGCAAAGGTCGAAAAGGGAAA

GAGCAAGAAGCTGAAGAGCGTCAAGGAACTGCTGGGAATCACAATCATGGAAAGAAGCAGCT

TCGAAAAGAACCCGATCGACTTCCTGGAAGCAAAGGGATACAAGGAAGTCAAGAAGGACCTG

ATCATCAAGCTGCCGAAGTACAGCCTGTTCGAACTGGAAAACGGAAGAAAGAGAATGCTGGC

AAGCGCAGGAGAACTGCAGAAGGGAAACGAACTGGCACTGCCGAGCAAGTACGTCAACTTCC

TGTACCTGGCAAGCCACTACGAAAAGCTGAAGGGAAGCCCGGAAGACAACGAACAGAAGCAG

CTGTTCGTCGAACAGCACAAGCACTACCTGGACGAAATCATCGAACAGATCAGCGAATTCAG

CAAGAGAGTCATCCTGGCAGACGCAAACCTGGACAAGGTCCTGAGCGCATACAACAAGCACA

GAGACAAGCCGATCAGAGAACAGGCAGAAAACATCATCCACCTGTTCACACTGACAAACCTG

GGAGCACCGGCAGCATTCAAGTACTTCGACACAACAATCGACAGAAAGAGATACACAAGCAC

AAAGGAAGTCCTGGACGCAACACTGATCCACCAGAGCATCACAGGACTGTACGAAACAAGAA

TCGACCTGAGCCAGCTGGGAGGAGACGGAGGAGGAAGCCCGAAGAAGAAGAGAAAGGTCTAG

CTAGCCATCACATTTAAAAGCATCTCAGCCTACCATGAGAATAAGAGAAAGAAAATGAAGAT

CAATAGCTTATTCATCTCTTTTTCTTTTTCGTTGGTGTAAAGCCAACACCCTGTCTAAAAAA

CATAAATTTCTTTAATCATTTTGCCTCTTTTCTCTGTGCTTCAATTAATAAAAAATGGAAAG

AACCTCGAG

SEQ ID NO: 2: Cas9 sequence 2 for transcription.
GGGTCCCGCAGTCGGCGTCCAGCGGCTCTGCTTGTTCGTGTGTGTGTCGTTGCAGGCCTTAT

TCGGATCCATGGATAAGAAGTACTCAATCGGGCTGGATATCGGAACTAATTCCGTGGGTTGG
```

-continued

```
GCAGTGATCACGGATGAATACAAAGTGCCGTCCAAGAAGTTCAAGGTCCTGGGGAACACCGA

TAGACACAGCATCAAGAAAAATCTCATCGGAGCCCTGCTGTTTGACTCCGGCGAAACCGCAG

AAGCGACCCGGCTCAAACGTACCGCGAGGCGACGCTACACCCGGCGGAAGAATCGCATCTGC

TATCTGCAAGAGATCTTTTCGAACGAAATGGCAAAGGTCGACGACAGCTTCTTCCACCGCCT

GGAAGAATCTTTCCTGGTGGAGGAGGACAAGAAGCATGAACGGCATCCTATCTTTGGAAACA

TCGTCGACGAAGTGGCGTACCACGAAAAGTACCCGACCATCTACCATCTGCGGAAGAAGTTG

GTTGACTCAACTGACAAGGCCGACCTCAGATTGATCTACTTGGCCCTCGCCCATATGATCAA

ATTCCGCGGACACTTCCTGATCGAAGGCGATCTGAACCCTGATAACTCCGACGTGGATAAGC

TTTTCATTCAACTGGTGCAGACCTACAACCAACTGTTCGAAGAAAACCCAATCAATGCTAGC

GGCGTCGATGCCAAGGCCATCCTGTCCGCCCGGCTGTCGAAGTCGCGGCGCCTCGAAAACCT

GATCGCACAGCTGCCGGGAGAGAAAAAGAACGGACTTTTCGGCAACTTGATCGCTCTCTCAC

TGGGACTCACTCCCAATTTCAAGTCCAATTTTGACCTGGCCGAGGACGCGAAGCTGCAACTC

TCAAAGGACACCTACGACGACGACTTGGACAATTTGCTGGCACAAATTGGCGATCAGTACGC

GGATCTGTTCCTTGCCGCTAAGAACCTTTCGGACGCAATCTTGCTGTCCGATATCCTGCGCG

TGAACACCGAAATAACCAAAGCGCCGCTTAGCGCCTCGATGATTAAGCGGTACGACGAGCAT

CACCAGGATCTCACGCTGCTCAAAGCGCTCGTGAGACAGCAACTGCCTGAAAAGTACAAGGA

GATCTTCTTCGACCAGTCCAAGAATGGGTACGCAGGGTACATCGATGGAGGCGCTAGCCAGG

AAGAGTTCTATAAGTTCATCAAGCCAATCCTGGAAAAGATGGACGGAACCGAAGAACTGCTG

GTCAAGCTGAACAGGGAGGATCTGCTCCGGAAACAGAGAACCTTTGACAACGGATCCATTCC

CCACCAGATCCATCTGGGTGAGCTGCACGCCATCTTGCGGCGCCAGGAGGACTTTTACCCAT

TCCTCAAGGACAACCGGGAAAAGATCGAGAAAATTCTGACGTTCCGCATCCCGTATTACGTG

GGCCCACTGGCGCGCGGCAATTCGCGCTTCGCGTGGATGACTAGAAAATCAGAGGAAACCAT

CACTCCTTGGAATTTCGAGGAAGTTGTGGATAAGGGAGCTTCGGCACAAAGCTTCATCGAAC

GAATGACCAACTTCGACAAGAATCTCCCAAACGAGAAGGTGCTTCCTAAGCACAGCCTCCTT

TACGAATACTTCACTGTCTACAACGAACTGACTAAAGTGAAATACGTTACTGAAGGAATGAG

GAAGCCGGCCTTTCTGTCCGGAGAACAGAAGAAAGCAATTGTCGATCTGCTGTTCAAGACCA

ACCGCAAGGTGACCGTCAAGCAGCTTAAAGAGGACTACTTCAAGAAGATCGAGTGTTTCGAC

TCAGTGGAAATCAGCGGGGTGGAGGACAGATTCAACGCTTCGCTGGGAACCTATCATGATCT

CCTGAAGATCATCAAGGACAAGGACTTCCTTGACAACGAGGAGAACGAGGACATCCTGGAAG

ATATCGTCCTGACCTTGACCCTTTTCGAGGATCGCGAGATGATCGAGGAGAGGCTTAAGACC

TACGCTCATCTCTTCGACGATAAGGTCATGAAACAACTCAAGCGCCGCCGGTACACTGGTTG

GGGCCGCCTCTCCCGCAAGCTGATCAACGGTATTCGCGATAAACAGAGCGGTAAAACTATCC

TGGATTTCCTCAAATCGGATGGCTTCGCTAATCGTAACTTCATGCAATTGATCCACGACGAC

AGCCTGACCTTTAAGGAGGACATCCAAAAAGCACAAGTGTCCGGACAGGGAGACTCACTCCA

TGAACACATCGCGAATCTGGCCGGTTCGCCGGCGATTAAGAAGGGAATTCTGCAAACTGTGA

AGGTGGTCGACGAGCTGGTGAAGGTCATGGGACGGCACAAACCGGAGAATATCGTGATTGAA

ATGGCCCGAGAAAACCAGACTACCCAGAAGGGCCAGAAAAACTCCCGCGAAAGGATGAAGCG

GATCGAAGAAGGAATCAAGGAGCTGGGCAGCCAGATCCTGAAAGAGCACCCGGTGGAAAACA

CGCAGCTGCAGAACGAGAAGCTCTACCTGTACTATTTGCAAAATGGACGGGACATGTACGTG

GACCAAGAGCTGGACATCAATCGGTTGTCTGATTACGACGTGGACCACATCGTTCCACAGTC

CTTTCTGAAGGATGACTCGATCGATAACAAGGTGTTGACTCGCAGCGACAAGAACAGAGGGA
```

-continued

```
AGTCAGATAATGTGCCATCGGAGGAGGTCGTGAAGAAGATGAAGAATTACTGGCGGCAGCTC

CTGAATGCGAAGCTGATTACCCAGAGAAAGTTTGACAATCTCACTAAAGCCGAGCGCGGCGG

ACTCTCAGAGCTGGATAAGGCTGGATTCATCAAACGGCAGCTGGTCGAGACTCGGCAGATTA

CCAAGCACGTGGCGCAGATCTTGGACTCCCGCATGAACACTAAATACGACGAGAACGATAAG

CTCATCCGGGAAGTGAAGGTGATTACCCTGAAAAGCAAACTTGTGTCGGACTTTCGGAAGGA

CTTTCAGTTTTACAAAGTGAGAGAAATCAACAACTACCATCACGCGCATGACGCATACCTCA

ACGCTGTGGTCGGTACCGCCCTGATCAAAAAGTACCCTAAACTTGAATCGGAGTTTGTGTAC

GGAGACTACAAGGTCTACGACGTGAGGAAGATGATAGCCAAGTCCGAACAGGAAATCGGGAA

AGCAACTGCGAAATACTTCTTTTACTCAAACATCATGAACTTTTTCAAGACTGAAATTACGC

TGGCCAATGGAGAAATCAGGAAGAGGCCACTGATCGAAACTAACGGAGAAACGGGCGAAATC

GTGTGGGACAAGGGCAGGGACTTCGCAACTGTTCGCAAAGTGCTCTCTATGCCGCAAGTCAA

TATTGTGAAGAAAACCGAAGTGCAAACCGGCGGATTTTCAAAGGAATCGATCCTCCCAAAGA

GAAATAGCGACAAGCTCATTGCACGCAAGAAAGACTGGGACCCGAAGAAGTACGGAGGATTC

GATTCGCCGACTGTCGCATACTCCGTCCTCGTGGTGGCCAAGGTGGAGAAGGGAAAGAGCAA

AAAGCTCAAATCCGTCAAAGAGCTGCTGGGGATTACCATCATGGAACGATCCTCGTTCGAGA

AGAACCCGATTGATTTCCTCGAGGCGAAGGGTTACAAGGAGGTGAAGAAGGATCTGATCATC

AAACTCCCCAAGTACTCACTGTTCGAACTGGAAAATGGTCGGAAGCGCATGCTGGCTTCGGC

CGGAGAACTCCAAAAAGGAAATGAGCTGGCCTTGCCTAGCAAGTACGTCAACTTCCTCTATC

TTGCTTCGCACTACGAAAAACTCAAAGGGTCACCGGAAGATAACGAACAGAAGCAGCTTTTC

GTGGAGCAGCACAAGCATTATCTGGATGAAATCATCGAACAAATCTCCGAGTTTTCAAAGCG

CGTGATCCTCGCCGACGCCAACCTCGACAAAGTCCTGTCGGCCTACAATAAGCATAGAGATA

AGCCGATCAGAGAACAGGCCGAGAACATTATCCACTTGTTCACCCTGACTAACCTGGGAGCC

CCAGCCGCCTTCAAGTACTTCGATACTACTATCGATCGCAAAAGATACACGTCCACCAAGGA

AGTTCTGGACGCGACCCTGATCCACCAAAGCATCACTGGACTCTACGAAACTAGGATCGATC

TGTCGCAGCTGGGTGGCGATGGCGGTGGATCTCCGAAAAAGAAGAGAAAGGTGTAATGAGCT

AGCCATCACATTTAAAAGCATCTCAGCCTACCATGAGAATAAGAGAAAGAAAATGAAGATCA

ATAGCTTATTCATCTCTTTTTCTTTTTCGTTGGTGTAAAGCCAACACCCTGTCTAAAAAACA

TAAATTTCTTTAATCATTTTGCCTCTTTTCTCTGTGCTTCAATTAATAAAAAATGGAAAGAA

CCTCGAG
```

Human TTR Guide Design and Human TTR with Cynomolgus Monkey Homology Guide Design Initial guide selection was performed in silico using a human reference genome (e.g., hg38) and user defined genomic regions of interest (e.g., TTR protein coding exons), for identifying PAMs in the regions of interest. For each identified PAM, analyses were performed and statistics reported. gRNA molecules were further selected and rank ordered based on a number of criteria (e.g., GC content, predicted on-target activity, and potential off-target activity). A total of 68 guide RNAs were designed toward TTR (ENSG00000118271) targeting the protein coding regions within Exon 1, 2, 3 and 4. Of the total 68 guides, 33 were 100% homologous in cynomolgus monkey ("cyno"). In addition, for 10 of the human TTR guides which were not perfectly homologous in cyno, "surrogate" guides were designed and made in parallel to perfectly match the corresponding cyno target sequence. These "surrogate" or "tool" guides may be screened in cyno, e.g., to approximate the activity and function of the homologous human guide sequence. Guide sequences and corresponding genomic coordinates are provided (Table 1). All of the guide RNAs were made as dual guide RNAs, and a subset of the guide sequences were made as modified single guide RNA (Table 2). Guide ID alignment across dual guide RNA (dgRNA) IDs, modified single guide RNA (sgRNA) IDs, the number of mismatches to the cyno genome as well as the cyno exact matched IDs are provided (Table 3). Where dgRNAs are used in the experiments detailed throughout the Examples, SEQ ID NO: 270 was used.

Cas9 mRNA and Guide RNA Delivery In Vitro

HEK293 Cas9 cell line. The human embryonic kidney adenocarcinoma cell line HEK293 constitutively expressing Spy Cas9 ("HEK293_Cas9") was cultured in DMEM media supplemented with 10% fetal bovine serum and 500 μg/ml G418. Cells were plated at a density of 10,000 cells/well in a 96-well plate 24 hours prior to transfection. Cells were transfected with Lipofectamine RNAiMAX (ThermoFisher, Cat. 13778150) per the manufacturer's protocol. Cells were transfected with a lipoplex containing individual crRNA (25 nM), trRNA (25 nM), Lipofectamine RNAiMAX (0.3 µL/well) and OptiMem.

HUH7 cell line. The human hepatocellular carcinoma cell line HUH7 (Japanese Collection of Research Bioresources Cell Bank, Cat. JCRB0403) was cultured in DMEM media supplemented with 10% fetal bovine serum. Cells were plated on at a density of 15,000 cells/well in a 96-well plate 20 hours prior to transfection. Cells were transfected with Lipofectamine MessengerMAX (ThermoFisher, Cat. LMRNA003) per the manufacturer's protocol. Cells were sequentially transfected with a lipoplex containing Spy Cas9 mRNA (100 ng), MessengerMAX (0.3 µL/well) and OptiMem followed by a separate lipoplex containing individual crRNA (25 nM), tracer RNA (25 nM), MessengerMAX (0.3 µL/well) and OptiMem.

HepG2 cell line. The human hepatocellular carcinoma cell line HepG2 (American Type Culture Collection, Cat. HB-8065) was cultured in DMEM media supplemented with 10% fetal bovine serum. Cells were counted and plated on Bio-coat collagen I coated 96-well plates (ThermoFisher, Cat. 877272) at a density of 10,000 cells/well in a 96-well plate 24 hours prior to transfection. Cells were transfected with Lipofectamine 2000 (ThermoFisher, Cat. 11668019) per the manufacturer's protocol. Cells were sequentially transfected with lipoplex containing Spy Cas9 mRNA (100 ng), Lipofectamine 2000 (0.2 µL/well) and OptiMem followed by a separate lipoplex containing individual crRNA (25 nM), tracer RNA (25 nM), Lipofectamine 2000 (0.2 µL/well) and OptiMem.

Primary liver hepatocytes. Primary human liver hepatocytes (PHH) and primary cynomolgus liver hepatocytes (PCH) (Gibco) were cultured per the manufacturer's protocol (Invitrogen, protocol 11.28.2012). In brief, the cells were thawed and resuspended in hepatocyte thawing medium with supplements (Gibco, Cat. CM7000) followed by centrifugation at 100 g for 10 minutes for human and 80 g for 4 minutes for cyno. The supernatant was discarded and the pelleted cells resuspended in hepatocyte plating medium plus supplement pack (Invitrogen, Cat. A1217601 and CM3000). Cells were counted and plated on Bio-coat collagen I coated 96-well plates (ThermoFisher, Cat. 877272) at a density of 33,000 cells/well for human or 60,000 cells/well for cyno (or 65,000 cells/well when assaying effects on TTR protein, described further below). Plated cells were allowed to settle and adhere for 6 or 24 hours in a tissue culture incubator at 37° C. and 5% $CO_2$ atmosphere. After incubation cells were checked for monolayer formation and media was replaced with hepatocyte culture medium with serum-free supplement pack (Invitrogen, Cat. A1217601 and CM4000).

Lipofectamine RNAiMax (ThermoFisher, Cat. 13778150) based transfections were conducted as per the manufacturer's protocol. Cells were sequentially transfected with a lipoplex containing Spy Cas9 mRNA (100 ng), Lipofectamine RNAiMax (0.4 µL/well) and OptiMem followed by a separate lipoplex containing crRNA (25 nM) and tracer RNA (25 nM) or sgRNA (25 nM), Lipofectamine RNAiMax (0.4 µL/well) and OptiMem.

Ribonucleotide formation was performed prior to electroporation or transfection of Spy Cas9 protein loaded with guide RNAs (RNPs) onto cells. For dual guide (dgRNAs), individual crRNA and trRNA was pre-annealed by mixing equivalent amounts of reagent and incubating at 95° C. for 2 min and cooling to room temperature. Single guide (sgRNAs) were boiled at 95° C. for 2 min and cooling to room temperature. The boiled dgRNA or sgRNA was incubated with Spy Cas9 protein in Optimem for 10 minutes at room temperature to form a ribonucleoprotein (RNP) complex.

For RNP electroporation into primary human and cyno hepatocytes, the cells are thawed and resuspended in Lonza electroporation Primary Cell P3 buffer at a concentration of 2500 cells per µL for human hepatocytes and 3500 cells per µL for cyno hepatocytes. A volume of 20 µL of resuspended cells and 5 µL of RNP are mixed together per guide. 20 µL of the mixture is placed into a Lonza electroporation plate. The cells were electroporated using the Lonza nucleofector with the preset protocol EX-147. Post electroporation, the cells are transferred into a Biocoat plate containing pre-warmed maintenance media and placed in a tissue culture incubator at 37° C. and 5% $CO_2$.

For RNP lipoplex transfections, cells were transfected with Lipofectamine RNAiMAX (ThermoFisher, Cat. 13778150) per the manufacturer's protocol. Cells were transfected with an RNP containing Spy Cas9 (10 nM), individual guide (10 nM), tracer RNA (10 nM), Lipofectamine RNAiMAX (1.0 µL/well) and OptiMem. RNP formation was performed as described above.

LNPs were formed either by microfluidic mixing of the lipid and RNA solutions using a Precision Nanosystems NanoAssemblr™ Benchtop Instrument, per the manufacturer's protocol, or cross-flow mixing.

LNP Formulation—NanoAssemblr

In general, the lipid nanoparticle components were dissolved in 100% ethanol with the lipid component of various molar ratios. The RNA cargos were dissolved in 25 mM citrate, 100 mM NaCl, pH 5.0, resulting in a concentration of RNA cargo of approximately 0.45 mg/mL. The LNPs were formulated with a lipid amine to RNA phosphate (N:P) molar ratio of about 4.5 or about 6, with the ratio of mRNA to gRNA at 1:1 by weight.

The LNPs were formed by microfluidic mixing of the lipid and RNA solutions using a Precision Nanosystems NanoAssemblr™ Benchtop Instrument, according to the manufacturer's protocol. A 2:1 ratio of aqueous to organic solvent was maintained during mixing using differential flow rates. After mixing, the LNPs were collected, diluted in water (approximately 1:1 v/v), held for 1 hour at room temperature, and further diluted with water (approximately 1:1 v/v) before final buffer exchange. The final buffer exchange into 50 mM Tris, 45 mM NaCl, 5% (w/v) sucrose, pH 7.5 (TSS) was completed with PD-10 desalting columns (GE). If required, formulations were concentrated by centrifugation with Amicon 100 kDa centrifugal filters (Millipore). The resulting mixture was then filtered using a 0.2 µm sterile filter. The final LNP was stored at −80° C. until further use.

LNP Formulation—Cross-Flow

Figure 2:
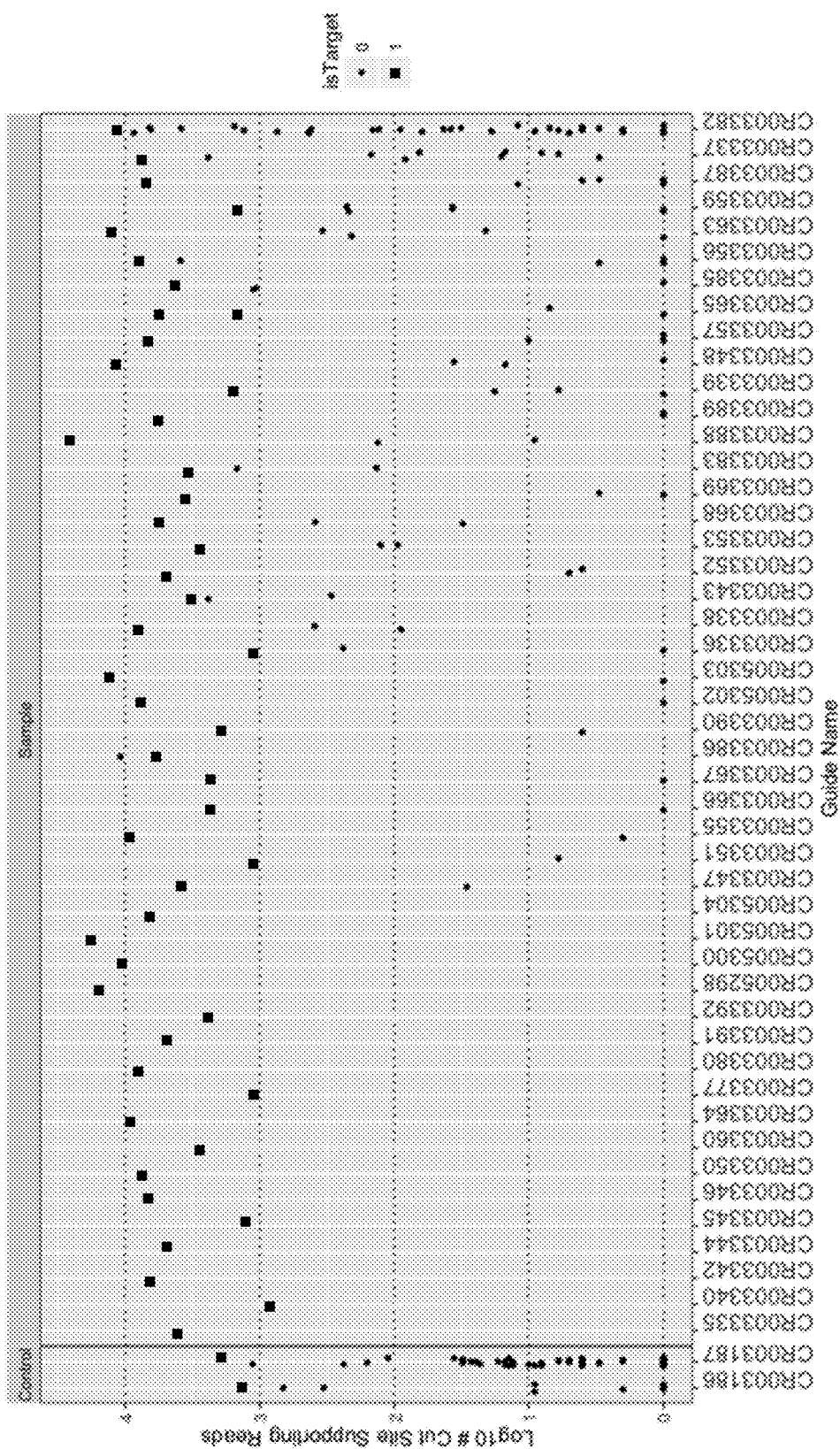
FIG. 2 shows off-target analysis in HEK293_Cas9 cells of certain dual guide RNAs targeting TTR. The on-target site is designated by a filled square for each dual guide RNA tested, whereas closed circles represent a potential off-target site.
Figure 3:
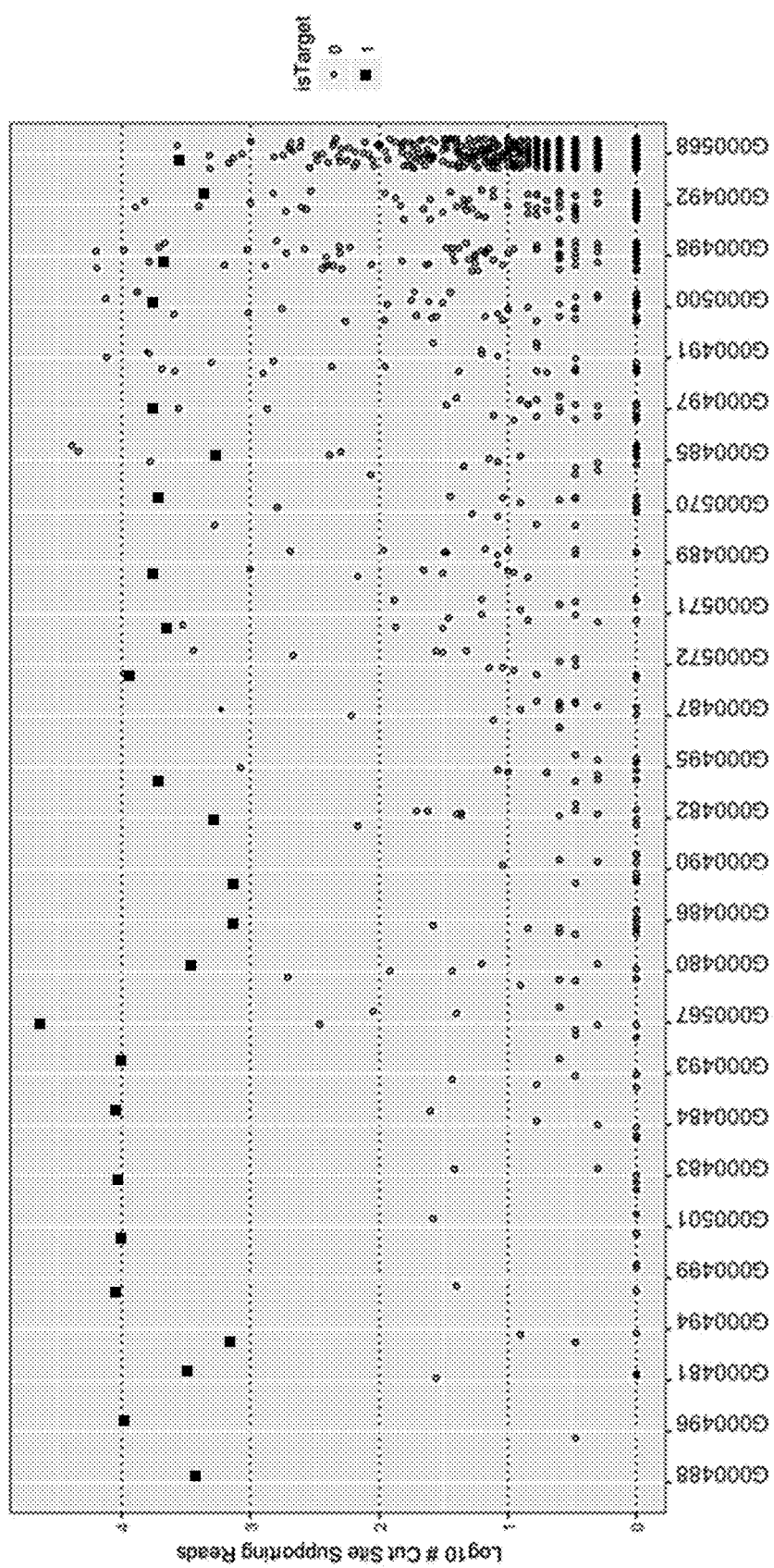
FIG. 3 shows off-target analysis in HEK_Cas9 cells of certain single guide RNAs targeting TTR. The on-target site is designated by a filled square for each single guide RNA tested, whereas open circles represent a potential off-target site.
Figure 4:
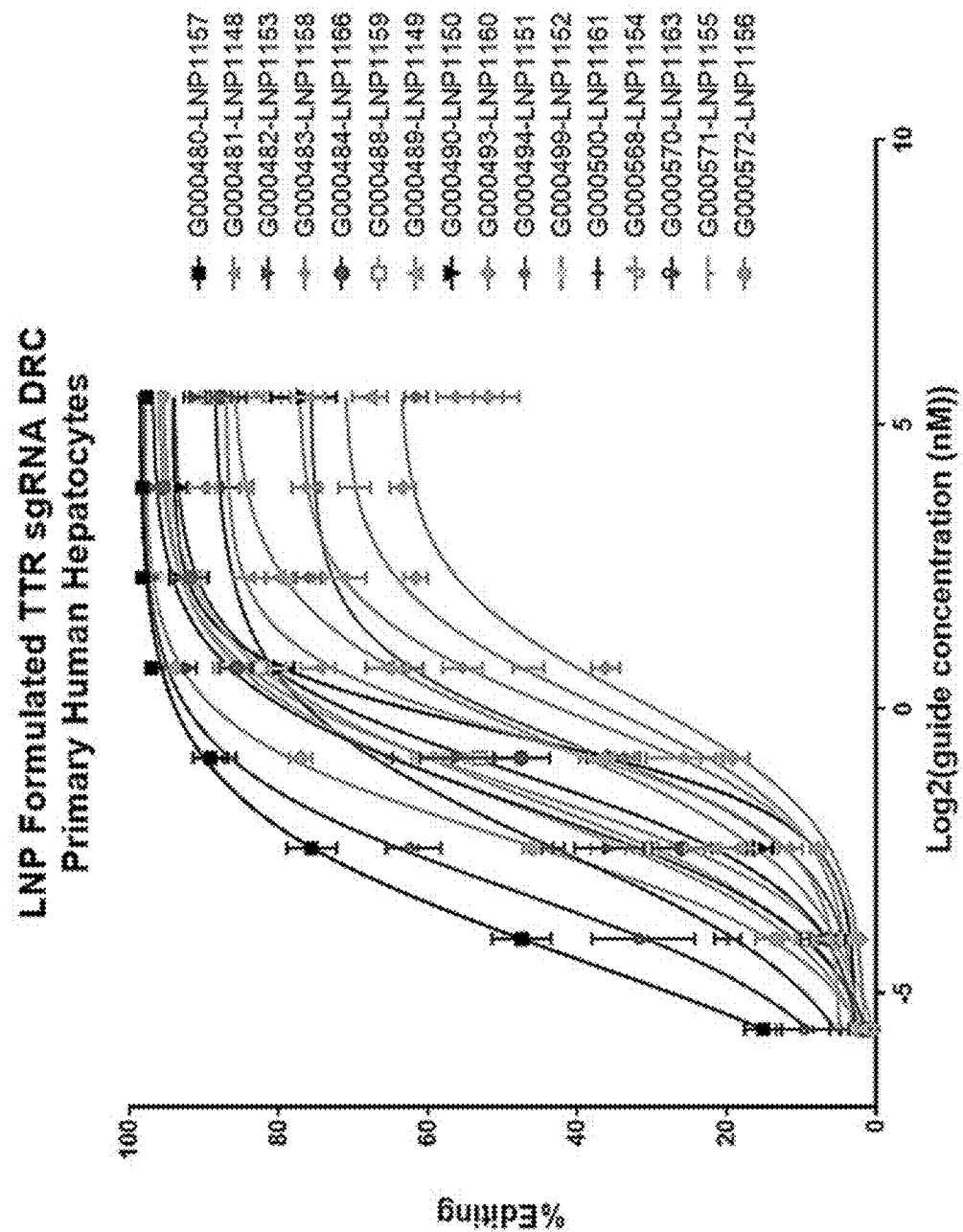
FIG. 4 shows dose response curves of lipid nanoparticle formulated human TTR specific sgRNAs on primary human hepatocytes.
Figure 5:
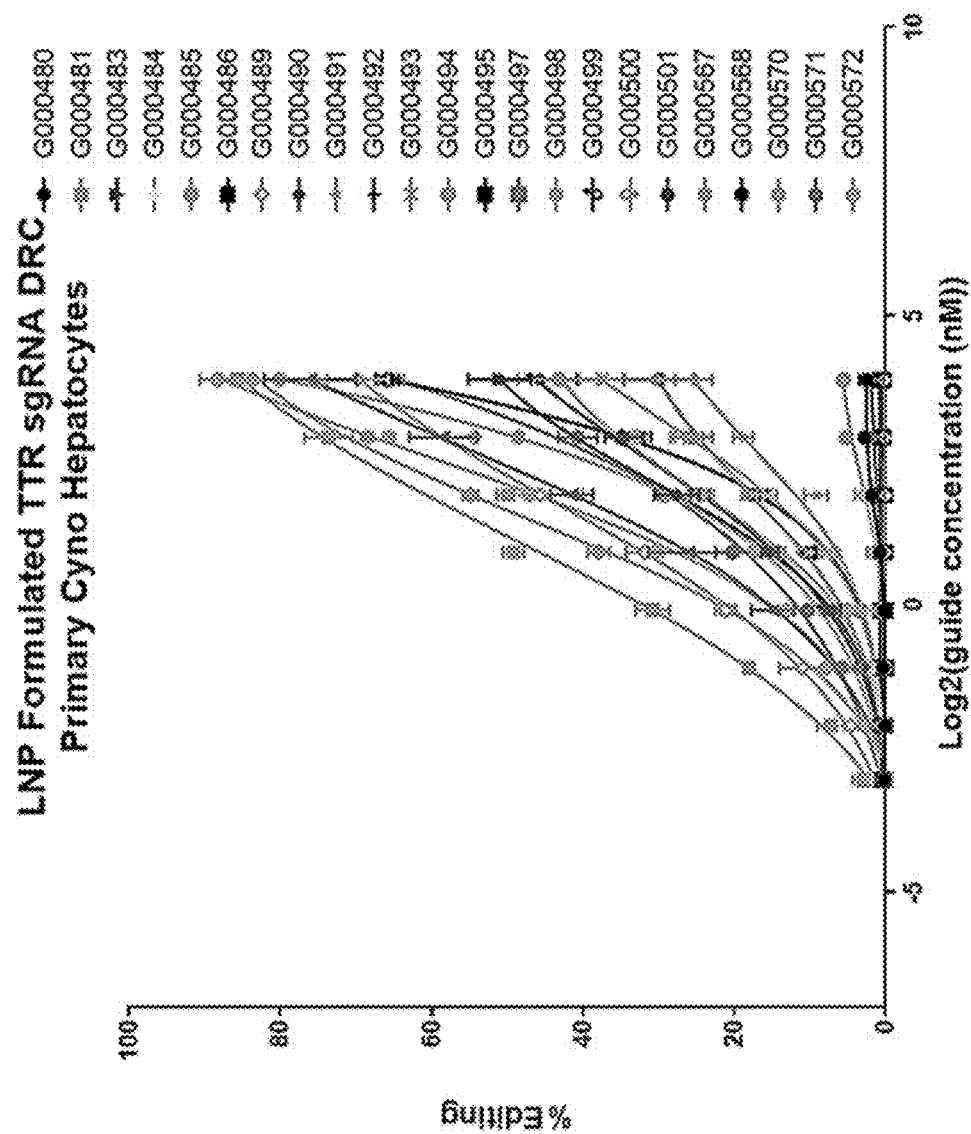
FIG. 5 shows dose response curves of lipid nanoparticle formulated human TTR specific sgRNAs on primary cyno hepatocytes.
Figure 6:
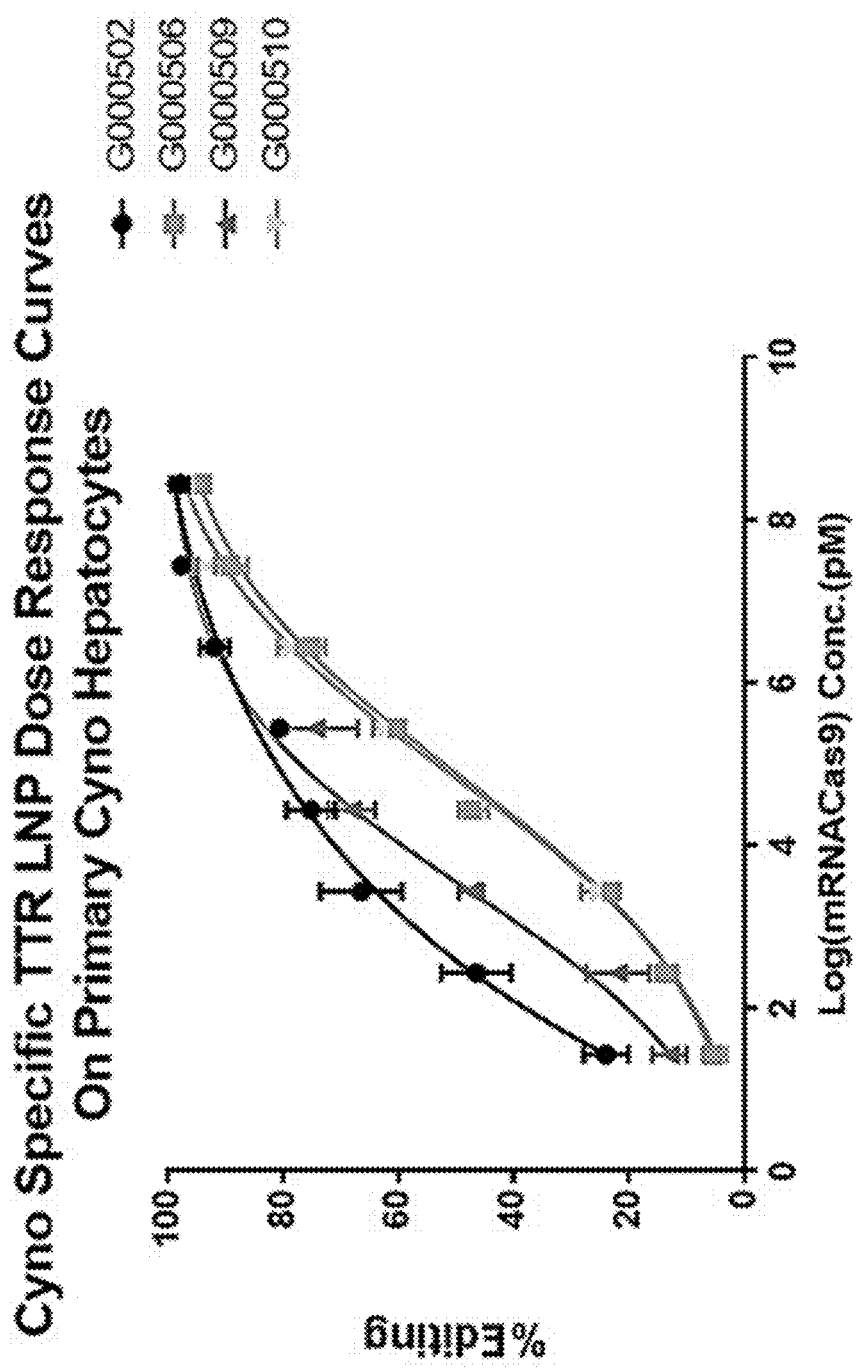
FIG. 6 shows dose response curves of lipid nanoparticle formulated cyno TTR specific sgRNAs on primary cyno hepatocytes.
Figure 7:
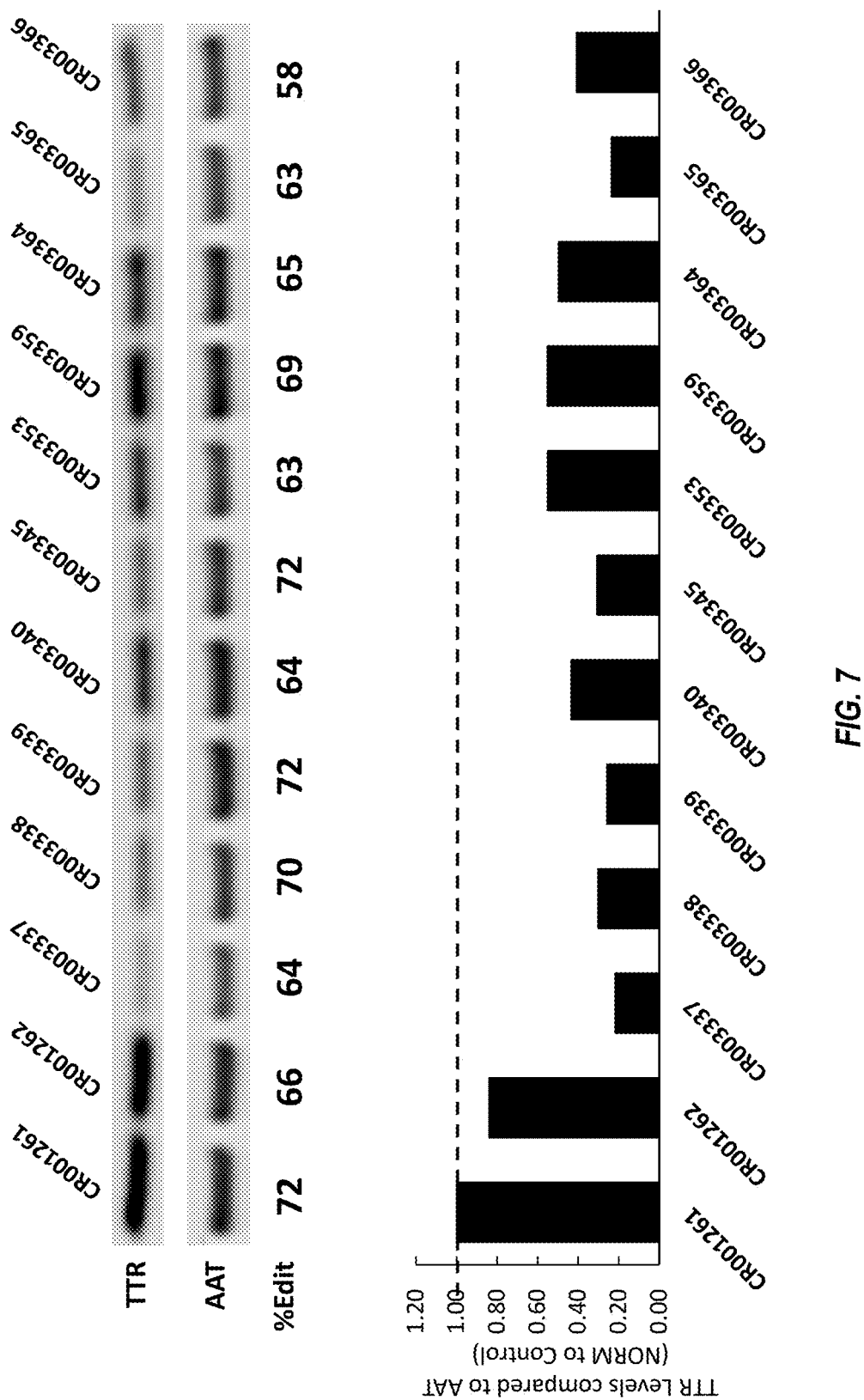
FIG. 7 shows percent editing (% edit) of TTR and reduction of secreted TTR following administration of the guide in HUH7 cells sequences provided on the x-axis. The values are normalized to the amount of alpha-1-antitrypsin (AAT) protein.

For LNPs prepared using the cross-flow technique, the LNPs were formed by impinging jet mixing of the lipid in ethanol with two volumes of RNA solutions and one volume of water. The lipid in ethanol is mixed through a mixing cross with the two volumes of RNA solution. A fourth stream of water is mixed with the outlet stream of the cross through an inline tee. (See WO2016010840 FIG. 2.) The LNPs were held for 1 hour at room temperature, and further diluted with water (approximately 1:1 v/v). Diluted LNPs were concentrated using tangential flow filtration on a flat sheet cartridge (Sartorius, 100 kD MWCO) and then buffer exchanged by diafiltration into 50 mM Tris, 45 mM NaCl, 5% (w/v) sucrose, pH 7.5 (TSS). Alternatively, the final buffer exchange into TSS was completed with PD-10 desalting columns (GE). If required, formulations were concentrated by centrifugation with Amicon 100 kDa centrifugal filters (Millipore). The resulting mixture was then filtered using a 0.2 μm sterile filter. The final LNP was stored at 4° C. or −80° C. until further use.

Formulation Analytics

Dynamic Light Scattering ("DLS") is used to characterize the polydispersity index ("pdi") and size of the LNPs of the present disclosure. DLS measures the scattering of light that results from subjecting a sample to a light source. PDI, as determined from DLS measurements, represents the distribution of particle size (around the mean particle size) in a population, with a perfectly uniform population having a PDI of zero. Average particle size and polydispersity are measured by dynamic light scattering (DLS) using a Malvern Zetasizer DLS instrument. LNP samples were diluted 30× in PBS prior to being measured by DLS. Z-average diameter which is an intensity based measurement of average particle size was reported along with number average diameter and pdi. A Malvern Zetasizer instrument is also used to measure the zeta potential of the LNP. Samples are diluted 1:17 (50 uL into 800 uL) in 0.1×PBS, pH 7.4 prior to measurement.

A fluorescence-based assay (Ribogreen®, ThermoFisher Scientific) is used to determine total RNA concentration and free RNA. Encapsulation efficiency is calculated as (Total RNA−Free RNA)/Total RNA. LNP samples are diluted appropriately with 1×TE buffer containing 0.2% Triton-X 100 to determine total RNA or 1×TE buffer to determine free RNA. Standard curves are prepared by utilizing the starting RNA solution used to make the formulations and diluted in 1×TE buffer+/−0.2% Triton-X 100. Diluted RiboGreen® dye (according to the manufacturer's instructions) is then added to each of the standards and samples and allowed to incubate for approximately 10 minutes at room temperature, in the absence of light. A SpectraMax M5 Microplate Reader (Molecular Devices) is used to read the samples with excitation, auto cutoff and emission wavelengths set to 488 nm, 515 nm, and 525 nm respectively. Total RNA and free RNA are determined from the appropriate standard curves.

Encapsulation efficiency is calculated as (Total RNA−Free RNA)/Total RNA. The same procedure may be used for determining the encapsulation efficiency of a DNA-based cargo component. For single-strand DNA Oligreen Dye may be used, and for double-strand DNA, Picogreen Dye.

Typically, when preparing LNPs, encapsulation was >80%, particle size was <120 nm, and pdi was <0.2.

LNP Delivery In Vivo

Unless otherwise noted, CD-1 female mice, ranging from 6-10 weeks of age were used in each study. Animals were weighed and grouped according to body weight for preparing dosing solutions based on group average weight. LNPs were dosed via the lateral tail vein in a volume of 0.2 mL per animal (approximately 10 mL per kilogram body weight). The animals were observed at approximately 6 hours post dose for adverse effects. Body weight was measured at twenty-four hours post-administration, and animals were euthanized at various time points by exsanguination via cardiac puncture under isoflourane anesthesia. Blood was collected into serum separator tubes or into tubes containing buffered sodium citrate for plasma as described herein. For studies involving in vivo editing, liver tissue was collected from the median lobe or from three independent lobes (e.g., the right median, left median, and left lateral lobes) from each animal for DNA extraction and analysis.

Transthyretin (TTR) ELISA Analysis Used in Animal Studies

Blood was collected and the serum was isolated as indicated. The total mouse TTR serum levels were determined using a Mouse Prealbumin (Transthyretin) ELISA Kit (Aviva Systems Biology, Cat. OKIA00111); rat TTR serum levels were measured using a rat specific ELISA kit (Aviva Systems Biology catalog number OKIA00159); human TTR serum levels were measured using a human specific ELISA kit (Aviva Systems Biology catalog number OKIA00081); each according to manufacture's protocol. Briefly, sera were serial diluted with kit sample diluent to a final dilution of 10,000-fold, or 5,000-fold when measuring human TTR in mouse sera. 100 ul of the prepared standard curve or diluted serum samples were added to the ELISA plate, incubated for 30 minutes at room temperature then washed 3 times with provided wash buffer. 100 uL of detection antibody was then added to each well and incubated for 20 minutes at room temperature followed by 3 washes. 100 uL of substrate is added then incubated for 10 minutes at room temperature before the addition of 100 uL stop solution. The absorbance of the contents was measured on the Spectramax M5 plate reader with analysis using SoftmaxPro version 7.0 software. Serum TTR levels were quantitated off the standard curve using 4 parameter logistic fit and expressed as ug/mL of serum or percent knockdown relative control (vehicle treated) animals.

Genomic DNA Isolation

Transfected cells were harvested post-transfection at 24, 48, or 72 hours. The genomic DNA was extracted from each well of a 96-well plate using 50 μL/well BuccalAmp DNA Extraction solution (Epicentre, Cat. QE09050) per manufacturer's protocol. All DNA samples were subjected to PCR and subsequent NGS analyses, as described herein.

Next-Generation Sequencing ("NGS") Analysis

To quantitatively determine the efficiency of editing at the target location in the genome, sequencing was utilized to identify the presence of insertions and deletions introduced by gene editing.

Primers were designed around the target site within the gene of interest (e.g. TTR), and the genomic area of interest was amplified.

Additional PCR was performed per the manufacturer's protocols (Illumina) to add chemistry for sequencing. The amplicons were sequenced on an Illumina MiSeq instrument. The reads were aligned to a reference genome (e.g., the human reference genome (hg38), the cynomologus reference genome (mf5), the rat reference genome (rn6), or the mouse reference genome (mm10)) after eliminating those having low quality scores. The resulting files containing the reads were mapped to the reference genome (BAM files), where reads that overlapped the target region of interest were selected and the number of wild type reads versus the number of reads which contain an insertion, substitution, or deletion was calculated.

The editing percentage (e.g., the "editing efficiency" or "percent editing" or "indel frequency") is defined as the total number of sequence reads with insertions/deletions ("indels") or substitutions over the total number of sequence reads, including wild type.

Analysis of Secreted Transthyretin ("TTR") Protein by Western Blot

Secreted levels of TTR protein in media were determined using western blotting methods. HepG2 cells were transfected as previously described with select guides from Table 1. Media changes were performed every 3 days post transfection. Six days post-transfection, the media was removed, and cells were washed once with media that did not contain fetal bovine serum (FBS). Media without serum was added to the cells and incubated at 37° C. After 4 hrs the media was removed and centrifuged to pellet any debris; cell number for each well was estimated based on the values obtained from a CTG assay on remaining cells and comparison to the plate average. After centrifugation, the media was transferred to a new plate and stored at −20° C. An acetone precipitation of the media was performed to precipitate any protein that had been secreted into the media. Four volumes of ice cold acetone were added to one volume of media. The solution was mixed well and kept at −20° C. for 90 min. The acetone:media mixture was centrifuged at 15,000×g and 4° C. for 15 min. The supernatant was discarded and the retained pellet was air dried to eliminate any residual acetone. The pellet was resuspended in 154 RIPA buffer (Boston Bio Products, Cat. BP-115) plus freshly added protease inhibitor mixture consisting of complete protease inhibitor cocktail (Sigma, Cat. 11697498001) and 1 mM DTT. Lysates were mixed with Laemmli buffer and denatured at 95° C. for 10 minutes. Western blots were run using the NuPage system on 12% Bis-Tris gels (ThermoFisher) per the manufacturer's protocol followed by wet transfer onto 0.45 μm nitrocellulose membrane (Bio-Rad, Cat. 1620115). Blots were blocked using 5% Dry Milk in TBS for 30 minutes on a lab rocker at room temperature. Blots were rinsed with TBST and probed with rabbit α-TTR monoclonal antibody (Abcam, Cat. Ab75815) at 1:1000 in TBST. Alpha-1 antitrypsin was used as a loading control (Sigma, Cat. HPA001292) at 1:1000 in TBST and incubated simultaneously with the TTR primary antibody. Blots were sealed in a bag and kept overnight at 4° C. on a lab rocker. After incubation, blots were rinsed 3 times for 5 min each in TBST and probed with secondary antibodies to Rabbit (ThermoFisher, Cat. PISA535571) at 1:25,000 in TBST for 30 min at room temperature. After incubation, blots were rinsed 3 times for 5 min each in TBST and 2 times with PBS. Blots were visualized and analyzed using a Licor Odyssey system.

Analysis of Intracellular TTR by Western Blot

The hepatocellular carcinoma cell line, HUH7, was transfected as previously described with select guides from Table 1. Six-days post-transfection, the media was removed and the cells were lysed with 50 μL/well RIPA buffer (Boston Bio Products, Cat. BP-115) plus freshly added protease inhibitor mixture consisting of complete protease inhibitor cocktail (Sigma, Cat. 11697498001), 1 mM DTT, and 250 U/ml Benzonase (EMD Millipore, Cat. 71206-3). Cells were kept on ice for 30 minutes at which time NaCl (1 M final concentration) was added. Cell lysates were thoroughly mixed and retained on ice for 30 minutes. The whole cell extracts ("WCE") were transferred to a PCR plate and centrifuged to pellet debris. A Bradford assay (Bio-Rad, Cat. 500-0001) was used to assess protein content of the lysates. The Bradford assay procedure was completed per the manufacturer's protocol. Extracts were stored at minus 20° C. prior to use. Western blots were performed to assess intracellular TTR protein levels. Lysates were mixed with Laemmli buffer and denatured at 95° C. for 10 min. Western blots were run using the NuPage system on 12% Bis-Tris gels (ThermoFisher) per the manufacturer's protocol followed by wet transfer onto 0.45 μm nitrocellulose membrane (Bio-Rad, Cat. 1620115). After transfer membranes were rinsed thoroughly with water and stained with Ponceau S solution (Boston Bio Products, Cat. ST-180) to confirm complete and even transfer. Blots were blocked using 5% Dry Milk in TBS for 30 minutes on a lab rocker at room temperature. Blots were rinsed with TBST and probed with rabbit α-TTR monoclonal antibody (Abcam, Cat. Ab75815) at 1:1000 in TBST. β-actin was used as a loading control (ThermoFisher, Cat. AM4302) at 1:2500 in TBST and incubated simultaneously with the TTR primary antibody. Blots were sealed in a bag and kept overnight at 4° C. on a lab rocker. After incubation, blots were rinsed 3 times for 5 minutes each in TBST and probed with secondary antibodies to Mouse and Rabbit (ThermoFisher, Cat. PI35518 and PISA535571) at 1:25,000 each in TBST for 30 min at room temperature. After incubation, blots were rinsed 3 times for 5 min each in TBST and 2 times with PBS. Blots were visualized and analyzed using a Licor Odyssey system.

Example 2. Screening of dgRNA Sequences

Cross Screening of TTR dgRNAs in Multiple Cell Types

Guides in dgRNA format targeting human TTR and the cynomologus matched sequences were delivered to HEK293 Cas9, HUH7 and HepG2 cell lines, as well as primary human hepatocytes and primary cynomolgus monkey hepatocytes as described in Example 1. Percent editing was determined for crRNAs comprising each guide sequence across each cell type and the guide sequences were then rank ordered based on highest % edit. The screening data for the guide sequences in Table 1 in all five cell lines are listed below (Table 4 through 11).

Table 4 shows the average and standard deviation for % Edit, % Insertion (Ins), and % Deletion (Del) for the TTR crRNAs in the human kidney adenocarcinoma cell line, HEK293 Cas9, which constitutively over expresses Spy Cas9 protein.

TABLE 4

TTR editing data in Hek_Cas9 cells transfected with dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003335 | 26.59 | 4.73 | 4.73 | 0.65 | 21.87 | 4.09 |
| CR003336 | 29.09 | 4.57 | 3.31 | 0.24 | 25.78 | 4.32 |
| CR003337 | 42.72 | 1.72 | 5.24 | 1.62 | 37.48 | 0.70 |
| CR003338 | 52.42 | 3.28 | 4.76 | 0.03 | 47.66 | 3.30 |
| CR003339 | 56.37 | 4.13 | 49.39 | 3.23 | 6.98 | 0.91 |
| CR003340 | 42.38 | 8.43 | 27.88 | 4.31 | 14.50 | 4.13 |
| CR003341 | 20.04 | 5.26 | 6.73 | 1.86 | 13.31 | 3.41 |
| CR003342 | 36.57 | 5.80 | 1.19 | 0.22 | 35.38 | 5.59 |
| CR003343 | 24.36 | 1.51 | 4.82 | 0.43 | 19.53 | 1.39 |
| CR003344 | 33.87 | 2.93 | 4.32 | 0.58 | 29.54 | 2.37 |
| CR003345 | 35.02 | 7.05 | 19.00 | 3.58 | 16.01 | 3.48 |
| CR003346 | 48.33 | 5.81 | 33.03 | 3.12 | 15.30 | 2.72 |
| CR003347 | 21.45 | 5.57 | 0.95 | 0.33 | 20.50 | 5.26 |
| CR003348 | 35.53 | 5.81 | 22.32 | 3.79 | 13.21 | 2.03 |
| CR003349 | 13.19 | 4.46 | 8.03 | 2.81 | 5.16 | 1.66 |
| CR003350 | 22.31 | 4.25 | 5.54 | 0.74 | 16.77 | 3.51 |
| CR003351 | 49.67 | 3.77 | 28.42 | 1.69 | 21.24 | 2.22 |
| CR003352 | 27.90 | 7.55 | 4.91 | 1.35 | 22.99 | 6.26 |
| CR003353 | 25.03 | 5.16 | 3.71 | 0.75 | 21.32 | 4.42 |
| CR003354 | 18.46 | 2.02 | 2.56 | 0.21 | 15.90 | 1.89 |
| CR003355 | 30.60 | 2.53 | 6.99 | 0.80 | 23.61 | 1.75 |
| CR003356 | 32.21 | 4.71 | 10.03 | 1.39 | 22.19 | 3.36 |
| CR003357 | 43.23 | 6.71 | 5.38 | 0.87 | 37.85 | 5.88 |
| CR003358 | 5.44 | 0.86 | 1.29 | 0.16 | 4.14 | 0.84 |
| CR003359 | 37.75 | 7.50 | 18.35 | 3.73 | 19.40 | 3.78 |
| CR003360 | 22.68 | 3.16 | 2.70 | 0.56 | 19.98 | 2.60 |
| CR003361 | 34.45 | 8.97 | 8.66 | 1.66 | 25.78 | 7.32 |
| CR003362 | 9.90 | 2.66 | 1.48 | 0.33 | 8.41 | 2.33 |
| CR003363 | 31.03 | 10.74 | 14.77 | 4.21 | 16.26 | 6.54 |
| CR003364 | 35.65 | 7.90 | 19.17 | 4.24 | 16.48 | 3.76 |
| CR003365 | 36.43 | 6.20 | 11.83 | 1.88 | 24.61 | 4.45 |
| CR003366 | 47.36 | 6.59 | 10.10 | 1.28 | 37.26 | 5.32 |
| CR003367 | 47.11 | 15.43 | 28.44 | 9.11 | 18.67 | 6.33 |

TABLE 4-continued

TTR editing data in Hek_Cas9 cells transfected with dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003368 | 40.35 | 10.13 | 3.73 | 0.96 | 36.61 | 9.17 |
| CR003369 | 33.10 | 7.26 | 9.06 | 1.12 | 24.04 | 6.16 |
| CR003370 | 34.22 | 5.69 | 4.49 | 0.67 | 29.73 | 5.06 |
| CR003371 | 25.60 | 8.33 | 3.84 | 1.41 | 21.76 | 6.92 |
| CR003372 | 15.24 | 7.92 | 3.25 | 1.61 | 11.99 | 6.31 |
| CR003373 | 13.55 | 2.40 | 1.31 | 0.21 | 12.25 | 2.19 |
| CR003374 | 10.91 | 0.88 | 0.81 | 0.10 | 10.10 | 0.81 |
| CR003375 | 11.63 | 3.18 | 0.78 | 0.17 | 10.85 | 3.05 |
| CR003376 | 28.16 | 4.49 | 1.35 | 0.18 | 26.81 | 4.52 |
| CR003377 | 24.70 | 4.44 | 2.71 | 0.54 | 21.99 | 3.91 |
| CR003378 | 20.97 | 2.67 | 4.49 | 0.49 | 16.48 | 2.18 |
| CR003379 | 26.32 | 2.91 | 5.34 | 0.61 | 20.98 | 2.30 |
| CR003380 | 47.64 | 5.74 | 3.64 | 0.24 | 44.00 | 5.52 |
| CR003381 | 22.04 | 5.74 | 3.82 | 1.26 | 18.23 | 4.64 |
| CR003382 | 29.95 | 3.13 | 4.46 | 0.45 | 25.49 | 2.73 |
| CR003383 | 40.47 | 0.64 | 25.12 | 0.45 | 15.35 | 0.66 |
| CR003384 | 17.45 | 1.32 | 1.45 | 0.23 | 16.00 | 1.42 |
| CR003385 | 26.19 | 5.62 | 7.36 | 1.57 | 18.82 | 4.06 |
| CR003386 | 33.12 | 10.65 | 2.94 | 0.63 | 30.18 | 10.03 |
| CR003387 | 24.68 | 5.93 | 7.75 | 1.99 | 16.92 | 3.94 |
| CR003388 | 19.23 | 4.41 | 1.41 | 0.39 | 17.82 | 4.07 |
| CR003389 | 34.18 | 5.09 | 10.30 | 2.12 | 23.87 | 3.02 |
| CR003390 | 28.02 | 3.77 | 4.31 | 0.25 | 23.71 | 3.61 |
| CR003391 | 44.81 | 4.67 | 0.61 | 0.07 | 44.19 | 4.63 |
| CR003392 | 21.67 | 7.52 | 0.85 | 0.26 | 20.82 | 7.27 |

Table 5 shows the average and standard deviation for % Edit, % Insertion (Ins), and % Deletion (Del) for the tested TTR crRNAs co-transfected with Spy Cas9 mRNA (SEQ ID NO:2) in the human hepatocellular carcinoma cell line, HUH7.

TABLE 5

TTR editing data in HUH7 cells transfected with Spy Cas9 mRNA and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003335 | 31.95 | 4.50 | 4.62 | 0.83 | 27.57 | 4.08 |
| CR003336 | 30.05 | 4.25 | 4.14 | 1.07 | 26.56 | 3.55 |
| CR003337 | 55.72 | 3.12 | 8.34 | 0.93 | 48.95 | 2.24 |
| CR003338 | 75.64 | 2.03 | 10.22 | 1.42 | 67.06 | 2.79 |
| CR003339 | 79.97 | 4.73 | 60.55 | 3.94 | 20.13 | 1.02 |
| CR003340 | 46.93 | 7.12 | 33.33 | 6.01 | 14.23 | 1.65 |
| CR003341 | 20.58 | 5.98 | 7.78 | 1.64 | 13.20 | 4.44 |
| CR003342 | 45.14 | 7.16 | 1.23 | 0.91 | 44.66 | 7.68 |
| CR003343 | 76.13 | 7.04 | 9.58 | 3.49 | 66.97 | 6.10 |
| CR003344 | 64.02 | 3.33 | 10.76 | 1.35 | 54.40 | 2.71 |
| CR003345 | 72.43 | 2.17 | 41.33 | 0.96 | 32.18 | 1.37 |
| CR003346 | 18.07 | 1.02 | 13.17 | 1.39 | 6.97 | 3.06 |
| CR003347 | 32.16 | 5.50 | 1.64 | 0.42 | 30.79 | 5.11 |
| CR003348 | 57.14 | 10.98 | 36.08 | 6.97 | 22.71 | 4.42 |
| CR003349 | 14.14 | 4.99 | 9.73 | 3.26 | 4.82 | 1.91 |
| CR003350 | 52.91 | 7.61 | 13.43 | 2.00 | 41.64 | 6.03 |
| CR003351 | 63.51 | 4.61 | 36.87 | 2.49 | 27.49 | 2.14 |
| CR003352 | 39.68 | 9.53 | 7.62 | 7.42 | 32.79 | 7.37 |
| CR003353 | 69.18 | 4.59 | 7.73 | 2.46 | 62.87 | 3.13 |
| CR003354 | 12.27 | 3.38 | 1.25 | 0.40 | 11.46 | 3.23 |
| CR003355 | 38.83 | 5.31 | 9.40 | 1.81 | 30.31 | 3.56 |
| CR003356 | 49.63 | 5.55 | 18.98 | 2.67 | 31.31 | 3.04 |
| CR003357 | 36.31 | 5.72 | 6.37 | 1.17 | 30.82 | 4.68 |
| CR003358 | 36.50 | 6.17 | 10.53 | 1.56 | 26.60 | 4.49 |
| CR003359 | 66.75 | 5.84 | 21.73 | 2.30 | 45.97 | 3.93 |
| CR003360 | 58.62 | 8.73 | 5.01 | 0.60 | 55.13 | 8.19 |
| CR003361 | 28.68 | 6.52 | 6.84 | 1.26 | 22.44 | 5.31 |
| CR003362 | 26.43 | 0.83 | 3.43 | 0.32 | 23.76 | 0.85 |
| CR003363 | 41.01 | 7.16 | 17.83 | 3.32 | 23.78 | 3.97 |
| CR003364 | 47.13 | 10.61 | 24.68 | 5.15 | 23.03 | 5.74 |

TABLE 5-continued

TTR editing data in HUH7 cells transfected with Spy Cas9 mRNA and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003365 | 60.68 | 5.25 | 17.77 | 1.57 | 43.82 | 3.73 |
| CR003366 | 69.98 | 8.84 | 20.77 | 3.10 | 50.32 | 5.69 |
| CR003367 | 66.29 | 4.48 | 33.62 | 4.14 | 33.48 | 0.51 |
| CR003368 | 31.57 | 11.73 | 3.08 | 0.92 | 29.69 | 11.32 |
| CR003369 | 24.19 | 6.89 | 7.12 | 2.27 | 17.38 | 4.76 |
| CR003370 | 39.16 | 11.59 | 4.83 | 1.79 | 35.55 | 10.35 |
| CR003371 | 40.47 | 7.68 | 6.07 | 0.89 | 35.65 | 7.01 |
| CR003372 | 21.52 | 6.02 | 4.89 | 1.66 | 17.25 | 4.58 |
| CR003373 | 27.29 | 4.45 | 3.31 | 0.66 | 25.12 | 4.12 |
| CR003374 | 3.10 | 0.68 | 0.45 | 0.24 | 2.87 | 0.54 |
| CR003375 | 2.38 | 0.22 | 0.26 | 0.14 | 2.25 | 0.12 |
| CR003376 | 19.42 | 5.60 | 1.37 | 0.45 | 18.55 | 5.28 |
| CR003377 | 34.93 | 5.47 | 5.59 | 0.88 | 29.89 | 4.71 |
| CR003378 | 40.73 | 4.63 | 9.73 | 1.85 | 32.27 | 2.91 |
| CR003379 | 19.18 | 5.17 | 3.38 | 0.77 | 16.48 | 4.32 |
| CR003380 | 31.76 | 5.81 | 3.29 | 0.57 | 29.29 | 5.42 |
| CR003381 | 99.70 | 0.17 | 1.92 | 0.20 | 99.70 | 0.17 |
| CR003382 | 34.47 | 5.71 | 0.14 | 0.16 | 34.47 | 5.71 |
| CR003383 | 42.89 | 10.14 | 2.14 | 0.56 | 41.19 | 9.67 |
| CR003384 | 17.03 | 1.95 | 0.84 | 0.30 | 16.29 | 1.84 |
| CR003386 | 69.40 | 19.41 | 0.53 | 0.23 | 69.34 | 19.32 |
| CR003387 | 25.64 | 3.69 | 0.23 | 0.07 | 25.55 | 3.62 |
| CR003388 | 59.48 | 4.29 | 3.88 | 0.68 | 56.45 | 4.45 |
| CR003389 | 62.32 | 1.97 | 13.19 | 1.18 | 50.90 | 1.02 |
| CR003390 | 18.97 | 4.82 | 3.31 | 0.91 | 16.49 | 3.98 |
| CR003391 | 61.31 | 13.21 | 2.10 | 0.51 | 59.70 | 12.76 |
| CR003392 | 28.37 | 8.58 | 1.93 | 0.73 | 26.98 | 7.94 |

Table 6 shows the average and standard deviation for % Edit, % Insertion (Ins), and % Deletion (Del) for the tested TTR and control crRNAs co-transfected with Spy Cas9 mRNA (SEQ ID NO:2) in the human hepatocellular carcinoma cell line, HepG2.

TABLE 6

TTR editing data in HepG2 cells transfected with Spy Cas9 mRNA and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR001261 (control) | 49.16 | 7.45 | 16.46 | 3.46 | 32.71 | 4.06 |
| CR001262 (control) | 63.33 | 5.66 | 59.88 | 4.92 | 3.45 | 0.86 |
| CR001263 (control) | 39.19 | 6.98 | 37.59 | 8.01 | 1.60 | 1.92 |
| CR001264 (control) | 57.09 | 12.14 | 47.47 | 9.25 | 9.61 | 2.89 |
| CR003335 | 37.19 | 2.12 | 32.96 | 1.67 | 4.23 | 0.59 |
| CR003336 | 31.31 | 5.47 | 30.48 | 5.10 | 0.83 | 0.75 |
| CR003337 | 61.93 | 2.68 | 59.28 | 2.11 | 2.65 | 1.39 |
| CR003338 | 68.00 | 6.09 | 65.40 | 6.78 | 2.60 | 1.17 |
| CR003339 | 68.21 | 7.67 | 12.37 | 1.47 | 55.84 | 6.31 |
| CR003340 | 37.76 | 6.01 | 6.12 | 1.95 | 31.65 | 4.07 |
| CR003341 | 15.60 | 5.49 | 9.94 | 3.38 | 5.66 | 2.13 |
| CR003342 | 11.06 | 6.71 | 10.78 | 6.69 | 0.28 | 0.03 |
| CR003343 | 45.41 | 15.20 | 40.05 | 10.79 | 5.36 | 5.20 |
| CR003344 | 33.43 | 6.11 | 29.81 | 5.09 | 3.62 | 1.13 |
| CR003345 | 10.58 | 9.25 | 6.12 | 5.38 | 4.45 | 3.87 |
| CR003346 | 0.13 | 0.05 | 0.07 | 0.02 | 0.05 | 0.03 |
| CR003347 | 22.57 | 10.94 | 21.08 | 11.19 | 1.49 | 0.90 |
| CR003348 | 38.44 | 10.45 | 17.04 | 5.04 | 21.40 | 5.89 |
| CR003349 | 8.36 | 2.19 | 4.46 | 1.75 | 3.91 | 0.76 |
| CR003350 | 29.60 | 5.17 | 25.16 | 4.56 | 4.44 | 0.67 |
| CR003351 | 57.54 | 5.67 | 31.98 | 2.63 | 25.57 | 3.08 |
| CR003352 | 44.28 | 8.71 | 39.51 | 7.10 | 4.77 | 1.79 |
| CR003353 | 60.40 | 11.37 | 56.71 | 9.95 | 3.68 | 1.45 |

TABLE 6-continued

TTR editing data in HepG2 cells transfected with Spy Cas9 mRNA and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003354 | 5.36 | 3.94 | 4.84 | 3.41 | 0.53 | 0.71 |
| CR003355 | 15.80 | 5.38 | 12.36 | 4.23 | 3.44 | 1.16 |
| CR003356 | 9.39 | 1.82 | 5.67 | 1.03 | 3.72 | 0.92 |
| CR003357 | 45.83 | 10.66 | 42.37 | 8.47 | 3.46 | 2.28 |
| CR003358 | 35.93 | 7.34 | 28.66 | 7.76 | 7.27 | 1.77 |
| CR003359 | 64.44 | 14.90 | 48.79 | 14.32 | 15.65 | 1.94 |
| CR003360 | 41.31 | 12.23 | 38.94 | 10.60 | 2.38 | 1.78 |
| CR003361 | 14.05 | 4.79 | 11.47 | 4.35 | 2.58 | 0.43 |
| CR003362 | 17.44 | 4.34 | 16.50 | 4.86 | 0.94 | 0.52 |
| CR003363 | 42.65 | 9.90 | 28.58 | 6.95 | 14.07 | 3.01 |
| CR003364 | 51.88 | 7.67 | 31.03 | 2.67 | 20.85 | 5.03 |
| CR003365 | 46.88 | 15.78 | 35.77 | 13.49 | 11.11 | 2.30 |
| CR003366 | 54.69 | 9.10 | 46.20 | 8.98 | 8.49 | 1.11 |
| CR003367 | 45.55 | 8.19 | 24.28 | 6.57 | 21.27 | 1.62 |
| CR003368 | 51.55 | 8.60 | 48.34 | 9.87 | 3.22 | 1.36 |
| CR003369 | 22.62 | 4.01 | 17.11 | 4.47 | 5.51 | 2.52 |
| CR003370 | 28.51 | 6.94 | 24.88 | 6.17 | 3.62 | 1.45 |
| CR003371 | 15.91 | 4.17 | 14.07 | 4.02 | 1.84 | 0.22 |
| CR003372 | 14.57 | 2.47 | 12.14 | 2.08 | 2.42 | 0.40 |
| CR003373 | 17.69 | 8.41 | 15.92 | 6.44 | 1.77 | 1.97 |
| CR003374 | 5.43 | 0.53 | 5.12 | 0.62 | 0.31 | 0.36 |
| CR003375 | 2.06 | 0.04 | 1.96 | 0.06 | 0.10 | 0.03 |
| CR003376 | 14.41 | 3.01 | 14.16 | 2.93 | 0.24 | 0.10 |
| CR003377 | 16.30 | 2.85 | 15.29 | 2.59 | 1.02 | 0.59 |
| CR003378 | 8.16 | 3.83 | 6.82 | 3.43 | 1.34 | 0.61 |
| CR003379 | 19.74 | 4.24 | 17.70 | 4.30 | 2.04 | 0.33 |
| CR003380 | 17.08 | 2.48 | 14.78 | 1.18 | 2.30 | 1.36 |
| CR003381 | 6.81 | 3.48 | 6.18 | 3.82 | 0.63 | 0.44 |
| CR003382 | 1.73 | 0.14 | 1.58 | 0.12 | 0.15 | 0.03 |
| CR003383 | 6.35 | 1.67 | 6.19 | 1.68 | 0.16 | 0.04 |
| CR003384 | 3.37 | 0.88 | 3.12 | 0.94 | 0.25 | 0.09 |
| CR003385 | 53.94 | 9.41 | 46.32 | 10.66 | 7.62 | 1.29 |
| CR003386 | 2.71 | 0.76 | 2.15 | 0.77 | 0.56 | 0.53 |
| CR003387 | 1.39 | 0.15 | 1.27 | 0.17 | 0.12 | 0.02 |
| CR003388 | 9.33 | 4.47 | 7.76 | 4.56 | 1.56 | 0.10 |
| CR003389 | 31.84 | 6.09 | 27.27 | 5.96 | 4.57 | 1.21 |
| CR003390 | 24.88 | 4.96 | 22.44 | 3.41 | 2.44 | 2.25 |
| CR003391 | 48.78 | 14.41 | 48.28 | 14.44 | 0.50 | 0.52 |
| CR003392 | 14.64 | 5.25 | 14.32 | 4.95 | 0.33 | 0.36 |
| CR005298 | 42.65 | 10.94 | 21.29 | 8.16 | 21.36 | 2.87 |
| CR005299 | 38.61 | 5.57 | 36.32 | 3.99 | 2.30 | 2.11 |
| CR005300 | 64.34 | 9.55 | 53.20 | 6.59 | 11.15 | 3.33 |
| CR005301 | 37.04 | 5.32 | 33.39 | 3.85 | 3.65 | 1.89 |
| CR005302 | 33.21 | 2.19 | 30.93 | 2.43 | 2.29 | 0.24 |
| CR005303 | 21.63 | 6.05 | 20.55 | 5.80 | 1.08 | 0.25 |
| CR005304 | 62.82 | 3.28 | 8.07 | 1.22 | 54.75 | 4.27 |
| CR005305 | 13.51 | 3.58 | 12.30 | 3.49 | 1.21 | 0.84 |
| CR005306 | 24.07 | 5.24 | 21.20 | 5.03 | 2.87 | 1.10 |
| CR005307 | 22.03 | 3.86 | 7.70 | 1.35 | 14.33 | 4.15 |

Table 7 shows the average and standard deviation for % Edit, % Insertion (Ins), and % Deletion (Del) for the tested TTR dgRNAs electroporated with Spy Cas9 protein (RNP) in primary human hepatocytes.

TABLE 7

TTR editing data in primary human hepatocytes electroporated with Spy Cas9 protein loaded with dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003335 | 72.20 | 4.53 | 69.70 | 4.36 | 2.50 | 0.30 |
| CR003336 | 39.17 | 3.04 | 38.43 | 3.20 | 0.70 | 0.17 |
| CR003337 | 54.27 | 2.70 | 53.23 | 3.05 | 1.30 | 0.26 |
| CR003338 | 83.03 | 4.84 | 80.87 | 4.63 | 2.13 | 0.25 |
| CR003339 | 43.00 | 2.66 | 8.93 | 1.86 | 34.07 | 1.72 |
| CR003340 | 12.03 | 1.55 | 5.60 | 1.32 | 6.50 | 0.53 |
| CR003341 | 11.43 | 0.71 | 7.03 | 0.50 | 4.40 | 1.21 |
| CR003342 | 32.77 | 3.63 | 31.87 | 3.28 | 0.90 | 0.35 |
| CR003343 | 77.10 | 2.21 | 75.63 | 2.01 | 1.50 | 0.36 |
| CR003344 | 39.40 | 3.86 | 33.30 | 2.52 | 6.10 | 1.31 |
| CR003345 | 48.07 | 6.24 | 34.53 | 2.95 | 13.57 | 3.74 |
| CR003346 | 35.67 | 1.80 | 20.83 | 1.65 | 14.83 | 1.66 |
| CR003347 | 82.30 | 5.93 | 81.97 | 5.98 | 0.43 | 0.15 |
| CR003348 | 28.53 | 1.79 | 11.30 | 2.46 | 17.27 | 0.86 |
| CR003349 | 4.10 | 0.17 | 2.33 | 0.46 | 1.87 | 0.25 |
| CR003350 | 28.13 | 3.50 | 22.40 | 2.41 | 5.73 | 1.22 |
| CR003351 | 51.77 | 5.11 | 30.83 | 3.32 | 20.97 | 2.43 |
| CR003352 | 29.83 | 4.18 | 25.63 | 3.67 | 4.30 | 0.56 |
| CR003353 | 84.83 | 4.68 | 82.23 | 4.05 | 2.63 | 0.74 |
| CR003354 | 2.50 | 0.36 | 2.43 | 0.32 | 0.03 | 0.06 |
| CR003355 | 12.53 | 1.54 | 10.60 | 2.36 | 1.97 | 1.17 |
| CR003356 | 9.97 | 2.68 | 7.80 | 2.01 | 2.23 | 0.85 |
| CR003357 | 36.23 | 4.02 | 35.47 | 4.11 | 0.77 | 0.61 |
| CR003358 | 5.70 | 1.42 | 4.93 | 1.36 | 0.80 | 0.26 |
| CR003359 | 63.77 | 7.07 | 56.33 | 5.81 | 7.50 | 1.35 |
| CR003360 | 32.23 | 3.09 | 31.67 | 2.97 | 0.63 | 0.31 |
| CR003361 | 4.10 | 0.36 | 3.73 | 0.42 | 0.37 | 0.06 |
| CR003362 | 7.03 | 1.30 | 6.87 | 1.20 | 0.20 | 0.20 |
| CR003363 | 9.43 | 8.22 | 7.80 | 6.86 | 1.63 | 1.44 |
| CR003364 | 23.30 | 5.20 | 16.93 | 4.96 | 6.53 | 0.55 |
| CR003365 | 42.37 | 3.88 | 35.57 | 1.88 | 6.83 | 2.00 |
| CR003366 | 34.70 | 3.26 | 31.63 | 2.98 | 3.10 | 1.15 |
| CR003367 | 39.20 | 5.31 | 22.93 | 4.14 | 16.37 | 1.46 |
| CR003368 | 28.47 | 3.29 | 27.63 | 2.90 | 0.80 | 0.66 |
| CR003369 | 3.67 | 1.16 | 3.30 | 1.06 | 0.40 | 0.20 |
| CR003370 | 15.27 | 1.75 | 14.43 | 1.72 | 0.90 | 0.20 |
| CR003371 | 16.20 | 2.13 | 14.47 | 2.37 | 1.87 | 0.81 |
| CR003372 | 12.17 | 2.69 | 10.47 | 2.63 | 1.77 | 0.12 |
| CR003373 | 0.87 | 0.21 | 0.83 | 0.25 | 0.07 | 0.12 |
| CR003374 | 0.80 | 0.17 | 0.70 | 0.26 | 0.10 | 0.10 |
| CR003375 | 1.33 | 1.10 | 1.27 | 1.08 | 0.07 | 0.06 |
| CR003376 | 1.90 | 1.06 | 1.87 | 1.00 | 0.03 | 0.06 |
| CR003377 | 10.23 | 1.53 | 10.13 | 1.51 | 0.10 | 0.10 |
| CR003378 | 4.60 | 1.92 | 3.87 | 1.19 | 0.73 | 0.67 |
| CR003379 | 6.57 | 1.00 | 6.30 | 0.70 | 0.27 | 0.31 |
| CR003380 | 5.37 | 2.57 | 5.27 | 2.54 | 0.10 | 0.10 |
| CR003381 | 6.20 | 2.74 | 5.83 | 2.61 | 0.50 | 0.10 |
| CR003382 | 8.40 | 2.07 | 8.10 | 1.87 | 0.43 | 0.21 |
| CR003383 | 8.57 | 0.75 | 3.37 | 0.67 | 5.27 | 0.46 |
| CR003384 | 1.87 | 0.67 | 1.73 | 0.57 | 0.23 | 0.12 |
| CR003385 | 40.87 | 6.86 | 38.43 | 6.41 | 2.53 | 0.45 |
| CR003386 | 4.90 | 1.20 | 4.47 | 1.14 | 0.47 | 0.25 |
| CR003387 | 1.87 | 0.25 | 1.70 | 0.26 | 0.20 | 0.10 |
| CR003388 | 5.70 | 0.40 | 5.47 | 0.40 | 0.27 | 0.12 |
| CR003389 | 27.67 | 2.76 | 27.20 | 2.88 | 0.50 | 0.36 |
| CR003390 | 15.97 | 3.86 | 15.80 | 3.99 | 0.23 | 0.15 |
| CR003391 | 29.77 | 3.85 | 29.57 | 3.85 | 0.27 | 0.06 |
| CR003392 | 4.13 | 1.21 | 4.00 | 1.15 | 0.17 | 0.06 |
| CR005298 | 39.90 | 2.92 | 22.37 | 3.04 | 17.57 | 0.42 |
| CR005299 | 8.65 | 0.78 | 8.30 | 0.99 | 0.35 | 0.21 |
| CR005300 | 57.47 | 1.69 | 53.47 | 1.86 | 4.10 | 0.92 |
| CR005301 | 25.37 | 1.65 | 24.00 | 2.26 | 1.60 | 0.82 |
| CR005302 | 61.10 | 5.20 | 60.10 | 4.77 | 1.00 | 0.46 |
| CR005303 | 53.57 | 8.52 | 53.07 | 8.36 | 0.53 | 0.47 |
| CR005304 | 67.00 | 5.80 | 5.53 | 1.37 | 61.63 | 6.98 |
| CR005305 | 3.83 | 0.78 | 3.53 | 0.61 | 0.40 | 0.17 |
| CR005306 | 9.43 | 1.63 | 8.07 | 2.17 | 1.37 | 0.72 |
| CR005307 | 8.17 | 1.20 | 5.20 | 0.87 | 3.00 | 0.82 |

Table 8 shows the average and standard deviation for % Edit, % Insertion (Ins), and % Deletion (Del) for the tested TTR and control dgRNAs transfected with Spy Cas9 protein (RNP) in primary human hepatocytes.

TABLE 8

TTR editing data in primary human hepatocytes transfected with Spy Cas9 loaded with dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR001261 | 32.51 | 1.00 | 12.50 | 0.47 | 20.01 | 0.59 |
| CR001262 | 50.09 | 1.48 | 45.25 | 1.69 | 4.83 | 0.31 |
| CR001263 | 15.25 | 2.41 | 14.83 | 2.37 | 0.42 | 0.10 |
| CR001264 | 45.30 | 3.48 | 23.87 | 2.09 | 21.43 | 1.68 |
| CR003335 | 51.14 | 4.27 | 49.51 | 4.04 | 1.63 | 0.25 |
| CR003336 | 30.70 | 2.41 | 30.11 | 2.48 | 0.58 | 0.11 |
| CR003337 | 49.43 | 4.75 | 47.54 | 4.49 | 1.88 | 0.47 |
| CR003338 | 61.34 | 3.55 | 59.13 | 3.44 | 2.22 | 0.11 |
| CR003339 | 45.06 | 9.83 | 8.85 | 1.65 | 36.21 | 8.34 |
| CR003340 | 10.44 | 2.44 | 5.94 | 1.34 | 4.50 | 1.16 |
| CR003341 | 19.66 | 3.67 | 14.64 | 3.31 | 5.02 | 0.37 |
| CR003342 | 20.66 | 2.55 | 19.85 | 2.54 | 0.81 | 0.15 |
| CR003343 | 43.25 | 4.47 | 41.61 | 4.26 | 1.63 | 0.33 |
| CR003344 | 35.45 | 13.12 | 30.97 | 11.72 | 4.48 | 1.51 |
| CR003345 | 28.90 | 6.33 | 21.00 | 5.23 | 7.91 | 1.81 |
| CR003346 | 4.11 | 1.36 | 2.27 | 0.53 | 1.84 | 0.85 |
| CR003347 | 66.35 | 4.48 | 66.11 | 4.51 | 0.24 | 0.08 |
| CR003348 | 23.18 | 2.16 | 13.74 | 1.17 | 9.44 | 0.99 |
| CR003349 | 10.83 | 1.57 | 9.00 | 1.41 | 1.83 | 0.32 |
| CR003350 | 24.84 | 2.74 | 19.77 | 1.91 | 5.07 | 0.89 |
| CR003351 | 40.28 | 1.31 | 23.92 | 0.70 | 16.36 | 0.78 |
| CR003352 | 30.48 | 1.93 | 27.27 | 2.31 | 3.21 | 0.38 |
| CR003353 | 61.54 | 4.13 | 59.38 | 4.04 | 2.16 | 0.11 |
| CR003354 | 10.31 | 1.47 | 10.07 | 1.50 | 0.23 | 0.11 |
| CR003355 | 19.11 | 0.92 | 17.69 | 0.79 | 1.42 | 0.44 |
| CR003356 | 7.53 | 1.78 | 6.24 | 1.51 | 1.29 | 0.32 |
| CR003357 | 49.35 | 2.53 | 48.45 | 2.54 | 0.90 | 0.13 |
| CR003358 | 31.62 | 5.97 | 25.95 | 5.03 | 5.67 | 1.04 |
| CR003359 | 59.47 | 6.05 | 50.96 | 5.69 | 8.51 | 0.54 |
| CR003360 | 31.47 | 4.12 | 30.27 | 4.21 | 1.19 | 0.22 |
| CR003361 | 13.08 | 1.48 | 12.52 | 1.45 | 0.56 | 0.18 |
| CR003362 | 11.65 | 1.24 | 11.10 | 1.06 | 0.56 | 0.36 |
| CR003363 | 27.65 | 2.84 | 21.47 | 2.39 | 6.18 | 0.61 |
| CR003364 | 35.29 | 3.50 | 23.93 | 2.63 | 11.36 | 1.16 |
| CR003365 | 47.78 | 3.67 | 40.24 | 3.12 | 7.54 | 0.72 |
| CR003366 | 42.74 | 3.41 | 37.95 | 2.88 | 4.79 | 0.60 |
| CR003367 | 31.19 | 4.60 | 16.06 | 2.66 | 15.13 | 1.94 |
| CR003368 | 34.83 | 5.05 | 33.83 | 5.09 | 1.00 | 0.10 |
| CR003369 | 12.98 | 0.26 | 11.67 | 0.21 | 1.31 | 0.11 |
| CR003370 | 20.06 | 1.79 | 18.80 | 1.65 | 1.26 | 0.28 |
| CR003371 | 18.80 | 2.73 | 17.23 | 2.34 | 1.57 | 0.43 |
| CR003372 | 17.56 | 2.26 | 15.74 | 2.16 | 1.81 | 0.10 |
| CR003373 | 3.64 | 0.29 | 3.44 | 0.30 | 0.19 | 0.07 |
| CR003374 | 2.65 | 0.33 | 2.52 | 0.33 | 0.14 | 0.02 |
| CR003375 | 5.04 | 0.66 | 4.93 | 0.66 | 0.11 | 0.01 |
| CR003376 | 5.00 | 1.10 | 4.86 | 1.10 | 0.14 | 0.03 |
| CR003377 | 12.77 | 2.00 | 12.45 | 1.84 | 0.31 | 0.18 |
| CR003378 | 8.66 | 1.90 | 8.24 | 1.74 | 0.42 | 0.19 |
| CR003379 | 16.86 | 2.62 | 16.51 | 2.62 | 0.34 | 0.08 |
| CR003380 | 8.17 | 1.42 | 7.71 | 1.47 | 0.46 | 0.10 |
| CR003381 | 7.15 | 0.73 | 6.88 | 0.67 | 0.27 | 0.07 |
| CR003382 | 2.44 | 0.06 | 2.28 | 0.05 | 0.15 | 0.03 |
| CR003383 | 4.76 | 0.40 | 4.52 | 0.42 | 0.24 | 0.09 |
| CR003384 | 3.56 | 0.26 | 3.39 | 0.26 | 0.17 | 0.01 |
| CR003385 | 41.15 | 6.06 | 38.15 | 5.59 | 3.00 | 0.48 |
| CR003386 | 3.22 | 0.25 | 2.97 | 0.27 | 0.25 | 0.02 |
| CR003387 | 1.79 | 0.11 | 1.68 | 0.09 | 0.11 | 0.04 |
| CR003388 | 5.43 | 1.03 | 4.38 | 1.00 | 1.05 | 0.25 |
| CR003389 | 19.87 | 4.39 | 19.19 | 4.52 | 0.68 | 0.24 |
| CR003390 | 16.09 | 2.84 | 15.85 | 2.91 | 0.24 | 0.09 |
| CR003391 | 34.72 | 8.29 | 34.46 | 8.35 | 0.26 | 0.06 |
| CR003392 | 10.07 | 1.06 | 9.93 | 1.02 | 0.14 | 0.04 |
| CR005298 | 32.07 | 1.02 | 21.12 | 1.02 | 10.95 | 0.15 |
| CR005299 | 19.37 | 0.61 | 18.79 | 0.51 | 0.58 | 0.13 |
| CR005300 | 57.23 | 6.24 | 53.62 | 5.44 | 3.61 | 0.87 |
| CR005301 | 31.37 | 3.02 | 29.53 | 2.88 | 1.84 | 0.15 |
| CR005302 | 48.29 | 5.22 | 47.32 | 5.32 | 0.97 | 0.14 |
| CR005303 | 36.45 | 4.83 | 36.06 | 4.72 | 0.39 | 0.11 |
| CR005304 | 49.45 | 6.85 | 4.32 | 0.31 | 45.13 | 6.74 |
| CR005305 | 7.07 | 1.43 | 6.73 | 1.30 | 0.34 | 0.17 |
| CR005306 | 18.81 | 1.82 | 16.24 | 1.57 | 2.57 | 0.35 |
| CR005307 | 18.73 | 1.68 | 10.18 | 0.92 | 8.55 | 0.88 |

Table 9 shows the average and standard deviation for % Edit, % Insertion (Ins), and % Deletion (Del) for the tested TTR and control dgRNAs co-transfected with Spy Cas9 mRNA (SEQ ID NO:2) in primary human hepatocytes.

TABLE 9

TTR editing data in primary human hepatocytes transfected with Spy Cas9 mRNA and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR001261 | 32.33 | 4.95 | 5.83 | 1.63 | 26.47 | 3.30 |
| CR001262 | 41.50 | 4.71 | 34.43 | 3.31 | 7.13 | 1.42 |
| CR001263 | 10.23 | 3.61 | 9.40 | 3.20 | 0.90 | 0.44 |
| CR001264 | 42.80 | 0.50 | 11.90 | 1.32 | 30.90 | 1.80 |
| CR003335 | 36.43 | 2.98 | 33.03 | 2.31 | 3.40 | 0.70 |
| CR003336 | 16.93 | 3.78 | 16.20 | 3.41 | 0.80 | 0.44 |
| CR003337 | 19.30 | 1.57 | 18.10 | 1.44 | 1.23 | 0.15 |
| CR003338 | 36.30 | 9.55 | 33.73 | 9.27 | 2.73 | 0.49 |
| CR003339 | 36.43 | 1.21 | 2.27 | 0.15 | 34.23 | 1.31 |
| CR003340 | 24.97 | 2.78 | 1.83 | 0.23 | 23.17 | 2.66 |
| CR003341 | 15.83 | 1.38 | 6.80 | 0.53 | 9.07 | 0.81 |
| CR003342 | 22.10 | 1.27 | 20.60 | 0.57 | 1.50 | 0.71 |
| CR003343 | 55.03 | 0.38 | 52.40 | 0.53 | 2.60 | 0.44 |
| CR003344 | 31.50 | 1.30 | 22.40 | 1.31 | 9.20 | 0.10 |
| CR003345 | 50.65 | 2.90 | 32.30 | 1.56 | 18.45 | 1.20 |
| CR003346 | 19.97 | 1.94 | 5.63 | 0.55 | 14.33 | 1.72 |
| CR003347 | 41.47 | 3.59 | 41.33 | 3.63 | 0.17 | 0.06 |
| CR003348 | 18.00 | 0.87 | 2.30 | 0.66 | 15.80 | 0.61 |
| CR003349 | 2.57 | 0.81 | 0.90 | 0.35 | 1.70 | 0.46 |
| CR003350 | 26.63 | 4.25 | 16.33 | 2.45 | 10.33 | 1.75 |
| CR003351 | 26.50 | 1.61 | 10.20 | 0.92 | 16.37 | 0.97 |
| CR003352 | 16.80 | 5.03 | 11.73 | 3.86 | 5.07 | 1.14 |
| CR003353 | 53.73 | 6.01 | 49.50 | 5.82 | 4.43 | 0.75 |
| CR003354 | 2.97 | 0.95 | 2.87 | 0.85 | 0.13 | 0.12 |
| CR003355 | 12.07 | 2.61 | 10.47 | 2.08 | 1.63 | 0.59 |
| CR003356 | 7.27 | 0.72 | 4.70 | 0.53 | 2.67 | 0.21 |
| CR003357 | 25.93 | 4.55 | 25.30 | 4.22 | 0.63 | 0.35 |
| CR003358 | 3.90 | 0.79 | 2.73 | 0.45 | 1.17 | 0.51 |
| CR003359 | 32.93 | 4.34 | 25.67 | 3.25 | 7.33 | 1.24 |
| CR003360 | 14.90 | 4.85 | 14.13 | 4.66 | 0.90 | 0.52 |
| CR003361 | 3.53 | 0.60 | 2.73 | 0.55 | 0.87 | 0.15 |
| CR003362 | 6.60 | 1.47 | 6.17 | 1.45 | 0.47 | 0.21 |
| CR003363 | 16.70 | 1.08 | 11.80 | 0.79 | 4.93 | 0.60 |
| CR003364 | 15.63 | 2.45 | 6.73 | 0.81 | 8.93 | 1.70 |
| CR003365 | 26.90 | 3.05 | 20.23 | 2.02 | 6.67 | 1.16 |
| CR003366 | 24.53 | 1.26 | 20.47 | 1.45 | 4.07 | 0.23 |
| CR003367 | 37.33 | 1.40 | 14.03 | 0.40 | 23.37 | 1.25 |
| CR003368 | 11.10 | 1.91 | 10.53 | 1.90 | 0.60 | 0.10 |
| CR003369 | 1.60 | 0.46 | 0.90 | 0.20 | 0.70 | 0.36 |
| CR003370 | 2.83 | 0.57 | 2.33 | 0.40 | 0.50 | 0.17 |
| CR003371 | 3.40 | 0.80 | 2.67 | 0.75 | 0.73 | 0.15 |
| CR003372 | 1.77 | 0.75 | 1.13 | 0.57 | 0.63 | 0.23 |
| CR003373 | 1.40 | 0.36 | 1.00 | 0.35 | 0.37 | 0.12 |
| CR003374 | 0.27 | 0.21 | 0.27 | 0.21 | 0.03 | 0.06 |
| CR003375 | 1.27 | 0.64 | 1.23 | 0.58 | 0.03 | 0.06 |
| CR003376 | 2.83 | 0.81 | 2.73 | 0.81 | 0.13 | 0.06 |
| CR003377 | 17.53 | 6.35 | 16.97 | 6.11 | 0.57 | 0.25 |
| CR003378 | 9.80 | 1.37 | 8.50 | 1.21 | 1.37 | 0.15 |
| CR003379 | 13.20 | 1.18 | 12.00 | 1.05 | 1.27 | 0.15 |
| CR003380 | 2.93 | 0.58 | 2.47 | 0.57 | 0.47 | 0.15 |
| CR003381 | 4.07 | 1.21 | 3.33 | 0.96 | 0.73 | 0.25 |
| CR003382 | 0.97 | 0.25 | 0.97 | 0.25 | 0.00 | 0.00 |
| CR003383 | 15.70 | 3.22 | 2.07 | 0.35 | 13.70 | 2.82 |
| CR003384 | 1.70 | 0.62 | 1.50 | 0.56 | 0.20 | 0.10 |
| CR003385 | 36.77 | 0.70 | 33.23 | 0.74 | 3.60 | 0.26 |
| CR003386 | 8.27 | 1.63 | 8.20 | 1.57 | 0.13 | 0.06 |
| CR003387 | 7.87 | 1.58 | 7.80 | 1.64 | 0.03 | 0.06 |
| CR003388 | 12.97 | 1.30 | 11.87 | 1.21 | 1.17 | 0.25 |
| CR003389 | 44.27 | 1.72 | 41.47 | 1.59 | 2.83 | 0.15 |
| CR003390 | 20.23 | 2.08 | 18.73 | 1.92 | 1.60 | 0.17 |
| CR003391 | 15.47 | 5.87 | 15.20 | 5.72 | 0.30 | 0.10 |
| CR003392 | 2.43 | 0.55 | 2.37 | 0.59 | 0.07 | 0.06 |
| CR005298 | 15.70 | 2.79 | 4.13 | 0.87 | 11.60 | 2.00 |
| CR005299 | 9.43 | 0.68 | 8.93 | 0.68 | 0.60 | 0.00 |
| CR005300 | 31.53 | 3.44 | 27.60 | 2.77 | 3.97 | 0.76 |
| CR005301 | 6.77 | 1.44 | 5.47 | 0.96 | 1.40 | 0.61 |
| CR005302 | 34.80 | 7.17 | 33.67 | 7.01 | 1.13 | 0.21 |

TABLE 9-continued

TTR editing data in primary human hepatocytes transfected with Spy Cas9 mRNA and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR005303 | 35.50 | 5.90 | 35.00 | 5.81 | 0.50 | 0.10 |
| CR005304 | 45.27 | 4.71 | 0.83 | 0.15 | 44.47 | 4.57 |
| CR005305 | 7.53 | 1.06 | 5.93 | 1.10 | 1.60 | 0.10 |
| CR005306 | 9.97 | 0.38 | 7.13 | 0.23 | 2.87 | 0.12 |
| CR005307 | 12.90 | 2.43 | 3.67 | 0.61 | 9.30 | 1.80 |

Table 10 shows the average and standard deviation for % Edit, % Insertion (Ins), and % Deletion (Del) for the tested TTR dgRNAs electroporated with Spy Cas9 protein (RNP) in primary cyno hepatocytes.

TABLE 10

TTR editing data in primary cyno hepatocytes electroporated with Spy Cas9 protein and dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR003336 | 8.18 | 1.93 | 8.10 | 1.94 | 0.07 | 0.01 |
| CR003337 | 24.94 | 5.80 | 24.10 | 4.71 | 0.84 | 1.10 |
| CR003338 | 44.94 | 9.99 | 44.89 | 9.97 | 0.05 | 0.01 |
| CR003339 | 8.95 | 0.89 | 4.93 | 0.64 | 4.02 | 0.25 |
| CR003340 | 12.53 | 2.22 | 7.72 | 0.13 | 4.80 | 2.09 |
| CR003341 | 8.43 | 10.53 | 7.66 | 9.91 | 0.77 | 0.63 |
| CR003344 | 35.72 | 4.67 | 33.81 | 5.29 | 1.91 | 0.61 |
| CR003345 | 52.92 | 3.26 | 30.74 | 0.78 | 22.19 | 2.48 |
| CR003346 | 1.91 | 0.86 | 1.82 | 0.82 | 0.09 | 0.04 |
| CR003347 | 72.41 | 0.38 | 72.15 | 0.73 | 0.25 | 0.34 |
| CR003352 | 1.25 | 0.20 | 1.16 | 0.21 | 0.09 | 0.01 |
| CR003353 | 4.75 | 0.43 | 4.67 | 0.47 | 0.08 | 0.04 |
| CR003358 | 20.47 | 0.30 | 19.01 | 0.51 | 1.46 | 0.21 |
| CR003359 | 46.17 | 1.14 | 40.66 | 2.00 | 5.51 | 0.86 |
| CR003360 | 29.47 | 0.63 | 29.05 | 1.00 | 0.42 | 0.37 |
| CR003361 | 4.53 | 0.14 | 4.46 | 0.18 | 0.08 | 0.04 |
| CR003362 | 4.59 | 0.80 | 4.36 | 0.77 | 0.22 | 0.03 |
| CR003363 | 15.64 | 1.92 | 13.24 | 2.65 | 2.39 | 0.73 |
| CR003364 | 19.62 | 2.54 | 14.27 | 2.72 | 5.35 | 0.17 |
| CR003365 | 10.31 | 1.81 | 9.33 | 1.80 | 0.97 | 0.01 |
| CR003366 | 18.52 | 0.71 | 17.62 | 0.33 | 0.90 | 0.39 |
| CR003368 | 18.56 | 3.89 | 18.30 | 3.77 | 0.26 | 0.11 |
| CR003369 | 1.53 | 0.25 | 1.28 | 0.40 | 0.25 | 0.15 |
| CR003370 | 2.52 | 0.64 | 2.40 | 0.63 | 0.12 | 0.01 |
| CR003371 | 1.83 | 0.38 | 1.69 | 0.41 | 0.14 | 0.03 |
| CR003372 | 2.15 | 0.30 | 1.83 | 0.33 | 0.32 | 0.04 |
| CR003382 | 10.86 | 2.04 | 8.54 | 1.93 | 2.33 | 0.11 |
| CR003383 | 8.86 | 2.30 | 4.31 | 0.69 | 4.55 | 1.61 |
| CR003384 | 3.75 | 0.35 | 2.50 | 0.37 | 1.25 | 0.02 |
| CR003385 | 30.96 | 1.61 | 26.84 | 2.20 | 4.12 | 0.59 |
| CR003386 | 5.54 | 1.42 | 3.51 | 1.26 | 2.03 | 0.15 |
| CR003387 | 4.72 | 0.03 | 4.55 | 0.08 | 0.17 | 0.11 |
| CR003388 | 6.81 | 0.17 | 6.59 | 0.28 | 0.22 | 0.11 |
| CR003389 | 18.83 | 4.99 | 18.05 | 4.92 | 0.78 | 0.07 |
| CR003390 | 16.87 | 3.88 | 16.49 | 3.48 | 0.39 | 0.39 |
| CR003391 | 36.44 | 1.09 | 35.73 | 1.37 | 0.71 | 0.28 |
| CR003392 | 7.02 | 0.97 | 6.63 | 0.59 | 0.38 | 0.37 |
| CR005299 | 13.48 | 2.96 | 13.23 | 2.74 | 0.26 | 0.22 |
| CR005301 | 46.76 | 1.75 | 46.34 | 2.19 | 0.42 | 0.44 |
| CR005302 | 1.34 | 0.19 | 1.26 | 0.19 | 0.08 | 0.00 |
| CR005303 | 59.28 | 1.05 | 58.72 | 1.06 | 0.56 | 0.00 |
| CR005305 | 11.28 | 0.39 | 11.13 | 0.39 | 0.15 | 0.00 |
| CR005307 | 4.56 | 0.71 | 2.01 | 0.49 | 2.55 | 0.21 |

Table 11 shows the average and standard deviation for % Edit, % Insertion (Ins), and % Deletion (Del) for the tested cyno specific TTR dgRNAs electroporated with Spy Cas9 protein (RNP) on primary cyno hepatocytes.

TABLE 11

TTR editing data in primary cyno hepatocytes electroporated with Spy Cas9 protein and cyno specific dgRNAs

| GUIDE ID | Avg % Edit | Std Dev % Edit | Avg % Insert | Std Dev % Insert | Avg % Deletion | Std Dev % Deletion |
|---|---|---|---|---|---|---|
| CR000689 | 24.41 | 1.67 | 18.11 | 2.41 | 6.30 | 0.93 |
| CR005364 | 27.70 | 0.74 | 0.58 | 0.29 | 27.11 | 0.60 |
| CR005365 | 64.94 | 2.03 | 0.10 | 0.04 | 64.85 | 2.05 |
| CR005366 | 77.00 | 1.17 | 0.33 | 0.27 | 76.67 | 0.99 |
| CR005367 | 50.79 | 0.53 | 0.53 | 0.25 | 50.26 | 0.36 |
| CR005368 | 27.60 | 2.07 | 0.33 | 0.45 | 27.27 | 2.32 |
| CR005369 | 42.01 | 0.33 | 8.09 | 0.55 | 33.92 | 0.31 |
| CR005370 | 63.52 | 3.21 | 0.59 | 0.33 | 62.93 | 2.88 |
| CR005371 | 8.42 | 0.69 | 0.31 | 0.12 | 8.10 | 0.57 |
| CR005372 | 17.98 | 1.39 | 0.83 | 0.77 | 17.16 | 0.71 |

Example 3. Screening of sgRNA Sequences

Cross Screening of TTR sgRNAs in Multiple Cell Types

Guides in modified sgRNA format targeting human and/or cyno TTR were delivered to primary human hepatocytes and primary cyno hepatocytes as described in Example 1. Percent editing was determined for crRNAs comprising each guide sequence across each cell type and the guide sequences were then rank ordered based on highest % edit. The screening data for the guide sequences in Table 2 in both cell lines are listed below (Table 12 through 15).

Table 12 shows the average and standard deviation for % Edit, % Insertion (Ins), and % Deletion (Del) for the tested TTR sgRNAs transfected with Spy Cas9 protein (RNP) in primary human hepatocytes.

TABLE 12

TTR editing data in primary human hepatocytes transfected with Spy Cas9 protein and sgRNAs

| GUIDE ID | Avg % Edit | Std Dev % Edit | Avg % Insert | Std Dev % Insert | Avg % Deletion | Std Dev % Deletion |
|---|---|---|---|---|---|---|
| G000480 | 81.80 | 1.98 | 77.15 | 2.19 | 4.70 | 0.28 |
| G000481 | 46.90 | 1.71 | 27.77 | 3.88 | 19.43 | 4.76 |
| G000482 | 66.67 | 2.35 | 56.57 | 4.14 | 10.10 | 1.85 |
| G000483 | 47.90 | 6.56 | 19.57 | 3.37 | 28.50 | 3.25 |
| G000484 | 62.97 | 0.90 | 29.23 | 0.21 | 33.83 | 0.95 |
| G000485 | 56.07 | 3.37 | 53.07 | 2.84 | 3.13 | 0.60 |
| G000486 | 69.73 | 6.86 | 9.83 | 1.93 | 59.93 | 5.63 |
| G000487 | 67.30 | 2.75 | 65.27 | 3.41 | 2.07 | 1.06 |
| G000488 | 61.27 | 1.95 | 26.30 | 1.55 | 35.00 | 1.30 |
| G000489 | 60.17 | 2.75 | 51.07 | 3.18 | 9.43 | 0.45 |
| G000490 | 55.90 | 7.88 | 46.13 | 7.55 | 9.80 | 0.69 |
| G000491 | 74.30 | 1.55 | 70.27 | 2.37 | 4.33 | 0.72 |
| G000492 | 60.97 | 5.81 | 57.90 | 4.64 | 3.13 | 1.35 |
| G000493 | 41.40 | 3.08 | 38.90 | 3.29 | 2.67 | 0.35 |
| G000494 | 62.23 | 3.30 | 61.47 | 3.25 | 0.77 | 0.31 |
| G000495 | 50.80 | 1.85 | 45.80 | 1.25 | 5.37 | 0.64 |
| G000496 | 72.33 | 1.63 | 44.73 | 2.14 | 27.67 | 1.46 |
| G000497 | 59.67 | 1.40 | 51.10 | 1.14 | 8.73 | 0.71 |
| G000498 | 72.80 | 3.75 | 60.17 | 3.12 | 12.70 | 0.72 |
| G000499 | 66.40 | 3.55 | 65.23 | 3.72 | 1.17 | 0.38 |
| G000500 | 65.53 | 1.21 | 62.00 | 1.11 | 3.83 | 0.40 |
| G000501 | 60.93 | 1.91 | 55.13 | 1.43 | 6.00 | 0.56 |

Table 13 shows the average and standard deviation at 12.5 nM for % Edit, % Insertion (Ins), and % Deletion (Del) for the tested TTR sgRNAs co-transfected with Spy Cas9 mRNA (SEQ ID NO:2) in primary human hepatocytes.

TABLE 13

TTR editing data in primary human hepatocytes transfected with Spy Cas9 mRNA and sgRNAs

| GUIDE ID | Avg % Edit | Std Dev % Edit | Avg % Insert | Std Dev % Insert | Avg % Deletion | Std Dev % Deletion |
|---|---|---|---|---|---|---|
| G000480 | 73.28 | 0.61 | 59.85 | 0.13 | 13.47 | 0.51 |
| G000481 | 34.30 | 5.26 | 14.62 | 2.59 | 19.77 | 2.72 |
| G000482 | 40.93 | 3.95 | 27.70 | 2.92 | 13.25 | 0.97 |
| G000483 | 27.82 | 2.93 | 4.05 | 0.51 | 23.85 | 2.43 |
| G000484 | 43.37 | 6.79 | 13.98 | 2.61 | 29.48 | 4.15 |
| G000485 | 30.82 | 5.76 | 28.87 | 5.50 | 1.97 | 0.28 |
| G000486 | 59.13 | 5.62 | 2.82 | 0.86 | 56.37 | 4.92 |
| G000487 | 49.57 | 0.99 | 47.38 | 0.89 | 2.27 | 0.24 |
| G000488 | 49.40 | 5.05 | 11.98 | 1.40 | 37.48 | 3.68 |
| G000489 | 24.25 | 2.82 | 14.17 | 2.01 | 10.28 | 1.38 |
| G000490 | 24.72 | 2.35 | 19.38 | 2.04 | 5.38 | 0.41 |
| G000491 | 45.93 | 1.22 | 42.42 | 1.06 | 3.60 | 0.33 |
| G000492 | 34.65 | 2.21 | 32.45 | 2.01 | 2.22 | 0.25 |
| G000493 | 11.55 | 1.35 | 10.65 | 1.58 | 0.97 | 0.30 |
| G000494 | 26.22 | 4.03 | 25.17 | 3.89 | 1.07 | 0.15 |
| G000495 | 47.77 | 1.88 | 43.40 | 1.91 | 4.45 | 0.17 |
| G000496 | 63.30 | 2.60 | 11.08 | 2.10 | 52.25 | 0.67 |
| G000497 | 40.33 | 3.32 | 34.48 | 2.71 | 5.85 | 0.61 |
| G000498 | 60.02 | 5.42 | 45.20 | 4.34 | 14.90 | 1.08 |
| G000499 | 39.30 | 6.04 | 38.58 | 5.86 | 0.77 | 0.12 |
| G000500 | 35.50 | 0.61 | 32.47 | 0.49 | 3.10 | 0.18 |
| G000501 | 40.32 | 1.50 | 33.82 | 2.04 | 6.62 | 0.55 |
| G000567 | 27.28 | 7.59 | 17.35 | 4.72 | 10.02 | 2.94 |
| G000568 | 43.75 | 5.83 | 43.00 | 5.81 | 0.80 | 0.18 |
| G000570 | 68.42 | 3.64 | 68.08 | 3.61 | 0.35 | 0.00 |
| G000571 | 20.47 | 3.41 | 14.47 | 2.72 | 6.13 | 0.78 |
| G000572 | 55.42 | 8.13 | 41.62 | 6.48 | 13.85 | 1.60 |

Table 14 shows the average and standard deviation for % Edit, % Insertion (Ins), and % Deletion (Del) for the tested TTR sgRNAs electroporated with Spy Cas9 protein (RNP) on primary cyno hepatocytes. Note that guides G000480 and G000488 have one mismatch to cyno, which may compromise their editing efficiency in cyno cells.

TABLE 14

TTR editing data in primary cyno hepatocytes electroporated with Spy Cas9 protein and sgRNAs

| GUIDE ID | Avg % Edit | Std Dev % Edit | Avg % Insert | Std Dev % Insert | Avg % Deletion | Std Dev % Deletion |
|---|---|---|---|---|---|---|
| G000480 | 10.20 | 0.56 | 9.83 | 0.81 | 0.37 | 0.25 |
| G000481 | 69.13 | 8.62 | 33.73 | 2.67 | 35.50 | 11.23 |
| G000482 | 75.17 | 2.34 | 55.23 | 2.00 | 20.03 | 0.85 |
| G000485 | 22.93 | 0.95 | 22.00 | 0.82 | 1.07 | 0.21 |
| G000486 | 79.90 | 0.79 | 11.90 | 0.85 | 68.07 | 0.35 |
| G000488 | 9.63 | 0.50 | 5.37 | 0.38 | 4.27 | 0.35 |
| G000489 | 67.53 | 1.15 | 53.53 | 1.56 | 14.17 | 0.64 |
| G000490 | 61.67 | 0.72 | 54.47 | 1.10 | 7.27 | 1.23 |
| G000491 | 66.20 | 1.11 | 64.37 | 0.47 | 1.90 | 0.70 |
| G000493 | 50.13 | 0.74 | 48.07 | 1.69 | 2.10 | 0.98 |
| G000494 | 81.53 | 0.71 | 79.57 | 0.49 | 2.07 | 0.67 |
| G000498 | 91.37 | 1.48 | 68.50 | 1.64 | 22.87 | 1.50 |
| G000499 | 83.40 | 0.36 | 82.00 | 0.20 | 1.43 | 0.55 |
| G000500 | 45.20 | 3.66 | 42.60 | 3.80 | 2.63 | 0.25 |

Table 15 shows the average and standard deviation for % Edit, % Insertion (Ins), and % Deletion (Del) for the tested cyno specific TTR sgRNAs electroporated with Spy Cas9 protein (RNP) on primary cyno hepatocytes.

TABLE 15

TTR editing data in primary cyno hepatocytes electroporated with Spy Cas9 protein and cyno specific sgRNAs (e.g., those having an analogous human gRNA, See Table 3)

| GUIDE ID | Avg % Edit | Std Dev % Edit | Avg % Insert | Std Dev % Insert | Avg % Deletion | Std Dev % Deletion |
|---|---|---|---|---|---|---|
| G000502 | 95.10 | 0.96 | 13.97 | 1.69 | 81.27 | 2.60 |
| G000503 | 58.53 | 2.40 | 52.07 | 1.68 | 6.50 | 2.46 |
| G000504 | 77.17 | 0.96 | 69.73 | 1.29 | 7.53 | 0.57 |
| G000505 | 95.53 | 1.06 | 95.50 | 1.01 | 0.10 | 0.10 |
| G000506 | 89.43 | 1.36 | 86.90 | 1.64 | 3.07 | 0.42 |
| G000507 | 71.17 | 3.22 | 67.03 | 2.39 | 4.60 | 1.65 |
| G000508 | 45.63 | 3.01 | 41.57 | 2.95 | 4.17 | 0.91 |
| G000509 | 93.03 | 0.81 | 43.60 | 1.30 | 49.73 | 1.76 |
| G000510 | 90.80 | 0.53 | 89.13 | 0.40 | 1.77 | 0.12 |
| G000511 | 62.77 | 1.63 | 60.87 | 1.55 | 2.00 | 0.35 |

Example 4. Screening of Lipid Nanoparticle (LNP) Formulations Containing Spy Ca9 mRNA and sgRNA Cross screening of LNP formulated TTR sgRNAs with Spy Cas9 mRNA in primary human hepatocytes and primary cyno hepatocytes.

Lipid nanoparticle formulations of modified sgRNAs targeting human TTR and the cyno matched sgRNA sequences were tested on primary human hepatocytes and primary cyno hepatocytes in a dose response curve. Primary human and cyno hepatocytes were plated as described in Example 1. Both cell lines were incubated at 37° C., 5% $CO_2$ for 24 hours prior to treatment with LNPs. The LNPs used in the experiments detailed in Tables 16-19 were prepared using the Nanoassemblr procedure, each containing the specified sgRNA and Cas9 mRNA (SEQ ID NO:2), each having Lipid. The LNPs contained Lipid A, Cholesterol, DSPC, and PEG2k-DMG in a 45:44:9:2 molar ratio, respectively, and had a N:P ratio of 4.5. LNPs were incubated in hepatocyte maintenance media containing 6% cyno serum at 37° C. for 5 minutes. Post incubation the LNPs were added onto the primary human or cyno hepatocytes in an 8 point 2-fold dose response curve starting at 100 ng mRNA. The cells were lysed 72 hours post treatment for NGS analysis as described in Example 1. Percent editing was determined for crRNAs comprising each guide sequence across each cell type and the guide sequences were then rank ordered based on highest % editing at 12.5 ng mRNA input and 3.9 nM guide concentration. The dose response curve data for the guide sequences in both cell lines is shown in FIGS. 4 through 7. The % editing at 12.5 ng mRNA input and 3.9 nM guide concentration are listed below (Table 16 through 18).

Table 16 shows the average and standard deviation at 12.5 ng of cas9 mRNA for % Edit, % Insertion (Ins), and % Deletion (Del) for the tested TTR sgRNAs formulated in lipid nanoparticles with Spy Cas9 mRNA on primary human hepatocytes as dose response curves. G000570 exhibited an uncharacteristic dose response curve compared to the other sgRNAs which may be an artifact of the experiment. The data are shown graphically in FIG. 4.

TABLE 16

TTR editing data in primary human hepatocytes treated with LNP formulated Spy Cas9 mRNA (SEQ ID NO: 2) and sgRNAs

| GUIDE ID | 12.5 ng mRNA, 3.9 nM sgRNA Avg % Edit | Std Dev % Edit |
|---|---|---|
| G000480 | 59.33 | 0.73 |
| G000481 | 24.37 | 0.37 |
| G000482 | 19.10 | 2.64 |
| G000483 | 7.37 | 0.67 |
| G000484 | 16.67 | 1.23 |
| G000485 | 14.23 | 2.36 |
| G000486 | 61.33 | 2.59 |
| G000487 | 17.37 | 0.95 |
| G000488 | 44.80 | 3.00 |
| G000489 | 16.85 | 0.06 |
| G000490 | 10.53 | 1.90 |
| G000491 | 31.60 | 2.33 |
| G000492 | 15.87 | 0.44 |
| G000493 | 7.33 | 0.73 |
| G000494 | 6.37 | 1.07 |
| G000495 | 23.97 | 1.66 |
| G000496 | 30.73 | 3.76 |
| G000497 | 15.10 | 3.30 |
| G000498 | 24.43 | 1.30 |
| G000499 | 16.07 | 1.67 |
| G000500 | 23.57 | 2.44 |
| G000501 | 32.30 | 2.49 |
| G000567 | 48.95 | 1.06 |
| G000568 | 54.60 | 3.68 |
| G000570 | 88.30 | 1.84 |
| G000572 | 55.45 | 1.20 |

Table 17 shows the average and standard deviation at 12.5 ng of mRNA and 3.9 nM guide concentration for % Edit, % Insertion (Ins), and % Deletion (Del) for the tested TTR sgRNAs formulated in lipid nanoparticles with Spy Cas9 mRNA on primary cyno hepatocytes as dose response curves. The data are shown graphically in FIG. 5.

TABLE 17

TTR editing data in primary cyno hepatocytes treated with LNP formulated Spy Cas9 mRNA (SEQ ID NO: 2) and sgRNAs

| GUIDE ID | 12.5 ng mRNA, 3.9 nM sgRNA, Avg % Edit | Std Dev % Edit |
|---|---|---|
| G000480 | 0.73 | 0.15 |
| G000481 | 49.20 | 1.39 |
| G000482 | 26.13 | 5.33 |
| G000483 | 0.73 | 0.60 |
| G000484 | 0.10 | 0.00 |
| G000485 | 1.43 | 1.02 |
| G000489 | 31.87 | 2.40 |
| G000490 | 15.23 | 1.08 |
| G000491 | 6.37 | 0.38 |
| G000492 | 0.70 | 0.28 |
| G000493 | 7.63 | 1.14 |
| G000494 | 14.30 | 1.06 |
| G000495 | 0.73 | 0.06 |
| G000497 | 0.23 | 0.06 |
| G000498 | 37.90 | 1.42 |
| G000499 | 14.63 | 0.70 |
| G000500 | 10.47 | 0.32 |
| G000501 | 1.37 | 0.31 |
| G000567 | 0.10 | 0.00 |
| G000568 | 9.25 | 0.21 |
| G000570 | 17.30 | 0.85 |
| G000571 | 20.20 | 2.26 |
| G000572 | 30.60 | 0.42 |

Table 18 shows the average and standard deviation at 12.5 ng of mRNA and 3.9 nM guide concentration for % Edit, % Insertion (Ins), and % Deletion (Del) for the tested cyno specific TTR sgRNAs formulated in lipid nanoparticles with Spy Cas9 mRNA on primary cyno hepatocytes as dose response curves. The data are shown graphically in FIG. 6.

TABLE 18

TTR editing data in primary cyno hepatocytes treated with LNP formulated Spy Cas9 mRNA (SEQ ID NO: 2) and cyno matched sgRNAs

| GUIDE ID | 12.5 ng mRNA, 3.9 nM sgRNA % Edit | Std Dev % Edit |
|---|---|---|
| G000502 | 80.70 | 0.14 |
| G000506 | 60.13 | 0.70 |
| G000509 | 74.47 | 7.28 |
| G000510 | 61.87 | 2.54 |

Cross Screening of LNP Formulated TTR sgRNAs with Spy Cas9 mRNA in Primary Human Hepatocytes and Primary Cyno Hepatocytes Lipid nanoparticle formulations of modified sgRNAs targeting human TTR and the cyno matched sgRNA sequences were tested on primary human hepatocytes and primary cyno hepatocytes in a dose response curve. Primary human and cyno hepatocytes were plated as described in Example 1. Both cell lines were incubated at 37° C., 5% $CO_2$ for 24 hours prior to treatment with LNPs. The LNPs used in the experiments detailed in Tables 20-22 were prepared using the cross-flow procedure described above but purified using PD-10 columns (GE Healthcare Life Sciences) and concentrated using Amicon centrifugal filter units (Millipore Sigma), each containing the specified sgRNA and Cas9 mRNA (SEQ ID NO:1). The LNPs contained Lipid A, Cholesterol, DSPC, and PEG2k-DMG in a 50:38:9:3 molar ratio, respectively, and had a N:P ratio of 6.0. LNPs were incubated in hepatocyte maintenance media containing 6% cyno serum at 37° C., 5% $CO_2$ for 5 minutes. Post incubation the LNPs were added onto the primary human or cyno hepatocytes in an 8 point 3-fold dose response curve starting at 300 ng mRNA. The cells were lysed 72 hours post treatment for NGS analysis as described in Example 1. Percent editing was determined for crRNAs comprising each guide sequence across each cell type and the guide sequences were then rank ordered based on EC50 values and maximum editing percent. The dose response curve data for the guide sequences in both cell lines is shown in FIGS. 4 through 7. The EC 50 values and maximum editing percent are listed below (Table 19 through 22).

Table 19 shows the EC50 and maximum editing the tested human specific TTR sgRNAs formulated in lipid nanoparticles with U-depleted Spy Cas9 mRNA on primary human hepatocytes as dose response curves. The data are shown graphically in FIG. 4.

TABLE 19

TTR editing data in primary human hepatocytes treated with LNP formulated Spy Cas9 mRNA and human specific sgRNAs

| GUIDE ID | EC50 | Max Editing |
|---|---|---|
| G000480 | 0.10 | 98.69 |
| G000481 | 1.43 | 87.05 |
| G000482 | 0.65 | 97.02 |

TABLE 19-continued

TTR editing data in primary human hepatocytes treated with LNP
formulated Spy Cas9 mRNA and human specific sgRNAs

| GUIDE ID | EC50 | Max Editing |
|---|---|---|
| G000483 | 1.88 | 77.39 |
| G000484 | 0.95 | 94.14 |
| G000488 | 0.72 | 95.83 |
| G000489 | 1.38 | 86.33 |
| G000490 | 1.52 | 94.16 |
| G000493 | 2.42 | 63.95 |
| G000494 | 1.28 | 75.70 |
| G000499 | 0.63 | 96.31 |
| G000500 | 0.39 | 88.70 |
| G000568 | 0.78 | 95.72 |
| G000570 | 0.23 | 98.22 |
| G000571 | 2.21 | 71.28 |
| G000572 | 0.42 | 97.94 |

Figure 16:
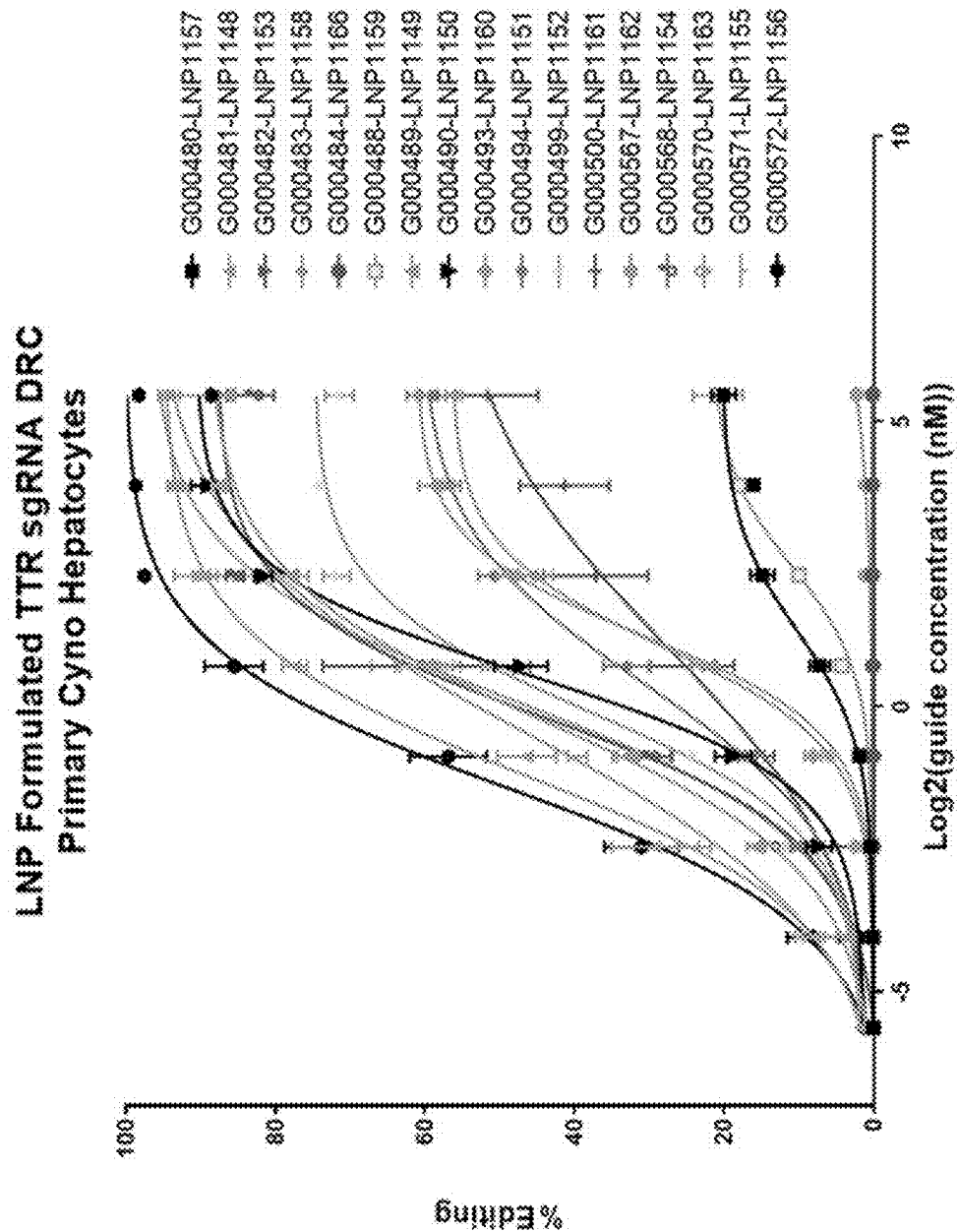
FIG. 16 shows dose response curves of lipid nanoparticle formulated human TTR specific sgRNAs on primary cyno hepatocytes.

Table 20 shows the EC50 and maximum editing the tested human specific TTR sgRNAs formulated in lipid nanoparticles with U-depleted Spy Cas9 mRNA on primary cyno hepatocytes as dose response curves. The data are shown graphically in FIG. 16.

TABLE 20

TTR editing data in primary cyno
hepatocytes treated with LNP formulated
Spy Cas9 mRNA and human specific sgRNAs

| GUIDE ID | EC50 | Max Editing |
|---|---|---|
| G000480 | 5.28 | 20.32 |
| G000481 | 0.93 | 95.07 |
| G000482 | 0.89 | 97.47 |
| G000483 | 4.40 | 56.52 |
| G000484 | 3.47 | 0.22 |
| G000488 | 11.56 | 21.63 |
| G000489 | 1.79 | 89.21 |
| G000490 | 3.09 | 90.76 |
| G000493 | 4.97 | 61.15 |
| G000494 | 2.77 | 60.84 |
| G000499 | 2.00 | 74.94 |
| G000500 | 4.42 | 58.04 |
| G000567 | 1.76 | 97.06 |
| G000568 | 1.87 | 87.93 |
| G000570 | 2.00 | 96.73 |
| G000571 | 1.55 | 97.03 |
| G000572 | 0.79 | 100.31 |

Figure 17:
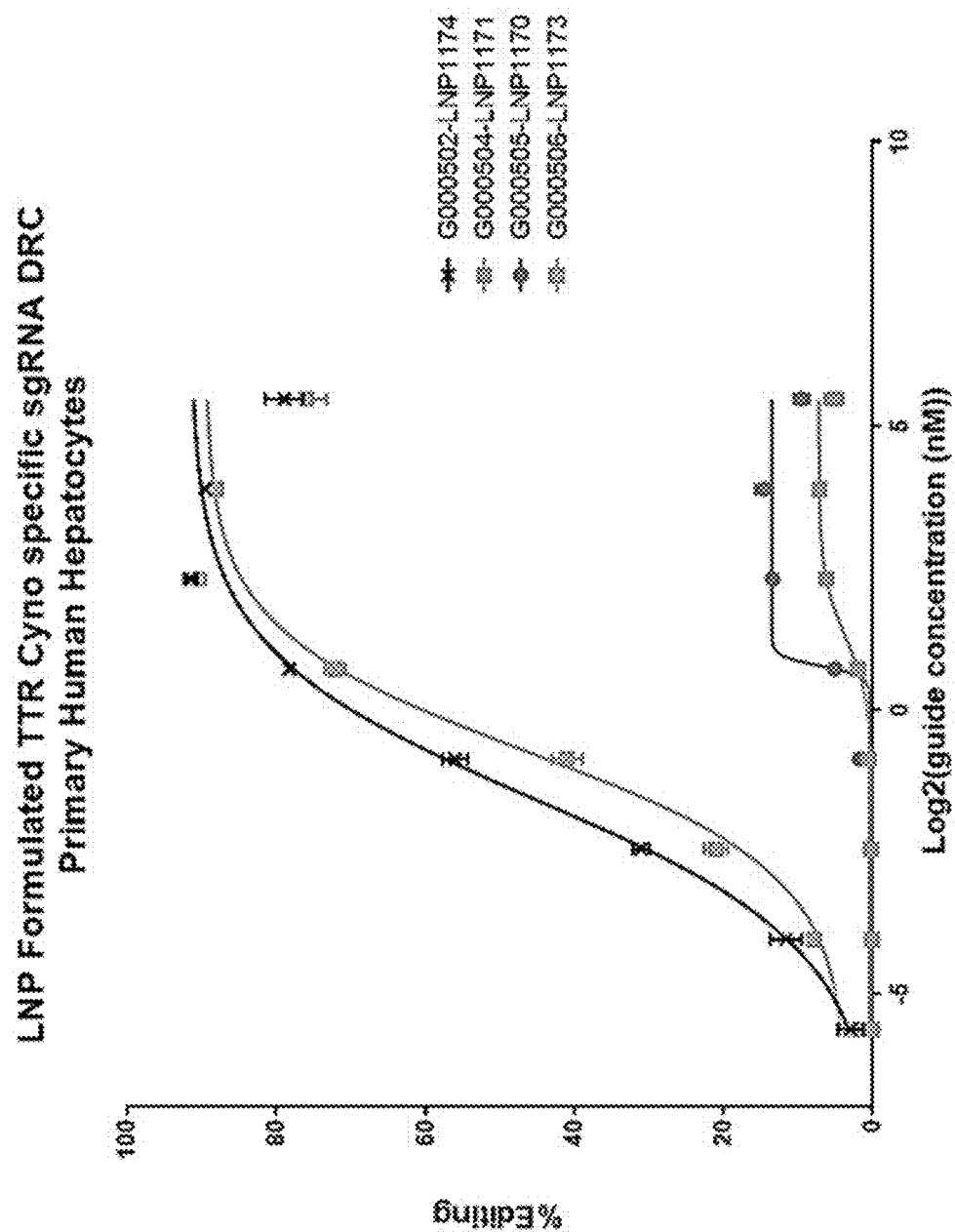
FIG. 17 shows dose response curves of lipid nanoparticle formulated cyno TTR specific sgRNAs on primary human hepatocytes.

Table 21 shows the EC50 and maximum editing the tested cyno matched TTR sgRNAs formulated in lipid nanoparticles with U-depleted Spy Cas9 mRNA on primary human hepatocytes as dose response curves. The data are shown graphically in FIG. 17.

TABLE 21

TTR editing data in primary human
hepatocytes treated with LNP formulated
Spy Cas9 mRNA and cyno specific sgRNAs

| GUIDE ID | EC50 | Max Editing |
|---|---|---|
| G000502 | 0.70 | 91.50 |
| G000504 | 5.16 | 7.16 |
| G000505 | 3.57 | 13.48 |
| G000506 | 1.26 | 89.49 |

Figure 18:
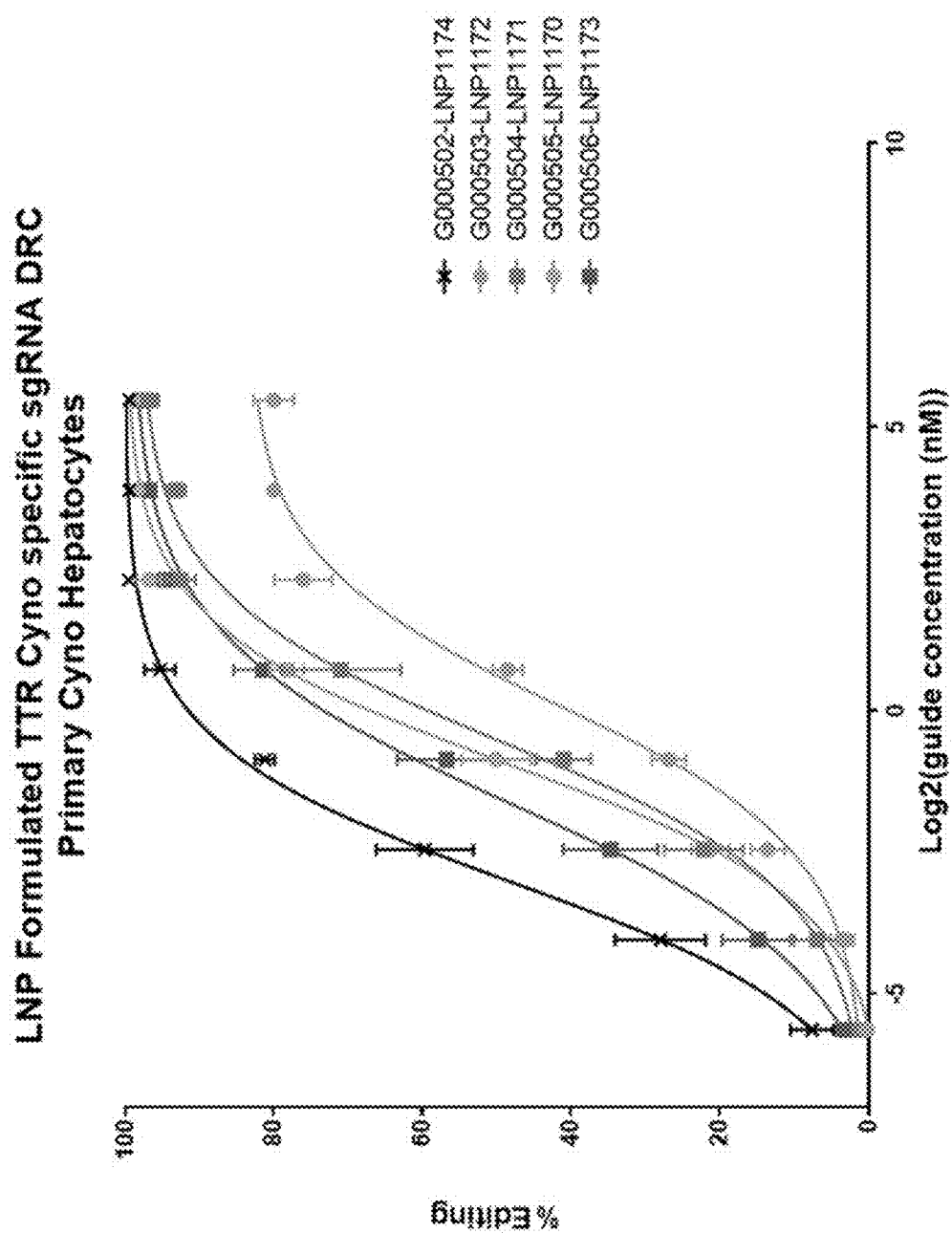
FIG. 18 shows dose response curves of lipid nanoparticle formulated cyno TTR specific sgRNAs on primary cyno hepatocytes.

Table 22 shows the EC50 and maximum editing the tested cyno matched TTR sgRNAs formulated in lipid nanoparticles with U-depleted Spy Cas9 mRNA on primary cyno hepatocytes as dose response curves. The data are shown graphically in FIG. 18.

TABLE 22

TTR editing data in primary cyno
hepatocytes treated with LNP formulated
Spy Cas9 mRNA and cyno specific sgRNAs

| GUIDE ID | EC50 | Max Editing |
|---|---|---|
| G000502 | 0.26 | 100.05 |
| G000503 | 2.26 | 83.41 |
| G000504 | 1.42 | 98.04 |
| G000505 | 1.10 | 99.97 |
| G000506 | 0.66 | 99.18 |

Example 5. Off-Target Analysis of TTR dgRNAs and sgRNAs

Off-Target Analysis of TTR Guides

An oligo insertion based assay (See, e.g., Tsai et al., Nature Biotechnology 33, 187-197; 2015) was used to determine potential off-target genomic sites cleaved by Cas9 targeting TTR. Forty-five dgRNAs from Table 1 (and two control guides with known off-target profiles) were screened in the HEK293 Cas9 cells. The human embryonic kidney adenocarcinoma cell line HEK293 constitutively expressing Spy Cas9 ("HEK293_Cas9") was cultured in DMEM media supplemented with 10% fetal bovine serum and 500 µg/ml G418. Cells were plated at a density of 30,000 cells/well in a 96-well plate 24 hours prior to transfection. Cells were transfected with Lipofectamine RNAiMAX (ThermoFisher, Cat. 13778150) per the manufacturer's protocol. Cells were transfected with a lipoplex containing individual crRNA (15 nM), trRNA (15 nM), and donor oligo with (10 nM) Lipofectamine RNAiMAX (0.3 µL/well) and OptiMem. Cells were lysed 24 hours post transfection and genomic DNA was extracting using Zymo's Quick gDNA 96 Extraction kit (catalog #D3012) following the manufacturer's recommended protocol. The gDNA was quantified using the Qubit High Sensitivity dsDNA kit (Life Technologies). Libraries were prepared per the previously described method in Tsai et al, 2015 with minor modifications. Sequencing was performed on Illumina's MiSeq and HiSeq 2500. The assay identified potential off-target sites for some of the crRNAs which are plotted in FIG. 2.

Table 23 shows the number of off-target integration sites detected in HekCas9 cells transfected with TTR dgRNAs along with a double stranded DNA oligo donor sequence.

TABLE 23

Number of off-target integration
sites detected for TTR dgRNAs
via an oligo insertion based assay

| GUIDE ID | # Sites |
|---|---|
| CR003335 | 0 |
| CR003336 | 2 |
| CR003337 | 10 |
| CR003338 | 2 |
| CR003339 | 3 |
| CR003340 | 0 |
| CR003342 | 0 |
| CR003343 | 2 |

TABLE 23-continued

Number of off-target integration
sites detected for TTR dgRNAs
via an oligo insertion based assay

| GUIDE ID | # Sites |
|---|---|
| CR003344 | 0 |
| CR003345 | 0 |
| CR003346 | 0 |
| CR003347 | 1 |
| CR003348 | 3 |
| CR003351 | 1 |
| CR003352 | 2 |
| CR003353 | 2 |
| CR003355 | 1 |
| CR003356 | 4 |
| CR003357 | 3 |
| CR003359 | 6 |
| CR003360 | 0 |
| CR003363 | 4 |
| CR003365 | 3 |
| CR003366 | 1 |
| CR003367 | 1 |
| CR003368 | 2 |
| CR003369 | 2 |
| CR003377 | 0 |
| CR003380 | 0 |
| CR003382 | 34 |
| CR003383 | 1 |
| CR003385 | 3 |
| CR003386 | 1 |
| CR003387 | 6 |
| CR003388 | 2 |
| CR003389 | 2 |
| CR003390 | 1 |
| CR003391 | 0 |
| CR003392 | 0 |
| CR005298 | 0 |
| CR005300 | 0 |
| CR005301 | 0 |
| CR005302 | 1 |
| CR005303 | 1 |
| CR005304 | 0 |

Additionally, a subset of the guides was assessed for off-target potential as modified sgRNAs in the Hek_Cas9 cells via the oligo based insertion method described above. The off-target results were plotted in FIG. 4.

Table 24 shows the number of off-target integration sites detected in HekCas9 cells transfected with TTR sgRNAs along with a double stranded DNA oligo donor sequence.

TABLE 24

Number of off-target integration
sites detected for TTR sgRNAs via
an insertion detection method

| GUIDE ID | # Sites |
|---|---|
| G000480 | 11 |
| G000481 | 3 |
| G000482 | 13 |
| G000483 | 5 |
| G000484 | 7 |
| G000485 | 22 |
| G000486 | 12 |
| G000487 | 14 |
| G000488 | 0 |
| G000489 | 19 |
| G000490 | 12 |
| G000491 | 28 |
| G000492 | 97 |
| G000493 | 7 |
| G000494 | 4 |

TABLE 24-continued

Number of off-target integration
sites detected for TTR sgRNAs via
an insertion detection method

| GUIDE ID | # Sites |
|---|---|
| G000495 | 13 |
| G000496 | 1 |
| G000497 | 26 |
| G000498 | 82 |
| G000499 | 4 |
| G000500 | 46 |
| G000501 | 4 |
| G000567 | 9 |
| G000568 | 937 |
| G000570 | 19 |
| G000571 | 16 |
| G000572 | 15 |

Example 6. Targeted Sequencing for Validating Potential Off-Target Sites

The HEK293_Cas9 cells used in Example 5 for detecting potential off-targets constitutively overexpress Cas9, leading to a higher number of potential off-target "hits" as compared to a transient delivery paradigm in various cell types. Further, when delivering sgRNAs (as opposed to dgRNAs), the number of potential off-target hits may be further inflated as sgRNA molecules are more stable than dgRNAs (especially when chemically modified). Accordingly, potential off-target sites identified by an oligo insertion method as used in Example 5 may be validated using targeted sequencing of the identified potential off-target sites.

In one approach, primary hepatocytes are treated with LNPs comprising Cas9 mRNA and a sgRNA of interest (e.g., a sgRNA having potential off-target sites for evaluation). The primary hepatocytes are then lysed and primers flanking the potential off-target site(s) are used to generate an amplicon for NGS analysis. Identification of indels at a certain level may validate potential off-target site, whereas the lack of indels found at the potential off-target site may indicate a false positive in the HEK293_Cas9 cell assay.

Example 7. Phenotypic Analysis

Western Blot Analysis of Secreted TTR

The hepatocellular carcinoma cell line, HepG2, was transfected as described in Example 1 with select guides from Table 1 in triplicate. Two days post-transfection, one replicate was harvested for genomic DNA and analysis by NGS sequencing for editing efficiency. Five days post-transfection, media without serum was replaced on one replicate. After 4 hrs the media was harvested for analysis of secreted TTR by WB as previously described. The data for % edit for each guide and reduction of extracellular TTR is provided in FIG. 7.

Western Blot Analysis of Intracellular TTR

The hepatocellular carcinoma cell line, HUH7, was transfected as described in Example 1 with crRNA comprising the guides from Table 1. The transfected pools of cells were retained in tissue culture and passaged for further analysis. At seven days post-transfection, cells were harvested and whole cell extracts (WCEs) were prepared and subjected to analysis by Western Blot as previously described.

WCEs were analyzed by Western Blot for reduction of TTR protein. Full length TTR protein has a predicted molecular weight of ~16 kD. A band at this molecular weight was observed in the control lanes in the Western Blot.

Figure 8:
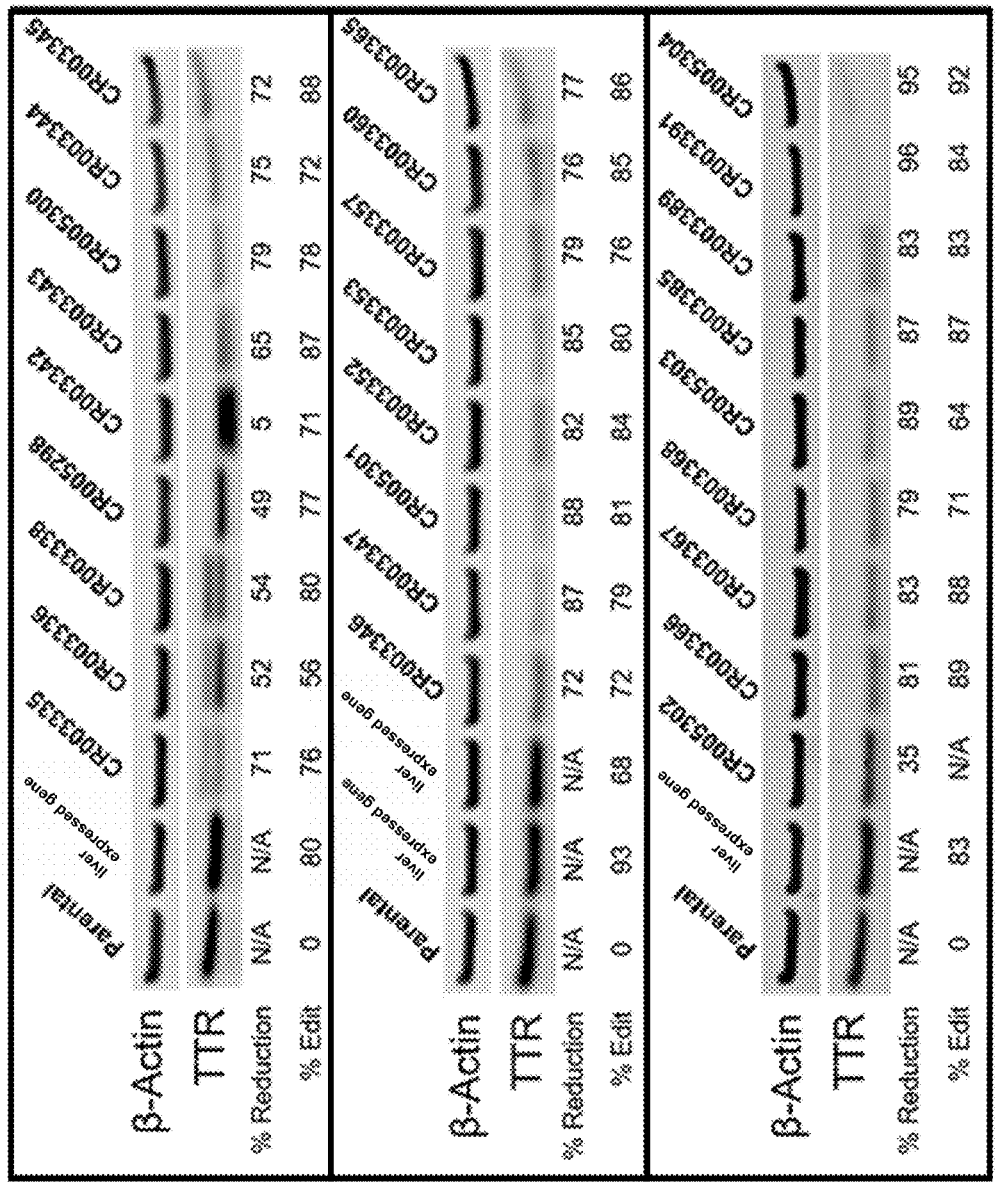
FIG. 8 shows western blot analysis of intracellular TTR following administration of targeted guides (listed in Table 1) in HUH7 cells.

Percent reduction of TTR protein was calculated using the Licor Odyssey Image Studio Ver 5.2 software. GAPDH was used as a loading control and probed simultaneously with TTR. A ratio was calculated for the densitometry values for GAPDH within each sample compared to the total region encompassing the TTR band. Percent reduction of TTR protein was determined after the ratios were normalized to control lanes. Results are shown in FIG. 8.

Example 8. LNP Delivery to Humanized TTR Mice and Mice Having Wt (Murine) TTR

Mice humanized with respect to the TTR gene were dosed with LNP formulations 701-704 containing the guides indicated in Table 25 (5 mice per formulation). These humanized TTR mice were engineered such that a region of the endogenous murine TTR locus was deleted and replaced with an orthologous human TTR sequence so that the locus encodes a human TTR protein. For comparison, 6 mice with murine TTR were dosed with LNP700, containing a guide (G000282) targeting murine TTR. LNPs with Formulation Numbers 1-5 in Table 25 were prepared using the Nanoassemblr procedure as described above while LNPs with Formulation Numbers 6-16 were prepared using the cross-flow procedure described above but purified using PD-10 columns (GE Healthcare Life Sciences) and concentrated using Amicon centrifugal filter units (Millipore Sigma). As negative controls, mice of the corresponding genotype were dosed with vehicle alone (Tris-saline-sucrose buffer (TSS)). The background of the humanized TTR mice administered LNPs with Formulation Numbers 2-5 in Table 25 was 50% 12956/SeaTac 50% C57BL/6NTac; the background of the humanized TTR mice administered LNPs having Formulation Numbers 6-16 in Table 25 as well as the mice with murine TTR (administered LNP700, Formulation Number 1) was 75% C57BL/6NTac 25% 12956/SeaTac.

TABLE 25

LNP formulations for dosing humanized TTR mice.

| Formulation Number | LNP | Guide | RNA concentration (mg/ml) | N:P Ratio | Molar Ratios (Lipid A, Cholesterol, DSPC, and PEG2k-DMG, respectively) |
|---|---|---|---|---|---|
| 1 | LNP700 | G000282 | 0.53 | 4.5 | 45:44:9:2 |
| 2 | LNP701 | G000481 | 0.46 | 4.5 | 45:44:9:2 |
| 3 | LNP702 | G000489 | 0.61 | 4.5 | 45:44:9:2 |
| 4 | LNP703 | G000494 | 0.57 | 4.5 | 45:44:9:2 |
| 5 | LNP704 | G000499 | 0.59 | 4.5 | 45:44:9:2 |
| 6 | LNP1148 | G000481 | 0.73 | 4.5 | 45:44:9:2 |
| 7 | LNP1152 | G000499 | 0.45 | 6.0 | 50:38:9:3 |
| 8 | LNP1153 | G000482 | 0.53 | 6.0 | 50:38:9:3 |
| 9 | LNP1155 | G000571 | 0.70 | 6.0 | 50:38:9:3 |
| 10 | LNP1156 | G000572 | 0.58 | 6.0 | 50:38:9:3 |
| 11 | LNP1157 | G000480 | 0.84 | 6.0 | 50:38:9:3 |
| 12 | LNP1159 | G000488 | 0.79 | 6.0 | 50:38:9:3 |
| 13 | LNP1160 | G000493 | 0.71 | 6.0 | 50:38:9:3 |
| 14 | LNP1161 | G000500 | 0.66 | 6.0 | 50:38:9:3 |
| 15 | LNP1162 | G000567 | 0.69 | 6.0 | 50:38:9:3 |
| 16 | LNP1163 | G000570 | 0.66 | 6.0 | 50:38:9:3 |

Figure 9:
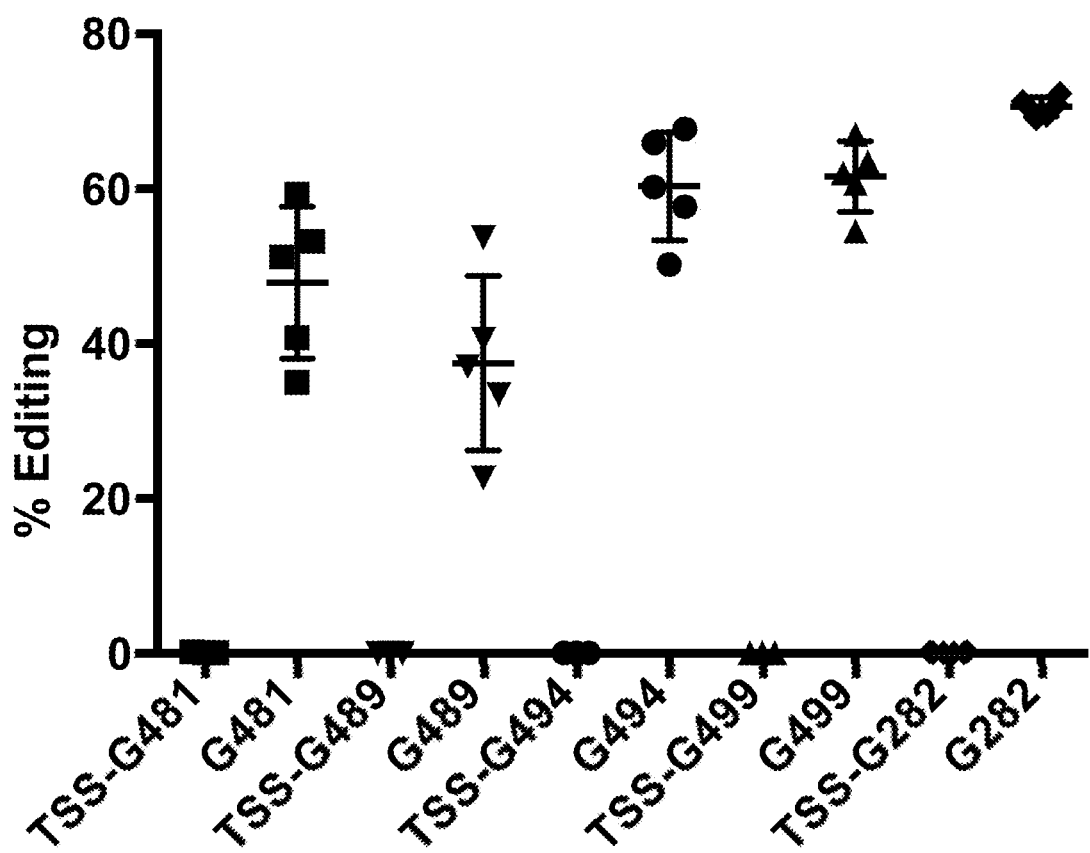
FIG. 9 shows percentage liver editing of TTR observed following administration of LNP formulations to mice with humanized (G481-G499) or murine (G282) TTR. Note: the first three '0's in each Guide ID is omitted from the Figure, for example "G481" is "G000481" in Tables 2 and 3.
Figure 10A:
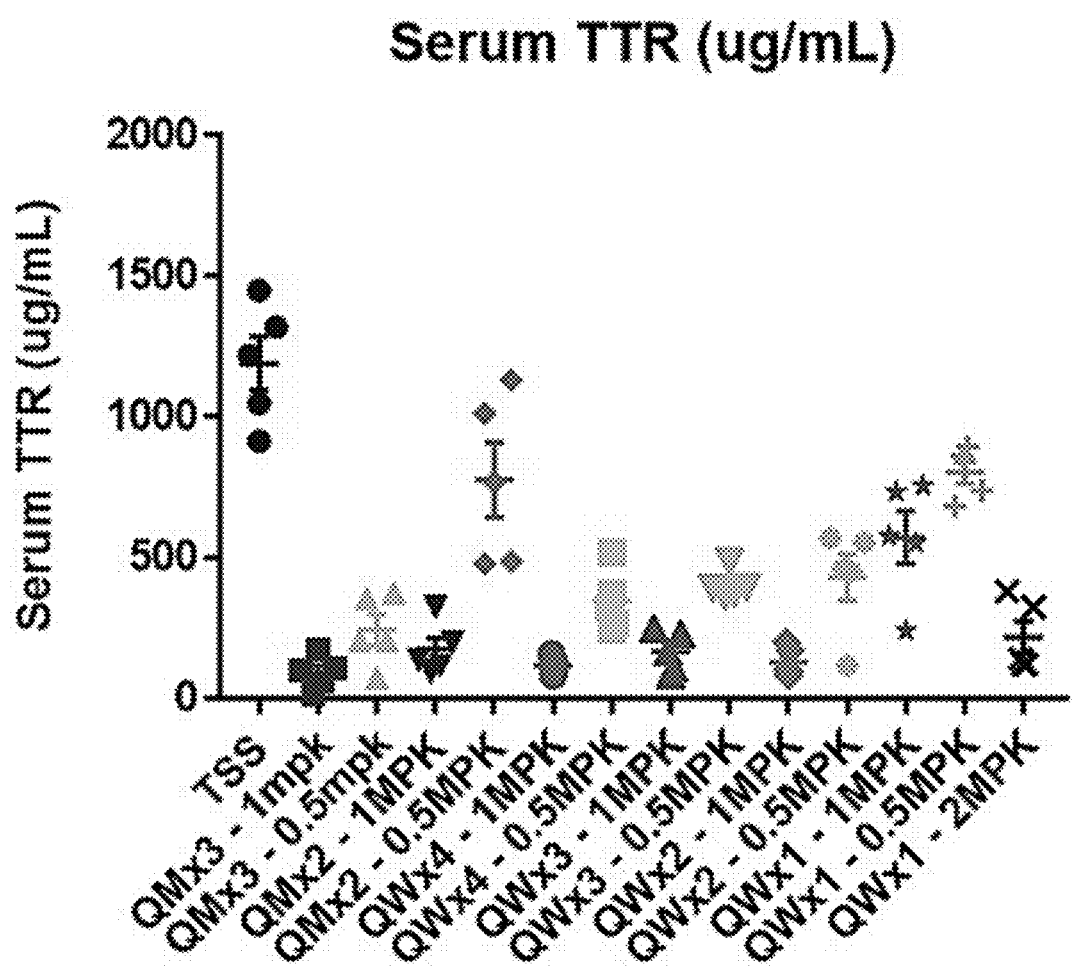
FIGS. 10A-B show serum TTR levels observed following the dosing regimens indicated on the horizontal axis as µg/ml (FIG. 10A) or percentage of TSS control (FIG. 10B). MPK=mg/kg throughout.
Figure 10B:
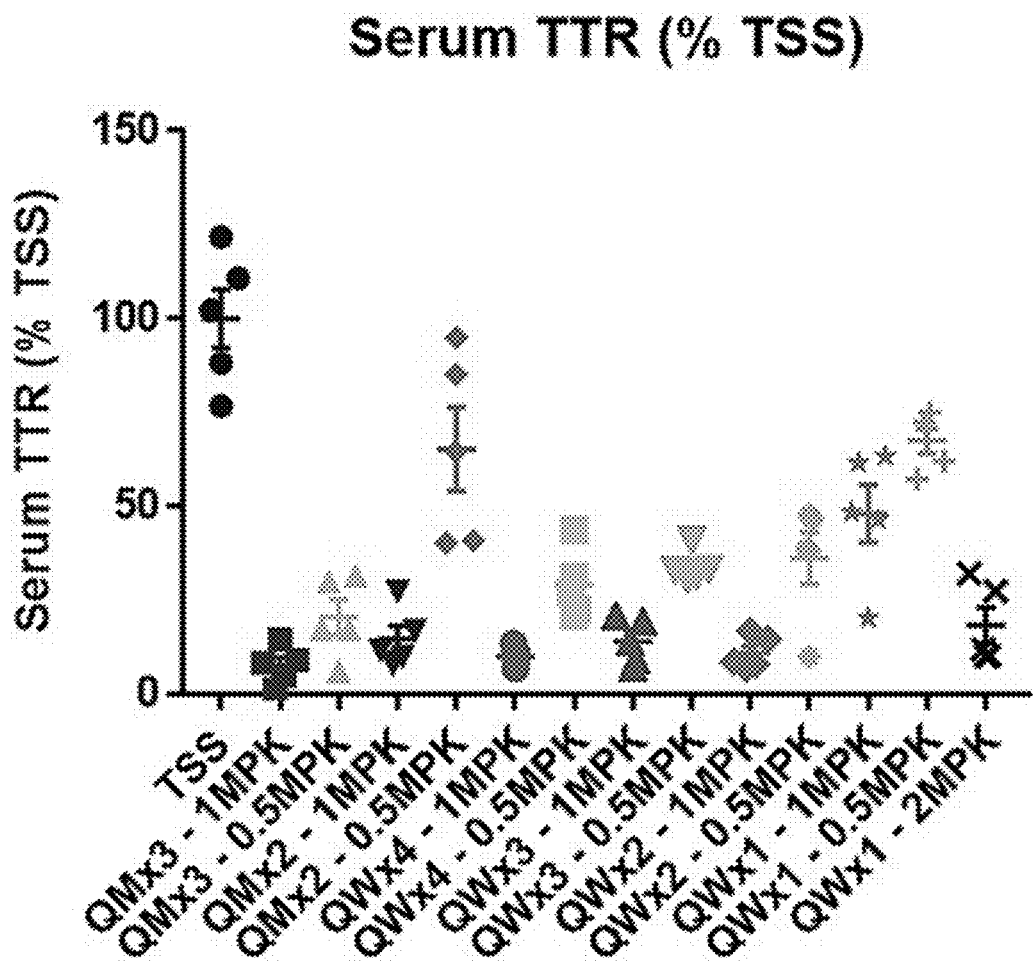
Figure 11A:
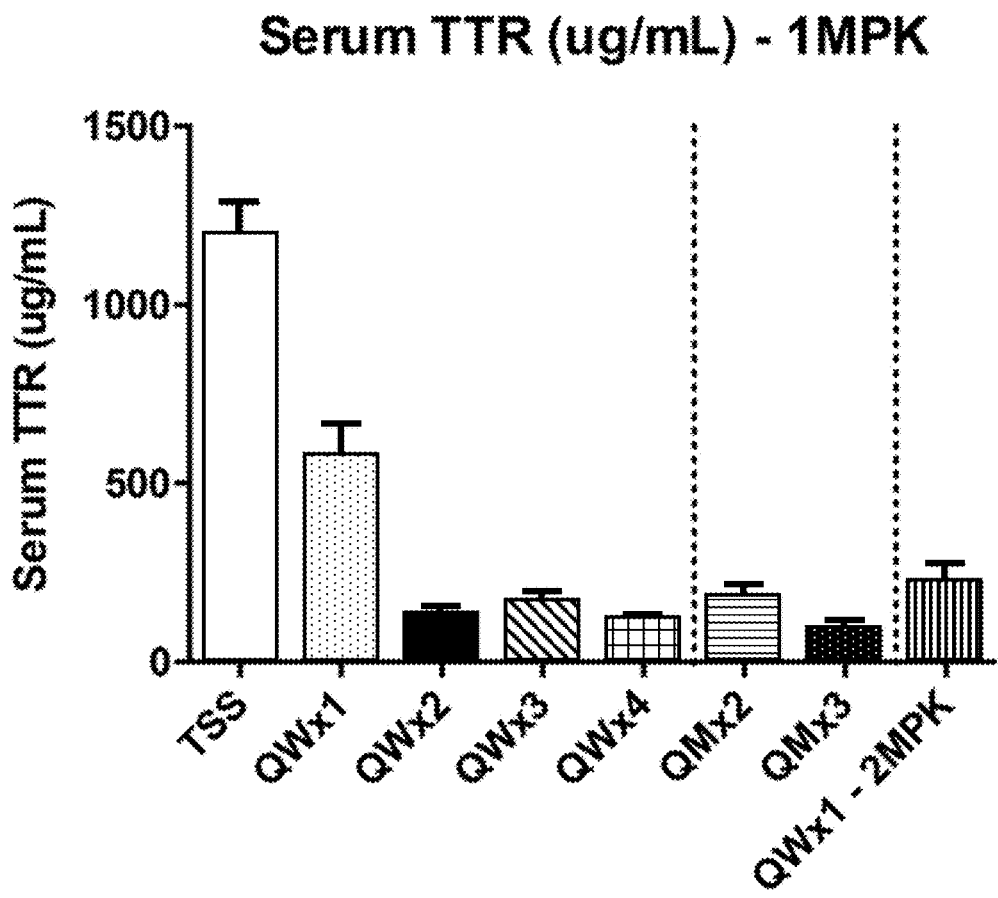
FIGS. 11A-B show serum TTR levels observed following the dosing regimens indicated on the horizontal axis for 1 mg/kg (FIG. 11A) or 0.5 mg/kg dosages (FIG. 11B). Data for a single 2 mg/kg dose is included as the right column in both panels.
Figure 11B:
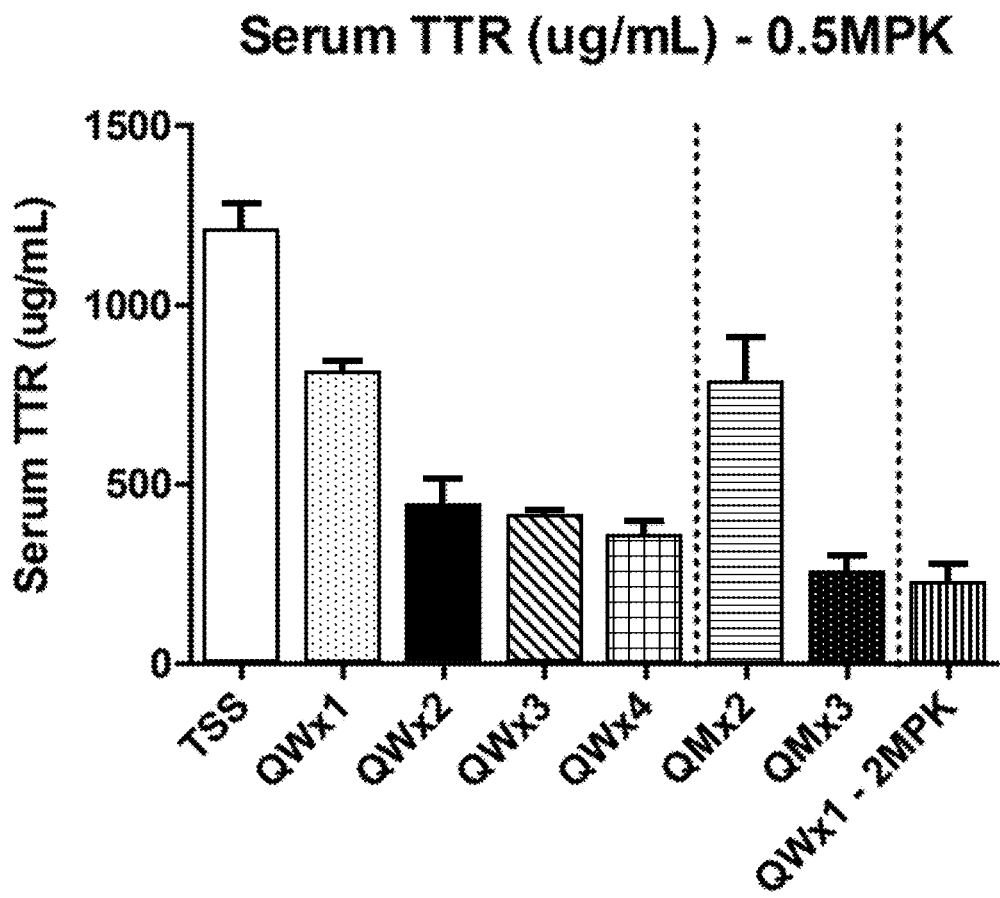
Figure 13:
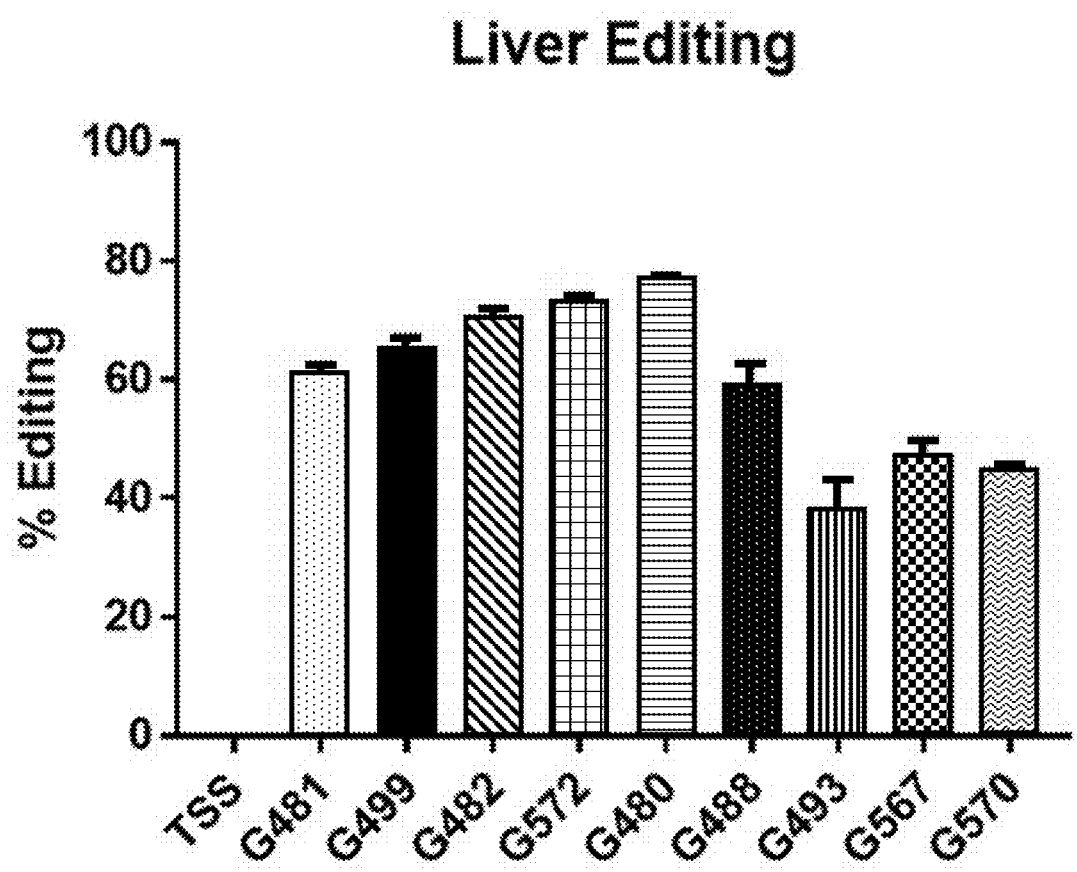
FIG. 13 shows percent liver editing observed following administration of LNP formulations to mice humanized with respect to the TTR gene. Note: the first three '0's in each Guide ID is omitted from the Figure, for example "G481" is "G000481" in Tables 2 and 3.

LNPs having Formulation numbers 1-5 contained Cas9 mRNA of SEQ ID NO:2 and LNPs having Formulation Numbers 6-16 contained Cas9 mRNA of SEQ ID NO: 1, all in a 1:1 ratio by weight to the guide. The LNPs contained Lipid A, Cholesterol, DSPC, and PEG2k-DMG in the molar ratios recited in Table 25, respectively. Dosing with LNPs having Formulation Numbers 1-5 was at 2 mg/kg (total RNA content) and dosing with LNPs having Formulation Numbers 6-16 was at 1 mg/kg (total RNA content). Liver editing results were determined using primers designed to amplify the region of interest for NGS analysis. Liver editing results for Formulation Numbers 1-5 are shown in FIG. 9 and indicate editing of the human TTR sequence with each of the four guides tested at a level >35% editing (mean values) with G000494 and G000499 providing values near 60%. Liver editing results for formulation numbers 6-8, 10-13, and 15-16 are shown in FIG. 13 and Table 26, which show efficient editing of the human TTR sequence with each of the formulations tested. Greater than 38% editing was seen for all formulations, with several formulations providing editing values greater than 60%. Formulations 9 and 14 are not shown due to the design of the PCR amplicon and a resulting low number of sequencing reads.

Figures 14A, 14B:
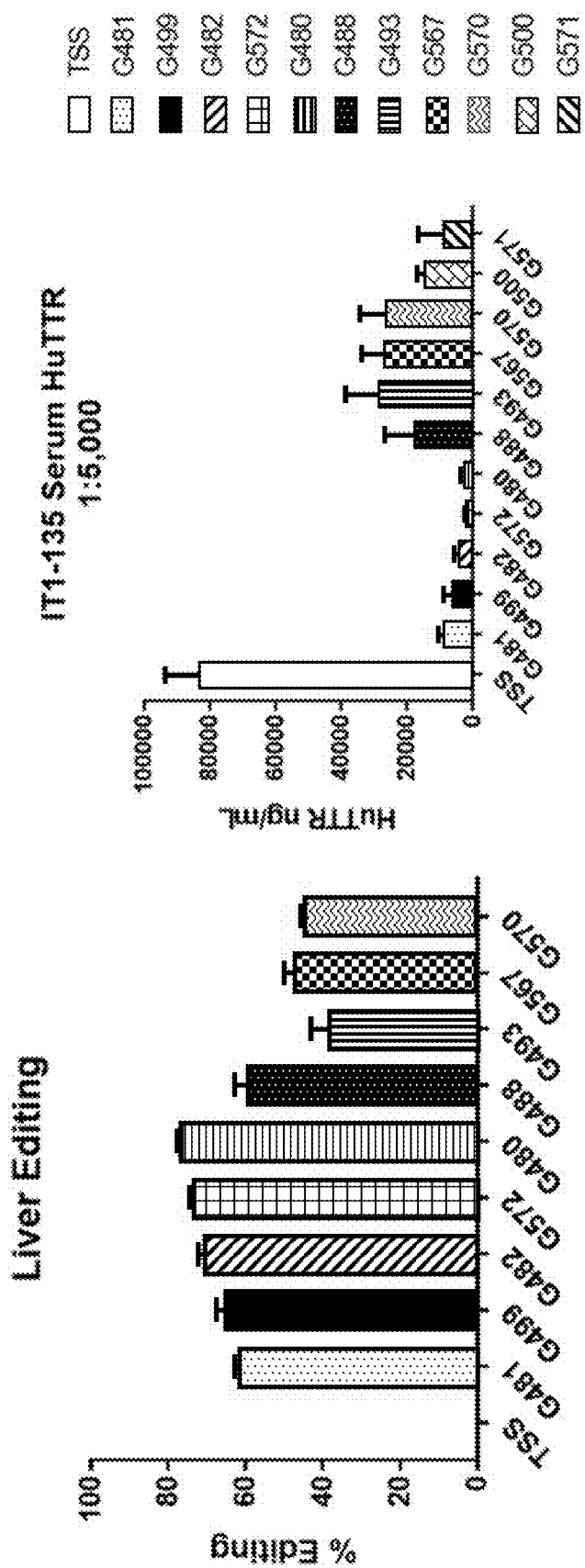
FIGS. 14A-B show that there is correlation between liver editing (FIG. 14A) and serum human TTR levels (FIG. 14B) following administration of LNP formulations to mice humanized with respect to the TTR gene. Note: the first three '0's in each Guide ID is omitted from the Figure, for example "G481" is "G000481" in Tables 2 and 3.

The level of human TTR in serum was measured in the mice provided formulation numbers 6-8, 10-13, and 15-16. See FIG. 14B. FIG. 14A is a repeat of FIG. 13 provided for comparison purposes. Knockdown of serum human TTR was detected for each formulation tested, which correlated with the amount of editing detected in liver (See FIG. 14A vs 14B, Table 26).

TABLE 26

| GUIDE ID | % Editing | Serum TTR(% TSS) |
|---|---|---|
| TSS (vehicle) | 0.06 | 100 |
| G481 | 61.28 | 10.52 |
| G499 | 65.66 | 8.39 |
| G482 | 70.86 | 4.65 |
| G572 | 73.52 | 2.11 |
| G480 | 77.34 | 3.48 |
| G488 | 59.125 | 27.78 |
| G493 | 38.55 | 49.73 |
| G567 | 47.525 | 44.24 |
| G570 | 45.5 | 41.73 |
| G571 | 33.88 | 11.39 |
| G500 | 44.44 | 34.28 |

Figure 26A:
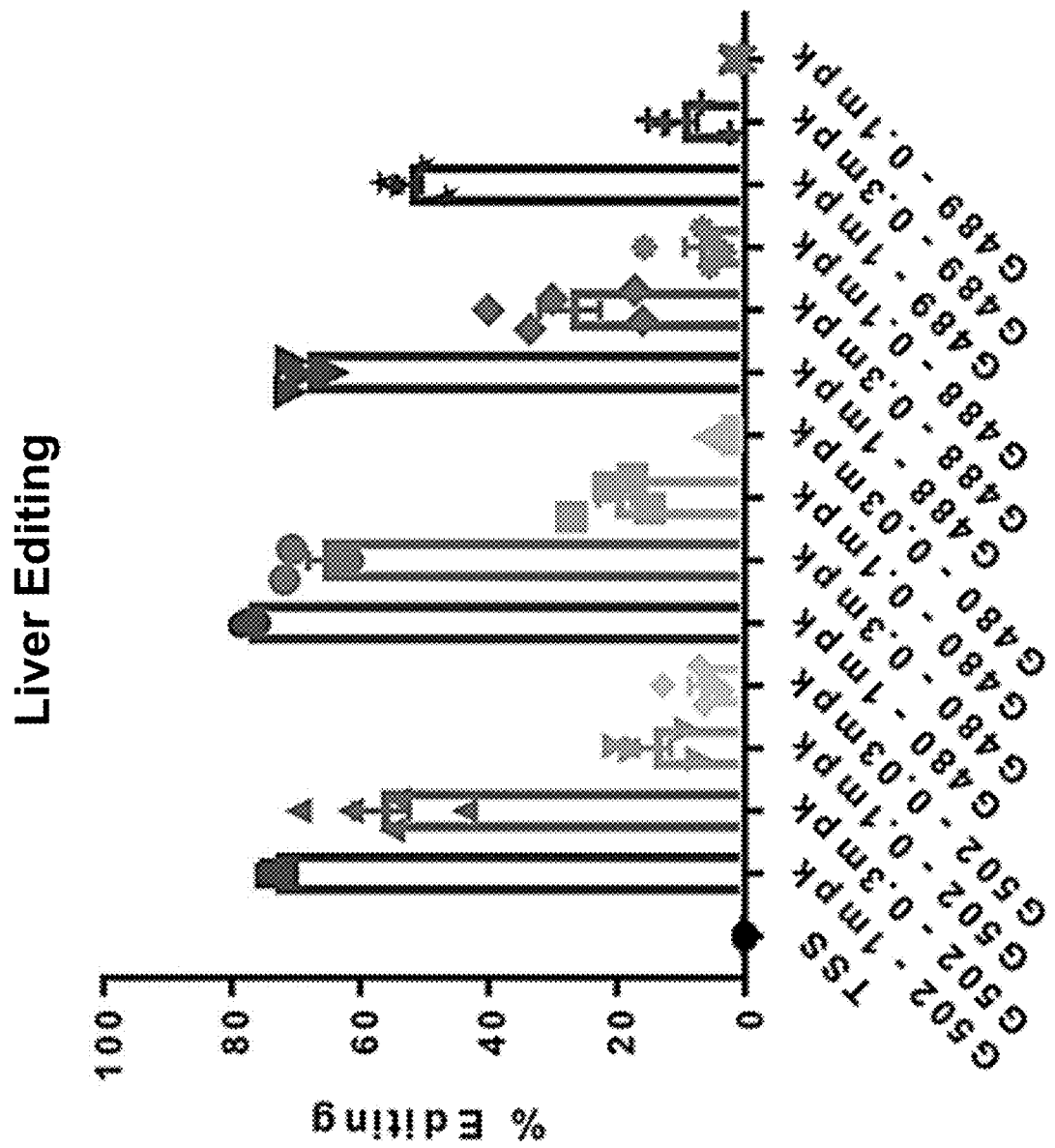
FIGS. 26A-C show liver TTR editing (FIG. 26A) and serum TTR results (in µg/mL (FIG. 26B) and as percentage of TSS-treated control (FIG. 26C)), respectively, from humanized TTR mice dosed with LNP formulations across a range of doses with guides G000480, G000488, G000489 and G000502 and containing Cas9 mRNA (SEQ ID NO: 1) in a 1:1 ratio by weight to the guide.
Figure 26B:
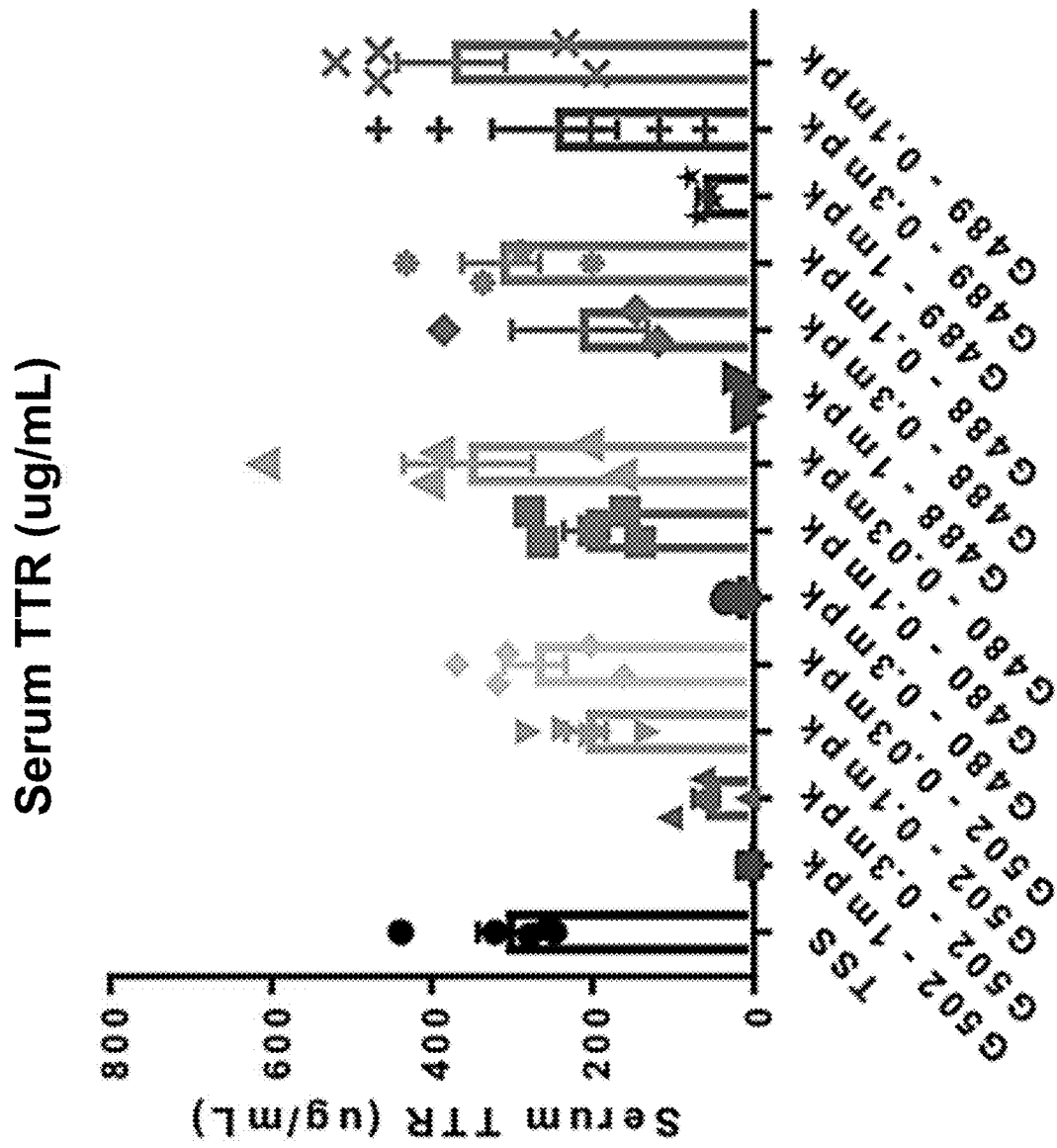
Figure 26C:
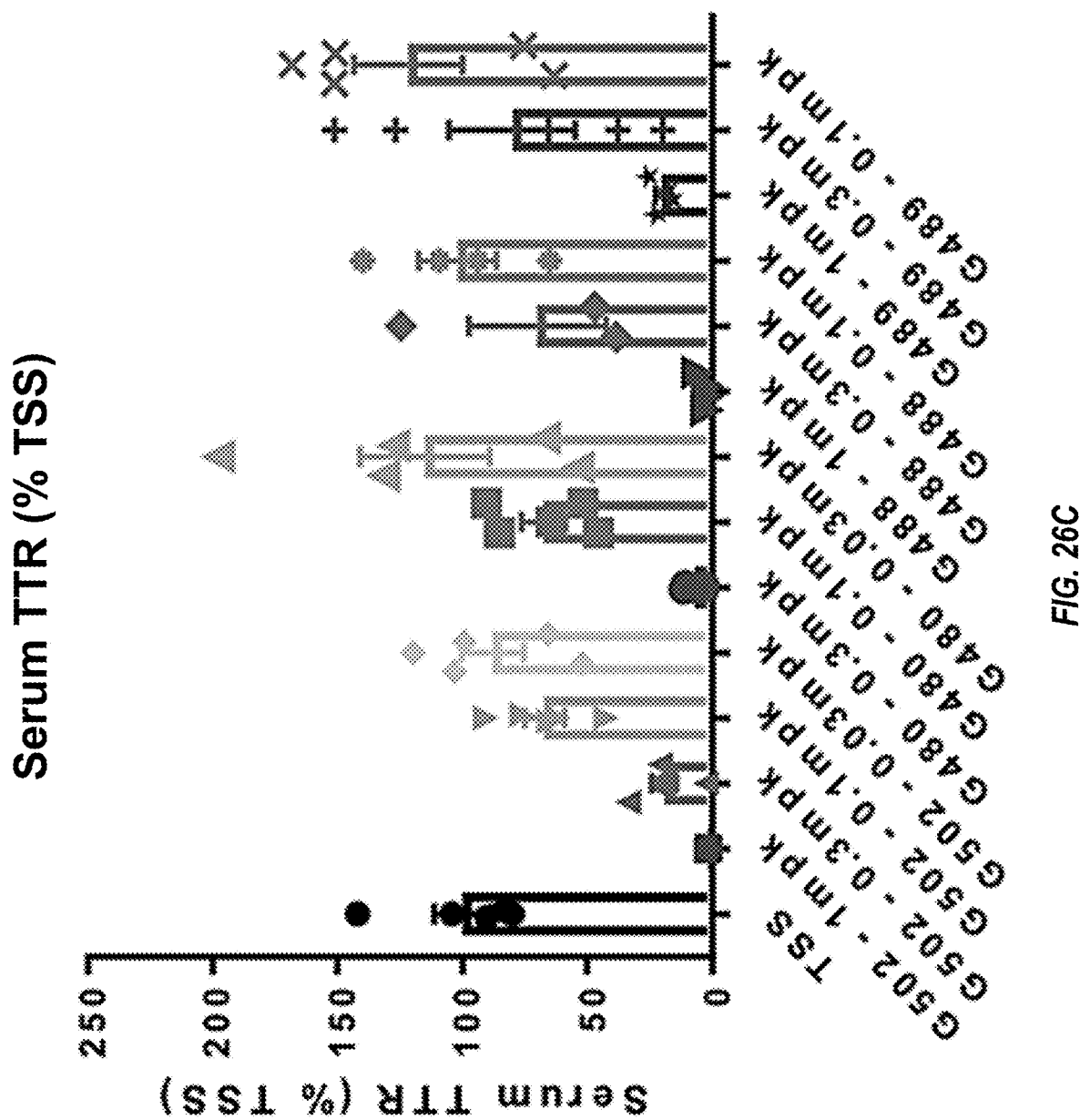

In another set of experiments, humanized TTR mice were dosed with LNP formulations across a range of doses with guides G000480, G000488, G000489 and G000502. The formulations contained Cas9 mRNA (SEQ ID NO: 1) in a 1:1 ratio by weight to the guide. The LNPs contained Lipid A, Cholesterol, DSPC, and PEG2k-DMG in a 50:38:9:3 molar ratio, respectively, and having a N:P ratio of 6. Dosing was at 1, 0.3, 0.1, or 0.03 mg/kg (n=5/group). The LNPs were prepared using the cross-flow procedure described above and purified and concentrated using PD-10 columns and Amicon centrifugal filter units, respectively. Liver editing results were determined using primers designed to amplify the region of interest for NGS analysis and serum human TTR levels were measured as described above. Results for liver editing are shown in FIG. 26A and serum human TTR levels in FIG. 26B-C. A dose response for both editing and serum TTR levels was evident.

Figure 27A:
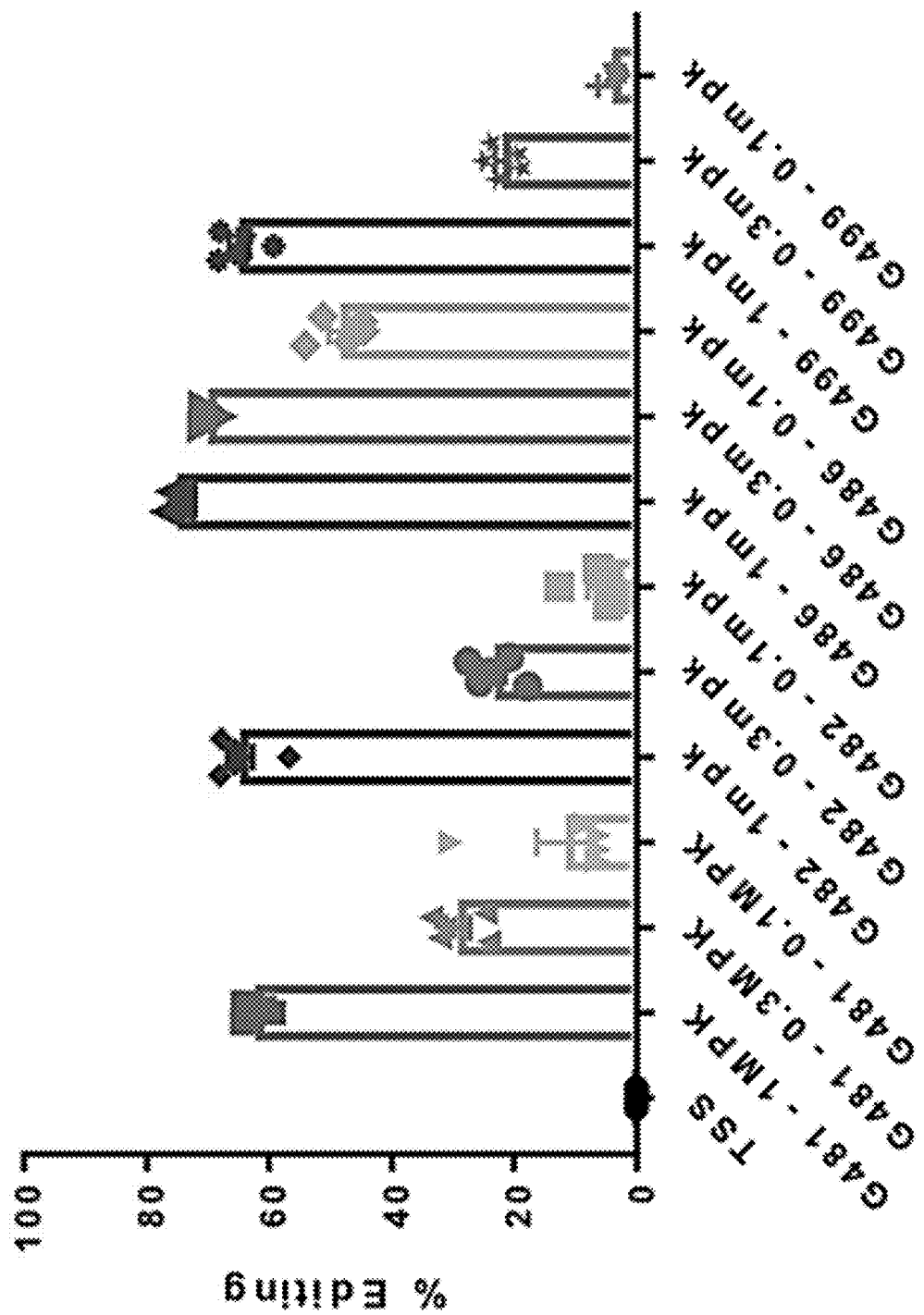
FIGS. 27A-C show liver TTR editing (FIG. 27A) and serum TTR results (in µg/mL (FIG. 27B) and as percentage of TSS-treated control (FIG. 27C)), respectively, from humanized TTR mice dosed with LNP formulations across a range of doses with guides G000481, G000482, G000486 and G000499 and containing Cas9 mRNA (SEQ ID NO: 1) in a 1:1 ratio by weight to the guide.
Figure 27B:
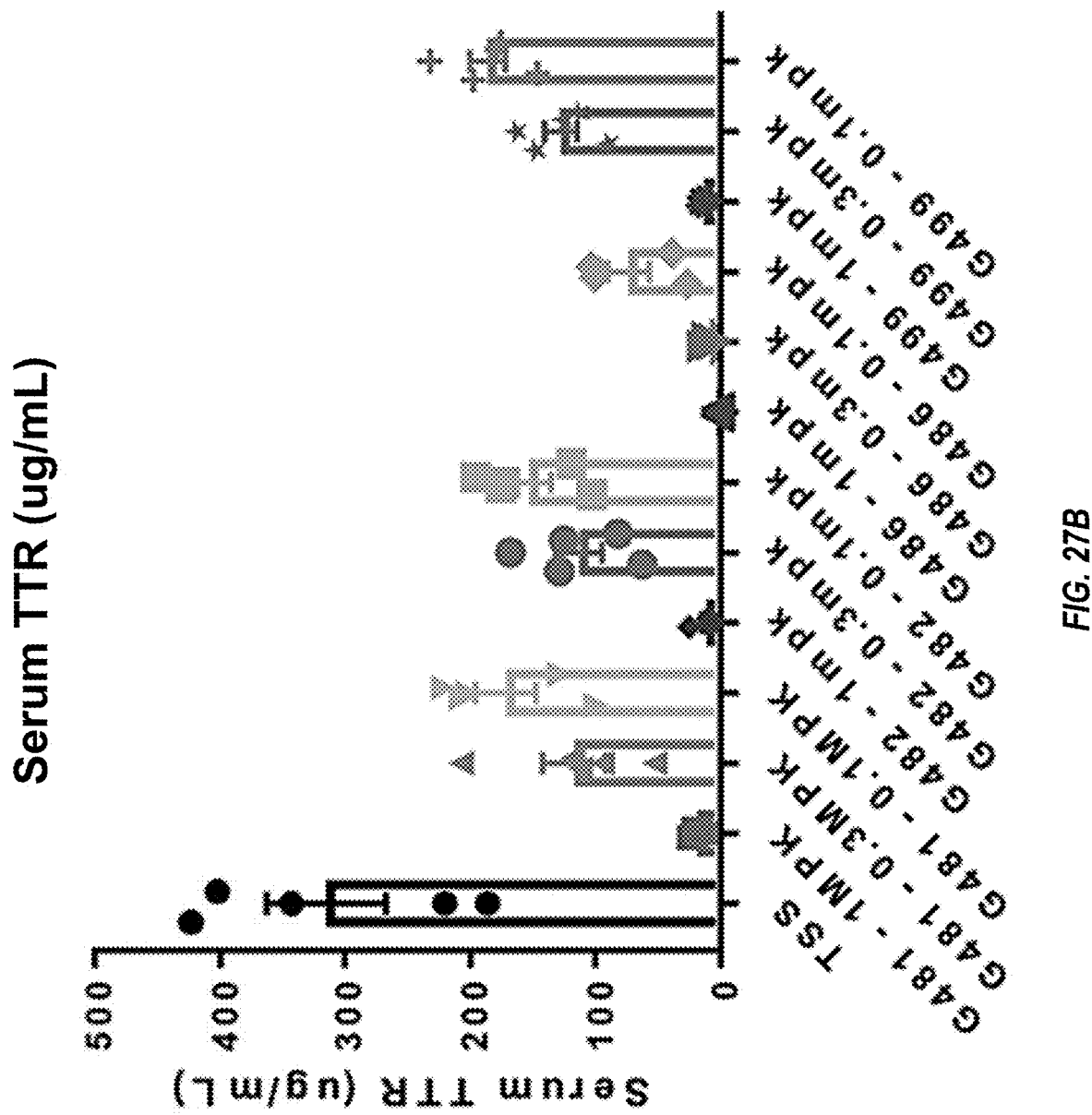
Figure 27C:
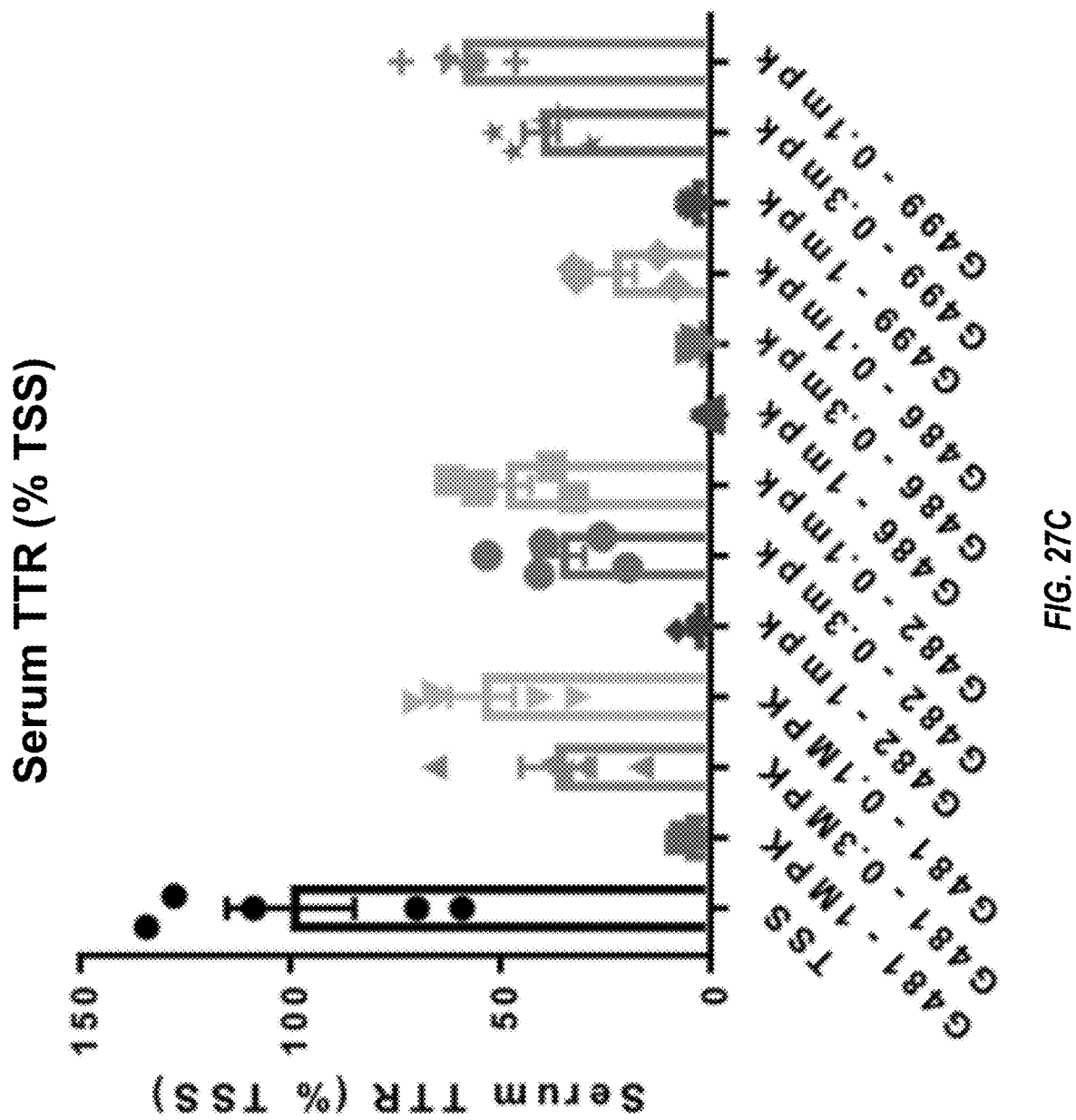

In another set of experiments, humanized TTR mice were dosed with LNP formulations across a range of doses with guides G000481, G000482, G000486 and G000499. The formulations contained Cas9 mRNA (SEQ ID NO: 1) in a 1:1 ratio by weight to the guide. The LNPs contained Lipid A, Cholesterol, DSPC, and PEG2k-DMG in a 50:38:9:3 molar ratio, respectively, and had an N:P ratio of 6. Dosing was at 1, 0.3, or 0.1 mg/kg (n=5/group). The LNPs were prepared using the cross-flow procedure described above and purified and concentrated using PD-10 columns and Amicon centrifugal filter units, respectively. Liver editing results were determined using primers designed to amplify the region of interest for NGS analysis and serum human TTR levels were measured as described above. Results for liver editing are shown in FIG. 27A and serum human TTR levels in FIG. 27B-C. A dose response for both editing and serum TTR levels was evident.

Figure 28A:
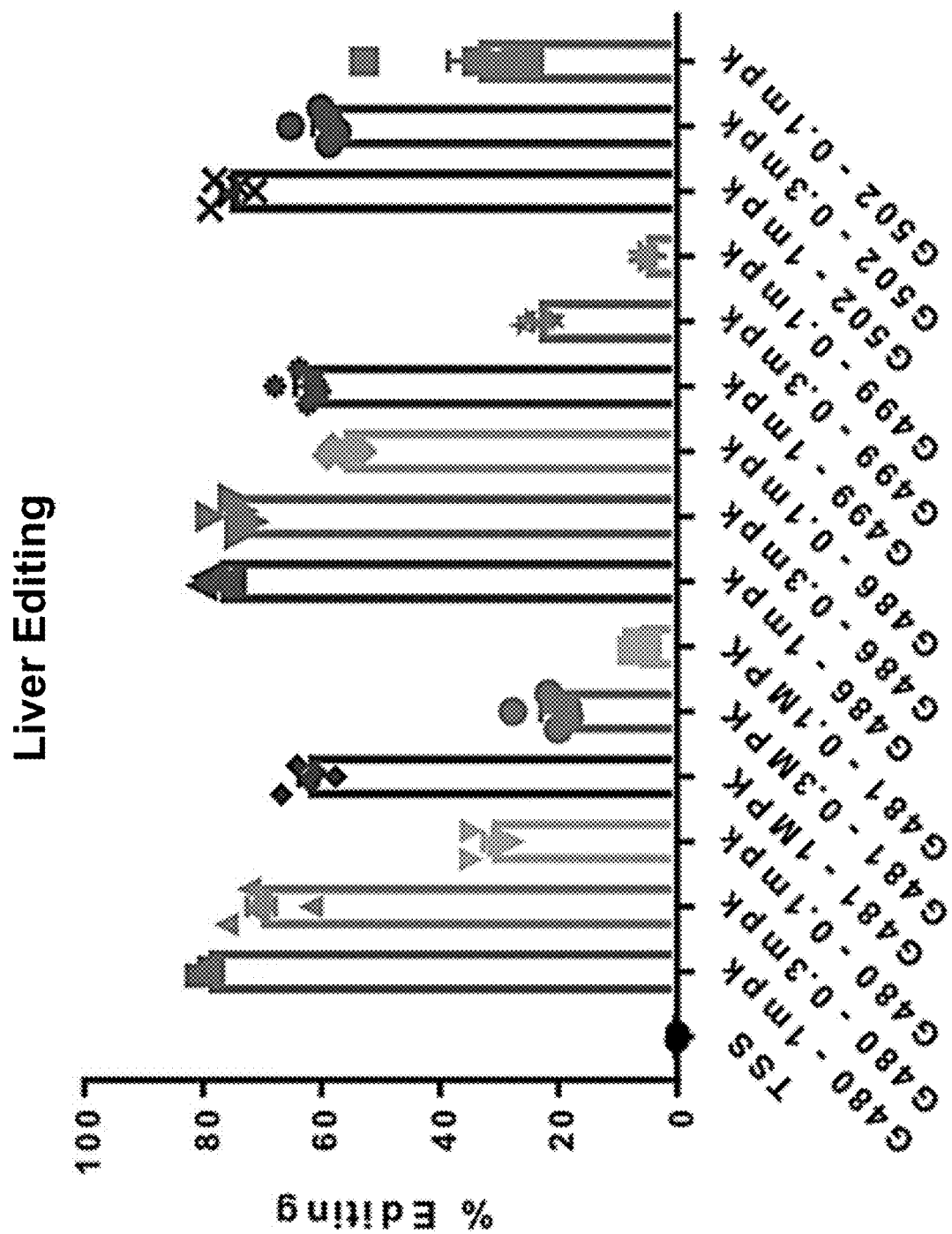
FIGS. 28A-C show liver TTR editing (FIG. 28A) and serum TTR results (in µg/mL (FIG. 28B) and as percentage of TSS-treated control (FIG. 28C)), respectively, from humanized TTR mice dosed with LNP formulations across a range of doses with guides G000480, G000481, G000486, G000499 and G000502 and containing Cas9 mRNA (SEQ ID NO: 1) in a 1:2 ratio by weight to the guide.
Figure 28B:
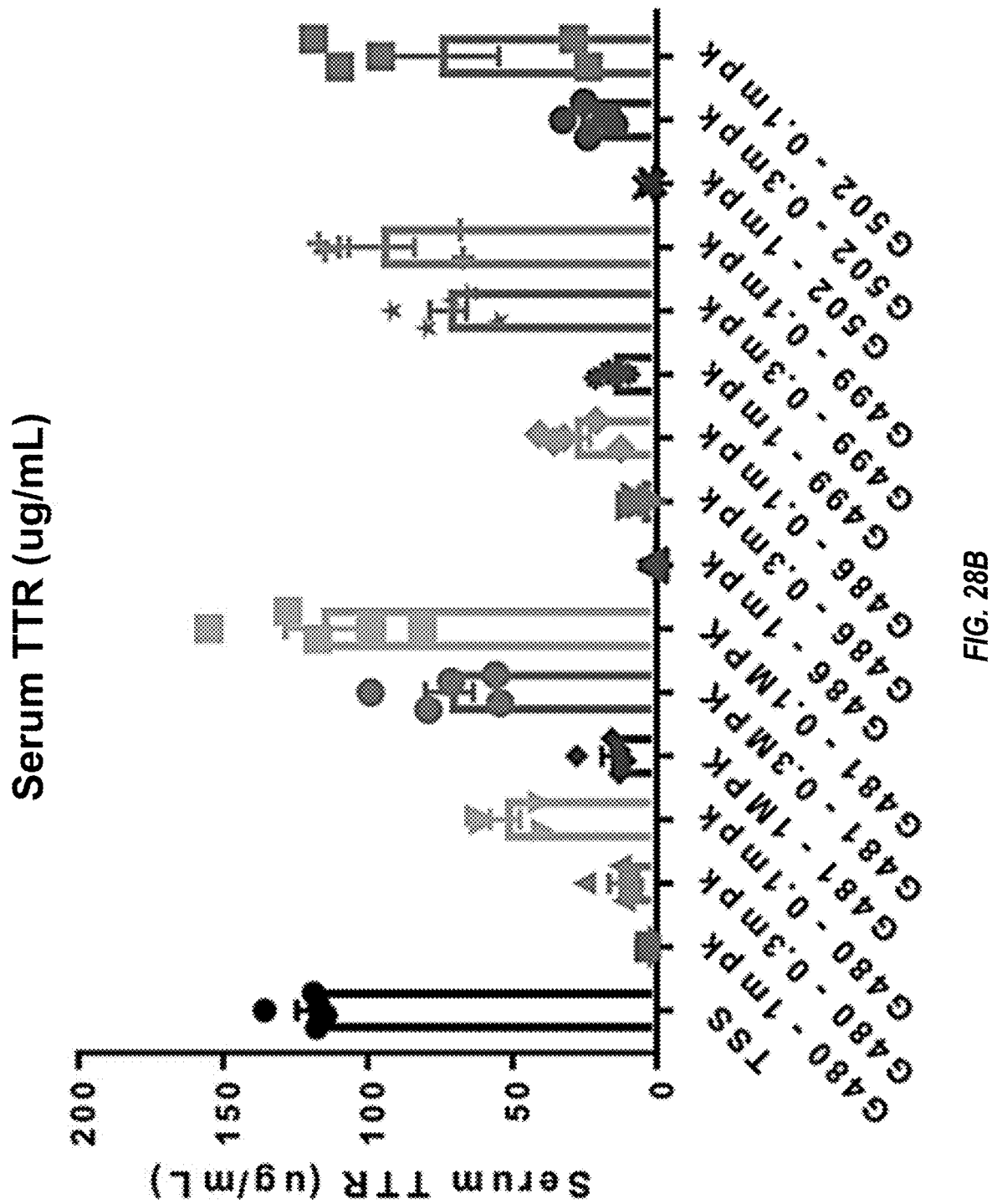
Figure 28C:
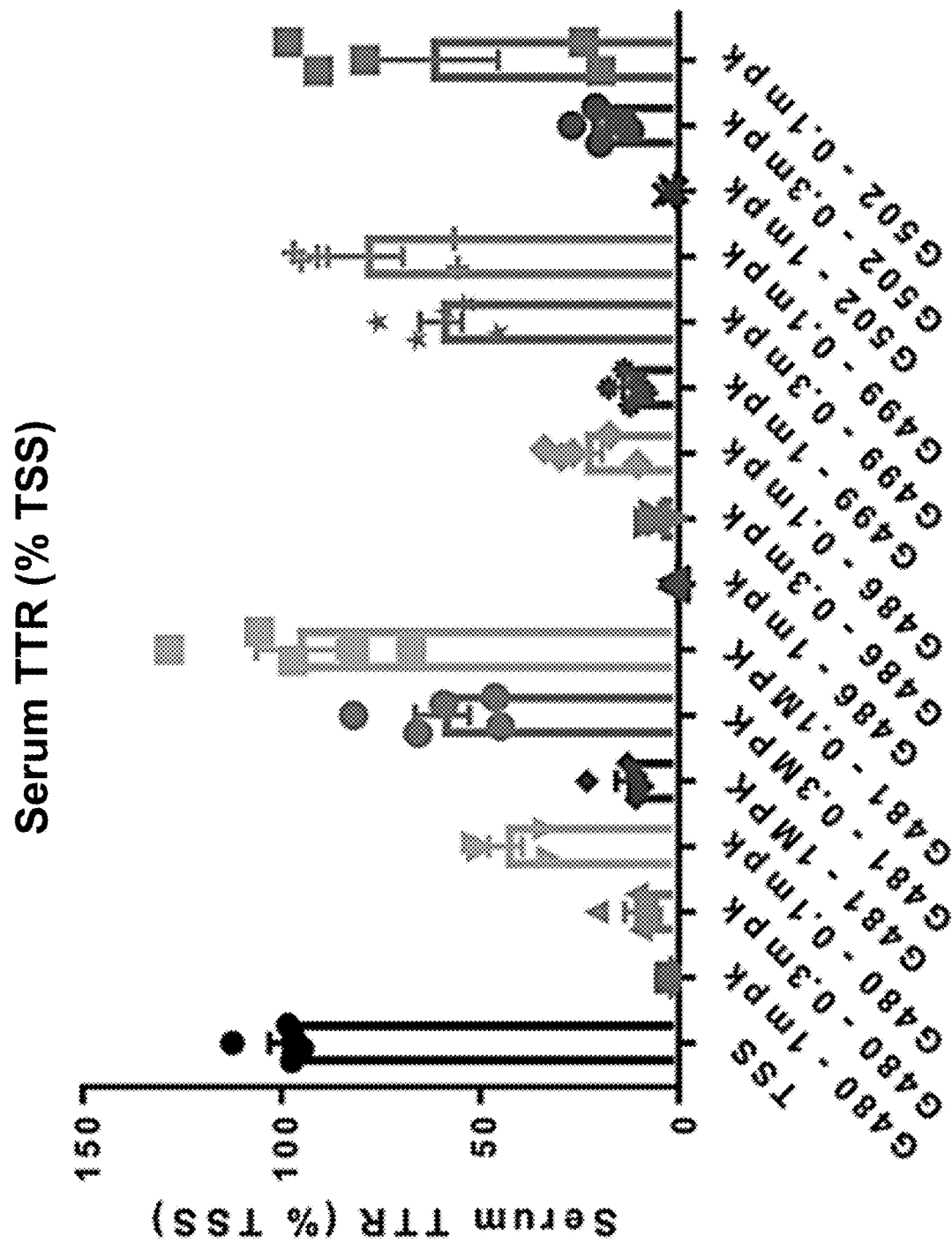

In another set of experiments, humanized TTR mice were dosed with LNP formulations across a range of doses with guides G000480, G000481, G000486, G000499 and G000502. The formulations contained Cas9 mRNA (SEQ ID NO: 1) in a 1:2 ratio by weight to the guide. The LNPs contained Lipid A, Cholesterol, DSPC, and PEG2k-DMG in a 50:38:9:3 molar ratio, respectively, and had an N:P ratio of 6. Dosing was at 1, 0.3, or 0.1 mg/kg (n=5/group). The LNPs were prepared using the cross-flow procedure described above and purified and concentrated using PD-10 columns and Amicon centrifugal filter units, respectively. Liver editing results were determined using primers designed to amplify the region of interest for NGS analysis and serum human TTR levels were measured as described above. Results for liver editing are shown in FIG. 28A and serum human TTR levels in FIG. 28B-C. A dose response for both editing and serum TTR levels was evident.

Figure 15A:
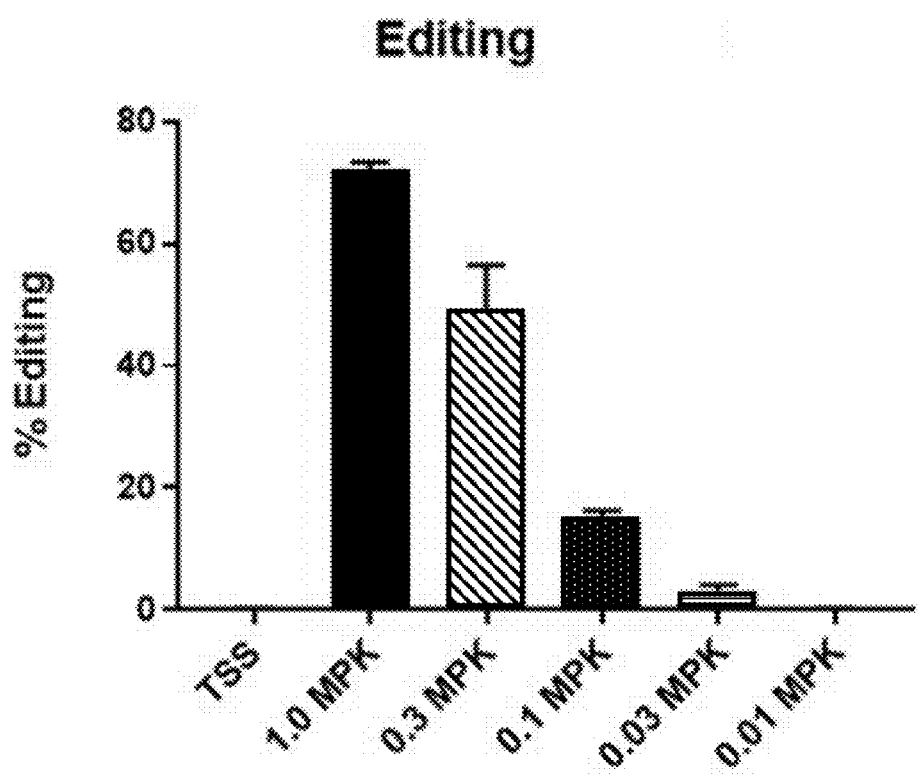
FIGS. 15A-B show that there is a dose response with respect to percent editing (FIG. 15A) and serum TTR levels (FIG. 15B) in wild type mice following administration of LNP formulations comprising guide G502, which is cross homologous between mouse and cyno.
Figure 15B:
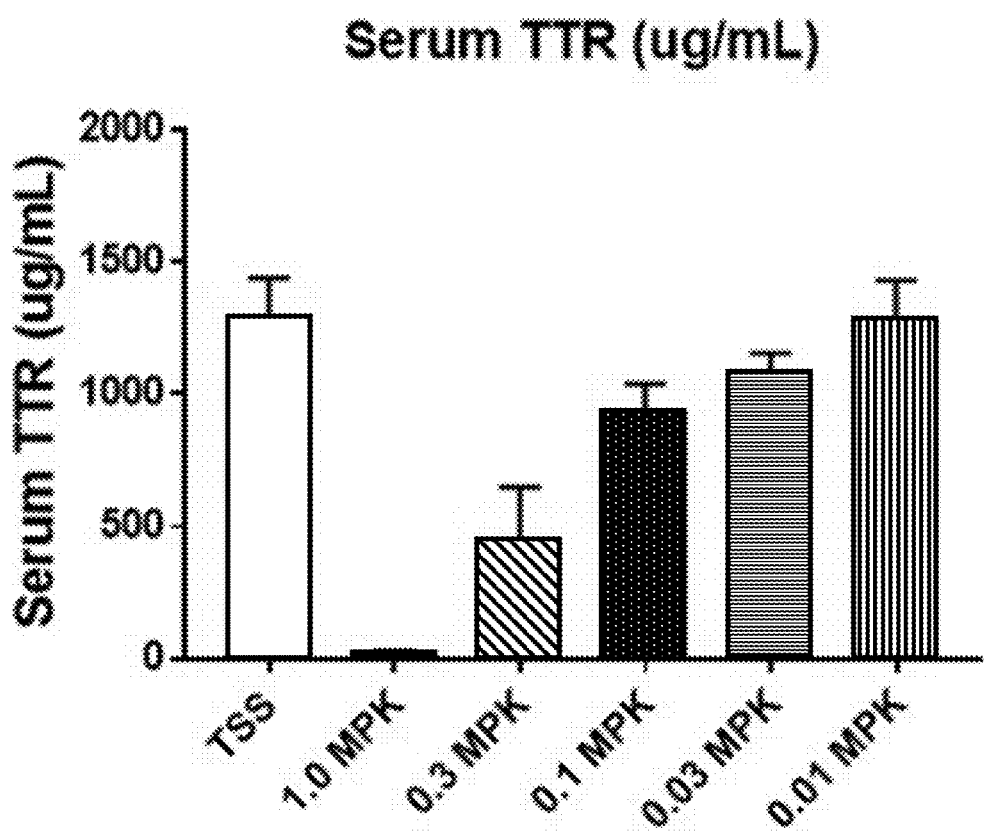

In separate experiments using wild type CD-1 mice, an LNP formulation comprising guide G000502, which is cross homologous between mouse and cyno, was tested in a dose response study. The formulation contained Cas9 mRNA (SEQ ID NO: 1) in a 1:1 ratio by weight to the guide. The LNP contained Lipid A, Cholesterol, DSPC, and PEG2k-DMG in a 45:44:9:2 molar ratio, respectively, and having a N:P ratio of 6. Dosing was at 1, 0.3, 0.1, 0.03, or 0.01 mg/kg (n=5/group). Liver editing results were determined using primers designed to amplify the region of interest for NGS analysis. Results for liver editing are shown in FIG. 15A and serum mouse TTR levels in FIG. 15B. A dose response for both editing and serum TTR levels was evident.

Example 9. LNP Delivery to Mice in Multiple Doses

Mice (females from Charles River Laboratory, aged approximately 6-7 weeks) were dosed with an LNP formulation LNP705, prepared using cross-flow and TFF procedures as described above containing G000282 ("G282") and Cas9 mRNA (SEQ ID NO: 2) in a 1:1 ratio by weight and a total RNA concentration of 0.5 mg/ml. The LNP had an N:P ratio of 4.5 and contained Lipid A, Cholesterol, DSPC, and PEG2k-DMG in a 45:44:9:2 molar ratio, respectively. Groups were dosed either once weekly up to one, two, three, or four weeks (QWx1-4) or once monthly up to two or three months (QMx2-3). Dosages were 0.5 mg/kg or 1 mg/kg (total RNA content). Control groups received a single dose on day 1 of 0.5, 1, or 2 mg/kg. Each group contained 5 mice. Serum TTR was analyzed by ELISA and at necropsy the liver, spleen and muscle were each collected for NGS editing analysis. Groups are shown in Table 27. X=sacrifice and necropsy. MPK=mg/kg.

TABLE 27

Study Groups

| Group | Duration/ Dose Regimen | Dose (MPK) | Total Dose (MPK) Given | Dose Day 1 | Dose Day 8 | Dose Day 15 | Dose Day 22 | NX Day 28 | Dose Day 43 | NX Day 49 |
|---|---|---|---|---|---|---|---|---|---|---|
| 1 | 4 Week Multi Dose/ QWx4 | 0 (TSS control) | 0 | X | X | X | X | X | | |
| 2 | 2 Month | 1 | 3 | X | | | X | | X | X |
| 3 | Multi Dose/ QMx3 | 0.5 | 1.5 | X | | | X | | X | X |
| 4 | 1 Month | 1 | 2 | X | | | X | X | | |
| 5 | Multi Dose/ QMx2 | 0.5 | 1 | X | | | X | X | | |
| 6 | 4 Week | 1 | 4 | X | X | X | X | X | | |
| 7 | Multi Dose/ QWx4 | 0.5 | 2 | X | X | X | X | X | | |
| 8 | 3 Week | 1 | 3 | | X | X | X | X | | |
| 9 | Multi Dose/ QWx3 | 0.5 | 1.5 | | X | X | X | X | | |
| 10 | 2 Week | 1 | 2 | | | X | X | X | | |
| 11 | Multi Dose/ QWx2 | 0.5 | 1 | | | X | X | X | | |
| 12 | Single Dose/ | 1 | 1 | | | | X | X | | |
| 13 | QWx1 | 0.5 | 0.5 | | | | X | X | | |
| 14 | | 2 | 2 | | | | Day 26 | Day 32 | | |

Figure 12A:
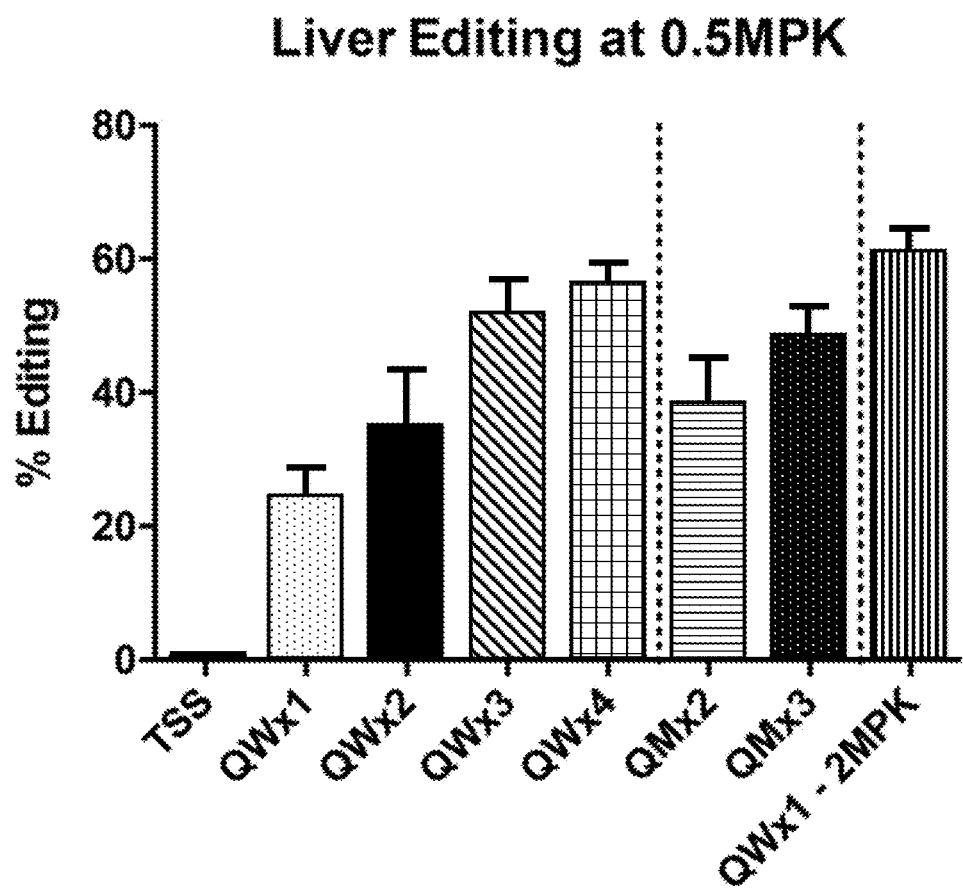
FIGS. 12A-B show percentage liver editing observed following the dosing regimens indicated on the horizontal axis for 1 mg/kg (FIG. 12A) or 0.5 mg/kg dosages (FIG. 12B).
Figure 12B:
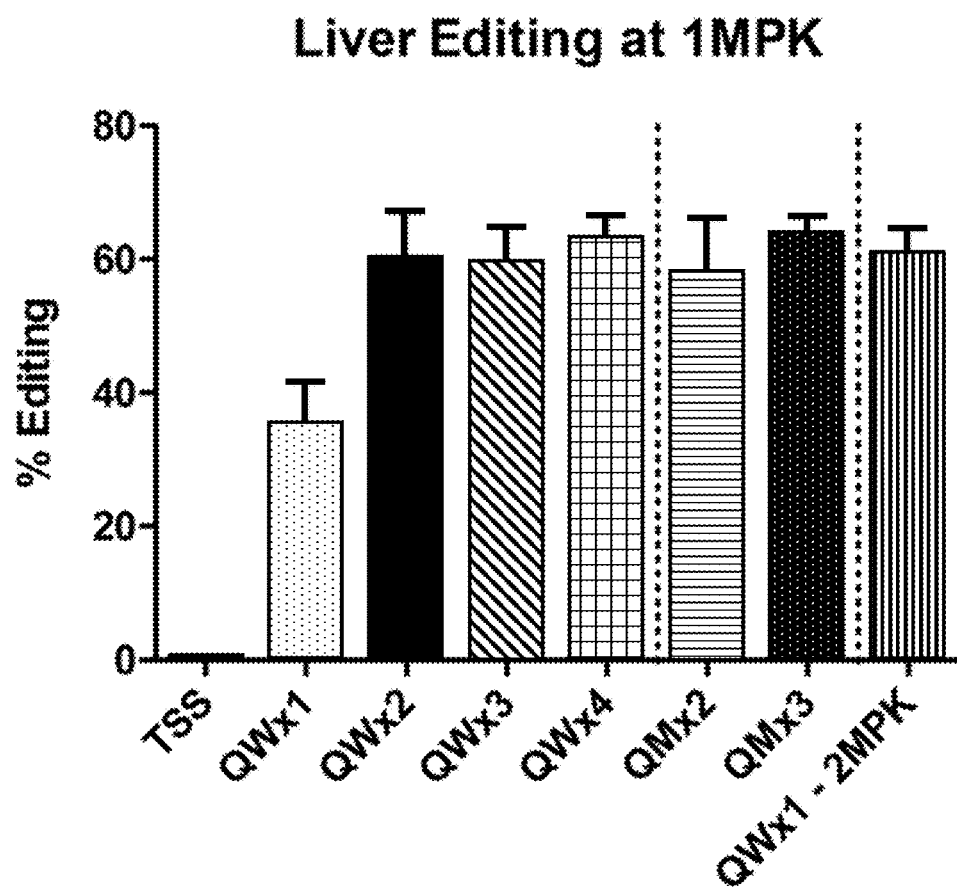
Figure 12C:
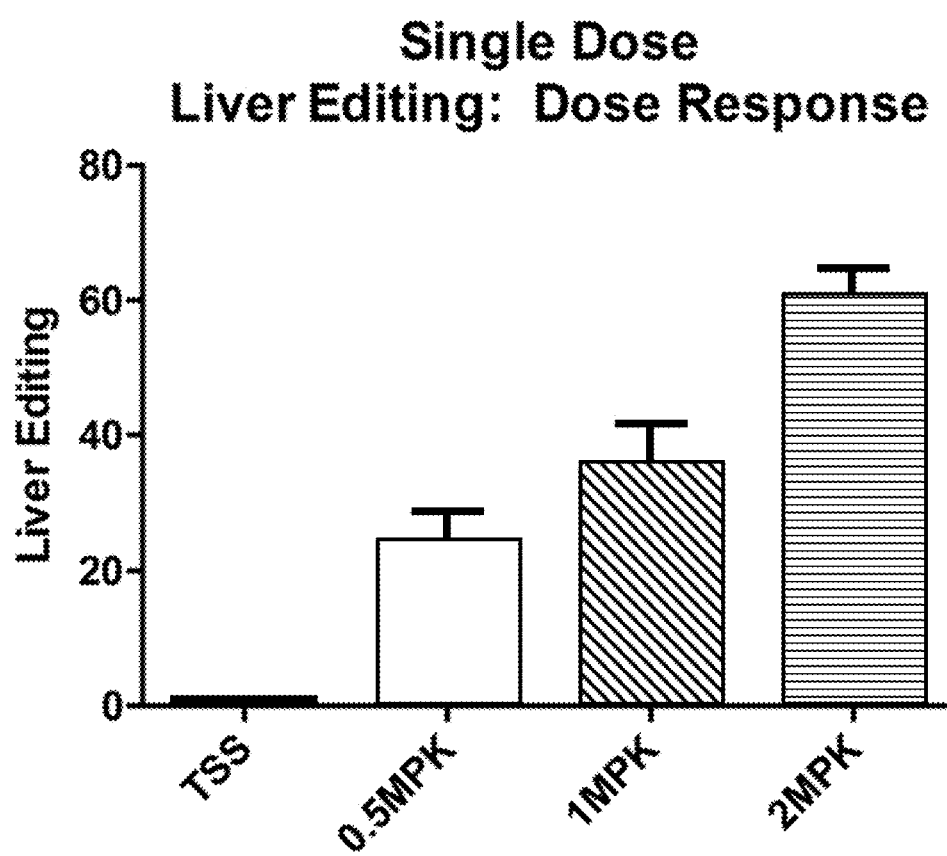
FIG. 12C shows percentage liver editing observed following a single dose at 0.5, 1, or 2 mg/kg.

Table 28 and FIGS. 10A-11B show serum TTR level results (% KD=% knockdown). Table 29 and FIGS. 12A-C show liver editing results.

TABLE 28

Serum TTR Results.

| Time Regimen | Dose | Serum TTR (μg/mL) | Serum TTR (% KD) |
|---|---|---|---|
| QW x4 | TSS | 1190.7 | — |
| QM x3 | 0.5 | 245.01 | 79.42 |
| QM x2 | 0.5 | 776.73 | 34.77 |
| QW x4 | 0.5 | 347.43 | 70.82 |
| QW x3 | 0.5 | 405.70 | 65.93 |
| QW x2 | 0.5 | 432.25 | 63.70 |
| QW x1 | 0.5 | 804.06 | 32.47 |
| QM x3 | 1 | 91.95 | 92.28 |
| QM x2 | 1 | 176.81 | 85.15 |
| QW x4 | 1 | 119.52 | 89.96 |

TABLE 28-continued

Serum TTR Results.

| Time Regimen | Dose | Serum TTR (µg/mL) | Serum TTR (% KD) |
|---|---|---|---|
| QW ×3 | 1 | 167.15 | 85.96 |
| QW ×2 | 1 | 130.98 | 89.00 |
| QW ×1 | 1 | 573.02 | 51.88 |
| QW ×1 | 2 | 219.07 | 81.60 |

TABLE 29

Liver Editing Results.

| Time Regimen | Dose | Liver Editing (%) |
|---|---|---|
| QW ×4 | TSS | 0.38 |
| QM ×3 | 0.5 | 48.18 |
| QM ×2 | 0.5 | 36.66 |
| QW ×4 | 0.5 | 56.03 |
| QW ×3 | 0.5 | 51.35 |
| QW ×2 | 0.5 | 34.77 |
| QW ×1 | 0.5 | 24.16 |
| QM ×3 | 1 | 63.40 |
| QM ×2 | 1 | 57.37 |
| QW ×4 | 1 | 62.89 |
| QW ×3 | 1 | 59.22 |
| QW ×2 | 1 | 60.12 |
| QW ×1 | 1 | 35.16 |
| QW ×1 | 2 | 60.57 |

The results show that it is possible to build up a cumulative dose and effect with multiple administrations over time, including at weekly or monthly intervals, to achieve increasing editing levels and % KD of TTR.

Example 10. RNA Cargo: Varying mRNA and gRNA Ratios

This study evaluated in vivo efficacy in mice of different ratios of gRNA to mRNA. CleanCap™ capped Cas9 mRNAs with the ORF of SEQ ID NO: 4, HSD 5' UTR, human albumin 3' UTR, a Kozak sequence, and a poly-A tail were made by IVT synthesis as indicated in Example 1 with N1-methylpseudouridine triphosphate in place of uridine triphosphate.

Figure 19A:
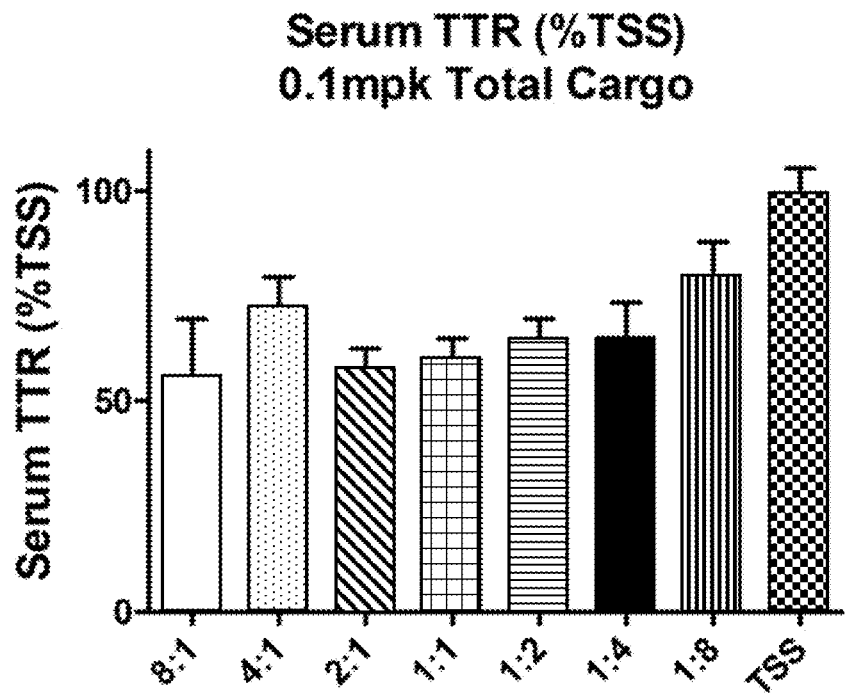
FIGS. 19A-D show serum TTR (% TSS.
Figure 19B:
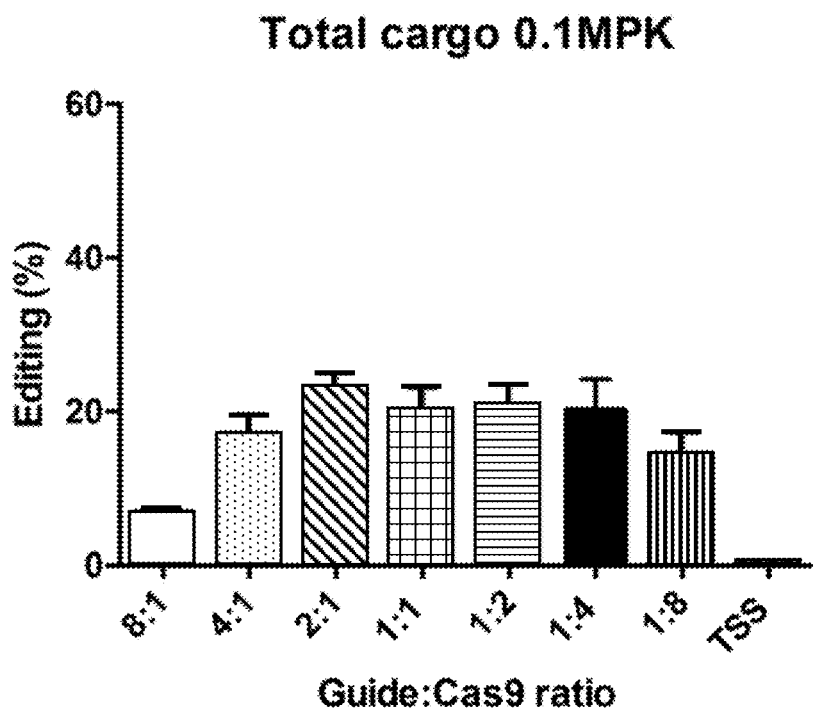

LNP formulations prepared from the mRNA described and G282 (SEQ ID NO: 124) as described in Example 1 with Lipid A, cholesterol, DSPC, and PEG2k-DMG in a 50:38:9:3 molar ratio and with an N:P ratio of 6. The gRNA:Cas9 mRNA weight ratios of the formulations were as shown in FIGS. 19A and 19B.

For in vivo characterization, the LNPs were administered to mice at 0.1 mg total RNA (mg guide RNA+mg mRNA) per kg (n=5 per group). At 7-9 days post-dose, animals were sacrificed, blood and the liver were collected, and serum TTR and liver editing were measured as described in Example 1. Serum TTR and liver editing results are shown in FIGS. 19A and 19B. Negative control mice were dosed with TSS vehicle.

Figure 19C:
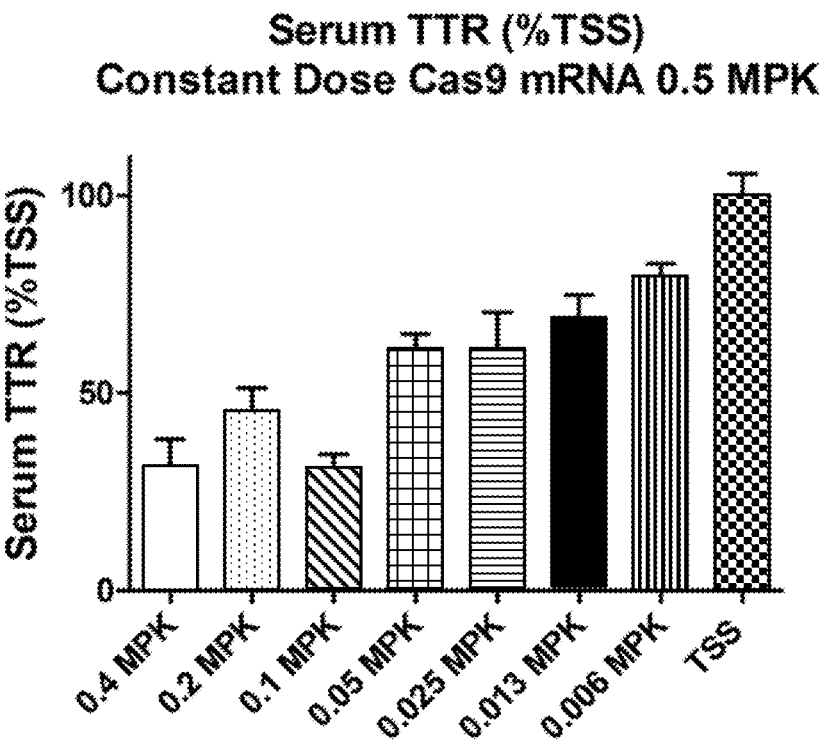
Figure 19D:
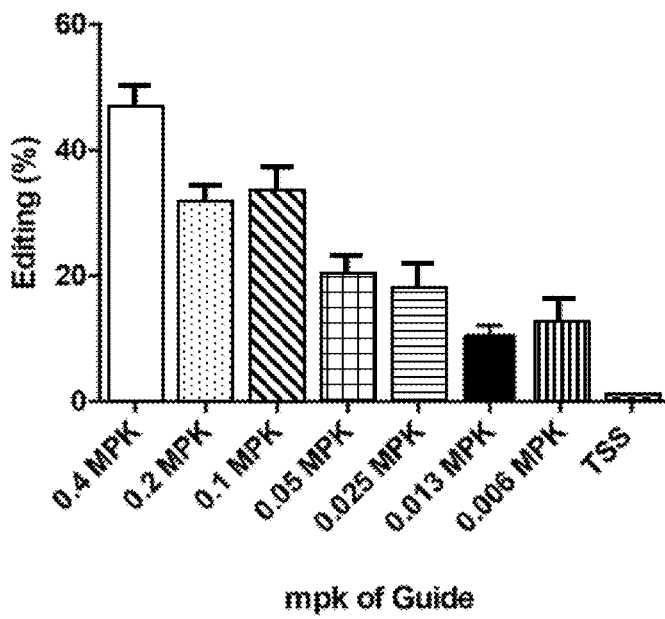

In addition, the above LNPs were administered to mice at a constant mRNA dose of 0.05 mg mRNA per kg (n=5 per group), while varying the gRNA dose from 0.06 mg per kg to 0.4 mg per kg. At 7-9 days post-dose, animals were sacrificed, blood and the liver were collected, and serum TTR and liver editing were measured. Serum TTR and liver editing results are shown in FIG. 19C and FIG. 19D. Negative control mice were dosed with TSS vehicle.

Example 11. Off-Target Analysis of TTR sgRNAs in Primary Human Hepatocytes

Figure 20:
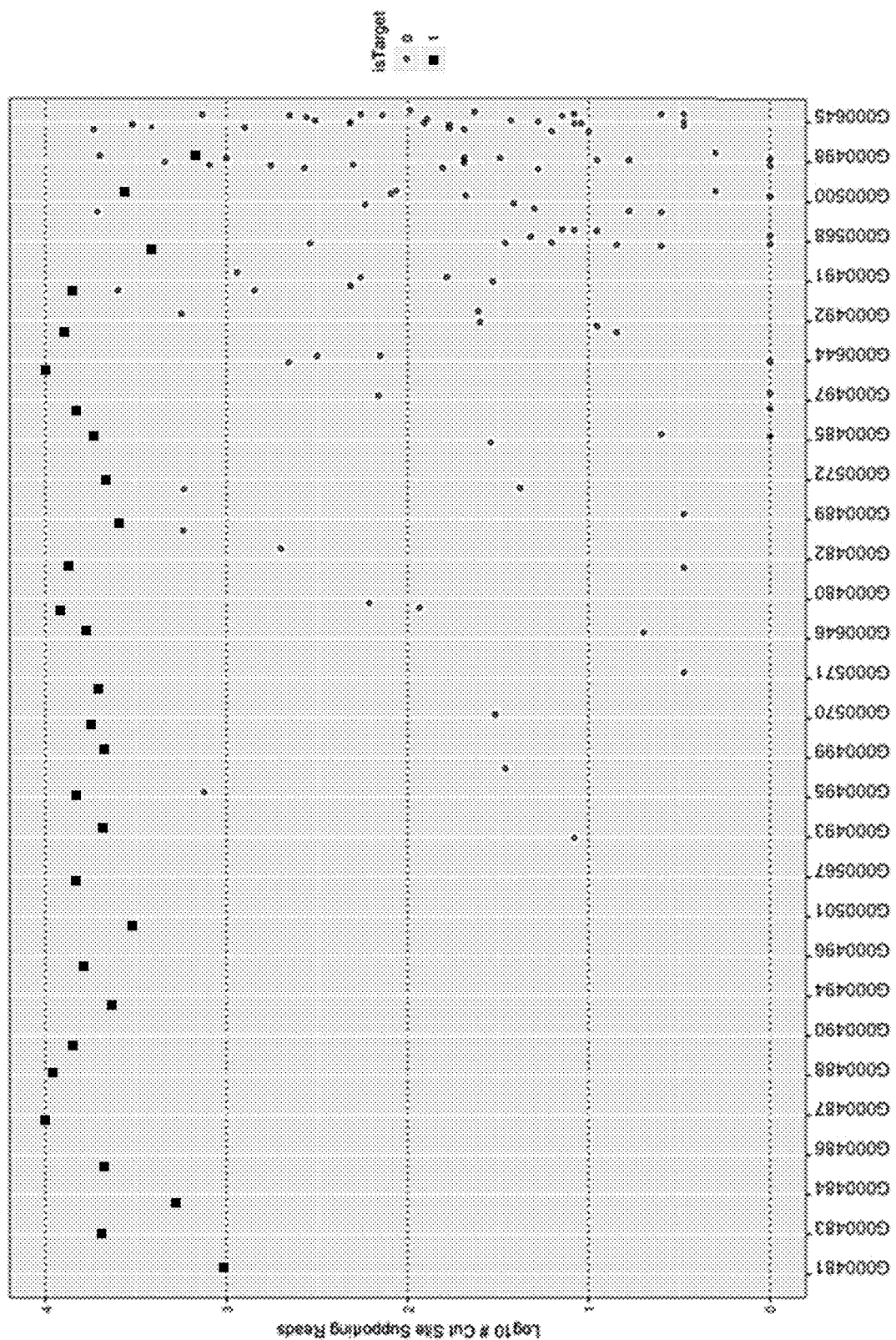
FIG. 20 shows off-target analysis of certain single guide RNAs in Primary Human Hepatocytes (PHH) targeting TTR. In the graph, filled squares represent the identification of the on-target cut site, while open circles represent the identification of potential off-target sites.
Figure 21A:
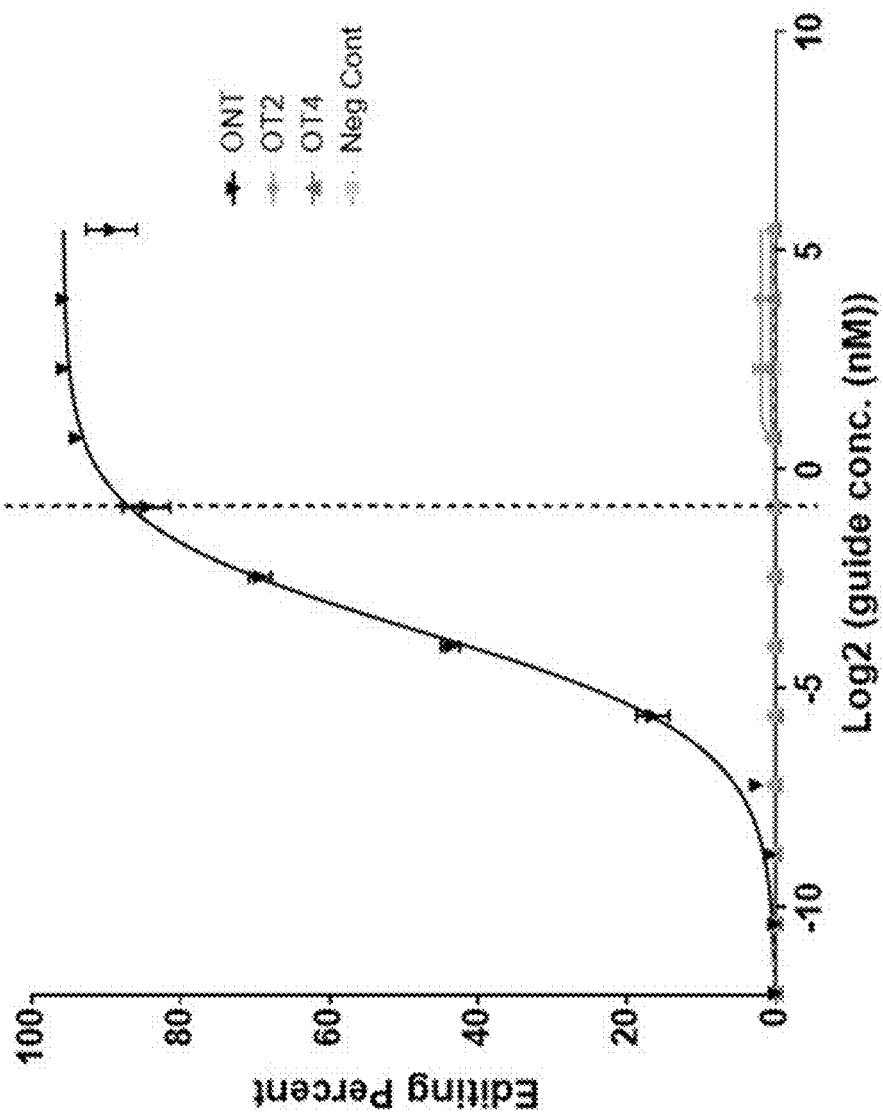
FIGS. 21A-B show percent editing on-target (ONT, FIG. 21A) and at two off-target sites (OT2 and OT4) in primary human hepatocytes following administration of lipid nanoparticle formulated G000480.
Figure 21B:
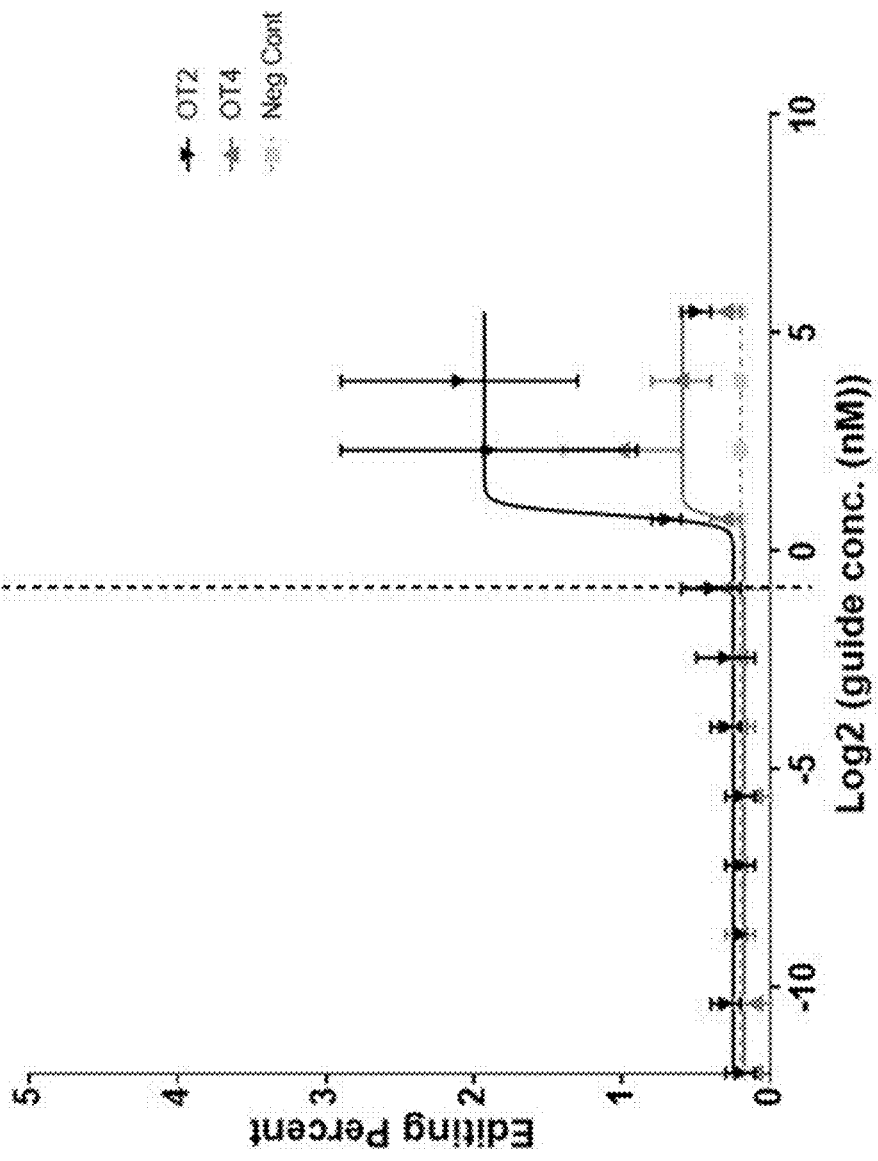
Figure 22A:
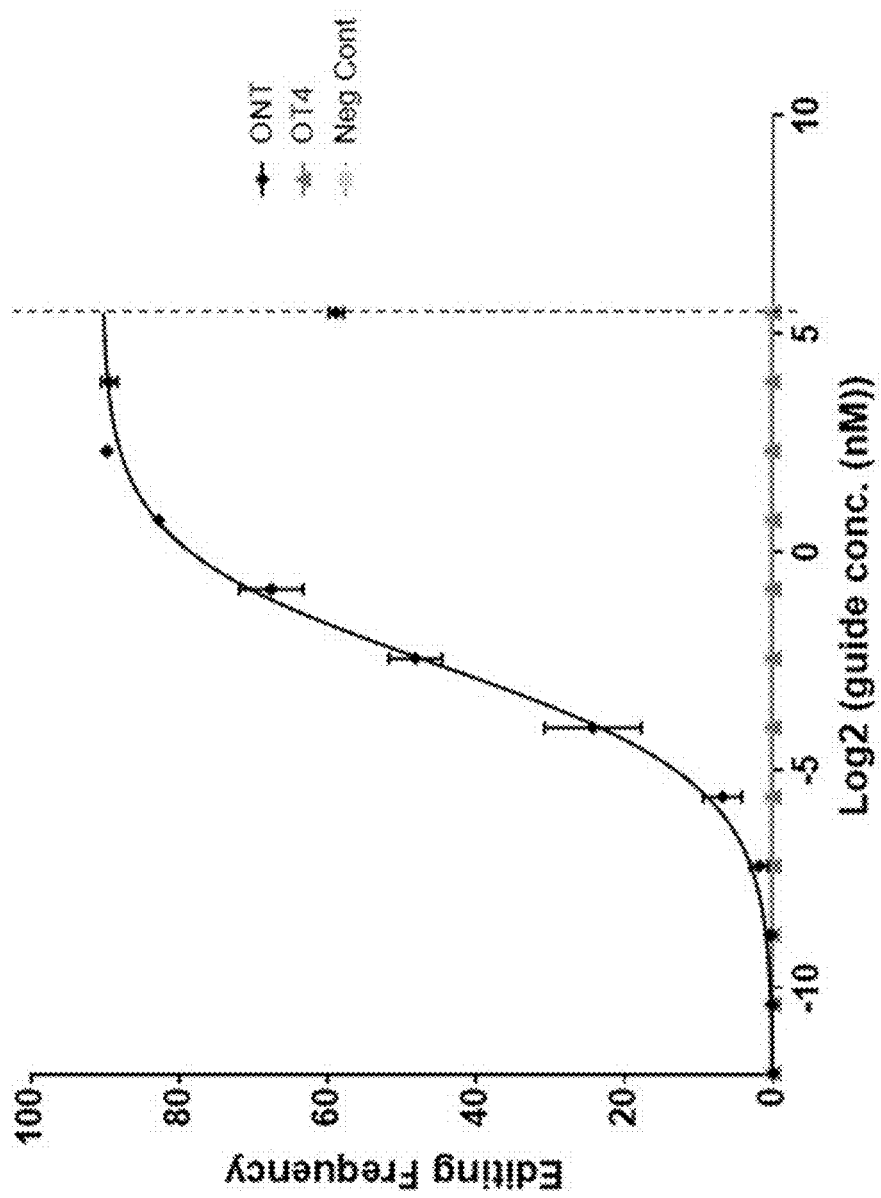
FIGS. 22A-B show percent editing on-target (ONT, FIG. 22A) and at an off-target site (OT4) in primary human hepatocytes following administration of lipid nanoparticle formulated G000486.
Figure 22B:
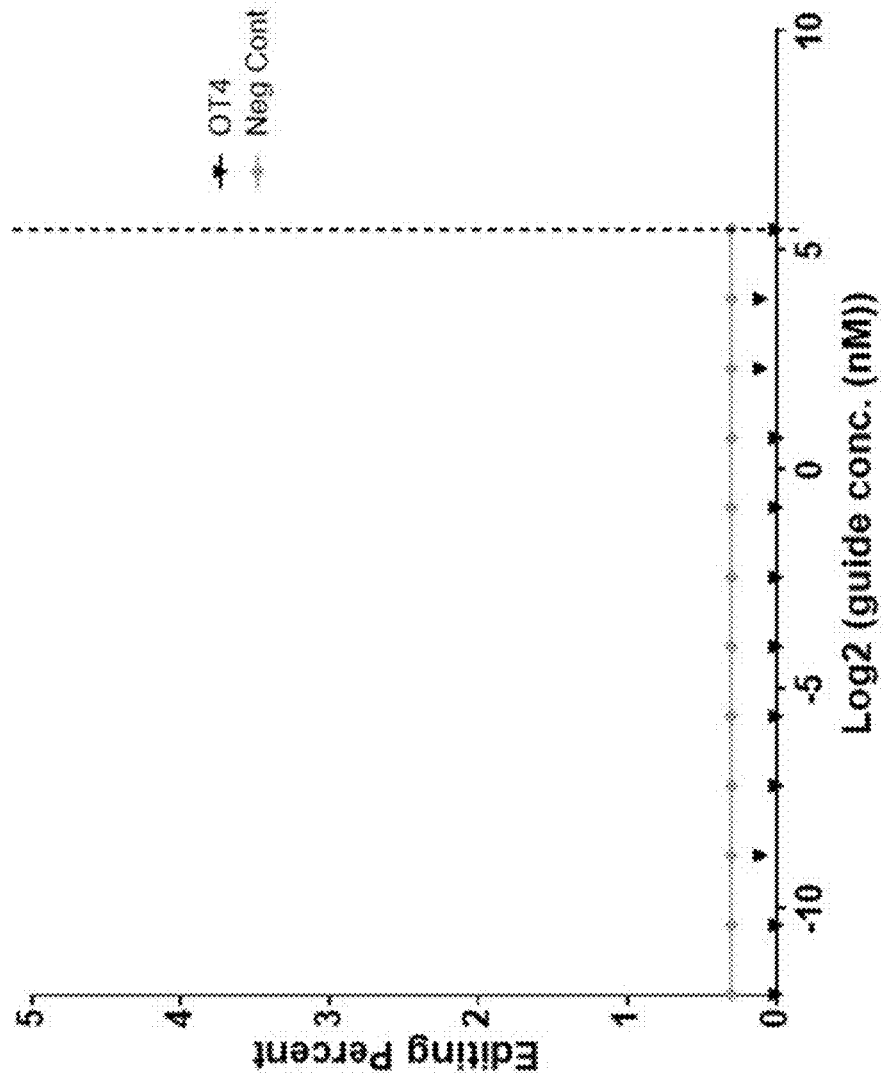

Off-target analysis of sgRNAs targeting TTR was performed in primary human hepatocytes (PHH) as described in Example 5, with the following modifications. PHH were plated at a density of 33,000 cells per well on collagen-coated 96-well plates as described in Example 1. Twenty-four hours post plating, cells were washed with media and transfected using Lipofectamine RNAiMAX (ThermoFisher, Cat. 13778150) as described in Example 1. Cells were transfected with a lipoplex containing 100 ng Cas9 mRNA, immediately followed by the addition of another lipoplex containing 25 nM of the sgRNA and 12.5 nM of the donor oligo (0.3 µL/well). Cells were lysed 48 hours post-transfection and gDNA was extracted and analyzed as further described in Example 5. The data is graphically represented in FIG. 20.

Table 30 shows the number of off-target integration sites detected in PHH, and compares to the number of sites that were detected in the HekCas9 cells used in Example 5. Fewer sites were detected in PHH for every guide tested as compared to the HekCas9 cell line, with no unique sites detected in PHH alone.

TABLE 30

Number of off-target integration sites detected for TTR sgRNAs in PHH via an oligo insertion based assay

| GUIDE ID | # Sites in PHH | # Sites in HekCas9 cells (Example 5) |
|---|---|---|
| G000480 | 2 | 11 |
| G000481 | 0 | 3 |
| G000482 | 2 | 13 |
| G000483 | 0 | 5 |
| G000484 | 0 | 7 |
| G000485 | 3 | 22 |
| G000486 | 0 | 12 |
| G000487 | 0 | 14 |
| G000488 | 0 | 0 |
| G000489 | 2 | 19 |
| G000490 | 0 | 12 |
| G000491 | 7 | 28 |
| G000492 | 5 | 97 |
| G000493 | 1 | 7 |
| G000494 | 0 | 4 |
| G000495 | 1 | 13 |
| G000496 | 0 | 1 |
| G000497 | 3 | 26 |
| G000498 | 19 | 82 |
| G000499 | 1 | 4 |
| G000500 | 12 | 46 |
| G000501 | 0 | 4 |
| G000567 | 0 | 9 |
| G000568 | 11 | 936 |
| G000570 | 1 | 19 |
| G000571 | 1 | 16 |
| G000572 | 2 | 15 |

Following the identification of potential off-target sites in PHH via the oligo insertion assay, certain potential sites were further evaluated by targeted amplicon sequencing, e.g., as described in Example 6. In addition to the potential off-target sites identified by the oligo insertion strategy, additional potential off-target sites identified by in silico prediction were included in the analysis.

To this end, PHH were treated with LNPs comprising 100 ng of Cas9 mRNA (SEQ ID NO:1) and the gRNA of interest at 14.68 nM (in a 1:1 ratio by weight), as described in Example 4. The LNPs were prepared using the cross-flow procedure described above and purified and concentrated using PD-10 columns and Amicon centrifugal filter units, respectively. The LNPs were formulated with an N:P ratio of 6.0 and contained Lipid A, Cholesterol, DSPC, and PEG2k-DMG in a 50:38:9:2 molar ratio, respectively. Following LNP treatment, isolated genomic DNA was analyzed by NGS (e.g., as described in Examples 1 and 6) to determine whether indels could be detected at the potential off-target site, which would be indicative of a Cas9-mediated cleavage event. Tables 31 and 32 show the potential off-target sites that were evaluated for the gRNAs G000480 and G000486, respectively.

As shown in FIGS. 21A-B and 22A-B and Table 33 below, indels were detected at low levels for only two of the potential off-target sites identified by the oligo insertion assay for G000480, and only one for G000486. No indels were detected at any of the in silico predicted sites for either guide. Further, indels were only detected at these sites using a near-saturating dose of LNP, as the indel rates observed at the on-target sites for G000480 and G000486 were ~97% and ~91%, respectively (See Table 33). The genomic coordinates of these sites are also reported in Tables 31 and 32, and each correspond to sequences that do not code for any protein.

A dose response assay was then performed in order to determine the highest dose of LNP in which no off-targets were detected. PHH were treated with LNPs comprising either G000480 or G000486 as described in Example 4. The doses ranged across 11 points with respect to gRNA concentration (0.001 nM, 0.002 nM, 0.007 nM, 0.02 nM, 0.06 nM, 0.19 nM, 0.57 nM, 1.72 nM, 5.17 nM, 15.51 nM, and 46.55 nM). As represented by the dashed vertical line in FIGS. 21A-B and 22A-B, the highest concentrations (with respect to the concentration of gRNA) at which the potential off-target sites were no longer detected for G000480 and G000486 were 0.57 nM and 15.51 nM, respectively, which resulted in on-target indel rates of 84.60% and 89.50%, respectively.

TABLE 31

Identified potential off target sites via insertion detection and in silico prediction for G000480 evaluated via targeted amplicon sequencing

| GUIDE ID | Off-target (OT) Site ID | Assay Used | Chromosomal Coordinates (hg38) | Strand |
| --- | --- | --- | --- | --- |
| G000480 | INS-OT.1 | Insertion Detection | chr7: 94767406-94767426 | + |
| G000480 | INS-OT.2 | Insertion Detection | chr2: 192658562-192658582 | + |
| G000480 | INS-OT.3 | Insertion Detection | chr7: 4834390-4834410 | + |
| G000480 | INS-OT.4 | Insertion Detection | chr20: 9216118-9216138 | − |
| G000480 | INS-OT.5 | Insertion Detection | chr10: 12547071-12547091 | + |
| G000480 | INS-OT.6 | Insertion Detection | chr6: 168377978-168377998 | − |
| G000480 | INS-OT.7 | Insertion Detection | chr12: 114144669-114144689 | − |
| G000480 | INS-OT.8 | Insertion Detection | chr10: 7376755-7376775 | + |
| G000480 | INS-OT.9 | Insertion Detection | chr2: 52950299-52950319 | + |
| G000480 | INS-OT.10 | Insertion Detection | chr8: 56579165-56579185 | − |
| G000480 | INS-OT.11 | Insertion Detection | chr1: 189992255-189992275 | + |
| G000480 | PRED-OT.1 | in silico prediction | chr10: 12547071-12547091 | + |
| G000480 | PRE-DOT.2 | in silico prediction | chrX: 119702782-119702802 | + |
| G000480 | PRED-OT.3 | in silico prediction | chr1: 116544586-116544606 | + |
| G000480 | PRED-OT.4 | in silico prediction | chr6: 88282884-88282904 | + |
| G000480 | PRED-OT.6 | in silico prediction | chr5: 121891868-121891888 | + |
| G000480 | PRED-OT.7 | in silico prediction | chr3: 52544945-52544965 | + |
| G000480 | PRED-OT.8 | in silico prediction | chr15: 36949639-36949659 | + |
| G000480 | PRED-OT.9 | in silico prediction | chr5: 33866486-33866506 | + |
| G000480 | PRED-OT.10 | in silico prediction | chr5: 159755754-159755774 | + |
| G000480 | PRED-OT.11 | in silico prediction | chr5: 31349859-31349879 | + |
| G000480 | PRED-OT.12 | in silico prediction | chr11: 79485652-79485672 | + |
| G000480 | PRED-OT.13 | in silico prediction | chr15: 29448864-29448884 | + |
| G000480 | PRED-OT.14 | in silico prediction | chr5: 171153565-171153585 | + |
| G000480 | PRED-OT.15 | in silico prediction | chr9: 84855273-84855293 | + |
| G000480 | PRED-OT.16 | in silico prediction | chr6: 159953060-159953080 | + |
| G000480 | PRED-OT.17 | in silico prediction | chr16: 51849024-51849044 | + |
| G000480 | PRED-OT.18 | in silico prediction | chr3: 24108809-24108829 | + |
| G000480 | PRED-OT.19 | in silico prediction | chr18: 41118310-41118330 | + |
| G000480 | PRED-OT.20 | in silico prediction | chr10: 108975241-108975261 | + |
| G000480 | PREDO-T.21 | in silico prediction | chr1: 44683633-44683653 | + |
| G000480 | PRED-OT.22 | in silico prediction | chr2: 196214849-196214869 | + |
| G000480 | PRED-OT.23 | in silico prediction | chr9: 117353544-117353564 | + |
| G000480 | PRED-OT.24 | in silico prediction | chr1: 55583322-55583342 | + |
| G000480 | PRED-OT.25 | in silico prediction | chr12: 28246827-28246847 | + |
| G000480 | PRED-OT.26 | in silico prediction | chr4: 54545361-54545381 | + |
| G000480 | PRED-OT.27 | in silico prediction | chr13: 22364836-22364856 | + |
| G000480 | PRED-OT.28 | in silico prediction | chr13: 80816049-80816069 | + |
| G000480 | PRED-OT.29 | in silico prediction | chr7: 39078622-39078642 | + |
| G000480 | PRED-OT.30 | in silico prediction | chr2: 59944386-59944406 | + |

"INS-OT.N" refers to an off-target site ID detected by oligo insertion, where N is an integer specified above;
"PRED-OT.N refers to an off-target site ID predicted via in silico methods, where N is an integer specified above.

TABLE 32

Identified potential off target sites via insertion detection and in silico prediction for G000486 evaluated via targeted amplicon sequencing

| GUIDE ID | Off-target (OT) Site ID | Assay Used | Chromosomal Coordinates (hg38) | Strand |
|---|---|---|---|---|
| G000486 | INS-OT.1 | Insertion Detection | chr14: 77332157-77332177 | + |
| G000486 | INS-OT.2 | Insertion Detection | chr14: 54672059-54672079 | − |
| G000486 | INS-OT.3 | Insertion Detection | chr4: 108513169-108513189 | − |
| G000486 | INS-OT.4 | Insertion Detection | chr5: 91397023-91397043 | − |
| G000486 | INS-OT.5 | Insertion Detection | chr9: 116626135-116626155 | − |
| G000486 | INS-OT.6 | Insertion Detection | chr6: 73201226-73201246 | + |
| G000486 | INS-OT.7 | Insertion Detection | chr16: 89368352-89368372 | − |
| G000486 | INS-OT.8 | Insertion Detection | chr7: 56308371-56308391 | − |
| G000486 | INS-OT.9 | Insertion Detection | chr21: 43605667-43605687 | + |
| G000486 | INS-OT.10 | Insertion Detection | chr5: 26758030-26758050 | + |
| G000486 | INS-OT.11 | Insertion Detection | chr17: 30656428-30656448 | + |
| G000486 | INS-OT.12 | Insertion Detection | chr8: 130486452-130486472 | + |
| G000486 | PRED-OT.1 | in silico prediction | chr11: 44707064-44707084 | + |
| G000486 | PRED-OT.2 | in silico prediction | chr5: 50775396-50775416 | + |
| G000486 | PRED-OT.3 | in silico prediction | chr4: 141623949-141623969 | + |
| G000486 | PRED-OT.4 | in silico prediction | chr1: 223481186-223481206 | + |
| G000486 | PRED-OT.5 | in silico prediction | chr6: 39951487-39951507 | + |
| G000486 | PRED-OT.6 | in silico prediction | chrY: 5456047-5456067 | + |
| G000486 | PRED-OT.8 | in silico prediction | chr6: 129868719-129868739 | + |
| G000486 | PRED-OT.9 | in silico prediction | chrX: 80450312-80450332 | + |
| G000486 | PRED-OT.10 | in silico prediction | chr7: 27256771-27256791 | + |
| G000486 | PRED-OT.11 | in silico prediction | chr3: 181416528-181416548 | + |
| G000486 | PRED-OT12 | in silico prediction | chr7: 146425020-146425040 | + |
| G000486 | PRED-OT.13 | in silico prediction | chr3: 16980977-16980997 | + |
| G000486 | PRED-OT.14 | in silico prediction | chr7: 118161002-118161022 | + |
| G000486 | PRED-OT.15 | in silico prediction | chr6: 102220539-102220559 | + |
| G000486 | PRED-OT.16 | in silico prediction | chr12: 127278991-127279011 | + |
| G000486 | PRED-OT.17 | in silico prediction | chr2: 67686631-67686651 | + |
| G000486 | PRED-OT.18 | in silico prediction | chr1: 114467665-114467685 | + |
| G000486 | PRED-OT.19 | in silico prediction | chr3: 194514436-194514456 | + |
| G000486 | PRED-OT.20 | in silico prediction | chr14: 31767581-31767601 | + |
| G000486 | PRED-OT.21 | in silico prediction | chr16: 28706209-28706229 | + |
| G000486 | PRED-OT.22 | in silico prediction | chr8: 110526279-110526299 | + |
| G000486 | PRED-OT.23 | in silico prediction | chr19: 2899814-2899834 | + |
| G000486 | PRED-OT.25 | in silico prediction | chr3: 130760261-130760281 | + |
| G000486 | PRED-OT.26 | in silico prediction | chr11: 2506046-2506066 | + |
| G000486 | PRED-OT.27 | in silico prediction | chr2: 153918318-153918338 | + |
| G000486 | PRED-OT.28 | in silico prediction | chr14: 40590226-40590246 | + |
| G000486 | PRED-OT.29 | in silico prediction | chr18: 806650-806670 | + |
| G000486 | PRED-OT.30 | in silico prediction | chr2: 117707480-117707500 | + |

"INS-OT.N" refers to an off-target site ID detected by oligo insertion, where N is an integer specified above;
"PRED-OT.N" refers to an off-target site ID predicted via in silico methods, where N is an integer specified.

TABLE 33

Detected Off Target sites in PHH treated with LNP containing 100 ng mRNA and 31.03 nM gRNA

| GUIDE ID | Off-target (OT) Site ID | Site Type | Indel Frequency (using LNP with 100 ng Cas9 mRNA and 14.68 nM gRNA) | Indel Frequency std. dev. |
|---|---|---|---|---|
| G000480 | n/a | On-Target | 97.33% | 1.10% |
| G000480 | INS-OT.2 | Off-Target | 1.43% | 0.40% |
| G000480 | INS-OT.4 | Off-Target | 0.97% | 0.25% |
| G000486 | n/a | On-Target | 91.33% | 1.97% |
| G000486 | INS-OT.4 | Off-Target | 0.47% | 0.06% |

Example 12. LNP Delivery to Humanized Mouse Model of ATTR

A well-established humanized transgenic mouse model of hereditary ATTR amyloidosis that expresses the V30M pathogenic mutant form of human TTR protein was used in this Example. This mouse model recapitulates the TTR deposition phenotype in tissues observed in ATTR patients, including within the peripheral nervous system and gastro-intestinal (GI) tract (See Santos et al., Neurobiol Aging. 2010 February; 31(2):280-9).

Mice (aged approximately 4-5 months) were dosed with LNP formulations prepared using the cross-flow and TFF procedures as described in Example 1. The LNPs were formulated with an N:P ratio of 6.0 and contained Lipid A, Cholesterol, DSPC, and PEG2k-DMG in a 50:38:9:2 molar ratio, respectively. The LNPs contained Cas9 mRNA (SEQ ID NO: 1) and either G000481 ("G481") or a non-targeting control guide G000395 ("G395"; SEQ ID NO: 273), in a 1:1 ratio of gRNA:mRNA by weight.

Mice were injected via the lateral tail vein as described in Example 1 with a single 1 mg/kg (of total RNA content) dose of LNP with an n=10/group. At 8 weeks post treatment, the mice were euthanized for sample collection. Human TTR protein levels were measured in serum and cerebrospinal fluid (CSF) by ELISA as previously described by Butler et al., Amyloid. 2016 June; 23(2):109-18. Liver tissue was assayed for editing levels as described in Example 1. Other tissues (stomach, colon, sciatic nerve, dorsal root ganglion (DRG)) were collected and processed for semi-quantitative immunohistochemistry as previously described by Gonsalves et al., Amyloid. 2014 September; 21(3): 175-184. Statistical analysis for the immunohistochemistry data was performed using Mann Whitney test with a p-value<0.0001.

Figure 23A:
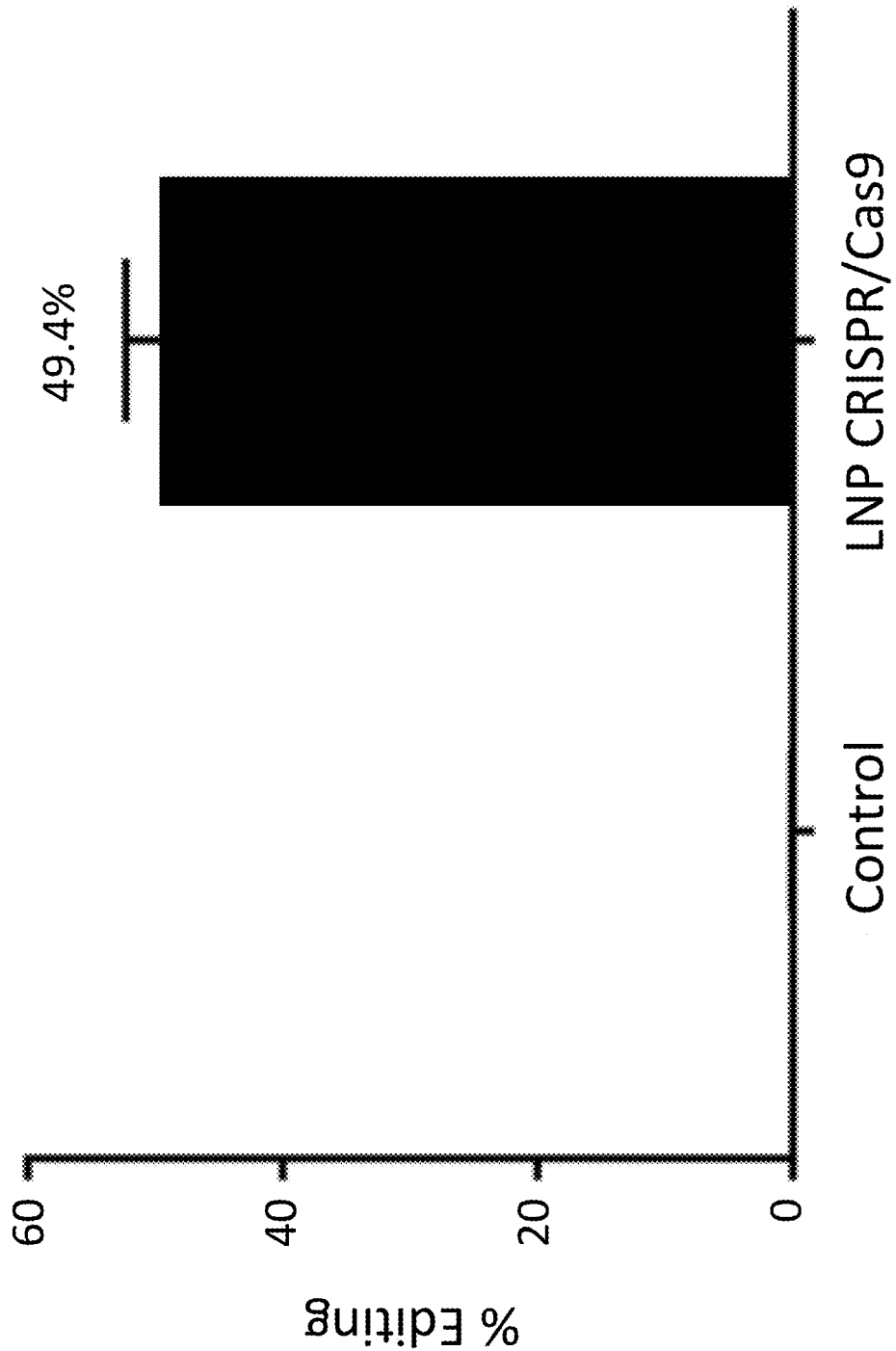
FIGS. 23A-B show percent editing (FIG. 23A) and number of insertion and deletion events at the TTR locus (FIG. 23B).
Figure 23B:
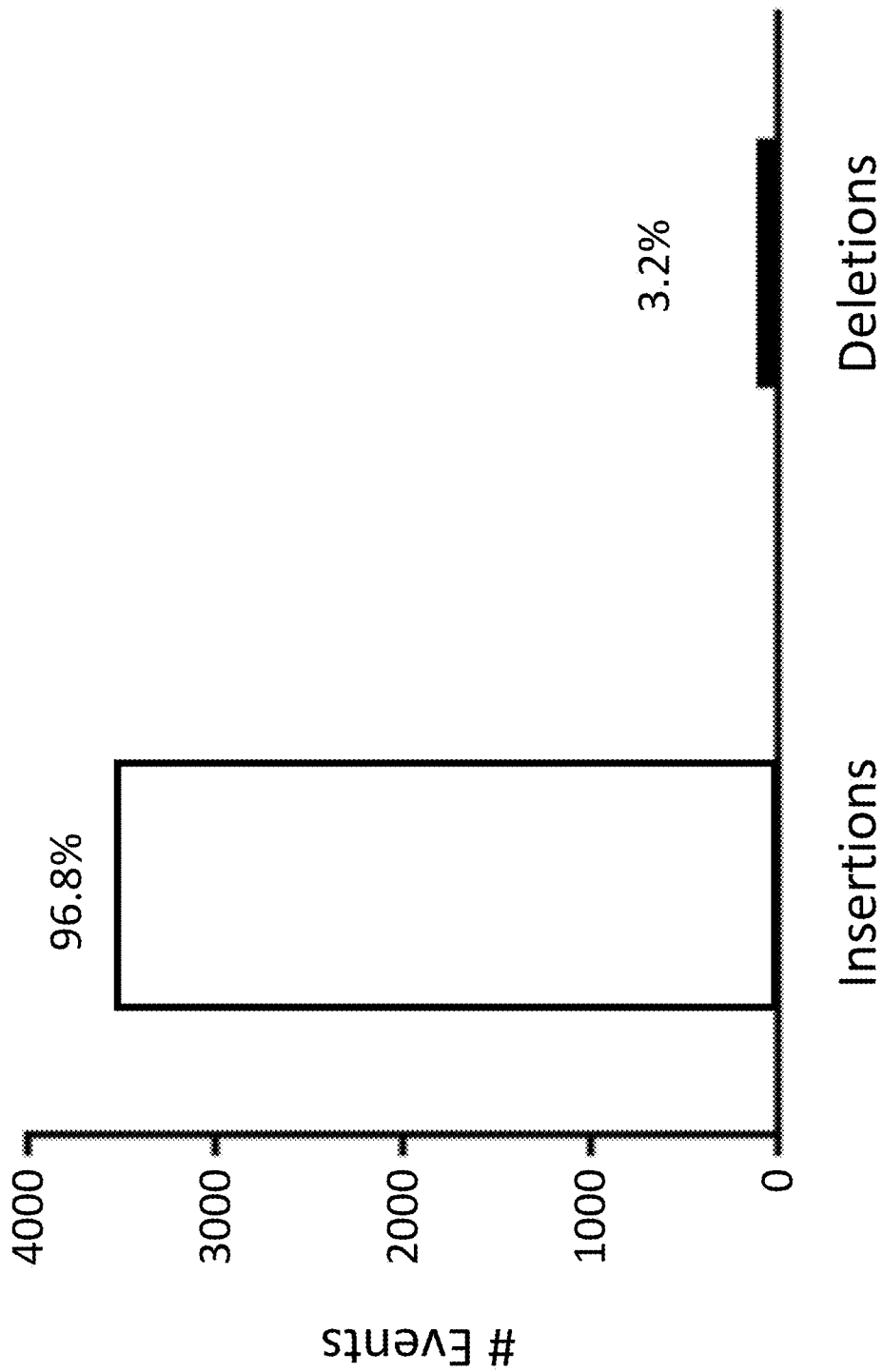

As shown in FIG. 23A-B, robust editing (49.4%) of TTR was observed in livers of the humanized mice following the single dose of LNP comprising G481, with no editing detected in the control group. Analysis of the editing events demonstrated that 96.8% of the events were insertions, with the remainder deletions.

Figure 24A:
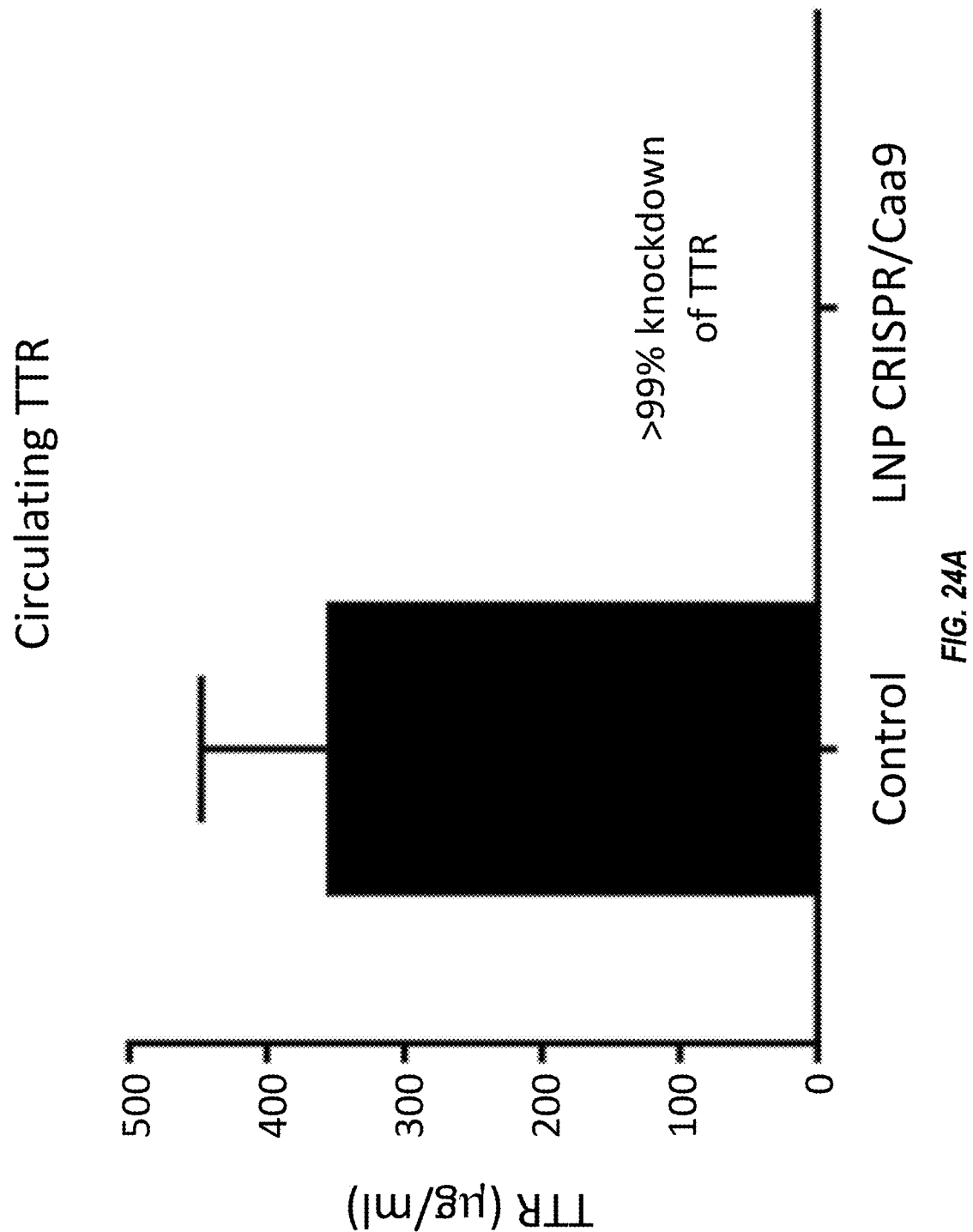
FIGS. 24A-B show TTR levels in circulating serum (FIG. 24A) and cerebrospinal fluid (CSF) (FIG. 24B), respectively, in µg/mL for control and treatment (dosed with lipid nanoparticle formulated TTR specific sgRNA) groups. Treatment resulted in >99% knockdown of TTR levels in serum.
Figure 24B:
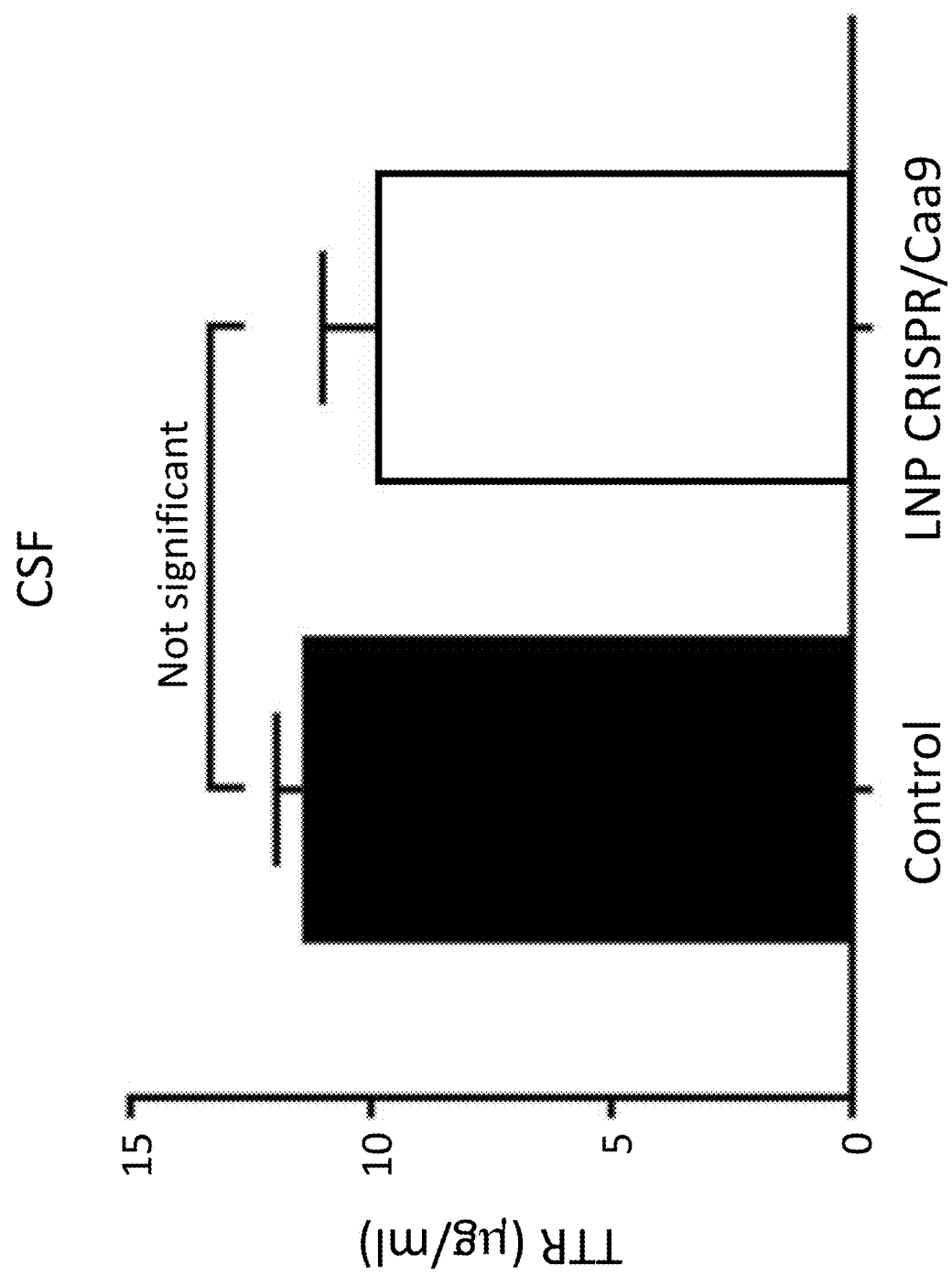

As shown in FIG. 24A-B, TTR protein levels were decreased in plasma but not in CSF from the treated mice, with greater than 99% knockdown of TTR plasma levels observed (p<0.001).

Figures 25A, 25B:
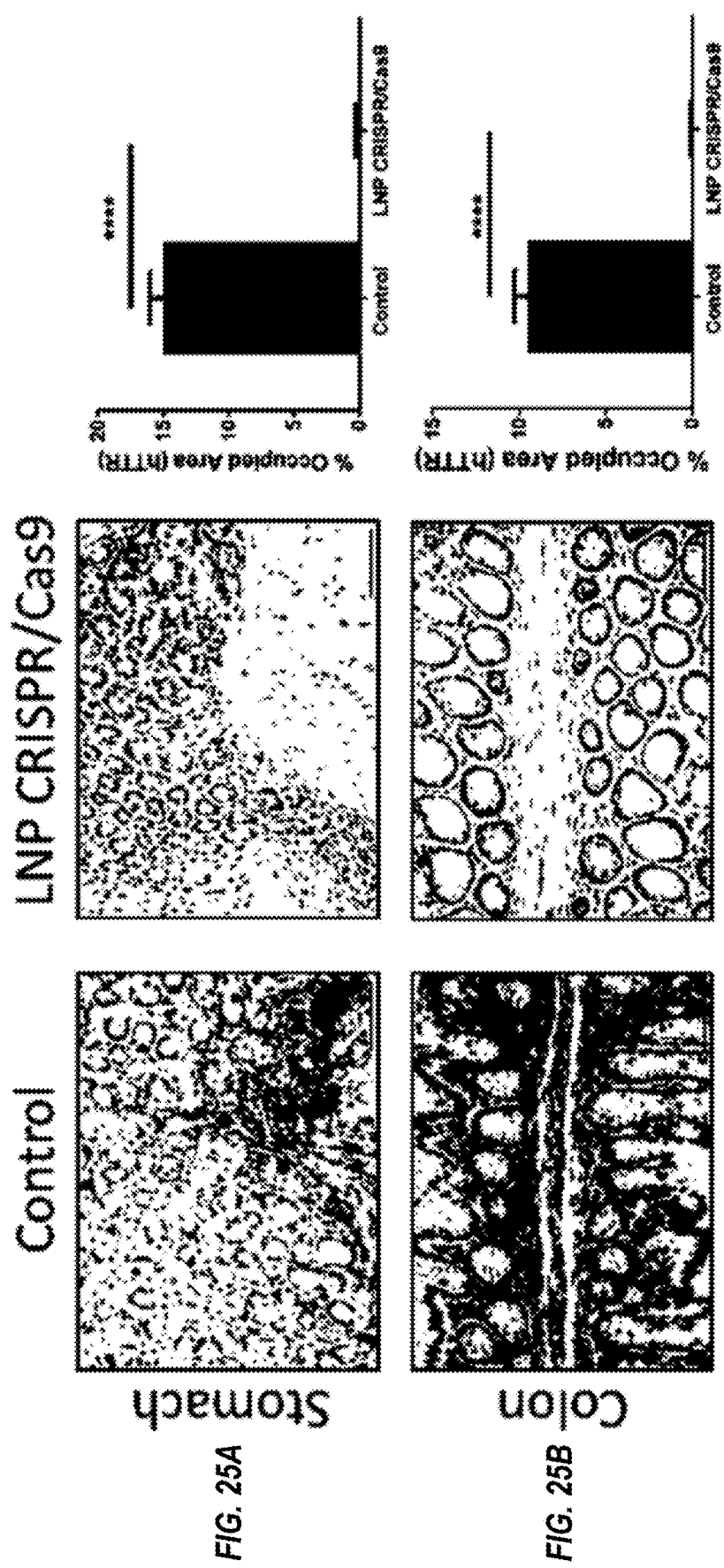
FIGS. 25A-D show immunohistochemistry images with staining for TTR in stomach (FIG. 25A), colon (FIG. 25B), sciatic nerve (FIG. 25C), and dorsal root ganglion (DRG) (FIG. 25D) from control and treatment (dosed with lipid nanoparticle formulated TTR specific sgRNA) mice. At right, bar graphs show reduction in TTR staining 8 weeks after treatment in treated mice as measured by percent occupied area for each tissue type.
Figures 25C, 25D:
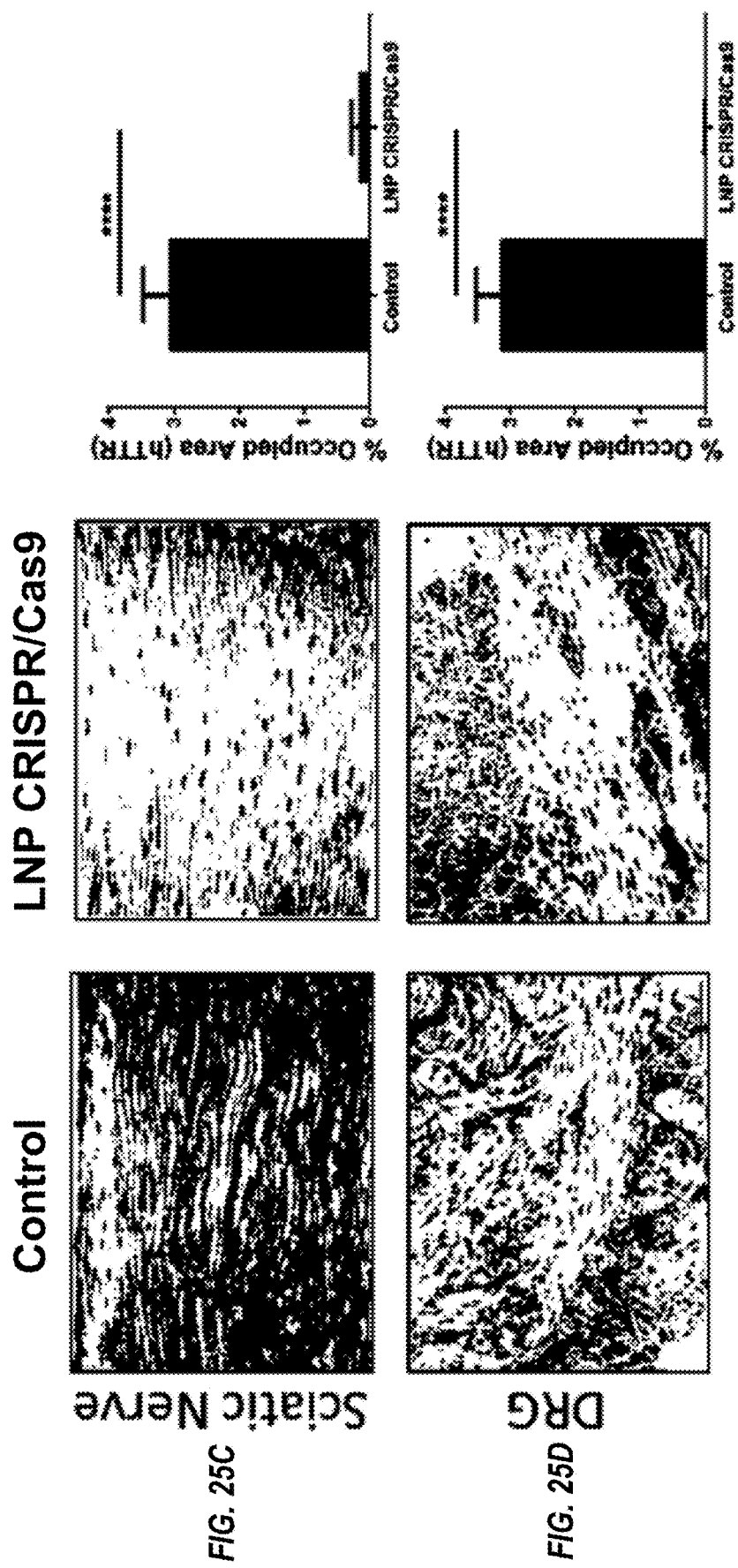

The near complete knockdown of TTR observed in the plasma of treated animals correlated with the clearance of TTR protein amyloid deposition in the assayed tissues. As shown in FIG. 25, control mice exhibited amyloid staining in tissues which resembles the pathophysiology observed in human subjects with ATTR. Decreasing circulating TTR by editing the HuTTR V30M locus resulted in a dramatic decrease of amyloid deposition in tissues. Approximately 85% or better reduction in TTR staining was observed across the treated tissues 8 weeks post-treatment (FIG. 25).

Example 13. TTR mRNA Knockdown in Primary Human Hepatocytes (PHH)

In one experiment, PHH were cultured and treated with LNPs comprising Cas9 mRNA (SEQ ID NO:1) and a gRNA of interest (See FIG. 29, Table 34), as described in Example 4. The LNPs were prepared using the cross-flow procedure described above and purified and concentrated using PD-10 columns and Amicon centrifugal filter units, respectively. The LNPs were formulated with an N:P ratio of 6.0 and contained Lipid A, Cholesterol, DSPC, and PEG2k-DMG in a 50:38:9:2 molar ratio, respectively. The LNPs comprised a gRNA:mRNA ratio of 1:2, and the cells were treated at a dose of 300 ng (with respect to the amount of mRNA cargo delivered).

Ninety-six (96) hours following LNP treatment (with biological triplicates for each condition), mRNA was purified from PHH cells using the Dynabeads mRNA DIRECT Kit (ThermoFisher Scientific) according to the manufacturer's protocol. Reverse Transcription (RT) was performed with Maxima reverse transcriptase (ThermoFisher Scientific) and a poly-dT primer. The resulting cDNA was purified with Ampure XP Beads (Agencourt). For Quantitative PCR, 2% of the purified cDNA was amplified with Taqman Fast Advanced Mastermix and 3 Taqman probe sets, TTR (Assay ID: Hs00174914_m1), GAPDH (Assay ID: Hs02786624_g1), and PPIB (Assay ID: Hs00168719_m1). The assays were run on the QuantStudio 7 Flex Real Time PCR System according to the manufacturer's instructions (Life Technologies). Relative expression of TTR mRNA was calculated by normalizing to the endogenous controls (GAPDH and PPIB) individually, and then averaged.

Figure 29:
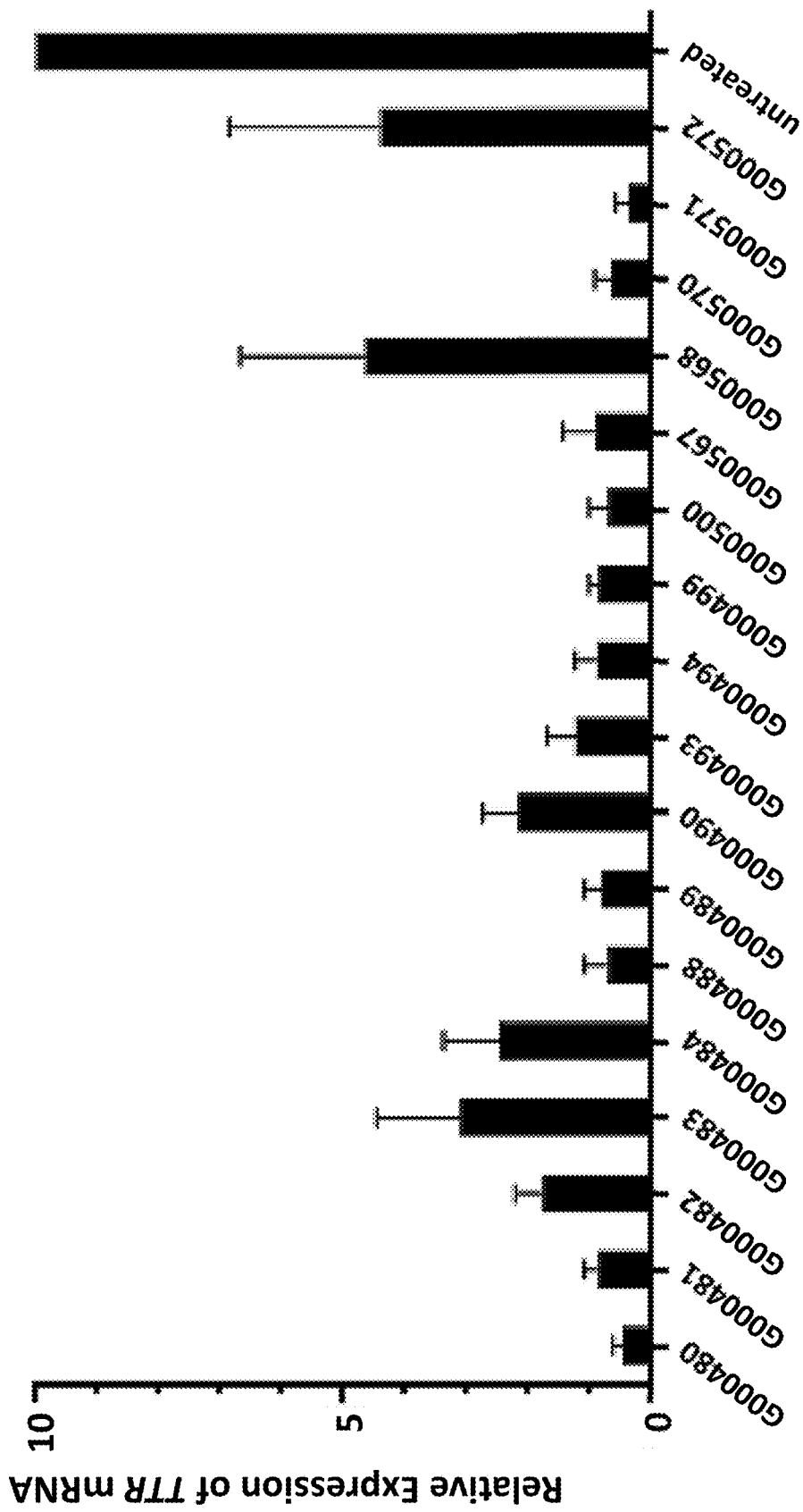
FIG. 29 shows relative expression of TTR mRNA in primary human hepatocytes (PHH) after treatment with LNPs comprising Cas9 mRNA and a gRNA as indicated, as compared to negative (untreated) controls.

As shown in FIG. 29 and reproduced numerically in Table 34 below, each of the LNP formulations tested resulted in knockdown of TTR mRNA, as compared to the negative (untreated) control. The groups in FIG. 29 and Table 34 are identified by the gRNA ID used in each LNP preparation. Relative expression of TTR mRNA is plotted in FIG. 29, whereas the percent knockdown of TTR mRNA is provided in Table 34.

TABLE 34

| GUIDE ID | Avg % Knockdown | Std Dev |
|---|---|---|
| G000480 | 95.19 | 1.68 |
| G000481 | 91.39 | 2.39 |
| G000482 | 82.31 | 4.51 |
| G000483 | 68.78 | 13.45 |
| G000484 | 75.22 | 9.05 |
| G000488 | 92.77 | 3.76 |
| G000489 | 91.85 | 2.77 |
| G000490 | 78.34 | 5.76 |
| G000493 | 87.53 | 4.54 |
| G000494 | 91.15 | 3.63 |
| G000499 | 91.38 | 1.71 |
| G000500 | 92.90 | 3.15 |
| G000567 | 90.89 | 5.39 |
| G000568 | 53.44 | 20.20 |
| G000570 | 93.38 | 2.66 |
| G000571 | 96.17 | 2.07 |
| G000572 | 55.92 | 24.53 |

In a separate experiment, TTR mRNA knockdown was evaluated following treatment with LNPs comprising G000480, G000486, and G000502. The LNPs were formulated and PHH were cultured and treated with the LNPs, each as described in the experiment above in this Example with the exception that the cells were treated at a dose of 100 ng (with respect to the amount of mRNA cargo delivered).

Ninety-six (96) hours following LNP treatment (single treatment for each condition), mRNA was purified from PHH cells using the Dynabeads mRNA DIRECT Kit (ThermoFisher Scientific) according to the manufacturer's protocol. Reverse Transcription (RT) was performed with the High Capacity cDNA Reverse Transcription Kit (ThermoFisher Scientific) according to the manufacturer's instructions. For Quantitative PCR, 2% of the cDNA was amplified with Taqman Fast Advanced Mastermix and 3 Taqman probe sets, TTR (Assay ID: Hs00174914_m1), GAPDH (Assay ID: Hs02786624_g1), and PPIB (Assay ID: Hs00168719_m1). The assays were run on the QuantStudio 7 Flex Real Time PCR System according to the manufacturer's instructions (Life Technologies). Relative expression of TTR mRNA was calculated by normalizing to the endogenous controls (GAPDH and PPIB) individually, and then averaged.

Figure 30:
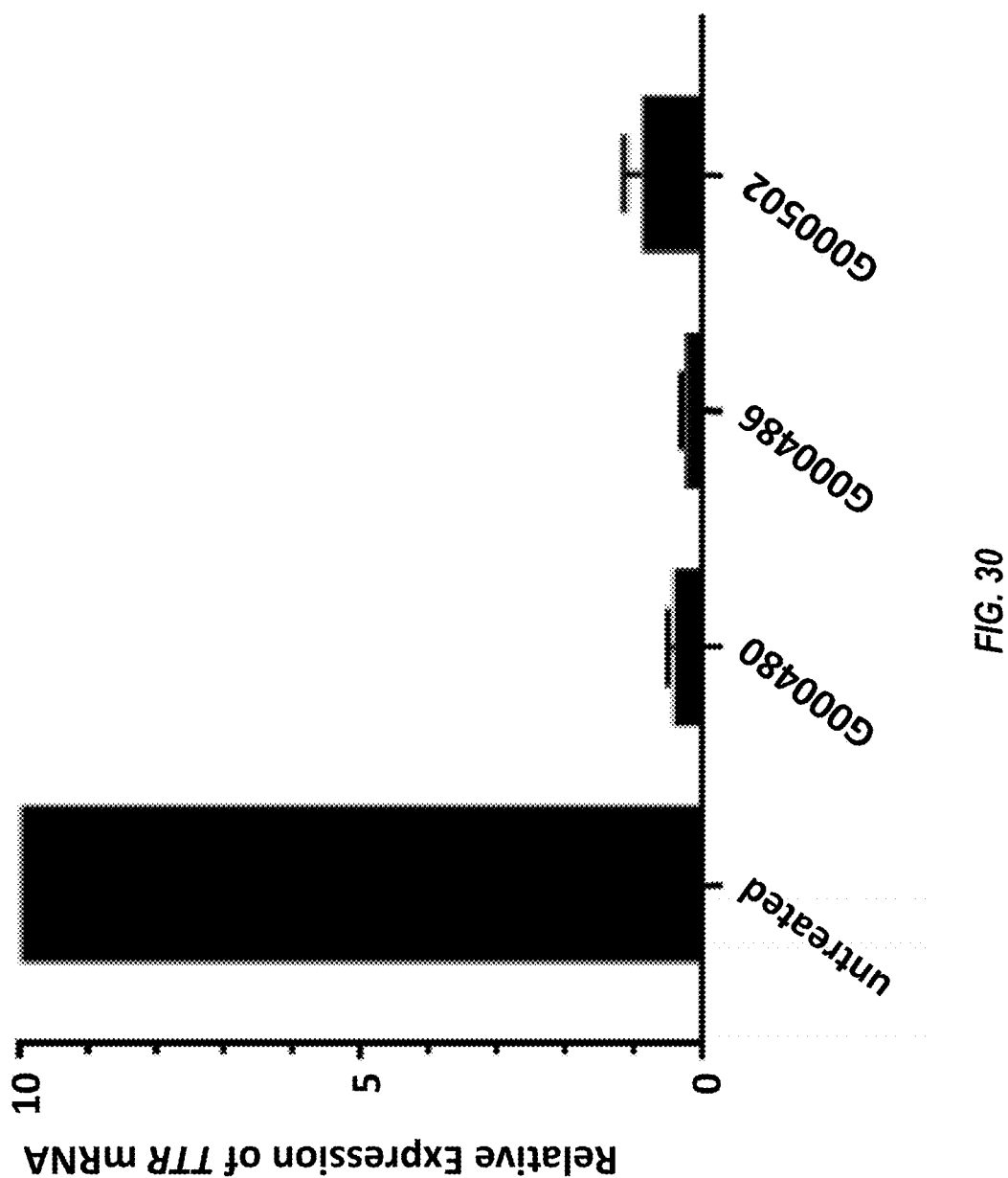
FIG. 30 shows relative expression of TTR mRNA in primary human hepatocytes (PHH) after treatment with LNPs comprising Cas9 mRNA and a gRNA as indicated, as compared to negative (untreated) controls.

As shown in FIG. 30 and reproduced numerically in Table 35 below, each of the LNP formulations tested resulted in knockdown of TTR mRNA, as compared to the negative (untreated) control. The groups in FIG. 30 and Table 35 are identified by the gRNA ID used in each LNP preparation. Relative expression of TTR mRNA is plotted in FIG. 30, whereas the percent knockdown of TTR mRNA is provided in Table 35.

TABLE 35

| GUIDE ID | Avg % Knockdown | Std Dev |
| --- | --- | --- |
| G000480 | 95.61 | 0.92 |
| G000486 | 97.36 | 0.63 |
| G000502 | 90.94 | 2.63 |

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
| --- | --- | --- |
| Cas9 transcript with 5' UTR of HSD, ORF corresponding to SEQ ID NO: 204, Kozak sequence, and 3' UTR of ALB | GGGTCCCGCAGTCGGCGTCCAGCGGCTCTGCTTGTTCGTGTGTGTCGTT GCAGGCCTTATTCGGATCCGCCACCATGGACAAGAAGTACAGCATCGGACT GGACATCGGAACAAACAGCGTCGGATGGGCAGTCATCACAGACGAATACAA GGTCCCGAGCAAGAAGTTCAAGGTCCTGGGAAACACAGACGACACAGCAT CAAGAAGAACCTGATCGGAGCACTGCTGTTCGACAGCGGAGAAACAGCAGA AGCAACAAGACTGAAGAGAACAGCAAGAAGAAGATACACAAGAAGAAAGAA CAGAATCTGCTACCTGCAGGAAATCTTCAGCAACGAAATGGCAAAGGTCGA CGACAGCTTCTTCCACAGACTGGAAGAAAGCTTCCTGGTCGAAGAAGACAA GAAGCACGAAAGACACCCGATCTTCGGAAACATCGTCGACGAAGTCGCATA CCACGAAAAGTACCCGACAATCTACCACCTGAGAAAGAAGCTGGTCGACAG CACAGACAAGGCAGACCTGAGACTGATCTACCTGGCACTGGCACACATGAT CAAGTTCAGAGGACACTTCCTGATCGAAGGAGACCTGAACCCGGACAACAG CGACGTCGACAAGCTGTTCATCCAGCTGGTCCAGACATACAACCAGCTGTT CGAAGAAACCCGATCAACGCAAGCGGAGTCGACGCAAAGGCAATCCTGAG CGCAAGACTGAGCAAGAGCAGAAGACTGGAAAACCTGATCGCACAGCTGCC GGGAGAAAAGAAGAACGGACTGTTCGGAAACCTGATCGCACTGAGCCTGGG ACTGACACCGAACTTCAAGAGCAACTTCGACCTGGCAGAGAACGCAAAGCT GCAGCTGAGCAAGGACACATACGACGACGACCTGGACAACCTGCTGGCACA GATCGGAGACCAGTACGCAGACCTGTTCCTGGCAGCAAAGAACCTGAGCGA CGCAATCCTGCTGAGCGACATCCTGAGAGTCAACACAGAAATCACAAAGGC ACCGCTGAGCGCAAGCATGATCAAGAGATACGACGAACACCACCAGGACCT GACACTGCTGAAGGCACTGGTCAGACAGCAGCTGCCGGAAAAGTACAAGGA AATCTTCTTCGACCAGAGCAAGAACGGATACGCAGGATACATCGACGGAGG AGCAAGCCAGGAAGAATTCTACAAGTTCATCAAGCCGATCCTGGAAAAGAT GGACGGAACAGAAGAACTGCTGGTCAAGCTGAACAGAGAAGACCTGCTGAG AAAGCAGAGAACATTCGACAACGGAAGCATCCCGCACCAGATCCACCTGGG AGAACTGCACGCAATCCTGAGAAGACAGGAAGACTTCTACCCGTTCCTGAA GGACAACAGAGAAAAGATCGAAAAGATCCTGACATTCAGAATCCCGTACTA CGTCGGACCGCTGGCAAGAGGAAACAGCAGATTCGCATGGATGACAAGAAA GAGCGAAGAAACAATCACACCGTGGAACTTCGAAGAAGTCGTCGACAAGGG AGCAAGCGCACAGAGCTTCATCGAAAGAATGACAAACTTCGACAAGAACCT GCCGAACGAAAAGGTCCTGCCGAAGCACAGCCTGCTGTACGAATACTTCAC AGTCTACAACGAACTGACAAAGGTCAAGTACGTCACAGAAGGAATGAGAAA GCCGGCATTCCTGAGCGGAGAACAGAAGAAGGCAATCGTCGACCTGCTGTT CAAGACAAACAGAAAGGTCACAGTCAAGCAGCTGAAGGAAGACTACTTCAA GAAGATCGAATGCTTCGACAGCGTCGAAATCAGCGGAGTCGAAGACAGATT CAACGCAAGCCTGGGAACATACCACGACCTGCTGAAGATCATCAAGGACAA GGACTTCCTGGACAACGAAGAAAACGAAGACATCCTGGAAGACATCGTCCT GACACTGACACTGTTCGAAGACAGAGAAATGATCGAAGAAAGACTGAAGAC ATACGCACACCTGTTCGACGACAAGGTCATGAAGCAGCTGAAGAGAAGAAG ATACACAGGATGGGGAAGACTGAGCAGAAAGCTGATCAACGGAATCAGAGA CAAGCAGAGCGGAAAGACAATCCTGGACTTCCTGAAGAGCGACGGATTCGC AAACAGAAACTTCATGCAGCTGATCCACGACGACAGCCTGACATTCAAGGA AGACATCCAGAAGGCACAGGTCAGCGGACAGGGAGACAGCCTGCACGAACA CATCGCAAACCTGGCAGGAAGCCCGGCAATCAAGAAGGGAATCCTGCAGAC AGTCAAGGTCGTCGACGAACTGGTCAAGGTCATGGGAAGACACAAGCCGGA AAACATCGTCATCGAAATGGCAAGAGAAAACCAGACAACACAGAAGGGACA GAAGAACAGCAGAGAAAGAATGAAGAGAATCGAAGAAGGAATCAAGGAACT GGGAAGCCAGATCCTGAAGGAACACCCGGTCGAAAACACACAGCTGCAGAA CGAAAAGCTGTACCTGTACTACCTGCAGAACGGAAGAGACATGTACGTCGA CCAGGAACTGGACATCAACAGACTGAGCGACTACGACGTCGACCACATCGT CCCGCAGAGCTTCCTGAAGGACGACAGCATCGACAACAAGGTCCTGACAAG | 1 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AAGCGACAAGAACAGAGGAAAGAGCGACAACGTCCCGAGCGAAGAAGTCGT<br>CAAGAAGATGAAGAACTACTGGAGACAGCTGCTGAACGCAAAGCTGATCAC<br>ACAGAGAAAGTTCGACAACCTGACAAAGGCAGAGAGGAGGACTGAGCGA<br>ACTGGACAAGGCAGGATTCATCAAGAGACAGCTGGTCGAAACAAGACAGAT<br>CACAAAGCACGTCGCACAGATCCTGGACAGCAGAATGAACACAAAGTACGA<br>CGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAAT<br>CAACAACTACCACCACGCACACGACGCATACCTGAACGCAGTCGTCGGAAC<br>AGCACTGATCAAGAAGTACCCGAAGCTGGAAAGCGAATTCGTCTACGGAGA<br>CTACAAGGTCTACGACGTCAGAAAGATGATCGCAAAGAGCGAACAGGAAAT<br>CGGAAAGGCAACAGCAAAGTACTTCTTCTACAGCAACATCATGAACTTCTT<br>CAAGACAGAAATCACACTGGCAAACGGAGAAATCAGAAAGAGACCGCTGAT<br>CGAAACAAACGGAGAAACAGGAGAAATCGTCTGGGACAAGGGAAGAGACTT<br>CGCAACAGTCAGAAAGGTCCTGAGCATGCCGCAGGTCAACATCGTCAAGAA<br>GACAGAAGTCCAGACAGGAGGATTCAGCAAGGAAAGCATCCTGCCGAAGAG<br>AAACAGCGACAAGCTGATCGCAAGAAAGAAGGACTGGGACCCGAAGAAGTA<br>CGGAGGATTCGACAGCCCGACAGTCGCATACAGCGTCCTGGTCGTCGCAAA<br>GGTCGAAAAGGGAAAGAGCAAGAAGCTGAAGAGCGTCAAGGAACTGCTGGG<br>AATCACAATCATGGAAAGAAGCAGCTTCGAAAAGAACCCGATCGACTTCCT<br>GGAAGCAAAGGGATACAAGGAAGTCAAGAAGGACCTGATCATCAAGCTGCC<br>GAAGTACAGCCTGTTCGAACTGGAAAACGGAAGAAAGAGAATGCTGGCAAG<br>CGCAGGAGAACTGCAGAAGGGAAACGAACTGGCACTGCCGAGCAAGTACGT<br>CAACTTCCTGTACCTGGCAAGCCACTACGAAAAGCTGAAGGGAAGCCCGGA<br>AGACAACGAACAGAAGCAGCTGTTCGTCGAACAGCACAAGCACTACCTGGA<br>CGAAATCATCGAACAGATCAGCGAATTCAGCAAGAGAGTCATCCTGGCAGA<br>CGCAAACCTGGACAAGGTCCTGAGCGCATACAACAAGCACAGAGACAAGCC<br>GATCAGAGAACAGGCAGAAAACATCATCCACCTGTTCACACTGACAAACCT<br>GGGAGCACCGGCAGCATTCAAGTACTTCGACACAACAATCGACAGAAAGAG<br>ATACACAAGCACAAAGGAAGTCCTGGACGCAACACTGATCCACCAGAGCAT<br>CACAGGACTGTACGAAACAAGAATCGACCTGAGCCAGCTGGGAGGAGACGG<br>AGGAGGAAGCCCGAAGAAGAAGAGAAAGGTCTAGCTAGCCATCACATTTAA<br>AAGCATCTCAGCCTACCATGAGAATAAGAGAAAGAAAATGAAGATCAATAG<br>CTTATTCATCTCTTTTTCTTTTTCGTTGGTGTAAAGCCAACACCCTGTCTA<br>AAAAACATAAATTTCTTTAATCATTTTGCCTCTTTTCTCTGTGCTTCAATT<br>AATAAAAAATGGAAAGAACCTCGAG | |
| Cas9 transcript comprising Cas9 ORF corresponding to SEQ ID NO: 205 using codons with generally high expression in humans | GGGTCCCGCAGTCGGCGTCCAGCGGCTCTGCTTGTTCGTGTGTGTGTCGTT<br>GCAGGCCTTATTCGGATCCATGCCTAAGAAAAAGCGGAAGGTCGACGGGGA<br>TAAGAAGTACTCAATCGGGCTGGATATCGGAACTAATTCCGTGGGTTGGGC<br>AGTGATCACGGATGAATACAAAGTGCCGTCCAAGAAGTTCAAGGTCCTGGG<br>GAACACCGATAGACACAGCATCAAGAAAAATCTCATCGGAGCCCTGCTGTT<br>TGACTCCGGCGAAACCGCAGAAGCGACCCGGCTCAAACGTACCGCGAGGCG<br>ACGCTACACCCGGCGGAAGAATCGCATCTGCTATCTGCAAGAGATCTTTTC<br>GAACGAAATGGCAAAGGTCGACGACAGCTTCTTCCACCGCCTGGAAGAATC<br>TTTCCTGGTGGAGGAGGACAAGAAGCATGAACGGCATCCTATCTTTGGAAA<br>CATCGTCGACGAAGTGGCGTACCACGAAAAGTACCCGACCATCTACCATCT<br>GCGGAAGAAGTTGGTTGACTCAACTGACAAGGCCGACCTCAGATTGATCTA<br>CTTGGCCCTCGCCCATATGATCAAATTCCGCGGACACTTCCTGATCGAAGG<br>CGATCTGAACCCTGATAACTCCGACGTGGATAAGCTTTTCATTCAACTGGT<br>GCAGACCTACAACCAACTGTTCGAAGAAAACCCAATCAATGCTAGCGGCGT<br>CGATGCCAAGGCCATCCTGTCCGCCCGGCTGTCGAAGTCGCGGCGCCTCGA<br>AAACCTGATCGCACAGCTGCCGGGAGAGAAAAAGAACGGACTTTTCGGCAA<br>CTTGATCGCTCTCTCACTGGGACTCACTCCCAATTTCAAGTCCAATTTTGA<br>CCTGGCCGAGGACGCGAAGCTGCAACTCTCAAAGGACACCTACGACGACGA<br>CTTGACAATTTGCTGGCACAAATTGGCGATCAGTACGCGGATCGTGTTCCT<br>TGCCGCTAAGAACCTTTCGGACGCAATCTTGCTGTCCGATATCCTGCGCGT<br>GAACACCGAAATAACCAAAGCGCCGCTTAGCGCCTCGATGATTAAGCGGTA<br>CGACGAGCATCACCAGGATCTCACGCTGCTCAAAGCGCTCGTGAGACAGCA<br>ACTGCCTGAAAAGTACAAGGAGATCTTCTTCGACCAGTCCAAGAATGGGTA<br>CGCAGGGTACATCGATGGAGGCGCTAGCCAGGAAGAGTTCTATAAGTTCAT<br>CAAGCCAATCCTGGAAAAGATGGACGGAACCGAAGAACTGCTGGTCAAGCT<br>GAACAGGGAGGATCTGCTCCGGAAACAGAGAACCTTTGACAACGGATCCAT<br>TCCCCACCAGATCCATCTGGGTGAGCTGCACGCCATCTTGCGGCGCCAGGA<br>GGACTTTTACCCATTCCTCAAGGACAACCGGGAAAAGATCGAGAAAATTCT<br>GACGTTCCGCATCCCGTATTACGTGGGCCCACTGGCGCGCGGCAATTCGCG<br>CTTCGCGTGGATGACTAGAAAATCAGAGGAAACCATCACTCCTTGGAATTT<br>CGAGGAAGTTGTGGATAAGGGAGCTTCGGCACAAAGCTTCATCGAACGAAT<br>GACCAACTTCGACAAGAATCTCCCAAACGAGAAGGTGCTTCCTAAGCACAG<br>CCTCCTTTACGAATACTTCACTGTCTACAACGAACTGACTAAAGTGAAATA<br>CGTTACTGAAGGAATGAGGAAGCCGGCCTTTCTGTCCGGAGAACAGAAGAA | 2 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AGCAATTGTCGATCTGCTGTTCAAGACCAACCGCAAGGTGACCGTCAAGCA<br>GCTTAAAGAGGACTACTTCAAGAAGATCGAGTGTTTCGACTCAGTGGAAAT<br>CAGCGGGGTGGAGGACAGATTCAACGCTTCGCTGGGAACCTATCATGATCT<br>CCTGAAGATCATCAAGGACAAGGACTTCCTTGACAACGAGGAGAACGAGGA<br>CATCCTGGAAGATATCGTCCTGACCTTGACCCTTTTCGAGGATCGCGAGAT<br>GATCGAGGAGAGGCTTAAGACCTACGCTCATCTCTTCGACGATAAGGTCAT<br>GAAACAACTCAAGCGCCGCCGGTACACTGGTTGGGGCCGCCTCTCCCGCAA<br>GCTGATCAACGGTATTCGCGATAAACAGAGCGGTAAAACTATCCTGGATTT<br>CCTCAAATCGGATGGCTTCGCTAATCGTAACTTCATGCAATTGATCCACGA<br>CGACAGCCTGACCTTTAAGGAGGACATCCAAAAAGCACAAGTGTCCGGACA<br>GGGAGACTCACTCCATGAACACATCGCGAATCTGGCCGGTTCGCCGGCGAT<br>TAAGAAGGGAATTCTGCAAACTGTGAAGGTGGTCGACGAGCTGGTGAAGGT<br>CATGGGACGGCACAAACCGGAGAATATCGTGATTGAAATGGCCCGAGAAAA<br>CCAGACTACCCAGAAGGGCCAGAAAAACTCCCGCGAAAGGATGAAGCGGAT<br>CGAAGAAGGAATCAAGGAGCTGGGCAGCCAGATCCTGAAAGAGCACCCGGT<br>GGAAAACACGCAGCTGCAGAACGAGAAGCTCTACCTGTACTATTTGCAAAA<br>TGGACGGGACATGTACGTGGACCAAGAGCTGGACATCAATCGGTTGTCTGA<br>TTACGACGTGGACCACATCGTTCCACAGTCCTTTCTGAAGGATGACTCGAT<br>CGATAACAAGGTGTTGACTCGCAGCGACAAGAACAGAGGGAAGTCAGATAA<br>TGTGCCATCGGAGGAGGTCGTGAAGAAGATGAAGAATTACTGGCGGCAGCT<br>CCTGAATGCGAAGCTGATTACCCAGAGAAAGTTTGACAATCTCACTAAAGC<br>CGAGCGCGGCGGACTCTCAGAGCTGGATAAGGCTGGATTCATCAAACGGCA<br>GCTGGTCGAGACTCGGCAGATTACCAAGCACGTGGCGCAGATCTTGGACTC<br>CCGCATGAACACTAAATACGACGAGAACGATAAGCTCATCCGGGAAGTGAA<br>GGTGATTACCCTGAAAAGCAAACTTGTGTCGGACTTTCGGAAGGACTTTCA<br>GTTTTACAAAGTGAGAGAAATCAACAACTACCATCACGCGCATGACGCATA<br>CCTCAACGCTGTGGTCGGTACCGCCCTGATCAAAAAGTACCCTAAACTTGA<br>ATCGGAGTTTGTGTACGGAGACTACAAGGTCTACGACGTGAGGAAGATGAT<br>AGCCAAGTCCGAACAGGAAATCGGGAAAGCAACTGCGAAATACTTCTTTTA<br>CTCAAACATCATGAACTTTTTCAAGACTGAAATTACGCTGGCCAATGGAGA<br>AATCAGGAAGAGGCCACTGATCGAAACTAACGGAGAAACGGGCGAAATCGT<br>GTGGGACAAGGGCAGGGACTTCGCAACTGTTCGCAAAGTGCTCTCTATGCC<br>GCAAGTCAATATTGTGAAGAAAACCGAAGTGCAAACCGGCGGATTTTCAAA<br>GGAATCGATCCTCCCAAAGAGAAATAGCGACAAGCTCATTGCACGCAAGAA<br>AGACTGGGACCCGAAGAAGTACGGAGGATTCGATTCGCCGACTGTCGCATA<br>CTCCGTCCTCGTGGTGCCAAGGTGGAGAAGGGAAAGAGCAAAAAGCTCAA<br>ATCCGTCAAAGAGCTGCTGGGGATTACCATCATGGAACGATCCTCGTTCGA<br>GAAGAACCCGATTGATTTCCTCGAGGCGAAGGGTTACAAGGAGGTGAAGAA<br>GGATCTGATCATCAAACTCCCCAAGTACTCACTGTTCGAACTGGAAAATGG<br>TCGGAAGCGCATGCTGGCTTCGGCCGGAGAACTCCAAAAAGGAAATGAGCT<br>GGCCTTGCCTAGCAAGTACGTCAACTTCCTCTATCTTGCTTCGCACTACGA<br>AAAACTCAAAGGGTCACCGGAAGATAACGAACAGAAGCAGCTTTTCGTGGA<br>GCAGCACAAGCATTATCTGGATGAAATCATCGAACAAATCTCCGAGTTTTC<br>AAAGCGCGTGATCCTCGCCGACGCCAACCTCGACAAAGTCCTGTCGGCCTA<br>CAATAAGCATAGAGATAAGCCGATCAGAGAACAGGCCGAGAACATTATCCA<br>CTTGTTCACCCTGACTAACCTGGGAGCCCCAGCCGCCTTCAAGTACTTCGA<br>TACTACTATCGATCGCAAAAGATACACGTCCACCAAGGAAGTTCTGGACGC<br>GACCCTGATCCACCAAAGCATCACTGGACTCTACGAAACTAGGATCGATCT<br>GTCGCAGCTGGGTGGCGATTGATAGTCTAGCCATCACATTTAAAAGCATCT<br>CAGCCTACCATGAGAATAAGAGAAAGAAAATGAAGATCAATAGCTTATTCA<br>TCTCTTTTTCTTTTTCGTTGGTGTAAAGCCAACACCCTGTCTAAAAAACAT<br>AAATTTCTTTAATCATTTTGCCTCTTTTCTCTGTGCTTCAATTAATAAAAA<br>ATGGAAAGAACCTCGAG | |
| modified sgRNA sequence ("N" may be any natural or non-natural nucleotide) | mN\*mN\*mN\*NNNNNNNNNNNNNNNNNNNGUUUUAGAmGmCmUmAmGmAmAm<br>UmAmGmCAAGUUAAAAUAAGGCUAGUCCGUUAUCAmAmCmUmUmGmAmAm<br>mAmAmGmUmGmGmCmAmCmCmGmAmGmUmCmGmGmUmGmCmU\*mU\*mU\*mU | 3 |
| 30/30/39 poly-A sequence | AAAAAAAAAAAAAAAAAAAAAAAAAAAAAAGCGAAAAAAAAAAAAAAAAAA<br>AAAAAAAAAAAACCGAAAAAAAAAAAAAAAAAAAAAAAAAAAAAAAAAAAA<br>AAA | 4 |

-continued

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
| --- | --- | --- |
| CR003335 gRNA targeting Human TTR (Exon 1) | CUGCUCCUCCUCUGCCUUGC | 5 |
| CR003336 gRNA targeting Human TTR (Exon 1) | CCUCCUCUGCCUUGCUGGAC | 6 |
| CR003337 gRNA targeting Human TTR (Exon 1) | CCAGUCCAGCAAGGCAGAGG | 7 |
| CR003338 gRNA targeting Human TTR (Exon 1) | AUACCAGUCCAGCAAGGCAG | 8 |
| CR003339 gRNA targeting Human TTR (Exon 1) | ACACAAAUACCAGUCCAGCA | 9 |
| CR003340 gRNA targeting Human TTR (Exon 1) | UGGACUGGUAUUUGUGUCUG | 10 |
| CR003341 gRNA targeting Human TTR (Exon 1) | CUGGUAUUUGUGUCUGAGGC | 11 |
| CR003342 gRNA targeting Human TTR (Exon 2) | CUUCUCUACACCCAGGGCAC | 12 |
| CR003343 gRNA targeting Human TTR (Exon 2) | CAGAGGACACUUGGAUUCAC | 13 |
| CR003344 gRNA targeting Human TTR (Exon 2) | UUUGAGCAUCAGAGGACACU | 14 |
| CR003345 gRNA targeting Human TTR (Exon 2) | UCUAGAACUUUGAGCAUGAG | 15 |

-continued

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| CR003346 gRNA targeting Human TTR (Exon 2) | AAAGUUCUAGAUGCUGUCCG | 16 |
| CR003347 gRNA targeting Human TTR (Exon 2) | CAUUGAUGGCAGGACUGCCU | 17 |
| CR003348 gRNA targeting Human TTR (Exon 2) | AGGCAGUCCUGCCAUCAAUG | 18 |
| CR003349 gRNA targeting Human TTR (Exon 2) | UGCACGGCCACAUUGAUGGC | 19 |
| CR003350 gRNA targeting Human TTR (Exon 2) | CACAUGCACGGCCACAUUGA | 20 |
| CR003351 gRNA targeting Human TTR (Exon 2) | AGCCUUUCUGAACACAUGCA | 21 |
| CR003352 gRNA targeting Human TTR (Exon 2) | GAAAGGCUGCUGAUGACACC | 22 |
| CR003353 gRNA targeting Human TTR (Exon 2) | AAAGGCUGCUGAUGACACCU | 23 |
| CR003354 gRNA targeting Human TTR (Exon 2) | ACCUGGGAGCCAUUUGCCUC | 24 |
| CR003355 gRNA targeting Human TTR (Exon 2) | CCCAGAGGCAAAUGGCUCCC | 25 |
| CR003356 gRNA targeting Human TTR (Exon 2) | GCAACUUACCCAGAGGCAAA | 26 |

-continued

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| CR003357 gRNA targeting Human TTR (Exon 2) | UUCUUUGGCAACUUACCCAG | 27 |
| CR003358 gRNA targeting Human TTR (Exon 3) | AUGCAGCUCUCCAGACUCAC | 28 |
| CR003359 gRNA targeting Human TTR (Exon 3) | AGUGAGUCUGGAGAGCUGCA | 29 |
| CR003360 gRNA targeting Human TTR (Exon 3) | GUGAGUCUGGAGAGCUGCAU | 30 |
| CR003361 gRNA targeting Human TTR (Exon 3) | GCUGCAUGGGCUCACAACUG | 31 |
| CR003362 gRNA targeting Human TTR (Exon 3) | GCAUGGGCUCACAACUGAGG | 32 |
| CR003363 gRNA targeting Human TTR (Exon 3) | ACUGAGGAGGAAUUUGUAGA | 33 |
| CR003364 gRNA targeting Human TTR (Exon 3) | CUGAGGAGGAAUUUGUAGAA | 34 |
| CR003365 gRNA targeting Human TTR (Exon 3) | UGUAGAAGGGAUAUACAAAG | 35 |
| CR003366 gRNA targeting Human TTR (Exon 3) | AAAUAGACACCAAAUCUUAC | 36 |
| CR003367 gRNA targeting Human TTR (Exon 3) | AGACACCAAAUCUUACUGGA | 37 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
| --- | --- | --- |
| CR003368 gRNA targeting Human TTR (Exon 3) | AAGUGCCUUCCAGUAAGAUU | 38 |
| CR003369 gRNA targeting Human TTR (Exon 3) | CUCUGCAUGCUCAUGGAAUG | 39 |
| CR003370 gRNA targeting Human TTR (Exon 3) | CCUCUGCAUGCUCAUGGAAU | 40 |
| CR003371 gRNA targeting Human TTR (Exon 3) | ACCUCUGCAUGCUCAUGGAA | 41 |
| CR003372 gRNA targeting Human TTR (Exon 3) | UACUCACCUCUGCAUGCUCA | 42 |
| CR003373 gRNA targeting Human TTR (Exon 4) | GUAUUCACAGCCAACGACUC | 43 |
| CR003374 gRNA targeting Human TTR (Exon 4) | GCGGCGGGGCCGGAGUCGU | 44 |
| CR003375 gRNA targeting Human TTR (Exon 4) | AAUGGUGUAGCGGCGGGGGC | 45 |
| CR003376 gRNA targeting Human TTR (Exon 4) | CGGCAAUGGUGUAGCGGCGG | 46 |
| CR003377 gRNA targeting Human TTR (Exon 4) | GCGGCAAUGGUGUAGCGGCG | 47 |
| CR003378 gRNA targeting Human TTR (Exon 4) | GGCGGCAAUGGUGUAGCGGC | 48 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| CR003379 gRNA targeting Human TTR (Exon 4) | GGGCGGCAAUGGUGUAGCGG | 49 |
| CR003380 gRNA targeting Human TTR (Exon 4) | GCAGGGCGGCAAUGGUGUAG | 50 |
| CR003381 gRNA targeting Human TTR (Exon 4) | GGGGCUCAGCAGGGCGGCAA | 51 |
| CR003382 gRNA targeting Human TTR (Exon 4) | GGAGUAGGGGCUCAGCAGGG | 52 |
| CR003383 gRNA targeting Human TTR (Exon 4) | AUAGGAGUAGGGGCUCAGCA | 53 |
| CR003384 gRNA targeting Human TTR (Exon 4) | AAUAGGAGUAGGGGCUCAGC | 54 |
| CR003385 gRNA targeting Human TTR (Exon 4) | CCCCUACUCCUAUUCCACCA | 55 |
| CR003386 gRNA targeting Human TTR (Exon 4) | CCGUGGUGGAAUAGGAGUAG | 56 |
| CR003387 gRNA targeting Human TTR (Exon 4) | GCCGUGGUGGAAUAGGAGUA | 57 |
| CR003388 gRNA targeting Human TTR (Exon 4) | GACGACAGCCGUGGUGGAAU | 58 |
| CR003389 gRNA targeting Human TTR (Exon 4) | AUUGGUGACGACAGCCGUGG | 59 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| CR003390 gRNA targeting Human TTR (Exon 4) | GGGAUUGGUGACGACAGCCG | 60 |
| CR003391 gRNA targeting Human TTR (Exon 4) | GGCUGUCGUCACCAAUCCCA | 61 |
| CR003392 gRNA targeting Human TTR (Exon 4) | AGUCCCUCAUUCCUUGGGAU | 62 |
| CR005298 gRNA targeting Human TTR (Exon 1) | UCCACUCAUUCUUGGCAGGA | 63 |
| CR005299 gRNA targeting Human TTR (Exon 4) | AGCCGUGGUGGAAUAGGAGU | 64 |
| CR005300 gRNA targeting Human TTR (Exon 1) | UCACAGAAACACUCACCGUA | 65 |
| CR005301 gRNA targeting Human TTR (Exon 1) | GUCACAGAAACACUCACCGU | 66 |
| CR005302 gRNA targeting Human TTR (Exon 2) | ACGUGUCUUCUCUACACCCA | 67 |
| CR005303 gRNA targeting Human TTR (Exon 2) | UGAAUCCAAGUGUCCUCUGA | 68 |
| CR005304 gRNA targeting Human TTR (Exon 2) | GGCCGUGCAUGUGUUCAGAA | 69 |
| CR005305 gRNA targeting Human TTR (Exon 3) | UAUAGGAAAACCAGUGAGUC | 70 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| CR005306 gRNA targeting Human TTR (Exon 3) | AAAUCUUACUGGAAGGCACU | 71 |
| CR005307 gRNA targeting Human TTR (Exon 4) | UGUCUGUCUUCUCUCAUAGG | 72 |
| CR000689 gRNA targeting Cyno TTR | ACACAAAUACCAGUCCAGCG | 73 |
| CR005364 gRNA targeting Cyno TTR | AAAGGCUGCUGAUGAGACCU | 74 |
| CR005365 gRNA targeting Cyno TTR | CAUUGACAGCAGGACUGCCU | 75 |
| CR005366 gRNA targeting Cyno TTR | AUACCAGUCCAGCGAGGCAG | 76 |
| CR005367 gRNA targeting Cyno TTR | CCAGUCCAGCGAGGCAGAGG | 77 |
| CR005368 gRNA targeting Cyno TTR | CCUCCUCUGCCUCGCUGGAC | 78 |
| CR005369 gRNA targeting Cyno TTR | AAAGUUCUAGAUGCCGUCCG | 79 |
| CR005370 gRNA targeting Cyno TTR | ACUUGUCUUCUCUAUACCCA | 80 |
| CR005371 gRNA targeting Cyno TTR | AAGUGACUUCCAGUAAGAUU | 81 |
| CR005372 gRNA targeting Cyno TTR | AAAAGGCUGCUGAUGAGACC | 82 |
| | Not Used | 83 |
| | Not Used | 84 |
| | Not Used | 85 |
| | Not Used | 86 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| G000480 sgRNA modified sequence targeting Human TTR | mA*mA*mA*GGCUGCUGAUGACACCUGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 87 |
| G000481 sgRNA modified sequence targeting Human TTR | mU*mC*mU*AGAACUUUGACCAUCAGGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 88 |
| G000482 sgRNA modified sequence targeting Human TTR | mU*mG*mU*AGAAGGGAUAUACAAAGGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 89 |
| G000483 sgRNA modified sequence targeting Human TTR | mU*mC*mC*ACUCAUUCUUGGCAGGAGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 90 |
| G000484 sgRNA modified sequence targeting Human TTR | mA*mG*mA*CACCAAAUCUUACUGGAGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 91 |
| G000485 sgRNA modified sequence targeting Human TTR | mC*mC*mU*CCUCUGCCUUGCUGGACGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 92 |
| G000486 sgRNA modified sequence targeting Human TTR | mA*mC*mA*CAAAUACCAGUCCAGCAGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 93 |
| G000487 sgRNA modified sequence targeting Human TTR | mU*mU*mC*UUUGGCAACUUACCCAGGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 94 |
| G000488 sgRNA modified sequence targeting Human TTR | mA*mA*mA*GUUCUAGAUGCUGUCCGGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 95 |
| G000489 sgRNA modified sequence targeting Human TTR | mU*mU*mU*GACCANCAGAGGACACUGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 96 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| G000490 sgRNA modified sequence targeting Human TTR | mA*mA*mA*UAGACACCAAAUCUUACGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 97 |
| G000491 sgRNA modified sequence targeting Human TTR | mA*mU*mA*CCAGUCCAGCTVAGGCAGGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 98 |
| G000492 sgRNA modified sequence targeting Human TTR | mC*mU*mU*CUCUACACCCAGGGCACGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 99 |
| G000493 sgRNA modified sequence targeting Human TTR | mA*mA*mG*UGCCUUCCAGUAAGAUUGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 100 |
| G000494 sgRNA modified sequence targeting Human TTR | mG*mU*mG*AGUCUGGAGAGCUGCAUGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 101 |
| G000495 sgRNA modified sequence targeting Human TTR | mC*mA*mG*AGGACACUUGGAUUCACGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 102 |
| G000496 sgRNA modified sequence targeting Human TTR | mG*mG*mC*CGUGCAUGUGUUCAGAAGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 103 |
| G000497 sgRNA modified sequence targeting Human TTR | mC*mU*mG*CUCCUCCUCUGCCUUGCGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 104 |
| G000498 sgRNA modified sequence targeting Human TTR | mA*mG*mU*GAGUCUGGAGAGCUGCAGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 105 |
| G000499 sgRNA modified sequence targeting Human TTR | mU*mG*mA*AUCCAAGUGUCCUCUGAGUUUUAGAmGmCmUmAmGmAmAmAm UmAmGmCAAGUUAAAAUAAGGCUAGUCCGUUAUCAmAmCmUmUmGmAmA mAmAmGmUmGmGmCmAmCmCmGmAmGmUmCmGmGmUmGmCmU*mU*mU*mU | 106 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| G000500 sgRNA modified sequence targeting Human TTR | mC*mC*mA*GUCCAGCAAGGCAGAGGGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 107 |
| G000501 sgRNA modified sequence targeting Human TTR | mU*mC*mA*CAGAAACACUCACCGUAGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 108 |
| G000567 sgRNA modified sequence targeting Human TTR | mG*mA*mA*AGGCUGCUGAUGACACCGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 109 |
| G000568 sgRNA modified sequence targeting Human TTR | mG*mG*mC*UGUCGUCACCAAUCCCAGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 110 |
| G000570 sgRNA modified sequence targeting Human TTR | mC*mA*mU*UGAUGGCAGGACUGCCUGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 111 |
| G000571 sgRNA modified sequence targeting Human TTR | mG*mU*mC*ACAGAAACACUCACCGUGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 112 |
| G000572 sgRNA modified sequence targeting Human TTR | mC*mC*mC*CUACUCCUAUUCCACCAGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 113 |
| G000502 sgRNA modified sequence targeting Cyno TTR | mA*mC*mA*CAAAUACCAGUCCAGCGGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 114 |
| G000503 sgRNA modified sequence targeting Cyno TTR | mA*mA*mA*AGGCUGCUGAUGAGACCGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 115 |
| G000504 sgRNA modified sequence targeting Cyno TTR | mA*mA*mA*GGCUGCUGAUGAGACCUGUUUUAGAmGmCmUmAmGmAmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 116 |

161

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| G000505 sgRNA modified sequence targeting Cyno TTR | mC*mA*mU*UGACAGCAGGACUGCCUGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 117 |
| G000506 sgRNA modified sequence targeting Cyno TTR | mA*mU*mA*CCAGUCCAGCGAGGCAGGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 118 |
| G000507 sgRNA modified sequence targeting Cyno TTR | mC*mC*mA*GUCCAGCGAGGCAGAGGGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 119 |
| G000508 sgRNA modified sequence targeting Cyno TTR | mC*mC*mU*CCUCUGCCUCGCUGGACGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 120 |
| G000509 sgRNA modified sequence targeting Cyno TTR | mA*mA*mA*GUUCUAGAUGCCGUCCGGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 121 |
| G000510 sgRNA modified sequence targeting Cyno TTR | mA*mC*mU*UGUCUUCUCUAUACCCAGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 122 |
| G000511 sgRNA modified sequence targeting Cyno TTR | mA*mA*mG*UGACUUCCAGUAAGAUUGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 123 |
| G000282 sgRNA modified sequence targeting Mouse TTR | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmGmUmGmGmCmAmCmCmGmAmGmUmCmGmGmUmGmCmU*mU*mU*mU | 124 |
| | Not used | 125 to 200 |
| DNA coding sequence of Cas9 using the thymidine analog of the minimal uridine codons listed in | ATGGACAAGAAGTACAGCATCGGACTGGACATCGGAACAAACAGCGTCGGATGGGCAGTCATCACAGACGAATACAAGGTCCCGAGCAAGAAGTTCAAGGTCCTGGGAAACACAGACAGACACAGCATCAAGAAGAACCTGATCGGAGCACTGCTGTTCGACAGCGGAGAAACAGCAGAAGCAACAAGACTGAAGAGAACAGCAAGAAGAAGATACACAAGAAGAAAGAACAGAATCTGCTACCTGCAGGAAATCTTCAGCAACGAAATGGCAAAGGTCGACGACAGCTTCTTCCACAGACTGGAAGAAAGCTTCCTGGTCGAAGAAGACAAGAAGCACGAAAGACACCCGATCTTCGGAAACATCGTCGACGAAGTCGCATACCACGAAAAGTACCCGACAATCTACCACCTGAGAAAGAAGCTGGTCGACAGCACAGACAAGGCAGACCTGAGACTGATCTACCTGGCACTGGCACACATGATCAAGTTCAGAGGACACTTCCTGATC | 201 |

| Description | Sequence | SEQ ID No. |
|---|---|---|
| Table 3, with start and stop codons | GAAGGAGACCTGAACCCGGACAACAGCGACGTCGACAAGCTGTTCATCCAG CTGGTCCAGACATACAACCAGCTGTTCGAAGAAACCCGATCAACGCAAGC GGAGTCGACGCAAAGGCAATCCTGAGCGCAAGACTGAGCAAGAGCAGAAGA CTGGAAAACCTGATCGCACAGCTGCCGGGAGAAAAGAAGAACGGACTGTTC GGAAACCTGATCGCACTGAGCCTGGGACTGACACCGAACTTCAAGAGCAAC TTCGACCTGGCAGAAGACGCAAAGCTGCAGCTGAGCAAGGACACATACGAC GACGACCTGGACAACCTGCTGGCACAGATCGGAGACCAGTACGCAGACCTG TTCCTGGCAGCAAAGAACCTGAGCGACGCAATCCTGCTGAGCGACATCCTG AGAGTCAACACAGAAATCACAAAGGCACCGCTGAGCGCAAGCATGATCAAG AGATACGACGAACACCACCAGGACCTGACACTGCTGAAGGCACTGGTCAGA CAGCAGCTGCCGGAAAAGTACAAGGAAATCTTCTTCGACCAGAGCAAGAAC GGATACGCAGGATACATCGACGGAGGAGCAAGCCAGGAAGAATTCTACAAG TTCATCAAGCCGATCCTGGAAAAGATGGACGGAACAGAAGAACTGCTGGTC AAGCTGAACAGAGAAGACCTGCTGAGAAAGCAGAGAACATTCGACAACGGA AGCATCCCGCACCAGATCCACCTGGGAGAACTGCACGCAATCCTGAGAAGA CAGGAAGACTTCTACCCGTTCCTGAAGGACAACAGAGAAAAGATCGAAAAG ATCCTGACATTCAGAATCCCGTACTACGTCGGACCGCTGGCAGAGAGGAAAC AGCAGATTCGCATGGATGACAAGAAAGAGCGAAGAAACAATCACACCGTGG AACTTCGAAGAAGTCGTCGACAAGGGAGCAAGCGCACAGAGCTTCATCGAA AGAATGACAAACTTCGACAAGAACCTGCCGAACGAAAAGGTCCTGCCGAAG CACAGCCTGCTGTACGAATACTTCACAGTCTACAACGAACTGACAAAGGTC AAGTACGTCACAGAAGGAATGAGAAAGCCGGCATTCCTGAGCGGAGAACAG AAGAAGGCAATCGTCGACCTGCTGTTCAAGACAAACAGAAAGGTCACAGTC AAGCAGCTGAAGGAAGACTACTTCAAGAAGATCGAATGCTTCGACAGCGTC GAAATCAGCGGAGTCGAAGACAGATTCAACGCAAGCCTGGGAACATACCAC GACCTGCTGAAGATCATCAAGGACAAGGACTTCCTGGACAACGAAGAAAAC GAAGACATCCTGGAAGACATCGTCCTGACACTGACACTGTTCGAAGACAGA GAAATGATCGAAGAAAGACTGAAGACATACGCACACCTGTTCGACGACAAG GTCATGAAGCAGCTGAAGAGAAGAAGATACACAGGATGGGGAAGACTGAGC AGAAAGCTGATCAACGGAATCAGAGACAAGCAGAGCGGAAAGACAATCCTG GACTTCCTGAAGAGCGACGGATTCGCAAACAGAAACTTCATGCAGCTGATC CACGACGACAGCCTGACATTCAAGGAAGACATCCAGAAGGCACAGGTCAGC GGACAGGGAGACAGCCTGCACGAACACATCGCAAACCTGGCAGGAAGCCCG GCAATCAAGAAGGGAATCCTGCAGACAGTCAAGGTCGTCGACGAACTGGTC AAGGTCATGGGAAGACACAAGCCGGAAAACATCGTCATCGAAATGGCAAGA GAAAACCAGACAACACAGAAGGGACAGAAGAACAGCAGAGAAAGAATGAAG AGAATCGAAGAAGGAATCAAGGAACTGGGAAGCCAGATCCTGAAGGAACAC CCGGTCGAAAACACACAGCTGCAGAACGAAAAGCTGTACCTGTACTACCTG CAGAACGGAAGAGACATGTACGTCGACCAGGAACTGGACATCAACAGACTG AGCGACTACGACGTCGACCACATCGTCCCGCAGAGCTTCCTGAAGGACGAC AGCATCGACAACAAGGTCCTGACAAGAAGCGACAAGAACAGAGGAAAGAGC GACAACGTCCCGAGCGAAGAAGTCGTCAAGAAGATGAAGAACTACTGGAGA CAGCTGCTGAACGCAAAGCTGATCACACAGAGAAAGTTCGACAACCTGACA AAGGCAGAGAGGAGGACTGAGCGAACTGGACAAGGCAGGATTCATCAAG AGACAGCTGGTCGAAACAAGACAGATCACAAAGCACGTCGCACAGATCCTG GACAGCAGAATGAACACAAAGTACGACGAAAACGACAAGCTGATCAGAGAA GTCAAGGTCATCACACTGAAGAGCAAGCTGGTCAGCGACTTCAGAAAGGAC TTCCAGTTCTACAAGGTCAGAGAAATCAACAACTACCACCACGCACACGAC GCATACCTGAACGCAGTCGTCGGAACAGCACTGATCAAGAAGTACCCGAAG CTGGAAAGCGAATTCGTCTACGGAGACTACAAGGTCTACGACGTCAGAAAG ATGATCGCAAAGAGCGAACAGGAAATCGGAAAGGCAACAGCAAAGTACTTC TTCTACAGCAACATCATGAACTTCTTCAAGACAGAAATCACACTGGCAAAC GGAGAAATCAGAAAGAGACCGCTGATCGAAACAAACGGAGAAACAGGAGAA ATCGTCTGGGACAAGGGAAGAGACTTCGCAACAGTCAGAAAGGTCCTGAGC ATGCCGCAGGTCAACATCGTCAAGAAGACAGAAGTCCAGACAGGAGGATTC AGCAAGGAAAGCATCCTGCCGAAGAGAAACAGCGACAAGCTGATCGCAAGA AAGAAGGACTGGGACCCGAAGAAGTACGGAGGATTCGACAGCCCGACAGTC GCATACAGCGTCCTGGTCGTCGCAAAGGTCGAAAAGGGAAAGAGCAAGAAG CTGAAGAGCGTCAAGGAACTGCTGGGAATCACAATCATGGAAAGAAGCAGC TTCGAAAAGAACCCGATCGACTTCCTGGAAGCAAAGGGATACAAGGAAGTC AAGAAGGACCTGATCATCAAGCTGCCGAAGTACAGCCTGTTCGAACTGGAA AACGGAAGAAAGAGAATGCTGGCAAGCGCAGGAGAACTGCAGAAGGGAAAC GAACTGGCACTGCCGAGCAAGTACGTCAACTTCCTGTACCTGGCAAGCCAC TACGAAAAGCTGAAGGGAAGCCCGGAAGACAACGAACAGAAGCAGCTGTTC GTCGAACAGCACAAGCACTACCTGGACGAAATCATCGAACAGATCAGCGAA TTCAGCAAGAGAGTCATCCTGGCAGACGCAAACCTGGACAAGGTCCTGAGC GCATACAACAAGCACAGAGACAAGCCGATCAGAGAACAGGCAGAAAACATC ATCCACCTGTTCACACTGACAAACCTGGGAGCACCGGCAGCATTCAAGTAC TTCGACACAACAATCGACAGAAAGAGATACACAAGCACAAAGGAAGTCCTG GACGCAACACTGATCCACCAGAGCATCACAGGACTGTACGAAACAAGAATC | |

| Description | Sequence | SEQ ID No. |
|---|---|---|
| | GACCTGAGCCAGCTGGGAGGAGACGGAGGAGGAAGCCCGAAGAAGAAGAGA<br>AAGGTCTAG | |
| DNA coding sequence of Cas9 using codons with generally high expression in humans | ATGGATAAGAAGTACTCAATCGGGCTGGATATCGGAACTAATTCCGTGGGT<br>TGGGCAGTGATCACGGATGAATACAAAGTGCCGTCCAAGAAGTTCAAGGTC<br>CTGGGGAACACCGATAGACACAGCATCAAGAAAAATCTCATCGGAGCCCTG<br>CTGTTTGACTCCGGCGAAACCGCAGAAGCGACCCGGCTCAAACGTACCGCG<br>AGGCGACGCTACACCCGGCGGAAGAATCGCATCTGCTATCTGCAAGAGATC<br>TTTTCGAACGAAATGGCAAAGGTCGACGACAGCTTCTTCCACCGCCTGGAA<br>GAATCTTTCCTGGTGGAGGAGGACAAGAAGCATGAACGGCATCCTATCTTT<br>GGAAACATCGTCGACGAAGTGGCGTACCACGAAAAGTACCCGACCATCTAC<br>CATCTGCGGAAGAAGTTGGTTGACTCAACTGACAAGGCCGACCTCAGATTG<br>ATCTACTTGGCCCTCGCCCATATGATCAAATTCCGCGGACACTTCCTGATC<br>GAAGGCGATCTGAACCCTGATAACTCCGACGTGGATAAGCTTTTCATTCAA<br>CTGGTGCAGACCTACAACCAACTGTTCGAAGAAAACCCAATCAATGCTAGC<br>GGCGTCGATGCCAAGGCCATCCTGTCCGCCCGGCTGTCGAAGTCGCGGCGC<br>CTCGAAAACCTGATCGCACAGCTGCCGGGAGAGAAAAAGAACGGACTTTTC<br>GGCAACTTGATCGCTCTCTCACTGGGACTCACTCCCAATTTCAAGTCCAAT<br>TTTGACCTGGCCGAGGACGCGAAGCTGCAACTCTCAAAGGACACCTACGAC<br>GACGACTTGGACAATTTGCTGGCACAAATTGGCGATCAGTACGCGGATCTG<br>TTCCTTGCCGCTAAGAACCTTTCGGACGCAATCTTGCTGTCCGATATCCTG<br>CGCGTGAACACCGAAATAACCAAAGCGCCGCTTAGCGCCTCGATGATTAAG<br>CGGTACGACGAGCATCACCAGGATCTCACGCTGCTCAAAGCGCTCGTGAGA<br>CAGCAACTGCCTGAAAAGTACAAGGAGATCTTCTTCGACCAGTCCAAGAAT<br>GGGTACGCAGGGTACATCGATGGAGGCGCTAGCCAGGAAGAGTTCTATAAG<br>TTCATCAAGCCAATCCTGGAAAAGATGGACGGAACCGAAGAACTGCTGGTC<br>AAGCTGAACAGGGAGGATCTGCTCCGGAAACAGAGAACCTTTGACAACGGA<br>TCCATTCCCCACCAGATCCATCTGGGTGAGCTGCACGCCATCTTGCGGCGC<br>CAGGAGGACTTTTACCCATTCCTCAAGGACAACCGGGAAAAGATCGAGAAA<br>ATTCTGACGTTCCGCATCCCGTATTACGTGGGCCCACTGGCGCGCGGCAAT<br>TCGCGCTTCGCGTGGATGACTAGAAAATCAGAGGAAACCATCACTCCTTGG<br>AATTTCGAGGAAGTTGTGGATAAGGGAGCTTCGGCACAAAGCTTCATCGAA<br>CGAATGACCAACTTCGACAAGAATCTCCCAAACGAGAAGGTGCTTCCTAAG<br>CACAGCCTCCTTTACGAATACTTCACTGTCTACAACGAACTGACTAAAGTG<br>AAATACGTTACTGAAGGAATGAGGAAGCCGGCCTTTCTGTCCGGAGAACAG<br>AAGAAAGCAATTGTCGATCTGCTGTTCAAGACCAACCGCAAGGTGACCGTC<br>AAGCAGCTTAAAGAGGACTACTTCAAGAAGATCGAGTGTTTCGACTCAGTG<br>GAAATCAGCGGGGTGGAGGACAGATTCAACGCTTCGCTGGGAACCTATCAT<br>GATCTCCTGAAGATCATCAAGGACAAGGACTTCCTTGACAACGAGGAGAAC<br>GAGGACATCCTGGAAGATATCGTCCTGACCTTGACCCTTTTCGAGGATCGC<br>GAGATGATCGAGGAGAGGCTTAAGACCTACGCTCATCTCTTCGACGATAAG<br>GTCATGAAACAACTCAAGCGCCGCCGGTACACTGGTTGGGGCCGCCTCTCC<br>CGCAAGCTGATCAACGGTATTCGCGATAAACAGAGCGGTAAAACTATCCTG<br>GATTTCCTCAAATCGGATGGCTTCGCTAATCGTAACTTCATGCAATTGATC<br>CACGACGACAGCCTGACCTTTAAGGAGGACATCCAAAAGCACAAGTGTCC<br>GGACAGGGAGACTCACTCCATGAACACATCGCGAATCTGGCCGGTTCGCCG<br>GCGATTAAGAAGGGAATTCTGCAAACTGTGAAGGTGGTCGACGAGCTGGTG<br>AAGGTCATGGGACGGCACAAACCGGAGAATATCGTGATTGAAATGGCCCGA<br>GAAAACCAGACTACCCAGAAGGGCCAGAAAAACTCCCGCGAAAGGATGAAG<br>CGGATCGAAGAAGGAATCAAGGAGCTGGGCAGCCAGATCCTGAAAGAGCAC<br>CCGGTGGAAAACACGCAGCTGCAGAACGAGAAGCTCTACCTGTACTATTTG<br>CAAAATGGACGGGACATGTACGTGGACCAAGAGCTGGACATCAATCGGTTG<br>TCTGATTACGACGTGGACCACATCGTTCCACAGTCCTTTCTGAAGGATGAC<br>TCGATCGATAACAAGGTGTTGACTCGCAGCGACAAGAACAGAGGGAAGTCA<br>GATAATGTGCCATCGGAGGAGGTCGTGAAGAAGATGAAGAATTACTGGCGG<br>CAGCTCCTGAATGCGAAGCTGATTACCCAGAGAAAGTTTGACAATCTCACT<br>AAAGCCGAGCGCGGCGGACTCTCAGAGCTGGATAAGGCTGGATTCATCAAA<br>CGGCAGCTGGTCGAGACTCGGCAGATTACCAAGCACGTGGCGCAGATCTTG<br>GACTCCCGCATGAACACTAAATACGACGAGAACGATAAGCTCATCCGGGAA<br>GTGAAGGTGATTACCCTGAAAAGCAAACTTGTGTCGGACTTTCGGAAGGAC<br>TTTCAGTTTTACAAAGTGAGAGAAATCAACAACTACCATCACGCGCATGAC<br>GCATACCTCAACGCTGTGGTCGGTACCGCCCTGATCAAAAAGTACCCTAAA<br>CTTGAATCGGAGTTTGTGTACGGAGACTACAAGGTCTACGACGTGAGGAAG<br>ATGATAGCCAAGTCCGAACAGGAAATCGGGAAAGCAACTGCGAAATACTTC<br>TTTTACTCAAACATCATGAACTTTTTCAAGACTGAAATTACGCTGGCCAAT<br>GGAGAAATCAGGAAGAGGCCACTGATCGAAACTAACGGAGAAACGGGCGAA<br>ATCGTGTGGGACAAGGGCAGGGACTTCGCAACTGTTCGCAAAGTGCTCTCT<br>ATGCCGCAAGTCAATATTGTGAAGAAAACCGAAGTGCAAACCGGCGGATTT<br>TCAAAGGAATCGATCCTCCCAAAGAGAAATAGCGACAAGCTCATTGCACGC<br>AAGAAAGACTGGGACCCCGAAGAAGTACGGAGGATTCGATTCGCCGACTGTC | 202 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GCATACTCCGTCCTCGTGGTGGCCAAGGTGGAGAAGGGAAAGAGCAAAAAG<br>CTCAAATCCGTCAAAGAGCTGCTGGGGATTACCATCATGGAACGATCCTCG<br>TTCGAGAAGAACCCGATTGATTTCCTCGAGGCGAAGGGTTACAAGGAGGTG<br>AAGAAGGATCTGATCATCAAACTCCCCAAGTACTCACTGTTCGAACTGGAA<br>AATGGTCGGAAGCGCATGCTGGCTTCGGCCGGAGAACTCCAAAAAGGAAAT<br>GAGCTGGCCTTGCCTAGCAAGTACGTCAACTTCCTCTATCTTGCTTCGCAC<br>TACGAAAAACTCAAAGGGTCACCGGAAGATAACGAACAGAAGCAGCTTTTC<br>GTGGGAGCAGCACAAGCATTATCTGGATGAAATCATCGAACAAATCTCCGAG<br>TTTTCAAAGCGCGTGATCCTCGCCGACGCCAACCTCGACAAAGTCCTGTCG<br>GCCTACAATAAGCATAGAGATAAGCCGATCAGAGAACAGGCCGAGAACATT<br>ATCCACTTGTTCACCCTGACTAACCTGGGAGCCCCAGCCGCCTTCAAGTAC<br>TTCGATACTACTATCGATCGCAAAAGATACACGTCCACCAAGGAAGTTCTG<br>GACGCGACCCTGATCCACCAAAGCATCACTGGACTCTACGAAACTAGGATC<br>GATCTGTCGCAGCTGGGTGGCGATGGCGGTGGATCTCCGAAAAAGAAGAGA<br>AAGGTGTAATGA | |
| Amino acid sequence of Cas9 with one nuclear localization signal (1xNLS) as the C terminal 7 amino acids | MDKKYSIGLDIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV<br>KQLKEDYFKKIECFDSVEISGVEDRFNASLGTYHDLLKIIKDKDFLDNEEN<br>EDILEDIVLTLTLFEDREMIEERLKTYAHLFDDKVMKQLKRRRYTGWGRLS<br>RKLINGIRDKQSGKTILDFLKSDGFANRNFMQLIHDDSLTFKEDIQKAQVS<br>GQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYL<br>QNGRDMYVDQELDINRLSDYDVDHIVPQSFLKDDSIDNKVLTRSDKNRGKS<br>DNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGE<br>IVWDKGRDFATVRKVLSMPQVNIVKKTEVQTGGFSKESILPKRNSDKLIAR<br>KKDWDPKKYGGFDSPTVAYSVLVVAKVEKGKSKKLKSVKELLGITIMERSS<br>FEKNPIDFLEAKGYKEVKKDLIIKLPKYSLFELENGRKRMLASAGELQKGN<br>ELALPSKYVNFLYLASHYEKLKGSPEDNEQKQLFVEQHKHYLDEIIEQISE<br>FSKRVILADANLDKVLSAYNKHRDKPIREQAENIIHLFTLTNLGAPAAFKY<br>FDTTIDRKRYTSTKEVLDATLIHQSITGLYETRIDLSQLGGDGGGSPKKKR<br>KV | 203 |
| Cas9 mRNA ORF using minimal uridine codons, with start and stop codons | AUGGACAAGAAGUACAGCAUCGGACUGGACAUCGGAACAAACAGCGUCGGA<br>UGGGCAGUCAUCACAGACGAAUACAAGGUCCCGAGCAAGAAGUUCAAGGUC<br>CUGGGAAACACAGACAGACACAGCAUCAAGAAGAACCUGAUCGGAGCACUG<br>CUGUUCGACAGCGGAGAAACAGCAGAAGCAACAAGACUGAAGAGAACAGCA<br>AGAAGAAGAUACACAAGAAGAAAGAACAGAAUCUGCUACCUGCAGGAAAUC<br>UUCAGCAACGAAAUGGCAAAGGUCGACGACAGCUUCUUCCACAGACUGGAA<br>GAAAGCUUCCUGGUCGAAGAAGACAAGAAGCACGAAAGACACCCGAUCUUC<br>GGAAACAUCGUCGACGAAGUCGCAUACCACGAAAAGUACCCGACAAUCUAC<br>CACCUGAGAAAGAAGCUGGUCGACAGCACAGACAAGGCAGACCUGAGACUG<br>AUCUACCUGGCACUGGCACACAUGAUCAAGUUCAGAGGACACUUCCUGAUC<br>GAAGGAGACCUGAACCCGGACAACAGCGACGUCGACAAGCUGUUCAUCCAG<br>CUGGUCCAGACAUACAACCAGCUGUUCGAAGAAAACCCGAUCAACGCAAGC<br>GGAGUCGACGCAAAGGCAAUCCUGAGCGCAAGACUGAGCAAGAGCAGAAGA<br>CUGGAAAACCUGAUCGCACAGCUGCCGGGAGAAAAGAAGAACGGACUGUUC<br>GGAAACCUGAUCGCACUGAGCCUGGGACUGACACCGAACUUCAAGAGCAAC<br>UUCGACCUGGCAGAAGACGCAAAGCUGCAGCUGAGCAAGGACACAUACGAC<br>GACGACCUGGACAACCUGCUGGCACAGAUCGGAGACCAGUACGCAGACCUG<br>UUCCUGGCAGCAAAGAACCUGAGCGACGCAAUCCUGCUGAGCGACAUCCUG<br>AGAGUCAACACAGAAAUCACAAAGGCACCGCUGAGCGCAAGCAUGAUCAAG<br>AGAUACGACGAACACCACCAGGACCUGACACUGCUGAAGGCACUGGUCAGA<br>CAGCAGCUGCCGGAAAAGUACAAGGAAAUCUUCUUCGACCAGAGCAAGAAC<br>GGAUACGCAGGAUACAUCGACGGAGGAGCAAGCCAGGAAGAAUUCUACAAG<br>UUCAUCAAGCCGAUCCUGGAAAAGAUGGACGGAACAGAAGAACUGCUGGUC<br>AAGCUGAACAGAGAAGACCUGCUGAGAAAGCAGAGAACAUUCGACAACGGA<br>AGCAUCCCGCACCAGAUCCACCUGGGAGAACUGCACGCAAUCCUGAGAAGA | 204 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CAGGAAGACUUCUACCCGUUCCUGAAGGACAACAGAGAAAAGAUCGAAAAG<br>AUCCUGACAUUCAGAAUCCCGUACUACGUCGGACCGCUGGCAAGAGGAAAC<br>AGCAGAUUCGCAUGGAUGACAAGAAAGAGCGAAGAAACAAUCACACCGUGG<br>AACUUCGAAGAAGUCGUCGACAAGGGAGCAAGCGCACAGAGCUUCAUCGAA<br>AGAAUGACAAACUUCGACAAGAACCUGCCGAACGAAAAGGUCCUGCCGAAG<br>CACAGCCUGCUGUACGAAUACUUCACAGUCUACAACGAACUGACAAAGGUC<br>AAGUACGUCACAGAAGGAAUGAGAAAGCCGGCAUUCCUGAGCGGAGAACAG<br>AAGAAGGCAAUCGUCGACCUGCUGUUCAAGACAAACAGAAAGGUCACAGUC<br>AAGCAGCUGAAGGAAGACUACUUCAAGAAGAUCGAAUGCUUCGACAGCGUC<br>GAAAUCAGCGGAGUCGAAGACAGAUUCAACGCAAGCCUGGGAACAUACCAC<br>GACCUGCUGAAGAUCAUCAAGGACAAGGACUUCCUGGACAACGAAGAAAAC<br>GAAGACAUCCUGGAAGACAUCGUCCUGACACUGACACUGUUCGAAGACAGA<br>GAAAUGAUCGAAGAAAGACUGAAGACAUACGCACACCUGUUCGACGACAAG<br>GUCAUGAAGCAGCUGAAGAGAAGAAGAUACACAGGAUGGGGAAGACUGAGC<br>AGAAAGCUGAUCAACGGAAUCAGAGACAAGCAGAGCGGAAAGACAAUCCUG<br>GACUUCCUGAAGAGCGACGGAUUCGCAAACAGAAACUUCAUGCAGCUGAUC<br>CACGACGACAGCCUGACAUUCAAGGAAGACAUCCAGAAGGCACAGGUCAGC<br>GGACAGGGAGACAGCCUGCACGAACACAUCGCAAACCUGGCAGGAAGCCCG<br>GCAAUCAAGAAGGGAAUCCUGCAGACAGUCAAGGUCGUCGACGAACUGGUC<br>AAGGUCAUGGGAAGACACAAGCCGGAAAACAUCGUCAUCGAAAUGGCAAGA<br>GAAAACCAGACAACACAGAAGGGACAGAAGAACAGCAGAGAAGAAUGAAG<br>AGAAUCGAAGAAGGAAUCAAGGAACUGGGAAGCCAGAUCCUGAAGGAACAC<br>CCGGUCGAAAACACACAGCUGCAGAACGAAAGCUGUACCUGUACUACCUG<br>CAGAACGGAAGAGACAUGUACGUCGACCAGGAACUGGACAUCAACAGACUG<br>AGCGACUACGACGUCGACCACAUCGUCCCGCAGAGCUUCCUGAAGGACGAC<br>AGCAUCGACAACAAGGUCCUGACAAGAAGCGACAAGAACAGAGGAAAGAGC<br>GACAACGUCCCGAGCGAAGAAGUCGUCAAGAAGAUGAAGAACUACUGGAGA<br>CAGCUGCUGAACGCAAAGCUGAUCACACAGAGAAAGUUCGACAACCUGACA<br>AAGGCAGAGAGAGGAGGACUGAGCGAACUGGACAAGGCAGGAUUCAUCAAG<br>AGACAGCUGGUCGAAACAAGACAGAUCACAAAGCACGUCGCACAGAUCCUG<br>GACAGCAGAAUGAACACAAAGUACGACGAAAACGACAAGCUGAUCAGAGAA<br>GUCAAGGUCAUCACACUGAAGAGCAAGCUGGUCAGCGACUUCAGAAAGGAC<br>UUCCAGUUCUACAAGGUCAGAGAAAUCAACAACUACCACCACGCACACGAC<br>GCAUACCUGAACGCAGUCGUCGGAACAGCACUGAUCAAGAAGUACCCGAAG<br>CUGGAAAGCGAAUUCGUCUACGGAGACUACAAGGUCUACGACGUCAGAAAG<br>AUGAUCGCAAAGAGCGAACAGGAAAUCGGAAAGGCAACAGCAAAGUACUUC<br>UUCUACAGCAACAUCAUGAACUUCUUCAAGACAGAAAUCACACUGGCAAAC<br>GGAGAAAUCAGAAAGAGACCGCUGAUCGAAACAAACGGAGAAACAGGAGAA<br>AUCGUCUGGGACAAGGGAAGAGACUUCGCAACAGUCAGAAAGGUCCUGAGC<br>AUGCCGCAGGUCAACAUCGUCAAGAAGACAGAAGUCCAGACAGGAGGAUUC<br>AGCAAGGAAAGCAUCCUGCCGAAGAGAAACAGCGACAAGCUGAUCGCAAGA<br>AAGAAGGACUGGGACCCGAAGAAGUACGGAGGAUUCGACAGCCCGACAGUC<br>GCAUACAGCGUCCUGGUCGUCGCAAAGGUCGAAAAGGGAAAGAGCAAGAAG<br>CUGAAGAGCGUCAAGGAACUGCUGGGAAUCACAAUCAUGGAAAGAAGCAGC<br>UUCGAAAAGAACCCGAUCGACUUCCUGGAAGCAAAGGGAUACAAGGAAGUC<br>AAGAAGGACCUGAUCAUCAAGCUGCCGAAGUACAGCCUGUUCGAACUGGAA<br>AACGGAAGAAAGAGAAUGCUGGCAAGCGCAGGAGAACUGCAGAAGGGAAAC<br>GAACUGGCACUGCCGAGCAAGUACGUCAACUUCCUGUACCUGGCAAGCCAC<br>UACGAAAAGCUGAAGGGAAGCCCGGAAGACAACGAACAGAAGCAGCUGUUC<br>GUCGAACAGCACAAGCACUACCUGGACGAAAUCAUCGAACAGAUCAGCGAA<br>UUCAGCAAGAGAGUCAUCCUGGCAGACGCAAACCUGGACAAGGUCCUGAGC<br>GCAUACAACAAGCACAGAGACAAGCCGAUCAGAGAACAGGCAGAAAACAUC<br>AUCCACCUGUUCACACUGACAAACCUGGGAGCACCGGCAGCAUUCAAGUAC<br>UUCGACACAACAAUCGACAGAAAGAGAUACACAAGCACAAAGGAAGUCCUG<br>GACGCAACACUGAUCCACCAGAGCAUCACAGGACUGUACGAAACAAGAAUC<br>GACCUGAGCCAGCUGGGAGGAGACGGAGGAGGAAGCCCGAAGAAGAAGAGA<br>AAGGUCUAG | |
| Cas9 mRNA ORF using codons with generally high expression in humans, with start and stop codons | AUGGAUAAGAAGUACUCAAUCGGGCUGGAUAUCGGAACUAAUUCCGUGGGU<br>UGGGCAGUGAUCACGGAUGAAUACAAAGUGCCGUCCAAGAAGUUCAAGGUC<br>CUGGGGAACACCGAUAGACACAGCAUCAAGAAAAAUCUCAUCGGAGCCCUG<br>CUGUUUGACUCCGGCGAAACCGCAGAAGCGACCCGGCUCAAACGUACCGCG<br>AGGCGACGCUACACCCGGCGAAGAAUCGCAUCUGCUAUCUGCAAGAGAUC<br>UUUUCGAACGAAAUGGCAAAGGUCGACAGCAGCUUCUUCCACCGCCUGGAA<br>GAAUCUUUCCUGGUGGAGGAGGACAAGAAGCAUGAACGGCAUCCUAUCUUU<br>GGAAACAUCGUCGACGAAGUGGCGUACCACGAAAAGUACCCGACCAUCUAC<br>CAUCUGCGGAAGAAGUUGGUUGACUCAACUGAACAAGGCCGACCUCAGAUUG<br>AUCUACUUGGCCCUCGCCCAUAUGAUCAAAUUCCGCGGACACUUCCUGAUC<br>GAAGGCGAUCUGAACCCUGAUAACUCCGACGUGGAUAAGCUUUUCAUUCAA<br>CUGGUGCAGACCUACAACCAACUGUUCGAAGAAAACCCAAUCAAUGCUAGC | 205 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GGCGUCGAUGCCAAGGCCAUCCUGUCCGCCCGGCUGUCGAAGUCGCGGCGC | |
| | CUCGAAAACCUGAUCGCACAGCUGCCGGGAGAGAAAAAGAACGGACUUUUC | |
| | GGCAACUUGAUCGCUCUCUCACUGGGACUCACUCCCAAUUUCAAGUCCAAU | |
| | UUUGACCUGGCCGAGGACGCGAAGCUGCAACUCUCAAAGGACACCUACGAC | |
| | GACGACUUGGACAAUUUGCUGGCACAAAUUGGCGAUCAGUACGCGGAUCUG | |
| | UUCCUUGCCGCUAAGAACCUUUCGGACGCAAUCUUGCUGUCCGAUAUCCUG | |
| | CGCGUGAACACCGAAAUAACCAAAGCGCCGCUUAGCGCCUCGAUGAUUAAG | |
| | CGGUACGACGAGCAUCACCAGGAUCUCACGCUGCUCAAAGCGCUCGUGAGA | |
| | CAGCAACUGCCUGAAAAGUACAAGGAGAUCUUCUUCGACCAGUCCAAGAAU | |
| | GGGUACGCAGGGUACAUCGAUGGAGGCGCUAGCCAGGAAGAGUUCUAUAAG | |
| | UUCAUCAAGCCAAUCCUGGAAAAGAUGGACGGAACCGAAGAACUGCUGGUC | |
| | AAGCUGAACAGGGAGGAUCUGCUCCGGAAACAGAGAACCUUUGACAACGGA | |
| | UCCAUUCCCCACCAGAUCCAUCUGGGUGAGCUGCACGCCAUCUUGCGGCGC | |
| | CAGGAGGACUUUUACCCAUUCCUCAAGGACAACCGGGAAAAGAUCGAGAAA | |
| | AUUCUGACGUUCCGCAUCCCGUAUUACGUGGGCCCACUGGCGCGCGGCAAU | |
| | UCGCGCUUCGCGUGGAUGACUAGAAAAUCAGAGGAAACCAUCACUCCUUGG | |
| | AAUUUCGAGGAAGUUGUGGAUAAGGGAGCUUCGGCACAAAGCUUCAUCGAA | |
| | CGAAUGACCAACUUCGACAAGAAUCUCCCAAACGAGAAGGUGCUUCCUAAG | |
| | CACAGCCUCCUUUACGAAUACUUCACUGUCUACAACGAACUGACUAAAGUG | |
| | AAAUACGUUACUGAAGGAAUGAGGAAGCCGGCCUUUCUGUCCGGAGAACAG | |
| | AAGAAAGCAAUUGUCGAUCUGCUGUUCAAGACCAACCGCAAGGUGACCGUC | |
| | AAGCAGCUUAAAGAGGACUACUUCAAGAAGAUCGAGUGUUUCGACUCAGUG | |
| | GAAAUCAGCGGGGUGGAGGACAGAUUCAACGCUUCGCUGGGAACCUAUCAU | |
| | GAUCUCCUGAAGAUCAUCAAGGACAAGGACUUCCUUGACAACGAGGAGAAC | |
| | GAGGACAUCCUGGAAGAUAUCGUCCUGACCUUGACCCUUUUCGAGGAUCGC | |
| | GAGAUGAUCGAGGAGAGGCUUAAGACCUACGCUCAUCUCUUCGACGAUAAG | |
| | GUCAUGAAACAACUCAAGCGCCGCCGGUACACUGGUUGGGGCCGCCUCUCC | |
| | CGCAAGCUGAUCAACGGUAUUCGCGAUAAACAGAGCGGUAAAACUAUCCUG | |
| | GAUUUCCUCAAAUCGGAUGGCUUCGCUAAUCGUAACUUCAUGCAAUUGAUC | |
| | CACGACGACAGCCUGACCUUUAAGGAGGACAUCCAAAAAGCACAAGUGUCC | |
| | GGACAGGGAGACUCACUCCAUGAACACAUCGCGAAUCUGGCCGGUUCGCCG | |
| | GCGAUUAAGAAGGGAAUUCUGCAAACUGUGAAGGUGGUCGACGAGCUGGUG | |
| | AAGGUCAUGGGACGGCACAAACCGGAGAAUAUCGUGAUUGAAAUGGCCCGA | |
| | GAAAACCAGACUACCCAGAAGGGCCAGAAAAAACUCCCGCGAAAGGAUGAAG | |
| | CGGAUCGAAGAAGGAAUCAAGGAGCUGGGCAGCCAGAUCCUGAAAGAGCAC | |
| | CCGGUGGAAAACACGCAGCUGCAGAACGAGAAGCUCUACCUGUACUAUUUG | |
| | CAAAAUGGACGGGACAUGUACGUGGACCAAGAGCUGGACAUCAAUCGGUUG | |
| | UCUGAUUACGACGUGGACCACAUCGUUCCACAGUCCUUUCUGAAGGAUGAC | |
| | UCGAUCGAUAACAAGGUGUUGACUCGCAGCGACAAGAACAGAGGGAAGUCA | |
| | GAUAAUGUGCCAUCGGAGGAGGUCGUGAAGAAGAUGAAGAAUUACUGGCGG | |
| | CAGCUCCUGAAUGCGAAGCUGAUUACCCAGAGAAAGUUUGACAAUCUCACU | |
| | AAAGCCGAGCGCGGCGGACUCUCAGAGCUGGAUAAGGCUGGAUUCAUCAAA | |
| | CGGCAGCUGGUCGAGACUCGGCAGAUUACCAAGCACGUGGCGCAGAUCUUG | |
| | GACUCCCGCAUGAACACUAAAUACGACGAGAACGAUAAGCUCAUCCGGGAA | |
| | GUGAAGGUGAUUACCCUGAAAAGCAAACUUGUGUCGGACUUUCGGAAGGAC | |
| | UUUCAGUUUUACAAAGUGAGAGAAAUCAACAACUACCAUCACGCGCAUGAC | |
| | GCAUACCUCAACGCUGUGGUCGGUACCGCCCUGAUCAAAAAGUACCCUAAA | |
| | CUUGAAUCGGAGUUUGUGUACGGAGACUACAAGGUCUACGACGUGAGGAAG | |
| | AUGAUAGCCAAGUCCGAACAGGAAAUCGGGAAAGCAACUGCGAAAUACUUC | |
| | UUUUACUCAAACAUCAUGAACUUUUUCAAGACUGAAAUUACGCUGGCCAAU | |
| | GGAGAAAUCAGGAAGAGGCCACUGAUCGAAACUAACGGAGAAACGGGCGAA | |
| | AUCGUGUGGGACAAGGGCAGGGACUUCGCAACUGUUCGCAAAGUGCUCUCU | |
| | AUGCCGCAAGUCAAUAUUGUGAAGAAAACCGAAGUGCAAACCGGCGGAUUU | |
| | UCAAAGGAAUCGAUCCUCCCAAAGAGAAAUAGCGACAAGCUCAUUGCACGC | |
| | AAGAAAGACUGGGACCCGAAGAAGUACGGAGGAUUCGAUUCGCCGACUGUC | |
| | GCAUACUCCGUCCUCGUGGUGGCCAAGGUGGAGAAGGGAAAGAGCAAAAAG | |
| | CUCAAAUCCGUCAAAGAGCUGCUGGGGAUUACCAUCAUGGAACGAUCCUCG | |
| | UUCGAGAAGAACCCGAUUGAUUUCCUCGAGGCGAAGGGUUACAAGGAGGUG | |
| | AAGAAGGAUCUGAUCAUCAAACUCCCCAAGUACUCACUGUUCGAACUGGAA | |
| | AAUGGUCGGAAGCGCAUGCUGGCUUCGGCCGGAGAACUCCAAAAAGGAAAU | |
| | GAGCUGGCCUUGCCUAGCAAGUACGUCAACUUCCUCUAUCUUGCUUCGCAC | |
| | UACGAAAAACUCAAAGGGUCACCGGAAGAUAACGAACAGAAGCAGCUUUUC | |
| | GUGGAGCAGCACAAGCAUUAUCUGGAUGAAAUCAUCGAACAAAUCUCCGAG | |
| | UUUUCAAAGCGCGUGAUCCUCGCCGACGCCAACCUCGACAAAGUCCUGUCG | |
| | GCCUACAAUAAGCAUAGAGAUAAGCCGAUCAGAGAACAGGCCGAGAACAUU | |
| | AUCCACUUGUUCACCCUGACUAACCUGGGAGCCCCAGCCGCCUUCAAGUAC | |
| | UUCGAUACUACUAUCGAUCGCAAAAGAUACACGUCCACCAAGGAAGUUCUG | |
| | GACGCGACCCUGAUCCACCAAAGCAUCACUGGACUCUACGAAACUAGGAUC | |
| | GAUCUGUCGCAGCUGGGUGGCGAUGGCGGUGGAUCUCCGAAAAAGAAGAGA | |
| | AAGGUGUAAUGA | |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
| --- | --- | --- |
| Cas9 nickase (D10A) amino acid sequence | MDKKYSIGLAIGTNSVGWAVITDEYKVPSKKFKVLGNTDRHSIKKNLIGAL LFDSGETAEATRLKRTARRRYTRRKNRICYLQEIFSNEMAKVDDSFFHRLE ESFLVEEDKKHERHPIFGNIVDEVAYHEKYPTIYHLRKKLVDSTDKADLRL IYLALAHMIKFRGHFLIEGDLNPDNSDVDKLFIQLVQTYNQLFEENPINAS GVDAKAILSARLSKSRRLENLIAQLPGEKKNGLFGNLIALSLGLTPNFKSN FDLAEDAKLQLSKDTYDDDLDNLLAQIGDQYADLFLAAKNLSDAILLSDIL RVNTEITKAPLSASMIKRYDEHHQDLTLLKALVRQQLPEKYKEIFFDQSKN GYAGYIDGGASQEEFYKFIKPILEKMDGTEELLVKLNREDLLRKQRTFDNG SIPHQIHLGELHAILRRQEDFYPFLKDNREKIEKILTFRIPYYVGPLARGN SRFAWMTRKSEETITPWNFEEVVDKGASAQSFIERMTNFDKNLPNEKVLPK HSLLYEYFTVYNELTKVKYVTEGMRKPAFLSGEQKKAIVDLLFKTNRKVTV KQLKEDYFKKIECFDSVEISGVEDRFNASLGTYHDLLKIIKDKDFLDNEEN EDILEDIVLTLTLFEDREMIEERLKTYAHLFDDKVMKQLKRRRYTGWGRLS RKLINGIRDKQSGKTILDFLKSDGFANRNFMQLIHDDSLTFKEDIQKAQVS GQGDSLHEHIANLAGSPAIKKGILQTVKVVDELVKVMGRHKPENIVIEMAR ENQTTQKGQKNSRERMKRIEEGIKELGSQILKEHPVENTQLQNEKLYLYYL QNGRDMYVDQELDINRLSDYDVDHIVPQSFLKDDSIDNKVLTRSDKNRGKS DNVPSEEVVKKMKNYWRQLLNAKLITQRKFDNLTKAERGGLSELDKAGFIK RQLVETRQITKHVAQILDSRMNTKYDENDKLIREVKVITLKSKLVSDFRKD FQFYKVREINNYHHAHDAYLNAVVGTALIKKYPKLESEFVYGDYKVYDVRK MIAKSEQEIGKATAKYFFYSNIMNFFKTEITLANGEIRKRPLIETNGETGE IVWDKGRDFATVRKVLSMPQVNIVKKTEVQTGGFSKESILPKRNSDKLIAR KKDWDPKKYGGFDSPTVAYSVLVVAKVEKGKSKKLKSVKELLGITIMERSS FEKNPIDFLEAKGYKEVKKDLIIKLPKYSLFELENGRKRMLASAGELQKGN ELALPSKYVNFLYLASHYEKLKGSPEDNEQKQLFVEQHKHYLDEIIEQISE FSKRVILADANLDKVLSAYNKHRDKPIREQAENIIHLFTLTNLGAPAAFKY FDTTIDRKRYTSTKEVLDATLIHQSITGLYETRIDLSQLGGDGGGSPKKKR KV | 206 |
| Cas9 nickase (D10A) mRNA ORF | AUGGACAAGAAGUACAGCAUCGGACUGGCAAUCGGAACAAACAGCGUCGGA UGGGCAGUCAUCACAGACGAAUACAAGGUCCCGAGCAAGAAGUUCAAGGUC CUGGGAAACACAGACAGACACAGCAUCAAGAAGAACCUGAUCGGAGCACUG CUGUUCGACAGCGGAGAAACAGCAGAAGCAACAAGACUGAAGAGAACAGCA AGAAGAAGAUACAAGAAGAAAGAACAGAAUCUGCUACCUGCAGGAAAUC UUCAGCAACGAAAUGGCAAAGGUCGACGACAGCUUCUUCCACAGACUGGAA GAAAGCUUCCUGGUCGAAGAAGACAAGAAGCACGAAAGACACCCCGAUCUUC GGAAACAUCGUCGACGAAGUCGCAUACCACGAAAAGUACCCGACAAUCUAC CACCUGAGAAAGAAGCUGGUCGACAGCACAGACAAGGCAGACCUGAGACUG AUCUACCUGGCACUGGCACACAUGAUCAAGUUCAGAGGACACUUCCUGAUC GAAGGAGACCUGAACCCGGACAACAGCGACGUCGACAAGCUGUUCAUCCAG CUGGUCCAGACAUACAACCAGCUGUUCGAAGAAAACCCGAUCAACGCAAGC GGAGUCGACGCAAAGGCAAUCCUGAGCGCAAGACUGAGCAAGAGCAGAAGA CUGGAAAACCUGAUCGCACAGCUGCCGGGAGAAAAGAAGAACGGACUGUUC GGAAACCUGAUCGCACUGAGCCUGGGACUGACACCGAACUUCAAGAGCAAC UUCGACCUGGCAGAAGACGCAAAGCUGCAGCUGAGCAAGGACACAUACGAC GACGACCUGGACAACCUGCUGGCACAGAUCGGAGACCAGUACGCAGACCUG UUCCUGGCAGCAAAGAACCUGAGCGACGCAAUCCUGCUGAGCGACAUCCUG AGAGUCAACACAGAAAUCACAAAGGCACCGCUGAGCGCAAGCAUGAUCAAG AGAUACGACGAACACCACCAGGACCUGACACUGCUGAAGGCACUGGUCAGA CAGCAGCUGCCGGAAAAGUACAAGGAAAUCUUCUUCGACCAGAGCAAGAAC GGAUACGCAGGAUACAUCGACGGAGGAGCAAGCCAGGAAGAAUUCUACAAG UUCAUCAAGCCGAUCCUGGAAAAGAUGGACGGAACAGAAGAACUGCUGGUC AAGCUGAACAGAGAAGACCUGCUGAGAAAGCAGAGAACAUUCGACAACGGA AGCAUCCCGCACCAGAUCCACCUGGGAGAACUGCACGCAAUCCUGAGAAGA CAGGAAGACUUCUACCCGUUCCUGAAGGACAACAGAGAAAAGAUCGAAAAG AUCCUGACAUUCAGAAUCCCGUACUACGUCGGACCGCUGGCAAGAGGAAAC AGCAGAUUCGCAUGGAUGACAAGAAAGAGCGAAGAAACAAUCACACCGUGG AACUUCGAAGAAGUCGUCGACAAGGGAGCAAGCGCACAGAGCUUCAUCGAA AGAAUGACAAACUUCGACAAGAACCUGCCGAACGAAAAGGUCCUGCCGAAG CACAGCCUGCUGUACGAAUACUUCACAGUCUACAACGAACUGACAAAGGUC AAGUACGUCACAGAAGGAAUGAGAAAGCCGGCAUUCCUGAGCGGAGAACAG AAGAAGGCAAUCGUCGACCUGCUGUUCAAGACAAACAGAAAGGUCACAGUC AAGCAGCUGAAGGAAGACUACUUCAAGAAGAUCGAAUGCUUCGACAGCGUC GAAAUCAGCGGAGUCGAAGACAGAUUCAACGCAAGCCUGGGAACAUACCAC GACCUGCUGAAGAUCAUCAAGGACAAGGACUUCCUGGACAACGAAGAAAAC GAAGACAUCCUGGAAGACAUCGUCCUGACACUGACACUGUUCGAAGACAGA GAAAUGAUCGAAGAAGACUGAAGACAUACGCACACCUGUUCGACGACAAG GUCAUGAAGCAGCUGAAGAGAAGAAGAUACACAGGAUGGGGAAGACUGAGC AGAAAGCUGAUCAACGGAAUCAGAGACAAGCAGAGCGGAAAGACAAUCCUG GACUUCCUGAAGAGCGACGGAUUCGCAAACAGAAACUUCAUGCAGCUGAUC | 207 |

| Description | Sequence | SEQ ID No. |
|---|---|---|
| | CACGACGACAGCCUGACAUUCAAGGAAGACAUCCAGAAGGCACAGGUCAGC<br>GGACAGGGAGACAGCCUGCACGAACACAUCGCAAACCUGGCAGGAAGCCCG<br>GCAAUCAAGAAGGGAAUCCUGCAGACAGUCAAGGUCGUCGACGAACUGGUC<br>AAGGUCAUGGGAAGACACAAGCCGGAAAACAUCGUCAUCGAAAUGGCAAGA<br>GAAAACCAGACAACACAGAAGGGACAGAAGAACAGCAGAGAAAGAAUGAAG<br>AGAAUCGAAGAAGGAAUCAAGGAACUGGGAAGCCAGAUCCUGAAGGAACAC<br>CCGGUCGAAAACACACAGCUGCAGAACGAAAAGCUGUACCUGUACUACCUG<br>CAGAACGGAAGAGACAUGUACGUCGACCAGGAACUGGACAUCAACAGACUG<br>AGCGACUACGACGUCGACCACAUCGUCCCGCAGAGCUUCCUGAAGGACGAC<br>AGCAUCGACAACAAGGUCCUGACAAGAAGCGACAAGAACAGAGGAAAGAGC<br>GACAACGUCCCGAGCGAAGAAGUCGUCAAGAAGAUGAAGAACUACUGGAGA<br>CAGCUGCUGAACGCAAAGCUGAUCACACAGAGAAAGUUCGACAACCUGACA<br>AAGGCAGAGAGAGGAGGACUGAGCGAACUGGACAAGGCAGGAUUCAUCAAG<br>AGACAGCUGGUCGAAACAAGACAGAUCACAAAGCACGUCGCACAGAUCCUG<br>GACAGCAGAAUGAACACAAAGUACGACGAAAACGACAAGCUGAUCAGAGAA<br>GUCAAGGUCAUCACACUGAAGAGCAAGCUGGUCAGCGACUUCAGAAAGGAC<br>UUCCAGUUCUACAAGGUCAGAGAAAUCAACAACUACCACCACGCACACGAC<br>GCAUACCUGAACGCAGUCGUCGGAACAGCACUGAUCAAGAAGUACCCGAAG<br>CUGGAAAGCGAAUUCGUCUACGGAGACUACAAGGUCUACGACGUCAGAAAG<br>AUGAUCGCAAAGAGCGAACAGGAAAUCGGAAAGGCAACAGCAAAGUACUUC<br>UUCUACAGCAACAUCAUGAACUUCUUCAAGACAGAAAUCACACUGGCAAAC<br>GGAGAAAUCAGAAAGAGACCGCUGAUCGAAACAAACGGAGAAACAGGAGAA<br>AUCGUCUGGGACAAGGGAAGAGACUUCGCAACAGUCAGAAAGGUCCUGAGC<br>AUGCCGCAGGUCAACAUCGUCAAGAAGACAGAAGUCCAGACAGGAGGAUUC<br>AGCAAGGAAAGCAUCCUGCCGAAGAGAAACAGCGACAAGCUGAUCGCAAGA<br>AAGAAGGACUGGGACCCGAAGAAGUACGGAGGAUUCGACAGCCCGACAGUC<br>GCAUACAGCGUCCUGGUCGUCGCAAAGGUCGAAAAGGGAAAGAGCAAGAAG<br>CUGAAGAGCGUCAAGGAACUGCUGGGAAUCACAAUCAUGGAAAGAAGCAGC<br>UUCGAAAAGAACCCGAUCGACUUCCUGGAAGCAAAGGGAUACAAGGAAGUC<br>AAGAAGGACCUGAUCAUCAAGCUGCCGAAGUACAGCCUGUUCGAACUGGAA<br>AACGGAAGAAAGAGAAUGCUGGCAAGCGCAGGAGAACUGCAGAAGGGAAAC<br>GAACUGGCACUGCCGAGCAAGUACGUCAACUUCCUGUACCUGGCAAGCCAC<br>UACGAAAAGCUGAAGGGAAGCCCGGAAGACAACGAACAGAAGCAGCUGUUC<br>GUCGAACAGCACAAGUACCUACCUGGACGAAAUCAUCGAACAGAUCAGCGAA<br>UUCAGCAAGAGAGUCAUCCUGGCAGACGCAAACCUGGACAAGGUCCUGAGC<br>GCAUACAACAAGCACAGAGACAAGCCGAUCAGAGAACAGGCAGAAAACAUC<br>AUCCACCUGUUCACACUGACAAACCUGGGAGCACCGGCAGCAUUCAAGUAC<br>UUCGACACAACAAUCGACAGAAAGAGAUACACAAGCACAAAGGAAGUCCUG<br>GACGCAACACUGAUCCACCAGAGCAUCACAGGACUGUACGAAACAAGAAUC<br>GACCUGAGCCAGCUGGGAGGAGACGGAGGAGGAAGCCCGAAGAAGAAGAGA<br>AAGGUCUAG | |
| dCas9 (D10A H840A) amino acid sequence | MDKKYSIGLAIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV<br>KQLKEDYFKKIECFDSVEISGVEDRFNASLGTYHDLLKIIKDKDFLDNEEN<br>EDILEDIVLTLTLFEDREMIEERLKTYAHLFDDKVMKQLKRRRYTGWGRLS<br>RKLINGIRDKQSGKTILDFLKSDGFANRNFMQLIHDDSLTFKEDIQKAQVS<br>GQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYL<br>QNGRDMYVDQELDINRLSDYDVDAIVPQSFLKDDSIDNKVLTRSDKNRGKS<br>DNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGE<br>IVWDKGRDFATVRKVLSMPQVNIVKKTEVQTGGFSKESILPKRNSDKLIAR<br>KKDWDPKKYGGFDSPTVAYSVLVVAKVEKGKSKKLKSVKELLGITIMERSS<br>FEKNPIDFLEAKGYKEVKKDLIIKLPKYSLFELENGRKRMLASAGELQKGN<br>ELALPSKYVNFLYLASHYEKLKGSPEDNEQKQLFVEQHKYLDEIIEQISE<br>FSKRVILADANLDKVLSAYNKHRDKPIREQAENIIHLFTLTNLGAPAAFKY<br>FDTTIDRKRYTSTKEVLDATLIHQSITGLYETRIDLSQLGGDGGGSPKKKR<br>KV | 208 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| dCas9 (D10A H840A) mRNA ORF | AUGGACAAGAAGUACAGCAUCGGACUGGCAAUCGGAACAAACAGCGUCGGA UGGGCAGUCAUCACAGACGAAUACAAGGUCCCGAGCAAGAAGUUCAAGGUC CUGGGAAACACAGACAGACACAGCAUCAAGAAGAACCUGAUCGGAGCACUG CUGUUCGACAGCGGAGAAACAGCAGAAGCAACAAGACUGAAGAGAACAGCA AGAAGAAGAUACACAAGAAGAAGAACAGAAUCUGCUACCUGCAGGAAAUC UUCAGCAACGAAAUGGCAAAGGUCGACGACAGCUUCUUCCACAGACUGGAA GAAAGCUUCCUGGUCGAAGAAGACAAGAAGCACGAAAGACACCCGAUCUUC GGAAACAUCGUCGACGAAGUCGCAUACCACGAAAAGUACCCGACAAUCUAC CACCUGAGAAGAAGCUGGUCGACAGCACAGACAAGGCAGACCUGAGACUG AUCUACCUGGCACUGGCACACAUGAUCAAGUUCAGAGGACACUUCCUGAUC GAAGGAGACCUGAACCCGGACAACAGCGACGUCGACAAGCUGUUCAUCCAG CUGGUCCAGACAUACAACCAGCUGUUCGAAGAAAACCCGAUCAACGCAAGC GGAGUCGACGCAAAGGCAAUCCUGAGCGCAAGACUGAGCAAGAGCAGAAGA CUGGAAAACCUGAUCGCACAGCUGCCGGGAGAAAAGAAGAACGGACUGUUC GGAAACCUGAUCGCACUGAGCCUGGGACUGACACCGAACUUCAAGAGCAAC UUCGACCUGGCAGAAGACGCAAAGCUGCAGCUGAGCAAGGACACAUACGAC GACGACCUGGACAACCUGCUGGCACAGAUCGGAGACCAGUACGCAGACCUG UUCCUGGCAGCAAAGAACCUGAGCGACGCAAUCCUGCUGAGCGACAUCCUG AGAGUCAACACAGAAAUCACAAAGGCACCGCUGAGCGCAAGCAUGAUCAAG AGAUACGACGAACACCACCAGGACCUGACACUGCUGAAGGCACUGGUCAGA CAGCAGCUGCCGGAAAAGUACAAGGAAAUCUUCUUCGACCAGAGCAAGAAC GGAUACGCAGGAUACAUCGACGGAGGAGCAAGCCAGGAAGAAUUCUACAAG UUCAUCAAGCCGAUCCUGGAAAAGAUGGACGGAACAGAAGAACUGCUGGUC AAGCUGAACAGAGAAGACCUGCUGAGAAAGCAGAGAACAUUCGACAACGGA AGCAUCCCGCACCAGAUCCACCUGGGAGAACUGCACGCAAUCCUGAGAAGA CAGGAAGACUUCUACCCGUUCCUGAAGGACAACAGAGAAAAGAUCGAAAAG AUCCUGACAUUCAGAAUCCCGUACUACGUCGGACCGCUGGCAAGAGGAAAC AGCAGAUUCGCAUGGAUGACAAGAAAGAGCGAAGAAACAAUCACACCGUGG AACUUCGAAGAAGUCGUCGACAAGGGAGCAAGCGCACAGAGCUUCAUCGAA AGAAUGACAAACUUCGACAAGAACCUGCCGAACGAAAAGGUCCUGCCGAAG CACAGCCUGCUGUACGAAUACUUCACAGUCUACAACGAACUGACAAAGGUC AAGUACGUCACAGAAGGAAUGAGAAAGCCGGCAUUCCUGAGCGGAGAACAG AAGAAGGCAAUCGUCGACCUGCUGUUCAAGACAAACAGAAAGGUCACAGUC AAGCAGCUGAAGGAAGACUACUUCAAGAAGAUCGAAUGCUUCGACAGCGUC GAAAUCAGCGGAGUCGAAGACAGAUUCAACGCAAGCCUGGGAACAUACCAC GACCUGCUGAAGAUCAUCAAGGACAAGGACUUCCUGGACAACGAAGAAAAC GAAGACAUCCUGGAAGACAUCGUCCUGACACUGACACUGUUCGAAGACAGA GAAAUGAUCGAAGAAAGACUGAAGACAUACGCACACCUGUUCGACGACAAG GUCAUGAAGCAGCUGAAGAGAAGAAGAUACACAGGAUGGGGAAGACUGAGC AGAAAGCUGAUCAACGGAAUCAGAGACAAGCAGAGCGGAAAGACAAUCCUG GACUUCCUGAAGAGCGACGGAUUCGCAAACAGAAACUUCAUGCAGCUGAUC CACGACGACAGCCUGACAUUCAAGGAAGACAUCCAGAAGGCACAGGUCAGC GGACAGGGAGACAGCCUGCACGAACACAUCGCAAACCUGGCAGGAAGCCCG GCAAUCAAGAAGGGAAUCCUGCAGACAGUCAAGGUCGUCGACGAACUGGUC AAGGUCAUGGGAAGACACAAGCCGGAAAACAUCGUCAUCGAAAUGGCAAGA GAAAACCAGACAACACAGAAGGGACAGAAGAACAGCAGAGAAAGAAUGAAG AGAAUCGAAGAAGGAAUCAAGGAACUGGGAAGCCAGAUCCUGAAGGAACAC CCGGUCGAAAACACACAGCUGCAGAACGAAAAGCUGUACCUGUACUACCUG CAGAACGGAAGAGACAUGUACGUCGACCAGGAACUGGACAUCAACAGACUG AGCGACUACGACGUCGACGCAAUCGUCCCGCAGAGCUUCCUGAAGGACGAC AGCAUCGACAACAAGGUCCUGACAAGAAGCGACAAGAACAGAGGGAAAGAGC GACAACGUCCCGAGCGAAGAAGUCGUCAAGAAGAUGAAGAACUACUGGAGA CAGCUGCUGAACGCAAAGCUGAUCACACAGAGAAAGUUCGACAACCUGACA AAGGCAGAGAGGAGGACUGAGCGAACUGGACAAGGCAGGAUUCAUCAAG AGACAGCUGGUCGAAACAAGACAGAUCACAAAGCACGUCGCACAGAUCCUG GACAGCAGAAUGAACACAAAGUACGACGAAAACGACAAGCUGAUCAGAGAA GUCAAGGUCAUCACACUGAAGAGCAAGCUGGUCAGCGACUUCAGAAAGGAC UUCCAGUUCUACAAGGUCAGAGAAAUCAACAACUACCACCACGCACACGAC GCAUACCUGAACGCAGUCGUCGGAACAGCACUGAUCAAGAAGUACCCGAAG CUGGAAAGCGAAUUCGUCUACGGAGACUACAAGGUCUACGACGUCAGAAAG AUGAUCGCAAAGAGCGAACAGGAAAUCGGAAAGGCAACAGCAAAGUACUUC UUCUACAGCAACAUCAUGAACUUCUUCAAGACAGAAAUCACACUGGCAAAC GGAGAAAUCAGAAAGAGACCGCUGAUCGAAACAAACGGAGAAACAGGAGAA AUCGUCUGGGACAAGGGAAGAGACUUCGCAACAGUCAGAAAGGUCCUGAGC AUGCCGCAGGUCAACAUCGUCAAGAAGACAGAAGUCCAGACAGGAGGAUUC AGCAAGGAAAGCAUCCUGCCGAAGAGAAACAGCGACAAGCUGAUCGCAAGA AAGAAGGACUGGGACCCGAAGAAGUACGGAGGAUUCGCAGCCCGACAGUC GCAUACAGCGUCCUGGUCGUCGCAAAGGUCGAAAAGGGAAAGAGCAAGAAG CUGAAGAGCGUCAAGGAACUGCUGGGAAUCACAAUCAUGGAAAGAAGCAGC | 209 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | UUCGAAAAGAACCCGAUCGACUUCCUGGAAGCAAAGGGAUACAAGGAAGUC AAGAAGGACCUGAUCAUCAAGCUGCCGAAGUACAGCCUGUUCGAACUGGAA AACGGAAGAAAGAGAAUGCUGGCAAGCGCAGGAGAACUGCAGAAGGGAAAC GAACUGGCACUGCCGAGCAAGUACGUCAACUUCCUGUACCUGGCAAGCCAC UACGAAAAGCUGAAGGGAAGCCCGGAAGACAACGAACAGAAGCAGCUGUUC GUCGAACAGCACAAGCACUACCUGGACGAAAUCAUCGAACAGAUCAGCGAA UUCAGCAAGAGAGUCAUCCUGGCAGACGCAAACCUGGACAAGGUCCUGAGC GCAUACAACAAGCACAGAGACAAGCCGAUCAGAGAACAGGCAGAAAACAUC AUCCACCUGUUCACACUGACAAACCUGGGAGCACCGGCAGCAUUCAAGUAC UUCGACACAACAAUCGACAGAAAGAGAUACACAAGCACAAAGGAAGUCCUG GACGCAACACUGAUCCACCAGAGCAUCACAGGACUGUACGAAACAAGAAUC GACCUGAGCCAGCUGGGAGGAGACGGAGGAGGAAGCCCGAAGAAGAAGAGA AAGGUCUAG | |
| Cas9 mRNA coding sequence using minimal uridine codons (no start or stop codons; suitable for inclusion in fusion protein coding sequence) | GACAAGAAGUACAGCAUCGGACUGGACAUCGGAACAAACAGCGUCGGAUGG GCAGUCAUCACAGACGAAUACAAGGUCCCGAGCAAGAAGUUCAAGGUCCUG GGAAACACAGACAGACACAGCAUCAAGAAGAACCUGAUCGGACACUGCUG UUCGACAGCGGAGAAACAGCAGAAGCAACAAGACUGAAGAGAACAGCAAGA AGAAGAUACACAAGAAGAAGAACAGAAUCUGCUACCUGCAGGAAAUCUUC AGCAACGAAAUGGCAAAGGUCGACGACAGCUUCUUCCACAGACUGGAAGAA AGCUUCCUGGUCGAAGAAGACAAGCACGACAAGAACACCCGAUCUUCGGA AACAUCGUCGACGAAGUCGCAUACCACGAAAAGUACCCGACAAUCUACCAC CUGAGAAAGAAGCUGGUCGACAGCACAGACAAGGCAGACCUGAGACUGAUC UACCUGGCACUGGCACACAUGAUCAAGUUCAGAGGACACUUCCUGAUCGAA GGAGACCUGAACCCGGACAACAGCGACGUCGACAAGCUGUUCAUCCAGCUG GUCCAGACAUACAACCAGCUGUUCGAAGAAAACCCGAUCAACGCAAGCGGA GUCGACGCAAAGGCAAUCCUGAGCGCAAGACUGAGCAAGAGCAGAAGACUG GAAAACCUGAUCGCACAGCUGCCGGGAGAAAAGAAGAACGGACUGUUCGGA AACCUGAUCGCACUGAGCCUGGGACUGACACCGAACUUCAAGAGCAACUUC GACCUGGCAGAAGACGCAAAGCUGCAGCUGAGCAAGGACACAUACGACGAC GACCUGGACAACCUGCUGGCACAGAUCGGAGACCAGUACGCAGACCUGUUC CUGGCAGCAAAGAACCUGAGCGACGCAAUCCUGCUGAGCGACAUCCUGAGA GUCAACACAGAAAUCACAAAGGCACCGCUGAGCGCAAGCAUGAUCAAGAGA UACGACGAACACCACCAGGACCUGACACUGCUGAAGGCACUGGUCAGACAG CAGCUGCCGGAAAAGUACAAGGAAAUCUUCUUCGACCAGAGCAAGAACGGA UACGCAGGAUACAUCGACGGAGGAGCAAGCCAGGAAGAAUUCUACAAGUUC AUCAAGCCGAUCCUGGAAAAGAUGGACGGAACAGAAGAACUGCUGGUCAAG CUGAACAGAGAAGACCUGCUGAGAAAGCAGAGAACAUUCGACAACGGAAGC AUCCCGCACCAGAUCCACCUGGGAGAACUGCACGCAAUCCUGAGAAGACAG GAAGACUUCUACCCGUUCCUGAAGGACAACAGAGAAAAGAUCGAAAAGAUC CUGACAUUCAGAAUCCCGUACUACGUCGGACCGCUGGCAAGAGGAAACAGC AGAUUCGCAUGGAUGACAAGAAAGAGCGAAGAAACAAUCACACCGUGGAAC UUCGAAGAAGUCGUCGACAAGGGAGCAAGCGCACAGAGCUUCAUCGAAAGA AUGACAAACUUCGACAAGAACCUGCCGAACGAAAAGGUCCUGCCGAAGCAC AGCCUGCUGUACGAAUACUUCACAGUCUACAACGAACUGACAAAGGUCAAG UACGUCACAGAAGGAAUGAGAAAGCCGGCAUUCCUGAGCGGAGAACAGAAG AAGGCAAUCGUCGACCUGCUGUUCAAGACAAACAGAAAGGUCACAGUCAAG CAGCUGAAGGAAGACUACUUCAAGAAGAUCGAAUGCUUCGACAGCGUCGAA AUCAGCGGAGUCGAAGACAGAUUCAACGCAAGCCUGGGAACAUACCACGAC CUGCUGAAGAUCAUCAAGGACAAGGACUUCCUGGACAACGAAGAAAACGAA GACAUCCUGGAAGACAUCGUCCUGACACUGACACUGUUCGAAGACAGAGAA AUGAUCGAAGAAAGACUGAAGACAUACGCACACCUGUUCGACGACAAGGUC AUGAAGCAGCUGAAGAGAAGAAGAUACACAGGAUGGGGAAGACUGAGCAGA AAGCUGAUCAACGGAAUCAGAGACAAGCAGAGCGGAAAGACAAUCCUGGAC UUCCUGAAGAGCGACGGAUUCGCAAACAGAAACUUCAUGCAGCUGAUCCAC GACGACAGCCUGACAUUCAAGGAAGACAUCCAGAAGGCACAGGUCAGCGGA CAGGGAGACAGCCUGCACGAACACAUCGCAAACCUGGCAGGAAGCCCCGGCA AUCAAGAAGGGAAUCCUGCAGACAGUCAAGGUCGUCGACGAACUGGUCAAG GUCAUGGGAAGACACAAGCCGGAAAACAUCGUCAUCGAAAUGGCAAGAGAA AACCAGACAACACAGAAGGACAGAAGAACAGCAGAGAAAGAAUGAAGAGA AUCGAAGAAGGAAUCAAGGAACUGGGAAGCCAGAUCCUGAAGGAACACCCG GUCGAAAACACACAGCUGCAGAACGAAAAGCUGUACCUGUACUACCUGCAG AACGGAAGAGACAUGUACGUCGACCAGGAACUGGACAUCAACAGACUGAGC GACUACGACGUCGACCACAUCGUCCCGCAGAGCUUCCUGAAGGACGACAGC AUCGACAACAAGGUCCUGACAAGAAGCGACAAGAACAGAGGAAAGAGCGAC AACGUCCCGAGCGAAGAAGUCGUCAAGAAGAUGAAGAACUACUGGAGACAG CUGCUGAACGCAAAGCUGAUCACACAGAGAAAGUUCGACAACCUGACAAAG GCAGAGAGGAGGACUGAGCGAACUGGACAAGGCAGGAUUCAUCAAGAGA CAGCUGGUCGAAACAAGACAGAUCACAAAGCACGUCGCACAGAUCCUGGAC AGCAGAAUGAACACAAAGUACGACGAAAACGACAAGCUGAUCAGAGAAGUC | 210 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AAGGUCAUCACACUGAAGAGCAAGCUGGUCAGCGACUUCAGAAAGGACUUC<br>CAGUUCUACAAGGUCAGAGAAAUCAACAACUACCACCACGCACACGACGCA<br>UACCUGAACGCAGUCGUCGGAACAGCACUGAUCAAGAAGUACCCGAAGCUG<br>GAAAGCGAAUUCGUCUACGGAGACUACAAGGUCUACGACGUCAGAAAGAUG<br>AUCGCAAAGAGCGAACAGGAAAUCGGAAAGGCAACAGCAAAGUACUUCUUC<br>UACAGCAACAUCAUGAACUUCUUCAAGACAGAAAUCACACUGGCAAACGGA<br>GAAAUCAGAAAGAGACCGCUGAUCGAAACAAACGGAGAAACAGGAGAAAUC<br>GUCUGGGACAAGGGAAGAGACUUCGCAACAGUCAGAAAGGUCCUGAGCAUG<br>CCGCAGGUCAACAUCGUCAAGAAGACAGAAGUCCAGACAGGAGGAUUCAGC<br>AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAGAGAAUGCUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCUGUUCACACUGACAAACCUGGGAGCACCGGCAGCAUUCAAGUACUUC<br>GACACAACAAUCGACAGAAAGAGAUACACAAGCACAAAGGAAGUCCUGGAC<br>GCAACACUGAUCCACCAGAGCAUCACAGGACUGUACGAAACAAGAAUCGAC<br>CUGAGCCAGCUGGGAGGAGACGGAGGAGGAAGCCCGAAGAAGAAGAGAAAG<br>GUC | |
| Cas9 nickase coding sequence using minimal uridine codons (no start or stop codons; suitable for inclusion in fusion protein coding sequence) | GACAAGAAGUACAGCAUCGGACUGGCAAUCGGAACAAACAGCGUCGGAUGG<br>GCAGUCAUCACAGACGAAUACAAGGUCCCGAGCAAGAAGUUCAAGGUCCUG<br>GGAAACACAGACAGACACAGCAUCAAGAAGAACCUGAUCGGAGCACUGCUG<br>UUCGACAGCGGAGAAACAGCAGAAGCAACAAGACUGAAGAGAACAGCAAGA<br>AGAAGAUACACAAGAAGAAAGAACAGAAAUCUGCUACCUGCAGGAAAUCUUC<br>AGCAACGAAAUGGCAAAGGUCGACGACAGCUUCUUCCACAGACUGGAAGAA<br>AGCUUCCUGGUCGAAGAAGACAAGAAGCACGAAAGACACCCGAUCUUCGGA<br>AACAUCGUCGACGAAGUCGCAUACCACGAAAAGUACCCGACAAUCUACCAC<br>CUGAGAAAGAAGCUGGUCGACAGCACAGACAAGGCAGACCUGAGACUGAUC<br>UACCUGGCACUGGCACACAUGAUCAAGUUCAGAGGACACUUCCUGAUCGAA<br>GGAGACCUGAACCCGGACAACAGCGACGUCGACAAGCUGUUCAUCCAGCUG<br>GUCCAGACAUACAACCAGCUGUUCGAAGAAAACCCGAUCAACGCAAGCGGA<br>GUCGACGCAAAGGCAAUCCUGAGCGCAAGACUGAGCAAGAGCAGAAGACUG<br>GAAAACCUGAUCGCACAGCUGCCGGGAGAAAAGAAGAACGGACUGUUCGGA<br>AACCUGAUCGCACUGAGCCUGGGACUGACACCGAACUUCAAGAGCAACUUC<br>GACCUGGCAGAAGACGCAAAGCUGCAGCUGAGCAAGGACACAUACGACGAC<br>GACCUGGACAACCUGCUGGCACAGAUCGGAGACCAGUACGCAGACCUGUUC<br>CUGGCAGCAAAGAACCUGAGCGACGCAAUCCUGCUGAGCGACAUCCUGAGA<br>GUCAACACAGAAAUCACAAAGGCACCGCUGAGCGCAAGCAUGAUCAAGAGA<br>UACGACGAACACCACCAGGACCUGACACUGCUGAAGGCACUGGUCAGACAG<br>CAGCUGCCGGAAAAGUACAAGGAAAUCUUCUUCGACCAGAGCAAGAACGGA<br>UACGCAGGAUACAUCGACGGAGGAGCAAGCCAGGAAGAAUUCUACAAGUUC<br>AUCAAGCCGAUCCUGGAAAAGAUGGACGGAACAGAAGAACUGCUGGUCAAG<br>CUGAACAGAGAAGACCUGCUGAGAAAGCAGAGAACAUUCGACAACGGAAGC<br>AUCCCGCACCAGAUCCACCUGGGAGAACUGCACGCAAUCCUGAGAAGACAG<br>GAAGACUUCUACCCGUUCCUGAAGGACAACAGAGAAAAGAUCGAAAAGAUC<br>CUGACAUUCAGAAUCCCGUACUACGUCGGACCGCUGGCAAGAGGAAACAGC<br>AGAUUCGCAUGGAUGACAAGAAAGAGCGAAGAAACAAUCACACCGUGGAAC<br>UUCGAAGAAGUCGUCGACAAGGGAGCAAGCGCACAGAGCUUCAUCGAAAGA<br>AUGACAAACUUCGACAAGAACCUGCCGAACGAAAAGGUCCUGCCGAAGCAC<br>AGCCUGCUGUACGAAUACUUCACAGUCUACAACGAACUGACAAAGGUCAAG<br>UACGUCACAGAAGGAAUGAGAAAGCCGGCAUUCCUGAGCGGAGAACAGAAG<br>AAGGCAAUCGUCGACCUGCUGUUCAAGACAAACAGAAAGGUCACAGUCAAG<br>CAGCUGAAGGAAGACUACUUCAAGAAGAUCGAAUGCUUCGACAGCGUCGAA<br>AUCAGCGGAGUCGAAGACAGAUUCAACGCAAGCCUGGGAACAUACCACGAC<br>CUGCUGAAGAUCAUCAAGGACAAGGACUUCCUGGACAACGAAGAAACGAA<br>GACAUCCUGGAAGACAUCGUCCUGACACUGACACUGUUCGAAGACAGAGAA<br>AUGAUCGAAGAAGACUGAAGACAUACGCACACCUGUUCGACGACAAGGUC<br>AUGAAGCAGCUGAAGAGAAGAAGAUACACAGGAUGGGGAAGACUGAGCAGA<br>AAGCUGAUCAACGGAAUCAGAGACAAGCAGAGCGGAAAGACAAUCCUGGAC<br>UUCCUGAAGAGCGACGGAUUCGCAAACAGAAACUUCAUGCAGCUGAUCCAC<br>GACGACAGCCUGACAUUCAAGGAAGACAUCCAGAAGGCACAGGUCAGCGGA<br>CAGGGAGACAGCCUGCACGAACACAUCGCAAACCUGGCAGGAAGCCCGGCA | 211 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AUCAAGAAGGGAAUCCUGCAGACAGUCAAGGUCGUCGACGAACUGGUCAAG GUCAUGGGAAGACACAAGCCGGAAAACAUCGUCAUCGAAAUGGCAAGAGAA AACCAGACAACACAGAAGGGACAGAAGAACAGCAGAGAAAGAAUGAAGAGA AUCGAAGAAGGAAUCAAGGAACUGGGAAGCCAGAUCCUGAAGGAACACCCG GUCGAAAACACACAGCUGCAGAACGAAAAGCUGUACCUGUACUACCUGCAG AACGGAAGAGACAUGUACGUCGACCAGGAACUGGACAUCAACAGACUGAGC GACUACGACGUCGACCACAUCGUCCCGCAGAGCUUCCUGAAGGACGACAGC AUCGACAACAAGGUCCUGACAAGAAGCGACAAGAACAGAGGGAAAGAGCGAC AACGUCCCGAGCGAAGAAGUCGUCAAGAAGAUGAAGAACUACUGGAGACAG CUGCUGAACGCAAAGCUGAUCACACAGAGAAAGUUCGACAACCUGACAAAG GCAGAGAGGAGGACUGAGCGAACUGGACAAGGCAGGAUUCAUCAAGAGA CAGCUGGUCGAAACAAGACAGAUCACAAAGCACGUCGCACAGAUCCUGGAC AGCAGAAUGAACACAAAGUACGACGAAAACGACAAGCUGAUCAGAGAAGUC AAGGUCAUCACACUGAAGAGCAAGCUGGUCAGCGACUUCAGAAAGGACUUC CAGUUCUACAAGGUCAGAGAAAUCAACAACUACCACCACGCACACGACGCA UACCUGAACGCAGUCGUCGGAACAGCACUGAUCAAGAAGUACCCGAAGCUG GAAAGCGAAUUCGUCUACGGAGACUACAAGGUCUACGACGUCAGAAAGAUG AUCGCAAAGAGCGAACAGGAAAUCGGAAAGGCAACAGCAAAGUACUUCUUC UACAGCAACAUCAUGAACUUCUUCAAGACAGAAAUCACACUGGCAAACGGA GAAAUCAGAAAGAGACCGCUGAUCGAAACAAACGGAGAAACAGGAGAAAUC GUCUGGGACAAGGGAAGAGACUUCGCAACAGUCAGAAAGGUCCUGAGCAUG CCGCAGGUCAACAUCGUCAAGAAGACAGAAGUCCAGACAGGAGGAUUCAGC AAGGAAAGCAUCCUGCCGAAGAGAAACAGCGACAAGCUGAUCGCAAGAAAG AAGGACUGGGACCCGAAGAAGUACGGAGGAUUCGACAGCCCGACAGUCGCA UACAGCGUCCUGGUCGUCGCAAAGGUCGAAAAGGGAAAGAGCAAGAAGCUG AAGAGCGUCAAGGAACUGCUGGGAAUCACAAUCAUGGAAAGAAGCAGCUUC GAAAAGAACCCGAUCGACUUCCUGGAAGCAAAGGGAUACAAGGAAGUCAAG AAGGACCUGAUCAUCAAGCUGCCGAAGUACAGCCUGUUCGAACUGGAAAAC GGAAGAAAGAGAAUGCUGGCAAGCGCAGGAGAACUGCAGAAGGGAAACGAA CUGGCACUGCCGAGCAAGUACGUCAACUUCCUGUACCUGGCAAGCCACUAC GAAAAGCUGAAGGGAAGCCCGGAAGACAACGAACAGAAGCAGCUGUUCGUC GAACAGCACAAGCACUACCUGGACGAAAUCAUCGAACAGAUCAGCGAAUUC AGCAAGAGAGUCAUCCUGGCAGACGCAAACCUGGACAAGGUCCUGAGCGCA UACAACAAGCACAGAGACAAGCCGAUCAGAGAACAGGCAGAAAACAUCAUC CACCUGUUCACACUGACAAACCUGGGAGCACCGGCAGCAUUCAAGUACUUC GACACAACAAUCGACAGAAAGAGAUACACAAGCACAAAGGAAGUCCUGGAC GCAACACUGAUCCACCAGAGCAUCACAGGACUGUACGAAACAAGAAUCGAC CUGAGCCAGCUGGGAGGAGACGGAGGAGGAAGCCCGAAGAAGAAGAGAAAG GUC | |
| dCas9 coding sequence using minimal uridine codons (no start or stop codons; suitable for inclusion in fusion protein coding sequence) | GACAAGAAGUACAGCAUCGGACUGGCAAUCGGAACAAACAGCGUCGGAUGG GCAGUCAUCACAGACGAAUACAAGGUCCCGAGCAAGAAGUUCAAGGUCCUG GGAAACACAGACAGACACAGCAUCAAGAAGAACCUGAUCGGAGCACUGCUG UUCGACAGCGGAGAAACAGCAGAAGCAACAAGACUGAAGAGAACAGCAAGA AGAAGAUACACAAGAAGAAAGAACAGAAUCUGCUACCUGCAGGAAAUCUUC AGCAACGAAAUGGCAAAGGUCGACGACAGCUUCUUCCACAGACUGGAAGAA AGCUUCCUGGUCGAAGAAGACAAGAAGCACGAAAGACACCCGAUCUUCGGA AACAUCGUCGACGAAGUCGCAUACCACGAAAAGUACCCGACAAUCUACCAC CUGAGAAAGAAGCUGGUCGACAGCACAGACAAGGCAGACCUGAGACUGAUC UACCUGGCACUGGCACACAUGAUCAAGUUCAGAGGACACUUCCUGAUCGAA GGAGACCUGAACCCGGACAACAGCGACGUCGACAAGCUGUUCAUCCAGCUG GUCCAGACAUACAACCAGCUGUUCGAAGAAAACCCGAUCAACGCAAGCGGA GUCGACGCAAAGGCAAUCCUGAGCGCAAGACUGAGCAAGAGCAGAAGACUG GAAAACCUGAUCGCACAGCUGCCGGGAGAAAAGAAGAACGGACUGUUCGGA AACCUGAUCGCACUGAGCCUGGGACUGACACCGAACUUCAAGAGCAACUUC GACCUGGCAGAAGACGCAAAGCUGCAGCUGAGCAAGGACACAUACGACGAC GACCUGGACAACCUGCUGGCACAGAUCGGAGACCAGUACGCAGACCUGUUC CUGGCAGCAAAGAACCUGAGCGACGCAAUCCUGCUGAGCGACAUCCUGAGA GUCAACACAGAAAUCACAAAGGCACCGCUGAGCGCAAGCAUGAUCAAGAGA UACGACGAACACCACCAGGACCUGACACUGCUGAAGGCACUGGUCAGACAG CAGCUGCCGGAAAAGUACAAGGAAAUCUUCUUCGACCAGAGCAAGAACGGA UACGCAGGAUACAUCGACGGAGGAGCAAGCCAGGAAGAAUUCUACAAGUUC AUCAAGCCGAUCCUGGAAAAGAUGGACGGAACAGAAGAACUGCUGGUCAAG CUGAACAGAGAAGACCUGCUGAGAAAGCAGAGAACAUUCGACAACGGAAGC AUCCCGCACCAGAUCCACCUGGGAGAACUGCACGCAAUCCUGAGAAGACAG GAAGACUUCUACCCGUUCCUGAAGGACAACAGAGAAAAGAUCGAAAAGAUC CUGACAUUCAGAAUCCCGUACUACGUCGGACCGCUGGCAAGAGGGAAACAGC AGAUUCGCAUGGAUGACAAGAAAGAGCGAAGAAACAAUCACACCGUGGAAC UUCGAAGAAGUCGUCGACAAGGGAGCAAGCGCACAGAGCUUCAUCGAAAGA AUGACAAACUUCGACAAGAACCUGCCGAACGAAAAGGUCCUGCCGAAGCAC | 212 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AGCCUGCUGUACGAAUACUUCACAGUCUACAACGAACUGACAAAGGUCAAG<br>UACGUCACAGAAGGAAUGAGAAAGCCGGCAUUCCUGAGCGGAGAACAGAAG<br>AAGGCAAUCGUCGACCUGCUGUUCAAGACAAACAGAAAGGUCACAGUCAAG<br>CAGCUGAAGGAAGACUACUUCAAGAAGAUCGAAUGCUUCGACAGCGUCGAA<br>AUCAGCGGAGUCGAAGACAGAUUCAACGCAAGCCUGGGAACAUACCACGAC<br>CUGCUGAAGAUCAUCAAGGACAAGGACUUCCUGGACAACGAAGAAAACGAA<br>GACAUCCUGGAAGACAUCGUCCUGACACUGACACUGUUCGAAGACAGAGAA<br>AUGAUCGAAGAAAGACUGAAGACAUACGCACACCUGUUCGACGACAAGGUC<br>AUGAAGCAGCUGAAGAGAAGAAGAUACACAGGAUGGGGAAGACUGAGCAGA<br>AAGCUGAUCAACGGAAUCAGAGACAAGCAGAGCGGAAAGACAAUCCUGGAC<br>UUCCUGAAGAGCGACGGAUUCGCAAACAGAAACUUCAUGCAGCUGAUCCAC<br>GACGACAGCCUGACAUUCAAGGAAGACAUCCAGAAGGCACAGGUCAGCGGA<br>CAGGGAGACAGCCUGCACGAACACAUCGCAAACCUGGCAGGAAGCCCGGCA<br>AUCAAGAAGGGAAUCCUGCAGACAGUCAAGGUCGUCGACGAACUGGUCAAG<br>GUCAUGGGAAGACACAAGCCGGAAAACAUCGUCAUCGAAAUGGCAAGAGAA<br>AACCAGACAACACAGAAGGGACAGAAGAACAGCAGAGAAAGAAUGAAGAGA<br>AUCGAAGAAGGAAUCAAGGAACUGGGAAGCCAGAUCCUGAAGGAACACCCG<br>GUCGAAAACACACAGCUGCAGAACGAAAAGCUGUACCUGUACUACCUGCAG<br>AACGGAAGAGACAUGUACGUCGACCAGGAACUGGACAUCAACAGACUGAGC<br>GACUACGACGUCGACGCAAUCGUCCCGCAGAGCUUCCUGAAGGACGACAGC<br>AUCGACAACAAGGUCCUGACAAGAAGCGACAAGAACAGAGGAAAGAGCGAC<br>AACGUCCCGAGCGAAGAAGUCGUCAAGAAGAUGAAGAACUACUGGAGACAG<br>CUGCUGAACGCAAAGCUGAUCACACAGAGAAAGUUCGACAACCUGACAAAG<br>GCAGAGAGGAGGACUGAGCGAACUGGACAAGGCAGGAUUCAUCAAGAGA<br>CAGCUGGUCGAAACAAGACAGAUCACAAAGCACGUCGCACAGAUCCUGGAC<br>AGCAGAAUGAACACAAAGUACGACGAAAACGACAAGCUGAUCAGAGAAGUC<br>AAGGUCAUCACACUGAAGAGCAAGCUGGUCAGCGACUUCAGAAAGGACUUC<br>CAGUUCUACAAGGUCAGAGAAAUCAACAACUACCACCACGCACACGACGCA<br>UACCUGAACGCAGUCGUCGGAACAGCACUGAUCAAGAAGUACCCGAAGCUG<br>GAAAGCGAAUUCGUCUACGGAGACUACAAGGUCUACGACGUCAGAAAGAUG<br>AUCGCAAAGAGCGAACAGGAAAUCGGAAAGGCAACAGCAAAGUACUUCUUC<br>UACAGCAACAUCAUGAACUUCUUCAAGACAGAAAUCACACUGGCAAACGGA<br>GAAAUCAGAAAGAGACCGCUGAUCGAAACAAACCGGAGAAACAGGAGAAAUC<br>GUCUGGGACAAGGGAAGAGACUUCGCAACAGUCAGAAAGGUCCUGAGCAUG<br>CCGCAGGUCAACAUCGUCAAGAAGACAGAAGUCCAGACAGGAGGAUUCAGC<br>AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAGAGAAUGCUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCUGUUCACACUGACAAACCUGGGAGCACCGGCAGCAUUCAAGUACUUC<br>GACACAACAAUCGACAGAAAGAGAUACACAAGCACAAAGGAAGUCCUGGAC<br>GCAACACUGAUCCACCAGAGCAUCACAGGACUGUACGAAACAAGAAUCGAC<br>CUGAGCCAGCUGGGAGGAGACGGAGGAGGAAGCCCGAAGAAGAAGAGAAAG<br>GUC | |
| Amino acid sequence of Cas9 (without NLS) | MDKKYSIGLDIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV<br>KQLKEDYFKKIECFDSVEISGVEDRFNASLGTYHDLLKIIKDKDFLDNEEN<br>EDILEDIVLTLTLFEDREMIEERLKTYAHLFDDKVMKQLKRRRYTGWGRLS<br>RKLINGIRDKQSGKTILDFLKSDGFANRNFMQLIHDDSLTFKEDIQKAQVS<br>GQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYL<br>QNGRDMYVDQELDINRLSDYDVDHIVPQSFLKDDSIDNKVLTRSDKNRGKS | 213 |

| Description | Sequence | SEQ ID No. |
|---|---|---|
| | DNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGE<br>IVWDKGRDFATVRKVLSMPQVNIVKKTEVQTGGFSKESILPKRNSDKLIAR<br>KKDWDPKKYGGFDSPTVAYSVLVVAKVEKGKSKKLKSVKELLGITIMERSS<br>FEKNPIDFLEAKGYKEVKKDLIIKLPKYSLFELENGRKRMLASAGELQKGN<br>ELALPSKYVNFLYLASHYEKLKGSPEDNEQKQLFVEQHKHYLDEIIEQISE<br>FSKRVILADANLDKVLSAYNKHRDKPIREQAENIIHLFTLTNLGAPAAFKY<br>FDTTIDRKRYTSTKEVLDATLIHQSITGLYETRIDLSQLGGD | |
| Cas9 mRNA ORF encoding SEQ ID NO: 213 using minimal uridine codons, with start and stop codons | AUGGACAAGAAGUACAGCAUCGGACUGGACAUCGGAACAAACAGCGUCGGA<br>UGGGCAGUCAUCACAGACGAAUACAAGGUCCCGAGCAAGAAGUUCAAGGUC<br>CUGGGAAACACAGACAGACACAGCAUCAAGAAGAACCUGAUCGGAGCACUG<br>CUGUUCGACAGCGGAGAAACAGCAGAAGCAACAAGACUGAAGAGAACAGCA<br>AGAAGAAGAUACACAAGAAGAAAGAACAGAAUCUGCUACCUGCAGGAAAUC<br>UUCAGCAACGAAAUGGCAAAGGUCGACGACAGCUUCUUCCACAGACUGGAA<br>GAAAGCUUCCUGGUCGAAGAAGACAAGAAGCACGAAAGACACCCGAUCUUC<br>GGAAACAUCGUCGACGAAGUCGCAUACCACGAAAAGUACCCGACAAUCUAC<br>CACCUGAGAAAGAAGCUGGUCGACAGCACAGACAAGGCAGACCUGAGACUG<br>AUCUACCUGGCACUGGCACACAUGAUCAAGUUCAGAGGACACUUCCUGAUC<br>GAAGGAGACCUGAACCCGGACAACAGCGACGUCGACAAGCUGUUCAUCCAG<br>CUGGUCCAGACAUACAACCAGCUGUUCGAAGAAAACCCGAUCAACGCAAGC<br>GGAGUCGACGCAAAGGCAAUCCUGAGCGCAAGACUGAGCAAGAGCAGAAGA<br>CUGGAAAACCUGAUCGCACAGCUGCCGGGAGAAAAGAAGAACGGACUGUUC<br>GGAAACCUGAUCGCACUGAGCCUGGGACUGACACCGAACUUCAAGAGCAAC<br>UUCGACCUGGCAGAAGACGCAAAGCUGCAGCUGAGCAAGGACACAUACGAC<br>GACGACCUGGACAACCUGCUGGCACAGAUCGGAGACCAGUACGCAGACCUG<br>UUCCUGGCAGCAAAGAACCUGAGCGACGCAAUCCUGCUGAGCGACAUCCUG<br>AGAGUCAACACAGAAAUCACAAAGGCACCGCUGAGCGCAAGCAUGAUCAAG<br>AGAUACGACGAACACCACCAGGACCUGACACUGCUGAAGGCACUGGUCAGA<br>CAGCAGCUGCCGGAAAAGUACAAGGAAAUCUUCUUCGACCAGAGCAAGAAC<br>GGAUACGCAGGAUACAUCGACGGAGGAGCAAGCCAGGAAGAAUUCUACAAG<br>UUCAUCAAGCCGAUCCUGGAAAAGAUGGACGGAACAGAAGAACUGCUGGUC<br>AAGCUGAACAGAGAAGACCUGCUGAGAAAGCAGAGAACAUUCGACAACGGA<br>AGCAUCCCGCACCAGAUCCACCUGGGAGAACUGCACGCAAUCCUGAGAAGA<br>CAGGAAGACUUCUACCCGUUCCUGAAGGACAACAGAGAAAAGAUCGAAAAG<br>AUCCUGACAUUCAGAAUCCCGUACUACGUCGGACCGCUGGCAAGAGGAAAC<br>AGCAGAUUCGCAUGGAUGACAAGAAAGAGCGAAGAAACAAUCACACCGUGG<br>AACUUCGAAGAAGUCGUCGACAAGGGAGCAAGCGCACAGAGCUUCAUCGAA<br>AGAAUGACAAACUUCGACAAGAACCUGCCGAACGAAAAGGUCCUGCCGAAG<br>CACAGCCUGCUGUACGAAUACUUCACAGUCUACAACGAACUGACAAAGGUC<br>AAGUACGUCACAGAAGGAAUGAGAAAGCCGGCAUUCCUGAGCGGAGAACAG<br>AAGAAGGCAAUCGUCGACCUGCUGUUCAAGACAAACAGAAAGGUCACAGUC<br>AAGCAGCUGAAGGAAGACUACUUCAAGAAGAUCGAAUGCUUCGACAGCGUC<br>GAAAUCAGCGGAGUCGAAGACAGAUUCAACGCAAGCCUGGGAACAUACCAC<br>GACCUGCUGAAGAUCAUCAAGGACAAGGACUUCCUGGACAACGAAGAAAAC<br>GAAGACAUCCUGGAAGACAUCGUCCUGACACUGACACUGUUCGAAGACAGA<br>GAAAUGAUCGAAGAAGACUGAGACAUACGCACACCUGUUCGACGACAAG<br>GUCAUGAAGCAGCUGAAGAGAAGAAGAUACACAGGAUGGGGACACUGAGC<br>AGAAAGCUGAUCAACGGAAUCAGAGACAAGCAGAGCGGAAAGACAAUCCUG<br>GACUUCCUGAAGAGCGACGGAUUCGCAAACAGAAACUUCAUGCAGCUGAUC<br>CACGACGACAGCCUGACAUUCAAGGAAGACAUCCAGAAGGCACAGGUCAGC<br>GGACAGGGAGACAGCCUGCACGAACACAUCGCAAACCUGGCAGGAAGCCCG<br>GCAAUCAAGAAGGGAAUCCUGCAGACAGUCAAGGUCGUCGACGAACUGGUC<br>AAGGUCAUGGGAAGACACAAGCCGGAAAACAUCGUCAUCGAAAUGGCAAGA<br>GAAAACCAGACAACACAGAAGGGACAGAAGAACAGCAGAGAAAGAAUGAAG<br>AGAAUCGAAGAAGGAAUCAAGGAACUGGGAAGCCAGAUCCUGAAGGAACAC<br>CCGGUCGAAAACACACAGCCUGCAGAACGAAAAGCUGUACCUGUACUACCUG<br>CAGAACGGAAGAGACAUGUACGUCGACCAGGAACUGGACAUCAACAGACUG<br>AGCGACUACGACGUCGACCACAUCGUCCCGCAGAGCUUCCUGAAGGACGAC<br>AGCAUCGACAACAAGGUCCUGACAAGAAGCGACAAGAACAGAGGAAAGAGC<br>GACAACGUCCCGAGCGAAGAAGUCGUCAAGAAGAUGAAGAACUACUGGAGA<br>CAGCUGCUGAACGCAAAGCUGAUCACACAGAGAAAGUUCGACAACCUGACA<br>AAGGCAGAGAGGAGGACUGAGCGAACUGGACAAGGCAGGAUUCAUCAAG<br>AGACAGCUGGUCGAAACAAGACAGAUCACAAAGCACGUCGCACAGAUCCUG<br>GACAGCAGAAUGAACACAAAGUACGACGAAAACGACAAGCUGAUCAGAGAA<br>GUCAAGGUCAUCACACUGAAGAGCAAGCUGGUCAGCGACUUCAGAAAGGAC<br>UUCCAGUUCUACAAGGUCAGAGAAAUCAACAACUACCACCACGCACACGAC<br>GCAUACCUGAACGCAGUCGUCGGAACAGCACUGAUCAAGAAGUACCCGAAG | 214 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CUGGAAAGCGAAUUCGUCUACGGAGACUACAAGGUCUACGACGUCAGAAAG<br>AUGAUCGCAAAGAGCGAACAGGAAAUCGGAAAGGCAACAGCAAAGUACUUC<br>UUCUACAGCAACAUCAUGAACUUCUUCAAGACAGAAAUCACACUGGCAAAC<br>GGAGAAAUCAGAAAGAGACCGCUGAUCGAAACAAACGGAGAAACAGGAGAA<br>AUCGUCUGGGACAAGGGAAGAGACUUCGCAACAGUCAGAAAGGUCCUGAGC<br>AUGCCGCAGGUCAACAUCGUCAAGAAGACAGAAGUCCAGACAGGAGGAUUC<br>AGCAAGGAAAGCAUCCUGCCGAAGAGAAACAGCGACAAGCUGAUCGCAAGA<br>AAGAAGGACUGGGACCCGAAGAAGUACGGAGGAUUCGACAGCCCGACAGUC<br>GCAUACAGCGUCCUGGUCGUCGCAAAGGUCGAAAAGGGAAAGAGCAAGAAG<br>CUGAAGAGCGUCAAGGAACUGCUGGGAAUCACAAUCAUGGAAAGAAGCAGC<br>UUCGAAAAGAACCCGAUCGACUUCCUGGAAGCAAAGGGAUACAAGGAAGUC<br>AAGAAGGACCUGAUCAUCAAGCUGCCGAAGUACAGCCUGUUCGAACUGGAA<br>AACGGAAGAAAGAGAAUGCUGGCAAGCGCAGGAGAACUGCAGAAGGGAAAC<br>GAACUGGCACUGCCGAGCAAGUACGUCAACUUCCUGUACCUGGCAAGCCAC<br>UACGAAAAGCUGAAGGGAAGCCCGGAAGACAACGAACAGAAGCAGCUGUUC<br>GUCGAACAGCACAAGCACUACCUGGACGAAAUCAUCGAACAGAUCAGCGAA<br>UUCAGCAAGAGAGUCAUCCUGGCAGACGCAAACCUGGACAAGGUCCUGAGC<br>GCAUACAACAAGCACAGAGACAAGCCGAUCAGAGAACAGGCAGAAAACAUC<br>AUCCACCUGUUCACACUGACAAACCUGGGAGCACCGGCAGCAUUCAAGUAC<br>UUCGACACAACAAUCGACAGAAAGAGAUACACAAGCACAAAGGAAGUCCUG<br>GACGCAACACUGAUCCACCAGAGCAUCACAGGACUGUACGAAACAAGAAUC<br>GACCUGAGCCAGCUGGGAGGAGACUAG | |
| Cas9 coding sequence encoding SEQ ID NO: 213 using minimal uridine codons (no start or stop codons; suitable for inclusion in fusion protein coding sequence) | GACAAGAAGUACAGCAUCGGACUGGACAUCGGAACAAACAGCGUCGGAUGG<br>GCAGUCAUCACAGACGAAUACAAGGUCCCGAGCAAGAAGUUCAAGGUCCUG<br>GGAAACACAGACAGACACAGCAUCAAGAAGAACCUGAUCGGAGCACUGCUG<br>UUCGACAGCGGAGAAACAGCAGAAGCAACAAGACUGAAGAGAACAGCAAGA<br>AGAAGAUACACAAGAAGAAAGAACAGAAAUCUGCUACCUGCAGGAAAUCUUC<br>AGCAACGAAAUGGCAAAGGUCGACAGCUUCUUCCACAGACUGGAAGAA<br>AGCUUCCUGGUCGAAGAAGACAAGAAGCACGAAAGACACCCGAUCUUCGGA<br>AACAUCGUCGACGAAGUCGCAUACCACGAAAAGUACCCGACAAUCUACCAC<br>CUGAGAAAGAAGCUGGUCGACAGCACAGACAAGGCAGACCUGAGACUGAUC<br>UACCUGGCACUGGCACACAUGAUCAAGUUCAGAGGACACUUCCUGAUCGAA<br>GGAGACCUGAACCCGGACAACAGCGACGUCGACAAGCUGUUCAUCCAGCUG<br>GUCCAGACAUACAACCAGCUGUUCGAAGAAAACCCGAUCAACGCAAGCGGA<br>GUCGACGCAAAGGCAAUCCUGAGCGCAAGACUGAGCAAGAGCAGAAGACUG<br>GAAAACCUGAUCGCACAGCUGCCGGGAGAAAAGAAGAACGGACUGUUCGGA<br>AACCUGAUCGCACUGAGCCUGGGACUGACACCGAACUUCAAGAGCAACUUC<br>GACCUGGCAGAAGACGCAAAGCUGCAGCUGAGCAAGGACACAUACGACGAC<br>GACCUGGACAACCUGCUGGCACAGAUCGGAGACCAGUACGCAGACCUGUUC<br>CUGGCAGCAAAGAACCUGAGCGACGCAAUCCUGCUGAGCGACAUCCUGAGA<br>GUCAACACAGAAAUCACAAAGGCACCGCUGAGCGCAAGCAUGAUCAAGAGA<br>UACGACGAACACCACCAGGACCUGACACUGCUGAAGGCACUGGUCAGACAG<br>CAGCUGCCGGAAAAGUACAAGGAAAUCUUCUUCGACCAGAGCAAGAACGGA<br>UACGCAGGAUACAUCGACGGAGGAGCAAGCCAGGAAGAAUUCUACAAGUUC<br>AUCAAGCCGAUCCUGGAAAAGAUGGACGGAACAGAAGAACUGCUGGUCAAG<br>CUGAACAGAGAAGACCUGCUGAGAAAGCAGAGAACAUUCGACAACGGAAGC<br>AUCCCGCACCAGAUCCACCUGGGAGAACUGCACGCAAUCCUGAGAAGACAG<br>GAAGACUUCUACCCGUUCCUGAAGGACAACAGAGAAAAGAUCGAAAAGAUC<br>CUGACAUUCAGAAUCCCGUACUACGUCGGACCGCUGGCAAGAGGAAACAGC<br>AGAUUCGCAUGGAUGACAAGAAAGAGCGAAGAAACAAUCACACCGUGGAAC<br>UUCGAAGAAGUCGUCGACAAGGGAGCAAGCGCACAGAGCUUCAUCGAAAGA<br>AUGACAAACUUCGACAAGAACCUGCCGAACGAAAAGGUCCUGCCGAAGCAC<br>AGCCUGCUGUACGAAUACUUCACAGUCUACAACGAACUGACAAAGGUCAAG<br>UACGUCACAGAAGGAAUGAGAAAGCCGGCAUUCCUGAGCGGAGAACAGAAG<br>AAGGCAAUCGUCGACCUGCUGUUCAAGACAAACAGAAAGGUCACAGUCAAG<br>CAGCUGAAGGAAGACUACUUCAAGAAGAUCGAAUGCUUCGACAGCGUCGAA<br>AUCAGCGGAGUCGAAGACAGAUUCAACGCAAGCCUGGGAACAUACCACGAC<br>CUGCUGAAGAUCAUCAAGGACAAGGACUUCCUGGACAACGAAGAAAACGAA<br>GACAUCCUGGAAGACAUCGUCCUGACACUGACACUGUUCGAAGACAGAGAA<br>AUGAUCGAAGAAGACUGAAGACAUACGCACACCUGUUCGACGACAAGGUC<br>AUGAAGCAGCUGAAGAGAAGAAGAUACACAGGAUGGGAAGACUGAGCAGA<br>AAGCUGAUCAACGGAAUCAGAGACAAGCAGAGCGGAAAGACAAUCCUGGAC<br>UUCCUGAAGAGCGACGGAUUCGCAAACAGAAACUUCAUGCAGCUGAUCCAC<br>GACGACAGCCUGACAUUCAAGGAAGACAUCCAGAAGGCACAGGUCAGCGGA<br>CAGGGAGACAGCCUGCACGAACACAUCGCAAACCUGGCAGGAAGCCCGGCA<br>AUCAAGAAGGGAAUCCUGCAGACAGUCAAGGUCGUCGACGAACUGGUCAAG<br>GUCAUGGGAAGACACAAGCCGGAAAACAUCGUCAUCGAAAUGGCAAGAGAA<br>AACCAGACAACACAGAAGGGACAGAAGAACAGCAGAGAAAGAAUGAAGAGA<br>AUCGAAGAAGGAAUCAAGGAACUGGGAAGCCAGAUCCUGAAGGAACACCCG | 215 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GUCGAAAACACACAGCUGCAGAACGAAAAGCUGUACCUGUACUACCUGCAG<br>AACGGAAGAGACAUGUACGUCGACCAGGAACUGGACAUCAACAGACUGAGC<br>GACUACGACGUCGACCACAUCGUCCCGCAGAGCUUCCUGAAGGACGACAGC<br>AUCGACAACAAGGUCCUGACAAGAAGCGACAAGAACAGAGGAAAGAGCGAC<br>AACGUCCCGAGCGAAGAAGUCGUCAAGAAGAUGAAGAACUACUGGAGACAG<br>CUGCUGAACGCAAAGCUGAUCACACAGAGAAAGUUCGACAACCUGACAAAG<br>GCAGAGAGGAGGACUGAGCGAACUGGACAAGGCAGGAUUCAUCAAGAGA<br>CAGCUGGUCGAAACAAGACAGAUCACAAAGCACGUCGCACAGAUCCUGGAC<br>AGCAGAAUGAACACAAAGUACGACGAAAACGACAAGCUGAUCAGAGAAGUC<br>AAGGUCAUCACACUGAAGAGCAAGCUGGUCAGCGACUUCAGAAAGGACUUC<br>CAGUUCUACAAGGUCAGAGAAAUCAACAACUACCACCACGCACACGACGCA<br>UACCUGAACGCAGUCGUCGGAACAGCACUGAUCAAGAAGUACCCGAAGCUG<br>GAAAGCGAAUUCGUCUACGGAGACUACAAGGUCUACGACGUCAGAAAGAUG<br>AUCGCAAAGAGCGAACAGGAAAUCGGAAAGGCAACAGCAAAGUACUUCUUC<br>UACAGCAACAUCAUGAACUUCUUCAAGACAGAAAUCACACUGGCAAACGGA<br>GAAAUCAGAAAGAGACCGCUGAUCGAAACAAACGGAGAAACAGGAGAAAUC<br>GUCUGGGACAAGGGAAGAGACUUCGCAACAGUCAGAAAGGUCCUGAGCAUG<br>CCGCAGGUCAACAUCGUCAAGAAGACAGAAGUCCAGACAGGAGGAUUCAGC<br>AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAAGAGAAUGCUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCUGUUCACACUGACAAACCUGGAGCACCGGCAGCAUUCAAGUACUUC<br>GACACAACAAUCGACAGAAAGAGAUACACAAGCACAAAGGAAGUCCUGGAC<br>GCAACACUGAUCCACCAGAGCAUCACAGGACUGUACGAAACAAGAAUCGAC<br>CUGAGCCAGCUGGGAGGAGAC | |
| Amino acid sequence of Cas9 nickase (without NLS) | MDKKYSIGLAIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV<br>KQLKEDYFKKIECFDSVEISGVEDRFNASLGTYHDLLKIIKDKDFLDNEEN<br>EDILEDIVLTLTLFEDREMIEERLKTYAHLFDDKVMKQLKRRRYTGWGRLS<br>RKLINGIRDKQSGKTILDFLKSDGFANRNFMQLIHDDSLTFKEDIQKAQVS<br>GQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYL<br>QNGRDMYVDQELDINRLSDYDVDHIVPQSFLKDDSIDNKVLTRSDKNRGKS<br>DNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETE<br>IVWDKGRDFATVRKVLSMPQVNIVKKTEVQTGGFSKESILPKRNSDKLIAR<br>KKDWDPKKYGGFDSPTVAYSVLVVAKVEKGKSKKLKSVKELLGITIMERSS<br>FEKNPIDFLEAKGYKEVKKDLIIKLPKYSLFELENGRKRMLASAGELQKGN<br>ELALPSKYVNFLYLASHYEKLKGSPEDNEQKQLFVEQHKHYLDEIIEQISE<br>FSKRVILADANLDKVLSAYNKHRDKPIREQAENIIHLFTLTNLGAPAAFKY<br>FDTTIDRKRYTSTKEVLDATLIHQSITGLYETRIDLSQLGGD | 216 |
| Cas9 nickase mRNA ORF encoding SEQ ID NO: 216 using minimal uridine | AUGGACAAGAAGUACAGCAUCGGACUGGCAAUCGGAACAAACAGCGUCGGA<br>UGGGCAGUCAUCACAGACGAAUACAAGGUCCCGAGCAAGAAGUUCAAGGUC<br>CUGGGAAACACAGACAGACACAGCAUCAAGAAGAACCUGAUCGGAGCACUG<br>CUGUUCGACAGCGGAGAAACAGCAGAAGCAACAAGACUGAAGAGAACAGCA<br>AGAAGAAGAUACACAAGAAGAAACAGAAUCUGCUACCUGCAGGAAAUC<br>UUCAGCAACGAAAUGGCAAAGGUCGACGACAGCUUCUUCCACAGACUGGAA<br>GAAAGCUUCCUGGUCGAAGAAGACAAGAAGCACGAAAGACACCCGAUCUUC | 217 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| codons as listed in Table 3, with start and stop codons | GGAAACAUCGUCGACGAAGUCGCAUACCACGAAAAGUACCCGACAAUCUAC CACCUGAGAAAGAAGCUGGUCGACAGCACAGACAAGGCAGACCUGAGACUG AUCUACCUGGCACUGGCACACAUGAUCAAGUUCAGAGGACACUUCCUGAUC GAAGGAGACCUGAACCCGGACAACAGCGACGUCGACAAGCUGUUCAUCCAG CUGGUCCAGACAUACAACCAGCUGUUCGAAGAAAACCCGAUCAACGCAAGC GGAGUCGACGCAAAGGCAAUCCUGAGCGCAAGACUGAGCAAGAGCAGAAGA CUGGAAAACCUGAUCGCACAGCUGCCGGGAGAAAAGAAGAACGGACUGUUC GGAAACCUGAUCGCACUGAGCCUGGGACUGACACCGAACUUCAAGAGCAAC UUCGACCUGGCAGAAGACGCAAAGCUGCAGCUGAGCAAGGACACAUACGAC GACGACCUGGACAACCUGCUGGCACAGAUCGGAGACCAGUACGCAGACCUG UUCCUGGCAGCAAAGAACCUGAGCGACGCAAUCCUGCUGAGCGACAUCCUG AGAGUCAACACAGAAAUCACAAAGGCACCGCUGAGCGCAAGCAUGAUCAAG AGAUACGACGAACACCACCAGGACCUGACACUGCUGAAGGCACUGGUCAGA CAGCAGCUGCCGGAAAAGUACAAGGAAAUCUUCUUCGACCAGAGCAAGAAC GGAUACGCAGGAUACAUCGACGGAGGAGCAAGCCAGGAAGAAUUCUACAAG UUCAUCAAGCCGAUCCUGGAAAAGAUGGACGGAACAGAAGAACUGCUGGUC AAGCUGAACAGAGAAGACCUGCUGAGAAAGCAGAGAACAUUCGACAACGGA AGCAUCCCGCACCAGAUCCACCUGGGAGAACUGCACGCAAUCCUGAGAAGA CAGGAAGACUUCUACCCGUUCCUGAAGGACAACAGAGAAAAGAUCGAAAAG AUCCUGACAUUCAGAAUCCCGUACUACGUCGGACCGCUGGCAAGAGGAAAC AGCAGAUUCGCAUGGAUGACAAGAAAGAGCGAAGAAACAAUCACACCGUGG AACUUCGAAGAAGUCGUCGACAAGGGAGCAAGCGCACAGAGCUUCAUCGAA AGAAUGACAAACUUCGACAAGAACCUGCCGAACGAAAAGGUCCUGCCGAAG CACAGCCUGCUGUACGAAUACUUCACAGUCUACAACGAACUGACAAAGGUC AAGUACGUCACAGAAGGAAUGAGAAAGCCGGCAUUCCUGAGCGGAGAACAG AAGAAGGCAAUCGUCGACCUGCUGUUCAAGACAAACAGAAAGGUCACAGUC AAGCAGCUGAAGGAAGACUACUUCAAGAAGAUCGAAUGCUUCGACAGCGUC GAAAUCAGCGGAGUCGAAGACAGAUUCAACGCAAGCCUGGGAACAUACCAC GACCUGCUGAAGAUCAUCAAGGACAAGGACUUCCUGGACAACGAAGAAAAC GAAGACAUCCUGGAAGACAUCGUCCUGACACUGACACUGUUCGAAGACAGA GAAAUGAUCGAAGAAAGACUGAAGACAUACGCACACCUGUUCGACGACAAG GUCAUGAAGCAGCUGAAGAGAAGAAGAUACACAGGAUGGGGAAGACUGAGC AGAAAGCUGAUCAACGGAAUCAGAGACAAGCAGAGCGGAAAGACAAUCCUG GACUUCCUGAAGAGCGACGGAUUCGCAAACAGAAACUUCAUGCAGCUGAUC CACGACGACAGCCUGACAUUCAAGGAAGACAUCCAGAAGGCACAGGUCAGC GGACAGGGAGACAGCCUGCACGAACACAUCGCAAACCUGGCAGGAAGCCCG GCAAUCAAGAAGGGAAUCCUGCAGACAGUCAAGGUCGUCGACGAACUGGUC AAGGUCAUGGGAAAGACACAAGCCGGAAAACAUCGUCAUCGAAAUGGCAAGA GAAAACCAGACAACACAGAAGGGACAGAAGAACAGCAGAGAAAGAAUGAAG AGAAUCGAAGAAGGAAUCAAGGAACUGGGAAGCCAGAUCCUGAAGGAACAC CCGGUCGAAAACACACAGCUGCAGAACGAAAAGCUGUACCUGUACUACCUG CAGAACGGAAGAGACAUGUACGUCGACCAGGAACUGGACAUCAACAGACUG AGCGACUACGACGUCGACCACAUCGUCCCGCAGAGCUUCCUGAAGGACGAC AGCAUCGACAACAAGGUCCUGACAAGAAGCGACAAGAACAGAGGAAAGAGC GACAACGUCCCGAGCGAAGAAGUCGUCAAGAAGAUGAAGAACUACUGGAGA CAGCUGCUGAACGCAAAGCUGAUCACACAGAGAAAGUUCGACAACCUGACA AAGGCAGAGAGGAGGACUGAGCGAACUGGACAAGGCAGGAUUCAUCAAG AGACAGCUGGUCGAAACAAGACAGAUCACAAAGCACGUCGCACAGAUCCUG GACAGCAGAAUGAACACAAAGUACGACGAAAACGACAAGCUGAUCAGAGAA GUCAAGGUCAUCACACUGAAGAGCAAGCUGGUCAGCGACUUCAGAAAGGAC UUCCAGUUCUACAAGGUCAGAGAAAUCAACAACUACCACCACGCACACGAC GCAUACCUGAACGCAGUCGUCGGAACAGCACUGAUCAAGAAGUACCCGAAG CUGGAAAGCGAAUUCGUCUACGGAGACUACAAGGUCUACGACGUCAGAAAG AUGAUCGCAAAGAGCGAACAGGAAAUCGGAAAGGCAACAGCAAAGUACUUC UUCUACAGCAACAUCAUGAACUUCUUCAAGACAGAAAUCACACUGGCAAAC GGAGAAAUCAGAAAGAGACCGCUGAUCGAAACAAACGGAGAAACAGGAGAA AUCGUCUGGGACAAGGGAAGAGACUUCGCAACAGUCAGAAAGGUCCUGAGC AUGCCGCAGGUCAACAUCGUCAAGAAGACAGAAGUCCAGACAGGAGGAUUC AGCAAGGAAAGCAUCCUGCCGAAGAGAAACAGCGACAAGCUGAUCGCAAGA AAGAAGGACUGGGACCCGAAGAAGUACGGAGGAUUCGACAGCCCGACAGUC GCAUACAGCGUCCUGGUCGUCGCAAAGGUCGAAAAGGGAAAGAGCAAGAAG CUGAAGAGCGUCAAGGAACUGCUGGGAAUCACAAUCAUGGAAAGAAGCAGC UUCGAAAAGAACCCGAUCGACUUCCUGGAAGCAAAGGGAUACAAGGAAGUC AAGAAGGACCUGAUCAUCAAGCUGCCGAAGUACAGCCUGUUCGAACUGGAA AACGGAAGAAAGAGAAUGCUGGCAAGCGCAGGAGAACUGCAGAAGGGAAAC GAACUGGCACUGCCGAGCAAGUACGUCAACUUCCUGUACCUGGCAAGCCAC UACGAAAAGCUGAAGGGAAGCCCGGAAGACAACGAACAGAAGCAGCUGUUC GUCGAACAGCACAAGCACUACCUGGACGAAAUCAUCGAACAGAUCAGCGAA UUCAGCAAGAGAGUCAUCCUGGCAGACGCAAACCUGGACAAGGUCCUGAGC GCAUACAACAAGCACAGAGACAAGCCGAUCAGAGAACAGGCAGAAAACAUC | |

| Description | Sequence | SEQ ID No. |
|---|---|---|
| | AUCCACCUGUUCACACUGACAAACCUGGGAGCACCGGCAGCAUUCAAGUAC UUCGACACAACAAUCGACAGAAAGAGAUACACAAGCACAAAGGAAGUCCUG GACGCAACACUGAUCCACCAGAGCAUCACAGGACUGUACGAAACAAGAAUC GACCUGAGCCAGCUGGGAGGAGACUAG | |
| Cas9 nickase coding sequence encoding SEQ ID NO: 216 using minimal uridine codons as listed in Table 3 (no start or stop codons; suitable for inclusion in fusion protein coding sequence) | GACAAGAAGUACAGCAUCGGACUGGCAAUCGGAACAAACAGCGUCGGAUGG GCAGUCAUCACAGACGAAUACAAGGUCCCGAGCAAGAAGUUCAAGGUCCUG GGAAACACAGACAGACACAGCAUCAAGAAGAACCUGAUCGGAGCACUGCUG UUCGACAGCGGAGAAACAGCAGAAGCAACAAGACUGAAGAGAACAGCAAGA AGAAGAUACACAAGAAGAAAGAACAGAAUCUGCUACCUGCAGGAAAUCUUC AGCAACGAAAUGGCAAAGGUCGACGACAGCUUCUUCCACAGACUGGAAGAA AGCUUCCUGGUCGAAGAAGACAAGAAGCACGAAAGACACCCGAUCUUCGGA AACAUCGUCGACGAAGUCGCAUACCACGAAAAGUACCCGACAAUCUACCAC CUGAGAAAGAAGCUGGUCGACAGCACAGACAAGGCAGACCUGAGACUGAUC UACCUGGCACUGGCACACAUGAUCAAGUUCAGAGGACACUUCCUGAUCGAA GGAGACCUGAACCCGGACAACAGCGACGUCGACAAGCUGUUCAUCCAGCUG GUCCAGACAUACAACCAGCUGUUCGAAGAAAACCCGAUCAACGCAAGCGGA GUCGACGCAAAGGCAAUCCUGAGCGCAAGACUGAGCAAGAGCAGAAGACUG GAAACCUGAUCGCACAGCUGCCGGGAGAAAAGAAGAACGGACUGUUCGGA AACCUGAUCGCACUGAGCCUGGGACUGACACCGAACUUCAAGAGCAACUUC GACCUGGCAGAAGACGCAAAGCUGCAGCUGAGCAAGGACACAUACGACGAC GACCUGGACAACCUGCUGGCACAGAUCGGAGACCAGUACGCAGACCUGUUC CUGGCAGCAAAGAACCUGAGCGACGCAAUCCUGCUGAGCGACAUCCUGAGA GUCAACACAGAAAUCACAAAGGCACCGCUGAGCGCAAGCAUGAUCAAGAGA UACGACGAACACCACCAGGACCUGACACUGCUGAAGGCACUGGUCAGACAG CAGCUGCCGGAAAAGUACAAGGAAAUCUUCUUCGACCAGAGCAAGAACGGA UACGCAGGAUACAUCGACGGAGGAGCAAGCCAGGAAGAAUUCUACAAGUUC AUCAAGCCGAUCCUGGAAAAGAUGGACGGAACAGAAGAACUGCUGGUCAAG CUGAACAGAGAAGACCUGCUGAGAAAGCAGAGAACAUUCGACAACGGAAGC AUCCCGCACCAGAUCCACCUGGGAGAACUGCACGCAAUCCUGAGAAGACAG GAAGACUUCUACCCGUUCCUGAAGGACAACAGAGAAAAGAUCGAAAAGAUC CUGACAUUCAGAAUCCCGUACUACGUCGGACCGCUGGCAAGAGGAAACAGC AGAUUCGCAUGGAUGACAAGAAAGAGCGAAGAAACAAUCACACCGUGGAAC UUCGAAGAAGUCGUCGACAAGGGAGCAAGCGCACAGAGCUUCAUCGAAAGA AUGACAAACUUCGACAAGAACCUGCCGAACGAAAAGGUCCUGCCGAAGCAC AGCCUGCUGUACGAAUACUUCACAGUCUACAACGAACUGACAAAGGUCAAG UACGUCACAGAAGGAAUGAGAAAGCCGGCAUUCCUGAGCGGAGAACAGAAG AAGGCAAUCGUCGACCUGCUGUUCAAGACAAACAGAAAGGUCACAGUCAAG CAGCUGAAGGAAGACUACUUCAAGAAGAUCGAAUGCUUCGACAGCGUCGAA AUCAGCGGAGUCGAAGACAGAUUCAACGCAAGCCUGGGAACAUACCACGAC CUGCUGAAGAUCAUCAAGGACAAGGACUUCCUGGACAACGAAGAAAACGAA GACAUCCUGGAAGACAUCGUCCUGACACUGACACUGUUCGAAGACAGAGAA AUGAUCGAAGAAAGACUGAAGACAUACGCACACCUGUUCGACGACAAGGUC AUGAAGCAGCUGAAGAGAAGAAGAUACACAGGAUGGGGAAGACUGAGCAGA AAGCUGAUCAACGGAAUCAGAGACAAGCAGAGCGGAAAGACAAUCCUGGAC UUCCUGAAGAGCGACGGAUUCGCAAACAGAAACUUCAUGCAGCUGAUCCAC GACGACAGCCUGACAUUCAAGGAAGACAUCCAGAAGGCACAGGUCAGCGGA CAGGGAGACAGCCUGCACGAACACAUCGCAAACCUGGCAGGAAGCCCGGCA AUCAAGAAGGGAAUCCUGCAGACAGUCAAGGUCGUCGACGAACUGGUCAAG GUCAUGGGAAGACACAAGCCGGAAAACAUCGUCAUCGAAAUGGCAAGAGAA AACCAGACAACACAGAAGGGACAGAAGAACAGCAGAGAAAGAAUGAAGAGA AUCGAAGAGGAAUCAAGGAACUGGGAAGCCAGAUCCUGAAGGAACACCCG GUCGAAAACACACAGCUGCAGAACGAAAAGCUGUACCUGUACUACCUGCAG AACGGAAGAGACAUGUACGUCGACCAGGAACUGGACAUCAACAGACUGAGC GACUACGACGUCGACCACAUCGUCCCGCAGAGCUUCCUGAAGGACGACAGC AUCGACAACAAGGUCCUGACAAGAAGCGACAAGAACAGAGGAAAGAGCGAC AACGUCCCGAGCGAAGAAGUCGUCAAGAAGAUGAAGAACUACUGGAGACAG CUGCUGAACGCAAAGCUGAUCACACAGAGAAAGUUCGACAACCUGACAAAG GCAGAGAGGAGGAGACUGAGCGAACUGGACAAGGCAGGAUUCAUCAAGAGA CAGCUGGUCGAAACAAGACAGAUCACAAAGCACGUCGCACAGAUCCUGGAC AGCAGAAUGAACACAAAGUACGACGAAAACGACAAGCUGAUCAGAGAAGUC AAGGUCAUCACACUGAAGAGCAAGCUGGUCAGCGACUUCAGAAAGGACUUC CAGUUCUACAAGGUCAGAGAAAUCAACAACUACCACCACGCACACGACGCA UACCUGAACGCAGUCGUCGGAACAGCACUGAUCAAGAAGUACCCGAAGCUG GAAAGCGAAUUCGUCUACGGAGACUACAAGGUCUACGACGUCAGAAAGAUG AUCGCAAAGAGCGAACAGGAAAUCGGAAAGGCAACAGCAAAGUACUUCUUC UACAGCAACAUCAUGAACUUCUUCAAGACAGAAAUCACACUGGCAAACGGA GAAAUCAGAAAGAGACCGCUGAUCGAAACAAACGGAGAAACAGGAGAAAUC GUCUGGGACAAGGGAAGAGACUUCGCAACAGUCAGAAAGGUCCUGAGCAUG CCGCAGGUCAACAUCGUCAAGAAGACAGAAGUCCAGACAGGAGGAUUCAGC | 218 |

-continued

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAGAGAAUGCUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCCUGUUCACACUGACAAACCUGGGAGCACCGGCAGCAUUCAAGUACUUC<br>GACACAACAAUCGACAGAAAGAGAUACACAAGCACAAAGGAAGUCCUGGAC<br>GCAACACUGAUCCACCGAGCAUCACAGGACUGUACGAAACAAGAAUCGAC<br>CUGAGCCAGCUGGGAGGAGAC | |
| Amino acid sequence of dCas9 (without NLS) | MDKKYSIGLAIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV<br>KQLKEDYFKKIECFDSVEISGVEDRFNASLGTYHDLLKIIKDKDFLDNEEN<br>EDILEDIVLTLTLFEDREMIEERLKTYAHLFDDKVMKQLKRRRYTGWGRLS<br>RKLINGIRDKQSGKTILDFLKSDGFANRNFMQLIHDDSLTFKEDIQKAQVS<br>GQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYL<br>QNGRDMYVDQELDINRLSDYDVDAIVPQSFLKDDSIDNKVLTRSDKNRGKS<br>DNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGE<br>IVWDKGRDFATVRKVLSMPQVNIVKKTEVQTGGFSKESILPKRNSDKLIAR<br>KKDWDPKKYGGFDSPTVAYSVLVVAKVEKGKSKKLKSVKELLGITIMERSS<br>FEKNPIDFLEAKGYKEVKKDLIIKLPKYSLFELENGRKRMLASAGELQKGN<br>ELALPSKYVNFLYLASHYEKLKGSPEDNEQKQLFVEQHKHYLDEIIEQISE<br>FSKRVILADANLDKVLSAYNKHRDKPIREQAENIIHLFTLTNLGAPAAFKY<br>FDTTIDRKRYTSTKEVLDATLIHQSITGLYETRIDLSQLGGD | 219 |
| dCas9 mRNA ORF encoding SEQ ID NO: 219 using minimal uridine codons as listed in Table 3, with start and stop codons | AUGGACAAGAAGUACAGCAUCGGACUGGCAAUCGGAACAAACAGCGUCGGA<br>UGGGCAGUCAUCACAGACGAAUACAAGGUCCCGAGCAAGAAGUUCAAGGUC<br>CUGGGAAACACAGACAGACACAGCAUCAAGAAGAACCUGAUCGGAGCACUG<br>CUGUUCGACAGCGGAGAAACAGCAGAAGCAACAAGACUGAAGAGAACAGCA<br>AGAAGAAGAUACACAAGAACAAGAAUCUGCUACCUGCAGGAAAUC<br>UUCAGCAACGAAAUGGCAAAGGUCGACGACAGCUUCUUCCACAGACUGGAA<br>GAAAGCUUCCUGGUCGAAGAAGCAAGAAGCACGAAAGACACCCGAUCUUC<br>GGAAACAUCGUCGACGAAGUCGCAUACCACGAAAAGUACCCGACAAUCUAC<br>CACCUGAGAAAGAAGCUGGUCGACAGCACAGACAAGGCAGACCUGAGACUG<br>AUCUACCUGGCACUGGCACACAUGAUCAAGUUCAGAGGACACUUCCUGAUC<br>GAAGGAGACCUGAACCCGGACAACAGCGACGUCGACAAGCUGUUCAUCCAG<br>CUGGUCCAGACAUACAACCAGCUGUUCGAAGAAACCCGAUCAACGCAAGC<br>GGAGUCGACGCAAAGGCAAUCCUGAGCGCAAGACUGAGCAAGAGCAGAAGA<br>CUGGAAAACCUGAUCGCACAGCUGCCGGGAGAAAAGAAGAACGGACUGUUC<br>GGAAACCUGAUCGCACUGAGCCUGGGACUGACACCGAACUUCAAGAGCAAC<br>UUCGACCUGGCAGAAGACGCAAAGCUGCAGCUGAGCAAGGACACAUACGAC<br>GACGACCUGGACAACCUGCUGGCACAGAUCGGAGACCAGUACGCAGACCUG<br>UUCCUGGCAGCAAAGAACCUGAGCGACGCAAUCCUGCUGAGCGACAUCCUG<br>AGAGUCAACACAGAAAUCACAAAGGCACCGCUGAGCGCAAGCAUGAUCAAG<br>AGAUACGACGAACACCACCAGGACCUGACACUGCUGAAGGCACUGGUCAGA<br>CAGCAGCUGCCGGAAAAGUACAAGGAAAUCUUCUUCGACCAGAGCAAGAAC<br>GGAUACGCAGGAUACAUCGACGGAGGAGCAAGCCAGGAAGAAUUCUACAAG<br>UUCAUCAAGCCGAUCCUGGAAAAGAUGGACGGAACAGAAGAACUGCUGGUC<br>AAGCUGAACAGAGAAGACCUGCUGAAAGCAGAGAACAUUCGACAACGGA<br>AGCAUCCCGCACCAGAUCCACCUGGGAGAACUGCACGCAAUCCUGAGAAGA | 220 |

| Description | Sequence | SEQ ID No. |
|---|---|---|
| | CAGGAAGACUUCUACCCGUUCCUGAAGGACAACAGAGAAAAGAUCGAAAAG<br>AUCCUGACAUUCAGAAUCCCGUACUACGUCGGACCGCUGGCAAGAGGAAAC<br>AGCAGAUUCGCAUGGAUGACAAGAAAGAGCGAAGAAACAAUCACACCGUGG<br>AACUUCGAAGAAGUCGUCGACAAGGGAGCAAGCGCACAGAGCUUCAUCGAA<br>AGAAUGACAAACUUCGACAAGAACCUGCCGAACGAAAAGGUCCUGCCGAAG<br>CACAGCCUGCUGUACGAAUACUUCACAGUCUACAACGAACUGACAAAGGUC<br>AAGUACGUCACAGAAGGAAUGAGAAAGCCGGCAUUCCUGAGCGGAGAACAG<br>AAGAAGGCAAUCGUCGACCUGCUGUUCAAGACAAACAGAAAGGUCACAGUC<br>AAGCAGCUGAAGGAAGACUACUUCAAGAAGAUCGAAUGCUUCGACAGCGUC<br>GAAAUCAGCGGAGUCGAAGACAGAUUCAACGCAAGCCUGGGAACAUACCAC<br>GACCUGCUGAAGAUCAUCAAGGACAAGGACUUCCUGGACAACGAAGAAAAC<br>GAAGACAUCCUGGAAGACAUCGUCCUGACACUGACACUGUUCGAAGACAGA<br>GAAAUGAUCGAAGAAAGACUGAAGACAUACGCACACCUGUUCGACGACAAG<br>GUCAUGAAGCAGCUGAAGAGAAGAAGAUACACAGGAUGGGGAAGACUGAGC<br>AGAAAGCUGAUCAACGGAAUCAGAGACAAGCAGAGCGGAAAGACAAUCCUG<br>GACUUCCUGAAGAGCGACGGAUUCGCAAACAGAAACUUCAUGCAGCUGAUC<br>CACGACGACAGCCUGACAUUCAAGGAAGACAUCCAGAAGGCACAGGUCAGC<br>GGACAGGGAGACAGCCUGCACGAACACAUCGCAAACCUGGCAGGAAGCCCG<br>GCAAUCAAGAAGGGAAUCCUGCAGACAGUCAAGGUCGUCGACGAACUGGUC<br>AAGGUCAUGGGAAGACACAAGCCGGAAAACAUCGUCAUCGAAAUGGCAAGA<br>GAAAACCAGACAACACAGAAGGGACAGAAGAACAGCAGAGAAAGAAUGAAG<br>AGAAUCGAAGAAGGAAUCAAGGAACUGGGAAGCCAGAUCCUGAAGGAACAC<br>CCGGUCGAAAACACACAGCUGCAGAACGAAAGCUGUACCUGUACUACCUG<br>CAGAACGGAAGAGACAUGUACGUCGACCAGGAACUGGACAUCAACAGACUG<br>AGCGACUACGACGUCGACGCAAUCGUCCCGCAGAGCUUCCUGAAGGACGAC<br>AGCAUCGACAACAAGGUCCUGACAAGAAGCGACAAGAACAGAGGAAAGAGC<br>GACAACGUCCCGAGCGAAGAAGUCGUCAAGAAGAUGAAGAACUACUGGAGA<br>CAGCUGCUGAACGCAAAGCUGAUCACACAGAGAAAGUUCGACAACCUGACA<br>AAGGCAGAGAGAGGAGGACUGAGCGAACUGGACAAGGCAGGAUUCAUCAAG<br>AGACAGCUGGUCGAAACAAGACAGAUCACAAAGCACGUCGCACAGAUCCUG<br>GACAGCAGAAUGAACACAAAGUACGACGAAAACGACAAGCUGAUCAGAGAA<br>GUCAAGGUCAUCACACUGAAGAGCAAGCUGGUCAGCGACUUCAGAAAGGAC<br>UUCCAGUUCUACAAGGUCAGAGAAAUCAACAACUACCACCACGCACACGAU<br>GCAUACCUGAACGCAGUCGUCGGAACAGCACUGAUCAAGAAGUACCCGAAG<br>CUGGAAAGCGAAUUCGUCUACGGAGACUACAAGGUCUACGACGUCAGAAAG<br>AUGAUCGCAAAGAGCGAACAGGAAAUCGGAAAGGCAACAGCAAAGUACUUC<br>UUCUACAGCAACAUCAUGAACUUCUUCAAGACAGAAAUCACACUGGCAAAC<br>GGAGAAAUCAGAAAGAGACCGCUGAUCGAAACAAACGGAGAAACAGGAGAA<br>AUCGUCUGGGACAAGGGAAGAGACUUCGCAACAGUCAGAAAGGUCCUGAGC<br>AUGCCGCAGGUCAACAUCGUCAAGAAGACAGAAGUCCAGACAGGAGGAUUC<br>AGCAAGGAAAGCAUCCUGCCGAAGAGAAACAGCGACAAGCUGAUCGCAAGA<br>AAGAAGGACUGGGACCCGAAGAAGUACGGAGGAUUCGACAGCCCGACAGUC<br>GCAUACAGCGUCCUGGUCGUCGCAAAGGUCGAAAAGGGAAAGAGCAAGAAG<br>CUGAAGAGCGUCAAGGAACUGCUGGGAAUCACAAUCAUGGAAAGAAGCAGC<br>UUCGAAAAGAACCCGAUCGACUUCCUGGAAGCAAAGGGAUACAAGGAAGUC<br>AAGAAGGACCUGAUCAUCAAGCUGCCGAAGUACAGCCUGUUCGAACUGGAA<br>AACGGAAGAAAGAGAAUGCUGGCAAGCGCAGGAGAACUGCAGAAGGGAAAC<br>GAACUGGCACUGCCGAGCAAGUACGUCAACUUCCUGUACCUGGCAAGCCAC<br>UACGAAAAGCUGAAGGGAAGCCCGGAAGACAACGAACAGAAGCAGCUGUUC<br>GUCGAACAGCACAAGCACUACCUGGACGAAAUCAUCGAACAGAUCAGCGAA<br>UUCAGCAAGAGAGUCAUCCUGGCAGACGCAAACCUGGACAAGGUCCUGAGC<br>GCAUACAACAAGCACAGAGACAAGCCGAUCAGAGAACAGGCAGAAAACAUC<br>AUCCACCUGUUCACACUGACAAACCUGGGAGCACCGGCAGCAUUCAAGUAC<br>UUCGACACAACAAUCGACAGAAAAGAGAUACAAGCACAAAGGAAGUCCUG<br>GACGCAACACUGAUCCACCAGAGCAUCACAGGACUGUACGAAACAAGAAUC<br>GACCUGAGCCAGCUGGGAGGAGACUAG | |
| dCas9 coding sequence encoding SEQ ID NO: 219 using minimal uridine codons as listed in Table 3 (no start or stop codons; suitable for | GACAAGAAGUACAGCAUCGGACUGGCAAUCGGAACAAACAGCGUCGGAUGG<br>GCAGUCAUCACAGACGAAUACAAGGUCCCGAGCAAGAAGUUCAAGGUCCUG<br>GGAAACACAGACAGACACAGCAUCAAGAAGAACCUGAUCGGAGCACUGCUG<br>UUCGACAGCGGAGAAACAGCAGAAGCAACAAGACUGAAGAGAACAGCAAGA<br>AGAAGAUACACAAGAAGAAAGAACAGAAUCUGCUACCUGCAGGAAAUCUUC<br>AGCAACGAAAUGGCAAAGGUCGACGACAGCUUCUUCCACAGACUGGAAGAA<br>AGCUUCCUGGUCGAAGAAGACAAGAAGCACGAAAGACACCCGAUCUUCGGA<br>AACAUCGUCGACGAAGUCGCAUACCACGAAAAGUACCCGACAAUCUACCAC<br>CUGAAAAGAAGCUGGUCGACAGCACAGACAAGGCAGACCUGAGACUGAUC<br>UACCUGGCACUGGCACACAUGAUCAAGUUCAGAGGACACUUCCUGAUCGAA<br>GGAGACCUGAACCCGGACAACAGCGACGUCGACAAGCUGUUCAUCCAGCUG<br>GUCCAGACAUACAACCAGCUGUUCGAAGAAAACCCGAUCAACGCAAGCGGA<br>GUCGACGCAAAGGCAAUCCUGAGCGCAAGACUGAGCAAGAGCAGAAGACUG | 221 |

| Description | Sequence | SEQ ID No. |
|---|---|---|
| inclusion in fusion protein coding sequence) | GAAAACCUGAUCGCACAGCUGCCGGGAGAAAAGAAGAACGGACUGUUCGGA AACCUGAUCGCACUGAGCCUGGGACUGACACCGAACUUCAAGAGCAACUUC GACCUGGCAGAAGACGCAAAGCUGCAGCUGAGCAAGGACACAUACGACGAC GACCUGGACAACCUGCUGGCACAGAUCGGAGACCAGUACGCAGACCUGUUC CUGGCAGCAAAGAACCUGAGCGACGCAAUCCUGCUGAGCGACAUCCUGAGA GUCAACACAGAAAUCACAAAGGCACCGCUGAGCGCAAGCAUGAUCAAGAGA UACGACGAACACCACCAGGACCUGACACUGCUGAAGGCACUGGUCAGACAG CAGCUGCCGGAAAAGUACAAGGAAAUCUUCUUCGACCAGAGCAAGAACGGA UACGCAGGAUACAUCGACGGAGGAGCAAGCCAGGAAGAAUUCUACAAGUUC AUCAAGCCGAUCCUGGAAAAGAUGGACGGAACAGAAGAACUGCUGGUCAAG CUGAACAGAGAAGACCUGCUGAGAAAGCAGAGAACAUUCGACAACGGAAGC AUCCCGCACCAGAUCCACCUGGGAGAACUGCACGCAAUCCUGAGAAGACAG GAAGACUUCUACCCGUUCCUGAAGGACAACAGAGAAAAGAUCGAAAAGAUC CUGACAUUCAGAAUCCCGUACUACGUCGGACCGCUGGCAAGAGGAAACAGC AGAUUCGCAUGGAUGACAAGAAAGAGCGAAGAAACAAUCACACCGUGGAAC UUCGAAGAAGUCGUCGACAAGGGAGCAAGCGCACAGAGCUUCAUCGAAAGA AUGACAAACUUCGACAAGAACCUGCCGAACGAAAAGGUCCUGCCGAAGCAC AGCCUGCUGUACGAAUACUUCACAGUCUACAACGAACUGACAAAGGUCAAG UACGUCACAGAAGGAAUGAGAAAGCCGGCAUUCCUGAGCGGAGAACAGAAG AAGGCAAUCGUCGACCUGCUGUUCAAGACAAACAGAAAGGUCACAGUCAAG CAGCUGAAGGAAGACUACUUCAAGAAGAUCGAAUGCUUCGACAGCGUCGAA AUCAGCGGAGUCGAAGACAGAUUCAACGCAAGCCUGGGAACAUACCACGAC CUGCUGAAGAUCAUCAAGGACAAGGACUUCCUGGACAACGAAGAAAACGAA GACAUCCUGGAAGACAUCGUCCUGACACUGACACUGUUCGAAGACAGAGAA AUGAUCGAAGAAAGACUGAAGACAUACGCACACCUGUUCGACGACAAGGUC AUGAAGCAGCUGAAGAGAAGAAGAUACACAGGAUGGGGAAGACUGAGCAGA AAGCUGAUCAACGGAAUCAGAGACAAGCAGAGCGGAAAGACAAUCCUGGAC UUCCUGAAGAGCGACGGAUUCGCAAACAGAAACUUCAUGCAGCUGAUCCAC GACGACAGCCUGACAUUCAAGGAAGACAUCCAGAAGGCACAGGUCAGCGGA CAGGGAGACAGCCUGCACGAACACAUCGCAAACCUGGCAGGAAGCCCGGCA AUCAAGAAGGGAAUCCUGCAGACAGUCAAGGUCGUCGACGAACUGGUCAAG GUCAUGGGAAGACACAAGCCGGAAAACAUCGUCAUCGAAAUGGCAAGAGAA AACCAGACAACACAGAAGGGACAGAAGAACAGCAGAGAAAGAAUGAAGAGA AUCGAAGAAGGAAUCAAGGAACUGGGAAGCCAGAUCCUGAAGGAACACCCG GUCGAAAACACACAGCUGCAGAACGAAAAGCUGUACCUGUACUACCUGCAG AACGGAAGAGACAUGUACGUCGACCAGGAACUGGACAUCAACAGACUGAGC GACUACGACGUCGACGCAAUCGUCCCGCAGAGCUUCCUGAAGGACGACAGC AUCGACAACAAGGUCCUGACAAGAAGCGACAAGAACAGAGGAAAGAGCGAC AACGUCCCGAGCGAAGAAGUCGUCAAGAAGAUGAAGAACUACUGGAGACAG CUGCUGAACGCAAAGCUGAUCACACAGAGAAAGUUCGACAACCUGACAAAG GCAGAGAGGAGGAGGACUGAGCGAACUGGACAAGGCAGGAUUCAUCAAGAGA CAGCUGGUCGAAACAAGACAGAUCACAAAGCACGUCGCACAGAUCCUGGAC AGCAGAAUGAACACAAAGUACGACGAAAACGACAAGCUGAUCAGAGAAGUC AAGGUCAUCACACUGAAGAGCAAGCUGGUCAGCGACUUCAGAAAGGACUUC CAGUUCUACAAGGUCAGAGAAAUCAACAACUACCACCACGCACACGACGCA UACCUGAACGCAGUCGUCGGAACAGCACUGAUCAAGAAGUACCCGAAGCUG GAAAGCGAAUUCGUCUACGGAGACUACAAGGUCUACGACGUCAGAAAGAUG AUCGCAAAGAGCGAACAGGAAAUCGGAAAGGCAACAGCAAAGUACUUCUUC UACAGCAACAUCAUGAACUUCUUCAAGACAGAAAUCACACUGGCAAACGGA GAAAUCAGAAGAGACCGCUGAUCGAAACAAACGGAGAAACAGGAGAAAUC GUCUGGGACAAGGGAAGAGACUUCGCAACAGUCAGAAAGGUCCUGAGCAUG CCGCAGGUCAACAUCGUCAAGAAGACAGAAGUCCAGACAGGAGGAUUCAGC AAGGAAAGCAUCCUGCCGAAGAGAAACAGCGACAAGCUGAUCGCAAGAAAG AAGGACUGGGACCCGAAGAAGUACGGAGGAUUCGACAGCCCGACAGUCGCA UACAGCGUCCUGGUCGUCGCAAAGGUCGAAAAGGGAAAGAGCAAGAAGCUG AAGAGCGUCAAGGAACUGCUGGGAAUCACAAUCAUGGAAAGAAGCAGCUUC GAAAAGAACCCGAUCGACUUCCUGGAAGCAAAGGGAUACAAGGAAGUCAAG AAGGACCUGAUCAUCAAGCUGCCGAAGUACAGCCUGUUCGAACUGGAAAAC GGAAGAAAGAGAAUGCUGGCAAGCGCAGGAGAACUGCAGAAGGGAAACGAA CUGGCACUGCCGAGCAAGUACGUCAACUUCCUGUACCUGGCAAGCCACUAC GAAAAGCUGAAGGGAAGCCCGGAAGACAACGAACAGAAGCAGCUGUUCGUC GAACAGCACAAGCACUACCUGGACGAAAUCAUCGAACAGAUCAGCGAAUUC AGCAAGAGAGUCAUCCUGGCAGACGCAAACCUGGACAAGGUCCUGAGCGCA UACAACAAGCACAGAGACAAGCCGAUCAGAGAACAGGCAGAAAACAUCAUC CACCUGUUCACACUGACAAACCUGGGAGCACCGGCAGCAUUCAAGUACUUC GACACAACAAUCGACAGAAAGAGAUACACAAGCACAAAGGAAGUCCUGGAC GCAACACUGAUCCACCAGAGCAUCACAGGACUGUACGAAACAAGAAUCGAC CUGAGCCAGCUGGGAGGAGACGGAGGAGGAAGC | |

-continued

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
| --- | --- | --- |
| Amino acid sequence of Cas9 with two nuclear localization signals (2xNLS) as the C terminal amino acids | MDKKYSIGLDIGTNSVGWAVITDEYKVPSKKFKVLGNTDRHSIKKNLIGAL LFDSGETAEATRLKRTARRRYTRRKNRICYLQEIFSNEMAKVDDSFFHRLE ESFLVEEDKKHERHPIFGNIVDEVAYHEKYPTIYHLRKKLVDSTDKADLRL IYLALAHMIKFRGHFLIEGDLNPDNSDVDKLFIQLVQTYNQLFEENPINAS GVDAKAILSARLSKSRRLENLIAQLPGEKKNGLFGNLIALSLGLTPNFKSN FDLAEDAKLQLSKDTYDDDLDNLLAQIGDQYADLFLAAKNLSDAILLSDIL RVNTEITKAPLSASMIKRYDEHHQDLTLLKALVRQQLPEKYKEIFFDQSKN GYAGYIDGGASQEEFYKFIKPILEKMDGTEELLVKLNREDLLRKQRTFDNG SIPHQIHLGELHAILRRQEDFYPFLKDNREKIEKILTFRIPYYVGPLARGN SRFAWMTRKSEETITPWNFEEVVDKGASAQSFIERMTNFDKNLPNEKVLPK HSLLYEYFTVYNELTKVKYVTEGMRKPAFLSGEQKKAIVDLLFKTNRKVTV KQLKEDYFKKIECFDSVEISGVEDRFNASLGTYHDLLKIIKDKDFLDNEEN EDILEDIVLTLTLFEDREMIEERLKTYAHLFDDKVMKQLKRRRYTGWGRLS RKLINGIRDKQSGKTILDFLKSDGFANRNFMQLIHDDSLTFKEDIQKAQVS GQGDSLHEHIANLAGSPAIKKGILQTVKVVDELVKVMGRHKPENIVIEMAR ENQTTQKGQKNSRERMKRIEEGIKELGSQILKEHPVENTQLQNEKLYLYYL QNGRDMYVDQELDINRLSDYDVDHIVPQSFLKDDSIDNKVLTRSDKNRGKS DNVPSEEVVKKMKNYWRQLLNAKLITQRKFDNLTKAERGGLSELDKAGFIK RQLVETRQITKHVAQILDSRMNTKYDENDKLIREVKVITLKSKLVSDFRKD FQFYKVREINNYHHAHDAYLNAVVGTALIKKYPKLESEFVYGDYKVYDVRK MIAKSEQEIGKATAKYFFYSNIMNFFKTEITLANGEIRKRPLIETNGETGE IVWDKGRDFATVRKVLSMPQVNIVKKTEVQTGGFSKESILPKRNSDKLIAR KKDWDPKKYGGFDSPTVAYSVLVVAKVEKGKSKKLKSVKELLGITIMERSS FEKNPIDFLEAKGYKEVKKDLIIKLPKYSLFELENGRKRMLASAGELQKGN ELALPSKYVNFLYLASHYEKLKGSPEDNEQKQLFVEQHKHYLDEIIEQISE FSKRVILADANLDKVLSAYNKHRDKPIREQAENIIHLFTLTNLGAPAAFKY FDTTIDRKRYTSTKEVLDATLIHQSITGLYETRIDLSQLGGDGSGSPKKKR KVDGSPKKKRKVDSG | 222 |
| Cas9 mRNA ORF encoding SEQ ID NO: 222 using minimal uridine codons, with start and stop codons | AUGGACAAGAAGUACAGCAUCGGACUGGACAUCGGAACAAACAGCGUCGGA UGGGCAGUCAUCACAGACGAAUACAAGGUCCCGAGCAAGAAGUUCAAGGUC CUGGGAAACACAGACAGACACAGCAUCAAGAAGAACCUGAUCGGAGCACUG CUGUUCGACAGCGGAGAAACAGCAGAAGCAACAAGACUGAAGAGAACAGCA AGAAGAAGAUACAAGAAGAAAGAAACAGAAUCUGCUACCUGCAGGAAAUC UUCAGCAACGAAAUGGCAAAGGUCGACGACAGCUUCUUCCACAGACUGGAA GAAAGCUUCCUGGUCGAAGAAGACAAGAAGCACGAAAGACACCCGAUCUUC GGAAACAUCGUCGACGAAGUCGCAUACCACGAAAAGUACCCGACAAUCUAC CACCUGAGAAAGAAGCUGGUCGACAGCACAGACAAGGCAGACCUGAGACUG AUCUACCUGGCACUGGCACACAUGAUCAAGUUCAGAGGACACUUCCUGAUC GAAGGAGACCUGAACCCGGACAACAGCGACGUCGACAAGCUGUUCAUCCAG CUGGUCCAGACAUACAACCAGCUGUUCGAAGAAAACCCGAUCAACGCAAGC GGAGUCGACGCAAAGGCAAUCCUGAGCGCAAGACUGAGCAAGAGCAGAAGA CUGGAAAACCUGAUCGCACAGCUGCCGGGAGAAAAGAAGAACGGACUGUUC GGAAACCUGAUCGCACUGAGCCUGGGACUGACACCGAACUUCAAGAGCAAC UUCGACCUGGCAGAAGACGCAAAGCUGCAGCUGAGCAAGGACACAUACGAC GACGACCUGGACAACCUGCUGGCACAGAUCGGAGACCAGUACGCAGACCUG UUCCUGGCAGCAAAGAACCUGAGCGACGCAAUCCUGCUGAGCGACAUCCUG AGAGUCAACACAGAAAUCACAAAGGCACCGCUGAGCGCAAGCAUGAUCAAG AGAUACGACGAACACCACCAGGACCUGACACUGCUGAAGGCACUGGUCAGA CAGCAGCUGCCGGAAAAGUACAAGGAAAUCUUCUUCGACCAGAGCAAGAAC GGAUACGCAGGAUACAUCGACGGAGGAGCAAGCCAGGAAGAAUUCUACAAG UUCAUCAAGCCGAUCCUGGAAAAGAUGGACGGAACAGAAGAACUGCUGGUC AAGCUGAACAGAGAAGACCUGCUGAGAAAGCAGAGAACAUUCGACAACGGA AGCAUCCCGCACCAGAUCCACCUGGGAGAACUGCACGCAAUCCUGAGAAGA CAGGAAGACUUCUACCCGUUCCUGAAGGACAACAGAGAAAAGAUCGAAAAG AUCCUGACAUUCAGAAUCCCGUACUACGUCGGACCGCUGGCAAGAGGAAAC AGCAGAUUCGCAUGGAUGACAAGAAAGAGCGAAGAAACAAUCACACCGUGG AACUUCGAAGAAGUCGUCGACAAGGGAGCAAGCGCACAGAGCUUCAUCGAA AGAAUGACAAACUUCGACAAGAACCUGCCGAACGAAAAGGUCCUGCCGAAG CACAGCCUGCUGUACGAAUACUUCACAGUCUACAACGAACUGACAAAGGUC AAGUACGUCACAGAAGGAAUGAGAAAGCCGGCAUUCCUGAGCGGAGAACAG AAGAAGGCAAUCGUCGACCUGCUGUUCAAGACAAACAGAAAGGUCACAGUC AAGCAGCUGAAGGAAGACUACUUCAAGAAGAUCGAAUGCUUCGACAGCGUC GAAAUCAGCGGAGUCGAAGACAGAUUCAACGCAAGCCUGGGAACAUACCAC GACCUGCUGAAGAUCAUCAAGGACAAGGACUUCCUGGACAACGAAGAAAAC GAAGACAUCCUGGAAGACAUCGUCCUGACACUGACACUGUUCGAAGACAGA GAAAUGAUCGAAGAAAGACUGAAGACAUACGCACACCUGUUCGACGACAAG GUCAUGAAGCAGCUGAAGAGAAGAAGAUACACAGGAUGGGGAAGACUGAGC AGAAAGCUGAUCAACGGAAUCAGAGACAAGCAGAGCGGAAAGACAAUCCUG GACUUCCUGAAGAGCGACGGAUUCGCAAACAGAAACUUCAUGCAGCUGAUC | 223 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CACGACGACAGCCUGACAUUCAAGGAAGACAUCCAGAAGGCACAGGUCAGC GGACAGGGAGACAGCCUGCACGAACACAUCGCAAACCUGGCAGGAAGCCCG GCAAUCAAGAAGGGAAUCCUGCAGACAGUCAAGGUCGUCGACGAACUGGUC AAGGUCAUGGGAAGACACAAGCCGGAAAACAUCGUCAUCGAAAUGGCAAGA GAAAACCAGACAACACAGAAGGGACAGAAGAACAGCAGAGAAAGAAUGAAG AGAAUCGAAGAAGGAAUCAAGGAACUGGGAAGCCAGAUCCUGAAGGAACAC CCGGUCGAAAACACACAGCUGCAGAACGAAAAGCUGUACCUGUACUACCUG CAGAACGGAAGAGACAUGUACGUCGACCAGGAACUGGACAUCAACAGACUG AGCGACUACGACGUCGACCACAUCGUCCCGCAGAGCUUCCUGAAGGACGAC AGCAUCGACAACAAGGUCCUGACAAGAAGCGACAAGAACAGAGGGAAAGAGC GACAACGUCCCGAGCGAAGAAGUCGUCAAGAAGAUGAAGAACUACUGGAGA CAGCUGCUGAACGCAAAGCUGAUCACACAGAGAAAGUUCGACAACCUGACA AAGGCAGAGAGAGGAGGACUGAGCGAACUGGACAAGGCAGGAUUCAUCAAG AGACAGCUGGUCGAAACAAGACAGAUCACAAAGCACGUCGCACAGAUCCUG GACAGCAGAAUGAACACAAAGUACGACGAAAACGACAAGCUGAUCAGAGAA GUCAAGGUCAUCACACUGAAGAGCAAGCUGGUCAGCGACUUCAGAAAGGAC UUCCAGUUCUACAAGGUCAGAGAAAUCAACAACUACCACCACGCACACGAC GCAUACCUGAACGCAGUCGUCGGAACAGCACUGAUCAAGAAGUACCCGAAG CUGGAAAGCGAAUUCGUCUACGGAGACUACAAGGUCUACGACGUCAGAAAG AUGAUCGCAAAGAGCGAACAGGAAAUCGGAAAGGCAACAGCAAAGUACUUC UUCUACAGCAACAUCAUGAACUUCUUCAAGACAGAAAUCACACUGGCAAAC GGAGAAAUCAGAAAGAGACCGCUGAUCGAAACAAACGGAGAAACAGGAGAA AUCGUCUGGGACAAGGGAAGAGACUUCGCAACAGUCAGAAAGGUCCUGAGC AUGCCGCAGGUCAACAUCGUCAAGAAGACAGAAGUCCAGACAGGAGGAUUC AGCAAGGAAAGCAUCCUGCCGAAGAGAAACAGCGACAAGCUGAUCGCAAGA AAGAAGGACUGGGACCCGAAGAAGUACGGAGGAUUCGACAGCCCGACAGUC GCAUACAGCGUCCUGGUCGUCGCAAAGGUCGAAAAGGGAAAGAGCAAGAAG CUGAAGAGCGUCAAGGAACUGCUGGGAAUCACAAUCAUGGAAAGAAGCAGC UUCGAAAAGAACCCGAUCGACUUCCUGGAAGCAAAGGGAUACAAGGAAGUC AAGAAGGACCUGAUCAUCAAGCUGCCGAAGUACAGCCUGUUCGAACUGGAA AACGGAAGAAAGAGAAUGCUGGCAAGCGCAGGAGAACUGCAGAAGGGAAAC GAACUGGCACUGCCGAGCAAGUACGUCAACUUCCUGUACCUGGCAAGCCAC UACGAAAAGCUGAAGGGAAGCCCGGAAGACAACGAACAGAAGCAGCUGUUC GUCGAACAGCACAAGCACUACCUGGACGAAAUCAUCGAACAGAUCAGCGAA UUCAGCAAGAGAGUCAUCCUGGCAGACGCAAACCUGGACAAGGUCCUGAGC GCAUACAACAAGCACAGAGACAAGCCGAUCAGAGAACAGGCAGAAAACAUC AUCCACCUGUUCACACUGACAAACCUGGGAGCACCGGCAGCAUUCAAGUAC UUCGACACAACAAUCGACAGAAAGAGAUACACAAGCACAAAGGAAGUCCUG GACGCAACACUGAUCCACCAGAGCAUCACAGGACUGUACGAAACAAGAAUC GACCUGAGCCAGCUGGGAGGAGACGGAGGAGGAAGCCCGAAGAAGAAGAGA AAGGUCCCGAAGAAGAAGAGAAAGGUC GGAAGCGGAAGCCCGAAGAAGAAGAGAAAGGUCGACGGAAGCCCGAAGAAG AAGAGAAAGGUCGACAGCGGAUAG | |
| Cas9 coding sequence encoding SEQ ID NO: 222 using minimal uridine codons (no start or stop codons; suitable for inclusion in fusion protein coding sequence) | GACAAGAAGUACAGCAUCGGACUGGACAUCGGAACAAACAGCGUCGGAUGG GCAGUCAUCACAGACGAAUACAAGGUCCCGAGCAAGAAGUUCAAGGUCCUG GGAAACACAGACAGACAGCAUCAAGAAGAACCUGAUCGGAGCACUGCUG UUCGACAGCGGAGAAACAGCCAGAAGCAACAAGACUGAAGAGAACAGCAAGA AGAAGAUACACAAGAAGAAAGAACAGAAUCUGCUACCUGCAGGAAAUCUUC AGCAACGAAAUGGCAAAGGUCGACGACAGCUUCUUCCACAGACUGGAAGAA AGCUUCCUGGUCGAAGAAGACAAGAAGCACGAAAGACACCCGAUCUUCGGA AACAUCGUCGACGAAGUCGCAUACCACGAAAAGUACCCGACAAUCUACCAC CUGAGAAAGAAGCUGGUCGACAGCACAGACAAGGCAGACCUGAGACUGAUC UACCUGGCACUGGCACACAUGAUCAAGUUCAGGGACACUUCCUGAUCGAA GGAGACCUGAACCCGGACAACAGCGACGUCGACAAGCUGUUCAUCCAGCUG GUCCAGACAUACAACCAGCUGUUCGAAGAAAACCCGAUCAACGCAAGCGGA GUCGACGCAAAGGCAAUCCUGAGCGCAAGACUGAGCAAGAGCAGAAGACUG GAAAACCUGAUCGCACAGCUGCCGGGAGAAAAGAAGAACGGACUGUUCGGA AACCUGAUCGCACUGAGCCUGGGACUGACACCGAACUUCAAGAGCAACUUC GACCUGGCAGAAGACGCAAAGCUGCAGCUGAGCAAGGACACAUACGACGAC GACCUGGACAACCUGCUGGCACAGAUCGGAGACCAGUACGCAGACCUGUUC CUGGCAGCAAAGAACCUGAGCGACGCAAUCCUGCUGAGCGACAUCCUGAGA GUCAACACAGAAAUCACAAAGGCACCGCUGAGCGCAAGCAUGAUCAAGAGA UACGACGAACACCACCAGGACCUGACACUGCUGAAGGCACUGGUCAGACAG CAGCUGCCGGAAAAGUACAAGGAAAUCUUCUUCGACCAGAGCAAGAACGGA UACGCAGGAUACAUCGACGGAGGAGCAAGCCAGGAAGAAUUCUACAAGUUC AUCAAGCCGAUCCUGGAAAAGAUGGACGGAACAGAAGAACUGCUGGUCAAG CUGAACAGAGAAGACCUGCUGAGAAAGCAGAGAACAUUCGACAACGGAAGC AUCCCGCACCAGAUCCACCUGGGAGAACUGCACGCAAUCCUGAGAAGACAG GAAGACUUCUACCCGUUCCUGAAGGACAACAGAGAAAAGAUCGAAAAGAUC | 224 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | CUGACAUUCAGAAUCCCGUACUACGUCGGACCGCUGGCAAGAGGAAACAGC<br>AGAUUCGCAUGGAUGACAAGAAAGAGCGAAGAAACAAUCACACCGUGGAAC<br>UUCGAAGAAGUCGUCGACAAGGGAGCAAGCGCACAGAGCUUCAUCGAAAGA<br>AUGACAAACUUCGACAAGAACCUGCCGAACGAAAAGGUCCUGCCGAAGCAC<br>AGCCUGCUGUACGAAUACUUCACAGUCUACAACGAACUGACAAAGGUCAAG<br>UACGUCACAGAAGGAAUGAGAAAGCCGGCAUUCCUGAGCGGAGAACAGAAG<br>AAGGCAAUCGUCGACCUGCUGUUCAAGACAAACAGAAAGGUCACAGUCAAG<br>CAGCUGAAGGAAGACUACUUCAAGAAGAUCGAAUGCUUCGACAGCGUCGAA<br>AUCAGCGGAGUCGAAGACAGAUUCAACGCAAGCCUGGGAACAUACCACGAC<br>CUGCUGAAGAUCAUCAAGGACAAGGACUUCCUGGACAACGAAGAAAACGAA<br>GACAUCCUGGAAGACAUCGUCCUGACACUGACACUGUUCGAAGACAGAGAA<br>AUGAUCGAAGAAGACUGAAGACAUACGCACACCUGUUCGACGACAAGGUC<br>AUGAAGCAGCUGAAGAGAAGAAGAUCACAGGAUGGGGAAGACUGAGCAGA<br>AAGCUGAUCAACGGAAUCAGAGACAAGCAGAGCGGAAAGACAAUCCUGGAC<br>UUCCUGAAGAGCGACGGAUUCGCAAACAGAAACUUCAUGCAGCUGAUCCAC<br>GACGACAGCCUGACAUUCAAGGAAGACAUCCAGAAGGCACAGGUCAGCGGA<br>CAGGGAGACAGCCUGCACGAACACAUCGCAAACCUGGCAGGAAGCCCGGCA<br>AUCAAGAAGGGAAUCCUGCAGACAGUCAAGGUCGUCGACGAACUGGUCAAG<br>GUCAUGGGAAGACACAAGCCGGAAAACAUCGUCAUCGAAAUGGCAAGAGAA<br>AACCAGACAACACAGAAGGGACAGAAGAACAGCAGAGAAAGAAUGAAGAGA<br>AUCAAGAAGGAAUCAAGGAACUGGGAAGCCAGAUCCUGAAGGAACACCCG<br>GUCGAAAACACACAGCUGCAGAACGAAAAGCUGUACCUGUACUACCUGCAG<br>AACGGAAGAGACAUGUACGUCGACCAGGAACUGGACAUCAACAGACUGAGC<br>GACUACGACGUCGACCACAUCGUCCCGCAGAGCUUCCUGAAGGACGACAGC<br>AUCGACAACAAGGUCCUGACAAGAAGCGACAAGAACAGAGGAAAGAGCGAC<br>AACGUCCCGAGCGAAGAAGUCGUCAAGAAGAUGAAGAACUACUGGAGACAG<br>CUGCUGAACGCAAAGCUGAUCACACAGAGAAAGUUCGACAACCUGACAAAG<br>GCAGAGAGGAGGAGGACUGAGCGAACUGGACAAGGCAGGAUUCAUCAAGAGA<br>CAGCUGGUCGAAACAAGACAGAUCACAAAGCACGUCGCACAGAUCCUGGAC<br>AGCAGAAUGAACACAAAGUACGACGAAAACGACAAGCUGAUCAGAGAAGUC<br>AAGGUCAUCACACUGAAGAGCAAGCUGGUCAGCGACUUCAGAAAGGACUUC<br>CAGUUCUACAAGGUCAGAGAAAUCAACAACUACCACCACGCACACGACGCA<br>UACCUGAACGCAGUCGUCGGAACAGCACUGAUCAAGAAGUACCCGAAGCUG<br>GAAAGCGAAUUCGUCUACGGAGACUACAAGGUCUACGACGUCAGAAAGAUG<br>AUCGCAAAGAGCGAACAGGAAAUCGGAAAGGCAACAGCAAAGUACUUCUUC<br>UACAGCAACAUCAUGAACUUCUUCAAGACAGAAAUCACACUGGCAAACGGA<br>GAAAUCAGAAAGAGACCGCUGAUCGAAACAAACGGAGAAACAGGAGAAAUC<br>GUCUGGGACAAGGGAAGAGACUUCGCAACAGUCAGAAAGGUCCUGAGCAUG<br>CCGCAGGUCAACAUCGUCAAGAAGACAGAAGUCCAGACAGGAGGAUUCAGC<br>AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAAGAGAAUGUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCUGUUCACACUGACAAACCUGGGAGCACCGGCAGCAUUCAAGUACUUC<br>GACACAACAAUCGACAGAAAGAGAUACACAAGCACAAAGGAAGUCCUGGAC<br>GCAACACUGAUCCACCAGAGCAUCACAGGACUGUACGAAACAAGAAUCGAC<br>CUGAGCCAGCUGGGAGGAGACGGAGGAGGAAGCCCGAAGAAGAAGAGAAAG<br>GUCCCGAAGAAGAAGAGAAAGGUC<br>GGAAGCGGAAGCCCGAAGAAGAAGAGAAAGGUCGACGGAAGCCCGAAGAAG<br>AAGAGAAAGGUCGACAGCGGA | |
| Amino acid sequence of Cas9 nickase with two nuclear localization signals as the C-terminal amino acids | MDKKYSIGLAIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV | 225 |

-continued

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | KQLKEDYFKKIECFDSVEISGVEDRFNASLGTYHDLLKIIKDKDFLDNEEN EDILEDIVLTLTLFEDREMIEERLKTYAHLFDDKVMKQLKRRRYTGWGRLS RKLINGIRDKQSGKTILDFLKSDGFANRNFMQLIHDDSLTFKEDIQKAQVS GQGDSLHEHIANLAGSPAIKKGILQTVKVVDELVKVMGRHKPENIVIEMAR ENQTTQKGQKNSRERMKRIEEGIKELGSQILKEHPVENTQLQNEKLYLYYL QNGRDMYVDQELDINRLSDYDVDHIVPQSFLKDDSIDNKVLTRSDKNRGKS DNVPSEEVVKKMKNYWRQLLNAKLITQRKFDNLTKAERGGLSELDKAGFIK RQLVETRQITKHVAQILDSRMNTKYDENDKLIREVKVITLKSKLVSDFRKD FQFYKVREINNYHHAHDAYLNAVVGTALIKKYPKLESEFVYGDYKVYDVRK MIAKSEQEIGKATAKYFFYSNIMNFFKTEITLANGEIRKRPLIETNGETGE IVWDKGRDFATVRKVLSMPQVNIVKKTEVQTGGFSKESILPKRNSDKLIAR KKDWDPKKYGGFDSPTVAYSVLVVAKVEKGKSKKLKSVKELLGITIMERSS FEKNPIDFLEAKGYKEVKKDLIIKLPKYSLFELENGRKRMLASAGELQKGN ELALPSKYVNFLYLASHYEKLKGSPEDNEQKQLFVEQHKHYLDEIIEQISE FSKRVILADANLDKVLSAYNKHRDKPIREQAENIIHLFTLTNLGAPAAFKY FDTTIDRKRYTSTKEVLDATLIHQSITGLYETRIDLSQLGGDSGSPKKKR KVDGSPKKKRKVDSG | |
| Cas9 nickase mRNA ORF encoding SEQ ID NO: 25 using minimal uridine codons as listed in Table 3, with start and stop codons | AUGGACAAGAAGUACAGCAUCGGACUGGCAAUCGGAACAAACAGCGUCGGA UGGGCAGUCAUCACAGACGAAUACAAGGUCCCGAGCAAGAAGUUCAAGGUC CUGGGAAACACAGACAGACACAGCAUCAAGAAGAACCUGGGAGCACUG CUGUUCGACAGCGGAGAAACAGCAGAAGCAACAAGACUGAAGAGAACAGCA AGAAGAAGAUACACAAGAAGAAAGAACAGAAUCUGCUACCUGCAGGAAAUC UUCAGCAACGAAAUGGCAAAGGUCGACGACAGCUUCUUCCACAGACUGGAA GAAAGCUUCCUGGUCGAAGAAGACAAGAAGCACGAAAGACACCCGAUCUUC GGAAACAUCGUCGACGAAGUCGCAUACCACGAAAAGUACCCGACAAUCUAC CACCUGAGAAAGAAGCUGGUCGACAGCACAGACAAGGCAGACCUGAGACUG AUCUACCUGGCACUGGCACACAUGAUCAAGUUCAGAGGACACUUCCUGAUC GAAGGAGACCUGAACCCGGACAACAGCGACGUCGACAAGCUGUUCAUCCAG CUGGUCCAGACAUACAACCAGCUGUUCGAAGAAAACCCGAUCAACGCAAGC GGAGUCGACGCAAAGGCAAUCCUGAGCGCAAGACUGAGCAAGAGCAGAAGA CUGGAAAACCUGAUCGCACAGCUGCCGGGAGAAAAGAAGAACGGACUGUUC GGAAACCUGAUCGCACUGAGCCUGGGACUGACACCGAACUUCAAGAGCAAC UUCGACCUGGCAGAAGACGCAAAGCUGCAGCUGAGCAAGGACACAUACGAC GACGACCUGGACAACCUGCUGGCACAGAUCGGAGACCAGUACGCAGACCUG UUCCUGGCAGCAAAGAACCUGAGCGACGCAAUCCUGCUGAGCGACAUCCUG AGAGUCAACACAGAAAUCACAAAGGCACCGCUGAGCGCAAGCAUGAUCAAG AGAUACGACGAACACCACCAGGACCUGACACUGCUGAAGGCACUGGUCAGA CAGCAGCUGCCGGAAAAGUACAAGGAAAUCUUCUUCGACCAGAGCAAGAAC GGAUACGCAGGAUACAUCGACGGAGGAGCAAGCCAGGAAGAAUUCUACAAG UUCAUCAAGCCGAUCCUGGAAAAGAUGGACGGAACAGAAGAACUGCUGGUC AAGCUGAACAGAGAAGACCUGCUGAGAAAGCAGAGAACAUUCGACAACGGA AGCAUCCCGCACCAGAUCCACCUGGGAGAACUGCACGCAAUCCUGAGAAGA CAGGAAGACUUCUACCCGUUCCUGAAGGACAACAGAGAAAAGAUCGAAAAG AUCCUGACAUUCAGAAUCCCGUACUACGUCGGACCGCUGGCAAGAGGAAAC AGCAGAUUCGCAUGGAUGACAAGAAAGAGCGAAGAAACAAUCACACCGUGG AACUUCGAAGAAGUCGUCGACAAGGGAGCAAGCGCACAGAGCUUCAUCGAA AGAAUGACAAACUUCGACAAGAACCUGCCGAACGAAAAGGUCCUGCCGAAG CACAGCCUGCUGUACGAAUACUUCACAGUCUACAACGAACUGACAAAGGUC AAGUACGUCACAGAAGGAAUGAGAAAGCCGGCAUUCCUGAGCGGAGAACAG AAGAAGGCAAUCGUCGACCUGCUGUUCAAGACAAACAGAAAGGUCACAGUC AAGCAGCUGAAGGAAGACUACUUCAAGAAGAUCGAAUGCUUCGACAGCGUC GAAAUCAGCGGAGUCGAAGACAGAUUCAACGCAAGCCUGGGAACAUACCAC GACCUGCUGAAGAUCAUCAAGGACAAGGACUUCCUGGACAACGAAGAAAAC GAAGACAUCCUGGAAGACAUCGUCCUGACACUGACACUGUUCGAAGACAGA GAAAUGAUCGAAGAAAGACUGAAGACAUACGCACACCUGUUCGACGACAAG GUCAUGAAGCAGCUGAAGAGAAGAAGAUACACAGGAUGGGGAAGACUGAGC AGAAAGCUGAUCAACGGAAUCAGAGACAAGCAGAGCGGAAAGACAAUCCUG GACUUCCUGAAGAGCGACGGAUUCGCAAACAGAAACUUCAUGCAGCUGAUC CACGACGACAGCCUGACAUUCAAGGAAGACAUCCAGAAGGCACAGGUCAGC GGACAGGGAGACAGCCUGCACGAACACAUCGCAAACCUGGCAGGAAGCCCG GCAAUCAAGAAGGGAAUCCUGCAGACAGUCAAGGUCGUCGACGAACUGGUC AAGGUCAUGGGAAGACACAAGCCGGAAAACAUCGUCAUCGAAAUGGCAAGA GAAAACCAGACAACACAGAAGGGACAGAAGAACAGCAGAGAAAGAAUGAAG AGAAUCGAAGAAGGAAUCAAGGAACUGGGAAGCCAGAUCCUGAAGGAACAC CCGGUCGAAAACACACAGCUGCAGAACGAAAAGCUGUACCUGUACUACCUG CAGAACGGAAGAGACAUGUACGUCGACCAGGAACUGGACAUCAACAGACUG AGCGACUACGACGUCGACCACAUCGUCCCGCAGAGCUUCCUGAAGGACGAC AGCAUCGACAACAAGGUCCUGACAAGAAGCGACAAGAACAGAGGAAAGAGC GACAACGUCCCGAGCGAAGAAGUCGUCAAGAAGAUGAAGAACUACUGGAGA | 226 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CAGCUGCUGAACGCAAAGCUGAUCACACAGAGAAAGUUCGACAACCUGACA<br>AAGGCAGAGAGGAGGACUGAGCGAACUGGACAAGGCAGGAUUCAUCAAG<br>AGACAGCUGGUCGAAACAAGACAGAUCACAAAGCACGUCGCACAGAUCCUG<br>GACAGCAGAAUGAACACAAAGUACGACGAAAACGACAAGCUGAUCAGAGAA<br>GUCAAGGUCAUCACACUGAAGAGCAAGCUGGUCAGCGACUUCAGAAAGGAC<br>UUCCAGUUCUACAAGGUCAGAGAAAUCAACAACUACCACCACGCACACGAC<br>GCAUACCUGAACGCAGUCGUCGGAACAGCACUGAUCAAGAAGUACCCGAAG<br>CUGGAAAGCGAAUUCGUCUACGGAGACUACAAGGUCUACGACGUCAGAAAG<br>AUGAUCGCAAAGAGCGAACAGGAAAUCGGAAAGGCAACAGCAAAGUACUUC<br>UUCUACAGCAACAUCAUGAACUUCUUCAAGACAGAAAUCACACUGGCAAAC<br>GGAGAAAUCAGAAAGAGACCGCUGAUCGAAACAAACGGAGAAACAGGAGAA<br>AUCGUCUGGGACAAGGGAAGAGACUUCGCAACAGUCAGAAAGGUCCUGAGC<br>AUGCCGCAGGUCAACAUCGUCAAGAAGACAGAAGUCCAGACAGGAGGAUUC<br>AGCAAGGAAAGCAUCCUGCCGAAGAGAAACAGCGACAAGCUGAUCGCAAGA<br>AAGAAGGACUGGGACCCGAAGAAGUACGGAGGAUUCGACAGCCCGACAGUC<br>GCAUACAGCGUCCUGGUCGUCGCAAAGGUCGAAAAGGGAAAGAGCAAGAAG<br>CUGAAGAGCGUCAAGGAACUGCUGGGAAUCACAAUCAUGGAAAGAAGCAGC<br>UUCGAAAAGAACCCGAUCGACUUCCUGGAAGCAAAGGGAUACAAGGAAGUC<br>AAGAAGGACCUGAUCAUCAAGCUGCCGAAGUACAGCCUGUUCGAACUGGAA<br>AACGGAAGAAAGAGAAUGCUGGCAAGCGCAGGAGAACUGCAGAAGGGAAAC<br>GAACUGGCACUGCCGAGCAAGUACGUCAACUUCCUGUACCUGGCAAGCCAC<br>UACGAAAAGCUGAAGGGAAGCCCGAAGACAACGAACAGAAGCAGCUGUUC<br>GUCGAACAGCACAAGCACUACCUGGACGAAAUCAUCGAACAGAUCAGCGAA<br>UUCAGCAAGAGAGUCAUCCUGGCAGACGCAAACCUGGACAAGGUCCUGAGC<br>GCAUACAACAAGCACAGAGACAAGCCGAUCAGAGAACAGGCAGAAAACAUC<br>AUCCACCUGUUCACACUGACAAACCUGGGAGCACCGGCAGCAUUCAAGUAC<br>UUCGACACAACAAUCGACAGAAAGAGAUACACAAGCACAAAGGAAGUCCUG<br>GACGCAACACUGAUCCACCAGAGCAUCACAGGACUGUACGAAACAAGAAUC<br>GACCUGAGCCAGCUGGGAGGAGACGAAGCGGAAGCCCGAAGAAGAAGAGA<br>AAGGUCGACGGAAGCCCGAAGAAGAAGAGAAAGGUCGACAGCGGAUAG | |
| Cas9 nickase coding sequence encoding SEQ ID NO: 25 using minimal uridine codons (no start or stop codons; suitable for inclusion in fusion protein coding sequence) | GACAAGAAGUACAGCAUCGGACUGGCAAUCGGAACAAACAGCGUCGGAUGG<br>GCAGUCAUCACAGACGAAUACAAGGUCCCGAGCAAGAAGUUCAAGGUCCUG<br>GGAAACACAGACAGACAGCAGCAUCAAGAAGAACCUGAUCGGAGCACUGCUG<br>UUCGACAGCGGAGAAACAGCAGAAGCAACAAGACUGAAGAGAACAGCAAGA<br>AGAAGAUACACAAGAAGAAAGAACAGAAUCUGCUACCUGCAGGAAAUCUUC<br>AGCAACGAAAUGGCAAAGGUCGACGACAGCUUCUUCCACAGACUGGAAGAA<br>AGCUUCCUGGUCGAAGAAGACAAGAAGCACGAAAGACACCCGACUUCGGA<br>AACAUCGUCGACGAAGUCGCAUACCACGAAAAGUACCCGACAAUCUACCAC<br>CUGAGAAAGAAGCUGGUCGACAGCACAGACAAGGCAGACCUGAGACUGAUC<br>UACCUGGCACUGGCACACAUGAUCAAGUUCAGAGGACACUUCCUGAUCGAA<br>GGAGACCUGAACCCGGACAACAGCGACGUCGACAAGCUGUUCAUCCAGCUG<br>GUCCAGACAUACAACCAGCUGUUCGAAGAAAACCCGAUCAACGCAAGCGGA<br>GUCGACGCAAAGGCAAUCCUGAGCGCAAGACUGAGCAAGAGCAGAAGACUG<br>GAAAACCUGAUCGCACAGCUGCCGGGAGAAAAGAAGAACGGACUGUUCGGA<br>AACCUGAUCGCACUGAGCCUGGGACUGACACCGAACUUCAAGAGCAACUUC<br>GACCUGGCAGAAGACGCAAAGCUGCAGCUGAGCAAGGACACAUACGACGAC<br>GACCUGGACAACCUGCUGGCACAGAUCGGAGACCAGUACGCAGACCUGUUC<br>CUGGCAGCAAAGAACCUGAGCGACGCAAUCCUGCUGAGCGACAUCCUGAGA<br>GUCAACACAGAAAUCACAAAGGCACCGCUGAGCGCAAGCAUGAUCAAGAGA<br>UACGACGAACACCACCAGGACCUGACACUGCUGAAGGCACUGGUCAGACAG<br>CAGCUGCCGGAAAAGUACAAGGAAAUCUUCUUCGACCAGAGCAAGAACGGA<br>UACGCAGGAUACAUCGACGGAGGAGCAAGCCAGGAAGAAUUCUACAAGUUC<br>AUCAAGCCGAUCCUGGAAAAGAUGGACGGAACAGAAGAACUGCUGGUCAAG<br>CUGAACAGAGAAGACCUGCUGAGAAAGCAGAGAACAUUCGACAACGGAAGC<br>AUCCCGCACCAGAUCCACCUGGGAGAACUGCACGCAAUCCUGAGAAGACAG<br>GAAGACUUCUACCCGUUCCUGAAGGACAACAGAGAAAAGAUCGAAAAGAUC<br>CUGACAUUCAGAAUCCCGUACUACGUCGGACCGCUGGCAAGAGGAAACAGC<br>AGAUUCGCAUGGAUGACAAGAAAGAGCGAAGAAACAAUCACACCGUGGAAC<br>UUCGAAGAAGUCGUCGACAAGGGAGCAAGCGCACAGAGCUUCAUCGAAAGA<br>AUGACAAACUUCGACAAGAACCUGCCGAACGAAAAGGUCCUGCCGAAGCAC<br>AGCCUGCUGUACGAAUACUUCACAGUCUACAACGAACUGACAAAGGUCAAG<br>UACGUCACAGAAGGAAUGAGAAAGCCGGCAUUCCUGAGCGGAGAACAGAAG<br>AAGGCAAUCGUCGACCUGCUGUUCAAGACAAACAGAAAGGUCACAGUCAAG<br>CAGCUGAAGGAAGACUACUUCAAGAAGAUCGAAUGCUUCGACAGCGUCGAA<br>AUCAGCGGAGUCGAAGACAGAUUCAACGCAAGCCUGGGAACAUACCACGAC<br>CUGCUGAAGAUCAUCAAGGACAAGGACUUCCUGGACAACGAAGAAAACGAA<br>GACAUCCUGGAAGACAUCGUCCUGACACUGACACUGUUCGAAGACAGAGAA<br>AUGAUCGAAGAAAGACUGAAGACAUACGCACACCUGUUCGACGACAAGGUC<br>AUGAAGCAGCUGAAGAGAAGAAGAUACACAGGAUGGGGAAGACUGAGCAGA | 227 |

| Description | Sequence | SEQ ID No. |
|---|---|---|
| | AAGCUGAUCAACGGAAUCAGAGACAAGCAGAGCGGAAAGACAAUCCUGGAC<br>UUCCUGAAGAGCGACGGAUUCGCAAACAGAAACUUCAUGCAGCUGAUCCAC<br>GACGACAGCCUGACAUUCAAGGAAGACAUCCAGAAGGCACAGGUCAGCGGA<br>CAGGGAGACAGCCUGCACGAACACAUCGCAAACCUGGCAGGAAGCCCGGCA<br>AUCAAGAAGGGAAUCCUGCAGACAGUCAAGGUCGUCGACGAACUGGUCAAG<br>GUCAUGGGAAGACACAAGCCGGAAAACAUCGUCAUCGAAAUGGCAAGAGAA<br>AACCAGACAACACAGAAGGGACAGAAGAACAGCAGAGAAAGAAUGAAGAGA<br>AUCGAAGAAGGAAUCAAGGAACUGGGAAGCCAGAUCCUGAAGGAACACCCG<br>GUCGAAAACACACAGCUGCAGAACGAAAAGCUGUACCUGUACUACCUGCAG<br>AACGGAAGAGACAUGUACGUCGACCAGGAACUGGACAUCAACAGACUGAGC<br>GACUACGACGUCGACCACAUCGUCCCGCAGAGCUUCCUGAAGGACGACAGC<br>AUCGACAACAAGGUCCUGACAAGAAGCGACAAGAACAGAGGAAAGAGCGAC<br>AACGUCCCGAGCGAAGAAGUCGUCAAGAAGAUGAAGAACUACUGGAGACAG<br>CUGCUGAACGCAAAGCUGAUCACACAGAGAAAGUUCGACAACCUGACAAAG<br>GCAGAGAGGAGGACUGAGCGAACUGGACAAGGCAGGAUUCAUCAAGAGA<br>CAGCUGGUCGAAACAAGACAGAUCACAAAGCACGUCGCACAGAUCCUGGAC<br>AGCAGAAUGAACACAAAGUACGACGAAAACGACAAGCUGAUCAGAGAGUC<br>AAGGUCAUCACACUGAAGAGCAAGCUGGUCAGCGACUUCAGAAAGGACUUC<br>CAGUUCUACAAGGUCAGAGAAAUCAACAACUACCACCACGCACACGACGCA<br>UACCUGAACGCAGUCGUCGGAACAGCACUGAUCAAGAAGUACCCGAAGCUG<br>GAAAGCGAAUUCGUCUACGGAGACUACAAGGUCUACGACGUCAGAAAGAUG<br>AUCGCAAAGAGCGAACAGGAAAUCGGAAAGGCAACAGCAAAGUACUUCUUC<br>UACAGCAACAUCAUGAACUUCUUCAAGACAGAAAUCACACUGGCAAACGGA<br>GAAAUCAGAAAGAGACCGCUGAUCGAAACAAACGGAGAAACAGGAGAAAUC<br>GUCUGGGACAAGGGAAGAGACUUCGCAACAGUCAGAAAGGUCCUGAGCAUG<br>CCGCAGGUCAACAUCGUCAAGAAGACAGAAGUCCAGACAGGAGGAUUCAGC<br>AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAGAGAAUGCUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCUGUUCACACUGACAAACCUGGGAGCACCGGCAGCAUUCAAGUACUUC<br>GACACAACAAUCGACAGAAAGAGAUACACAAGCACAAAGGAAGUCCUGGAC<br>GCAACACUGAUCCACCAGAGCAUCACAGGACUGUACGAAACAAGAAUCGAC<br>CUGAGCCAGCUGGGAGGAGAC<br>GGAAGCGGAAGCCCGAAGAAGAAGAGAAAGGUCGACGGAAGCCCGAAGAAG<br>AAGAGAAAGGUCGACAGCGGA | |
| Amino acid sequence of dCas9 with two nuclear localization signals as the C-terminal amino acids | MDKKYSIGLAIGTNSVGWAVITDEYKVPSKKFKVLGNTDRHSIKKNLIGAL<br>LFDSGETAEATRLKRTARRRYTRRKNRICYLQEIFSNEMAKVDDSFFHRLE<br>ESFLVEEDKKHERHPIFGNIVDEVAYHEKYPTIYHLRKKLVDSTDKADLRL<br>IYLALAHMIKFRGHFLIEGDLNPDNSDVDKLFIQLVQTYNQLFEENPINAS<br>GVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKN<br>GYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGN<br>SRFAWMTRKSEETITPWNFEEVVDKGASAQSFIERMTNFDKNLPNEKVLPK<br>HSLLYEYFTVYNELTKVKYVTEGMRKPAFLSGEQKKAIVDLLFKTNRKVTV<br>KQLKEDYFKKIECFDSVEISGVEDRFNASLGTYHDLLKIIKDKDFLDNEEN<br>EDILEDIVLTLTLFEDREMIEERLKTYAHLFDDKVMKQLKRRRYTGWGRLS<br>RKLINGIRDKQSGKTILDFLKSDGFANRNFMQLIHDDSLTFKEDIQKAQVS<br>GQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYL<br>QNGRDMYVDQELDINRLSDYDVDAIVPQSFLKDDSIDNKVLTRSDKNRGKS<br>DNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGE<br>IVWDKGRDFATVRKVLSMPQVNIVKKTEVQTGGFSKESILPKRNSDKLIAR<br>KKDWDPKKYGGFDSPTVAYSVLVVAKVEKGKSKKLKSVKELLGITIMERSS<br>FEKNPIDFLEAKGYKEVKKDLIIKLPKYSLFELENGRKRMLASAGELQKGN<br>ELALPSKYVNFLYLASHYEKLKGSPEDNEQKQLFVEQHKHYLDEIIEQISE | 228 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | FSKRVILADANLDKVLSAYNKHRDKPIREQAENIIHLFTLTNLGAPAAFKY FDTTIDRKRYTSTKEVLDATLIHQSITGLYETRIDLSQLGGDGSGSPKKKR KVDGSPKKKRKVDSG | |
| dCas9 mRNA ORF encoding SEQ ID NO: 228 using minimal uridine codons, with start and stop codons | AUGGACAAGAAGUACAGCAUCGGACUGGCAAUCGGAACAAACAGCGUCGGA UGGGCAGUCAUCACAGACGAAUACAAGGUCCCGAGCAAGAAGUUCAAGGUC CUGGGAAACACAGACAGACACAGCAUCAAGAAGAACCUGAUCGGAGCACUG CUGUUCGACAGCGGAGAAACAGCAGAAGCAACAAGACUGAAGAGAACAGCA AGAAGAAGAUACACAAGAAGAAAGAACAGAAAUCUGCUACCUGCAGGAAAUC UUCAGCAACGAAAUGGCAAAGGUCGACGACAGCUUCUUCCACAGACUGGAA GAAAGCUUCCUGGUCGAAGAAGACAAGAAGCACGAAAGACACCCGAUCUUC GGAAACAUCGUCGACGAAGUCGCAUACCACGAAAAGUACCCGACAAUCUAC CACCUGAAAGAAGCUGGUCGACAGCACAGACAAGGCAGACCUGGACACUG AUCUACCUGGCACUGGCACACAUGAUCAAGUUCAGAGGACACUUCCUGAUC GAAGGAGACCUGAACCCGGACAACAGCGACGUCGACAAGCUGUUCAUCCAG CUGGUCCAGACAUACAACCAGCUGUUCGAAGAAAACCCGAUCAACGCAAGC GGAGUCGACGCAAAGGCAAUCCUGAGCGCAAGACUGAGCAAGAGCAGAAGA CUGGAAAACCUGAUCGCACAGCUGCCGGGAGAAAAGAAGAACGGACUGUUC GGAAACCUGAUCGCACUGAGCCUGGGACUGACACCGAACUUCAAGAGCAAC UUCGACCUGGCAGAAGACGCAAAGCUGCAGCUGAGCAAGGACACAUACGAC GACGACCUGGACAACCUGCUGGCACAGAUCGGAGACCAGUACGCAGACCUG UUCCUGGCAGCAAAGAACCUGAGCGACGCAAUCCUGCUGAGCGACAUCCUG AGAGUCAACACAGAAAUCACAAAGGCACCGCUGAGCGCAAGCAUGAUCAAG AGAUACGACGAACACCACCAGGACCUGACACUGCUGAAGGCACUGGUCAGA CAGCAGCUGCCGGAAAAGUACAAGGAAAUCUUCUUCGACCAGAGCAAGAAC GGAUACGCAGGAUACAUCGACGGAGGAGCAAGCCAGGAAGAAUUCUACAAG UUCAUCAAGCCGAUCCUGGAAAAGAUGGACGGAACAGAAGAACUGCUGGUC AAGCUGAACAGAGAAGACCUGCUGAGAAAGCAGAGAACAUUCGACAACGGA AGCAUCCCGCACCAGAAUCCACCUGGGAGAACUGCACGCAAUCCUGAGAAGA CAGGAAGACUUCUACCCGUUCCUGAAGGACAACAGAGAAAAGAUCGAAAAG AUCCUGACAUUCAGAAUCCCGUACUACGUCGGACCGCUGGCAAGAGGAAAC AGCAGAUUCGCAUGGAUGACAAGAAAGAGCGAAGAAACAAUCACACCGUGG AACUUCGAAGAAGUCGUCGACAAGGGAGCAAGCGCACAGAGCUUCAUCGAA AGAAUGACAAACUUCGACAAGAACCUGCCGAACGAAAAGGUCCUGCCGAAG CACAGCCUGCUGUACGAAUACUUCACAGUCUACAACGAACUGACAAAGGUC AAGUACGUCACAGAAGGAAUGAGAAAGCCGGCAUUCCUGAGCGGAGAACAG AAGAAGGCAAUCGUCGACCUGCUGUUCAAGACAAACAGAAAGGUCACAGUC AAGCAGCUGAAGGAAGACUACUUCAAGAAGAUCGAAUGCUUCGACAGCGUC GAAAUCAGCGGAGUCGAAGACAGAUUCAACGCAAGCCUGGGAACAUACCAC GACCUGCUGAAGAUCAUCAAGGACAAGGACUUCCUGGACAACGAAGAAAAC GAAGACAUCCUGGAAGACAUCGUCCUGACACUGACACUGUUCGAAGACAGA GAAAUGAUCGAAGAAAGACUGAAGACAUACGCACACCUGUUCGACGACAAG GUCAUGAAGCAGCUGAAGAGAAGAAGAUACACAGGAUGGGGAAGACUGAGC AGAAAGCUGAUCAACGGAAUCAGAGACAAGCAGAGCGGAAAGACAAUCCUG GACUUCCUGAAGAGCGACGGAUUCGCAAACAGAAACUUCAUGCAGCUGAUC CACGACGACAGCCUGACAUUCAAGGAAGACAUCCAGAAGGCACAGGUCAGC GGACAGGGAGACAGCCUGCACGAACACAUCGCAAACCUGGCAGGAAGCCCG GCAAUCAAGAAGGGAAUCCUGCAGACAGUCAAGGUCGUCGACGAACUGGUC AAGGUCAUGGGAAGACACAAGCCGGAAAACAUCGUCAUCGAAAUGGCAAGA GAAAACCAGACAACACAGAAGGGACAGAAGAACAGCAGAGAAAGAAUGAAG AGAAUCGAAGAAGGAAUCAAGGAACUGGGAAGCCAGAUCCUGAAGGAACAC CCGGUCGAAAACACACAGCCUGCAGAACGAAAGCUGUACCUGUACUACCUG CAGAACGGAAGAGACAUGUACGUCGACCAGGAACUGGACAUCAACAGACUG AGCGACUACGACGUCGACGCAAUCGUCCCGCAGAGCUUCCUGAAGGACGAC AGCAUCGACAACAAGGUCCUGACAAGAAGCGACAAGAACAGAGGAAAGAGC GACAACGUCCCGAGCGAAGAAGUCGUCAAGAAGAUGAAGAACUACUGGAGA CAGCUGCUGAACGCAAAGCUGAUCACACAGAGAAAGUUCGACAACCUGACA AAGGCAGAGAGGAGGACUGAGCGAACUGGACAAGGCAGGAUUCAUCAAG AGACAGCUGGUCGAAACAAGACAGAUCACAAAGCACGUCGCACAGAUCCUG GACAGCAGAAUGAACACAAAGUACGACGAAAACGACAAGCUGAUCAGAGAA GUCAAGGUCAUCACACUGAAGAGCAAGCUGGUCAGCGACUUCAGAAAGGAC UUCCAGUUCUACAAGGUCAGAGAAAUCAACAACUACCACCACGCACACGAC GCAUACCUGAACGCAGUCGUCGGAACAGCACUGAUCAAGAAGUACCCGAAG CUGGAAAGCGAAUUCGUCUACGGAGACUACAAGGUCUACGACGUCAGAAAG AUGAUCGCAAAGAGCGAACAGGAAAUCGGAAAGGCAACAGCAAAGUACUUC UUCUACAGCAACAUCAUGAACUUCUUCAAGACAGAAAUCACACUGGCAAAC GGAGAAAUCAGAAAGAGACCGCUGAUCGAAACAAACGGAGAAACAGGAGAA AUCGUCUGGGACAAGGGAAGAGACUUCGCAACAGUCAGAAAGGUCCUGAGC AUGCCGCAGGUCAACAUCGUCAAGAAGACAGAAGUCCAGACAGGAGGAUUC AGCAAGGAAAGCAUCCUGCCGAAGAGAAACAGCGACAAGCUGAUCGCAAGA | 229 |

-continued

| Description | Sequence | SEQ ID No. |
|---|---|---|
| | AAGAAGGACUGGGACCCGAAGAAGUACGGAGGAUUCGACAGCCCGACAGUC<br>GCAUACAGCGUCCUGGUCGUCGCAAAGGUCGAAAAGGGAAAGAGCAAGAAG<br>CUGAAGAGCGUCAAGGAACUGCUGGGAAUCACAAUCAUGGAAAGAAGCAGC<br>UUCGAAAAGAACCCGAUCGACUUCCUGGAAGCAAAGGGAUACAAGGAAGUC<br>AAGAAGGACCUGAUCAUCAAGCUGCCGAAGUACAGCCUGUUCGAACUGGAA<br>AACGGAAGAAAGAGAAUGCUGGCAAGCGCAGGAGAACUGCAGAAGGGAAAC<br>GAACUGGCACUGCCGAGCAAGUACGUCAACUUCCUGUACCUGGCAAGCCAC<br>UACGAAAAGCUGAAGGGAAGCCCGGAAGACAACGAACAGAAGCAGCUGUUC<br>GUCAACAGCACAAGCACUACCUGGACGAAAUCAUCGAACAGAUCAGCGAA<br>UUCAGCAAGAGAGUCAUCCUGGCAGACGCAAACCUGGACAAGGUCCUGAGC<br>GCAUACAACAAGCACAGAGACAAGCCGAUCAGAGAACAGGCAGAAAACAUC<br>AUCCACCUGUUCACACUGACAAACCUGGGAGCACCGGCAGCAUUCAAGUAC<br>UUCGACACAACAAUCGACAGAAAAGAGAUACACAAGCACAAAGGAAGUCCUG<br>GACGCAACACUGAUCCACCAGAGCAUCACAGGACUGUACGAAACAAGAAUC<br>GACCUGAGCCAGCUGGGAGGAGAC<br>GGAAGCGGAAGCCCGAAGAAGAAGAGAAAGGUCGACGGAAGCCCGAAGAAG<br>AAGAGAAAGGUCGACAGCGGAUAG | |
| dCas9 coding sequence encoding SEQ ID NO: 228 using minimal uridine codons (no start or stop codons; suitable for inclusion in fusion protein coding sequence) | GACAAGAAGUACAGCAUCGGACUGGCAAUCGGAACAAACAGCGUCGGAUGG<br>GCAGUCAUCACAGACGAAUACAAGGUCCCGAGCAAGAAGUUCAAGGUCCUG<br>GGAAACACAGACAGACACAGCAUCAAGAAGAACCUGAUCGGAGCACUGCUG<br>UUCGACAGCGGAGAAACAGCAGAAGCAACAAGACUGAAGAGAACAGCAAGA<br>AGAAGAUACACAAGCAAGAAGAACAGAAUCUGCUACCUGCAGGAAAUCUUC<br>AGCAACGAAAUGGCAAAGGUCGACGACAGCUUCUUCCACAGACUGGAAGAA<br>AGCUUCCUGGUCGAAGAAGACAAGAAGCACGAAAGACACCCGAUCUUCGGA<br>AACAUCGUCGACGAAGUCGCAUACCACGAAAAGUACCCGACAAUCUACCAC<br>CUGAGAAAGAAGCUGGUCGACAGCACAGACAAGGCAGACCUGAGACUGAUC<br>UACCUGGCACUGGCACACAUGAUCAAGUUCAGAGGACACUUCCUGAUCGAA<br>GGAGACCUGAACCCGGACAACAGCGACGUCGACAAGCUGUUCAUCCAGCUG<br>GUCCAGACAUACAACCAGCUGUUCGAAGAAAACCCGAUCAACGCAAGCGGA<br>GUCGACGCAAAGGCAAUCCUGAGCGCAAGACUGAGCAAGAGCAGAAGACUG<br>GAAAACCUGAUCGCACAGCUGCCGGGAGAAAAGAAGAACGGACUGUUCGGA<br>AACCUGAUCGCACUGAGCCUGGGACUGACACCGAACUUCAAGAGCAACUUC<br>GACCUGGCAGAAGACGCAAAGCUGCAGCUGAGCAAGGACACAUACGACGAC<br>GACCUGGACAACCUGCUGGCACAGAUCGGAGACCAGUACGCAGACCUGUUC<br>CUGGCAGCAAAGAACCUGAGCGACGCAAUCCUGCUGAGCGACAUCCUGAGA<br>GUCAACACAGAAAUCACAAAGGCACCGCUGAGCGCAAGCAUGAUCAAGAGA<br>UACGACGAACACCACCAGGACCUGACACUGCUGAAGGCACUGGUCAGACAG<br>CAGCUGCCGGAAAAGUACAAGGAAAUCUUCUUCGACCAGAGCAAGAACGGA<br>UACGCAGGAUACAUCGACGGAGGAGCAAGCCAGGAAGAAUUCUACAAGUUC<br>AUCAAGCCGAUCCUGGAAAAGAUGGACGGAACAGAAGAACUGCUGGUCAAG<br>CUGAACAGAGAAGACCUGCUGAGAAAGCAGAGAACAUUCGACAACGGAAGC<br>AUCCCGCACCAGAUCCACCUGGGAGAACUGCACGCAAUCCUGAGAAGACAG<br>GAAGACUUCUACCCGUUCCUGAAGGACAACAGAGAAAAGAUCGAAAAGAUC<br>CUGACAUUCAGAAUCCCGUACUACGUCGGACCGCUGGCAAGAGGAAACAGC<br>AGAUUCGCAUGGAUGACAAGAAAGAGCGAAGAAACAAUCACCGUGGAC<br>UUCGAAGAAGUCGUCGACAAGGGAGCAAGCGCACAGAGCUUCAUCGAAAGA<br>AUGACAAACUUCGACAAGAACCUGCCGAACGAAAAGGUCCUGCCGAAGCAC<br>AGCCUGCUGUACGAAUACUUCACAGUCUACAACGAACUGACAAAGGUCAAG<br>UACGUCACAGAAGGAAUGAGAAAGCCGGCAUUCCUGAGCGGAGAACAGAAG<br>AAGGCAAUCGUCGACCUGCUGUUCAAGACAAACAGAAAGGUCACAGUCAAG<br>CAGCUGAAGGAAGACUACUUCAAGAAGAUCGAAUGCUUCGACAGCGUCGAA<br>AUCAGCGGAGUCGAAGACAGAUUCAACGCAAGCCUGGGAACAUACCACGAC<br>CUGCUGAAGAUCAUCAAGGACAAGGACUUCCUGGACAACGAAGAAAACAGA<br>GACAUCCUGGAAGACAUCGUCCUGACACUGACACUGUUCGAAGACAGAGAA<br>AUGAUCGAAGAAGACUGAAGACAUACGCACACCUGUUCGACGACAAGGUC<br>AUGAAGCAGCUGAAGAGAAGAAGAUACACAGGAUGGGAAGACUGAGCAGA<br>AAGCUGAUCAACGGAAUCAGAGACAAGCAGAGCGGAAAGACAAUCCUGGAC<br>UUCCUGAAGAGCGACGGAUUCGCAAACAGAAACUUCAUGCAGCUGAUCCAC<br>GACGACAGCCUGACAUUCAAGGAAGACAUCCAGAAGGCACAGGUCAGCGGA<br>CAGGGAGACAGCCUGCACGAACACAUCGCAAACCUGGCAGGAAGCCCGGCA<br>AUCAAGAAGGGAAUCCUGCAGACAGUCAAGGUCGUCGACGAACUGGUCAAG<br>GUCAUGGGAAGACACAAGCCGGAAAACAUCGUCAUCGAAAUGGCAAGAGAA<br>AACCAGACAACACAGAAGGGACAGAAGAACAGCAGAGAAAGAUGAAGAGA<br>AUCGAAGAAGGAAUCAAGGAACUGGGAAGCCAGAUCCUGAAGGAACACCCG<br>GUCGAAAACACACAGCUGCAGAACGAAAAGCUGUACCUGUACUACCUGCAG<br>AACGGAAGAGACAUGUACGUCGACCAGGAACUGGACAUCAACAGACUGAGC<br>GACUACGACGUCGACGCAAUCGUCCCGCAGAGCUUCCUGAAGGACGACAGC<br>AUCGACAACAAGGUCCUGACAAGAAGCGACAAGAACAGAGGAAAGAGCGAC<br>AACGUCCCGAGCGAAGAAGUCGUCAAGAAGAUGAAGAACUACUGGAGACAG | 230 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | CUGCUGAACGCAAAGCUGAUCACACAGAGAAAGUUCGACAACCUGACAAAG<br>GCAGAGAGAGGAGGACUGAGCGAACUGGACAAGGCAGGAUUCAUCAAGAGA<br>CAGCUGGUCGAAACAAGACAGAUCACAAAGCACGUCGCACAGAUCCUGGAC<br>AGCAGAAUGAACACAAAGUACGACGAAAACGACAAGCUGAUCAGAGAAGUC<br>AAGGUCAUCACACUGAAGAGCAAGCUGGUCAGCGACUUCAGAAAGGACUUC<br>CAGUUCUACAAGGUCAGAGAAAUCAACAACUACCACCACGCACACGACGCA<br>UACCUGAACGCAGUCGUCGGAACAGCACUGAUCAAGAAGUACCCGAAGCUG<br>GAAAGCGAAUUCGUCUACGGAGACUACAAGGUCUACGACGUCAGAAAGAUG<br>AUCGCAAAGAGCGAACAGGAAAUCGGAAAGGCAACAGCAAAGUACUUCUUC<br>UACAGCAACAUCAUGAACUUCUUCAAGACAGAAAUCACACUGGCAAACGGA<br>GAAAUCAGAAAGAGACCGCUGAUCGAAACAAACGGAGAAACAGGAGAAAUC<br>GUCUGGGACAAGGGAAGAGACUUCGCAACAGUCAGAAAGGUCCUGAGCAUG<br>CCGCAGGUCAACAUCGUCAAGAAGACAGAAGUCCAGACAGGAGGAUUCAGC<br>AAGGAAAGCAUCCUGCCGAAGAGAAACAGCGACAAGCUGAUCGCAAGAAAG<br>AAGGACUGGGACCCGAAGAAGUACGGAGGAUUCGACAGCCCGACAGUCGCA<br>UACAGCGUCCUGGUCGUCGCAAAGGUCGAAAAGGGAAAGAGCAAGAAGCUG<br>AAGAGCGUCAAGGAACUGCUGGGAAUCACAAUCAUGGAAAGAAGCAGCUUC<br>GAAAAGAACCCGAUCGACUUCCUGGAAGCAAAGGGAUACAAGGAAGUCAAG<br>AAGGACCUGAUCAUCAAGCUGCCGAAGUACAGCCUGUUCGAACUGGAAAAC<br>GGAAGAAAGAGAAUGCUGGCAAGCGCAGGAGAACUGCAGAAGGGAAACGAA<br>CUGGCACUGCCGAGCAAGUACGUCAACUUCCUGUACCUGGCAAGCCACUAC<br>GAAAAGCUGAAGGGAAGCCCGGAAGACAACGAACAGAAGCAGCUGUUCGUC<br>GAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCA<br>UACAACAAGCACAGAGACAAGCCGAUCAGAGAACAGGCAGAAAACAUCAUC<br>CACCUGUUCACACUGACAAACCUGGGAGCACCGGCAGCAUUCAAGUACUUC<br>GACACAACAAUCGACAGAAAGAGAUACACAAGCACAAAGGAAGUCCUGGAC<br>GCAACACUGAUCCACCAGAGCAUCACAGGACUGUACGAAACAAGAAUCGAC<br>CUGAGCCAGCUGGGAGGAGACGGAAGCGGAAGCCCGAAGAAGAAGAGAAAG<br>GUCGACGGAAGCCCGAAGAAGAAGAGAAAGGUCGACAGCGGA | |
| T7 Promoter | TAATACGACTCACTATA | 231 |
| Human beta-globin 5' UTR | ACATTTGCTTCTGACACAACTGTGTTCACTAGCAACCTCAAACAGACACC | 232 |
| Human beta-globin 3' UTR | GCTCGCTTTCTTGCTGTCCAATTTCTATTAAAGGTTCCTTTGTTCCCTAAG<br>TCCAACTACTAAACTGGGGGATATTATGAAGGGCCTTGAGCATCTGGATTC<br>TGCCTAATAAAAAACATTTATTTTCATTGC | 233 |
| Human alpha-globin 5' UTR | CATAAACCCTGGCGCGCTCGCGGCCCGGCACTCTTCTGGTCCCCACAGACT<br>CAGAGAGAACCCACC | 234 |
| Human alpha-globin 3' UTR | GCTGGAGCCTCGGTGGCCATGCTTCTTGCCCCTTGGGCCTCCCCCCAGCCC<br>CTCCTCCCCTTCCTGCACCCGTACCCCCGTGGTCTTTGAATAAAGTCTGAG<br>TGGGCGGC | 235 |
| *Xenopus laevis* beta-globin 5' UTR | AAGCTCAGAATAAACGCTCAACTTTGGCC | 236 |
| *Xenopus laevis* beta-globin 3' UTR | ACCAGCCTCAAGAACACCCGAATGGAGTCTCTAAGCTACATAATACCAACT<br>TACACTTTACAAAATGTTGTCCCCCAAAATGTAGCCATTCGTATCTGCTCC<br>TAATAAAAAGAAAGTTTCTTCACATTCT | 237 |
| Bovine Growth Hormone 5' UTR | CAGGGTCCTGTGGACAGCTCACCAGCT | 238 |
| Bovine Growth Hormone 3' UTR | TTGCCAGCCATCTGTTGTTTGCCCCTCCCCCGTGCCTTCCTTGACCCTGGA<br>AGGTGCCACTCCCACTGTCCTTTCCTAATAAAATGAGGAAATTGCATCGCA | 239 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| *Mus musculus* hemoglobin alpha, adult chain 1 (Hba-a1), 3' UTR | GCTGCCTTCTGCGGGGCTTGCCTTCTGGCCATGCCCTTCTTCTCTCCCTTG CACCTGTACCTCTTGGTCTTTGAATAAAGCCTGAGTAGGAAG | 240 |
| HSD17B4 5' UTR | TCCCGCAGTCGGCGTCCAGCGGCTCTGCTTGTTCGTGTGTGTGTCGTTGCA GGCCTTATTC | 241 |
| G282 single guide RNA targeting the mouse TTR gene | mU*mU*mA*CAGCCACGUCUACAGCAGUUUUAGAmGmCmUmAmGmAmAmAm UmAmGmCAAGUUAAAAUAAGGCUAGUCCGUUAUCAmAmCmUmGmAmAmA mAmAmGmUmGmGmCmAmCmCmGmAmGmUmCmGmGmUmGmCmU*mU*mU*mU | 242 |
| | Not used | 243 |
| Cas9 transcript with 5' UTR of HSD, ORF corresponding to SEQ ID NO: 204, and 3' UTR of ALB | GGGTCCCGCAGTCGGCGTCCAGCGGCTCTGCTTGTTCGTGTGTGTCGTT GCAGGCCTTATTCGGATCCATGGACAAGAAGTACAGCATCGGACTGGACAT CGGAACAAACAGCGTCGATGGGCAGTCATCACAGACGAATACAAGGTCCC GAGCAAGAAGTTCAAGGTCCTGGGAAACACAGACAGACACAGCATCAAGAA GAACCTGATCGGAGCACTGCTGTTCGACAGCGGAGAAACAGCAGAAGCAAC AAGACTGAAGAGAACAGCAAGAAGAAGATACACAAGAAGAAAGAACAGAAT CTGCTACCTGCAGGAAATCTTCAGCAACGAAATGGCAAAGGTCGACGACAG CTTCTTCCACAGACTGGAAGAAAGCTTCCTGGTCGAAGAAGACAAGAAGCA CGAAAGACACCCGATCTTCGGAAACATCGTCGACGAAGTCGCATACCACGA AAAGTACCCGACAATCTACCACCTGAGAAAGAAGCTGGTCGACAGCACAGA CAAGGCAGACCTGAGACTGATCTACCTGGCACTGGCACACATGATCAAGTT CAGAGGACACTTCCTGATCGAAGGAGACCTGAACCCGGACAACAGCGACGT CGACAAGCTGTTCATCCAGCTGGTCCAGACATACAACCAGCTGTTCGAAGA AAACCCGATCAACGCAAGCGGAGTCGACGCAAAGGCAATCCTGAGCGCAAG ACTGAGCAAGAGCAGAAGACTGGAAAACCTGATCGCACAGCTGCCGGGAGA AAAGAAGAACGGACTGTTCGGAAACCTGATCGCACTGAGCCTGGGACTGAC ACCGAACTTCAAGAGCAACTTCGACCTGGCAGAAGACGCAAAGCTGCAGCT GAGCAAGGACACATACGACGACGACCTGGACAACCTGCTGGCACAGATCGG AGACCAGTACGCAGACCTGTTCCTGGCAGCAAAGAACCTGAGCGACGCAAT CCTGCTGAGCGACATCCTGAGAGTCAACACAGAAATCACAAAGGCACCGCT GAGCGCAAGCATGATCAAGAGATACGACGAACACCACCAGGACCTGACACT GCTGAAGGCACTGGTCAGACAGCAGCTGCCGGAAAAGTACAAGGAAATCTT CTTCGACCAGAGCAAGAACGGATACGCAGGATACATCGACGGAGGAGCAAG CCAGGAAGAATTCTACAAGTTCATCAAGCCGATCCTGGAAAAGATGGACGG AACAGAAGAACTGCTGGTCAAGCTGAACAGAGAAGACCTGCTGAGAAAGCA GAGAACATTCGACAACGGAAGCATCCCGCACCAGATCCACCTGGGAGAACT GCACGCAATCCTGAGAAGACAGGAAGACTTCTACCCGTTCCTGAAGGACAA CAGAGAAAAGATCGAAAAGATCCTGACATTCAGAATCCCGTACTACGTCGG ACCGCTGGCAAGAGGAAACAGCAGATTCGCATGGATGACAAGAAAGAGCGA AGAAACAATCACACCGTGGAACTTCGAAGAAGTCGTCGACAAGGGAGCAAG CGCACAGAGCTTCATCGAAAGAATGACAAACTTCGACAAGAACCTGCCGAA CGAAAAGGTCCTGCCGAAGCACAGCCTGCTGTATGAATACTTCACAGTCTA CAACGAACTGACAAAGGTCAAGTACGTCACAGAAGGAATGAGAAAGCCGGC ATTCCTGAGCGGAGAACAGAAGAAGGCAATCGTCGACCTGCTGTTCAAGAC AAACAGAAAGGTCACAGTCAAGCAGCTGAAGGAAGACTACTTCAAGAAGAT CGAATGCTTCGACAGCGTCGAAATCAGCGGAGTCGAAGACAGATTCAACGC AAGCCTGGGAACATACCACGACCTGCTGAAGATCATCAAGGACAAGGACTT CCTGGACAACGAAGAAAACGAAGACATCCTGGAAGACATCGTCCTGACACT GACACTGTTCGAAGACAGAGAAATGATCGAAGAAAGACTGAAGACATACGC ACACCTGTTCGACGACAAGGTCATGAAGCAGCTGAAGAGAAGAAGATACAC AGGATGGGGAAGACTGAGCAGAAAGCTGATCAACGGAATCAGACACAAGCA GAGCGGAAAGACAATCCTGGACTTCCTGAAGAGCGACGGATTCGCAAACAG AAACTTCATGCAGCTGATCCACGACGACAGCCTGACATTCAAGGAAGACAT CCAGAAGGCACAGGTCAGCGGACAGGGAGACAGCCTGCACGAACACATCGC AAACCTGGCAGGAAGCCCGGCAATCAAGAAGGGAATCCTGCAGACAGTCAA GGTCGTCGACGAACTGGTCAAGGTCATGGGAAGACACAAGCCGGAAAACAT CGTCATCGAAATGGCAAGAGAAAACCAGACAACACAGAAGGGACAGAAGCA CAGCAGAGAAAGAATGAAGAGAATCGAAGAAGGAATCAAGGAACTGGGAAG CCAGATCCTGAAGGAACACCCGGTCGAAAACACACAGCTGCAGAACGAAAA GCTGTACCTGTACTACCTGCAGAACGGAAGAGACATGTACGTCGACCAGGA ACTGGACATCAACAGACTGAGCGACTACGACGTCGACCACATCGTCCCGCA GAGCTTCCTGAAGGACGACAGCATCGACAACAAGGTCCTGACAAGAAGCGA | 244 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CAAGAACAGAGGAAAGAGCGACAACGTCCCGAGCGAAGAAGTCGTCAAGAA<br>GATGAAGAACTACTGGAGACAGCTGCTGAACGCAAAGCTGATCACACAGAG<br>AAAGTTCGACAACCTGACAAAGGCAGAGAGAGGAGGACTGAGCGAACTGGA<br>CAAGGCAGGATTCATCAAGAGACAGCTGGTCGAAACAAGACAGATCACAAA<br>GCACGTCGCACAGATCCTGGACAGCAGAATGAACACAAAGTACGACGAAAA<br>CGACAAGCTGATCAGAGAAGTCAAGGTCATCACACTGAAGAGCAAGCTGGT<br>CAGCGACTTCAGAAAGGACTTCCAGTTCTACAAGGTCAGAGAAATCAACAA<br>CTACCACCACGCACACGACGCATACCTGAACGCAGTCGTCGGAACAGCACT<br>GATCAAGAAGTACCCGAAGCTGGAAAGCGAATTCGTCTACGGAGACTACAA<br>GGTCTACGACGTCAGAAAGATGATCGCAAAGAGCGAACAGGAAATCGGAAA<br>GGCAACAGCAAAGTACTTCTTCTACAGCAACATCATGAACTTCTTCAAGAC<br>AGAAATCACACTGGCAAACGGAGAAATCAGAAAGAGACCGCTGATCGAAAC<br>AAACGGAGAAACAGGAGAAATCGTCTGGGACAAGGGAAGAGACTTCGCAAC<br>AGTCAGAAAGGTCCTGAGCATGCCGCAGGTCAACATCGTCAAGAAGACAGA<br>AGTCCAGACAGGAGGATTCAGCAAGGAAAGCATCCTGCCGAAGAGAAACAG<br>CGACAAGCTGATCGCAAGAAAGAAGGACTGGGACCCGAAGAAGTACGGAGG<br>ATTCGACAGCCCGACAGTCGCATACAGCGTCCTGGTCGTCGCAAAGGTCGA<br>AAAGGGAAAGAGCAAGAAGCTGAAGAGCGTCAAGGAACTGCTGGGAATCAC<br>AATCATGGAAAGAAGCAGCTTCGAAAAGAACCCGATCGACTTCCTGGAAGC<br>AAAGGGATACAAGGAAGTCAAGAAGGACCTGATCATCAAGCTGCCGAAGTA<br>CAGCCTGTTCGAACTGGAAAACGGAAGAAAGAGAATGCTGGCAAGCGCAGG<br>AGAACTGCAGAAGGGAAACGAACTGGCACTGCCGAGCAAGTACGTCAACTT<br>CCTGTACCTGGCAAGCCACTACGAAAAGCTGAAGGGAAGCCCGGAAGACAA<br>CGAACAGAAGCAGCTGTTCGTCGAACAGCACAAGCACTACCTGGACGAAAT<br>CATCGAACAGATCAGCGAATTCAGCAAGAGAGTCATCCTGGCAGACGCAAA<br>CCTGGACAAGGTCCTGAGCGCATACAACAAGCACAGAGACAAGCCGATCAG<br>AGAACAGGCAGAAAACATCATCCACCTGTTCACACTGACAAACCTGGGAGC<br>ACCGGCAGCATTCAAGTACTTCGACACAACAATCGACAGAAAGAGATACAC<br>AAGCACAAAGGAAGTCCTGGACGCAACACTGATCCACCAGAGCATCACAGG<br>ACTGTACGAAACAAGAATCGACCTGAGCCAGCTGGGAGGAGACGGAGGAGG<br>AAGCCCGAAGAAGAAGAGAAAGGTCTAGCTAGCCATCACATTTAAAAGCAT<br>CTCAGCCTACCATGAGAATAAGAGAAAGAAAATGAAGATCAATAGCTTATT<br>CATCTCTTTTTCTTTTTCGTTGGTGTAAAGCCAACACCCTGTCTAAAAAAC<br>ATAAATTTCTTTAATCATTTTGCCTCTTTTCTCTGTGCTTCAATTAATAAA<br>AAATGGAAAGAACCTCGAG | |
| Alternative Cas9 ORF with 19.36% U content | ATGGATAAGAAGTACTCGATCGGGCTGGATATCGGAACTAATTCCGTGGGT<br>TGGGCAGTGATCACGGATGAATACAAAGTGCCGTCCAAGAAGTTCAAGGTC<br>CTGGGGAACACCGATAGACACAGCATCAAGAAGAATCTCATCGGAGCCCTG<br>CTGTTTGACTCCGGCGAAACCGCAGAAGCGACCCGGCTCAAACGTACCGCG<br>AGGCGACGCTACACCCGGCGGAAGAATCGCATCTGCTATCTGCAAGAAATC<br>TTTTCGAACGAAATGGCAAAGGTGGACGACAGCTTCTTCCACCGCCTGGAA<br>GAATCTTTCCTGGTGGAGGAGGACAAGAAGCATGAACGGCATCCTATCTTT<br>GGAAACATCGTGGACGAAGTGGCGTACCACGAAAAGTACCCGACCATCTAC<br>CATCTGCGGAAGAAGTTGGTTGACTCAACTGACAAGGCCGACCTCAGATTG<br>ATCTACTTGGCCCTCGCCCATATGATCAAATTCCGCGGACACTTCCTGATC<br>GAAGGCGATCTGAACCCTGATAACTCCGACGTGGATAAGCTGTTCATTCAA<br>CTGGTGCAGACCTACAACCAACTGTTCGAAGAAAACCCAATCAATGCCAGC<br>GGCGTCGATGCCAAGGCCATCCTGTCCGCCCGGCTGTCGAAGTCGCGGCGC<br>CTCGAAAACCTGATCGCACAGCTGCCGGGAGAAGAAGAACGGACTTTTC<br>GGCAACTTGATCGCTCTCTCACTGGGACTCACTCCCAATTTCAAGTCCAAT<br>TTTGACCTGGCCGAGGACGCGAAGCTGCAACTCTCAAAGGACACCTACGAC<br>GACGACTTGGACAATTTGCTGGCACAAATTGGCGATCAGTACGCGGATCTG<br>TTCCTTGCCGCTAAGAACCTTTCGGACGCAATCTTGCTGTCCGATATCCTG<br>CGCGTGAACACCGAAATAACCAAAGCGCCGCTTAGCGCCTCGATGATTAAG<br>CGGTACGACGAGCATCACCAGGATCTCACGCTGCTCAAAGCGCTCGTGAGA<br>CAGCAACTGCCTGAAAAGTACAAGGAGATTTTCTTCGACCAGTCCAAGAAT<br>GGGTACGCAGGGTACATCGATGGAGGCGCCAGCCAGGAAGAGTTCTATAAG<br>TTCATCAAGCCAATCCTGGAAAAGATGGACGGAACCGAAGAACTGCTGGTC<br>AAGCTGAACAGGGAGGATCTGCTCCGCAAACAGAGAACCTTTGACAACGGA<br>AGCATTCCACACCAGATCCATCTGGGTGAGCTGCACGCCATCTTGCGGCGC<br>CAGGAGGACTTTTACCCATTCCTCAAGGACAACCGGGAAAAGATCGAGAAA<br>ATTCTGACGTTCCGCATCCCGTATTACGTGGGCCCACTGGCGCGCGGCAAT<br>TCGCGCTTCGCGTGGATGACTAGAAAATCAGAGGAAACCATCACTCCTTGG<br>AATTTCGAGGAAGTTGTGGATAAGGGAGCTTCGGCACAATCCTTCATCGAA<br>CGAATGACCAACTTCGACAAGAATCTCCCAAACGAGAAGGTGCTTCCTAAG<br>CACAGCCTCCTTTACGAATACTTCACTGTCTACAACGAACTGACTAAAGTG<br>AAATACGTTACTGAAGGAATGAGGAAGCCGGCCTTTCTGAGCGGAGAACAG<br>AAGAAAGCGATTGTCGATCTGCTGTTCAAGACCAACCGCAAGGTGACCGTC<br>AAGCAGCTTAAAGAGGACTACTTCAAGAAGATCGAGTGTTTCGACTCAGTG | 245 |

225
-continued

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GAAATCAGCGGAGTGGAGGACAGATTCAACGCTTCGCTGGGAACCTATCAT<br>GATCTCCTGAAGATCATCAAGGACAAGGACTTCCTTGACAACGAGGAGAAC<br>GAGGACATCCTGGAAGATATCGTCCTGACCTTGACCCTTTTCGAGGATCGC<br>GAGATGATCGAGGAGAGGCTTAAGACCTACGCTCATCTCTTCGACGATAAG<br>GTCATGAAACAACTCAAGCGCCGCCGGTACACTGGTTGGGGCCGCCTCTCC<br>CGCAAGCTGATCAACGGTATTCGCGATAAACAGAGCGGTAAAACTATCCTG<br>GATTTCCTCAAATCGGATGGCTTCGCTAATCGTAACTTCATGCAGTTGATC<br>CACGACGACAGCCTGACCTTTAAGGAGGACATCCAGAAAGCACAAGTGAGC<br>GGACAGGGAGACTCACTCCATGAACACATCGCGAATCTGGCCGGTTCGCCG<br>GCGATTAAGAAGGGAATCCTGCAAACTGTGAAGGTGGTGGACGAGCTGGTG<br>AAGGTCATGGGACGGCACAAACCGGAGAATATCGTGATTGAAATGGCCCGA<br>GAAAACCAGACTACCCAGAAGGGCCAGAAGAACTCCCGCGAAAGGATGAAG<br>CGGATCGAAGAAGGAATCAAGGAGCTGGGCAGCCAGATCCTGAAAGAGCAC<br>CCGGTGGAAAACACGCAGCTGCAGAACGAGAAGCTCTACCTGTACTATTTG<br>CAAAATGGACGGGACATGTACGTGGACCAAGAGCTGGACATCAATCGGTTG<br>TCTGATTACGACGTGGACCACATCGTTCCACAGTCCTTTCTGAAGGATGAC<br>TCCATCGATAACAAGGTGTTGACTCGCAGCGACAAGAACAGAGGGAAGTCA<br>GATAATGTGCCATCGGAGGAGGTCGTGAAGAAGATGAAGAATTACTGGCGG<br>CAGCTCCTGAATGCGAAGCTGATTACCCAGAGAAAGTTTGACAATCTCACT<br>AAAGCCGAGCGCGGCGGACTCTCAGAGCTGGATAAGGCTGGATTCATCAAA<br>CGGCAGCTGGTCGAGACTCGGCAGATTACCAAGCACGTGGCGCAGATCCTG<br>GACTCCCGCATGAACACTAAATACGACGAGAACGATAAGCTCATCCGGGAA<br>GTGAAGGTGATTACCCTGAAAAGCAAACTTGTGTCGGACTTTCGGAAGGAC<br>TTTCAGTTTTACAAAGTGAGAGAAATCAACAACTACCATCACGCGCATGAC<br>GCATACCTCAACGCTGTGGTCGGCACCGCCCTGATCAAGAAGTACCCTAAA<br>CTTGAATCGGAGTTTGTGTACGGAGACTACAAGGTCTACGACGTGAGGAAG<br>ATGATAGCCAAGTCCGAACAGGAAATCGGGAAAGCAACTGCGAAATACTTC<br>TTTTACTCAAACATCATGAACTTCTTCAAGACTGAAATTACGCTGGCCAAT<br>GGAGAAATCAGGAAGAGGCCACTGATCGAAACTAACGGAGAAACGGGCGAA<br>ATCGTGTGGGACAAGGGCAGGGACTTCGCAACTGTTCGCAAAGTGCTCTCT<br>ATGCCGCAAGTCAATATTGTGAAGAAAACCGAAGTGCAAACCGGCGGATTT<br>TCAAAGGAATCGATCCTCCCAAAGAGAAATAGCGACAAGCTCATTGCACGC<br>AAGAAAGACTGGGACCCGAAGAAGTACGGAGGATTCGATTCGCCGACTGTC<br>GCATACTCCGTCCTCGTGGTGGCCAAGGTGGAGAAGGGAAAGAGCAAGAAG<br>CTCAAATCCGTCAAAGAGCTGCTGGGGATTACCATCATGGAACGATCCTCG<br>TTCGAGAAGAACCCGATTGATTTCCTGGAGGCGAAGGGTTACAAGGAGGTG<br>AAGAAGGATCTGATCATCAAACTGCCCAAGTACTCACTGTTCGAACTGGAA<br>AATGGTCGGAAGCGCATGCTGGCTTCGGCCGGAGAACTCCAGAAAGGAAAT<br>GAGCTGGCCTTGCCTAGCAAGTACGTCAACTTCCTCTATCTTGCTTCGCAC<br>TACGAGAAACTCAAAGGGTCACCGGAAGATAACGAACAGAAGCAGCTTTTC<br>GTGGAGCAGCACAAGCATTATCTGGATGAAATCATCGAACAAATCTCCGAG<br>TTTTCAAAGCGCGTGATCCTCGCCGACGCCAACCTCGACAAAGTCCTGTCG<br>GCCTACAATAAGCATAGAGATAAGCCGATCAGAGAACAGGCCGAGAACATT<br>ATCCACTTGTTCACCCTGACTAACCTGGGAGCTCCAGCCGCCTTCAAGTAC<br>TTCGATACTACTATCGACCGCAAAAGATACACGTCCACCAAGGAAGTTCTG<br>GACGCGACCCTGATCCACCAAAGCATCACTGGACTCTACGAAACTAGGATC<br>GATCTGTCGCAGCTGGGTGGCGATGGTGGCGGTGGATCCTACCCATACGAC<br>GTGCCTGACTACGCCTCCGGAGGTGGTGGCCCAAGAAGAAACGGAAGGTG<br>TGATAG | |
| Cas9 transcript with 5' UTR of HSD, ORF corresponding to SEQ ID NO: 245, Kozak sequence, and 3' UTR of ALB | GGGTCCCGCAGTCGGCGTCCAGCGGCTCTGCTTGTTCGTGTGTGTCGTT<br>GCAGGCCTTATTCGGATCTGCCACCATGGATAAGAAGTACTCGATCGGGCT<br>GGATATCGGAACTAATTCCGTGGGTTGGGCAGTGATCACGGATGAATACAA<br>AGTGCCGTCCAAGAAGTTCAAGGTCCTGGGAACACCGATAGACACAGCAT<br>CAAGAAGAATCTCATCGGAGCCCTGCTGTTTGACTCCGGCGAAACCGCAGA<br>AGCGACCCGGCTCAAACGTACCGCGAGGCGACGCTACACCCGGCGGAAGAA<br>TCGCATCTGCTATCTGCAAGAAATCTTTTCGAACGAAATGGCAAAGGTGGA<br>CGACAGCTTCTTCCACCGCCTGGAAGAATCTTTCCTGGTGGAGGAGGACAA<br>GAAGCATGAACGGCATCTATCTTTGAAACATCGTGGACGAAGTGGCGTA<br>CCACGAAAAGTACCCGACCATCTACCATCTGCGGAAGAAGTTGGTTGACTC<br>AACTGACAAGGCCGACCTCAGATTGATCTACTTGGCCCTCGCCCATATGAT<br>CAAATTCCGCGGACACTTCCTGATCGAAGGCGATCTGAACCCTGATAACTC<br>CGACGTGGATAAGCTGTTCATTCAACTGGTGCAGACCTACAACCAACTGTT<br>CGAAGAAAACCCAATCAATGCCAGCGGCGTCGATGCCAAGGCCATCCTGTC<br>CGCCCGGCTGTCGAAGTCGCGGCGCCTCGAAAACCTGATCGCACAGCTGCC<br>GGGAGAGAAGAAGAACGGACTTTTCGGCAACTTGATCGCTCTCTCACTGGG<br>ACTCACTCCCAATTTCAAGTCCAATTTTGACCTGGCCGAGGACGCGAAGCT<br>GCAACTCTCAAAGGACACCTACGACGACGACTTGGACAATTTGCTGGCACA<br>AATTGGCGATCAGTACGCGGATCTGTTCCTTGCCGCTAAGAACCTTTCGGA<br>CGCAATCTTGCTGTCCGATATCCTGCGCGTGAACACCGAAATAACCAAAGC | 246 |

| Description | Sequence | SEQ ID No. |
|---|---|---|
| | GCCGCTTAGCGCCTCGATGATTAAGCGGTACGACGAGCATCACCAGGATCT<br>CACGCTGCTCAAAGCGCTCGTGAGACAGCAACTGCCTGAAAAGTACAAGGA<br>GATTTTCTTCGACCAGTCCAAGAATGGGTACGCAGGGTACATCGATGGAGG<br>CGCCAGCCAGGAAGAGTTCTATAAGTTCATCAAGCCAATCCTGGAAAAGAT<br>GGACGGAACCGAAGAACTGCTGGTCAAGCTGAACAGGGAGGATCTGCTCCG<br>CAAACAGAGAACCTTTGACAACGGAAGCATTCCACACCAGATCCATCTGGG<br>TGAGCTGCACGCCATCTTGCGGCGCCAGGAGGACTTTTACCCATTCCTCAA<br>GGACAACCGGGAAAAGATCGAGAAAATTCTGACGTTCCGCATCCCGTATTA<br>CGTGGGCCCACTGGCGCGCGGCAATTCGCGCTTCGCGTGGATGACTAGAAA<br>ATCAGAGGAAACCATCACTCCTTGGAATTTCGAGGAAGTTGTGGATAAGGG<br>AGCTTCGGCACAATCCTTCATCGAACGAATGACCAACTTCGACAAGAATCT<br>CCCAAACGAGAAGGTGCTTCCTAAGCACAGCCTCCTTTACGAATACTTCAC<br>TGTCTACAACGAACTGACTAAAGTGAAATACGTTACTGAAGGAATGAGGAA<br>GCCGGCCTTTCTGAGCGGAGAACAGAAGAAAGCGATTGTCGATCTGCTGTT<br>CAAGACCAACCGCAAGGTGACCGTCAAGCAGCTTAAAGAGGACTACTTCAA<br>GAAGATCGAGTGTTTCGACTCAGTGGAAATCAGCGGAGTGGAGGACAGATT<br>CAACGCTTCGCTGGGAACCTATCATGATCTCCTGAAGATCATCAAGGACAA<br>GGACTTCCTTGACAACGAGGAGAACGAGGACATCCTGGAAGATATCGTCCT<br>GACCTTGACCCTTTTCGAGGATCGCGAGATGATCGAGGAGAGGCTTAAGAC<br>CTACGCTCATCTCTTCGACGATAAGGTCATGAAACAACTCAAGCGCCGCCG<br>GTACACTGGTTGGGGCCGCCTCTCCCGCAAGCTGATCAACGGTATTCGCGA<br>TAAACAGAGCGGTAAAACTATCCTGGATTTCCTCAAATCGGATGGCTTCGC<br>TAATCGTAACTTCATGCAGTTGATCCACGACGACAGCCTGACCTTTAAGGA<br>GGACATCCAGAAAGCACAAGTGAGCGGACAGGGAGACTCACTCCATGAACA<br>CATCGCGAATCTGGCCGGTTCGCCGGCGATTAAGAAGGGAATCCTGCAAAC<br>TGTGAAGGTGGTGGACGAGCTGGTGAAGGTCATGGGACGGCACAAACCGGA<br>GAATATCGTGATTGAAATGGCCCGAGAAAACCAGACTACCCAGAAGGGCCA<br>GAAGAACTCCCGCGAAAGGATGAAGCGGATCGAAGAAGGAATCAAGGAGCT<br>GGGCAGCCAGATCCTGAAAGAGCACCCGGTGGAAAACACGCAGCTGCAGAA<br>CGAGAAGCTCTACCTGTACTATTTGCAAAATGGACGGGACATGTACGTGGA<br>CCAAGAGCTGGACATCAATCGGTTGTCTGATTACGACGTGGACCACATCGT<br>TCCACAGTCCTTTCTGAAGGATGACTCCATCGATAACAAGGTGTTGACTCG<br>CAGCGACAAGAACAGAGGGAAGTCAGATAATGTGCCATCGGAGGAGGTCGT<br>GAAGAAGATGAAGAATTACTGGCGGCAGCTCCTGAATGCGAAGCTGATTAC<br>CCAGAGAAAGTTTGACAATCTCACTAAAGCCGAGCGCGGCGGACTCTCAGA<br>GCTGGATAAGGCTGGATTCATCAAACGGCAGCTGGTCGAGACTCGGCAGAT<br>TACCAAGCACGTGGCGCAGATCCTGGACTCCCGCATGAACACTAAATACGA<br>CGAGAACGATAAGCTCATCCGGGAAGTGAAGGTGATTACCCTGAAAAGCAA<br>ACTTGTGTCGGACTTTCGGAAGGACTTTCAGTTTTACAAAGTGAGAGAAAT<br>CAACAACTACCATCACGCGCATGACGCATACCTCAACGCTGTGGTCGGCAC<br>CGCCCTGATCAAGAAGTACCCTAAACTTGAATCGGAGTTTGTGTACGGAGA<br>CTACAAGGTCTACGACGTGAGGAAGATGATAGCCAAGTCCGAACAGGAAAT<br>CGGGAAAGCAACTGCGAAATACTTCTTTTACTCAAACATCATGAACTTCTT<br>CAAGACTGAAATTACGCTGGCCAATGGAGAAATCAGGAAGAGGCCACTGAT<br>CGAAACTAACGGAGAAACGGGCGAAATCGTGTGGGACAAGGGCAGGGACTT<br>CGCAACTGTTCGCAAAGTGCTCTCTATGCCGCAAGTCAATATTGTGAAGAA<br>AACCGAAGTGCAAACCGGCGGATTTTCAAAGGAATCGATCCTCCCAAAGAG<br>AAATAGCGACAAGCTCATTGCACGCAAGAAAGACTGGGACCCGAAGAAGTA<br>CGGAGGATTCGATTCGCCGACTGTCGCATACTCCGTCCTCGTGGTGGCCAA<br>GGTGGAGAAGGGAAAGAGCAAGAAGCTCAAATCCGTCAAAGAGCTGCTGGG<br>GATTACCATCATGGAACGATCCTCGTTCGAGAAGAACCCGATTGATTTCCT<br>GGAGGCGAAGGGTTACAAGGAGGTGAAGAAGGATCTGATCATCAAACTGCC<br>CAAGTACTCCACTGTTCGAACTGGAAAATGGTCGGAAGCGCATGCTGGCTTC<br>GGCCGGAGAACTCCAGAAAGGAAATGAGCTGGCCTTGCCTAGCAAGTACGT<br>CAACTTCCTCTATCTTGCTTCGCACTACGAGAAACTCAAAGGGTCACCGGA<br>AGATAACGAACAGAAGCAGCTTTTCGTGGAGCAGCACAAGCATTATCTGGA<br>TGAAATCATCGAACAAATCTCCGAGTTTTCAAAGCGCGTGATCCTCGCCGA<br>CGCCAACCTCGACAAAGTCCTGTCGGCCTACAATAAGCATAGAGATAAGCC<br>GATCAGAGAACAGGCCGAGAACATTATCCACTTGTTCACCCTGACTAACCT<br>GGGAGCTCCAGCCGCCTTCAAGTACTTCGATACTACTATCGACCGCAAAAG<br>ATACACGTCCACCAAGGAAGTTCTGGACGCGACCCTGATCCACCAAAGCAT<br>CACTGGACTCTACGAAACTAGGATCGATCTGTCGCAGCTGGGTGGCGATGG<br>TGGCGGTGGATCCTACCCATACGACGTGCCTGACTACGCCTCCGGAGGTGG<br>TGGCCCCAAGAAGAAACGGAAGGTGTGATAGCTAGCCATCACATTTAAAAG<br>CATCTCAGCCTACCATGAGAATAAGAGAAAGAAATGAAGATCAATAGCTT<br>ATTCATCTCTTTTTCTTTTTCGTTGGTGTAAAGCCAACACCCTGTCTAAAA<br>AACATAAATTTCTTTAATCATTTTGCCTCTTTTCTCTGTGCTTCAATTAAT<br>AAAAAATGGAAAGAACCTCGAG | |

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| Cas9 transcript with 5' UTR of HSD, ORF corresponding to SEQ ID NO: 245, and 3' UTR of ALB | GGGTCCCGCAGTCGGCGTCCAGCGGCTCTGCTTGTTCGTGTGTGTGTCGTT GCAGGCCTTATTCGGATCTATGGATAAGAAGTACTCGATCGGGCTGGATAT CGGAACTAATTCCGTGGGTTGGGCAGTGATCACGGATGAATACAAAGTGCC GTCCAAGAAGTTCAAGGTCCTGGGGAACACCGATAGACACAGCATCAAGAA GAATCTCATCGGAGCCCTGCTGTTTGACTCCGGCGAAACCGCAGAAGCGAC CCGGCTCAAACGTACCGCGAGGCGACGCTACACCCGGCGGAAGAATCGCAT CTGCTATCTGCAAGAAATCTTTTCGAACGAAATGGCAAAGGTGGACGACAG CTTCTTCCACCGCCTGGAAGAATCTTTCCTGGTGGAGGAGGACAAGAAGCA TGAACGGCATCCTATCTTTTGGAAACATCGTGGACGAAGTGGCGTACCACGA AAAGTACCCGACCATCTACCATCTGCGGAAGAAGTTGGTTGACTCAACTGA CAAGGCCGACCTCAGATTGATCTACTTGGCCCTCGCCCATATGATCAAATT CCGCGGACACTTCCTGATCGAAGGCGATCTGAACCCTGATAACTCCGACGT GGATAAGCTGTTCATTCAACTGGTGCAGACCTACAACCAACTGTTCGAAGA AAACCCAATCAATGCCAGCGGCGTCGATGCCAAGGCCATCCTGTCCGCCCG GCTGTCGAAGTCGCGGCGCCTCGAAACCTGATCGCACAGCTGCCGGGAGA GAAGAAGAACGGACTTTTCGGCAACTTGATCGCTCTCTCACTGGGACTCAC TCCCAATTTCAAGTCCAATTTTGACCTGGCCGAGGACGCGAAGCTGCAACT CTCAAAGGACACCTACGACGACGACTTGGACAATTTGCTGGCACAAATTGG CGATCAGTACGCGGATCTGTTCCTTGCCGCTAAGAACCTTTCGGACGCAAT CTTGCTGTCCGATATCCTGCGCGTGAACACCGAAATAACCAAAGCGCCGCT TAGCGCCTCGATGATTAAGCGGTACGACGAGCATCACCAGGATCTCACGCT GCTCAAAGCGCTCGTGAGACAGCAACTGCCTGAAAAGTACAAGGAGATTTT CTTCGACCAGTCCAAGAATGGGTACGCAGGGTACATCGATGGAGGCGCCAG CCAGGAAGAGTTCTATAAGTTCATCAAGCCAATCCTGGAAAAGATGGACGG AACCGAAGAACTGCTGGTCAAGCTGAACAGGGAGGATCTGCTCCGCAAACA GAGAACCTTTGACAACGGAAGCATTCCACACCAGATCCATCTGGGTGAGCT GCACGCCATCTTGCGGCGCCAGGAGGACTTTTACCCATTCCTCAAGGACAA CCGGGAAAAGATCGAGAAAATTCTGACGTTCCGCATCCCGTATTACGTGGG CCCACTGGCGCGCGGCAATTCGCGCTTCGCGTGGATGACTAGAAAATCAGA GGAAACCATCACTCCTTGGAATTTCGAGGAAGTTGTGGATAAGGGAGCTTC GGCACAATCCTTCATCGAACGAATGACCAACTTCGACAAGAATCTCCCAAA CGAGAAGGTGCTTCCTAAGCACAGCCTCCTTTACGAATACTTCACTGTCTA CAACGAACTGACTAAAGTGAAATACGTTACTGAAGGAATGAGGAAGCCGGC CTTTCTGAGCGGAGAACAGAAGAAAGCGATTGTCGATCTGCTGTTCAAGAC CAACCGCAAGGTGACCGTCAAGCAGCTTAAAGAGGACTACTTCAAGAAGAT CGAGTGTTTCGACTCAGTGGAAATCAGCGGAGTGGAGGACAGATTCAACGC TTCGCTGGGAACCTATCATGATCTCCTGAAGATCATCAAGGACAAGGACTT CCTTGACAACGAGGAGAACGAGGACATCCTGGAAGATATCGTCCTGACCTT GACCCTTTTCGAGGATCGCGAGATGATCGAGGAGAGGCTTAAGACCTACGC TCATCTCTTCGACGATAAGGTCATGAAACAACTCAAGCGCCGCCGGTACAC TGGTTGGGGCCGCCTCTCCCGCAAGCTGATCAACGGTATTCGCGATAAACA GAGCGGTAAAACTATCCTGGATTTCCTCAAATCGGATGGCTTCGCTAATCG TAACTTCATGCAGTTGATCCACGACGACAGCCTGACCTTTAAGGAGGACAT CCAGAAAGCACAAGTGAGCGGACAGGGAGACTCACTCCATGAACACATCGC GAATCTGGCCGGTTCGCCGGCGATTAAGAAGGGAATCCTGCAAACTGTGAA GGTGGTGGACGAGCTGGTGAAGGTCATGGGACGGCACAAACCGGAGAATAT CGTGATTGAAATGGCCCGAGAAAACCAGACTACCCAGAAGGGCCAGAAGCA CTCCCGCGAAAGGATGAAGCGGATCGAAGAAGGAATCAAGGAGCTGGGCAG CCAGATCCTGAAAGAGCACCCGGTGGAAAAACACGCAGCTGCAGAACGAGAA GCTCTACCTGTACTATTTGCAAAATGGACGGGACATGTACGTGGACCAAGA GCTGGACATCAATCGGTTGTCTGATTACGACGTGGACCACATCGTTCCACA GTCCTTTCTGAAGGATGACTCCATCGATAACAAGGTGTTGACTCGCAGCGA CAAGAACAGAGGGAAGTCAGATAATGTGCCATCGGAGGAGGTCGTGAAGAA GATGAAGAATTACTGGCGGCAGCTCCTGAATGCGAAGCTGATTACCCAGAG AAAGTTTGACAATCTCACTAAAGCCGAGCGCGGCGGACTCTCAGAGCTGGA TAAGGCTGGATTCATCAAACGGCAGCTGGTCGAGACTCGGCAGATTACCAA GCACGTGGCGCAGATCCTGGACTCCCGCATGAACACTAAATACGACGAGAA CGATAAGCTCATCCGGGAAGTGAAGGTGATTACCCTGAAAAGCAAACTTGT GTCGGACTTTCGGAAGGACTTTCAGTTTTACAAAGTGAGAGAAATCAACAA CTACCATCACGCGCATGACGCATACCTCAACGCTGTGGTCGGCACCGCCCT GATCAAGAAGTACCCTAAACTTGAATCGGAGTTTGTGTACGGAGACTACAA GGTCTACGACGTGAGGAAGATGATAGCCAAGTCCGAACAGGAAATCGGGAA AGCAACTGCGAAATACTTCTTTTACTCAAACATCATGAACTTCTTCAAGAC TGAAATTACGCTGGCCAATGGAGAAATCAGGAAGAGGCCACTGATCGAAAC TAACGGAGAAACGGGCGAAATCGTGTGGGACAAGGGCAGGGACTTCGCAAC TGTTCGCAAAGTGCTCTCTATGCCGCAAGTCAATATTGTGAAGAAAACCGA AGTGCAAACCGGCGGATTTTCAAAGGAATCGATCCTCCCAAAGAGAAATAG CGACAAGCTCATTGCACGCAAGAAAGACTGGGACCCGAAGAAGTACGGAGG ATTCGATTCGCCGACTGTCGCATACTCCGTCCTCGTGGTGGCCAAGGTGGA GAAGGGAAAGAGCAAGAAGCTCAAATCCGTCAAAGAGCTGCTGGGGATTAC | 247 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CATCATGGAACGATCCTCGTTCGAGAAGAACCCGATTGATTTCCTGGAGGC GAAGGGTTACAAGGAGGTGAAGAAGGATCTGATCATCAAACTGCCCAAGTA CTCACTGTTCGAACTGGAAAATGGTCGGAAGCGCATGCTGGCTTCGGCCGG AGAACTCCAGAAAGGAAATGAGCTGGCCTTGCCTAGCAAGTACGTCAACTT CCTCTATCTTGCTTCGCACTACGAGAAACTCAAAGGGTCACCGGAAGATAA CGAACAGAAGCAGCTTTTCGTGGAGCAGCACAAGCATTATCTGGATGAAAT CATCGAACAAATCTCCGAGTTTTCAAAGCGCGTGATCCTCGCCGACGCCAA CCTCGACAAAGTCCTGTCGGCCTACAATAAGCATAGAGATAAGCCGATCAG AGAACAGGCCGAGAACATTATCCACTTGTTCACCCTGACTAACCTGGGAGC TCCAGCCGCCTTCAAGTACTTCGATACTACTATCGACCGCAAAAGATACAC GTCCACCAAGGAAGTTCTGGACGCGACCCTGATCCACCAAAGCATCACTGG ACTCTACGAAACTAGGATCGATCTGTCGCAGCTGGGTGGCGATGGTGGCGG TGGATCCTACCCATACGACGTGCCTGACTACGCCTCCGGAGGTGGTGGCCC CAAGAAGAAACGGAAGGTGTGATAGCTAGCCATCACATTTAAAAGCATCTC AGCCTACCATGAGAATAAGAGAAAGAAAATGAAGATCAATAGCTTATTCAT CTCTTTTTCTTTTCGTTGGTGTAAAGCCAACACCCTGTCTAAAAACATA AATTTCTTTAATCATTTTGCCTCTTTTCTCTGTGCTTCAATTAATAAAAAA TGGAAAGAACCTCGAG | |
| | Not used | 248 |
| Cas9 transcript comprising Kozak sequence with Cas9 ORF using codons with generally high expression in humans | GGGTCCCGCAGTCGGCGTCCAGCGGCTCTGCTTGTTCGTGTGTGTCGTT GCAGGCCTTATTCGGATCCGCCACCATGCCTAAGAAAAAGCGGAAGGTCGA CGGGGATAAGAAGTACTCAATCGGGCTGGATATCGGAACTAATTCCGTGGG TTGGGCAGTGATCACGGATGAATACAAAGTGCCGTCCAAGAAGTTCAAGGT CCTGGGGAACACCGATAGACACAGCATCAAGAAAAATCTCATCGGAGCCCT GCTGTTTGACTCCGGCGAAACCGCAGAAGCGACCCGGCTCAAACGTACCGC GAGGCGACGCTACACCCGGCGGAAGAATCGCATCTGCTATCTGCAAGAGAT CTTTTCGAACGAAATGGCAAAGGTCGACGACAGCTTCTTCCACCGCCTGGA AGAATCTTTCCTGGTGGAGGAGGACAAGAAGCATGAACGGCATCCTATCTT TGGAAACATCGTCGACGAAGTGGCGTACCACGAAAAGTACCCGACCATCTA CCATCTGCGGAAGAAGTTGGTTGACTCAACTGACAAGGCCGACCTCAGATT GATCTACTTGGCCCTCGCCCATATGATCAAATTCCGCGGACACTTCCTGAT CGAAGGCGATCTGAACCCTGATAACTCCGACGTGGATAAGCTTTTCATTCA ACTGGTGCAGACCTACAACCAACTGTTCGAAGAAAACCCAATCAATGCTAG CGGCGTCGATGCCAAGGCCATCCTGTCCGCCCGGCTGTCGAAGTCGCGGCG CCTCGAAAACCTGATCGCACAGCTGCCGGGAGAGAAAAAGAACGGACTTTT CGGCAACTTGATCGCTCTCTCACTGGGACTCACTCCCAATTTCAAGTCCAA TTTTGACCTGGCCGAGGACGCGAAGCTGCAACTCTCAAAGGACACCTACGA CGACGACTTGGACAATTTGCTGGCACAAATTGGCGATCAGTACGCGGATCT GTTCCTTGCCGCTAAGAACCTTTCGGACGCAATCTTGCTGTCCGATATCCT GCGCGTGAACACCGAAATAACCAAAGCGCCGCTTAGCGCCTCGATGATTAA GCGGTACGACGAGCATCACCAGGATCTCACGCTGCTCAAAGCGCTCGTGAG ACAGCAACTGCCTGAAAAGTACAAGGAGATCTTCTTCGACCAGTCCAAGAA TGGGTACGCAGGGTACATCGATGGAGGCGCTAGCCAGGAAGAGTTCTATAA GTTCATCAAGCCAATCCTGGAAAAGATGGACGGAACCGAAGAACTGCTGGT CAAGCTGAACAGGGAGGATCTGCTCCGGAAACAGAGAACCTTTGACAACGG ATCCATTCCCCACCAGATCCATCTGGGTGAGCTGCACGCCATCTTGCGGCG CCAGGAGGACTTTTACCCATTCCTCAAGGACAACCGGGAAAAGATCGAGAA AATTCTGACGTTCCGCATCCCGTATTACGTGGGCCCACTGGCGCGCGGCAA TTCGCGCTTCGCGTGGATGACTAGAAAATCAGAGGAAACCATCACTCCTTG GAATTTCGAGGAAGTTGTGGATAAGGGAGCTTCGGCACAAAGCTTCATCGA ACGAATGACCAACTTCGACAAGAATCTCCCAAACGAGAAGGTGCTTCCTAA GCACAGCCTCCTTTACGAATACTTCACTGTCTACAACGAACTGACTAAAGT GAAATACGTTACTGAAGGAATGAGGAAGCCGGCCTTTCTGTCCGGAGAACA GAAGAAAGCAATTGTCGATCTGCTGTTCAAGACCAACCGCAAGGTGACCGT CAAGCAGCTTAAAGAGGACTACTTCAAGAAGATCGAGTGTTTCGACTCAGT GGAAATCAGCGGGGTGGAGGACAGATTCAACGCTTCGCTGGGAACCTATCA TGATCTCCTGAAGATCATCAAGGACAAGGACTTCCTTGACAACGAGGAGAA CGAGGACATCCTGGAAGATATCGTCCTGACCTTGACCCTTTTCGAGGATCG CGAGATGATCGAGGAGAGGCTTAAGACCTACGCTCATCTCTTCGACGATAA GGTCATGAAACAACTCAAGCGCCGCCGGTACACTGGTTGGGGCCGCCTCTC CCGCAAGCTGATCAACGGTATTCGCGATAAACAGAGCGGTAAAACTATCCT GGATTTCCTCAAATCGGATGGCTTCGCTAATCGTAACTTCATGCAATTGAT CCACGACGACAGCCTGACCTTTAAGGAGGACATCCAAAAAGCACAAGTGTC CGGACAGGGAGACTCACTCCATGAACACATCGCGAATCTGGCCGGTTCGCC GGCGATTAAGAAGGGAATTCTGCAAACTGTGAAGGTGGTCGACGAGCTGGT GAAGGTCATGGGACGGCACAAACCGGAGAATATCGTGATTGAAATGGCCCG AGAAAACCAGACTACCCAGAAGGGCCAGAAAAACTCCCGCGAAAGGATGAA GCGGATCGAAGAAGGAATCAAGGAGCTGGGCAGCCAGATCCTGAAAGAGCA | 249 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | CCCGGTGGAAAACACGCAGCTGCAGAACGAGAAGCTCTACCTGTACTATTT<br>GCAAAATGGACGGGACATGTACGTGGACCAAGAGCTGGACATCAATCGGTT<br>GTCTGATTACGACGTGGACCACATCGTTCCACAGTCCTTTCTGAAGGATGA<br>CTCGATCGATAACAAGGTGTTGACTCGCAGCGACAAGAACAGAGGGAAGTC<br>AGATAATGTGCCATCGGAGGAGGTCGTGAAGAAGATGAAGAATTACTGGCG<br>GCAGCTCCTGAATGCGAAGCTGATTACCCAGAGAAAGTTTGACAATCTCAC<br>TAAAGCCGAGCGCGGCGGACTCTCAGAGCTGGATAAGGCTGGATTCATCAA<br>ACGGCAGCTGGTCGAGACTCGGCAGATTACCAAGCACGTGGCGCAGATCTT<br>GGACTCCCGCATGAACACTAAATACGACGAGAACGATAAGCTCATCCGGGA<br>AGTGAAGGTGATTACCCTGAAAAGCAAACTTGTGTCGGACTTTCGGAAGGA<br>CTTTCAGTTTTACAAAGTGAGAGAAATCAACAACTACCATCACGCGCATGA<br>CGCATACCTCAACGCTGTGGTCGGTACCGCCCTGATCAAAAAGTACCCTAA<br>ACTTGAATCGGAGTTTGTGTACGGAGACTACAAGGTCTACGACGTGAGGAA<br>GATGATAGCCAAGTCCGAACAGGAAATCGGGAAAGCAACTGCGAAATACTT<br>CTTTTACTCAAACATCATGAACTTTTTCAAGACTGAAATTACGCTGGCCAA<br>TGGAGAAATCAGGAAGAGGCCACTGATCGAAACTAACGGAGAAACGGGCGA<br>AATCGTGTGGGACAAGGGCAGGGACTTCGCAACTGTTCGCAAAGTGCTCTC<br>TATGCCGCAAGTCAATATTGTGAAGAAAACCGAAGTGCAAACCGGCGGATT<br>TTCAAAGGAATCGATCCTCCCAAAGAGAAATAGCGACAAGCTCATTGCACG<br>CAAGAAAGACTGGGACCCGAAGAAGTACGGAGGATTCGATTCGCCGACTGT<br>CGCATACTCCGTCCTCGTGGTGGCCAAGGTGGAGAAGGGAAAGAGCAAAGA<br>GCTCAAATCCGTCAAAGAGCTGCTGGGGATTACCATCATGGAACGATCCTC<br>GTTCGAGAAGAACCCGATTGATTTCCTCGAGGCGAAGGGTTACAAGGAGGT<br>GAAGAAGGATCTGATCATCAAACTCCCCAAGTACTCACTGTTCGAACTGGA<br>AAATGGTCGGAAGCGCATGCTGGCTTCGGCCGGAGAACTCCAAAAAGGAAA<br>TGAGCTGGCCTTGCCTAGCAAGTACGTCAACTTCCTCTATCTTGCTTCGCA<br>CTACGAAAAACTCAAAGGGTCACCGGAAGATAACGAACAGAAGCAGCTTTT<br>CGTGGAGCAGCACAAGCATTATCTGGATGAAATCATCGAACAAATCTCCGA<br>GTTTTCAAAGCGCGTGATCCTCGCCGACGCCAACCTCGACAAAGTCCTGTC<br>GGCCTACAATAAGCATAGAGATAAGCCGATCAGAGAACAGGCCGAGAACAT<br>TATCCACTTGTTCACCCTGACTAACCTGGGAGCCCCAGCCGCCTTCAAGTA<br>CTTCGATACTACTATCGATCGCAAAAGATACACGTCCACCAAGGAAGTTCT<br>GGACGCGACCCTGATCCACCAAAGCATCACTGGACTCTACGAAACTAGGAT<br>CGATCTGTCGCAGCTGGGTGGCGATTGATAGTCTAGCCATCACATTTAAAA<br>GCATCTCAGCCTACCATGAGAATAAGAGAAAGAAAATGAAGATCAATAGCT<br>TATTCATCTCTTTTTCTTTTTCGTTGGTGTAAAGCCAACACCCTGTCTAAA<br>AAACATAAATTTCTTTAATCATTTTGCCTCTTTTCTCTGTGCTTCAATTAA<br>TAAAAAATGGAAAGAACCTCGAG | |
| Cas9 ORF<br>with splice<br>junctions<br>removed;<br>12.75% U<br>content | ATGGACAAGAAGTACAGCATCGGACTGGACATCGGAACAAACAGCGTCGGA<br>TGGGCAGTCATCACAGACGAATACAAGGTCCCGAGCAAGAAGTTCAAGGTC<br>CTGGGAAACACAGACAGACACAGCATCAAGAAGAACCTGATCGGACACTG<br>CTGTTCGACAGCGGAGAAAACAGCAGAAGCAACAAGACTGAAGAGAACAGCA<br>AGAAGAAGATACACAAGAAGAAAGAACAGAATCTGCTACCTGCAGGAAATC<br>TTCAGCAACGAAATGGCAAAGGTCGACGACAGCTTCTTCCACcggCTGGAA<br>GAAAGCTTCCTGGTCGAAGAAGACAAGAAGCACGAAAGACACCCGATCTTC<br>GGAAACATCGTCGACGAAGTCGCATACCACGAAAAGTACCCGACAATCTAC<br>CACCTGAGAAAGAAGCTGGTCGACAGCACAGACAAGGCAGACCTGAGACTG<br>ATCTACCTGGCACTGGCACACATGATCAAGTTCAGAGGACACTTCCTGATC<br>GAAGGAGACCTGAACCCGGACAACAGCGACGTCGACAAGCTGTTCATCCAG<br>CTGGTCCAGACATACAACCAGCTGTTCGAAGAAAACCCGATCAACGCAAGC<br>GGAGTCGACGCAAAGGCAATCCTGAGCGCAAGACTGAGCAAGAGCAGAAGA<br>CTGGAAAACCTGATCGCACAGCTGCCGGGAGAAAAGAAGAACGGACTGTTC<br>GGAAACCTGATCGCACTGAGCCTGGGACTGACACCGAACTTCAAGAGCAAC<br>TTCGACCTGGCAGAAGACGCAAAGCTGCAGCTGAGCAAGGACACATACGAC<br>GACGACCTGGACAACCTGCTGGCACAGATCGGAGACCAGTACGCAGACCTG<br>TTCCTGGCAGCAAAGAACCTGAGCGACGCAATCCTGCTGAGCGACATCCTG<br>AGAGTCAACACAGAAATCACAAAGGCACCGCTGAGCGCAAGCATGATCAAG<br>AGATACGACGAACACCACCAGGACCTGACACTGCTGAAGGCACTGGTCAGA<br>CAGCAGCTGCCGGAAAAGTACAAGGAAATCTTCTTCGACCAGAGCAAGAAC<br>GGATACGCAGGATACATCGACGGAGGAGCAAGCCAGGAAGAATTCTACAAG<br>TTCATCAAGCCGATCCTGGAAAAGATGGACGGAACAGAAGAACTGCTGGTC<br>AAGCTGAACAGAGAAGACCTGCTGAGAAAGCAGAGAACATTCGACAACGGA<br>AGCATCCCGCACCAGATCCACCTGGGAGAACTGCACGCAATCCTGAGAAGA<br>CAGGAAGACTTCTACCCGTTCCTGAAGGACAACAGAGAAAAGATCGAAAAG<br>ATCCTGACATTCAGAATCCCGTACTACGTCGGACCGCTGGCAAGAGGAAAC<br>AGCAGATTCGCATGGATGACAAGAAAGAGCGAAGAAACAATCACACCGTGG<br>TACTTCGAAGAAGTCGTCGACAAGGGAGCAAGCGCACAGAGCTTCATCGAA<br>AGTATGACTAACTTCGACTAGTACCTGCCGTACGTATAGGTCCTGCCGTAG<br>CACAGCCTGCTGTACGTATACTTCACAGTCTACTACGTACTGACTAAGGTC | 250 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | TAGTACGTCACAGTAGGTATGAGTAAGCCGGCATTCCTGAGCGGAGTACAG<br>TAGTAGGCTATCGTCGACCTGCTGTTCTAGACTAACAGTAAGGTCACAGTC<br>TAGCAGCTGTAGGTAGACTACTTCTAGTAGATCGTATGCTTCGACAGCGTC<br>GTAATCAGCGGAGTCGTAGACAGATTCTACGCTAGCCTGGGTACATACCAC<br>GACCTGCTGTAGATCATCTAGGACTAGGACTTCCTGGACTACGTAGTATAC<br>GTAGACATCCTGGTAGACATCGTCCTGACACTGACACTGTTCGTAGACAGA<br>GTAATGATCGTAGTAAGACTGTAGACATACGCACACCTGTTCGACGACTAG<br>GTCATGTAGCAGCTGTAGAGTAGTAGATACACAGGATGGGGTAGACTGAGC<br>AGAAAGCTGATCAACGGAATCAGAGACAAGCAGAGCGGAAAGACAATCCTG<br>GACTTCCTGTAGAGCGACGGATTCGCTAACAGTAACTTCATGCAGCTGATC<br>CACGACGACAGCCTGACATTCAAGGAAGACATCCAGAAGGCACAGGTCAGC<br>GGACAGGGAGACAGCCTGCACGAACACATCGCAAACCTGGCAGGAAGCCCG<br>GCAATCAAGAAGGGAATCCTGCAGACAGTCAAGGTCGTCGACGAACTGGTC<br>AAGGTCATGGGAAGACACAAGCCGGAAAACATCGTCATCGAAATGGCAAGA<br>GAAACCAGACAACACAGAAGGGACAGAAGAACAGCAGAGAAGAATGAAG<br>AGAATCGAAGAAGGAATCAAGGAACTGGGAAGCCAGATCCTGAAGGAACAC<br>CCGGTCGAAAACACACAGCTGCAGAACGAAAAGCTGTACCTGTACTACCTG<br>CAaAACGGAAGAGACATGTACGTCGACCAGGAACTGGACATCAACAGACTG<br>AGCGACTACGACGTCGACCACATCGTCCCGCAGAGCTTCCTGAAGGACGAC<br>AGCATCGACAACAAGGTCCTGACAAGAAGCGACAAGAACAGAGGAAAGAGC<br>GACAACGTCCCGAGCGAAGAAGTCGTCAAGAAGATGAAGAACTACTGGAGA<br>CAGCTGCTGAACGCAAAGCTGATCACACAGAGAAAGTTCGACAACCTGACA<br>AAGGCAGAGAGGAGGACTGAGCGAACTGGACAAGGCAGGATTCATCAAG<br>AGACAGCTGGTCGAAACAAGACAGATCACAAAGCACGTCGCACAGATCCTG<br>GACAGCAGAATGAACACAAAGTACGACGAAAACGACAAGCTGATCAGAGAA<br>GTCAAGGTCATCACACTGAAGAGCAAGCTGGTCAGCGACTTCAGAAAGGAC<br>TTCCAGTTCTACAAGGTCAGAGAAATCAACAACTACCACCACGCACACGAC<br>GCATACCTGAACGCAGTCGTCGGAACAGCACTGATCAAGAAGTACCCGAAG<br>CTGGAAAGCGAATTCGTCTACGGAGACTACAAGGTCTACGACGTCAGAAAG<br>ATGATCGCAAAGAGCGAACAGGAAATCGGAAAGGCAACAGCAAAGTACTTC<br>TTCTACAGCAACATCATGAACTTCTTCAAGACAGAAATCACACTGGCAAAC<br>GGAGAAATCAGAAAGAGACCGCTGATCGAAACAAACGGAGAAACAGGAGAA<br>ATCGTCTGGGACAAGGGAAGAGACTTCGCAACAGTCAGAAAGGTCCTGAGC<br>ATGCCGCAGGTCAACATCGTCAAGAAGACAGAAGTCCAGACAGGAGGATTC<br>AGCAAGGAAAGCATCCTGCCGAAGAGAAACAGCGACAAGCTGATCGCAAGA<br>AAGAAGGACTGGGACCCGAAGAAGTACGGAGGATTCGACAGCCCGACAGTC<br>GCATACAGCGTCCTGGTCGTCGCAAAGGTCGAAAAGGGAAAGAGCAAGAAG<br>CTGAAGAGCGTCAAGGAACTGCTGGGAATCACAATCATGGAAGAAGCAGC<br>TTCGAAAAGAACCCGATCGACTTCCTGGAAGCAAAGGGATACAAGGAAGTC<br>AAGAAGGACCTGATCATCAAGCTGCCGAAGTACAGCCTGTTCGAACTGGAA<br>AACGGAAGAAAGAGAATGCTGGCAAGCGCAGGAGAACTGCAGAAGGGAAAC<br>GAACTGGCACTGCCGAGCAAGTACGTCAACTTCCTGTACCTGGCAAGCCAC<br>TACGAAAAGCTGAAGGGAAGCCCGGAAGACAACGAACAGAAGCAGCTGTTC<br>GTCGAACAGCACAAGCACTACCTGGACGAAATCATCGAACAGATCAGCGAA<br>TTCAGCAAGAGAGTCATCCTGGCAGACGCAAACCTGGACAAGGTCCTGAGC<br>GCATACAACAAGCACAGAGACAAGCCGATCAGAGAACAGGCAGAAAACATC<br>ATCCACCTGTTCACACTGACAAACCTGGGAGCACCGGCAGCATTCAAGTAC<br>TTCGACACAACAATCGACAGAAAGAGATACACAAGCACAAGGAAGTCCTG<br>GACGCAACACTGATCCACCAGAGCATCACAGGACTGTACGAAACAAGAATC<br>GACCTGAGCCAGCTGGGAGGAGACGGAGGAGGAAGCCCGAAGAAGAAGAGA<br>AAGGTCTAG | |
| Cas9 transcript with 5' UTR of HSD, ORF corresponding to SEQ ID NO: 250, Kozak sequence, and 3' UTR of ALB | GGGTCCCGCAGTCGGCGTCCAGCGGCTCTGCTTGTTCGTGTGTGTGTCGTT<br>GCAGGCCTTATTCGGATCCGCCACCATGGACAAGAAGTACAGCATCGGACT<br>GGACATCGGAACAAACAGCGTCGGATGGGCAGTCATCACAGACGAATACAA<br>GGTCCCGAGCAAGAAGTTCAAGGTCCTGGGAAACACAGACAGACACAGCAT<br>CAAGAAGAACCTGATCGGAGCACTGCTGTTCGACAGCGGAGAAACAGCAGA<br>AGCAACAAGACTGAAGAGAACAGCAAGAAGAAGATACACAAGAAGAAAGAA<br>CAGAATCTGCTACCTGCAGGAAATCTTCAGCAACGAAATGGCAAAGGTCGA<br>CGACAGCTTCTTCCACcggCTGGAAGAAAAGCTTCCTGGTCGAAGAAGACAA<br>GAAGCACGAAAGACACCCGATCTTCGGAAACATCGTCGACGAAGTCGCATA<br>CCACGAAAAGTACCCGACAATCTACCACCTGAGAAAGAAGCTGGTCGACAG<br>CACAGACAAGGCAGACCTGAGACTGATCTACCTGGCACTGGCACACATGAT<br>CAAGTTCAGAGGACACTTCCTGATCGAAGGAGACCTGAACCCGGACAACAG<br>CGACGTCGACAAGCTGTTCATCCAGCTGGTCCAGACATACAACCAGCTGTT<br>CGAAGAAACCCGATCAACGCAAGCGGAGTCGACGCAAAGGCAATCCTGAG<br>CGCAAGACTGAGCAAGAGCAGAAGACTGGAAAACCTGATCGCACAGCTGCC<br>GGGAGAAAAGAAGAACGGACTGTTCGGAAACCTGATCGCACTGAGCCTGGG<br>ACTGACACCGAACTTCAAGAGCAACTTCGACCTGGCAGAAGACGCAAAGCT<br>GCAGCTGAGCAAGGACACATACGACGACGACCTGGACAACCTGCTGGCACA | 251 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GATCGGAGACCAGTACGCAGACCTGTTCCTGGCAGCAAAGAACCTGAGCGA<br>CGCAATCCTGCTGAGCGACATCCTGAGAGTCAACACAGAAATCACAAAGGC<br>ACCGCTGAGCGCAAGCATGATCAAGAGATACGACGAACACCACCAGGACCT<br>GACACTGCTGAAGGCACTGGTCAGACAGCAGCTGCCGGAAAAGTACAAGGA<br>AATCTTCTTCGACCAGAGCAAGAACGGATACGCAGGATACATCGACGGAGG<br>AGCAAGCCAGGAAGAATTCTACAAGTTCATCAAGCCGATCCTGGAAAAGAT<br>GGACGGAACAGAAGAACTGCTGGTCAAGCTGAACAGAGAAGACCTGCTGAG<br>AAAGCAGAGAACATTCGACAACGGAAGCATCCCGCACCAGATCCACCTGGG<br>AGAACTGCACGCAATCCTGAGAAGACAGGAAGACTTCTACCCGTTCCTGAA<br>GGACAACAGAGAAAAGATCGAAAAGATCCTGACATTCAGAATCCCGTACTA<br>CGTCGGACCGCTGGCAAGAGGAAACAGCAGATTCGCATGGATGACAAGAAA<br>GAGCGAAGAAACAATCACACCGTGGAACTTCGAAGAAGTCGTCGACAAGGG<br>AGCAAGCGCACAGAGCTTCATCGAAAGAATGACAAACTTCGACAAGAACCT<br>GCCGAACGAAAAGGTCCTGCCGAAGCACAGCCTGCTGTACGAATACTTCAC<br>AGTCTACAACGAACTGACAAAGGTCAAGTACGTCACAGAAGGAATGAGAAA<br>GCCGGCATTCCTGAGCGGAGAACAGAAGAAGGCAATCGTCGACCTGCTGTT<br>CAAGACAAACAGAAAGGTCACAGTCAAGCAGCTGAAGGAAGACTACTTCAA<br>GAAGATCGAATGCTTCGACAGCGTCGAAATCAGCGGAGTCGAAGACAGATT<br>CAACGCAAGCCTGGGAACATACCACGACCTGCTGAAGATCATCAAGGACAA<br>GGACTTCCTGGACAACGAAGAAAACGAAGACATCCTGGAAGACATCGTCCT<br>GACACTGACACTGTTCGAAGACAGAGAAATGATCGAAGAAAGACTGAAGAC<br>ATACGCACACCTGTTCGACGACAAGGTCATGAAGCAGCTGAAGAGAAGAAG<br>ATACACAGGATGGGAAGACTGAGCAGAAAGCTGATCAACGGAATCAGAGA<br>CAAGCAGAGCGGAAAGACAATCCTGGACTTCCTGAAGAGCGACGGATTCGC<br>AAACAGAAACTTCATGCAGCTGATCCACGACGACAGCCTGACATTCAAGGA<br>AGACATCCAGAAGGCACAGGTCAGCGGACAGGGAGACAGCCTGCACGAACA<br>CATCGCAAACCTGGCAGGAAGCCCGGCAATCAAGAAGGGAATCCTGCAGAC<br>AGTCAAGGTCGTCGACGAACTGGTCAAGGTCATGGGAAGACACAAGCCGGA<br>AAACATCGTCATCGAAATGGCAAGAGAAAACCAGACAACACAGAAGGGACA<br>GAAGAACAGCAGAGAAGAATGAAGAGAATCGAAGAAGGAATCAAGGAACT<br>GGGGAAGCCAGATCCTGAAGGAACACCCGGTCGAAAACACACAGCTGCAGAA<br>CGAAAAGCTGTACCTGTACTACCTGCAaAACGGAAGAGACATGTACGTCGA<br>CCAGGAACTGGACATCAACAGACTGAGCGACTACGACGTCGACCACATCGT<br>CCCGCAGAGCTTCCTGAAGGACGACAGCATCGACAACAAGGTCCTGACAAG<br>AAGCGACAAGAACAGAGGAAAGAGCGACAACGTCCCGAGCGAAGAAGTCGT<br>CAAGAAGATGAAGAACTACTGGAGACAGCTGCTGAACGCAAAGCTGATCAC<br>ACAGAGAAAGTTCGACAACCTGACAAAGGCAGAGAGAGGAGGACTGAGCGA<br>ACTGGACAAGGCAGGATTCATCAAGAGACAGCTGGTCGAAACAAGACAGAT<br>CACAAAGCACGTCGCACAGATCCTGGACAGCAGAATGAACACAAAGTACGA<br>CGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAAT<br>CAACAACTACCACCACGCACACGACGCATACCTGAACGCAGTCGTCGGAAC<br>AGCACTGATCAAGAAGTACCCGAAGCTGGAAAGCGAATTCGTCTACGGAGA<br>CTACAAGGTCTACGACGTCAGAAAGATGATCGCAAAGAGCGAACAGGAAAT<br>CGGAAAGGCAACAGCAAAGTACTTCTTCTACAGCAACATCATGAACTTCTT<br>CAAGACAGAAATCACACTGGCAAACGGAGAAATCAGAAAGAGACCGCTGAT<br>CGAAACAAACGGAGAAACAGGAGAAATCGTCTGGGACAAGGGAAGAGACTT<br>CGCAACAGTCAGAAAGGTCCTGAGCATGCCGCAGGTCAACATCGTCAAGAA<br>GACAGAAGTCCAGACAGGAGGATTCAGCAAGGAAAGCATCCTGCCGAAGAG<br>AAACAGCGACAAGCTGATCGCAAGAAAGAAGGACTGGGACCCGAAGAAGTA<br>CGGAGGATTCGACAGCCCGACAGTCGCATACAGCGTCCTGGTCGTCGCAAA<br>GGTCGAAAAGGGAAAGAGCAAGAAGCTGAAGAGCGTCAAGGAACTGCTGGG<br>AATCACAATCATGGAAAGAAGCAGCTTCGAAAAGAACCCGATCGACTTCCT<br>GGAAGCAAAGGGATACAAGGAAGTCAAGAAGGACCTGATCATCAAGCTGCC<br>GAAGTACAGCCTGTTCGAACTGGAAAACGGAAGAAAGAGAATGCTGGCAAG<br>CGCAGGAGAACTGCAGAAGGGAAACGAACTGGCACTGCCGAGCAAGTACGT<br>CAACTTCCTGTACCTGGCAAGCCACTACGAAAAGCTGAAGGGAAGCCCGGA<br>AGACAACGAACAGAAGCAGCTGTTCGTCGAACAGCACAAGCACTACCTGGA<br>CGAAATCATCGAACAGATCAGCGAATTCAGCAAGAGAGTCATCCTGGCAGA<br>CGCAAACCTGGACAAGGTCCTGAGCGCATACAACAAGCACAGAGACAAGCC<br>GATCAGAGAACAGGCAGAAAACATCATCCACCTGTTCACACTGACAAACCT<br>GGGAGCACCGGCAGCATTCAAGTACTTCGACACAACAATCGACAGAAAGAG<br>ATACACAAGCACAAAGGAAGTCCTGGACGCAACACTGATCCACCAGAGCAT<br>CACAGGACTGTACGAAACAAGAATCGACCTGAGCCAGCTGGGAGGAGACGG<br>AGGAGGAAGCCCGAAGAAGAAGAGAAAGGTCTAGCTAGCCATCACATTTAA<br>AAGCATCTCAGCCTACCATGAGAATAAGAGAAAGAAAATGAAGATCAATAG<br>CTTATTCATCTCTTTTTCTTTTTCGTTGGTGTAAAGCCAACACCCTGTCTA<br>AAAAACATAAATTTCTTTAATCATTTTGCCTCTTTTCTCTGTGCTTCAATT<br>AATAAAAAATGGAAAGAACCTCGAG | |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| Cas9 ORF with minimal uridine codons frequently used in humans in general; 12.75% U content | ATGGACAAGAAGTACAGCATCGGCCTGGACATCGGCACCAACAGCGTGGGC TGGGCCGTGATCACCGACGAGTACAAGGTGCCCAGCAAGAAGTTCAAGGTG CTGGGCAACACCGACAGACACAGCATCAAGAAGAACCTGATCGGCGCCCTG CTGTTCGACAGCGGCGAGACCGCCGAGGCCACCAGACTGAAGAGAACCGCC AGAAGAAGATACACCAGAAGAAAGAACAGAATCTGCTACCTGCAGGAGATC TTCAGCAACGAGATGGCCAAGGTGGACGACAGCTTCTTCCACAGACTGGAG GAGAGCTTCCTGGTGGAGGAGGACAAGAAGCACGAGAGACACCCCATCTTC GGCAACATCGTGGACGAGGTGGCCTACCACGAGAAGTACCCCACCATCTAC CACCTGAGAAAGAAGCTGGTGGACAGCACCGACAAGGCCGACCTGAGACTG ATCTACCTGGCCCTGGCCCACATGATCAAGTTCAGAGGCCACTTCCTGATC GAGGGCGACCTGAACCCCGACAACAGCGACGTGGACAAGCTGTTCATCCAG CTGGTGCAGACCTACAACCAGCTGTTCGAGGAGAACCCCATCAACGCCAGC GGCGTGGACCGCAAGGCCATCCTGAGCGCCAGACTGAGCAAGAGCAGAAGA CTGGAGAACCTGATCGCCCAGCTGCCCGGCGAGAAGAAGAACGGCCTGTTC GGCAACCTGATCGCCCTGAGCCTGGGCCTGACCCCCAACTTCAAGAGCAAC TTCGACCTGGCCGAGGACGCCAAGCTGCAGCTGAGCAAGGACACCTACGAC GACGACCTGGACAACCTGCTGGCCCAGATCGGCGACCAGTACGCCGACCTG TTCCTGGCCGCCAAGAACCTGAGCGACGCCATCCTGCTGAGCGACATCCTG AGAGTGAACACCGAGATCACCAAGGCCCCCCTGAGCGCCAGCATGATCAAG AGATACGACGAGCACCACCAGGACCTGACCCTGCTGAAGGCCCTGGTGAGA CAGCAGCTGCCCGAGAAGTACAAGGAGATCTTCTTCGACCAGAGCAAGAAC GGCTACGCCGGCTACATCGACGGCGGCGCCAGCCAGGAGGAGTTCTACAAG TTCATCAAGCCCATCCTGGAGAAGATGGACGGCACCGAGGAGCTGCTGGTG AAGCTGAACAGAGAGGACCTGCTGAGAAAGCAGAGAACCTTCGACAACGGC AGCATCCCCCACCAGATCCACCTGGGCGAGCTGCACGCCATCCTGAGAAGA CAGGAGGACTTCTACCCCTTCCTGAAGGACAACAGAGAGAAGATCGAGAAG ATCCTGACCTTCAGAATCCCCTACTACGTGGGCCCCCTGGCCAGAGGCAAC AGCAGATTCGCCTGGATGACCAGAAAGAGCGAGGAGACCATCACCCCCTGG AACTTCGAGGAGGTGGTGGACAAGGGCGCCAGCGCCCAGAGCTTCATCGAG AGAATGACCAACTTCGACAAGAACCTGCCCAACGAGAAGGTGCTGCCCAAG CACAGCCTGCTGTACGAGTACTTCACCGTGTACAACGAGCTGACCAAGGTG AAGTACGTGACCGAGGGCATGAGAAAGCCCGCCTTCCTGAGCGGCGAGCAG AAGAAGGCCATCGTGGACCTGCTGTTCAAGACCAACAGAAAGGTGACCGTG AAGCAGCTGAAGGAGGACTACTTCAAGAAGATCGAGTGCTTCGACAGCGTG GAGATCAGCGGCGTGGAGGACAGATTCAACGCCAGCCTGGGCACCTACCAC GACCTGCTGAAGATCATCAAGGACAAGGACTTCCTGGACAACGAGGAGAAC GAGGACATCCTGGAGGACATCGTGCTGACCCTGACCCTGTTCGAGGACAGA GAGATGATCGAGGAGAGACTGAAGACCTACGCCCACCTGTTCGACGACAAG GTGATGAAGCAGCTGAAGAGAAGAAGATACACCGGCTGGGGCAGACTGAGC AGAAAGCTGATCAACGGCATCAGAGACAAGCAGAGCGGCAAGACCATCCTG GACTTCCTGAAGAGCGACGGCTTCGCCAACAGAAACTTCATGCAGCTGATC CACGACGACAGCCTGACCTTCAAGGAGGACATCCAGAAGGCCCAGGTGAGC GGCCAGGGCGACAGCCTGCACGAGCACATCGCCAACCTGGCCGGCAGCCCC GCCATCAAGAAGGGCATCCTGCAGACCGTGAAGGTGGTGGACGAGCTGGTG AAGGTGATGGGCAGACACAAGCCCGAGAACATCGTGATCGAGATGGCCAGA GAGAACCAGACCACCCAGAAGGGCCAGAAGAACAGCAGAGAGAGAATGAAG AGAATCGAGGAGGGCATCAAGGAGCTGGGCAGCCAGATCCTGAAGGAGCAC CCCGTGGAGAACACCCAGCTGCAGAACGAGAAGCTGTACCTGTACTACCTG CAGAACGGCAGAGACATGTACGTGGACCAGGAGCTGGACATCAACAGACTG AGCGACTACGACGTGGACCACATCGTGCCCCAGAGCTTCCTGAAGGACGAC AGCATCGACAACAAGGTGCTGACCAGAAGCGACAAGAACAGAGGCAAGAGC GACAACGTGCCCAGCGAGGAGGTGGTGAAGAAGATGAAGAACTACTGGAGA CAGCTGCTGAACGCCAAGCTGATCACCCAGAGAAAGTTCGACAACCTGACC AAGGCCGAGAGAGGCGGCCTGAGCGAGCTGGACAAGGCCGGCTTCATCAAG AGACAGCTGGTGGAGACCAGACAGATCACCAAGCACGTGGCCCAGATCCTG GACAGCAGAATGAACACCAAGTACGACGAGAACGACAAGCTGATCAGAGAG GTGAAGGTGATCACCCTGAAGAGCAAGCTGGTGAGCGACTTCAGAAAGGAC TTCCAGTTCTACAAGGTGAGAGAGATCAACAACTACCACCACGCCCACGAC GCCTACCTGAACGCCGTGGTGGGCACCGCCCTGATCAAGAAGTACCCCAAG CTGGAGAGCGAGTTCGTGTACGGCGACTACAAGGTGTACGACGTGAGAAAG ATGATCGCCAAGAGCGAGCAGGAGATCGGCAAGGCCACCGCCAAGTACTTC TTCTACAGCAACATCATGAACTTCTTCAAGACCGAGATCACCCTGGCCAAC GGCGAGATCAGAAAGAGACCCCTGATCGAGACCAACGGCGAGACCGGCGAG ATCGTGTGGGACAAGGGCAGAGACTTCGCCACCGTGAGAAAGGTGCTGAGC ATGCCCCAGGTGAACATCGTGAAGAAGACCGAGGTGCAGACCGGCGGCTTC AGCAAGGAGAGCATCCTGCCCAAGAGAAACAGCGACAAGCTGATCGCCAGA AAGAAGGACTGGGACCCCAAGAAGTACGGCGGCTTCGACAGCCCCACCGTG GCCTACAGCGTGCTGGTGGTGGCCAAGGTGGAGAAGGGCAAGAGCAAGAAG CTGAAGAGCGTGAAGGAGCTGCTGGGCATCACCATCATGGAGAGAAGCAGC TTCGAGAAGAACCCCATCGACTTCCTGGAGGCCAAGGGCTACAAGGAGGTG | 252 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | AAGAAGGACCTGATCATCAAGCTGCCCAAGTACAGCCTGTTCGAGCTGGAG AACGGCAGAAAGAGAATGCTGGCCAGCGCCGGCGAGCTGCAGAAGGGCAAC GAGCTGGCCCTGCCCAGCAAGTACGTGAACTTCCTGTACCTGGCCAGCCAC TACGAGAAGCTGAAGGGCAGCCCCGAGGACAACGAGCAGAAGCAGCTGTTC GTGGAGCAGCACAAGCACTACCTGGACGAGATCATCGAGCAGATCAGCGAG TTCAGCAAGAGAGTGATCCTGGCCGACGCCAACCTGGACAAGGTGCTGAGC GCCTACAACAAGCACAGAGACAAGCCCATCAGAGAGCAGGCCGAGAACATC ATCCACCTGTTCACCCTGACCAACCTGGGCGCCCCCGCCGCCTTCAAGTAC TTCGACACCACCATCGACAGAAAGAGATACACCAGCACCAAGGAGGTGCTG GACGCCACCCTGATCCACCAGAGCATCACCGGCCTGTACGAGACCAGAATC GACCTGAGCCAGCTGGGCGGCGACGGCGGCGGCAGCCCCAAGAAGAAGAGA AAGGTGTGA | |
| Cas9 transcript with 5' UTR of HSD, ORF corresponding to SEQ ID NO: 252, Kozak sequence, and 3' UTR of ALB | GGGTCCCGCAGTCGGCGTCCAGCGGCTCTGCTTGTTCGTGTGTGTCGTT GCAGGCCTTATTCGGATCCGCCACCATGGACAAGAAGTACAGCATCGGCCT GGACATCGGCACCAACAGCGTGGGCTGGGCCGTGATCACCGACGAGTACAA GGTGCCCAGCAAGAAGTTCAAGGTGCTGGGCAACACCGACAGACACAGCAT CAAGAAGAACCTGATCGGCGCCCTGCTGTTCGACAGCGGCGAGACCGCCGA GGCCACCAGACTGAAGAGAACCGCCAGAAGAAGATACACCAGAAGAAGAA CAGAATCTGCTACCTGCAGGAGATCTTCAGCAACGAGATGGCCAAGGTGGA CGACAGCTTCTTCCACAGACTGGAGGAGTCCTTCCTGGTGGAGGAGGACAA GAAGCACGAGAGACACCCCATCTTCGGCAACATCGTGGACGAGGTGGCCTA CCACGAGAAGTACCCCACCATCTACCACCTGAGAAAGAAGCTGGTGGACAG CACCGACAAGGCCGACCTGAGACTGATCTACCTGGCCCTGGCCCACATGAT CAAGTTCAGAGGCCACTTCCTGATCGAGGGCGACCTGAACCCCGACAACAG CGACGTGGACAAGCTGTTCATCCAGCTGGTGCAGACCTACAACCAGCTGTT CGAGGAGAACCCCATCAACGCCAGCGGCGTGGACGCCAAGGCCATCCTGAG CGCCAGACTGAGCAAGAGCAGAAGACTGGAGAACCTGATCGCCCAGCTGCC CGGCGAGAAGAAGAACGGCCTGTTCGGCAACCTGATCGCCCTGAGCCTGGG CCTGACCCCCAACTTCAAGAGCAACTTCGACCTGGCCGAGGACGCCAAGCT GCAGCTGAGCAAGGACACCTACGACGACGACCTGGACAACCTGCTGGCCCA GATCGGCGACCAGTACGCCGACCTGTTCCTGGCCGCCAAGAACCTGAGCGA CGCCATCCTGCTGAGCGACATCCTGAGAGTGAACACCGAGATCACCAAGGC CCCCCTGAGCGCCAGCATGATCAAGAGATACGACGAGCACCACCAGGACCT GACCCTGCTGAAGGCCCTGGTGAGACAGCAGCTGCCCGAGAAGTACAAGGA GATCTTCTTCGACCAGAGCAAGAACGGCTACGCCGGCTACATCGACGGCGG CGCCAGCCAGGAGGAGTTCTACAAGTTCATCAAGCCCATCCTGGAGAAGAT GGACGGCACCGAGGAGCTGCTGGTGAAGCTGAACAGAGAGGACCTGCTGAG AAAGCAGAGAACCTTCGACAACGGCAGCATCCCCCACCAGATCCACCTGGG CGAGCTGCACGCCATCCTGAGAAGACAGGAGGACTTCTACCCCTTCCTGAA GGACAACAGAGAGAAGATCGAGAAGATCCTGACCTTCAGAATCCCCTACTA CGTGGGCCCCCTGGCCAGAGGCAACAGCAGATTCGCCTGGATGACCAGAAA GAGCGAGGAGACCATCACCCCCTGGAACTTCGAGGAGGTGGTGGACAAGGG CGCCAGCGCCCAGAGCTTCATCGAGAGAATGACCAACTTCGACAAGAACCT GCCCAACGAGAAGGTGCTGCCCAAGCACAGCCTGCTGTACGAGTACTTCAC CGTGTACAACGAGCTGACCAAGGTGAAGTACGTGACCGAGGGCATGAGAAA GCCCGCCTTCCTGAGCGGCGAGCAGAAGAAGGCCATCGTGGACCTGCTGTT CAAGACCAACAGAAAGGTGACCGTGAAGCAGCTGAAGGAGGACTACTTCAA GAAGATCGAGTGCTTCGACAGCGTGGAGATCAGCGGCGTGGAGGACAGATT CAACGCCAGCCTGGGCACCTACCACGACCTGCTGAAGATCATCAAGGACAA GGACTTCCTGGACAACGAGGAGAACGAGGACATCCTGGAGGACATCGTGCT GACCCTGACCCTGTTCGAGGACAGAGAGATGATCGAGGAGAGACTGAAGAC CTACGCCCACCTGTTCGACGACAAGGTGATGAAGCAGCTGAAGAGAAGAAG ATACACCGGCTGGGGCAGACTGAGCAGAAAGCTGATCAACGGCATCAGAGA CAAGCAGAGCGGCAAGACCATCCTGGACTTCCTGAAGAGCGACGGCTTCGC CAACAGAAACTTCATGCAGCTGATCCACGACGACAGCCTGACCTTCAAGGA GGACATCCAGAAGGCCCAGGTGAGCGGCCAGGGCGACAGCCTGCACGAGCA CATCGCCAACCTGGCCGGCAGCCCCGCCATCAAGAAGGGCATCCTGCAGAC CGTGAAGGTGGTGGACGAGCTGGTGAAGGTGATGGGCAGACAAGCCCGA GAACATCGTGATCGAGATGGCCAGAGAGAACCAGACCACCCAGAAGGGCCA GAAGAACAGCAGAGAGAGAATGAAGAGAATCGAGGAGGGCATCAAGGAGCT GGGCAGCCAGATCCTGAAGGAGCACCCCGTGGAGAACACCCAGCTGCAGAA CGAGAAGCTGTACCTGTACTACCTGCAGAACGGCAGAGACATGTACGTGGA CCAGGAGCTGGACATCAACAGACTGAGCGACTACGACGTGGACCACATCGT GCCCCAGAGCTTCCTGAAGGACGACAGCATCGACAACAAGGTGCTGACCAG AAGCGACAAGAACAGAGGCAAGAGCGACAACGTGCCCAGCGAGGAGGTGGT GAAGAAGATGAAGAACTACTGGAGACAGCTGCTGAACGCCAAGCTGATCAC CCAGAGAAAGTTCGACAACCTGACCAAGGCCGAGAGGCGGCCTGAGCGA GCTGGACAAGGCCGGCTTCATCAAGAGACAGCTGGTGGAGACCAGACAGAT CACCAAGCACGTGGCCCAGATCCTGGACAGCAGAATGAACACCAAGTACGA | 253 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CGAGAACGACAAGCTGATCAGAGAGGTGAAGGTGATCACCCTGAAGAGCAA<br>GCTGGTGAGCGACTTCAGAAAGGACTTCCAGTTCTACAAGGTGAGAGAGAT<br>CAACAACTACCACCACGCCCACGACGCCTACCTGAACGCCGTGGTGGGCAC<br>CGCCCTGATCAAGAAGTACCCCAAGCTGGAGAGCGAGTTCGTGTACGGCGA<br>CTACAAGGTGTACGACGTGAGAAAGATGATCGCCAAGAGCGAGCAGGAGAT<br>CGGCAAGGCCACCGCCAAGTACTTCTTCTACAGCAACATCATGAACTTCTT<br>CAAGACCGAGATCACCCTGGCCAACGGCGAGATCAGAAAGAGACCCCTGAT<br>CGAGACCAACGGCGAGACCGGCGAGATCGTGTGGGACAAGGGCAGAGACTT<br>CGCCACCGTGAGAAAGGTGCTGAGCATGCCCCAGGTGAACATCGTGAAGAA<br>GACCGAGGTGCAGACCGGCGGCTTCAGCAAGGAGAGCATCCTGCCCAAGAG<br>AAACAGCGACAAGCTGATCGCCAGAAAGAAGGACTGGGACCCCAAGAAGTA<br>CGGCGGCTTCGACAGCCCCACCGTGGCCTACAGCGTGCTGGTGGTGGCCAA<br>GGTGGAGAAGGGCAAGAGCAAGAAGCTGAAGAGCGTGAAGGAGCTGCTGGG<br>CATCACCATCATGGAGAGAAGCAGCTTCGAGAAGAACCCCATCGACTTCCT<br>GGAGGCCAAGGGCTACAAGGAGGTGAAGAAGGACCTGATCATCAAGCTGCC<br>CAAGTACAGCCTGTTCGAGCTGGAGAACGGCAGAAAGAGAATGCTGGCCAG<br>CGCCGGCGAGCTGCAGAAGGGCAACGAGCTGGCCCTGCCCAGCAAGTACGT<br>GAACTTCCTGTACCTGGCCAGCCACTACGAGAAGCTGAAGGGCAGCCCCGA<br>GGACAACGAGCAGAAGCAGCTGTTCGTGGAGCAGCACAAGCACTACCTGGA<br>CGAGATCATCGAGCAGATCAGCGAGTTCAGCAAGAGAGTGATCCTGGCCGA<br>CGCCAACCTGGACAAGGTGCTGAGCGCCTACAACAAGCACAGAGACAAGCC<br>CATCAGAGAGCAGGCCGAGAACATCATCCACCTGTTCACCCTGACCAACCT<br>GGGCGCCCCCGCCGCCTTCAAGTACTTCGACACCACCATCGACAGAAAGAG<br>ATACACCAGCACCAAGGAGGTGCTGGACGCCACCCTGATCCACCAGAGCAT<br>CACCGGCCTGTACGAGACCAGAATCGACCTGAGCCAGCTGGGCGGCGACGG<br>CGGCGGCAGCCCCAAGAAGAAGAGAAAGGTGTGACTAGCCATCACATTTAA<br>AAGCATCTCAGCCTACCATGAGAATAAGAGAAAGAAAATGAAGATCAATAG<br>CTTATTCATCTCTTTTTCTTTTTCGTTGGTGTAAAGCCAACACCCTGTCTA<br>AAAAACATAAATTTCTTTAATCATTTTGCCTCTTTTCTCTGTGCTTCAATT<br>AATAAAAAATGGAAAGAACCTCGAG | |
| Cas9 ORF with minimal uridine codons infrequently used in humans in general; 12.75% U content | ATGGACAAAAAATACAGCATAGGGCTAGACATAGGGACGAACAGCGTAGGG<br>TGGGCGGTAATAACGGACGAATACAAAGTACCGAGCAAAAAATTCAAAGTA<br>CTAGGGAACACGGACCGACACAGCATAAAAAAAAACCTAATAGGGGCGCTA<br>CTATTCGACAGCGGGGAAACGGCGGAAGCGACGCGACTAAAACGAACGGCG<br>CGACGACGATACACGCGACGAAAAAACCGAATATGCTACCTACAAGAAATA<br>TTCAGCAACGAAATGGCGAAAGTAGACGACAGCTTCTTCCACCGACTAGAA<br>GAAAGCTTCCTAGTAGAAGAGACAAAAAACACGAACGACACCCGATATTC<br>GGGAACATAGTAGACGAAGTAGCGTACCACGAAAAATACCCGACGATATAC<br>CACCTACGAAAAAACTAGTAGACAGCACGGACAAAGCGGACCTACGACTA<br>ATATACCTAGCGCTAGCGCACATGATAAAATTCCGAGGGCACTTCCTAATA<br>GAAGGGGACCTAAACCCGGACAACAGCGACGTAGACAAACTATTCATACAA<br>CTAGTACAAACGTACAACCAACTATTCGAAGAAAACCCGATAAACGCGAGC<br>GGGGTAGACGCGAAAGCGATACTAAGCGCGCGACTAAGCAAAAGCCGACGA<br>CTAGAAAACCTAATAGCGCAACTACCGGGGGAAAAAAAAACGGGCTATTC<br>GGGAACCTAATAGCGCTAAGCCTAGGGCTAACGCCGAACTTCAAAAGCAAC<br>TTCGACCTAGCGGAAGACGCGAAACTACAACTAAGCAAAGACACGTACGAC<br>GACGACCTAGACAACCTACTAGCGCAAATAGGGGACCAATACGCGGACCTA<br>TTCCTAGCGGCGAAAAACCTAAGCGACGCGATACTACTAAGCGACATACTA<br>CGAGTAAACACGGAAATAACGAAAGCGCCGCTAAGCGCGAGCATGATAAAA<br>CGATACGACGAACACCACCAAGACCTAACGCTACTAAAAGCGCTAGTACGA<br>CAACAACTACCGGAAAAATACAAAGAAATATTCTTCGACCAAAGCAAAAAC<br>GGGTACGCGGGGTACATAGACGGGGGGGCGAGCCAAGAAGAATTCTACAAA<br>TTCATAAAACCGATACTAGAAAAAAATGGACGGGACGGAAGAACTACTAGTA<br>AAACTAAACCGAGAAGACCTACTACGAAAACAACGAACGTTCGACAACGGG<br>AGCATACCGCACCAAATACACCTAGGGGAACTACACGCGATACTACGACGA<br>CAAGAAGACTTCTACCCGTTCCTAAAAGACAACCGAGAAAAATAGAAAAA<br>ATACTAACGTTCCGAATACCGTACTACGTAGGGCCGCTAGCGCGAGGGAAC<br>AGCCGATTCGCGTGGATGACGCGAAAAAGCGAAGAAACGATAACGCCGTGG<br>AACTTCGAAGAAGTAGTAGACAAAGGGGCGAGCGCGCAAAGCTTCATAGAA<br>CGAATGACGAACTTCGACAAAAAACCTACCGAACGAAAAGTACTACCGAAA<br>CACAGCCTACTATACGAATACTTCACGGTATACAACGAACTAACGAAAGTA<br>AAATACGTAACGGAAGGGATGCGAAAACCGGCGTTCCTAAGCGGGGAACAA<br>AAAAAGCGATAGTAGACCTACTATTCAAAACGAACCGAAAAGTAACGGTA<br>AAACAACTAAAAGAAGACTACTTCAAAAAAATAGAATGCTTCGACAGCGTA<br>GAAATAAGCGGGGTAGAAGACCGATTCAACGCGAGCCTAGGGACGTACCAC<br>GACCTACTAAAAATAATAAAAGACAAAGACTTCCTAGACAACGAAGAAAAC<br>GAAGACATACTAGAAGACATAGTACTAACGCTAACGCTATTCGAAGACCGA<br>GAAATGATAGAAGAACGACTAAAAACGTACGCGCACCTATTCGACGACAAA<br>GTAATGAAACAACTAAAACGACGACGATACACGGGGTGGGGCGACTAAGC | 254 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CGAAAACTAATAAACGGGATACGAGACAAACAAAGCGGGAAAACGATACTA<br>GACTTCCTAAAAAGCGACGGGTTCGCGAACCGAAACTTCATGCAACTAATA<br>CACGACGACAGCCTAACGTTCAAAGAAGACATACAAAAAGCGCAAGTAAGC<br>GGGCAAGGGGACAGCCTACACGAACACATAGCGAACCTAGCGGGGAGCCCG<br>GCGATAAAAAAAGGGATACTACAAACGGTAAAAGTAGTAGACGAACTAGTA<br>AAAGTAATGGGGCGACACAAACCGGAAAACATAGTAATAGAAATGGCGCGA<br>GAAAACCAAACGACGCAAAAAGGGCAAAAAAACAGCCGAGAACGAATGAAA<br>CGAATAGAAGAAGGGATAAAAGAACTAGGGAGCCAAATACTAAAAGAACAC<br>CCGGTAGAAAACACGCAACTACAAAACGAAAAACTATACCTATACTACCTA<br>CAAAACGGGCGAGACATGTACGTAGACCAAGAACTAGACATAAACCGACTA<br>AGCGACTACGACGTAGACCACATAGTACCGCAAAGCTTCCTAAAAGACGAC<br>AGCATAGACAACAAAGTACTAACGCGAAGCGACAAAAACCGAGGGAAAAGC<br>GACAACGTACCGAGCGAAGAAGTAGTAAAAAAAATGAAAAACTACTGGCGA<br>CAACTACTAAACGCGAAACTAATAACGCAACGAAAATTCGACAACCTAACG<br>AAAGCGGAACGAGGGGGGCTAAGCGAACTAGACAAAGCGGGGTTCATAAAA<br>CGACAACTAGTAGAAACGCGACAAATAACGAAACACGTAGCGCAAATACTA<br>GACAGCCGAATGAACACGAAATACGACGAAAACGACAAACTAATACGAGAA<br>GTAAAAGTAATAACGCTAAAAAGCAAACTAGTAAGCGACTTCCGAAAAGAC<br>TTCCAATTCTACAAAGTACGAGAAATAAACAACTACCACCACGCGCACGAC<br>GCGTACCTAAACGCGGTAGTAGGGACGGCGCTAATAAAAAAATACCCGAAA<br>CTAGAAAGCGAATTCGTATACGGGGACTACAAAGTATACGACGTACGAAAA<br>ATGATAGCGAAAAGCGAACAAGAAATAGGGAAAGCGACGGCGAAATACTTC<br>TTCTACAGCAACATAATGAACTTCTTCAAAACGGAAATAACGCTAGCGAAC<br>GGGGAAATACGAAAACGACCGCTAATAGAAACGAACGGGGAAACGGGGGAA<br>ATAGTATGGGACAAAGGGCGAGACTTCGCGACGGTACGAAAAGTACTAAGC<br>ATGCCGCAAGTAAACATAGTAAAAAAAACGGAAGTACAAACGGGGGGGTTC<br>AGCAAAGAAAGCATACTACCGAAACGAAACAGCGACAAACTAATAGCGCGA<br>AAAAAAGACTGGGACCCGAAAAAATACGGGGGGTTCGACAGCCCGACGGTA<br>GCGTACAGCGTACTAGTAGTAGCGAAAGTAGAAAAAGGGAAAAGCAAAAAA<br>CTAAAAAGCGTAAAAGAACTACTAGGGATAACGATAATGGAACGAAGCAGC<br>TTCGAAAAAAACCCGATAGACTTCCTAGAAGCGAAAGGGTACAAAGAAGTA<br>AAAAAAGACCTAATAATAAAACTACCGAAATACAGCCTATTCGAACTAGAA<br>AACGGGCGAAAACGAATGCTAGCGAGCGCGGGGGAACTACAAAAAGGGAAC<br>GAACTAGCGCTACCGAGCAAATACGTAAACTTCCTATACCTAGCGAGCCAC<br>TACGAAAAACTAAAAGGGAGCCCGGAAGACAACGAACAAAAACAACTATTC<br>GTAGAACAACACAAACACTACCTAGACGAAATAATAGAACAAATAAGCGAA<br>TTCAGCAAACGAGTAATACTAGCGGACGCGAACCTAGACAAAGTACTAAGC<br>GCGTACAACAAACACCGAGACAAACCGATACGAGAACAAGCGGAAAACATA<br>ATACACCTATTCACGCTAACGAACCTAGGGGCGCCGGCGGCGTTCAAATAC<br>TTCGACACGACGATAGACCGAAAACGATACACGAGCACGAAAGAAGTACTA<br>GACGCGACGCTAATACACCAAAGCATAACGGGGCTATACGAAACGCGAATA<br>GACCTAAGCCAACTAGGGGGGACGGGGGGGGAGCCCGAAAAAAAACGA<br>AAAGTATGA | |
| Cas9 transcript with 5' UTR of HSD, ORF corresponding to SEQ ID NO: 254, Kozak sequence, and 3' UTR of ALB | GGGTCCCGCAGTCGGCGTCCAGCGGCTCTGCTTGTTCGTGTGTGTGTCGTT<br>GCAGGCCTTATTCGGATCCGCCACCATGGACAAAAAATACAGCATAGGGCT<br>AGACATAGGGACGAACAGCGTAGGGTGGGCGGTAATAACGGACGAATACAA<br>AGTACCGAGCAAAAAATTCAAAGTACTAGGGAACACGGACCGACACAGCAT<br>AAAAAAAAACCTAATAGGGGCGCTACTATTCGACAGCGGGGAAACGGCGGA<br>AGCGACGCGACTAAAACGAACGGCGCGACGATACACGCGACGAAAAAA<br>CCGAATATGCTACCTACAAGAAATATTCAGCAACGAAATGGCGAAAGTAGA<br>CGACAGCTTCTTCCACCGACTAGAAGAAAGCTTCCTAGTAGAAGAAGACAA<br>AAAACACGAACGACACCCGATATTCGGGAACATAGTAGACGAAGTAGCGTA<br>CCACGAAAAATACCCGACGATATACCACCTACGAAAAAAACTAGTAGCAG<br>CACGGACAAAGCGGACCTACGACTAATATACCTAGCGCTAGCGCACATGAT<br>AAAATTCCGAGGGCACTTCCTAATAGAAGGGGACCTAAACCCGGACAACAG<br>CGACGTAGACAAACTATTCATCAACTAGTACAAACGTACAACCAACTATT<br>CGAAGAAACCCGATAAACGCGAGCGGGGTAGACGCGAAAGCGATACTAAG<br>CGCGCGACTAAGCAAAAGCCGACGACTAGAAAACCTAATAGCGCAACTACC<br>GGGGGAAAAAAAAAACGGGCTATTCGGGAACCTAATAGCGCTAAGCCTACC<br>GCTAACGCCGAACTTCAAAAGCAACTTCGACCTAGCGGAAGACGCGAAACT<br>ACAACTAAGCAAAGACACGTACGACGACGACCTAGACAACCTACTAGCGCA<br>AATAGGGGACCAATACGCGGACCTATTCCTAGCGGCGAAAAACCTAAGCGA<br>CGCGATACTACTAAGCGACATACTACGAGTAAAACACGGAAATACGAAAGC<br>GCCGCTAAGCGCGAGCATGATAAAACGATACGACGAACACCACCAAGACCT<br>AACGCTACTAAAAGCGCTAGTACGACAACAACTACCGGAAAAATACAAAGA<br>AATATTCTTCGACCAAAGCAAAAACGGGTACGCGGGTACATAGACGGGGG<br>GGCGAGCCAAGAAGAATTCTACAAATTCATAAAACCGATACTAGAAAAAAT<br>GGACGGGACGGAAGAACTACTAGTAAAACTAAACCGAGAAGACCTACTACG<br>AAAACAACGAACGTTCGACAACGGGAGCATACCGCACCCAAATACACCTAGG | 255 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | GGAACTACACGCGATACTACGACGACAAGAAGACTTCTACCCGTTCCTAAA AGACAACCGAGAAAAATAGAAAAAATACTAACGTTCCGAATACCGTACTA CGTAGGGCCGCTAGCGCGAGGGAACAGCCGATTCGCGTGGATGACGCGAAA AAGCGAAGAAACGATAACGCCGTGGAACTTCGAAGAAGTAGTAGACAAAGG GGCGAGCGCGCAAAGCTTCATAGAACGAATGACGAACTTCGACAAAAACCT ACCGAACGAAAAAGTACTACCGAAACACAGCCTACTATACGAATACTTCAC GGTATACAACGAACTAACGAAAGTAAAATACGTAACGGAAGGGATGCGAAA ACCGGCGTTCCTAAGCGGGGAACAAAAAAAAGCGATAGTAGACCTACTATT CAAAACGAACCGAAAAGTAACGGTAAAACAACTAAAAGAAGACTACTTCAA AAAAATAGAATGCTTCGACAGCGTAGAAATAAGCGGGGTAGAAGACCGATT CAACGCGAGCCTAGGGACGTACCACGACCTACTAAAAATAATAAAAGACAA AGACTTCCTAGACAACGAAGAAAACGAAGACATACTAGAAGACATAGTACT AACGCTAACGCTATTCGAAGACCGAGAAATGATAGAAGAACGACTAAAAAC GTACGCGCACCTATTCGACGACAAAGTAATGAAACAACTAAAACGACGACG ATACACGGGTGGGGCGACTAAGCCGAAAACTAATAAACGGGATACGAGA CAAACAAAGCGGGAAAACGATACTAGACTTCCTAAAAAGCGACGGGTTCGC GAACCGAAACTTCATGCAACTAATACACGACGACAGCCTAACGTTCAAAGA AGACATACAAAAAGCGCAAGTAAGCGGGCAAGGGGACAGCCTACACGAACA CATAGCGAACCTAGCGGGGAGCCCGGCGATAAAAAAAGGGATACTACAAAC GGTAAAAGTAGTAGACGAACTAGTAAAAGTAATGGGGCGACACAAACCGGA AAACATAGTAATAGAAATGGCGCGAGAAAACCAAACGACGCAAAAAGGGCA AAAAACAGCCGAGAACGAATGAAACGAATAGAAGAAGGGATAAAAGAACT AGGGAGCCAAATACTAAAAGAACACCCGGTAGAAAACACGCAACTACAAAA CGAAAAACTATACCTATACTACCTACAAAACGGGCGAGACATGTACGTAGA CCAAGAACTAGACATAAACCGACTAAGCGACTACGACGTAGACCACATAGT ACCGCAAAGCTTCCTAAAAGACGACAGCATAGACAACAAAGTACTAACGCG AAGCGACAAAACCGAGGGAAAAGCGACAACGTACCGAGCGAAGAAGTAGT AAAAAAAATGAAAAACTACTGGCGACAACTACTAAACGCGAAACTAATAAC GCAACGAAAATTCGACAACCTAACGAAAGCGGAACGAGGGGGGCTAAGCGA ACTAGACAAAGCGGGGTTCATAAAACGACAACTAGTAGAAACGCGACAAAT AACGAAACACGTAGCGCAAATACTAGACAGCCGAATGAACACGAAATACGA CGAAAACGACAAACTAATACGAGAAGTAAAAGTAATAACGCTAAAAGCAA ACTAGTAAGCGACTTCCGAAAAGACTTCCAATTCTACAAAGTACGAGAAAT AAACAACTACCACCACGCGCACGACGCGTACCTAAACGCGGTAGTAGGGAC GGCGCTAATAAAAAAATACCCGAAACTAGAAAGCGAATTCGTATACGGGGA CTACAAAGTATACGACGTACGAAAAATGATAGCGAAAAGCGAACAAGAAAT AGGGAAAGCGACGGCGAAATACTTCTTCTACAGCAACATAATGAACTTCTT CAAAACGAAATAACGCTAGCGAACGGGGAAATACGAAAACGACCGCTAAT AGAAACGAACGGGGAAACGGGGGAAATAGTATGGGACAAAGGGCGAGACTT CGCGACGGTACGAAAAGTACTAAGCATGCCGCAAGTAAACATAGTAAAAAA AACGGAAGTACAAACGGGGGGGTTCAGCAAAGAAAGCATACTACCGAAACG AAACAGCGACAAACTAATAGCGCGAAAAAAAGACTGGGACCCGAAAAAATA CGGGGGGTTCGACAGCCCGACGGTAGCGTACAGCGTACTAGTAGTAGCGAA AGTAGAAAAAGGGAAAGCAAAAACTAAAAGCGTAAAAGAACTACTAGG GATAACGATAATGGAACGAAGCAGCTTCGAAAAAAACCCGATAGACTTCCT AGAAGCGAAAGGGTACAAAGAAGTAAAAAAAGACCTAATAATAAAACTACC GAAATACAGCCTATTCGAACTAGAAAACGGGCGAAAACGAATGCTAGCGAG CGCGGGGGAACTACAAAAAGGGAACGAACTAGCGCTACCGAGCAAATACGT AAACTTCCTATACCTAGCGAGCCACTACGAAAAACTAAAAGGGAGCCCGGA AGACAACGAACAAAACAACTATTCGTAGAACAACACAAACACTACCTAGA CGAAATAATAGAACAAATAAGCGAATTCAGCAAACGAGTAATACTAGCGGA CGCGAACCTAGACAAAGTACTAAGCGCGTACAACAAACACCGAGACAAACC GATACGAGAACAAGCGGAAAACATAATACACCTATTCACGCTAACGAACCT AGGGGCGCCGGCGGCGTTCAAATACTTCGACACGACGATAGACCGAAAACG ATACACGAGCACGAAAGAAGTACTAGACGCGACGCTAATACACCAAAGCAT AACGGGGCTATACGAAACGCGAATAGACCTAAGCCAACTAGGGGGGGACGG GGGGGGGAGCCCGAAAAAAAAACGAAAGTATGACTAGCCATCACATTTAA AAGCATCTCAGCCTACCATGAGAATAAGAGAAAGAAATGAAGATCAATAG CTTATTCATCTCTTTTTCTTTTCGTTGGTGTAAAGCCAACACCCTGTCTA AAAAACATAAATTTCTTTAATCATTTTGCCTCTTTTCTCTGTGCTTCAATT AATAAAAAATGGAAAGAACCTCGAG | |
| Cas9 transcript with AGG as first three nucleotides for use with CleanCap ™, 5' UTR of | AGGTCCCGCAGTCGGCGTCCAGCGGCTCTGCTTGTTCGTGTGTGTGTCGTT GCAGGCCTTATTCGGATCCGCCACCATGGACAAGAAGTACAGCATCGGACT GGACATCGGAACAAACAGCGTCGGATGGGCAGTCATCACAGACGAATACAA GGTCCCGAGCAAGAAGTTCAAGGTCCTGGGAAACACAGACAGACACAGCAT CAAGAAGAACCTGATCGGAGCACTGCTGTTCGACAGCGGAGAAACAGCAGA AGCAACAAGACTGAAGAGAACAGCAAGAAGAAGATACACAAGAAGAAGAA CAGAATCTGCTACCTGCAGGAAATCTTCAGCAACGAAATGGCAAAGGTCGA CGACAGCTTCTTCCACAGACTGGAAGAAAGCTTCCTGGTCGAAGAAGACAA | 256 |

| Description | Sequence | SEQ ID No. |
|---|---|---|
| HSD, ORF corresponding to SEQ ID NO: 204, Kozak sequence, and 3' UTR of ALB | GAAGCACGAAAGACACCCGATCTTCGGAAACATCGTCGACGAAGTCGCATA CCACGAAAAGTACCCGACAATCTACCACCTGAGAAAGAAGCTGGTCGACAG CACAGACAAGGCAGACCTGAGACTGATCTACCTGGCACTGGCACACATGAT CAAGTTCAGAGGACACTTCCTGATCGAAGGAGACCTGAACCCGGACAACAG CGACGTCGACAAGCTGTTCATCCAGCTGGTCCAGACATACAACCAGCTGTT CGAAGAAAACCCGATCAACGCAAGCGGAGTCGACGCAAAGGCAATCCTGAG CGCAAGACTGAGCAAGAGCAGAAGACTGGAAAACCTGATCGCACAGCTGCC GGGAGAAAAGAAGAACGGACTGTTCGGAAACCTGATCGCACTGAGCCTGGG ACTGACACCGAACTTCAAGAGCAACTTCGACCTGGCAGAAGACGCAAAGCT GCAGCTGAGCAAGGACACATACGACGACGACCTGGACAACCTGCTGGCACA GATCGGAGACCAGTACGCAGACCTGTTCCTGGCAGCAAAGAACCTGAGCGA CGCAATCCTGCTGAGCGACATCCTGAGAGTCAACACAGAAATCACAAAGGC ACCGCTGAGCGCAAGCATGATCAAGAGATACGACGAACACCACCAGGACCT GACACTGCTGAAGGCACTGGTCAGACAGCAGCTGCCGGAAAAGTACAAGGA AATCTTCTTCGACCAGAGCAAGAACGGATACGCAGGATACATCGACGGAGG AGCAAGCCAGGAAGAATTCTACAAGTTCATCAAGCCGATCCTGGAAAAGAT GGACGGAACAGAAGAACTGCTGGTCAAGCTGAACAGAAGAACCTGCTGAG AAAGCAGAGAACATTCGACAACGGAAGCATCCCGCACCAGATCCACCTGGG AGAACTGCACGCAATCCTGAGAAGACAGGAAGACTTCTACCCGTTCCTGAA GGACAACAGAGAAAAGATCGAAAAGATCCTGACATTCAGAATCCCGTACTA CGTCGACCGCTGGCAAGAGGAAACAGCAGATTCGCATGGATGACAAGAAA GAGCGAAGAAACAATCACACCGTGGAACTTCGAAGAAGTCGTCGACAAGGG AGCAAGCGCACAGAGCTTCATCGAAAGAATGACAAACTTCGACAAGAACCT GCCGAACGAAAAGGTCCTGCCGAAGCACAGCCTGCTGTACGAATACTTCAC AGTCTACAACGAACTGACAAAGGTCAAGTACGTCACAGAAGGAATGAGAAA GCCGGCATTCCTGAGCGGAGAACAGAAGAAGGCAATCGTCGACCTGCTGTT CAAGACAAACAGAAAGGTCACAGTCAAGCAGCTGAAGGAAGACTACTTCAA GAAGATCGAATGCTTCGACAGCGTCGAAATCAGCGGAGTCGAAGACAGATT CAACGCAAGCCTGGGAACATACCACGACCTGCTGAAGATCATCAAGGACAA GGACTTCCTGGACAACGAAGAAAACGAAGACATCCTGGAAGACATCGTCCT GACACTGACACTGTTCGAAGACAGAGAAATGATCGAAGAAAGACTGAAGAC ATACGCACACCTGTTCGACGACAAGGTCATGAAGCAGCTGAAGAGAAGAAG ATACACAGGATGGGGAAGACTGAGCAGAAAGCTGATCAACGGAATCAGAGA CAAGCAGAGCGGAAAGACAATCCTGGACTTCCTGAAGAGCGACGGATTCGC AAACAGAAACTTCATGCAGCTGATCCACGACGACAGCCTGACATTCAAGGA AGACATCCAGAAGGCACAGGTCAGCGGACAGGGAGACAGCCTGCACGAACA CATCGCAAACCTGGCAGGAAGCCCGGCAATCAAGAAGGGAATCCTGCAGAC AGTCAAGGTCGTCGACGAACTGGTCAAGGTCATGGGAAGACACAAGCCGGA AAACATCGTCATCGAAATGGCAAGAGAAAACCAGACAACACAGAAGGGACA GAAGAACAGCAGAGAAAGAATGAAGAGAATCGAAGAAGGAATCAAGGAACT GGGAAGCCAGATCCTGAAGGAACACCCGGTCGAAAACACACAGCTGCAGAA CGAAAAGCTGTACCTGTACTACCTGCAGAACGGAAGAGACATGTACGTCGA CCAGGAACTGGACATCAACAGACTGAGCGACTACGACGTCGACCACATCGT CCCGCAGAGCTTCCTGAAGGACGACAGCATCGACAACAAGGTCCTGACAAG AAGCGACAAGAACAGAGGAAAGAGCGACAACGTCCCGAGCGAAGAAGTCGT CAAGAAGATGAAGAACTACTGGAGACAGCTGCTGAACGCAAAGCTGATCAC ACAGAGAAAGTTCGACAACCTGACAAAGGCAGAGAGAGGAGGACTGAGCGA ACTGGACAAGGCAGGATTCATCAAGAGACAGCTGGTCGAAACAAGACAGAT CACAAAGCACGTCGCACAGATCCTGGACAGCAGAATGAACACAAAGTACGA CGAAAACGACAAGCTGATCAGAGAAGTCAAGGTCATCACACTGAAGAGCAA GCTGGTCAGCGACTTCAGAAAGGACTTCCAGTTCTACAAGGTCAGAGAAAT CAACAACTACCACCACGCACACGACGCATACCTGAACGCAGTCGTCGGAAC AGCACTGATCAAGAAGTACCCGAAGCTGGAAAGCGAATTCGTCTACGGAGA CTACAAGGTCTACGACGTCAGAAAGATGATCGCAAAGAGCGAACAGGAAAT CGGAAAGGCAACAGCAAAGTACTTCTTCTACAGCAACATCATGAACTTCTT CAAGACAGAAATCACACTGGCAAACGGAGAAATCAGAAAGAGACCGCTGAT CGAAACAAACGGAGAAACAGGAGAAATCGTCTGGGACAAGGGAAGAGACTT CGCAACAGTCAGAAAGGTCCTGAGCATGCCGCAGGTCAACATCGTCAAGAA GACAGAAGTCCAGACAGGAGGATTCAGCAAGGAAAGCATCCTGCCGAAGAG AAACAGCGACAAGCTGATCGCAAGAAAGAAGGACTGGGACCCGAAGAAGTA CGGAGGATTCGACAGCCCGACAGTCGCATACAGCGTCCTGGTCGTCGCAAA GGTCGAAAAGGGAAAGAGCAAGAAGCTGAAGAGCGTCAAGGAACTGCTGGG AATCACAATCATGGAAAGAAGCAGCTTCGAAAAGAACCCGATCGACTTCCT GGAAGCAAAGGGATACAAGGAAGTCAAGAAGGACCTGATCATCAAGCTGCC GAAGTACAGCCTGTTCGAACTGGAAAACGGAAGAAAGAGAATGCTGGCAAG CGCAGGAGAACTGCAGAAGGGAAACGAACTGGCACTGCCGAGCAAGTACGT CAACTTCCTGTACCTGGCAAGCCACTACGAAAAGCTGAAGGGAAGCCCGGA AGACAACGAACAGAAGCAGCTGTTCGTCGAACAGCACAAGCACTACCTGGA CGAAATCATCGAACAGATCAGCGAATTCAGCAAGAGAGTCATCCTGGCAGA CGCAAACCTGGACAAGGTCCTGAGCGCATACAACAAGCACAGAGACAAGCC | |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | GATCAGAGAACAGGCAGAAAACATCATCCACCTGTTCACACTGACAAACCT<br>GGGAGCACCGGCAGCATTCAAGTACTTCGACACAACAATCGACAGAAAGAG<br>ATACACAAGCACAAAGGAAGTCCTGGACGCAACACTGATCCACCAGAGCAT<br>CACAGGACTGTACGAAACAAGAATCGACCTGAGCCAGCTGGGAGGAGACGG<br>AGGAGGAAGCCCGAAGAAGAAGAGAAAGGTCTAGCTAGCCATCACATTTAA<br>AAGCATCTCAGCCTACCATGAGAATAAGAGAAAGAAAATGAAGATCAATAG<br>CTTATTCATCTCTTTTTCTTTTTCGTTGGTGTAAAGCCAACACCCTGTCTA<br>AAAAACATAAATTTCTTTAATCATTTTGCCTCTTTTCTCTGTGCTTCAATT<br>AATAAAAAATGGAAAGAACCTCGAG | |
| Cas9 transcript with 5' UTR from CMV, ORF corresponding to SEQ ID NO: 204, Kozak sequence, and 3' UTR of ALB | GGGCAGATCGCCTGGAGACGCCATCCACGCTGTTTTGACCTCCATAGAAGA<br>CACCGGGACCGATCCAGCCTCCGCGGCCGGGAACGGTGCATTGGAACGCGG<br>ATTCCCCGTGCCAAGAGTGACTCACCGTCCTTGACACGGCCACCATGGACA<br>AGAAGTACAGCATCGGACTGGACATCGGAACAAACAGCGTCGGATGGGCAG<br>TCATCACAGACGAATACAAGGTCCCGAGCAAGAAGTTCAAGGTCCTGGGAA<br>ACACAGACAGACACAGCATCAAGAAGAACCTGATCGGAGCACTGCTGTTCG<br>ACAGCGGAGAAACAGCAGAAGCAACAAGACTGAAGAGAACAGCAAGAAGAA<br>GATACACAAGCAAGAAAGAACAGAATCTGCTACCTGCAGGAAATCTTCAGCA<br>ACGAAATGGCAAAGGTCGACGACAGCTTCTTCCACAGACTGGAAGAAAGCT<br>TCCTGGTCGAAGAAGACAAGAAGCACGAAAGACACCCGATCTTCGGAAACA<br>TCGTCGACGAAGTCGCATACCACGAAAAGTACCCGACAATCTACCACCTGA<br>GAAAGAAGCTGGTCGACAGCACAGACAAGGCAGACCTGAGACTGATCTACC<br>TGGCACTGGCACACATGATCAAGTTCAGAGGACACTTCCTGATCGAAGGAG<br>ACCTGAACCCGGACAACAGCGACGTCGACAAGCTGTTCATCCAGCTGGTCC<br>AGACATACAACCAGCTGTTCGAAGAAAACCCGATCAACGCAAGCGGAGTCG<br>ACGCAAAGGCAATCCTGAGCGCAAGACTGAGCAAGAGCAGAAGACTGGAAA<br>ACCTGATCGCACAGCTGCCGGGAGAAAAGAAGAACGGACTGTTCGGAAACC<br>TGATCGCACTGAGCCTGGGACTGACACCGAACTTCAAGAGCAACTTCGACC<br>TGGCAGAAGACGCAAAGCTGCAGCTGAGCAAGGACACATACGACGACGACC<br>TGGACAACCTGCTGGCACAGATCGGAGACCAGTACGCAGACCTGTTCCTGG<br>CAGCAAAGAACCTGAGCGACGCAATCCTGCTGAGCGACATCCTGAGAGTCA<br>ACACAGAAATCACAAAGGCACCGCTGAGCGCAAGCATGATCAAGAGATACG<br>ACGAACACCACCAGGACCTGACACTGCTGAAGGCACTGGTCAGACAGCAGC<br>TGCCGGAAAAGTACAAGGAAATCTTCTTCGACCAGAGCAAGAACGGATACG<br>CAGGATACATCGACGGAGGAGCAAGCCAGGAAGAATTCTACAAGTTCATCA<br>AGCCGATCCTGGAAAAGATGGACGGAACAGAAGAACTGCTGGTCAAGCTGA<br>ACAGAGAAGACCTGCTGAGAAAGCAGAGAACATTCGACAACGGAAGCATCC<br>CGCACCAGATCCACCTGGGAGAACTGCACGCAATCCTGAGAAGACAGGAAG<br>ACTTCTACCCGTTCCTGAAGGACAACAGAGAAAAGATCGAAAAGATCCTGA<br>CATTCAGAATCCCGTACTACGTCGGACCGCTGGCAAGAGGAAACAGCAGAT<br>TCGCATGGATGACAAGAAAGAGCGAAGAAACAATCACACCGTGGAACTTCG<br>AAGAAGTCGTCGACAAGGGAGCAAGCGCACAGAGCTTCATCGAAGAATGA<br>CAAACTTCGACAAGAACCTGCCGAACGAAAAGGTCCTGCCGAAGCACAGCC<br>TGCTGTACGAATACTTCACAGTCTACAACGAACTGACAAAGGTCAAGTACG<br>TCACAGAAGGAATGAGAAAGCCGGCATTCCTGAGCGGAGAACAGAAGAAGG<br>CAATCGTCGACCTGCTGTTCAAGACAAACAGAAAGGTCACAGTCAAGCAGC<br>TGAAGGAAGACTACTTCAAGAAGATCGAATGCTTCGACAGCGTCGAAATCA<br>GCGGAGTCGAAGACAGATTCAACGCAAGCCTGGGAACATACCACGACCTGC<br>TGAAGATCATCAAGGACAAGGACTTCCTGGACAACGAAGAAACGAAGACA<br>TCCTGGAAGACATCGTCCTGACACTGACACTGTTCGAAGACAGAGAAATGA<br>TCGAAGAAAGACTGAAGACATACGCACACCTGTTCGACGACAAGGTCATGA<br>AGCAGCTGAAGAGAAGAAGATACACAGGATGGGGAAGACTGAGCAGAAAGC<br>TGATCAACGGAATCAGAGACAAGCAGAGCGGAAAGACAATCCTGGACTTCC<br>TGAAGAGCGACGGATTCGCAAACAGAAACTTCATGCAGCTGATCCACGACG<br>ACAGCCTGACATTCAAGGAAGACATCCAGAAGGCACAGGTCAGCGGACAGG<br>GAGACAGCCTGCACGAACACATCGCAAACCTGGCAGGAAGCCCGGCAATCA<br>AGAAGGGAATCCTGCAGACAGTCAAGGTCGTCGACGAACTGGTCAAGGTCA<br>TGGGAAGACACAAGCCGGAAAACATCGTCATCGAAATGGCAAGAGAAAACC<br>AGACAACACAGAAGGGACAGAAGAACAGCAGAGAAAGAATGAAGAGAATCG<br>AAGAAGGAATCAAGGAACTGGGAAGCCAGATCCTGAAGGAACACCCGGTCG<br>AAAACACACAGCTGCAGAACGAAAAGCTGTACCTGTACTACCTGCAGAACG<br>GAAGAGACATGTACGTCGACCAGGAACTGGACATCAACAGACTGAGCGACT<br>ACGACGTCGACCACATCGTCCCGCAGAGCTTCCTGAAGGACGACAGCATCG<br>ACAACAAGGTCCTGACAAGAAGCGACAAGAACAGAGGAAAGAGCGACAACG<br>TCCCGAGCGAAGAAGTCGTCAAGAAGATGAAGAACTACTGGAGACAGCTGC<br>TGAACGCAAAGCTGATCACACAGAGAAAGTTCGACAACCTGACAAAGGCAG<br>AGAGAGGAGGACTGAGCGAACTGGACAAGGCAGGATTCATCAAGAGACAGC<br>TGGTCGAAACAAGACAGATCACAAAGCACGTCGCACAGATCCTGGACAGCA<br>GAATGAACACAAAGTACGACGAAAACGACAAGCTGATCAGAGAAGTCAAGG<br>TCATCACACTGAAGAGCAAGCTGGTCAGCGACTTCAGAAAGGACTTCCAGT | 257 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | TCTACAAGGTCAGAGAAATCAACAACTACCACCACGCACACGACGCATACC<br>TGAACGCAGTCGTCGGAACAGCACTGATCAAGAAGTACCCGAAGCTGGAAA<br>GCGAATTCGTCTACGGAGACTACAAGGTCTACGACGTCAGAAAGATGATCG<br>CAAAGAGCGAACAGGAAATCGGAAAGGCAACAGCAAAGTACTTCTTCTACA<br>GCAACATCATGAACTTCTTCAAGACAGAAATCACACTGGCAAACGGAGAAA<br>TCAGAAAGAGACCGCTGATCGAAACAAACGGAGAAACAGGAGAAATCGTCT<br>GGGACAAGGGAAGAGACTTCGCAACAGTCAGAAAGGTCCTGAGCATGCCGC<br>AGGTCAACATCGTCAAGAAGACAGAAGTCCAGACAGGAGGATTCAGCAAGG<br>AAAGCATCCTGCCGAAGAGAAACAGCGACAAGCTGATCGCAAGAAAGAAGG<br>ACTGGGACCCGAAGAAGTACGGAGGATTCGACAGCCCGACAGTCGCATACA<br>GCGTCCTGGTCGTCGCAAAGGTCGAAAAGGGAAAGAGCAAGAAGCTGAAGA<br>GCGTCAAGGAACTGCTGGGAATCACAATCATGGAAGAAGCAGCTTCGAAA<br>AGAACCCGATCGACTTCCTGGAAGCAAAGGGATACAAGGAAGTCAAGAAGG<br>ACCTGATCATCAAGCTGCCGAAGTACAGCCTGTTCGAACTGGAAAACGGAA<br>GAAAGAGAATGCTGGCAAGCGCAGGAGAACTGCAGAAGGGAAACGAACTGG<br>CACTGCCGAGCAAGTACGTCAACTTCCTGTACCTGGCAAGCCACTACGAAA<br>AGCTGAAGGGAAGCCCGGAAGACAACGAACAGAAGCAGCTGTTCGTCGAAC<br>AGCACAAGCACTACCTGGACGAAATCATCGAACAGATCAGCGAATTCAGCA<br>AGAGAGTCATCCTGGCAGACGCAAACCTGGACAAGGTCCTGAGCGCATACA<br>ACAAGCACAGAGACAAGCCGATCAGAGAACAGGCAGAAAACATCATCCACC<br>TGTTCACACTGACAAACCTGGGAGCACCGGCAGCATTCAAGTACTTCGACA<br>CAACAATCGACAGAAAGAGATACACAAGCACAAAGGAAGTCCTGGACGCAA<br>CACTGATCCACCAGAGCATCACAGGACTGTACGAAACAAGAATCGACCTGA<br>GCCAGCTGGGAGGAGACGGAGGAGGAAGCCCGAAGAAGAAGAGAAAGGTCT<br>AGCTAGCCATCACATTTAAAAGCATCTCAGCCTACCATGAGAATAAGAGAA<br>AGAAAATGAAGATCAATAGCTTATTCATCTCTTTTTCTTTTTCGTTGGTGT<br>AAAGCCAACACCCTGTCTAAAAAACATAAATTTCTTTAATCATTTTGCCTC<br>TTTTCTCTGTGCTTCAATTAATAAAAAATGGAAAGAACCTCGAG | |
| Cas9 transcript with 5' UTR from HBB, ORF corresponding to SEQ ID NO: 204, Kozak sequence, and 3' UTR of HBB | GGGACATTTGCTTCTGACACAACTGTGTTCACTAGCAACCTCAAACAGACA<br>CCGGATCTGCCACCATGGACAAGAAGTACAGCATCGGACTGGACATCGGAA<br>CAAACAGCGTCGGATGGGCAGTCATCACAGACGAATACAAGGTCCCGAGCA<br>AGAAGTTCAAGGTCCTGGGAAACACAGACAGACACAGCATCAAGAAGAACC<br>TGATCGGAGCACTGCTGTTCGACAGCGGAGAAACAGCAGAAGCAACAAGAC<br>TGAAGAGAACAGCAAGAAGAAGATACAAGAAGAAAGAACAGAATCTGCT<br>ACCTGCAGGAAATCTTCAGCAACGAAATGGCAAAGGTCGACGACAGCTTCT<br>TCCACAGACTGGAAGAAAGCTTCCTGGTCGAAGAAGACAAGAAGCACGAAA<br>GACACCCGATCTTCGGAAACATCGTCGACGAAGTCGCATACCACGAAAAGT<br>ACCCGACAATCTACCACCTGAGAAAGAAGCTGGTCGACAGCACAGACAAGG<br>CAGACCTGAGACTGATCTACCTGGCACTGGCACACATGATCAAGTTCAGAG<br>GACACTTCCTGATCGAAGGAGACCTGAACCCGGACAACAGCGACGTCGACA<br>AGCTGTTCATCCAGCTGGTCCAGACATACAACCAGCTGTTCGAAGAAAACC<br>CGATCAACGCAAGCGGAGTCGACGCAAAGGCAATCCTGAGCGCAAGACTGA<br>GCAAGAGCAGAAGACTGGAAAACCTGATCGCACAGCTGCCGGGAGAAAAGA<br>AGAACGGACTGTTCGGAAACCTGATCGCACTGAGCCTGGGACTGACACCGA<br>ACTTCAAGAGCAACTTCGACCTGGCAGAAGACGCAAAGCTGCAGCTGAGCA<br>AGGACACATACGACGACGACCTGGACAACCTGCTGGCACAGATCGGAGACC<br>AGTACGCAGACCTGTTCCTGGCAGCAAAGAACCTGAGCGACGCAATCCTGC<br>TGAGCGACATCCTGAGAGTCAACACAGAAATCACAAAGGCACCGCTGAGCG<br>CAAGCATGATCAAGAGATACGACGAACACCACCAGGACCTGACACTGCTGA<br>AGGCACTGGTCAGACAGCAGCTGCCGGAAAAGTACAAGGAAATCTTCTTCG<br>ACCAGAGCAAGAACGGATACGCAGGATACATCGACGGAGGAGCAAGCCAGG<br>AAGAATTCTACAAGTTCATCAAGCCGATCCTGGAAAAGATGGACGGAACAG<br>AAGAACTGCTGGTCAAGCTGAACAGAGAAGACCTGCTGAGAAAGCAGAGAA<br>CATTCGACAACGGAAGCATCCCGCACCAGATCCACCTGGGAGAACTGCACG<br>CAATCCTGAGAAGACAGGAAGACTTCTACCCGTTCCTGAAGGACAACAGAG<br>AAAAGATCGAAAAGATCCTGACATTCAGAATCCCGTACTACGTCGGACCGC<br>TGGCAAGAGGAAACAGCAGATTCGCATGGATGACAAGAAAGAGCGAAGAAA<br>CAATCACACCGTGGAACTTCGAAGAAGTCGTCGACAAGGGAGCAAGCGCAC<br>AGAGCTTCATCGAAAGAATGACAAACTTCGACAAGAACCTGCCGAACGAAA<br>AGGTCCTGCCGAAGCACAGCCTGCTGTACGAATACTTCACAGTCTACAACG<br>AACTGACAAAGGTCAAGTACGTCACAGAAGGAATGAGAAAGCCGGCATTCC<br>TGAGCGGAGAACAGAAGAAGGCAATCGTCGACCTGCTGTTCAAGACAAACA<br>GAAAGGTCACAGTCAAGCAGCTGAAGGAAGACTACTTCAAGAAGATCGAAT<br>GCTTCGACAGCGTCGAAATCAGCGGAGTCGAAGACAGATTCAACGCAAGCC<br>TGGGAACATACCACGACCTGCTGAAGATCATCAAGGACAAGGACTTCCTGG<br>ACAACGAAGAAAACGAAGACATCCTGGAAGACATCGTCCTGACACTGACAC<br>TGTTCGAAGACAGAGAAATGATCGAAGAAGACTGAAGACATACGCACACC<br>TGTTCGACGACAAGGTCATGAAGCAGCTGAAGAGAAGAAGATACACAGGAT<br>GGGGAAGACTGAGCAGAAAGCTGATCAACGGAATCAGAGACAAGCAGAGCG | 258 |

| Description | Sequence | SEQ ID No. |
|---|---|---|
| | GAAAGACAATCCTGGACTTCCTGAAGAGCGACGGATTCGCAAACAGAAACT<br>TCATGCAGCTGATCCACGACGACAGCCTGACATTCAAGGAAGACATCCAGA<br>AGGCACAGGTCAGCGGACAGGGAGACAGCCTGCACGAACACATCGCAAACC<br>TGGCAGGAAGCCCGGCAATCAAGAAGGGAATCCTGCAGACAGTCAAGGTCG<br>TCGACGAACTGGTCAAGGTCATGGGAAGACACAAGCCGGAAAACATCGTCA<br>TCGAAATGGCAAGAGAAAACCAGACAACACAGAAGGGACAGAAGAACAGCA<br>GAGAAAGAATGAAGAGAATCGAAGAAGGAATCAAGGAACTGGGAAGCCAGA<br>TCCTGAAGGAACACCCGGTCGAAAACACACAGCTGCAGAACGAAAAGCTGT<br>ACCTGTACTACCTGCAGAACGGAAGAGACATGTACGTCGACCAGGAACTGG<br>ACATCAACAGACTGAGCGACTACGACGTCGACCACATCGTCCCGCAGAGCT<br>TCCTGAAGGACGACAGCATCGACAACAAGGTCCTGACAAGAAGCGACAAGA<br>ACAGAGGAAAGAGCGACAACGTCCCGAGCGAAGAAGTCGTCAAGAAGATGA<br>AGAACTACTGGACAGCTGCTGAACGCAAAGCTGATCACACAGAGAAAGT<br>TCGACAACCTGACAAAGGCAGAGAGAGGAGGACTGAGCGAACTGGACAAGG<br>CAGGATTCATCAAGAGACAGCTGGTCGAAACAAGACAGATCACAAAGCACG<br>TCGCACAGATCCTGGACAGCAGAATGAACACAAAGTACGACGAAAACGACA<br>AGCTGATCAGAGAAGTCAAGGTCATCACACTGAAGAGCAAGCTGGTCAGCG<br>ACTTCAGAAAGGACTTCCAGTTCTACAAGGTCAGAGAAATCAACAACTACC<br>ACCACGCACACGACGCATACCTGAACGCAGTCGTCGGAACAGCACTGATCA<br>AGAAGTACCCGAAGCTGGAAAGCGAATTCGTCTACGGAGACTACAAGGTCT<br>ACGACGTCAGAAAGATGATCGCAAAGAGCGAACAGGAAATCGGAAAGGCAA<br>CAGCAAAGTACTTCTTCTACAGCAACATCATGAACTTCTTCAAGACAGAAA<br>TCACACTGGCAAACGGAGAAATCAGAAAGAGACCGCTGATCGAAACAAACG<br>GAGAAACAGGAGAAATCGTCTGGGACAAGGGAAGAGACTTCGCAACAGTCA<br>GAAAGGTCCTGAGCATGCCGCAGGTCAACATCGTCAAGAAGACAGAAGTCC<br>AGACAGGAGGATTCAGCAAGGAAAGCATCCTGCCGAAGAGAAACAGCGACA<br>AGCTGATCGCAAGAAAGAAGGACTGGGACCCGAAGAAGTACGGAGGATTCG<br>ACAGCCCGACAGTCGCATACAGCGTCCTGGTCGTCGCAAAGGTCGAAAAGG<br>GAAAGAGCAAGAAGCTGAAGAGCGTCAAGGAACTGCTGGGAATCACAATCA<br>TGGAAAGAAGCAGCTTCGAAAAGAACCCGATCGACTTCCTGGAAGCAAAGG<br>GATACAAGGAAGTCAAGAAGGACCTGATCATCAAGCTGCCGAAGTACAGCC<br>TGTTCGAACTGGAAAACGGAAGAAAGAGAATGCTGGCAAGCGCAGGAGAAC<br>TGCAGAAGGGAAACGAACTGGCACTGCCGAGCAAGTACGTCAACTTCCTGT<br>ACCTGGCAAGCCACTACGAAAAGCTGAAGGGAAGCCCGGAAGACAACGAAA<br>AGAAGCAGCTGTTCGTCGAACAGCACAAGCACTACCTGGACGAAATCATCG<br>AACAGATCAGCGAATTCAGCAAGAGAGTCATCCTGGCAGACGCAAACCTGG<br>ACAAGGTCCTGAGCGCATACAACAAGCACAGAGACAAGCCGATCAGAGAAC<br>AGGCAGAAAACATCATCCACCTGTTCACACTGACAAACCTGGGAGCACCGG<br>CAGCATTCAAGTACTTCGACACAACAATCGACAGAAAGAGATACACAAGCA<br>CAAAGGAAGTCCTGGACGCAACACTGATCCACCAGAGCATCACAGGACTGT<br>ACGAAACAAGAATCGACCTGAGCCAGCTGGGAGGAGACGGAGGAGGAAGCC<br>CGAAGAAGAAGAGAAAGGTCTAGCTAGCGCTCGCTTTCTTGCTGTCCAATT<br>TCTATTAAAGGTTCCTTTGTTCCCTAAGTCCAACTACTAAACTGGGGGATA<br>TTATGAAGGGCCTTGAGCATCTGGATTCTGCCTAATAAAAAACATTTATTT<br>TCATTGCCTCGAG | |
| Cas9<br>transcript<br>with 5' UTR<br>from XBG,<br>ORF<br>corresponding<br>to SEQ ID<br>NO: 204,<br>Kozak<br>sequence,<br>and 3' UTR<br>of XBG | GGGAAGCTCAGAATAAACGCTCAACTTTGGCCGGATCTGCCACCATGGACA<br>AGAAGTACAGCATCGGACTGGACATCGGAACAAACAGCGTCGGATGGGCAG<br>TCATCACAGACGAATACAAGGTCCCGAGCAAGAAGTTCAAGGTCCTGGGAA<br>ACACAGACAGACACAGCATCAAGAAGAACCTGATCGGAGCACTGCTGTTCG<br>ACAGCGGAGAAACAGCAGAAGCAACAAGCTGAAGAGAACAGCAAGAAGAA<br>GATACACAAGAAGAAAGAACAGAATCTGCTACCTGCAGGAAATCTTCAGCA<br>ACGAAATGGCAAAGGTCGACGACAGCTTCTTCCACAGACTGGAAGAAAGCT<br>TCCTGGTCGAAGAAGACAAGAAGCACGAAAGACACCCGATCTTCGGAAACA<br>TCGTCGACGAAGTCGCATACCACGAAAAGTACCCGACAATCTACCACCTGA<br>GAAAGAAGCTGGTCGACAGCACAGACAAGGCAGACCTGAGACTGATCTACC<br>TGGCACTGGCACACATGATCAAGTTCAGAGGACACTTCCTGATCGAAGGAG<br>ACCTGAACCCGGACAACAGCGACGTCGACAAGCTGTTCATCCAGCTGGTCC<br>AGACATACAACCAGCTGTTCGAAGAAAACCCGATCAACGCAAGCGGAGTCG<br>ACGCAAAGGCAATCCTGAGCGCAAGACTGAGCAAGAGCAGAAGACTGGAAA<br>ACCTGATCGCACAGCTGCCGGGAGAAAAGAAGAACGGACTGTTCGGAAACC<br>TGATCGCACTGAGCCTGGGACTGACACCGAACTTCAAGAGCAACTTCGACC<br>TGGCAGAAGACGCAAAGCTGCAGCTGAGCAAGGACACATACGACGACGACC<br>TGGACAACCTGCTGGCACAGATCGGAGACCAGTACGCAGACCTGTTCCTGG<br>CAGCAAAGAACCTGAGCGACGCAATCCTGCTGAGCGACATCCTGAGAGTCA<br>ACACAGAAATCACAAAGGCACCGCTGAGCGCAAGCATGATCAAGAGATACG<br>ACGAACACCACCAGGACCTGACACTGCTGAAGGCACTGGTCAGACAGCAGC<br>TGCCGGAAAAGTACAAGGAAATCTTCTTCGACCAGAGCAAGAACGGATACG<br>CAGGATACATCGACGGAGGAGCAAGCCAGGAAGAATTCTACAAGTTCATCA<br>AGCCGATCCTGGAAAAGATGGACGGAACAGAAGAACTGCTGGTCAAGCTGA | 259 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | ACAGAGAAGACCTGCTGAGAAAGCAGAGAACATTCGACAACGGAAGCATCC<br>CGCACCAGATCCACCTGGGAGAACTGCACGCAATCCTGAGAAGACAGGAAG<br>ACTTCTACCCGTTCCTGAAGGACAACAGAGAAAAGATCGAAAAGATCCTGA<br>CATTCAGAATCCCGTACTACGTCGGACCGCTGGCAAGAGGAAACAGCAGAT<br>TCGCATGGATGACAAGAAAGAGCGAAGAAACAATCACACCGTGGAACTTCG<br>AAGAAGTCGTCGACAAGGGAGCAAGCGCACAGAGCTTCATCGAAAGAATGA<br>CAAACTTCGACAAGAACCTGCCGAACGAAAAGGTCCTGCCGAAGCACAGCC<br>TGCTGTACGAATACTTCACAGTCTACAACGAACTGACAAAGGTCAAGTACG<br>TCACAGAAGGAATGAGAAAGCCGGCATTCCTGAGCGGAGAACAGAAGAAGG<br>CAATCGTCGACCTGCTGTTCAAGACAAACAGAAAGGTCACAGTCAAGCAGC<br>TGAAGGAAGACTACTTCAAGAAGATCGAATGCTTCGACAGCGTCGAAATCA<br>GCGGAGTCGAAGACAGATTCAACGCAAGCCTGGGAACATACCACGACCTGC<br>TGAAGATCATCAAGGACAAGGACTTCCTGGACAACGAAGAAAACGAAGACA<br>TCCTGGAAGACATCGTCCTGACACTGACACTGTTCGAAGACAGAGAAATGA<br>TCGAAGAAGACTGAAGACATACGCACACCTGTTCGACGACAAGGTCATGA<br>AGCAGCTGAAGAGAAGAAGATACACAGGATGGGGAAGACTGAGCAGAAAGC<br>TGATCAACGGAATCAGAGACAAGCAGAGCGGAAAGACAATCCTGGACTTCC<br>TGAAGAGCGACGGATTCGCAAACAGAAACTTCATGCAGCTGATCCACGACG<br>ACAGCCTGACATTCAAGGAAGCATCCAGAAGGCACAGGTCAGCGGACAGG<br>GAGACAGCCTGCACGAACACATCGCAAACCTGGCAGGAAGCCCGGCAATCA<br>AGAAGGGAATCCTGCAGACAGTCAAGGTCGTCGACGAACTGGTCAAGGTCA<br>TGGGAAGACACAAGCCGGAAAACATCGTCATCGAAATGGCAAGAGAAAACC<br>AGACAACACAGAAGGGACAGAAGAACAGCAGAGAAAGAATGAAGAGAATCG<br>AAGAAGGAATCAAGGAACTGGGAAGCCAGATCCTGAAGGAACACCCGGTCG<br>AAAACACACAGCTGCAGAACGAAAAGCTGTACCTGTACTACCTGCAGAACG<br>GAAGAGACATGTACGTCGACCAGGAACTGGACATCAACAGACTGAGCGACT<br>ACGACGTCGACCACATCGTCCCGCAGAGCTTCCTGAAGGACGACAGCATCG<br>ACAACAAGGTCCTGACAAGAAGCGACAAGAACAGAGGAAAGAGCGACAACG<br>TCCCGAGCGAAGAAGTCGTCAAGAAGATGAAGAACTACTGGAGACAGCTGC<br>TGAACGCAAAGCTGATCACACAGAGAAAGTTCGACAACCTGACAAAGGCAG<br>AGAGAGGAGGACTGAGCGAACTGGACAAGGCAGGATTCATCAAGAGACAGC<br>TGGTCGAAACAAGACAGATCACAAAGCACGTCGCACAGATCCTGGACAGCA<br>GAATGAACACAAAGTACGACGAAAACGACAAGCTGATCAGAGAAGTCAAGG<br>TCATCACACTGAAGAGCAAGCTGGTCAGCGACTTCAGAAAGGACTTCCAGT<br>TCTACAAGGTCAGAGAAATCAACAACTACCACCACGCACACGACGCATACC<br>TGAACGCAGTCGTCGGAACAGCACTGATCAAGAAGTACCCGAAGCTGGAAA<br>GCGAATTCGTCTACGGAGACTACAAGGTCTACGACGTCAGAAAGATGATCG<br>CAAAGAGCGAACAGGAAATCGGAAAGGCAACAGCAAAGTACTTCTTCTACA<br>GCAACATCATGAACTTCTTCAAGACAGAAATCACACTGGCAAACGGAGAAA<br>TCAGAAAGAGACCGCTGATCGAAACAAACGGAGAAACAGGAGAAATCGTCT<br>GGGACAAGGGAAGAGACTTCGCAACAGTCAGAAAGGTCCTGAGCATGCCGC<br>AGGTCAACATCGTCAAGAAGACAGAAGTCCAGACAGGAGGATTCAGCAGG<br>AAAGCATCCTGCCGAAGAGAAACAGCGACAAGCTGATCGCAAGAAAGAAGG<br>ACTGGGACCCGAAGAAGTACGGAGGATTCGACAGCCCGACAGTCGCATACA<br>GCGTCCTGGTCGTCGCAAAGGTCGAAAAGGGAAAGAGCAAGAAGCTGAAGA<br>GCGTCAAGGAACTGCTGGGAATCACAATCATGGAAAGAAGCAGCTTCGAAA<br>AGAACCCGATCGACTTCCTGGAAGCAAAGGGATACAAGGAAGTCAAGAAGG<br>ACCTGATCATCAAGCTGCCGAAGTACAGCCTGTTCGAACTGGAAAACGGAA<br>GAAAGAGAATGCTGGCAAGCGCAGGAGAACTGCAGAAGGGAAACGAACTGG<br>CACTGCCGAGCAAGTACGTCAACTTCCTGTACCTGGCAAGCCACTACGAAA<br>AGCTGAAGGGAAGCCCGGAAGACAACGAACAGAAGCAGCTGTTCGTCGAAC<br>AGCACAAGCACTACCTGGACGAAATCATCGAACAGATCAGCGAATTCAGCA<br>AGAGAGTCATCCTGGCAGACGCAAACCTGGACAAGGTCCTGAGCGCATACA<br>ACAAGCACAGAGACAAGCCGATCAGAGAACAGGCAGAAAACATCATCCACC<br>TGTTCACACTGACAAACCTGGGAGCACCGGCAGCATTCAAGTACTTCGACA<br>CAACAATCGACAGAAAGAGATACACAAGCACAAAGGAAGTCCTGGACGCAA<br>CACTGATCCACCAGAGCATCACAGGACTGTACGAAACAAGAATCGACCTGA<br>GCCAGCTGGGAGGAGACGGAGGAGGAAGCCCGAAGAAGAAGAGAAAGGTCT<br>AGCTAGCACCAGCCTCAAGAACACCCGAATGGAGTCTCTAAGCTACATAAT<br>ACCAACTTACACTTTACAAAATGTTGTCCCCCAAAATGTAGCCATTCGTAT<br>CTGCTCCTAATAAAAAGAAAGTTTCTTCACATTCTCTCGAG | |
| Cas9 transcript with AGG as first three nucleotides for use with CleanCap ™, 5' UTR from | AGGAAGCTCAGAATAAACGCTCAACTTTGGCCGGATCTGCCACCATGGACA<br>AGAAGTACAGCATCGGACTGGACATCGGAACAAACAGCGTCGGATGGGCAG<br>TCATCACAGACGAATACAAGGTCCCGAGCAAGAAGTTCAAGGTCCTGGGAA<br>ACACAGACAGACACAGCATCAAGAAGAACCTGATCGGAGCACTGCTGTTCG<br>ACAGCGGAGAAACAGCAGAAGCAACAAGACTGAAGAGAACAGCAAGAAGAA<br>GATACACAAGAAGAAAGAACAGAATCTGCTACCTGCAGGAAATCTTCAGCA<br>ACGAAATGGCAAAGGTCGACGACAGCTTCTTCCACAGACTGGAAGAAAGCT<br>TCCTGGTCGAAGAAGACAAGAAGCACGAAAGACACCCGATCTTCGGAAACA | 260 |

| Description | Sequence | SEQ ID No. |
|---|---|---|
| XBG, ORF corresponding to SEQ ID NO: 204, Kozak sequence, and 3' UTR of XBG | TCGTCGACGAAGTCGCATACCACGAAAAGTACCCGACAATCTACCACCTGA GAAAGAAGCTGGTCGACAGCACAGACAAGGCAGACCTGAGACTGATCTACC TGGCACTGGCACACATGATCAAGTTCAGAGGACACTTCCTGATCGAAGGAG ACCTGAACCCGGACAACAGCGACGTCGACAAGCTGTTCATCCAGCTGGTCC AGACATACAACCAGCTGTTCGAAGAAAACCCGATCAACGCAAGCGGAGTCG ACGCAAAGGCAATCCTGAGCGCAAGACTGAGCAAGAGCAGAAGACTGGAAA ACCTGATCGCACAGCTGCCGGGAGAAAAGAAGAACGGACTGTTCGGAAACC TGATCGCACTGAGCCTGGGACTGACACCGAACTTCAAGAGCAACTTCGACC TGGCAGAAGACGCAAAGCTGCAGCTGAGCAAGGACACATACGACGACGACC TGGACAACCTGCTGGCACAGATCGGAGACCAGTACGCAGACCTGTTCCTGG CAGCAAAGAACCTGAGCGACGCAATCCTGCTGAGCGACATCCTGAGAGTCA ACACAGAAATCACAAAGGCACCGCTGAGCGCAAGCATGATCAAGAGATACG ACGAACACCACCAGGACCTGACACTGCTGAAGGCACTGGTCAGACAGCAGC TGCCGGAAAAGTACAAGGAAATCTTCTTCGACCAGAGCAAGAACGGATACG CAGGATACATCGACGGAGGAGCAAGCCAGGAAGAATTCTACAAGTTCATCA AGCCGATCCTGGAAAAGATGGACGGAACAGAAGAACTGCTGGTCAAGCTGA ACAGAGAAGACCTGCTGAGAAAGCAGAGAACATTCGACAACGGAAGCATCC CGCACCAGATCCACCTGGGAGAACTGCACGCAATCCTGAGAAGACAGGAAG ACTTCTACCCGTTCCTGAAGGACAACAGAGAAAAGATCGAAAAGATCCTGA CATTCAGAATCCCGTACTACGTCGGACCGCTGGCAAGAGGAAACAGCAGAT TCGCATGGATGACAAGAAAGAGCGAAGAAACAATCACACCGTGGAACTTCG AAGAAGTCGTCGACAAGGGAGCAAGCGCACAGAGCTTCATCGAAAGAATGA CAAACTTCGACAAGAACCTGCCGAACGAAAAGGTCCTGCCGAAGCACAGCC TGCTGTACGAATACTTCACAGTCTACAACGAACTGACAAAGGTCAAGTACG TCACAGAAGGAATGAGAAAGCCGGCATTCCTGAGCGGAGAACAGAAGAAGG CAATCGTCGACCTGCTGTTCAAGACAAACAGAAAGGTCACAGTCAAGCAGC TGAAGGAAGACTACTTCAAGAAGATCGAATGCTTCGACAGCGTCGAAATCA GCGGAGTCGAAGACAGATTCAACGCAAGCCTGGGAACATACCACGACCTGC TGAAGATCATCAAGGACAAGGACTTCCTGGACAACGAAGAAAACGAAGACA TCCTGGAAGACATCGTCCTGACACTGACACTGTTCGAAGACAGAGAAATGA TCGAAGAAGACTGAAGACATACGCACACCTGTTCGACGACAAGGTCATGA AGCAGCTGAAGAGAAGAAGATACACAGGATGGGGAAGACTGAGCAGAAAGC TGATCAACGGAATCAGAGACAAGCAGAGCGGAAAGACAATCCTGGACTTCC TGAAGAGCGACGGATTCGCAAACAGAAACTTCATGCAGCTGATCCACGACG ACAGCCTGACATTCAAGGAAGACATCCAGAAGGCACAGGTCAGCGGACAGG GAGACAGCCTGCACGAACACATCGCAAACCTGGCAGGAAGCCCGGCAATCA AGAAGGGAATCCTGCAGACAGTCAAGGTCGTCGACGAACTGGTCAAGGTCA TGGGAAGACACAAGCCGGAAAACATCGTCATCGAAATGGCAAGAGAAAACC AGACAACACAGAAGGGACAGAAGAACAGCAGAGAAAGAATGAAGAGAATCG AAGAAGGAATCAAGGAACTGGGAAGCCAGATCCTGAAGGAACACCCGGTCG AAAACACACAGCTGCAGAACGAAAAGCTGTACCTGTACTACCTGCAGAACG GAAGAGACATGTACGTCGACCAGGAACTGGACATCAACAGACTGAGCGACT ACGACGTCGACCACATCGTCCCGCAGAGCTTCCTGAAGGACGACAGCATCG ACAACAAGGTCCTGACAAGAAGCGACAAGAACAGAGGAAAGAGCGACAACG TCCCGAGCGAAGAAGTCGTCAAGAAGATGAAGAACTACTGGAGACAGCTGC TGAACGCAAAGCTGATCACACAGAGAAAGTTCGACAACCTGACAAAGGCAG AGAGAGGAGGACTGAGCGAACTGGACAAGGCAGGATTCATCAAGAGACAGC TGGTCGAAACAAGACAGATCACAAAGCACGTCGCACAGATCCTGGACAGCA GAATGAACACAAAGTACGACGAAAACGACAAGCTGATCAGAGAAGTCAAGG TCATCACACTGAAGAGCAAGCTGGTCAGCGACTTCAGAAAGGACTTCCAGT TCTACAAGGTCAGAGAAATCAACAACTACCACCACGCACACGACGCATACC TGAACGCAGTCGTCGGAACAGCACTGATCAAGAAGTACCCGAAGCTGGAAA GCGAATTCGTCTACGGAGACTACAAGGTCTACGACGTCAGAAAGATGATCG CAAAGAGCGAACAGGAAATCGGAAAGGCAACAGCAAAGTACTTCTTCTACA GCAACATCATGAACTTCTTCAAGACAGAAATCACACTGGCAAACGGAGAAA TCAGAAAGAGACCGCTGATCGAAACAAACGGAGAAACAGGAGAAATCGTCT GGGACAAGGGAAGAGACTTCGCAACAGTCAGAAAGGTCCTGAGCATGCCGC AGGTCAACATCGTCAAGAAGACAGAAGTCCAGACAGGAGGATTCAGCAAGG AAAGCATCCTGCCGAAGAGAAACAGCGACAAGCTGATCGCAAGAAAGAGG ACTGGGACCCGAAGAAGTACGGAGGATTCGACAGCCCGACAGTCGCATACA GCGTCCTGGTCGTCGCAAAGGTCGAAAAGGGAAAGAGCAAGAAGCTGAAGA GCGTCAAGGAACTGCTGGGAATCACAATCATGGAAAGAAGCAGCTTCGAAA AGAACCCGATCGACTTCCTGGAAGCAAAGGGATACAAGGAAGTCAAGAAGG ACCTGATCATCAAGCTGCCGAAGTACAGCCTGTTCGAACTGGAAAACGGAA GAAAGAGAATGCTGGCAAGCGCAGGAGAACTGCAGAAGGGAAACGAACTGG CACTGCCGAGCAAGTACGTCAACTTCCTGTACCTGGCAAGCCACTACGAAA AGCTGAAGGGAAGCCCGGAAGACAACGAACAGAAGCAGCTGTTCGTCGAAC AGCACAAGCACTACCTGGACGAAATCATCGAACAGATCAGCGAATTCAGCA AGAGAGTCATCCTGGCAGACGCAAACCTGGACAAGGTCCTGAGCGCATACA ACAAGCACAGAGACAAGCCGATCAGAGAACAGGCAGAAAACATCATCCACC | |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | TGTTCACACTGACAAACCTGGGAGCACCGGCAGCATTCAAGTACTTCGACA CAACAATCGACAGAAAGAGATACACAAGCACAAAGGAAGTCCTGGACGCAA CACTGATCCACCAGAGCATCACAGGACTGTACGAAACAAGAATCGACCTGA GCCAGCTGGGAGGAGACGGAGGAGGAAGCCCGAAGAAGAAGAGAAAGGTCT AGCTAGCACCAGCCTCAAGAACACCCGAATGGAGTCTCTAAGCTACATAAT ACCAACTTACACTTTACAAAATGTTGTCCCCCAAAATGTAGCCATTCGTAT CTGCTCCTAATAAAAAGAAAGTTTCTTCACATTCTCTCGAG | |
| Cas9 transcript with AGG as first three nucleotides for use with CleanCap ™, 5' UTR from HSD, ORF corresponding to SEQ ID NO: 204, Kozak sequence, and 3' UTR of ALB | AGGTCCCGCAGTCGGCGTCCAGCGGCTCTGCTTGTTCGTGTGTGTGTCGTT GCAGGCCTTATTCGGATCCGCCACCATGGACAAGAAGTACAGCATCGGACT GGACATCGGAACAAACAGCGTCGGATGGGCAGTCATCACAGACGAATACAA GGTCCCGAGCAAGAAGTTCAAGGTCCTGGGAAACACAGACAGACACAGCAT CAAGAAGAACCTGATCGGAGCACTGCTGTTCGACAGCGGAGAAACAGCAGA AGCAACAAGACTGAAGAGAACAGCAAGAAGAAGATACACAAGAAGAAAGAA CAGAATCTGCTACCTGCAGGAAATCTTCAGCAACGAAATGGCAAAGGTCGA CGACAGCTTCTTCCACAGACTGGAAGAAAGCTTCCTGGTCGAAGAAGACAA GAAGCACGAAAGACACCCGATCTTCGGAAACATCGTCGACGAAGTCGCATA CCACGAAAAGTACCCGACAATCTACCACCTGAGAAAGAAGCTGGTCGACAG CACAGACAAGGCAGACCTGAGACTGATCTACCTGGCACTGGCACACATGAT CAAGTTCAGAGGACACTTCCTGATCGAAGGAGACCTGAACCCGGACAACAG CGACGTCGACAAGCTGTTCATCCAGCTGGTCCAGACATACAACCAGCTGTT CGAAGAAAACCCGATCAACGCAAGCGGAGTCGACGCAAAGGCAATCCTGAG CGCAAGACTGAGCAAGAGCAGAAGACTGGAAAACCTGATCGCACAGCTGCC GGGAGAAAAGAAGAACGGACTGTTCGGAAACCTGATCGCACTGAGCCTGGG ACTGACACCGAACTTCAAGAGCAACTTCGACCTGGCAGAAGACGCAAAGCT GCAGCTGAGCAAGGACACATACGACGACGACCTGGACAACCTGCTGGCACA GATCGGAGACCAGTACGCAGACCTGTTCCTGGCAGCAAAGAACCTGAGCGA CGCAATCCTGCTGAGCGACATCCTGAGAGTCAACACAGAAATCACAAAGGC ACCGCTGAGCGCAAGCATGATCAAGAGATACGACGAACACCACCAGGACCT GACACTGCTGAAGGCACTGGTCAGACAGCAGCTGCCGGAAAAGTACAAGGA AATCTTCTTCGACCAGAGCAAGAACGGATACGCAGGATACATCGACGGAGG AGCAAGCCAGGAAGAATTCTACAAGTTCATCAAGCCGATCCTGGAAAAGAT GGACGGAACAGAAGAACTGCTGGTCAAGCTGAACAGAGAAGACCTGCTGAG AAAGCAGAGAACATTCGACAACGGAAGCATCCCGCACCAGATCCACCTGGG AGAACTGCACGCAATCCTGAGAAGACAGGAAGACTTCTACCCGTTCCTGAA GGACAACAGAGAAAAGATCGAAAAGATCCTGACATTCAGAATCCCGTACTA CGTCGGACCGCTGGCAAGAGGAAACAGCAGATTCGCATGGATGACAAGAAA GAGCGAAGAAACAATCACACCGTGGAACTTCGAAGAAGTCGTCGACAAGGG AGCAAGCGCACAGAGCTTCATCGAAAGAATGACAAACTTCGACAAGAACCT GCCGAACGAAAAGGTCCTGCCGAAGCACAGCCTGCTGTACGAATACTTCAC AGTCTACAACGAACTGACAAAGGTCAAGTACGTCACAGAAGGAATGAGAAA GCCGGCATTCCTGAGCGGAGAACAGAAGAAGGCAATCGTCGACCTGCTGTT CAAGACAAACAGAAAGGTCACAGTCAAGCAGCTGAAGGAAGACTACTTCAA GAAGATCGAATGCTTCGACAGCGTCGAAATCAGCGGAGTCGAAGACAGATT CAACGCAAGCCTGGGAACATACCACGACCTGCTGAAGATCATCAAGGACAA GGACTTCCTGGACAACGAAGAAAACGAAGACATCCTGGAAGACATCGTCCT GACACTGACACTGTTCGAAGACAGAGAAATGATCGAAGAAAGACTGAAGAC ATACGCACACCTGTTCGACGACAAGGTCATGAAGCAGCTGAAGAGAAGAAG ATACACAGGATGGGGAAGACTGAGCAGAAAGCTGATCAACGGAATCAGAGA CAAGCAGAGCGGAAAGACAATCCTGGACTTCCTGAAGAGCGACGGATTCGC AAACAGAAACTTCATGCAGCTGATCCACGACGACAGCCTGACATTCAAGGA AGACATCCAGAAGGCACAGGTCAGCGGACAGGGAGACAGCCTGCACGAACA CATCGCAAACCTGGCAGGAAGCCCGGCAATCAAGAAGGGAATCCTGCAGAC AGTCAAGGTCGTCGACGAACTGGTCAAGGTCATGGGAAGACACAAGCCGGA AAACATCGTCATCGAAATGGCAAGAGAAAACCAGACAACACAGAAGGGACA GAAGAACAGCAGAGAAAGAATGAAGAGAATCGAAGAAGGAATCAAGGAACT GGGAAGCCAGATCCTGAAGGAACACCCGGTCGAAAACACACAGCTGCAGAA CGAAAAGCTGTACCTGTACTACCTGCAGAACGGAAGAGACATGTACGTCGA CCAGGAACTGGACATCAACAGACTGAGCGACTACGACGTCGACCACATCGT CCCGCAGAGCTTCCTGAAGGACGACAGCATCGACAACAAGGTCCTGACAAG AAGCGACAAGAACAGAGGAAAGAGCGACAACGTCCCGAGCGAAGAAGTCGT CAAGAAGATGAAGAACTACTGGAGACAGCTGCTGAACGCAAAGCTGATCAC ACAGAGAAAGTTCGACAACCTGACAAAGGCAGAGAGGAGGACTGAGCGA ACTGGACAAGGCAGGATTCATCAAGAGACAGCTGGTCGAAACAAGACAGAT CACAAAGCACGTCGCACAGATCCTGGACAGCAGAATGAACACAAAGTACGA CGAAAACGACAAGCTGATCAGAGAAGTCAAGGTCATCACACTGAAGAGCAA GCTGGTCAGCGACTTCAGAAAGGACTTCCAGTTCTACAAGGTCAGAGAAAT CAACAACTACCACCACGCACACGACGCATACCTGAACGCAGTCGTCGGAAC AGCACTGATCAAGAAGTACCCGAAGCTGGAAAGCGAATTCGTCTACGGAGA CTACAAGGTCTACGACGTCAGAAAGATGATCGCAAAGAGCGAACAGGAAAT | 261 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | CGGAAAGGCAACAGCAAAGTACTTCTTCTACAGCAACATCATGAACTTCTT<br>CAAGACAGAAATCACACTGGCAAACGGAGAAATCAGAAAGAGACCGCTGAT<br>CGAAACAAACGGAGAAACAGGAGAAATCGTCTGGGACAAGGGAAGAGACTT<br>CGCAACAGTCAGAAAGGTCCTGAGCATGCCGCAGGTCAACATCGTCAAGAA<br>GACAGAAGTCCAGACAGGAGGATTCAGCAAGGAAAGCATCCTGCCGAAGAG<br>AAACAGCGACAAGCTGATCGCAAGAAAGAAGGACTGGGACCCGAAGAAGTA<br>CGGAGGATTCGACAGCCCGACAGTCGCATACAGCGTCCTGGTCGTCGCAAA<br>GGTCGAAAAGGGAAAGAGCAAGAAGCTGAAGAGCGTCAAGGAACTGCTGGG<br>AATCACAATCATGGAAAGAAGCAGCTTCGAAAAGAACCCGATCGACTTCCT<br>GGAAGCAAAGGGATACAAGGAAGTCAAGAAGGACCTGATCATCAAGCTGCC<br>GAAGTACAGCCTGTTCGAACTGGAAAACGGAAGAAAGAGAATGCTGGCAAG<br>CGCAGGAGAACTGCAGAAGGGAAACGAACTGGCACTGCCGAGCAAGTACGT<br>CAACTTCCTGTACCTGGCAAGCCACTACGAAAAGCTGAAGGGAAGCCCGGA<br>AGACAACGAACAGAAGCAGCTGTTCGTCGAACAGCACAAGCACTACCTGGA<br>CGAAATCATCGAACAGATCAGCGAATTCAGCAAGAGAGTCATCCTGGCAGA<br>CGCAAACCTGGACAAGGTCCTGAGCGCATACAACAAGCACAGAGACAAGCC<br>GATCAGAGAACAGGCAGAAAACATCATCCACCTGTTCACACTGACAAACCT<br>GGGAGCACCGGCAGCATTCAAGTACTTCGACACAACAATCGACAGAAAGAG<br>ATACACAAGCACAAAGGAAGTCCTGGACGCAACACTGATCCACCAGAGCAT<br>CACAGGACTGTACGAAACAAGAATCGACCTGAGCCAGCTGGGAGGAGACGG<br>AGGAGGAAGCCCGAAGAAGAAGAGAAAGGTCTAGCTAGCCATCACATTTAA<br>AAGCATCTCAGCCTACCATGAGAATAAGAGAAAGAAAATGAAGATCAATAG<br>CTTATTCATCTCTTTTTCTTTTTCGTTGGTGTAAAGCCAACACCCTGTCTA<br>AAAAACATAAATTTCTTTAATCATTTTGCCTCTTTTCTCTGTGCTTCAATT<br>AATAAAAAATGGAAAGAACCTCGAG | |
| 30/30/39 poly-A sequence | Not used | 262 |
| poly-A 100 sequence | AAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAA | 263 |
| G209 single guide RNA targeting the mouse TTR gene | AAATAAGAGAGAAAAGAAGAGTAAGAAGAAATATAAGAGCCACC | 264 |
| ORF encoding *Neisseria meningitidis* Cas9 using minimal uridine codons, with start and stop codons | ATGGCAGCATTCAAGCCGAACTCGATCAACTACATCCTGGGACTGGACATC<br>GGAATCGCATCGGTCGGATGGGCAATGGTCGAAATCGACGAAGAAGAAAAC<br>CCGATCAGACTGATCGACCTGGGAGTCAGAGTCTTCGAAAGAGCGAAGTC<br>CCGAAGACAGGAGACTCGCTGGCAATGGCAAGAAGACTGGCAAGATCGGTC<br>AGAAGACTGACAAGAAGAAGAGCACACAGACTGCTGAGAACAAGAAGACTG<br>CTGAAGAGAGAAGGAGTCCTGCAGGCAGCAAACTTCGACGAAAACGGACTG<br>ATCAAGTCGCTGCCGAACACACCGTGGCAGCTGAGAGCAGCAGCACTGGAC<br>AGAAAGCTGACACCGCTGGAATGGTCGGCAGTCCTGCTGCACCTGATCAAG<br>CACAGAGGATACCTGTCGCAGAGAAGAACGAAGGAGAAACAGCAGACAAG<br>GAACTGGGAGCACTGCTGAAGGGAGTCGCAGGAAACGCACACGCACTGCAG<br>ACAGGAGACTTCAGAACACCGGCAGAACTGGCACTGAACAAGTTCGAAAAG<br>GAATCGGGACACATCAGAAACCAGAGATCGGACTACTCGCACACATTCTCG<br>AGAAAGGACCTGCAGGCAGAACTGATCCTGCTGTTCGAAAAGCAGAAGGAA<br>TTCGGAAACCCGCACGTCTCGGGAGGACTGAAGGAAGGAATCGAAACACTG<br>CTGATGACACAGAGACCGGCACTGTCGGGAGACGCAGTCCAGAAGATGCTG<br>GGACACTGCACATTCGAACCGGCAGAACCGAAGGCAGCAAAGAACACATAC<br>ACAGCAGAAAGATTCATCTGGCTGACAAAGCTGAACAACCTGAGAATCCTG<br>GAACAGGGATCGGAAAGACCGCTGACAGACACAGAAAGAGCAACACTGATG<br>GACGAACCGTACAGAAAGTCGAAGCTGACATACGCACAGGCAAGAAAGCTG<br>CTGGGACTGGAAGACACAGCATTCTTCAAGGGACTGAGATACGGAAAGGAC<br>AACGCAGAAGCATCGACACTGATGAAATGAAGGCATACCACGCAATCTCG<br>AGAGCACTGGAAAAGGAAGGACTGAAGGACAAGAAGTCGCCGCTGAACCTG<br>TCGCCGGAACTGCAGGACGAAATCGGAACAGCATTCTCGCTGTTCAAGACA<br>GACGAAGACATCACAGGAAGACTGAAGGACAGAATCCAGCCGGAAATCCTG<br>GAAGCACTGCTGAAGCACATCTCGTTCGACAAGTTCGTCCAGATCTCGCTG<br>AAGGCACTGAGAAGAATCGTCCCGCTGATGGAACAGGGAAAGAGATACGAC<br>GAAGCATGCGCAGAAATCTACGGAGACCACTACGGAAAGAAGAACACAGAA<br>GAAAAGATCTACCTGCCGCCGATCCCGGCAGACGAAATCAGAAACCCGGTC<br>GTCCTGAGAGCACTGTCGCAGGCAAGAAAGGTCATCAACGGAGTCGTCAGA<br>AGATACGGATCGCCGGCAAGAATCCACATCGAAACAGCAAGAGAAGTCGGA<br>AAGTCGTTCAAGGACAGAAAGGAAATCGAAAAGAGACAGGAAGAAAACAGA | 265 |

-continued

Sequence Table
The following sequence table provides a listing of sequences disclosed herein.
It is understood that if a DNA sequence (comprising Ts) is referenced with
respect to an RNA, then Ts should be replaced with Us (which may be modified
or unmodified depending on the context), and vice versa.

| Description | Sequence | SEQ ID No. |
|---|---|---|
| | AAGGACAGAGAAAAGGCAGCAGCAAAGTTCAGAGAATACTTCCCGAACTTC<br>GTCGGAGAACCGAAGTCGAAGGACATCCTGAAGCTGAGACTGTACGAACAG<br>CAGCACGGAAAGTGCCTGTACTCGGGAAAGGAAATCAACCTGGGAAGACTG<br>AACGAAAAGGGATACGTCGAAATCGACCACGCACTGCCGTTCTCGAGAACA<br>TGGGACGACTCGTTCAACAACAAGGTCCTGGTCCTGGGATCGGAAAACCAG<br>AACAAGGGAAACCAGACACCGTACGAATACTTCAACGGAAAGGACAACTCG<br>AGAGAATGGCAGGAATTCAAGGCAAGAGTCGAAACATCGAGATTCCCGAGA<br>TCGAAGAAGCAGAGAATCCTGCTGCAGAAGTTCGACGAAGACGGATTCAAG<br>GAAAGAAACCTGAACGACACAAGATACGTCAACAGATTCCTGTGCCAGTTC<br>GTCGCAGACAGAATGAGACTGACAGGAAAGGGAAAGAAGAGAGTCTTCGCA<br>TCGAACGGACAGATCACAAACCTGCTGAGAGGATTCTGGGGACTGAGAAAG<br>GTCAGAGCAGAAAACGACAGACACCACGCACTGGACGCAGTCGTCGTCGCA<br>TGCTCGACAGTCGCAATGCAGCAGAAGATCACAAGATTCGTCAGATACAAG<br>GAAATGAACGCATTCGACGGAAAGACAATCGACAAGGAAACAGGAGAAGTC<br>CTGCACCAGAAGACACACTTCCCGCAGCCGTGGGAATTCTTCGCACAGGAA<br>GTCATGATCAGAGTCTTCGGAAAGCCGGACGGAAAGCCGGAATTCGAAGAA<br>GCAGACACACTGGAAAAGCTGAGAACACTGCTGGCAGAAAAGCTGTCGTCG<br>AGACCGGAAGCAGTCCACGAATACGTCACACCGCTGTTCGTCTCGAGAGCA<br>CCGAACAGAAAGATGTCGGGACAGGGACACATGGAAACAGTCAAGTCGGCA<br>AAGAGACTGGACGAAGGAGTCTCGGTCCTGAGAGTCCCGCTGACACAGCTG<br>AAGCTGAAGGACCTGGAAAAGATGGTCAACAGAGAAAGAGAACCGAAGCTG<br>TACGAAGCACTGAAGGCAAGACTGGAAGCACACAAGGACGACCCGGCAAAG<br>GCATTCGCAGAACCGTTCTACAAGTACGACAAGGCAGGAAACAGAACACAG<br>CAGGTCAAGGCAGTCAGAGTCGAACAGGTCCAGAAGACAGGAGTCTGGGTC<br>AGAAACCACAACGGAATCGCAGACAACGCAACAATGGTCAGAGTAGACGTC<br>TTCGAAAAGGGAGACAAGTACTACCTGGTCCCGATCTACTCGTGGCAGGTC<br>GCAAAGGGAATCCTGCCGGACAGAGCAGTCGTCCAGGGAAAGGACGAAGAA<br>GACTGGCAGCTGATCGACGACTCGTTCAACTTCAAGTTCTCGCTGCACCCG<br>AACGACCTGGTCGAAGTCATCACAAAGAAGGCAAGAATGTTCGGATACTTC<br>GCATCGTGCCACAGAGGAACAGGAAACATCAACATCAGAATCCACGACCTG<br>GACCACAAGATCGGAAAGAACGGAATCCTGGAAGGAATCGGAGTCAAGACA<br>GCACTGTCGTTCCAGAAGTACCAGATCGACGAACTGGGAAAGGAAATCAGA<br>CCGTGCAGACTGAAGAAGAGACCGCCGGTCAGATCCGAAAGAGAACAGCA<br>GACGGATCGGAATTCGAATCGCCGAAGAAGAAGAGAAAGGTCGAATGA | |
| ORF encoding *Neisseria meningitidis* Cas9 using minimal uridine codons (no start or stop codons; suitable for inclusion in fusion protein coding sequence) | GCAGCATTCAAGCCGAACTCGATCAACTACATCCTGGGACTGGACATCGGA<br>ATCGCATCGGTCGGATGGGCAATGGTCGAAATCGACGAAGAAGAAAACCCG<br>ATCAGACTGATCGACCTGGGAGTCAGAGTCTTCGAAAGAGCAGAAGTCCCG<br>AAGACAGGAGACTCGCTGGCAATGGCAAGAAGACTGGCAAGATCGGTCAGA<br>AGACTGACAAGAAGAAGAGCACACAGACTGCTGAGAACAAGAAGACTGCTG<br>AAGAGAGAAGGAGTCCTGCAGGCAGCAAACTTCGACGAAAACGGACTGATC<br>AAGTCGCTGCCGAACACACCGTGGCAGCTGAGAGCAGCAGCACTGGACAGA<br>AAGCTGACACCGCTGGAATGGTCGGCAGTCCTGCTGCACCTGATCAAGCAC<br>AGAGGATACCTGTCGCAGAGAAAGAACGAAGGAGAAACAGCAGACAAGGAA<br>CTGGGAGCACTGCTGAAGGGAGTCGCAGGAAACGCACACGCACTGCAGACA<br>GGAGACTTCAGAACACCGGCAGAACTGGCACTGAACAAGTTCGAAAAGGAA<br>TCGGGACACATCAGAAACCAGAGATCGGACTACTCGCACACATTCTCGAGA<br>AAGGACCTGCAGGCAGAACTGATCCTGCTGTTCGAAAAGCAGAAGGAATTC<br>GGAAACCCGCACGTCTCGGGAGGACTGAAGGAAGGAATCGAAACACTGCTG<br>ATGACACAGAGACCGGCACTGTCGGGAGACGCAGTCCAGAAGATGCTGGGA<br>CACTGCACATTCGAACCGGCAGAACCGAAGGCAGCAAAGAACACATACACA<br>GCAGAAAGATTCATCTGGCTGACAAAGCTGAACAACCTGAGAATCCTGGAA<br>CAGGGATCGGAAAGACCGCTGACAGACACAGAAAGAGCAACACTGATGGAC<br>GAACCGTACAGAAAGTCGAAGCTGACATACGCACAGGCAAGAAAGCTGCTG<br>GGACTGGAAGACACAGCATTCTTCAAGGGACTGAGATACGGAAAGGACAAC<br>GCAGAAGCATCGACACTGATGGAAATGAAGGCATACCACGCAATCTCGAGA<br>GCACTGGAAAGGAAGGACTGAAGGACAAGAAGTCGCCGCTGAACCTGTCG<br>CCGGAACTGCAGGACGAAATCGGAACAGCATTCTCGCTGTTCAAGACAGAC<br>GAAGACATCACAGGAAGACTGAAGGACAGAATCCAGCCGGAAATCCTGGAA<br>GCACTGCTGAAGCACATCTCGTTCGACAAGTTCGTCCAGATCTCGCTGAAG<br>GCACTGAGAAGAATCGTCCCGCTGATGGAACAGGGAAAGAGATACGACGAA<br>GCATGCGCAGAAATCTACGGAGACCACTACGGAAAGAAGAACACAGAAGAA<br>AAGATCTACCTGCCGCCGATCCCGGCAGACGAAATCAGAAACCCGGTCGTC<br>CTGAGAGCACTGTCGCAGGCAAGAAAGGTCATCAACGGAGTCGTCAGAAGA<br>TACGGATCGCCGGCAAGAATCCACATCGAAACAGCAAGAGAAGTCGGAAAG<br>TCGTTCAAGGACAGAAAGGAAATCGAAAAGAGACAGGAAGAAAACAGAAAG<br>GACAGAGAAAGGCAGCAGCAAAGTTCAGAGAATACTTCCCGAACTTCGTC<br>GGAGAACCGAAGTCGAAGGACATCCTGAAGCTGAGACTGTACGAACAGCAG<br>CACGGAAAGTGCCTGTACTCGGGAAAGGAAATCAACCTGGGAAGACTGAAC<br>GAAAAGGGATACGTCGAAATCGACCACGCACTGCCGTTCTCGAGAACATGG | 266 |

Sequence Table
The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GACGACTCGTTCAACAACAAGGTCCTGGTCCTGGGATCGGAAAACCAGAAC<br>AAGGGAAACCAGACACCGTACGAATACTTCAACGGAAAGGACAACTCGAGA<br>GAATGGCAGGAATTCAAGGCAAGAGTCGAAACATCGAGATTCCCGAGATCG<br>AAGAAGCAGAGAATCCTGCTGCAGAAGTTCGACGAAGACGGATTCAAGGAA<br>AGAAACCTGAACGACACAAGATACGTCAACAGATTCCTGTGCCAGTTCGTC<br>GCAGACAGAATGAGACTGACAGGAAAGGGAAAGAAGAGAGTCTTCGCATCG<br>AACGGACAGATCACAAACCTGCTGAGAGGATTCTGGGGACTGAGAAAGGTC<br>AGAGCAGAAAACGACAGACACCACGCACTGGACGCAGTCGTCGTCGCATGC<br>TCGACAGTCGCAATGCAGCAGAAGATCACAAGATTCGTCAGATACAAGGAA<br>ATGAACGCATTCGACGGAAAGACAATCGACAAGGAAACAGGAGAAGTCCTG<br>CACCAGAAGACACACTTCCCGCAGCCGTGGGAATTCTTCGCACAGGAAGTC<br>ATGATCAGAGTCTTCGGAAAGCCGGACGGAAAGCCGGAATTCGAAGAAGCA<br>GACACACTGGAAAAGCTGAGAACACTGCTGGCAGAAAAGCTGTCGTCGAGA<br>CCGGAAGCAGTCCACGAATACGTCACACCGCTGTTCGTCTCGAGAGCACCG<br>AACAGAAAGATGTCGGGACAGGGACACATGGAAACAGTCAAGTCGGCAAAG<br>AGACTGGACGAAGGAGTCTCGGTCCTGAGAGTCCCGCTGACACAGCTGAAG<br>CTGAAGGACCTGGAAAAGATGGTCAACAGAGAAAGAGAACCGAAGCTGTAC<br>GAAGCACTGAAGGCAAGACTGGAAGCACACAAGGACGACCCGGCAAAGGCA<br>TTCGCAGAACCGTTCTACAAGTACGACAAGGCAGGAAACAGAACACAGCAG<br>GTCAAGGCAGTCAGAGTCGAACAGGTCCAGAAGACAGGAGTCTGGGTCAGA<br>AACCACAACGGAATCGCAGACAACGCAACAATGGTCAGAGTAGACGTCTTC<br>GAAAAGGGAGACAAGTACTACCTGGTCCCGATCTACTCGTGGCAGGTCGCA<br>AAGGGAATCCTGCCGGACAGAGCAGTCGTCAGGGAAAGGACGAAGAAGAC<br>TGGCAGCTGATCGACGACTCGTTCAACTTCAAGTTCTCGCTGCACCCGAAC<br>GACCTGGTCGAAGTCATCACAAAGAAGGCAAGAATGTTCGGATACTTCGCA<br>TCGTGCCACAGAGGAACAGGAAACATCAACATCAGAATCCACGACCTGGAC<br>CACAAGATCGGAAAGAACGGAATCCTGGAAGGAATCGGAGTCAAGACAGCA<br>CTGTCGTTCCAGAAGTACCAGATCGACGAACTGGGAAAGGAAATCAGACCG<br>TGCAGACTGAAGAAGAGACCGCCGGTCAGATCCGGAAAGAGAACAGCAGAC<br>GGATCGGAATTCGAATCGCCGAAGAAGAAGAGAAAGGTCGAA | |
| Transcript comprising SEQ ID NO: 265 (encoding *Neisseria meningitidis* Cas9) | GGGAGACCCAAGCTG<u>GCTAGC</u>GTTTAAACTT<u>AAGCTT</u>GGATCCGCCACCAT<br>GGCAGCATTCAAGCCGAACTCGATCAACTACATCCTGGGACTGGACATCGG<br>AATCGCATCGGTCGGATGGGCAATGGTCGAAATCGACGAAGAAGAAACCC<br>GATCAGATCGATCGACCTGGGAGTCAGAGTCTTCGAAAGAGCAGAAGTCCC<br>GAAGACAGGAGACTCGCTGGCAATGGCAAGAAGACTGGCAAGATCGGTCAG<br>AAGACTGACAAGAAGAAGAGCACACAGACTGCTGAGAACAAGAAGACTGCT<br>GAAGAGAGAAGGAGTCCTGCAGGCAGCAAACTTCGACGAAAACGGACTGAT<br>CAAGTCGCTGCCGAACACACCGTGGCAGCTGAGAGCAGCAGCACTGGACAG<br>AAAGCTGACACCGCTGGAATGGTCGGCAGTCCTGCTGCACCTGATCAAGCA<br>CAGAGGATACCTGTCGCAGAGAAAGAACGAAGGAGAAACAGCAGACAAGGA<br>ACTGGGAGCACTGCTGAAGGGAGTCGCAGGAAACGCACACGCACTGCAGAC<br>AGGAGACTTCAGAACACCGGCAGAACTGGCACTGAACAAGTTCGAAAAGGA<br>ATCGGGACACATCAGAAACCAGAGATCGGACTACTCGCACACATTCTCGAG<br>AAAGGACCTGCAGGCAGAACTGATCCTGCTGTTCGAAAAGCAGAAGGAATT<br>CGGAAACCCGCACGTCTCGGGAGGACTGAAGGAAGGAATCGAAAACACTGCT<br>GATGACACAGAGACCGGCACTGTCGGGAGACGCAGTCCAGAAGATGCTGGG<br>ACACTGCACATTCGAACCGGCAGAACCGAAGGCAGCAAAGAACACATACAC<br>AGCAGAAAGATTCATCTGGCTGACAAAGCTGAACAACCTGAGAATCCTGGA<br>ACAGGGATCGGAAAGACCGCTGACAGACACAGAAAGAGCAACACTGATGGA<br>CGAACCGTACAGAAAGTCGAAGCTGACATACGCACAGGCAAGAAAGCTGCT<br>GGGACTGGAAGACACAGCATTCTTCAAGGGACTGAGATACGGAAAGGACAA<br>CGCAGAAGCATCGACACTGATGGAAATGAAGGCATACCACGCAATCTCGAG<br>AGCACTGGAAAAGGAAGGACTGAAGGACAAGAAGTCGCCGCTGAACCTGTC<br>GCCGGAACTGCAGGACGAAATCGGAACAGCATTCTCGCTGTTCAAGACAGA<br>CGAAGACATCACAGGAAGACTGAAGGACAGAATCCAGCCGGAAATCCTGGA<br>AGCACTGCTGAAGCACATCTCGTTCGACAAGTTCGTCCAGATCTCGCTGAA<br>GGCACTGAGAAGAATCGTCCCGCTGATGGAACAGGGAAAGAGATACGACGA<br>AGCATGCGCAGAAATCTACGAGACCACTACGGAAAGAAGAACACAGAAGA<br>AAAGATCTACCTGCCGCCGATCCCGGCAGACGAAATCAGAAACCCGGTCGT<br>CCTGAGAGCACTGTCGCAGGCAAGAAAGGTCATCAACGGAGTCGTCAGAAG<br>ATACGGATCGCCGGCAAGAATCCACATCGAAACAGCAAGAGAAGTCGGAAA<br>GTCGTTCAAGGACAGAAAGGAAATCGAAAAGAGACAGGAAGAAAACAGAAA<br>GGACAGAGAAAAGGCAGCAAAGTTCAGAGAATACTTCCCGAACTTCGT<br>CGGAGAACCGAAGTCGAAGGACATCCTGAAGCTGAGACTGTACGAACAGCA<br>GCACGGAAAGTGCCTGTACTCGGGAAAGGAAATCAACCTGGGAAGACTGAA<br>CGAAAAGGGATACGTCGAAATCGACCACGCACTGCCGTTCTCGAGAACATG<br>GGACGACTCGTTCAACAACAAGGTCCTGGTCCTGGGATCGGAAAACCAGAA<br>CAAGGGAAACCAGACACCGTACGAATACTTCAACGGAAAGGACAACTCGAG<br>AGAATGGCAGGAATTCAAGGCAAGAGTCGAAACATCGAGATTCCCGAGATC | 267 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| | GAAGAAGCAGAGAATCCTGCTGCAGAAGTTCGACGAAGACGGATTCAAGGA AAGAAACCTGAACGACACAAGATACGTCAACAGATTCCTGTGCCAGTTCGT CGCAGACAGAATGAGACTGACAGGAAAGGGAAGAAGAGAGTCTTCGCATC GAACGGACAGATCACAAACCTGCTGAGAGGATTCTGGGGACTGAGAAAGGT CAGAGCAGAAAACGACAGACACCACGCACTGGACGCAGTCGTCGTCGCATG CTCGACAGTCGCAATGCAGCAGAAGATCACAAGATTCGTCAGATACAAGGA AATGAACGCATTCGACGGAAAGACAATCGACAAGGAAACAGGAGAAGTCCT GCACCAGAAGACACACTTCCCGCAGCCGTGGGAATTCTTCGCACAGGAAGT CATGATCAGAGTCTTCGGAAAGCCGGACGGAAAGCCGGAATTCGAAGAAGC AGACACACTGGAAAAGCTGAGAACACTGCTGGCAGAAAAGCTGTCGTCGAG ACCGGAAGCAGTCCACGAATACGTCACACCGCTGTTCGTCTCGAGAGCACC GAACAGAAAGATGTCGGGACAGGGACACATGGAAACAGTCAAGTCGGCAAA GAGACTGGACGAAGGAGTCTCGGTCCTGAGAGTCCCGCTGACACAGCTGAA GCTGAAGGACCTGGAAAAGATGGTCAACAGAGAAAGAGAACCGAAGCTGTA CGAAGCACTGAAGGCAAGACTGGAAGCACACAAGGACGACCCGGCAAAGGC ATTCGCAGAACCGTTCTACAAGTACGACAAGGCAGGAAACAGAACACAGCA GGTCAAGGCAGTCAGAGTCGAACAGGTCCAGAAGACAGGAGTCTGGGTCGA AAACCACAACGGAATCGCAGACAACGCAACAATGGTCAGAGTAGACGTCTT CGAAAAGGGAGACAAGTACTACCTGGTCCCGATCTACTCGTGGCAGGTCGC AAAGGGAATCCTGCCGGACAGAGCAGTCGTCCAGGGAAAGGACGAAGAAGA CTGGCAGCTGATCGACGACTCGTTCAACTTCAAGTTCTCGCTGCACCCGAA CGACCTGGTCGAAGTCATCACAAAGAAGGCAAGAATGTTCGGATACTTCGC ATCGTGCCACAGAGGAACAGGAAACATCAACATCAGAATCCACGACCTGGA CCACAAGATCGGAAAGAACGGAATCCTGGAAGGAATCGGAGTCAAGACAGC ACTGTCGTTCCAGAAGTACCAGATCGACGAACTGGGAAAGGAAATCAGACC GTGCAGACTGAAGAAGAGACCGCCGGTCAGATCCGGAAAGAGAACAGCAGA CGGATCGGAATTCGAATCGCCGAAGAAGAAGAGAAAGGTCGAATGATAGCT AG<u>CTCGAG</u>TCTAGAGGGCCCGTTTAAACCCGCTGATCAGCCTCGACTGTGC CTTCTAGTTGCCAGCCATCTGTTGTTTGCCCCTCCCCCGTGCCTTCCTTGA CCCTGGAAGGTGCC<u>ACTCCCACTGTCCTTTCCTAATAAAATGAGGAAATTG CATCGCATTGTCTGAGTAGGTGTCATTCTATTCTGGGGGGTGGGGTGGGGC AGGACAGCAAGGGGGAGGATTGGGAAGACAATAGCAGGCATGCTGGGGATG CGGTGGGCTCTATGG | |
| Amino acid sequence of *Neisseria meningitidis* Cas9 | MAAFKPNSINYILGLDIGIASVGWAMVEIDEEENPIRLIDLGVRVFERAEV PKTGDSLAMARRLARSVRRLTRRRAHRLLRTRRLLKREGVLQAANFDENGL IKSLPNTPWQLRAAALDRKLTPLEWSAVLLHLIKHRGYLSQRKNEGETADK ELGALLKGVAGNAHALQTGDFRTPAELALNKFEKESGHIRNQRSDYSHTFS RKDLQAELILLFEKQKEFGNPHVSGGLKEGIETLLMTQRPALSGDAVQKML GHCTFEPAEPKAAKNTYTAERFIWLTKLNNLRILEQGSERPLTDTERATLM DEPYRKSKLTYAQARKLLGLEDTAFFKGLRYGKDNAEASTLMEMKAYHAIS RALEKEGLKDKKSPLNLSPELQDEIGTAFSLFKTDEDITGRLKDRIQPEIL EALLKHISFDKFVQISLKALRRIVPLMEQGKRYDEACAEIYGDHYGKKNTE EKIYLPPIPADEIRNPVVLRALSQARKVINGVVRRYGSPARIHIETAREVG KSFKDRKEIEKRQEENRKDREKAAAKFREYFPNFVGEPKSKDILKLRLYEQ QHGKCLYSGKEINLGRLNEKGYVEIDHALPFSRTWDDSFNNKVLVLGSENQ NKGNQTPYEYFNGKDNSREWQEFKARVETSRFPRSKKQRILLQKFDEDGFK ERNLNDTRYVNRFLCQFVADRMRLTGKGKKRVFASNGQITNLLRGFWGLRK VRAENDRHHALDAVVVACSTVAMQQKITRFVRYKEMNAFDGKTIDKETGEV LHQKTHFPQPWEFFAQEVMIRVFGKPDGKPEFEEADTLEKLRTLLAEKLSS RPEAVHEYVTPLFVSRAPNRKMSGQGHMETVKSAKRLDEGVSVLRVPLTQL KLKDLEKMVNREREPKLYEALKARLEAHKDDPAKAFAEPFYKYDKAGNRTQ QVKAVRVEQVQKTGVWVRNHNGIADNATMVRVDVFEKGDKYYLVPIYSWQV AKGILPDRAVVQGKDEEDWQLIDDSFNFKFSLHPNDLVEVITKKARMFGYF ASCHRGTGNINIRIHDLDHKIGKNGILEGIGVKTALSFQKYQIDELGKEIR PCRLKKRPPVRSGKRTADGSEFESPKKKRKVE | 268 |
| G390 single guide RNA targeting the rat TTR gene | mG*mC*mC*GAGUCUGGAGAGCUGCAGUUUUAGAmGmCmUmAmGmAmAm UmAmGmCAAGUUAAAAUAAGGCUAGUCCGUUAUCAmAmCmUmUmGmAmAmA mAmAmGmUmGmGmCmAmCmCmGmAmGmUmCmGmGmUmGmCmU*mU*mU*mU | 269 |
| trRNA | AACAGCAUAGCAAGUUAAAAUAAGGCUAGUCCGUUAUCAACUUGAAAAGU GGCACCGAGUCGGUGCUUUUUUU | 270 |
| | Not Used | 271 |
| G534 single guide RNA | mA*mC*mG*CAAUAUCAGUCCAGCGGUUUUAGAmGmCmUmAmGmAmAmAm UmAmGmCAAGUUAAAAUAAGGCUAGUCCGUUAUCAmAmCmUmUmGmAmAmA | 272 |

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

| Description | Sequence | SEQ ID No. |
|---|---|---|
| targeting the rat TTR gene | mAmAmGmUmGmGmCmAmCmCmGmAmGmUmCmGmGmUmGmCmU*mU*mU*mU | |
| G000395 5' truncated inactive sgRNA modified sequence | mG*mC*mA*AUGGUGUAGCGGGUUUUAGAmGmCmUmAmGmAmAmAmUmAmG mCAAGUUAAAAUAAGGCUAGUCCGUUAUCAmAmCmUmUmGmAmAmAmAmAm GmUmGmGmCmAmCmCmGmAmGmUmCmGmGmUmGmCmU*mU*mU*mU | 273 |
| SV40 NLS | PKKKRKV | 274 |
| Alternate SV40 NLS | PKKKRRV | 275 |
| Nucleoplasmin NLS | KRPAATKKAGQAKKKK | 276 |
| Exemplary Kozak sequence | gccRccAUGG | 277 |
| Exemplary Kozak sequence | gccgccRccAUGG | 278 |

* = PS linkage ; 'm' = 2'-O-Me nucleotide

---

What is claimed is:

1. A composition comprising a single guide RNA (sgRNA) comprising in 5' to 3' order, 1) one of the following (i)-(iii): (i) a guide sequence comprising the sequence of SEQ ID NO: 23; (ii) a guide sequence that is at least 17, 18, or 19 contiguous nucleotides of the sequence of SEQ ID NO: 23; or (iii) a guide sequence that is at least 90% identical to the sequence of SEQ ID NO: 23; and 2) the sequence of SEQ ID NO: 125, wherein the sequence of SEQ ID NO: 125 comprises a modification pattern of nucleotides 21-100 of SEQ ID NO: 3 (GUUUUAGAmGmCmUmAmGmAmA-mAmUmAmGmCAAGUUAAAAUAAGGCUAGUC CGUUAUCAmAmCmUmUmGmAmAmAmAmG-mUmGmGmCmAmCmCmGmAmG mUmCmGmGmUmGmCmU*mU*mU*mU), wherein a * indicates a phosphorothioate (PS) linkage and a lower case "m" indicates that the nucleotide is 2'-O-Me modified.

2. The composition of claim 1, wherein the sgRNA comprises the sequence of SEQ ID NO: 87.

3. The composition of claim 1, wherein the sgRNA comprises a sequence that is at least 97% identical to the sequence of SEQ ID NO: 87.

4. The composition of claim 1, wherein the sgRNA comprises a modification pattern of SEQ ID NO: 3, wherein each N in SEQ ID NO: 3 is any natural or non-natural nucleotide, wherein the N's in SEQ ID NO: 3 form the guide sequence.

5. The composition of claim 1, wherein the sgRNA further comprises:
   (a) PS bonds between the first four nucleotides; or
   (b) 2'-O-Me modified nucleotides at the first three nucleotides at the 5' end.

6. The composition of claim 1, wherein the sgRNA further comprises:
   (a) PS bonds between the first four nucleotides; and
   (b) 2'-O-Me modified nucleotides at the first three nucleotides at the 5' end.

7. The composition of claim 1, wherein the sgRNA is associated with a lipid nanoparticle (LNP).

8. The composition of claim 7, wherein the LNP comprises one or more of an ionizable lipid, a neutral lipid, a helper lipid, or a stealth lipid.

9. The composition of claim 8, wherein
   (i) the ionizable lipid is Lipid A or Lipid B;
   (ii) the neutral lipid is DSPC;
   (iii) the helper lipid is cholesterol;
   (iv) the stealth lipid is PEG-DMG; or
   (v) a combination of any two or more of (i)-(iv).

10. The composition of claim 1, wherein the composition further comprises an RNA-guided DNA binding agent or an mRNA that encodes an RNA-guided DNA binding agent.

11. The composition of claim 10, wherein the RNA-guided DNA binding agent is Cas9.

12. The composition of claim 11, wherein the mRNA encoding the RNA-guided DNA binding agent comprises an open reading frame (ORF) comprising a sequence that is at least 90% identical to any one of SEQ ID NOs: 201, 204, 210, 214, 215, 223, 224, 250, 252, or 254.

13. A pharmaceutical formulation comprising the composition of claim 1 and a pharmaceutically acceptable carrier.

14. A lipid nanoparticle (LNP) comprising the composition of claim 1 and a nucleic acid encoding an RNA-guided DNA binding agent.

15. An isolated cell comprising the composition of claim 1.

16. The cell of claim 15, wherein the cell is a hepatocyte.

17. A composition comprising a single guide RNA (sgRNA) comprising the sequence of SEQ ID NO: 87 (mA*mA*mA*GGCUGCUGAUGACACCUGUUU-UAGAmGmCmUmAmGmAmAmAmUm AmGmCAAGUUAAAAUAAGGCUAGUCCGUUAUCA-mAmCmUmUmGmAmAmAmAm AmGmUmGmGmC-mAmCmCmGmAmGmUm-CmGmGmUmGmCmU*mU*mU*mU), wherein a * indicates a phosphorothioate (PS) linkage and a lower case "m" indicates that the nucleotide is 2'-O-Me modified.

18. A composition comprising (i) a single guide RNA (sgRNA) comprising the sequence of SEQ ID NO: 87 (mA*mA*mA*GGCUGCUGAUGACACCUGUUUU-AGAmGmCmUmAmGmAmAmAmUm AmGmCAAGUUAAAAUAAGGCUAGUCCGUUAUCA-mAmCmUmUmGmAmAmAmAm AmGmUmGmGmC-mAmCmCmGmAmGmUmCm-GmGmUmGmCmU*mU*mU*mU), wherein a* indicates a phosphorothioate (PS) linkage and a lower case "m" indicates that the nucleotide is 2'-O-Me modified, and (ii) a Cas9 or a nucleic acid encoding the Cas9.

19. The composition of claim 18, wherein the nucleic acid encoding the Cas9 comprises an open reading frame (ORF) comprising a sequence that is at least 90% identical to any one of SEQ ID NOs: 201, 204, 210, 214, 215, 223, 224, 250, 252, or 254.

20. A lipid nanoparticle (LNP) formulation comprising (i) a single guide RNA (sgRNA) comprising the sequence of SEQ ID NO: 87 (mA*mA*mA*GGC-UGCUGAUGACACCUGUUUUAGAmGmCmUmAmG-mAmAmAmUm AmGmCAAGUUAAAAUAAGGCUA-GUCCGUUAUCAmAmCmUmUmGmAmAmAmAm AmGmUmGmGmCmAmCmCmGmAmGmUmCmGm-GmUmGmCmU*mU*mU*mU), wherein a * indicates a phosphorothioate (PS) linkage and a lower case "m" indicates that the nucleotide is 2'-O-Me modified, and (ii) a nucleic acid encoding a Cas9."

21. The LNP formulation of claim 20, wherein the LNP comprises an ionizable lipid, a neutral lipid, a helper lipid, or a stealth lipid.

22. The LNP formulation of claim 21, wherein
   (i) the ionizable lipid is Lipid A or Lipid B;
   (ii) the neutral lipid is DSPC;
   (iii) the helper lipid is cholesterol; and
   (iv) the stealth lipid is PEG-DMG; or
   (v) a combination of any two or more of (i)-(iv).

23. The LNP formulation of claim 21, wherein the LNP comprises Lipid A, DSPC, cholesterol, and PEG-DMG.

24. The composition of claim 18, wherein the Cas9 is a *S. pyogenes* (Spy) Cas9.

* * * * *

SEQUENCE LISTING

```
Sequence total quantity: 278
SEQ ID NO: 1                    moltype = DNA  length = 4411
FEATURE                         Location/Qualifiers
misc_feature                    1..4411
                                note = Synthetic: Cas9 transcript with 5 UTR of HSD, ORF
                                  corresponding to SEQ ID NO: 204, Kozak sequence, and 3 UTR
                                  of ALB
source                          1..4411
                                mol_type = other DNA
                                organism = synthetic construct
SEQUENCE: 1
gggtcccgca gtcggcgtcc agcggctctg cttgttcgtg tgtgtgtcgt tgcaggcctt   60
attcggatcc gccaccatgg acaagaagta cagcatcgga ctggacatcg aacaaacag   120
cgtcggatgg gcagtcatca cagacgaata caaggtcccg agcaagaagt tcaaggtcct   180
gggaaacaca gacagacaca gcatcaagaa gaacctgatc ggagcactgc tgttcgacag   240
cggagaaaca gcagaagcaa caagactgaa gagaacagca agaagaagat acacaagaag   300
aaagaacaga atctgctacc tgcaggaaat cttcagcaac gaaatggcaa aggtcgacga   360
cagcttcttc cacagactgg aagaaagctt cctggtcgaa gaagacaaga agcacgaaag   420
acacccgatc ttcggaaaca tcgtcgacga agtcgcatac cacgaaaagt acccgacaat   480
ctaccacctg agaagaagc tggtcgacag cacagacaag gcagacctga gactgatcta   540
cctggcactg gcacacatga tcaagttcag aggacacttc ctgatcgaag agacctgaa   600
cccggacaac agcgacgtcg acaagctgtt catccagctg gtccagacat acaaccagct   660
gttcgaagaa aacccgatca acgcaagcgg agtcgacgca aaggcaatcc tgagcgcaag   720
actgagcaag agcagaagac tggaaaacct gatcgcacag ctgccgggag aaaagaagaa   780
cggactgttc ggaaacctga tcgcactgag cctgggactg acaccgaact tcaagagcaa   840
cttcgacctg gcagaagacg caaagctgca gctgagcaag gacacatacg acgacgact   900
ggacaacctg ctggcacaga tcggacacca gtacgcagac ctgttcctgg cagcaaagaa   960
cctgagcgac gcaatcctgc tgagcgacat cctgagagtc aacacagaaa tcacaaaggc  1020
accgctgagc gcaagcatga tcaagagata cgacgaacac caccggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agaacattc gacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
```

```
ggcaagagga aacagcagat tcgcatggat gacaagaaag agcgaagaaa caatcacacc 1500
gtggaacttc gaagaagtcg tcgacaaggg agcaagcgca cagagcttca tcgaaagaat 1560
gacaaacttc gacaagaacc tgccgaacga aaaggtcctg ccgaagcaca gcctgctgta 1620
cgaatacttc acagtctaca acgaactgac aaaggtcaag tacgtcacag aaggaatgag 1680
aaagccggca ttcctgagcg gagaacagaa gaaggcaatc gtcgacctgc tgttcaagac 1740
aaacagaaag gtcacagtca agcagctgaa ggaagactac ttcaagaaga tcgaatgctt 1800
cgacagcgtc gaaatcagcg gagtcgaaga cagattcaac gcaagcctgg aacatacca 1860
cgacctgctg aagatcatca aggacaagga cttcctggac aacgaagaaa acgaagacat 1920
cctggaagac atcgtcctga cactgacact gttcgaagac agagaaatga tcgaagaaag 1980
actgaagaca tacgcacacc tgttcgacga caaggtcatg aagcagctga agagaagaag 2040
atacacagga tggggaagac tgagcagaaa gctgatcaac ggaatcagag acaagcagag 2100
cggaaagaca atcctggact tcctgaagag cgacggattc gcaaacagaa acttcatgca 2160
gctgatccac gacgacagcc tgacattcaa ggaagacatc cagaaggcac aggtcagcgg 2220
acagggagac agcctgcacg aacacatcgc aaacctggca ggaagcccgg caatcaagaa 2280
gggaatcctg cagacagtca aggtcgtcga cgaactggtc aaggtcatgg aagacacaa 2340
gccgaaaaac atcgtcatcg aaatggcaag agaaaaccag acaacacaga agggacagaa 2400
gaacagcaga gaaagaatga agagaatcga gaaggaatc aaggaactgg aagccagat 2460
cctgaaggaa caccggtcg aaaacacaca gctgcagaac gaaaagctgt acctgtacta 2520
cctgcagaac ggaagagaca tgtacgtcga ccaggaactg gacatcaaca gactgagcga 2580
ctacgacgtc gaccacatcg tcccgcagag cttcctgaag gacgacagca tcgacaacaa 2640
ggtcctgaca agaagcgaca gaacagagg aaagagcgac aacgtcccga gcgaagaagt 2700
cgtcaagaag atgaagaact actggagaca gctgctgaac gcaaagctga tcacacagag 2760
aaagttcgac aacctgacaa aggcagagag aggaggactg agcgaactgg acaaggcagg 2820
attcatcaag agacagctgg tcgaaacaag acagatcaca aagcacgtcg cacagatcct 2880
ggacagcaga atgaacacaa agtacgacga aaacgacaag ctgatcagag aagtcaaggt 2940
catcacactg aagagcaagc tggtcagcga cttccagt tctacaaggt 3000
cagagaaatc aacaactacc accacgcaca cgacgcatac ctgaacgcag tcgtcggaac 3060
agcactgatc aagaagtacc cgaagctgga aagcgaattc gtctacgag actcaaggt 3120
ctacgacgtc agaagatga tcgcaaagag cgaacaggaa atcggaaagg caacagcaaa 3180
gtacttcttc tacagcaaca tcatgaactt cttcaagaca gaaatccac tggcaaacgg 3240
agaaatcaga aagagaccgc tgatcgaaac aaacgagaa acaggagaaa tcgtctggga 3300
caagggaaga gacttcgcaa cagtcagaaa ggtcctgagc atgccgcagg tcaacatcgt 3360
caagaagaca gaagtccaga caggaggatt cagcaaggaa agcatcctgc cgaagagaaa 3420
cagcgacaag ctgatcgcaa gaaagaagga ctgggaccg aagaagtacg gaggattcga 3480
cagcccgaca gtcgcataca gcgtcctggt cgtcgcaaag gtcgaaaagg gaaagagcaa 3540
gaagctgaag agcgtcaagg aactgctggg aatcacaatc atggaaaga gcagcttcga 3600
aaagaacccg atcgacttcc tggaagcaaa gggatacaag gaagtcaaga aggacctgat 3660
catcaagctg ccgaagtaca gcctgttcga actggaaaac ggaagaaaga gaatgctggc 3720
aagcgcagga gaactgcaga agggaaacga actggcactg ccgagcaagt acgtcaactt 3780
cctgtacctg gcaagccact acgaaaagct gaagggaagc ccggaagaca cgaacagaa 3840
gcagctgttc gtcgaacagc acaagcacta cctggacgaa atcatcgaac agatcagcga 3900
attcagcaag agagtcatcc tggcagacgc aaacctggac aaggtcctga gcgcatacaa 3960
caagcacaga gacaagccga tcagagaaca ggcagaaaac atcatccacc tgttcacact 4020
gacaaacctg ggagcaccgg cagcattcaa gtacttcgac acaacaatcg acagaaagag 4080
atacacaagc acaaggaag tcctggacga aacactgatc caccagagca tcacaggact 4140
gtacgaaaca agaatcgacc tgagccagct gggaggagac ggaggaggaa gcccgaagaa 4200
gaagagaaag gtctagctag ccatcacatt taaaagcatc tcagcctacc atgagaataa 4260
gagaaagaaa atgaagatca atagcttatt catctctttt tcttttttcgt tggtgtaaag 4320
ccaacaccct gtctaaaaaa cataaatttc tttaatcatt ttgcctcttt tctctgtgct 4380
tcaattaata aaaatggaa agaacctcga g 4411
```

```
SEQ ID NO: 2           moltype = DNA   length = 4403
FEATURE                Location/Qualifiers
misc_feature           1..4403
                       note = Synthetic: Cas9 transcript comprising Cas9 ORF
                         corresponding to SEQ ID NO: 205 using codons with
                         generally high expression in humans
source                 1..4403
                       mol_type = other DNA
                       organism = synthetic construct
SEQUENCE: 2
gggtcccgca gtcggcgtcc agcggctctg cttgttcgtg tgtgtgtcgt tgcaggcctt 60
attcggatcc atgcctaaga aaaagcggaa ggtcgacggg gataagaagt actcaatcgg 120
gctggatatc ggaactaatt ccgtgggttg ggcagtgatc acggatgaat acaaagtgcc 180
gtccaagaag ttcaaggtcc tggggaacac cgatagacac agcatcaaga aaaatctcat 240
cggagccctg ctgtttgact ccggcgaaac cgcagaagcg acccggctca acgtaccgc 300
gaggcgacgc tacacccgc ggaagaatcg catctgctat ctgcaagaga tcttttcgaa 360
cgaaatggca aaggtcgacg acagcttctt ccaccgcctg gaagaatctt tcctggtgga 420
ggaggacaag aagcatgaac ggcatcctat ctttggaaac atcgtcgacg aagtggctga 480
ccacgaaaag tacccgacca tctaccatct gcggaagaag ttggttgact caactgacaa 540
ggccgacctc agattgatct acttggcct cgcccatatg atcaaattcc gcggacactt 600
cctgatcgaa ggcgatctga accctgataa ctccgacgtg ataagcttt tcattcaact 660
ggtgcagacc tacaaccaac tgttcgaaga aaacccaatc aatgctagcg gcgtcgatgc 720
caaggccatc ctgtccgccc ggctgtcgaa gtcgcggac ctcgaaaacc tgatcgcact 780
gctgccggga gagaaaaaga acggactttt cggcaacttg atcgctctct cactgggact 840
cactcccaat ttcaagtcca ttttgaccct ggccgaggac gcgaagctgc aactctcaaa 900
ggacacctac gacgacgact tggacaattt gctggcacaa attggcgatc agtacgcgga 960
tctgttcctt gccgctaaga acctttcgga cgcaatcttg ctgtccgata tcctgcgcgt 1020
gaacaccgaa ataaccaaag cgccgcttag cgcctcgatg attaagcggt acgacgagca 1080
```

```
tcaccaggat ctcacgctgc tcaaagcgct cgtgagacag caactgcctg aaaagtacaa    1140
ggagatcttc ttcgaccagt ccaagaatgg gtacgcaggg tacatcgatg gaggcgctag    1200
ccaggaagag ttctataagt tcatcaagcc aatcctggaa aagatggacg gaaccgaaga    1260
actgctggtc aagctgaaca gggaggatct gctccggaaa cagagaacct ttgacaacgg    1320
atccattccc caccagatcc atctgggtga gctgcacgtc atcttgcggc gccaggagga    1380
cttttaccca ttcctcaagg acaaccggga aaagatcgag aaaattctga cgttccgcat    1440
cccgtattac gtgggcccac tggcgcgcgg caattcgcgc ttcgcgtgga tgactagaaa    1500
atcagaggaa accatcactc cttggaattt cgaggaagtt gtggataagg gagcttcggc    1560
acaaagcttc atcgaacgaa tgaccaactt cgacaagaat ctcccaaacg agaaggtgct    1620
tcctaagcac agcctccttt acgaatactt cactgtctac aacgaactga ctaaagtgaa    1680
atacgttact gaaggaatga ggaagccggc ctttctgtcc ggagaacaga agaaagcaat    1740
tgtcgatctg ctgttcaaga ccaaccgcaa ggtgaccgtc aagcagctta agaggactac    1800
cttcaagaag atcgagtgtt tcgactcagt ggaaatcagc ggggtggagg acagattcaa    1860
cgcttcgctg ggaacctatc atgatctcct gaagatcatc aaggacaagg acttccttga    1920
caacgaggag aacgaggaca tcctggaaga tatcgtcctg accttgaccc ttttcgagga    1980
tcgcgagatg atcgaggaga ggcttaagac ctacgctcat ctcttcgacg ataaggtcat    2040
gaaacaactc aagcgccgcc ggtacactgg ttggggccgc ctctcccgca agctgatcaa    2100
cggtattcgc gataaacaga gcggtaaaac tatcctggat ttcctcaaat cggatggctt    2160
cgctaatcgt aacttcatgc aattgatcca cgacgacagc ctgacccttta aggaggacat    2220
ccaaaaagca caagtgtccg gacagggaga ctcactccat gaacacatcg cgaatctggc    2280
cggttcgccg gcgattaaga agggaattct gcaaactgtg aaggtggtcg acgagctggt    2340
gaaggtcatg ggacggcaca aacggagaa tatcgtgatt gaaatggccc gagaaaacca    2400
gactacccag aagggccaga aaactcccg cgaaaggatg aagcggatcg aagaaggaat    2460
caaggagctg ggcagccaga tcctgaaaga gcacccggtg aaaacacgc agctgcagaa    2520
cgagaagctc tacctgtact atttgcaaaa tggacgggac atgtacgtgg accaagagct    2580
ggacatcaat cggttgtctg attaccacgt ggaccacatc gttccacagt cctttctgaa    2640
ggatgactcg atcgataaca aggtgttgac tcgcagcgca aagaacagag ggaagtcaga    2700
taatgtgcca tcggaggagg tcgtgaagaa gatgaagaat tactggcggc agctcctgaa    2760
tgcgaagctg attacccaga gaaagtttga caatctcact aaagccgagc gcggcggact    2820
ctcagagctg gataaggctg gattcatcaa acggcagctg gtcgagactc ggcagattac    2880
caagcacgtg gcgcagatct tggactcccg catgaacact aaatacgacg agaacgataa    2940
gctcatccgg gaagtgaagg tgattaccct gaaaagcaaa cttgtgtcgg actttcggaa    3000
ggactttcag ttttacaaag tgagagaaat caacaactac catcacgcgc atgacgcata    3060
cctcaacgct gtggtcggta ccgccctgat caaaaagtac cctaaacttg aatcggagtt    3120
tgtgtacgga gactacaagg tctacgacgt gaggaagatg atagccaagt ccgaacagga    3180
aatcgggaaa gcaactgcga aatacttctt ttactcaaac atcatgaact ttttcaagac    3240
tgaaattacg ctgccaatg gagaaatcag gaagaggcca ctgatcgaaa ctaacggaga    3300
aacgggcgaa atcgtgtggg acaagggcag ggacttcgca actgttcgca aagtgctctc    3360
tatgccgcaa gtcaatattg tgaagaaaac cgaagtgcaa accggcggat tttcaaagga    3420
atcgatcctc ccaaagagaa atagcgacaa gctcattgca cgcaagaaag actgggaccc    3480
gaagaagtac ggaggattcg attcgccgac tgtcgcatac tccgtcctcg tggtggccaa    3540
ggtggagaag ggaaagagca aaagctcaa atccgtcaaa gagctgctgg ggattaccat    3600
catggaacga tcctcgttcg agaagaaccc gattgatttc ctcgaggcga agggttacaa    3660
ggaggtgaag aaggatctga tcatcaaact ccccaagtac tcactgttcg aactggaaaa    3720
tggtcggaag cgcatgctgg cttcggccgg agaactccaa aaaggaaatg agctggcctt    3780
gcctagcaag tacgtcaact tcctctatct tgcttcgcac tacgaaaaac tcaaagggtc    3840
accggaagat aacgaacaga agcagctttt cgtggagcag cacaagcatt atctggatga    3900
aatcatcgaa caaatctccg agttttcaaa gcgcgtgatc ctcgccgacg ccaacctcga    3960
caaagtcctg tcgcctaca ataagcatag agataagccg atcagagaac aggccgagaa    4020
cattatccac ttgttcaccc tgactaacct gggagcccca gccgccttca gtacttcga    4080
tactactatc gatcgcaaaa gatacacgtc caccaaggaa gttctggaca cgaccctgat    4140
ccaccaaagc atcactggac tctacgaaac taggatcgat ctgtcgcagc tgggtggcga    4200
ttgatagtct agcatcaca tttaaaagca tctcagccta ccatgagaat aagagaaaga    4260
aaatgaagat caatagctta ttcatctctt tttcttttttc gttggtgtaa agccaacacc    4320
ctgtctaaaa aacataaatt tctttaatca ttttgcctct tttctctgtg cttcaattaa    4380
taaaaatgg aaagaacctc gag                                             4403
SEQ ID NO: 3             moltype = RNA   length = 100
FEATURE                  Location/Qualifiers
misc_feature             1..100
                         note = Synthetic: modified sgRNA sequence
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 3
nnnnnnnnnn nnnnnnnnnn gttttagagc tagaaatagc aagttaaaat aaggctagtc    60
cgttatcaac ttgaaaaagt ggcaccgagt cggtgctttt                         100
```

```
SEQ ID NO: 4              moltype = DNA  length = 105
FEATURE                   Location/Qualifiers
misc_feature              1..105
                          note = Synthetic: 30/30/39 poly-A sequence
source                    1..105
                          mol_type = other DNA
                          organism = synthetic construct
SEQUENCE: 4
aaaaaaaaaa aaaaaaaaaa aaaaaaaaaa gcgaaaaaaa aaaaaaaaaa aaaaaaaaaa    60
aaaccgaaaa aaaaaaaaaa aaaaaaaaaa aaaaaaaaaa aaaaa                   105

SEQ ID NO: 5              moltype = RNA  length = 20
FEATURE                   Location/Qualifiers
misc_feature              1..20
                          note = Synthetic: CR003335 gRNA targeting Human TTR (Exon 1)
source                    1..20
                          mol_type = other RNA
                          organism = synthetic construct
SEQUENCE: 5
ctgctcctcc tctgccttgc                                                20

SEQ ID NO: 6              moltype = RNA  length = 20
FEATURE                   Location/Qualifiers
misc_feature              1..20
                          note = Synthetic: CR003336 gRNA targeting Human TTR (Exon 1)
source                    1..20
                          mol_type = other RNA
                          organism = synthetic construct
SEQUENCE: 6
cctcctctgc cttgctggac                                                20

SEQ ID NO: 7              moltype = RNA  length = 20
FEATURE                   Location/Qualifiers
misc_feature              1..20
                          note = Synthetic: CR003337 gRNA targeting Human TTR (Exon 1)
source                    1..20
                          mol_type = other RNA
                          organism = synthetic construct
SEQUENCE: 7
ccagtccagc aaggcagagg                                                20

SEQ ID NO: 8              moltype = RNA  length = 20
FEATURE                   Location/Qualifiers
misc_feature              1..20
                          note = Synthetic: CR003338 gRNA targeting Human TTR (Exon 1)
source                    1..20
                          mol_type = other RNA
                          organism = synthetic construct
SEQUENCE: 8
ataccagtcc agcaaggcag                                                20

SEQ ID NO: 9              moltype = RNA  length = 20
FEATURE                   Location/Qualifiers
misc_feature              1..20
                          note = Synthetic: CR003339 gRNA targeting Human TTR (Exon 1)
source                    1..20
                          mol_type = other RNA
                          organism = synthetic construct
SEQUENCE: 9
acacaaatac cagtccagca                                                20

SEQ ID NO: 10             moltype = RNA  length = 20
FEATURE                   Location/Qualifiers
misc_feature              1..20
                          note = Synthetic: CR003340 gRNA targeting Human TTR (Exon 1)
source                    1..20
                          mol_type = other RNA
                          organism = synthetic construct
SEQUENCE: 10
tggactggta tttgtgtctg                                                20

SEQ ID NO: 11             moltype = RNA  length = 20
FEATURE                   Location/Qualifiers
misc_feature              1..20
                          note = Synthetic: CR003341 gRNA targeting Human TTR (Exon 1)
source                    1..20
                          mol_type = other RNA
                          organism = synthetic construct
```

```
SEQUENCE: 11
ctggtatttg tgtctgaggc                                               20

SEQ ID NO: 12           moltype = RNA  length = 20
FEATURE                 Location/Qualifiers
misc_feature            1..20
                        note = Synthetic: CR003342 gRNA targeting Human TTR (Exon 2)
source                  1..20
                        mol_type = other RNA
                        organism = synthetic construct
SEQUENCE: 12
cttctctaca cccagggcac                                               20

SEQ ID NO: 13           moltype = RNA  length = 20
FEATURE                 Location/Qualifiers
misc_feature            1..20
                        note = Synthetic: CR003343 gRNA targeting Human TTR (Exon 2)
source                  1..20
                        mol_type = other RNA
                        organism = synthetic construct
SEQUENCE: 13
cagaggacac ttggattcac                                               20

SEQ ID NO: 14           moltype = RNA  length = 20
FEATURE                 Location/Qualifiers
misc_feature            1..20
                        note = Synthetic: CR003344 gRNA targeting Human TTR (Exon 2)
source                  1..20
                        mol_type = other RNA
                        organism = synthetic construct
SEQUENCE: 14
tttgaccatc agaggacact                                               20

SEQ ID NO: 15           moltype = RNA  length = 20
FEATURE                 Location/Qualifiers
misc_feature            1..20
                        note = Synthetic: CR003345 gRNA targeting Human TTR (Exon 2)
source                  1..20
                        mol_type = other RNA
                        organism = synthetic construct
SEQUENCE: 15
tctagaactt tgaccatcag                                               20

SEQ ID NO: 16           moltype = RNA  length = 20
FEATURE                 Location/Qualifiers
misc_feature            1..20
                        note = Synthetic: CR003346 gRNA targeting Human TTR (Exon 2)
source                  1..20
                        mol_type = other RNA
                        organism = synthetic construct
SEQUENCE: 16
aaagttctag atgctgtccg                                               20

SEQ ID NO: 17           moltype = RNA  length = 20
FEATURE                 Location/Qualifiers
misc_feature            1..20
                        note = Synthetic: CR003347 gRNA targeting Human TTR (Exon 2)
source                  1..20
                        mol_type = other RNA
                        organism = synthetic construct
SEQUENCE: 17
cattgatggc aggactgcct                                               20

SEQ ID NO: 18           moltype = RNA  length = 20
FEATURE                 Location/Qualifiers
misc_feature            1..20
                        note = Synthetic: CR003348 gRNA targeting Human TTR (Exon 2)
source                  1..20
                        mol_type = other RNA
                        organism = synthetic construct
SEQUENCE: 18
aggcagtcct gccatcaatg                                               20

SEQ ID NO: 19           moltype = RNA  length = 20
FEATURE                 Location/Qualifiers
misc_feature            1..20
                        note = Synthetic: CR003349 gRNA targeting Human TTR (Exon 2)
source                  1..20
                        mol_type = other RNA
```

```
                        organism = synthetic construct
SEQUENCE: 19
tgcacggcca cattgatggc                                                   20

SEQ ID NO: 20           moltype = RNA  length = 20
FEATURE                 Location/Qualifiers
misc_feature            1..20
                        note = Synthetic: CR003350 gRNA targeting Human TTR (Exon 2)
source                  1..20
                        mol_type = other RNA
                        organism = synthetic construct
SEQUENCE: 20
cacatgcacg gccacattga                                                   20

SEQ ID NO: 21           moltype = RNA  length = 20
FEATURE                 Location/Qualifiers
misc_feature            1..20
                        note = Synthetic: CR003351 gRNA targeting Human TTR (Exon 2)
source                  1..20
                        mol_type = other RNA
                        organism = synthetic construct
SEQUENCE: 21
agcctttctg aacacatgca                                                   20

SEQ ID NO: 22           moltype = RNA  length = 20
FEATURE                 Location/Qualifiers
misc_feature            1..20
                        note = Synthetic: CR003352 gRNA targeting Human TTR (Exon 2)
source                  1..20
                        mol_type = other RNA
                        organism = synthetic construct
SEQUENCE: 22
gaaaggctgc tgatgacacc                                                   20

SEQ ID NO: 23           moltype = RNA  length = 20
FEATURE                 Location/Qualifiers
misc_feature            1..20
                        note = Synthetic: CR003353 gRNA targeting Human TTR (Exon 2)
source                  1..20
                        mol_type = other RNA
                        organism = synthetic construct
SEQUENCE: 23
aaaggctgct gatgacacct                                                   20

SEQ ID NO: 24           moltype = RNA  length = 20
FEATURE                 Location/Qualifiers
misc_feature            1..20
                        note = Synthetic: CR003354 gRNA targeting Human TTR (Exon 2)
source                  1..20
                        mol_type = other RNA
                        organism = synthetic construct
SEQUENCE: 24
acctgggagc catttgcctc                                                   20

SEQ ID NO: 25           moltype = RNA  length = 20
FEATURE                 Location/Qualifiers
misc_feature            1..20
                        note = Synthetic: CR003355 gRNA targeting Human TTR (Exon 2)
source                  1..20
                        mol_type = other RNA
                        organism = synthetic construct
SEQUENCE: 25
cccagaggca aatggctccc                                                   20

SEQ ID NO: 26           moltype = RNA  length = 20
FEATURE                 Location/Qualifiers
misc_feature            1..20
                        note = Synthetic: CR003356 gRNA targeting Human TTR (Exon 2)
source                  1..20
                        mol_type = other RNA
                        organism = synthetic construct
SEQUENCE: 26
gcaacttacc cagaggcaaa                                                   20

SEQ ID NO: 27           moltype = RNA  length = 20
FEATURE                 Location/Qualifiers
misc_feature            1..20
                        note = Synthetic: CR003357 gRNA targeting Human TTR (Exon 2)
source                  1..20
```

```
                            mol_type = other RNA
                            organism = synthetic construct
SEQUENCE: 27
ttctttggca acttacccag                                                    20

SEQ ID NO: 28               moltype = RNA   length = 20
FEATURE                     Location/Qualifiers
misc_feature                1..20
                            note = Synthetic: CR003358 gRNA targeting Human TTR (Exon 3)
source                      1..20
                            mol_type = other RNA
                            organism = synthetic construct
SEQUENCE: 28
atgcagctct ccagactcac                                                    20

SEQ ID NO: 29               moltype = RNA   length = 20
FEATURE                     Location/Qualifiers
misc_feature                1..20
                            note = Synthetic: CR003359 gRNA targeting Human TTR (Exon 3)
source                      1..20
                            mol_type = other RNA
                            organism = synthetic construct
SEQUENCE: 29
agtgagtctg gagagctgca                                                    20

SEQ ID NO: 30               moltype = RNA   length = 20
FEATURE                     Location/Qualifiers
misc_feature                1..20
                            note = Synthetic: CR003360 gRNA targeting Human TTR (Exon 3)
source                      1..20
                            mol_type = other RNA
                            organism = synthetic construct
SEQUENCE: 30
gtgagtctgg agagctgcat                                                    20

SEQ ID NO: 31               moltype = RNA   length = 20
FEATURE                     Location/Qualifiers
misc_feature                1..20
                            note = Synthetic: CR003361 gRNA targeting Human TTR (Exon 3)
source                      1..20
                            mol_type = other RNA
                            organism = synthetic construct
SEQUENCE: 31
gctgcatggg ctcacaactg                                                    20

SEQ ID NO: 32               moltype = RNA   length = 20
FEATURE                     Location/Qualifiers
misc_feature                1..20
                            note = Synthetic: CR003362 gRNA targeting Human TTR (Exon 3)
source                      1..20
                            mol_type = other RNA
                            organism = synthetic construct
SEQUENCE: 32
gcatgggctc acaactgagg                                                    20

SEQ ID NO: 33               moltype = RNA   length = 20
FEATURE                     Location/Qualifiers
misc_feature                1..20
                            note = Synthetic: CR003363 gRNA targeting Human TTR (Exon 3)
source                      1..20
                            mol_type = other RNA
                            organism = synthetic construct
SEQUENCE: 33
actgaggagg aatttgtaga                                                    20

SEQ ID NO: 34               moltype = RNA   length = 20
FEATURE                     Location/Qualifiers
misc_feature                1..20
                            note = Synthetic: CR003364 gRNA targeting Human TTR (Exon 3)
source                      1..20
                            mol_type = other RNA
                            organism = synthetic construct
SEQUENCE: 34
ctgaggagga atttgtagaa                                                    20

SEQ ID NO: 35               moltype = RNA   length = 20
FEATURE                     Location/Qualifiers
misc_feature                1..20
                            note = Synthetic: CR003365 gRNA targeting Human TTR (Exon 3)
```

```
source                          1..20
                                mol_type = other RNA
                                organism = synthetic construct
SEQUENCE: 35
tgtagaaggg atatacaaag                                                     20

SEQ ID NO: 36                   moltype = RNA  length = 20
FEATURE                         Location/Qualifiers
misc_feature                    1..20
                                note = Synthetic: CR003366 gRNA targeting Human TTR (Exon 3)
source                          1..20
                                mol_type = other RNA
                                organism = synthetic construct
SEQUENCE: 36
aaatagacac caaatcttac                                                     20

SEQ ID NO: 37                   moltype = RNA  length = 20
FEATURE                         Location/Qualifiers
misc_feature                    1..20
                                note = Synthetic: CR003367 gRNA targeting Human TTR (Exon 3)
source                          1..20
                                mol_type = other RNA
                                organism = synthetic construct
SEQUENCE: 37
agacaccaaa tcttactgga                                                     20

SEQ ID NO: 38                   moltype = RNA  length = 20
FEATURE                         Location/Qualifiers
misc_feature                    1..20
                                note = Synthetic: CR003368 gRNA targeting Human TTR (Exon 3)
source                          1..20
                                mol_type = other RNA
                                organism = synthetic construct
SEQUENCE: 38
aagtgccttc cagtaagatt                                                     20

SEQ ID NO: 39                   moltype = RNA  length = 20
FEATURE                         Location/Qualifiers
misc_feature                    1..20
                                note = Synthetic: CR003369 gRNA targeting Human TTR (Exon 3)
source                          1..20
                                mol_type = other RNA
                                organism = synthetic construct
SEQUENCE: 39
ctctgcatgc tcatggaatg                                                     20

SEQ ID NO: 40                   moltype = RNA  length = 20
FEATURE                         Location/Qualifiers
misc_feature                    1..20
                                note = Synthetic: CR003370 gRNA targeting Human TTR (Exon 3)
source                          1..20
                                mol_type = other RNA
                                organism = synthetic construct
SEQUENCE: 40
cctctgcatg ctcatggaat                                                     20

SEQ ID NO: 41                   moltype = RNA  length = 20
FEATURE                         Location/Qualifiers
misc_feature                    1..20
                                note = Synthetic: CR003371 gRNA targeting Human TTR (Exon 3)
source                          1..20
                                mol_type = other RNA
                                organism = synthetic construct
SEQUENCE: 41
acctctgcat gctcatggaa                                                     20

SEQ ID NO: 42                   moltype = RNA  length = 20
FEATURE                         Location/Qualifiers
misc_feature                    1..20
                                note = Synthetic: CR003372 gRNA targeting Human TTR (Exon 3)
source                          1..20
                                mol_type = other RNA
                                organism = synthetic construct
SEQUENCE: 42
tactcacctc tgcatgctca                                                     20

SEQ ID NO: 43                   moltype = RNA  length = 20
FEATURE                         Location/Qualifiers
misc_feature                    1..20
```

```
                         note = Synthetic: CR003373 gRNA targeting Human TTR (Exon 4)
source                   1..20
                         mol_type = other RNA
                         organism = synthetic construct
SEQUENCE: 43
gtattcacag ccaacgactc                                                       20

SEQ ID NO: 44            moltype = RNA   length = 20
FEATURE                  Location/Qualifiers
misc_feature             1..20
                         note = Synthetic: CR003374 gRNA targeting Human TTR (Exon 4)
source                   1..20
                         mol_type = other RNA
                         organism = synthetic construct
SEQUENCE: 44
gcggcggggg ccggagtcgt                                                       20

SEQ ID NO: 45            moltype = RNA   length = 20
FEATURE                  Location/Qualifiers
misc_feature             1..20
                         note = Synthetic: CR003375 gRNA targeting Human TTR (Exon 4)
source                   1..20
                         mol_type = other RNA
                         organism = synthetic construct
SEQUENCE: 45
aatggtgtag cggcggggc                                                        20

SEQ ID NO: 46            moltype = RNA   length = 20
FEATURE                  Location/Qualifiers
misc_feature             1..20
                         note = Synthetic: CR003376 gRNA targeting Human TTR (Exon 4)
source                   1..20
                         mol_type = other RNA
                         organism = synthetic construct
SEQUENCE: 46
cggcaatggt gtagcggcgg                                                       20

SEQ ID NO: 47            moltype = RNA   length = 20
FEATURE                  Location/Qualifiers
misc_feature             1..20
                         note = Synthetic: CR003377 gRNA targeting Human TTR (Exon 4)
source                   1..20
                         mol_type = other RNA
                         organism = synthetic construct
SEQUENCE: 47
gcggcaatgg tgtagcggcg                                                       20

SEQ ID NO: 48            moltype = RNA   length = 20
FEATURE                  Location/Qualifiers
misc_feature             1..20
                         note = Synthetic: CR003378 gRNA targeting Human TTR (Exon 4)
source                   1..20
                         mol_type = other RNA
                         organism = synthetic construct
SEQUENCE: 48
ggcggcaatg gtgtagcggc                                                       20

SEQ ID NO: 49            moltype = RNA   length = 20
FEATURE                  Location/Qualifiers
misc_feature             1..20
                         note = Synthetic: CR003379 gRNA targeting Human TTR (Exon 4)
source                   1..20
                         mol_type = other RNA
                         organism = synthetic construct
SEQUENCE: 49
gggcggcaat ggtgtagcgg                                                       20

SEQ ID NO: 50            moltype = RNA   length = 20
FEATURE                  Location/Qualifiers
misc_feature             1..20
                         note = Synthetic: CR003380 gRNA targeting Human TTR (Exon 4)
source                   1..20
                         mol_type = other RNA
                         organism = synthetic construct
SEQUENCE: 50
gcagggcggc aatggtgtag                                                       20

SEQ ID NO: 51            moltype = RNA   length = 20
FEATURE                  Location/Qualifiers
```

```
misc_feature          1..20
                      note = Synthetic: CR003381 gRNA targeting Human TTR (Exon 4)
source                1..20
                      mol_type = other RNA
                      organism = synthetic construct
SEQUENCE: 51
ggggctcagc agggcggcaa                                                      20

SEQ ID NO: 52         moltype = RNA  length = 20
FEATURE               Location/Qualifiers
misc_feature          1..20
                      note = Synthetic: CR003382 gRNA targeting Human TTR (Exon 4)
source                1..20
                      mol_type = other RNA
                      organism = synthetic construct
SEQUENCE: 52
ggagtagggg ctcagcaggg                                                      20

SEQ ID NO: 53         moltype = RNA  length = 20
FEATURE               Location/Qualifiers
misc_feature          1..20
                      note = Synthetic: CR003383 gRNA targeting Human TTR (Exon 4)
source                1..20
                      mol_type = other RNA
                      organism = synthetic construct
SEQUENCE: 53
ataggagtag gggctcagca                                                      20

SEQ ID NO: 54         moltype = RNA  length = 20
FEATURE               Location/Qualifiers
misc_feature          1..20
                      note = Synthetic: CR003384 gRNA targeting Human TTR (Exon 4)
source                1..20
                      mol_type = other RNA
                      organism = synthetic construct
SEQUENCE: 54
aataggagta ggggctcagc                                                      20

SEQ ID NO: 55         moltype = RNA  length = 20
FEATURE               Location/Qualifiers
misc_feature          1..20
                      note = Synthetic: CR003385 gRNA targeting Human TTR (Exon 4)
source                1..20
                      mol_type = other RNA
                      organism = synthetic construct
SEQUENCE: 55
cccctactcc tattccacca                                                      20

SEQ ID NO: 56         moltype = RNA  length = 20
FEATURE               Location/Qualifiers
misc_feature          1..20
                      note = Synthetic: CR003386 gRNA targeting Human TTR (Exon 4)
source                1..20
                      mol_type = other RNA
                      organism = synthetic construct
SEQUENCE: 56
ccgtggtgga ataggagtag                                                      20

SEQ ID NO: 57         moltype = RNA  length = 20
FEATURE               Location/Qualifiers
misc_feature          1..20
                      note = Synthetic: CR003387 gRNA targeting Human TTR (Exon 4)
source                1..20
                      mol_type = other RNA
                      organism = synthetic construct
SEQUENCE: 57
gccgtggtgg aataggagta                                                      20

SEQ ID NO: 58         moltype = RNA  length = 20
FEATURE               Location/Qualifiers
misc_feature          1..20
                      note = Synthetic: CR003388 gRNA targeting Human TTR (Exon 4)
source                1..20
                      mol_type = other RNA
                      organism = synthetic construct
SEQUENCE: 58
gacgacagcc gtggtggaat                                                      20

SEQ ID NO: 59         moltype = RNA  length = 20
```

```
FEATURE                  Location/Qualifiers
misc_feature             1..20
                         note = Synthetic: CR003389 gRNA targeting Human TTR (Exon 4)
source                   1..20
                         mol_type = other RNA
                         organism = synthetic construct SEQUENCE: 59
attggtgacg acagccgtgg                                                        20

SEQ ID NO: 60            moltype = RNA  length = 20
FEATURE                  Location/Qualifiers
misc_feature             1..20
                         note = Synthetic: CR003390 gRNA targeting Human TTR (Exon 4)
source                   1..20
                         mol_type = other RNA
                         organism = synthetic construct SEQUENCE: 60
gggattggtg acgacagccg                                                        20

SEQ ID NO: 61            moltype = RNA  length = 20
FEATURE                  Location/Qualifiers
misc_feature             1..20
                         note = Synthetic: CR003391 gRNA targeting Human TTR (Exon 4)
source                   1..20
                         mol_type = other RNA
                         organism = synthetic construct SEQUENCE: 61
ggctgtcgtc accaatccca                                                        20

SEQ ID NO: 62            moltype = RNA  length = 20
FEATURE                  Location/Qualifiers
misc_feature             1..20
                         note = Synthetic: CR003392 gRNA targeting Human TTR (Exon 4)
source                   1..20
                         mol_type = other RNA
                         organism = synthetic construct SEQUENCE: 62
agtccctcat tccttgggat                                                        20

SEQ ID NO: 63            moltype = RNA  length = 20
FEATURE                  Location/Qualifiers
misc_feature             1..20
                         note = Synthetic: CR005298 gRNA targeting Human TTR (Exon 1)
source                   1..20
                         mol_type = other RNA
                         organism = synthetic construct SEQUENCE: 63
tccactcatt cttggcagga                                                        20

SEQ ID NO: 64            moltype = RNA  length = 20
FEATURE                  Location/Qualifiers
misc_feature             1..20
                         note = Synthetic: CR005299 gRNA targeting Human TTR (Exon 4)
source                   1..20
                         mol_type = other RNA
                         organism = synthetic construct SEQUENCE: 64
agccgtggtg gaataggagt                                                        20

SEQ ID NO: 65            moltype = RNA  length = 20
FEATURE                  Location/Qualifiers
misc_feature             1..20
                         note = Synthetic: CR005300 gRNA targeting Human TTR (Exon 1)
source                   1..20
                         mol_type = other RNA
                         organism = synthetic construct SEQUENCE: 65
tcacagaaac actcaccgta                                                        20

SEQ ID NO: 66            moltype = RNA  length = 20
FEATURE                  Location/Qualifiers
misc_feature             1..20
                         note = Synthetic: CR005301 gRNA targeting Human TTR (Exon 1)
source                   1..20
                         mol_type = other RNA
                         organism = synthetic construct SEQUENCE: 66
gtcacagaaa cactcaccgt                                                        20
```

```
SEQ ID NO: 67            moltype = RNA   length = 20
FEATURE                  Location/Qualifiers
misc_feature             1..20
                         note = Synthetic: CR005302 gRNA targeting Human TTR (Exon 2)
source                   1..20
                         mol_type = other RNA
                         organism = synthetic construct
SEQUENCE: 67
acgtgtcttc tctacaccca                                                    20

SEQ ID NO: 68            moltype = RNA   length = 20
FEATURE                  Location/Qualifiers
misc_feature             1..20
                         note = Synthetic: CR005303 gRNA targeting Human TTR (Exon 2)
source                   1..20
                         mol_type = other RNA
                         organism = synthetic construct
SEQUENCE: 68
tgaatccaag tgtcctctga                                                    20

SEQ ID NO: 69            moltype = RNA   length = 20
FEATURE                  Location/Qualifiers
misc_feature             1..20
                         note = Synthetic: CR005304 gRNA targeting Human TTR (Exon 2)
source                   1..20
                         mol_type = other RNA
                         organism = synthetic construct
SEQUENCE: 69
ggccgtgcat gtgttcagaa                                                    20

SEQ ID NO: 70            moltype = RNA   length = 20
FEATURE                  Location/Qualifiers
misc_feature             1..20
                         note = Synthetic: CR005305 gRNA targeting Human TTR (Exon 3)
source                   1..20
                         mol_type = other RNA
                         organism = synthetic construct
SEQUENCE: 70
tataggaaaa ccagtgagtc                                                    20

SEQ ID NO: 71            moltype = RNA   length = 20
FEATURE                  Location/Qualifiers
misc_feature             1..20
                         note = Synthetic: CR005306 gRNA targeting Human TTR (Exon 3)
source                   1..20
                         mol_type = other RNA
                         organism = synthetic construct
SEQUENCE: 71
aaatcttact ggaaggcact                                                    20

SEQ ID NO: 72            moltype = RNA   length = 20
FEATURE                  Location/Qualifiers
misc_feature             1..20
                         note = Synthetic: CR005307 gRNA targeting Human TTR (Exon 4)
source                   1..20
                         mol_type = other RNA
                         organism = synthetic construct
SEQUENCE: 72
tgtctgtctt ctctcatagg                                                    20

SEQ ID NO: 73            moltype = RNA   length = 20
FEATURE                  Location/Qualifiers
misc_feature             1..20
                         note = Synthetic: CR000689 gRNA targeting Cyno TTR
source                   1..20
                         mol_type = other RNA
                         organism = synthetic construct
SEQUENCE: 73
acacaaatac cagtccagcg                                                    20

SEQ ID NO: 74            moltype = RNA   length = 20
FEATURE                  Location/Qualifiers
misc_feature             1..20
                         note = Synthetic: CR005364 gRNA targeting Cyno TTR
source                   1..20
                         mol_type = other RNA
                         organism = synthetic construct
SEQUENCE: 74
aaaggctgct gatgagacct                                                    20
```

```
SEQ ID NO: 75              moltype = RNA   length = 20
FEATURE                    Location/Qualifiers
misc_feature               1..20
                           note = Synthetic: CR005365 gRNA targeting Cyno TTR
source                     1..20
                           mol_type = other RNA
                           organism = synthetic construct
SEQUENCE: 75
cattgacagc aggactgcct                                                     20

SEQ ID NO: 76              moltype = RNA   length = 20
FEATURE                    Location/Qualifiers
misc_feature               1..20
                           note = Synthetic: CR005366 gRNA targeting Cyno TTR
source                     1..20
                           mol_type = other RNA
                           organism = synthetic construct
SEQUENCE: 76
ataccagtcc agcgaggcag                                                     20

SEQ ID NO: 77              moltype = RNA   length = 20
FEATURE                    Location/Qualifiers
misc_feature               1..20
                           note = Synthetic: CR005367 gRNA targeting Cyno TTR
source                     1..20
                           mol_type = other RNA
                           organism = synthetic construct
SEQUENCE: 77
ccagtccagc gaggcagagg                                                     20

SEQ ID NO: 78              moltype = RNA   length = 20
FEATURE                    Location/Qualifiers
misc_feature               1..20
                           note = Synthetic: CR005368 gRNA targeting Cyno TTR
source                     1..20
                           mol_type = other RNA
                           organism = synthetic construct
SEQUENCE: 78
cctcctctgc ctcgctggac                                                     20

SEQ ID NO: 79              moltype = RNA   length = 20
FEATURE                    Location/Qualifiers
misc_feature               1..20
                           note = Synthetic: CR005369 gRNA targeting Cyno TTR
source                     1..20
                           mol_type = other RNA
                           organism = synthetic construct
SEQUENCE: 79
aaagttctag atgccgtccg                                                     20

SEQ ID NO: 80              moltype = RNA   length = 20
FEATURE                    Location/Qualifiers
misc_feature               1..20
                           note = Synthetic: CR005370 gRNA targeting Cyno TTR
source                     1..20
                           mol_type = other RNA
                           organism = synthetic construct
SEQUENCE: 80
acttgtcttc tctataccca                                                     20

SEQ ID NO: 81              moltype = RNA   length = 20
FEATURE                    Location/Qualifiers
misc_feature               1..20
                           note = Synthetic: CR005371 gRNA targeting Cyno TTR
source                     1..20
                           mol_type = other RNA
                           organism = synthetic construct
SEQUENCE: 81
aagtgacttc cagtaagatt                                                     20

SEQ ID NO: 82              moltype = RNA   length = 20
FEATURE                    Location/Qualifiers
misc_feature               1..20
                           note = Synthetic: CR005372 gRNA targeting Cyno TTR
source                     1..20
                           mol_type = other RNA
                           organism = synthetic construct
SEQUENCE: 82
```

-continued

```
aaaaggctgc tgatgagacc                                                20

SEQ ID NO: 83          moltype =    length =
SEQUENCE: 83
000

SEQ ID NO: 84          moltype =    length =
SEQUENCE: 84
000

SEQ ID NO: 85          moltype =    length =
SEQUENCE: 85
000

SEQ ID NO: 86          moltype =    length =
SEQUENCE: 86
000

SEQ ID NO: 87          moltype = RNA   length = 100
FEATURE                Location/Qualifiers
misc_feature           1..100
                       note = Synthetic: G000480 sgRNA modified sequence targeting
                        Human TTR
modified_base          1..3
                       mod_base = OTHER
                       note = PS linkage, 2'-O-Me nucleotide
modified_base          29..40
                       mod_base = OTHER
                       note = 2'-O-Me nucleotide
modified_base          69..96
                       mod_base = OTHER
                       note = 2'-O-Me nucleotide
modified_base          97..100
                       mod_base = OTHER
                       note = PS linkage, 2'-O-Me nucleotide
source                 1..100
                       mol_type = other RNA
                       organism = synthetic construct
SEQUENCE: 87
aaaggctgct gatgacacct gttttagagc tagaaatagc aagttaaaat aaggctagtc    60
cgttatcaac ttgaaaaagt ggcaccgagt cggtgctttt                         100

SEQ ID NO: 88          moltype = RNA   length = 100
FEATURE                Location/Qualifiers
misc_feature           1..100
                       note = Synthetic: G000481 sgRNA modified sequence targeting
                        Human TTR
modified_base          1..3
                       mod_base = OTHER
                       note = PS linkage, 2'-O-Me nucleotide
modified_base          29..40
                       mod_base = OTHER
                       note = 2'-O-Me nucleotide
modified_base          69..96
                       mod_base = OTHER
                       note = 2'-O-Me nucleotide
modified_base          97..100
                       mod_base = OTHER
                       note = PS linkage, 2'-O-Me nucleotide
source                 1..100
                       mol_type = other RNA
                       organism = synthetic construct
SEQUENCE: 88
tctagaactt tgaccatcag gttttagagc tagaaatagc aagttaaaat aaggctagtc    60
cgttatcaac ttgaaaaagt ggcaccgagt cggtgctttt                         100

SEQ ID NO: 89          moltype = RNA   length = 100
FEATURE                Location/Qualifiers
misc_feature           1..100
                       note = Synthetic: G000482 sgRNA modified sequence targeting
                        Human TTR
modified_base          1..3
                       mod_base = OTHER
                       note = PS linkage, 2'-O-Me nucleotide
modified_base          29..40
                       mod_base = OTHER
                       note = 2'-O-Me nucleotide
modified_base          69..96
                       mod_base = OTHER
```

```
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 89
tgtagaaggg atatacaaag gttttagagc tagaaatagc aagttaaaat aaggctagtc    60
cgttatcaac ttgaaaaagt ggcaccgagt cggtgctttt                         100

SEQ ID NO: 90           moltype = RNA  length = 100
FEATURE                 Location/Qualifiers
misc_feature            1..100
                        note = Synthetic: G000483 sgRNA modified sequence targeting
                         Human TTR
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 90
tccactcatt cttggcagga gttttagagc tagaaatagc aagttaaaat aaggctagtc    60
cgttatcaac ttgaaaaagt ggcaccgagt cggtgctttt                         100

SEQ ID NO: 91           moltype = RNA  length = 100
FEATURE                 Location/Qualifiers
misc_feature            1..100
                        note = Synthetic: G000484 sgRNA modified sequence targeting
                         Human TTR
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 91
agacaccaaa tcttactgga gttttagagc tagaaatagc aagttaaaat aaggctagtc    60
cgttatcaac ttgaaaaagt ggcaccgagt cggtgctttt                         100

SEQ ID NO: 92           moltype = RNA  length = 100
FEATURE                 Location/Qualifiers
misc_feature            1..100
                        note = Synthetic: G000485 sgRNA modified sequence targeting
                         Human TTR
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
```

```
SEQUENCE: 92
cctcctctgc cttgctggac gttttagagc tagaaatagc aagttaaaat aaggctagtc    60
cgttatcaac ttgaaaaagt ggcaccgagt cggtgctttt                         100

SEQ ID NO: 93           moltype = RNA   length = 100
FEATURE                 Location/Qualifiers
misc_feature            1..100
                        note = Synthetic: G000486 sgRNA modified sequence targeting
                         Human TTR
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 93
acacaaatac cagtccagca gttttagagc tagaaatagc aagttaaaat aaggctagtc    60
cgttatcaac ttgaaaaagt ggcaccgagt cggtgctttt                         100

SEQ ID NO: 94           moltype = RNA   length = 100
FEATURE                 Location/Qualifiers
misc_feature            1..100
                        note = Synthetic: G000487 sgRNA modified sequence targeting
                         Human TTR
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 94
ttctttggca acttacccag gttttagagc tagaaatagc aagttaaaat aaggctagtc    60
cgttatcaac ttgaaaaagt ggcaccgagt cggtgctttt                         100

SEQ ID NO: 95           moltype = RNA   length = 100
FEATURE                 Location/Qualifiers
misc_feature            1..100
                        note = Synthetic: G000488 sgRNA modified sequence targeting
                         Human TTR
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 95
aaagttctag atgctgtccg gttttagagc tagaaatagc aagttaaaat aaggctagtc    60
cgttatcaac ttgaaaaagt ggcaccgagt cggtgctttt                         100

SEQ ID NO: 96           moltype = RNA   length = 100
FEATURE                 Location/Qualifiers
misc_feature            1..100
```

```
                              note = Synthetic: G000489 sgRNA modified sequence targeting
                                  Human TTR
modified_base                 1..3
                              mod_base = OTHER
                              note = PS linkage, 2'-O-Me nucleotide
modified_base                 29..40
                              mod_base = OTHER
                              note = 2'-O-Me nucleotide
modified_base                 69..96
                              mod_base = OTHER
                              note = 2'-O-Me nucleotide
modified_base                 97..100
                              mod_base = OTHER
                              note = PS linkage, 2'-O-Me nucleotide
source                        1..100
                              mol_type = other RNA
                              organism = synthetic construct
SEQUENCE: 96
tttgaccatc agaggacact gttttagagc tagaaatagc aagttaaaat aaggctagtc    60
cgttatcaac ttgaaaaagt ggcaccgagt cggtgctttt                         100

SEQ ID NO: 97             moltype = RNA  length = 100
FEATURE                   Location/Qualifiers
misc_feature              1..100
                              note = Synthetic: G000490 sgRNA modified sequence targeting
                                  Human TTR
modified_base             1..3
                              mod_base = OTHER
                              note = PS linkage, 2'-O-Me nucleotide
modified_base             29..40
                              mod_base = OTHER
                              note = 2'-O-Me nucleotide
modified_base             69..96
                              mod_base = OTHER
                              note = 2'-O-Me nucleotide
modified_base             97..100
                              mod_base = OTHER
                              note = PS linkage, 2'-O-Me nucleotide
source                    1..100
                              mol_type = other RNA
                              organism = synthetic construct
SEQUENCE: 97
aaatagacac caaatcttac gttttagagc tagaaatagc aagttaaaat aaggctagtc    60
cgttatcaac ttgaaaaagt ggcaccgagt cggtgctttt                         100

SEQ ID NO: 98             moltype = RNA  length = 100
FEATURE                   Location/Qualifiers
misc_feature              1..100
                              note = Synthetic: G000491 sgRNA modified sequence targeting
                                  Human TTR
modified_base             1..3
                              mod_base = OTHER
                              note = PS linkage, 2'-O-Me nucleotide
modified_base             29..40
                              mod_base = OTHER
                              note = 2'-O-Me nucleotide
modified_base             69..96
                              mod_base = OTHER
                              note = 2'-O-Me nucleotide
modified_base             97..100
                              mod_base = OTHER
                              note = PS linkage, 2'-O-Me nucleotide
source                    1..100
                              mol_type = other RNA
                              organism = synthetic construct
SEQUENCE: 98
ataccagtcc agcaaggcag gttttagagc tagaaatagc aagttaaaat aaggctagtc    60
cgttatcaac ttgaaaaagt ggcaccgagt cggtgctttt                         100

SEQ ID NO: 99             moltype = RNA  length = 100
FEATURE                   Location/Qualifiers
misc_feature              1..100
                              note = Synthetic: G000492 sgRNA modified sequence targeting
                                  Human TTR
modified_base             1..3
                              mod_base = OTHER
                              note = PS linkage, 2'-O-Me nucleotide
modified_base             29..40
                              mod_base = OTHER
```

```
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 99
cttctctaca cccagggcac gttttagagc tagaaatagc aagttaaaat aaggctagtc    60
cgttatcaac ttgaaaaagt ggcaccgagt cggtgctttt                        100

SEQ ID NO: 100            moltype = RNA  length = 100
FEATURE                   Location/Qualifiers
misc_feature              1..100
                          note = Synthetic: G000493 sgRNA modified sequence targeting
                           Human TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 100
aagtgccttc cagtaagatt gttttagagc tagaaatagc aagttaaaat aaggctagtc    60
cgttatcaac ttgaaaaagt ggcaccgagt cggtgctttt                        100

SEQ ID NO: 101            moltype = RNA  length = 100
FEATURE                   Location/Qualifiers
misc_feature              1..100
                          note = Synthetic: G000494 sgRNA modified sequence targeting
                           Human TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 101
gtgagtctgg agagctgcat gttttagagc tagaaatagc aagttaaaat aaggctagtc    60
cgttatcaac ttgaaaaagt ggcaccgagt cggtgctttt                        100

SEQ ID NO: 102            moltype = RNA  length = 100
FEATURE                   Location/Qualifiers
misc_feature              1..100
                          note = Synthetic: G000495 sgRNA modified sequence targeting
                           Human TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
```

```
source                   1..100
                         mol_type = other RNA
                         organism = synthetic construct
SEQUENCE: 102
cagaggacac ttggattcac gttttagagc tagaaatagc aagttaaaat aaggctagtc    60
cgttatcaac ttgaaaaagt ggcaccgagt cggtgctttt                         100

SEQ ID NO: 103           moltype = RNA   length = 100
FEATURE                  Location/Qualifiers
misc_feature             1..100
                         note = Synthetic: G000496 sgRNA modified sequence targeting
                          Human TTR
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 103
ggccgtgcat gtgttcagaa gttttagagc tagaaatagc aagttaaaat aaggctagtc    60
cgttatcaac ttgaaaaagt ggcaccgagt cggtgctttt                         100

SEQ ID NO: 104           moltype = RNA   length = 100
FEATURE                  Location/Qualifiers
misc_feature             1..100
                         note = Synthetic: G000497 sgRNA modified sequence targeting
                          Human TTR
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 104
ctgctcctcc tctgccttgc gttttagagc tagaaatagc aagttaaaat aaggctagtc    60
cgttatcaac ttgaaaaagt ggcaccgagt cggtgctttt                         100

SEQ ID NO: 105           moltype = RNA   length = 100
FEATURE                  Location/Qualifiers
misc_feature             1..100
                         note = Synthetic: G000498 sgRNA modified sequence targeting
                          Human TTR
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 105
agtgagtctg gagagctgca gttttagagc tagaaatagc aagttaaaat aaggctagtc    60
cgttatcaac ttgaaaaagt ggcaccgagt cggtgctttt                         100
```

```
SEQ ID NO: 106            moltype = RNA   length = 100
FEATURE                   Location/Qualifiers
misc_feature              1..100
                          note = Synthetic: G000499 sgRNA modified sequence targeting
                            Human TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 106
tgaatccaag tgtcctctga gttttagagc tagaaatagc aagttaaaat aaggctagtc    60
cgttatcaac ttgaaaaagt ggcaccgagt cggtgctttt                         100

SEQ ID NO: 107            moltype = RNA   length = 100
FEATURE                   Location/Qualifiers
misc_feature              1..100
                          note = Synthetic: G000500 sgRNA modified sequence targeting
                            Human TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 107
ccagtccagc aaggcagagg gttttagagc tagaaatagc aagttaaaat aaggctagtc    60
cgttatcaac ttgaaaaagt ggcaccgagt cggtgctttt                         100

SEQ ID NO: 108            moltype = RNA   length = 100
FEATURE                   Location/Qualifiers
misc_feature              1..100
                          note = Synthetic: G000501 sgRNA modified sequence targeting
                            Human TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 108
tcacagaaac actcaccgta gttttagagc tagaaatagc aagttaaaat aaggctagtc    60
cgttatcaac ttgaaaaagt ggcaccgagt cggtgctttt                         100

SEQ ID NO: 109            moltype = RNA   length = 100
FEATURE                   Location/Qualifiers
misc_feature              1..100
                          note = Synthetic: G000567 sgRNA modified sequence targeting
                            Human TTR
modified_base             1..3
                          mod_base = OTHER
```

```
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 109
gaaaggctgc tgatgacacc gttttagagc tagaaatagc aagttaaaat aaggctagtc    60
cgttatcaac ttgaaaaagt ggcaccgagt cggtgctttt                         100

SEQ ID NO: 110           moltype = RNA  length = 100
FEATURE                  Location/Qualifiers
misc_feature             1..100
                         note = Synthetic: G000568 sgRNA modified sequence targeting
                          Human TTR
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 110
ggctgtcgtc accaatccca gttttagagc tagaaatagc aagttaaaat aaggctagtc    60
cgttatcaac ttgaaaaagt ggcaccgagt cggtgctttt                         100

SEQ ID NO: 111           moltype = RNA  length = 100
FEATURE                  Location/Qualifiers
misc_feature             1..100
                         note = Synthetic: G000570 sgRNA modified sequence targeting
                          Human TTR
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
modified_base            97..100
                         mod_base = OTHER
                         note = PS linkage, 2'-O-Me nucleotide
source                   1..100
                         mol_type = other RNA
                         organism = synthetic construct
SEQUENCE: 111
cattgatggc aggactgcct gttttagagc tagaaatagc aagttaaaat aaggctagtc    60
cgttatcaac ttgaaaaagt ggcaccgagt cggtgctttt                         100

SEQ ID NO: 112           moltype = RNA  length = 100
FEATURE                  Location/Qualifiers
misc_feature             1..100
                         note = Synthetic: G000571 sgRNA modified sequence targeting
                          Human TTR
modified_base            1..3
                         mod_base = OTHER
                         note = PS linkage, 2'-O-Me nucleotide
modified_base            29..40
                         mod_base = OTHER
                         note = 2'-O-Me nucleotide
modified_base            69..96
                         mod_base = OTHER
                         note = 2'-O-Me nucleotide
```

```
modified_base              97..100
                           mod_base = OTHER
                           note = PS linkage, 2'-O-Me nucleotide
source                     1..100
                           mol_type = other RNA
                           organism = synthetic construct
SEQUENCE: 112
gtcacagaaa cactcaccgt gttttagagc tagaaatagc aagttaaaat aaggctagtc    60
cgttatcaac ttgaaaaagt ggcaccgagt cggtgctttt                         100

SEQ ID NO: 113             moltype = RNA  length = 100
FEATURE                    Location/Qualifiers
misc_feature               1..100
                           note = Synthetic: G000572 sgRNA modified sequence targeting
                            Human TTR
modified_base              1..3
                           mod_base = OTHER
                           note = PS linkage, 2'-O-Me nucleotide
modified_base              29..40
                           mod_base = OTHER
                           note = 2'-O-Me nucleotide
modified_base              69..96
                           mod_base = OTHER
                           note = 2'-O-Me nucleotide
modified_base              97..100
                           mod_base = OTHER
                           note = PS linkage, 2'-O-Me nucleotide
source                     1..100
                           mol_type = other RNA
                           organism = synthetic construct
SEQUENCE: 113
cccctactcc tattccacca gttttagagc tagaaatagc aagttaaaat aaggctagtc    60
cgttatcaac ttgaaaaagt ggcaccgagt cggtgctttt                         100

SEQ ID NO: 114             moltype = RNA  length = 100
FEATURE                    Location/Qualifiers
misc_feature               1..100
                           note = Synthetic: G000502 sgRNA modified sequence targeting
                            Cyno TTR
modified_base              1..3
                           mod_base = OTHER
                           note = PS linkage, 2'-O-Me nucleotide
modified_base              29..40
                           mod_base = OTHER
                           note = 2'-O-Me nucleotide
modified_base              69..96
                           mod_base = OTHER
                           note = 2'-O-Me nucleotide
modified_base              97..100
                           mod_base = OTHER
                           note = PS linkage, 2'-O-Me nucleotide
source                     1..100
                           mol_type = other RNA
                           organism = synthetic construct
SEQUENCE: 114
acacaaatac cagtccagcg gttttagagc tagaaatagc aagttaaaat aaggctagtc    60
cgttatcaac ttgaaaaagt ggcaccgagt cggtgctttt                         100

SEQ ID NO: 115             moltype = RNA  length = 100
FEATURE                    Location/Qualifiers
misc_feature               1..100
                           note = Synthetic: G000503 sgRNA modified sequence targeting
                            Cyno TTR
modified_base              1..3
                           mod_base = OTHER
                           note = PS linkage, 2'-O-Me nucleotide
modified_base              29..40
                           mod_base = OTHER
                           note = 2'-O-Me nucleotide
modified_base              69..96
                           mod_base = OTHER
                           note = 2'-O-Me nucleotide
modified_base              97..100
                           mod_base = OTHER
                           note = PS linkage, 2'-O-Me nucleotide
source                     1..100
                           mol_type = other RNA
                           organism = synthetic construct
SEQUENCE: 115
```

```
aaaaggctgc tgatgagacc gttttagagc tagaaatagc aagttaaaat aaggctagtc   60
cgttatcaac ttgaaaaagt ggcaccgagt cggtgctttt                        100

SEQ ID NO: 116            moltype = RNA   length = 100
FEATURE                   Location/Qualifiers
misc_feature              1..100
                          note = Synthetic: G000504 sgRNA modified sequence targeting
                            Cyno TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 116
aaaggctgct gatgagacct gttttagagc tagaaatagc aagttaaaat aaggctagtc   60
cgttatcaac ttgaaaaagt ggcaccgagt cggtgctttt                        100

SEQ ID NO: 117            moltype = RNA   length = 100
FEATURE                   Location/Qualifiers
misc_feature              1..100
                          note = Synthetic: G000505 sgRNA modified sequence targeting
                            Cyno TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 117
cattgacagc aggactgcct gttttagagc tagaaatagc aagttaaaat aaggctagtc   60
cgttatcaac ttgaaaaagt ggcaccgagt cggtgctttt                        100

SEQ ID NO: 118            moltype = RNA   length = 100
FEATURE                   Location/Qualifiers
misc_feature              1..100
                          note = Synthetic: G000506 sgRNA modified sequence targeting
                            Cyno TTR
modified_base             1..3
                          mod_base = OTHER
                          note = PS linkage, 2'-O-Me nucleotide
modified_base             29..40
                          mod_base = OTHER
                          note = 2'-O-Me nucleotide
modified_base             69..96
                          mod_base = OTHER
                          note = 2'-O-Me nucleotide
modified_base             97..100
                          mod_base = OTHER
                          note = PS linkage, 2'-O-Me nucleotide
source                    1..100
                          mol_type = other RNA
                          organism = synthetic construct
SEQUENCE: 118
ataccagtcc agcgaggcag gttttagagc tagaaatagc aagttaaaat aaggctagtc   60
cgttatcaac ttgaaaaagt ggcaccgagt cggtgctttt                        100

SEQ ID NO: 119            moltype = RNA   length = 100
FEATURE                   Location/Qualifiers
misc_feature              1..100
                          note = Synthetic: G000507 sgRNA modified sequence targeting
```

```
                            Cyno TTR
modified_base               1..3
                            mod_base = OTHER
                            note = PS linkage, 2'-O-Me nucleotide
modified_base               29..40
                            mod_base = OTHER
                            note = 2'-O-Me nucleotide
modified_base               69..96
                            mod_base = OTHER
                            note = 2'-O-Me nucleotide
modified_base               97..100
                            mod_base = OTHER
                            note = PS linkage, 2'-O-Me nucleotide
source                      1..100
                            mol_type = other RNA
                            organism = synthetic construct
SEQUENCE: 119
ccagtccagc gaggcagagg gttttagagc tagaaatagc aagttaaaat aaggctagtc    60
cgttatcaac ttgaaaaagt ggcaccgagt cggtgctttt                        100

SEQ ID NO: 120              moltype = RNA  length = 100
FEATURE                     Location/Qualifiers
misc_feature                1..100
                            note = Synthetic: G000508 sgRNA modified sequence targeting
                             Cyno TTR
modified_base               1..3
                            mod_base = OTHER
                            note = PS linkage, 2'-O-Me nucleotide
modified_base               29..40
                            mod_base = OTHER
                            note = 2'-O-Me nucleotide
modified_base               69..96
                            mod_base = OTHER
                            note = 2'-O-Me nucleotide
modified_base               97..100
                            mod_base = OTHER
                            note = PS linkage, 2'-O-Me nucleotide
source                      1..100
                            mol_type = other RNA
                            organism = synthetic construct
SEQUENCE: 120
cctcctctgc ctcgctggac gttttagagc tagaaatagc aagttaaaat aaggctagtc    60
cgttatcaac ttgaaaaagt ggcaccgagt cggtgctttt                        100

SEQ ID NO: 121              moltype = RNA  length = 100
FEATURE                     Location/Qualifiers
misc_feature                1..100
                            note = Synthetic: G000509 sgRNA modified sequence targeting
                             Cyno TTR
modified_base               1..3
                            mod_base = OTHER
                            note = PS linkage, 2'-O-Me nucleotide
modified_base               29..40
                            mod_base = OTHER
                            note = 2'-O-Me nucleotide
modified_base               69..96
                            mod_base = OTHER
                            note = 2'-O-Me nucleotide
modified_base               97..100
                            mod_base = OTHER
                            note = PS linkage, 2'-O-Me nucleotide
source                      1..100
                            mol_type = other RNA
                            organism = synthetic construct
SEQUENCE: 121
aaagttctag atgccgtccg gttttagagc tagaaatagc aagttaaaat aaggctagtc    60
cgttatcaac ttgaaaaagt ggcaccgagt cggtgctttt                        100

SEQ ID NO: 122              moltype = RNA  length = 100
FEATURE                     Location/Qualifiers
misc_feature                1..100
                            note = Synthetic: G000510 sgRNA modified sequence targeting
                             Cyno TTR
modified_base               1..3
                            mod_base = OTHER
                            note = PS linkage, 2'-O-Me nucleotide
modified_base               29..40
                            mod_base = OTHER
                            note = 2'-O-Me nucleotide
```

```
modified_base              69..96
                           mod_base = OTHER
                           note = 2'-O-Me nucleotide
modified_base              97..100
                           mod_base = OTHER
                           note = PS linkage, 2'-O-Me nucleotide
source                     1..100
                           mol_type = other RNA
                           organism = synthetic construct
SEQUENCE: 122
acttgtcttc tctataccca gttttagagc tagaaatagc aagttaaaat aaggctagtc      60
cgttatcaac ttgaaaaagt ggcaccgagt cggtgctttt                           100

SEQ ID NO: 123             moltype = RNA   length = 100
FEATURE                    Location/Qualifiers
misc_feature               1..100
                           note = Synthetic: G000511 sgRNA modified sequence targeting
                            Cyno TTR
modified_base              1..3
                           mod_base = OTHER
                           note = PS linkage, 2'-O-Me nucleotide
modified_base              29..40
                           mod_base = OTHER
                           note = 2'-O-Me nucleotide
modified_base              69..96
                           mod_base = OTHER
                           note = 2'-O-Me nucleotide
modified_base              97..100
                           mod_base = OTHER
                           note = PS linkage, 2'-O-Me nucleotide
source                     1..100
                           mol_type = other RNA
                           organism = synthetic construct
SEQUENCE: 123
aagtgacttc cagtaagatt gttttagagc tagaaatagc aagttaaaat aaggctagtc      60
cgttatcaac ttgaaaaagt ggcaccgagt cggtgctttt                           100

SEQ ID NO: 124             moltype = RNA   length = 100
FEATURE                    Location/Qualifiers
misc_feature               1..100
                           note = Synthetic: G000282 sgRNA modified sequence targeting
                            Mouse TTR
modified_base              1..3
                           mod_base = OTHER
                           note = PS linkage, 2'-O-Me nucleotide
modified_base              29..40
                           mod_base = OTHER
                           note = 2'-O-Me nucleotide
modified_base              69..96
                           mod_base = OTHER
                           note = 2'-O-Me nucleotide
modified_base              97..100
                           mod_base = OTHER
                           note = PS linkage, 2'-O-Me nucleotide
source                     1..100
                           mol_type = other RNA
                           organism = synthetic construct
SEQUENCE: 124
ttacagccac gtctacagca gttttagagc tagaaatagc aagttaaaat aaggctagtc      60
cgttatcaac ttgaaaaagt ggcaccgagt cggtgctttt                           100

SEQ ID NO: 125             moltype = RNA   length = 80
FEATURE                    Location/Qualifiers
misc_feature               1..80
                           note = Synthetic
source                     1..80
                           mol_type = other RNA
                           organism = synthetic construct
SEQUENCE: 125
gttttagagc tagaaatagc aagttaaaat aaggctagtc cgttatcaac ttgaaaaagt      60
ggcaccgagt cggtgctttt                                                  80

SEQ ID NO: 126             moltype = RNA   length = 22
FEATURE                    Location/Qualifiers
misc_feature               1..22
                           note = Synthetic
source                     1..22
                           mol_type = other RNA
                           organism = synthetic construct
```

SEQUENCE: 126
gttttagagc tatgctgttt tg                                      22

SEQ ID NO: 127        moltype =    length =
SEQUENCE: 127
000

SEQ ID NO: 128        moltype =    length =
SEQUENCE: 128
000

SEQ ID NO: 129        moltype =    length =
SEQUENCE: 129
000

SEQ ID NO: 130        moltype =    length =
SEQUENCE: 130
000

SEQ ID NO: 131        moltype =    length =
SEQUENCE: 131
000

SEQ ID NO: 132        moltype =    length =
SEQUENCE: 132
000

SEQ ID NO: 133        moltype =    length =
SEQUENCE: 133
000

SEQ ID NO: 134        moltype =    length =
SEQUENCE: 134
000

SEQ ID NO: 135        moltype =    length =
SEQUENCE: 135
000

SEQ ID NO: 136        moltype =    length =
SEQUENCE: 136
000

SEQ ID NO: 137        moltype =    length =
SEQUENCE: 137
000

SEQ ID NO: 138        moltype =    length =
SEQUENCE: 138
000

SEQ ID NO: 139        moltype =    length =
SEQUENCE: 139
000

SEQ ID NO: 140        moltype =    length =
SEQUENCE: 140
000

SEQ ID NO: 141        moltype =    length =
SEQUENCE: 141
000

SEQ ID NO: 142        moltype =    length =
SEQUENCE: 142
000

SEQ ID NO: 143        moltype =    length =
SEQUENCE: 143
000

SEQ ID NO: 144        moltype =    length =
SEQUENCE: 144
000

SEQ ID NO: 145        moltype =    length =
SEQUENCE: 145
000

| | | |
|---|---|---|
| SEQ ID NO: 146<br>SEQUENCE: 146<br>000 | moltype = | length = |
| SEQ ID NO: 147<br>SEQUENCE: 147<br>000 | moltype = | length = |
| SEQ ID NO: 148<br>SEQUENCE: 148<br>000 | moltype = | length = |
| SEQ ID NO: 149<br>SEQUENCE: 149<br>000 | moltype = | length = |
| SEQ ID NO: 150<br>SEQUENCE: 150<br>000 | moltype = | length = |
| SEQ ID NO: 151<br>SEQUENCE: 151<br>000 | moltype = | length = |
| SEQ ID NO: 152<br>SEQUENCE: 152<br>000 | moltype = | length = |
| SEQ ID NO: 153<br>SEQUENCE: 153<br>000 | moltype = | length = |
| SEQ ID NO: 154<br>SEQUENCE: 154<br>000 | moltype = | length = |
| SEQ ID NO: 155<br>SEQUENCE: 155<br>000 | moltype = | length = |
| SEQ ID NO: 156<br>SEQUENCE: 156<br>000 | moltype = | length = |
| SEQ ID NO: 157<br>SEQUENCE: 157<br>000 | moltype = | length = |
| SEQ ID NO: 158<br>SEQUENCE: 158<br>000 | moltype = | length = |
| SEQ ID NO: 159<br>SEQUENCE: 159<br>000 | moltype = | length = |
| SEQ ID NO: 160<br>SEQUENCE: 160<br>000 | moltype = | length = |
| SEQ ID NO: 161<br>SEQUENCE: 161<br>000 | moltype = | length = |
| SEQ ID NO: 162<br>SEQUENCE: 162<br>000 | moltype = | length = |
| SEQ ID NO: 163<br>SEQUENCE: 163<br>000 | moltype = | length = |
| SEQ ID NO: 164<br>SEQUENCE: 164<br>000 | moltype = | length = |
| SEQ ID NO: 165<br>SEQUENCE: 165<br>000 | moltype = | length = |

| | | |
|---|---|---|
| SEQ ID NO: 166 SEQUENCE: 166 000 | moltype = | length = |
| SEQ ID NO: 167 SEQUENCE: 167 000 | moltype = | length = |
| SEQ ID NO: 168 SEQUENCE: 168 000 | moltype = | length = |
| SEQ ID NO: 169 SEQUENCE: 169 000 | moltype = | length = |
| SEQ ID NO: 170 SEQUENCE: 170 000 | moltype = | length = |
| SEQ ID NO: 171 SEQUENCE: 171 000 | moltype = | length = |
| SEQ ID NO: 172 SEQUENCE: 172 000 | moltype = | length = |
| SEQ ID NO: 173 SEQUENCE: 173 000 | moltype = | length = |
| SEQ ID NO: 174 SEQUENCE: 174 000 | moltype = | length = |
| SEQ ID NO: 175 SEQUENCE: 175 000 | moltype = | length = |
| SEQ ID NO: 176 SEQUENCE: 176 000 | moltype = | length = |
| SEQ ID NO: 177 SEQUENCE: 177 000 | moltype = | length = |
| SEQ ID NO: 178 SEQUENCE: 178 000 | moltype = | length = |
| SEQ ID NO: 179 SEQUENCE: 179 000 | moltype = | length = |
| SEQ ID NO: 180 SEQUENCE: 180 000 | moltype = | length = |
| SEQ ID NO: 181 SEQUENCE: 181 000 | moltype = | length = |
| SEQ ID NO: 182 SEQUENCE: 182 000 | moltype = | length = |
| SEQ ID NO: 183 SEQUENCE: 183 000 | moltype = | length = |
| SEQ ID NO: 184 SEQUENCE: 184 000 | moltype = | length = |
| SEQ ID NO: 185 SEQUENCE: 185 | moltype = | length = |

```
SEQ ID NO: 186          moltype =    length =
SEQUENCE: 186
000

SEQ ID NO: 187          moltype =    length =
SEQUENCE: 187
000

SEQ ID NO: 188          moltype =    length =
SEQUENCE: 188
000

SEQ ID NO: 189          moltype =    length =
SEQUENCE: 189
000

SEQ ID NO: 190          moltype =    length =
SEQUENCE: 190
000

SEQ ID NO: 191          moltype =    length =
SEQUENCE: 191
000

SEQ ID NO: 192          moltype =    length =
SEQUENCE: 192
000

SEQ ID NO: 193          moltype =    length =
SEQUENCE: 193
000

SEQ ID NO: 194          moltype =    length =
SEQUENCE: 194
000

SEQ ID NO: 195          moltype =    length =
SEQUENCE: 195
000

SEQ ID NO: 196          moltype =    length =
SEQUENCE: 196
000

SEQ ID NO: 197          moltype =    length =
SEQUENCE: 197
000

SEQ ID NO: 198          moltype =    length =
SEQUENCE: 198
000

SEQ ID NO: 199          moltype =    length =
SEQUENCE: 199
000

SEQ ID NO: 200          moltype =    length =
SEQUENCE: 200
000

SEQ ID NO: 201          moltype = DNA   length = 4140
FEATURE                 Location/Qualifiers
misc_feature            1..4140
                        note = Synthetic: DNA coding sequence of Cas9 using the
                         thymidine analog of the minimal uridine codons listed in
                         Table 3, with start and stop codons
source                  1..4140
                        mol_type = other DNA
                        organism = synthetic construct
SEQUENCE: 201
atggacaaga agtacagcat cggactggac atcggaacaa acagcgtcgg atgggcagtc    60
atcacagacg aatacaaggt cccgagcaag aagttcaagg tcctgggaaa cacagacaga   120
cacagcatca agaagaacct gatcggagcc ctgctgttcg acagcggaga aacagcagaa   180
gcaacaagac tgaagagaac agcaagaaga agatacacaa gaagaaagaa cagaatctgc   240
tacctgcagg aaatcttcag caacgaaatg gcaaaggtcg acgacagctt cttccacaga   300
ctggaagaaa gcttcctggt cgaagaagac aagaagcacg aaagacaccc gatcttcgga   360
aacatcgtcg acgaagtcgc ataccacgaa aagtaccega caatctacca cctgagaaag   420
```

```
aagctggtcg acagcacaga caaggcagac ctgagactga tctacctggc actggcacac  480
atgatcaagt tcagaggaca cttcctgatc gaaggagacc tgaacccgga caacagcgac  540
gtcgacaagc tgttcatcca gctggtccag acatacaacc agctgttcga agaaaacccg  600
atcaacgcaa gcgagtcga cgcaaaggca atcctgagcg caagactgag caagagcaga  660
agactggaaa acctgatcgc acagctgccg ggagaaaaga agaacggact gttcggaaac  720
ctgatcgcac tgagcctggg actgacaccg aacttcaaga gcaacttcga cctggcagaa  780
gacgcaaagc tgcagctgag caaggacaca tacgacgacg acctggacaa cctgctggca  840
cagatcggag accagtacgc agacctgttc ctggcagcaa agaacctgag cgacgcaatc  900
ctgctgagcg acatcctgag agtcaacaca gaaatcacaa aggcaccgct gagcgcaagc  960
atgatcaaga gatacgacga acaccaccag gacctgacac tgctgaaggc actggtcaga 1020
cagcagctgc cggaaaagta caaggaaatc ttcttcgacc agagcaagaa cggatacgca 1080
ggatacatcg acgaggagc aagccaggaa gaattctaca agttcatcaa gccgatcctg 1140
gaaaagatgg acggaacaga agaactgctg gtcaagctga acagagaaga cctgctgaga 1200
aagcagagaa cattcgacaa cggaagcatc ccgcaccaga tccacctggg agaactgcac 1260
gcaatcctga agacaggaa agacttctac ccgttcctga aggacaacag agaaaagatc 1320
gaaaagatcc tgacattcag aatcccgtac tacgtcggac cgctggcaag aggaaacagc 1380
agattcgcat ggatgacaag aaagagcgaa gaaaacatca caccgtggaa cttcgaagaa 1440
gtcgtcgaca agggagcaag cgcacagagc ttcatcgaaa gaatgacaaa cttcgacaag 1500
aacctgccga cgaaaaggt cctgccgaag cacagcctgc tgtacgaata cttcacagtc 1560
tacaacgaac tgcaaaaggt caagtacgtc acagaaggaa tgagaaagcc ggcattcctg 1620
agcggagaac agaagaaggc aatcgtcgac ctgctgttca agacaaacag aaaggtcaca 1680
gtcaagcagc tgaaggaaga ctacttcaag aagatcgaat gcttcgacag cgtcgaaatc 1740
agcggagtcg aagacagatt caacgcaagc ctgggaacat accacgacct gctgaagatc 1800
atcaaggaca aggacttcct ggacaacgaa gaaaacgaag acatcctgga agacatcgtc 1860
ctgacactga cactgttcga agacagagaa atgatcgaag aaagactgaa gacatacgca 1920
cacctgttcg acgacaaggt catgaagcag ctgaagagaa gaagatacac aggatgggga 1980
agactgagca gaaagctgat caacggaatc agagacaagc agagcggaaa gacaatcctg 2040
gacttcctga gagcgacgg attcgcaaac agaaacttca tgcagctgat ccacgacgac 2100
agcctgacat tcaaggaaga catccagaag gcacaggtca gcggacaggg agacagcctg 2160
cacgaacaca tcgcaaacct ggcaggaagc ccggcaatca gaaagggaat cctgcagaca 2220
gtcaaggtcg tcgacgaact ggtcaaggtc atgggaagac acaagccgga aaacatcgtc 2280
atcgaaatgg caagagaaaa ccagacaaca cagaagggac agaagaacag cagagaaaga 2340
atgaagagaa tcgaagaagg aatcaaggaa ctgggaagcc agatcctgaa ggaacacccg 2400
gtcgaaaaca cacagctgca gaacgaaaag ctgtacctgt actacctgca gaacggaaga 2460
gacatgtacg tcgaccagga actggacatc aacagactga gcgactacga cgtcgaccac 2520
atcgtcccgc agagcttcct gaaggacgac agcatcgaca caaggtcct gacaagaagc 2580
gacaagaaca gaggaaagag cgacaacgtc ccgagcgaag aagtcgtcaa gaagatgaag 2640
aactactgga gacagctgct gaacgcaaag ctgatcacac agagaaagtt cgacaacctg 2700
acaaaggcag agagaggagg actgagcgaa ctggacaagg caggattcat caagagacag 2760
ctggtcgaaa caagacagat cacaaagcac gtcgcacaga tcctggacag cagaatgaac 2820
acaaagtacg acgaaaacga caagctgatc agagaagtca aggtcatcac actgaagagc 2880
aagctggtca gcgacttcag aaaggacttc cagttctaca aggtcagaga aatcaacaac 2940
taccaccacg cacacgacgc atacctgaac gcagtcgtcg gaaccgcact gatcaagaag 3000
taccccgaagc tggaaagcga attcgtctac ggagactaca aggtcacga cgtcagaaag 3060
atgatcgcaa agagcgaaca ggaaatcgga aaggcaacag caagtactt cttctacagc 3120
aacatcatga acttcttcaa gacagaaatc acactggcaa acggagaaat cagaaagaga 3180
ccgctgatcg aaacaaacgg agaaacagga gaaatcgtct gggacaaggg aagagacttc 3240
gcaacagtca gaaaggtcct gagcatgccg caggtcaaca tcgtcaagaa gacagaagtc 3300
cagacaggag gattcagcaa ggaaagcatc ctgccgaaga aaacagcga caagctgatc 3360
gcaagaaaga aggactggga cccgaagaag tacgaggat cgacagccc gacagtcgca 3420
tacagcgtcc tggtcgtcgc aaaggtcgaa aagggaaaga gcaagaagct gaagagcgtc 3480
aaggaactgc tgggaatcac aatcatggaa agaagcagct cgaaaagaa cccgatcgac 3540
ttcctggaag caagggata caaggaagtc aagaaggacc tgatcatcaa gctgccgaag 3600
tacagcctgt tcgaactgga aaacggaaga agagaatgc tggcaagcgc aggagaactg 3660
cagaagggaa acgaactggc actgccgagc aagtacgtca acttcctgta cctggcaagc 3720
cactacgaaa agctgaaggg aagcccggaa gacaacgaac agaagcagct gttcgtcgaa 3780
cagcacaagc actacctgga cgaaatcatc gaacagatca gcgaattcag caagagagtc 3840
atcctggcag acgcaaacct ggacaaggtc ctgagcgcat acaacaagca gagagacaag 3900
ccgatcagag aacaggcaga aaacatcatc cacctgttca cactgacaaa cctgggagca 3960
ccggcagcat tcaagtactt cgacacaaca atcgacagaa agagatacac aagcacaaag 4020
gaagtcctgg acgcaacact gatccaccag agcatcacag gactgtacga acaagaatc 4080
gacctgagcc agctgggagg agacggagga ggaagcccga agaagaagag aaaggtctag 4140
```

SEQ ID NO: 202       moltype = DNA   length = 4143
FEATURE              Location/Qualifiers
misc_feature         1..4143
                     note = Synthetic: DNA coding sequence of Cas9 using codons
                     with generally high expression in humans
source               1..4143
                     mol_type = other DNA
                     organism = synthetic construct
SEQUENCE: 202

```
atggataaga agtactcaat cgggctggat atcggaacta attccgtggg ttgggcagtg   60
atcacggatg aatacaaagt gccgtccaag aagttcaagg tcctggggaa caccgataga  120
cacagcatca agaaaaatct catcggagcc ctgctgtttg actccggcga aaccgcagaa  180
gcgaccggc tcaaacgtac cgcgaggcga cgctacaccc ggcggaagaa tcgcatctgc  240
tatctgcaag agatctttc gaacgaaatg gcaaggtcg acgacagctt cttccaccgc  300
ctggaagaat ctttcctggt ggaggaggac aagaagcatg aacggcatcc tatctttgga  360
aacatcgtcg acgaagtggc gtaccacgaa aagtacccga ccatctacca tctgcggaag  420
```

-continued

```
aagttggttg actcaactga caaggccgac ctcagattga tctacttggc cctcgcccat   480
atgatcaaat tccgcggaca cttcctgatc gaaggcgatc tgaaccctga taactccgac   540
gtggataagc ttttcattca actggtgcag acctacaacc aactgttcga agaaaaccca   600
atcaatgcta gcggcgtcga tgccaaggcc atcctgtccg cccggctgtc gaagtcgcgg   660
cgcctcgaaa acctgatcgc acagctgccg ggagagaaaa agaacggact tttcggcaac   720
ttgatcgctc tctcactggg actcactccc aatttcaagt ccatttttga cctggccgag   780
gacgcgaagc tgcaactctc aaaggacacc tacgacgacg acttggacaa tttgctggca   840
caaattggcg atcagtacgc ggatctgttc cttgccgcta agaacctttc ggacgcaatc   900
ttgctgtccg atatcctgcg cgtgaacacc gaaataaacg aagcgccgct tagcgcctcg   960
atgattaagc ggtacgacga gcatccaccg gatctcacgc tgctcaaagc gctcgtgaga  1020
cagcaactgc ctgaaaagta caaggagatc ttcttcgacc agtccaagaa tgggtacgca  1080
gggtacatcg atggaggcgc tagccaggaa gagttctata agttcatcaa gccaatcctg  1140
gaaaagatgg acggaaccga agaactgctg gtcaagctga caggggaggga tctgctccgg  1200
aaacagacaca cctttgacaa cggatccatt ccccaccaga tccatctggg tgagctgcac  1260
gccatcttgc ggcgccagga ggactttttac ccattcctca aggacaaccg ggaaaagatc  1320
gagaaaattc tgacgttccg catcccgtat tacgtgggcc cactggcgcg cggcaattcg  1380
cgcttcgcgt ggatgactag aaaatcagag gaaaccatca ctccttggaa tttcgaggaa  1440
gttgtggata agggagcttc ggcacaaagc ttcatcgaac agtaccacga cttcgacaag  1500
aatctcccaa acgagaaggt gcttcctaag cacagcctcc tttacgaata cttcactgtc  1560
tacaacgaac tgactaaagt gaaatacgtt actgaaggaa tgaggaagcc ggcctttctg  1620
tccgagaac agaagaaagc aattgtcgat ctgctgttca agaccaaccg caaggtgacc  1680
gtcaagcagc ttaaagagga ctacttcaag aagatcgagt gtttcgactc agtggaaatc  1740
agcggggtgg aggacagatt caacgcttcg ctgggaacct atcatgatct cctgaagatc  1800
atcaaggaca aggacttcct tgacaacgag gagaacgagg acatcctgga agatatcgtc  1860
ctgaccttga cccttttcga ggatcgcgag atgatcgagg agaggcttaa gacctacgct  1920
catctcttcg acgataaggt catgaaacaa ctcaagcgcc gccggtacac tggttggggc  1980
cgcctctccc gcaagctgat caacggtatt cgcgataaac agagcggtaa aactatcctg  2040
gatttcctca aatcggatgg cttcgctaat cgtaacttca tgcaattgat ccacgacgac  2100
agcctgacct ttaaggagga catccaaaaa gcacaagtgt ccggacaggg agactcactc  2160
catgaacaca tcgcgaatct ggccggttcg ccggcgatta agaagggaat tctgcaaact  2220
gtgaaggtgg tcgacgagct ggtgaaggtc atgggacggc acaaaccgga gaatatcgtg  2280
attgaaatgg cccgagaaaa ccagactacc cagaagggcc agaaaaactc ccgcgaaagg  2340
atgaagcgga tcgaagaagg aatcaaggag ctgggcagcc agatcctgaa agagcacccg  2400
gtggaaaaca cgcagctgca gaacgagaag tctctacctg tactatttgca aaatggacgg  2460
gacatgtacg tggaccaaga gctggacatc aatcggttgt ctgattacga cgtggaccac  2520
atcgttccac agtccttttct gaaggatgac tcgatcgata caaggtgtt gactcgcagc  2580
gacaagaaca gagggaagtc agataatgtg ccatcgagg aggtcgtgaa gaagatgaag  2640
aattactggc ggcagctcct gaatgcgaag ctgattaccg agagaaagtt tgacaatctc  2700
actaaagccg agcgcggcgg actctcagag ctggataagg ctggattcat caaacggcag  2760
ctggtcgaga ctcggcagat taccaagcac gtgcgcaga tcttggactc ccgcatgaac  2820
actaaatacg acgagaacga taagctcatc cgggaagtga aggtgattac cctgaaaagc  2880
aaacttgtgt cggactttcg gaaggacttt cagtttttaca aagtgagaga aatcaacaac  2940
taccatcacg cgcatgacgc atacctcaac gctgtggtcg gtaccgccct gatcaaaaag  3000
taccctaaac ttgaatcgga gtttgtgtac ggagactaca aggtctacga cgtgaggaag  3060
atgatagcca gtccgaaca ggaaatcggg aaagcaactg cgaaatactt cttttactca  3120
aacatcatga acttttttcaa gactgaaatt acgctggcca atggagaaat caggaagagg  3180
ccactgatcg aaactaacgg agaaacgggc gaaatgtttg gggacaaggg cagggacttc  3240
gcaactgttc gcaaagtgct ctctatgccg caagtcaata ttgtgaagaa accgaagtg  3300
caaaccggcg gattttcaaa ggaatcgatc ctcccaaaga gaaatagcga caagctcatt  3360
gcacgcaaga aagactggga cccgaagaag tacgaggat tcgattcgcc gactgtcgca  3420
tactccgtcc tcgtggtggc caaggtggaa aagggaaaga gcaaaaagct caaatccgca  3480
aaagagctgc tggggattac catcatgaa cgatcctcgt tcgagaagaa cccgattgat  3540
ttcctcgagg cgaagggtta caaggaggtg aagaaggatc tgatcatcaa actccccaag  3600
tactcactgt tcgaactgga aaatggtcgg aagcgcatgc tggcttcggc cggagaactc  3660
caaaaaggaa atgagctggc cttgcctagc aagtacgtca acttcctcta tcttgcttcg  3720
cactacgaaa aactcaaagg gtcaccggaa gataacgaac agaagcagct tttcgtggaa  3780
cagcacaagc attatctgga tgaaatcatc gaacaaatct ccgagttttc aaagcgcgtg  3840
atcctcgccg acgccaacct cgacaaagtc ctgtcggcct acaataagca tagagataag  3900
ccgatcagag aacaggccga gaacattatc cacttgttca ccctgactaa cctgggagcc  3960
ccagccgcct tcaagtactt cgatactact atcgatcgca aaagatacac gtccaccaag  4020
gaagttctgg acgcgaccct gatccaccaa agcatcactg gactctacga aactaggatc  4080
gatctgtcgc agctgggtgg cgatggcggt ggatctccga aaaagaagag aaaggtgtaa  4140
tga                                                                4143
```

```
SEQ ID NO: 203         moltype = AA  length = 1379
FEATURE                Location/Qualifiers
REGION                 1..1379
                       note = Synthetic: Amino acid sequence of Cas9 with one
                        nuclear localization signal (1xNLS) as the C-terminal 7
                        amino acids
source                 1..1379
                       mol_type = protein
                       organism = synthetic construct
SEQUENCE: 203
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
```

```
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWPKK YGGFDSPTVA    1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDGG GSPKKKRKV   1379

SEQ ID NO: 204         moltype = RNA   length = 4140
FEATURE                Location/Qualifiers
misc_feature           1..4140
                       note = Synthetic: Cas9 mRNA ORF using minimal uridine
                        codons, with start and stop codons
source                 1..4140
                       mol_type = other RNA
                       organism = synthetic construct
SEQUENCE: 204
atggacaaga agtacagcat cggactggac atcggaacaa acagcgtcgg atgggcagtc     60
atcacagacg aatacaaggt cccgacaaag aagttcaagg tcctgggaaa cacagacaga    120
cacagcatca agaagaacct gatcggagca ctgctgttcg acagcggaga aacagcagaa    180
gcaacaagac tgaagagaac agcaagaaga agatacacaa gaagaaagaa cagaatctgc    240
tacctgcagg aaatcttcag caacgaaatg gcaaggtcg acgacagctt cttccacaga    300
ctggaagaaa gcttcctggt cgaagaagaa aagaagcacg aagagaccc gatcttcgga    360
aacatcgtcg acgaagtcgc ataccacgaa aagtacccga caatctacca cctgagaaag    420
aagctggtcg acagcacaga caaggcagac ctgagactga tctacctggc actggcacac    480
atgatcaagt tcagaggaca cttcctgatc gaaggagacc tgaacccgga caacagcgac    540
gtcgacaagc tgttcatcca gctggtccag acatacaacc agctgttcga agaaaacccg    600
atcaacagca gcggagtcga cgcaaaggca atcctgagcg caagactgag caagagcaga    660
agactggaaa acctgatcgc acagctgccg ggagaaaaga gaacggact gttcggaaac    720
ctgatcgcac tgagcctggg actgacaccg aacttcaaga gcaacttcga cctggcagaa    780
gacgcaaagc tgcagctgag caaggacaca tacgacgacg acctggacaa cctgctggca    840
cagatcggag accagtacgc agacctgttc ctggcagcaa agaacctgag cgacgcaatc    900
ctgctgagcg acatcctgag agtcaacaca gaaatcacaa aggcaccgct gagcgcaagc    960
atgatcaaga gatacgacga acaccaccag gacctgacac tgctgaaggc actggtcaga   1020
cagcagctgc cggaaaagta caaggaaatc ttcttcgacc agagcaagaa cggatacgca   1080
ggatacatcg acggaggagc aagccaggaa gaattctaca agttcatcaa gccgatcctg   1140
gaaaagatgg acggaacaga gaactgctg gtcaagctga cagagaaga cctgctgaga   1200
aagcagagaa cattcgacaa cggaagcatc ccgcaccaga tccacctggg agaactgcac   1260
gcaatcctga agacagga agacttctac ccgttcctga aggacaacag agaaaagatc   1320
gaaaagatcc tgacattcag aatcccgtac tacgtcggca gcctggcagg aggaaacgc   1380
agattcgcat ggatgacaag aaagagcgaa gaaacaatca caccgtggaa cttcgaagaa   1440
gtcgtcgaca agggagcaag cgcacagagc ttcatcgaaa gaatgacaaa cttcgacaag   1500
aacctgccga cgaaaaggt cctgccgaag cacagcctgc tgtacgaata cttcacagtc   1560
tacaacgaac tgacaaaggt caagtacgtc acagaaggaa tgagaaagcc ggcattcctg   1620
agcggagaac agaagaaggc aatcgtcgac ctgctgttca gacaaacag aaaggtcaca   1680
gtcaagcagc tgaaggaaga ctacttcaag aagatcgaat gcttcgacag cgtcgaaatc   1740
agcggagtcg aagacagatt caacgcaagc ctgggaacat accacgacct gctgaagatc   1800
atcaaggaca aggacttcct ggacaacgaa gaaaacgaag acatcctgga agacatcgtc   1860
ctgacactga cactgttcga agacagagaa atgatcgaag aaagactgaa gacatacgca   1920
cacctgttcg acgacaaggt catgaagcag ctgaagagaa gagatacac aggatgggga   1980
agactgagca gaaagctgat caacggaatc agagacaagc agagcggaaa gacaatcctg   2040
gacttcctga agagcgacgg attcgcaaac agaaacttca tgcagctgat ccacgacgac   2100
agcctgacat tcaaggaaga catccagaag cacaggtcg gcgacaaggg agacagcctg   2160
cacgaacaca tcgcaaacct ggcaggaagc ccggcaatca gaaagggaat cctgcagaca   2220
gtcaaggtcg tcgacgaact ggtcaaggtc atgggaagac acaagccgga aaacatcgtc   2280
atcgaaatgg caagagaaaa ccagacaaca cagaagggac agaagaacag cagagaaaga   2340
atgaagagaa tcgaagaagg aatcaaggaa ctgggaagcc agatcctgaa ggaacacccg   2400
gtcgaaaaca cacagctgca gaacgaaaag ctgtacctgt actacctgca gaacggaaga   2460
gacatgtacg tcgaccagga actggacatc aacagactga gcgactacga cgtcgaccac   2520
atcgtcccgc agagcttcct gaaggacgac agcatcgaca caaggtcct gacaagaagc   2580
gacaagaaca gaggaaagag cgacaacgtc ccgagcgaag agtcgtcaa agagatgaag   2640
aactactgga gacagctgct gaacgcaaag ctgatcacac agagaaagtt cgacaacctg   2700
acaaaggcag agagaggagg actgagcgaa ctggacaagg cagatttcat caagagacag   2760
ctggtcgaaa caagacagat cacaaagcac gtcgcacaga tcctggacag cagaatgaac   2820
acaaagtacg acgaaaacga caagctgatc agagaagtca aggtcatcac actgaagagc   2880
aagctggtca gcgacttcag aaaggacttc cagttctaca aggtcagaga aatcaacaac   2940
taccaccacg cacacgacgc atacctgaac gcagtcgtcg gaacagcact gatcaagaag   3000
tacccgaagc tggaaagcga attcgtctac ggagactaca aggtctacga cgtcagaaag   3060
```

```
atgatcgcaa agagcgaaca ggaaatcgga aaggcaacag caaagtactt cttctacagc    3120
aacatcatga acttcttcaa gacagaaatc acactggcaa acggagaaat cagaaagaga    3180
ccgctgatcg aaacaaacgg agaaacagga gaaatcgtct gggacaaggg aagagacttc    3240
gcaacagtca gaaaggtcct gagcatgccg caggtcaaca tcgtcaagaa gacagaagtc    3300
cagacaggag gattcagcaa ggaaagcatc ctgccgaaga gaaacagcga caagctgatc    3360
gcaagaaaga aggactggga cccgaagaag tacggaggat tcgacagccc gacagtcgca    3420
tacagcgtcc tggtcgtcgc aaaggtcgaa aagggaaaga gcaagaagct gaagagcgtc    3480
aaggaactgc tgggaatcac aatcatgaa agaagcagct tcgaaaagaa cccgatcgac    3540
ttcctggaag caaagggata caaggaagtc aagaaggacc tgatcatcaa gctgccgaag    3600
tacagcctgt tcgaactgga aaacggaaga agagaaatgc tggcaagcgc aggagaactg    3660
cagaagggaa acgaactggc actgccgagc aagtacgtca acttcctgta cctggcaagc    3720
cactacgaaa agctgaaggg aagcccggaa gacaacgaac agaagcagct gttcgtcgaa    3780
cagcacaagc actacctgga cgaaatcatc gaacagatca gcgaattcag caagagagtc    3840
atcctggcag acgcaaacct ggacaaggtc tgagcgcta acaacaagca cagacaaag    3900
ccgatcagag aacaggcaga aaacatcatc cacctgttca cactgacaaa cctgggagca    3960
ccggcagcat tcaagtactt cgacacaaca atcgacagaa agagatacac aagcacaaag    4020
gaagtcctgg acgcaacact gatccaccag agcatcacag gactgtacga aacaagaatc    4080
gacctgagcc agctgggagg agacggagga ggaagcccga gaagaagag aaaggtctag    4140
```

SEQ ID NO: 205      moltype = RNA   length = 4143
FEATURE             Location/Qualifiers
misc_feature        1..4143
                    note = Synthetic: Cas9 mRNA ORF using codons with generally
                    high expression in humans, with start and stop codons
source              1..4143
                    mol_type = other RNA
                    organism = synthetic construct SEQUENCE: 205
```
atggataaga agtactcaat cgggctggat atcggaacta attccgtggg ttgggcagtg    60
atcacggatg aatacaaagt gccgtccaag aagttcaagg tcctggggaa caccgataga    120
cacagcatca agaaaaatct catcggagcc ctgctgtttg actccggcga aaccgcagaa    180
gcgacccggc tcaaacgtac cgcgaggcga cgctacaccc ggcggaagaa tcgcatctgc    240
tatctgcaag agatcttttc gaacgaaatg gcaaggtcg acgacagctt cttccaccgc    300
ctggaagaat ctttcctggt ggaggaggac aagaagcatg aacggcatcc tatctttgga    360
aacatcgtcg acgaagtggc gtaccacgaa agtacccga ccatctacca tctgcggaag    420
aagttggttg actcaactga caaggccgac ctcagattga tctacttggc cctgcccat    480
atgatcaaat tccgcggaca cttcctgatc gaaggcgatc tgaaccctga taactccgac    540
gtggataagc ttttcattca actggtgcag acctacaacc aactgttcga agaaaaccca    600
atcaatgcta gcggcgtcga tgccaaggcc atcctgtccg cccggctgtc gaagtcgcga    660
cgcctcgaaa acctgatcgc acagctgccg ggagagaaaa agaacggact tttcggcaac    720
ttgatcgctc tctcactggg actcactccc aatttcaagt ccaattttga cctgccgag    780
gacgcgaagc tgcaactctc aaaggacacc tacgacacg acttggacaa tttgctggca    840
caaattggcg atcagtacgc ggatctgttc cttgccgcta agaaccttc ggacgcaatc    900
ttgctgtccg atatcctgcg cgtgaacacc gaaataacca aagcgccgct tagcgcctcg    960
atgattaagc ggtacgacga gcatcaccag gatctcacgc tgctcaaagc gctcgtgaga    1020
cagcaactgc ctgaaaagta caaggagatc ttcttcgacc agtccaagaa tgggtacgca    1080
gggtacatcg atgggggcgc tagccaggaa gagttctata gttcatcaa gccaatcctg    1140
gaaaagatgg acggaaccga agaactgctg gtcaagctga acaggaggag tctgctccga    1200
aaacagaaa cctttgacaa cggatccatt ccccaccaga tccatctggg tgagctgcac    1260
gccatcttgg ggcgcagga ggactttac ccattcctca aggacaaccg ggaaaagatc    1320
gagaaaattc tgacgttccg catcccgtat tacgtgggcc cactggcgcg cggcaattcg    1380
cgcttcgcgt ggatgactag aaaatcagag gaaaccatca ctccttggaa tttcgaggaa    1440
gttgtggata agggagcttc ggcacaaagc ttcatcgaac gaatgaccaa cttcgacaag    1500
aatctcccaa acgagaaggt gcttcctaag cacagcctcc tttacgaata cttcactgtc    1560
tacaacgaac tgactaaagt gaaatacgtt actgaaggaa tgaggaagcc ggccttctg    1620
tccggagaac agaagaaagc aattgtcgat ctgctgttca gaccaaccg caaggtgacc    1680
gtcaagcagc ttaaagagga ctacttcaag aagatcgagt gttcgactc agtggaaatc    1740
agcggggtgg aggacagatt caacgcttcg ctgggaacct atcatgatct cctgaagatc    1800
atcaaggaca aggacttcct tgacaacgag gagaacgagg acatcctgga agatatcgtc    1860
ctgaccttga ccctttttga ggatcgcgag atgatcgag agaggcttaa gacctacgct    1920
catctcttcg acgataaggt catgaaacaa ctcaagcgcc gccggtacac tggttggggc    1980
cgcctctccc gcaagctgat caacggtatt cgcgataaac agagcggtaa aactatcctg    2040
gatttcctca aatcggatgg cttcgctaat cgtaacttca tgcaattgat ccacgacgac    2100
agcctgacct ttaaggagga catccaaaaa gcacaagtgc cggacaggg agactcctcg    2160
catgaacaca tcgcgaatct ggccggttcg ccggcgatta gaagggaat tctgcaaact    2220
gtgaaggtgg tcgacgagct ggtcaaggtc atggacggc acaaaccgga gaatatcgtg    2280
attgaaatgc ccgagaaaa ccagactacc cagaagggcc agaaaactc ccgcgaaagg    2340
atgaagcgga tcgaagaagg aatcaaggag ctgggcagcc agatcctgaa agagcaccg    2400
gtgcagaaca cgcagctgca gaacgagaag ctctaccgt actatttgta aatggacag    2460
gacatgtacg tggaccaaga gctggacatc aatcggttgt ctgattacga cgtgaccac    2520
atcgttccac agtcctttct gaaggatgac tcgatcgata caaggtgtt gactcgcagc    2580
gacaagaaca gagggaagtc agataatgtg ccatcggagg aggtcgtgaa gagatgaag    2640
aattactggc ggcagctcct gaatgcgaag ctgattaccc agagaaagtt tgacaatctc    2700
acgaaagccg agcgcggcgg actctcaagg ctggataagg ctggattcat caaacgcag    2760
ctggtcgaga ctcggcagat taccaagcac gtgcgcagga tcttggactc ccgcatgaac    2820
actaaatacg acgagaacga taagctcatc cgggaagtga aggtgattac cctgaaaagc    2880
aaacttgtgt cggactttcg gaaggacttt cagtttaca aagtgagaga atcaacaac    2940
taccatcacg cgcatgacgc atacctcaac gctgtggtcg gtaccgccct gatcaaaaag    3000
tacccctaaac ttgaatcgga gtttgtgtac ggagactaca aggtctacga cgtgaggaag    3060
```

-continued

```
atgatagcca agtccgaaca ggaaatcggg aaagcaactg cgaaatactt cttttactca    3120
aacatcatga acttttcaa gactgaaatt acgctggcca atggagaaat caggaagagg    3180
ccactgatcg aaactaacgg agaaacgggc gaaatcgtgt gggacaaggg cagggacttc    3240
gcaactgttc gcaaagtgct ctctatgccg caagtcaata ttgtgaagaa aaccgaagtg    3300
caaaccggcg gattttcaaa ggaatcgatc ctcccagaga aaatagcca caagctcatt    3360
gcacgcaaga aagactggga cccgaagaag tacggaggat tcgattcgcc gactgtcgca    3420
tactccgtcc tcgtggtggc caaggtggag aagggaaaga gcaaaaagct caaatccgtc    3480
aaagagctgc tggggattac catcatgaa cgatcctcgt tcgagaagaa cccgattgat    3540
ttcctcgagg cgaagggtta caaggaggtg aagaaggatc tgatcatcaa actccccaag    3600
tactcactgt tcgaactgga aaatggtcgg aagcgcatgc tggcttcggc cggagaactc    3660
caaaaaggaa atgagctggc cttgcctagc aagtacgtca acttcctcta tcttgcttcg    3720
cactacgaaa aactcaaagg gtcaccgaaa gataacgaac agaagcagct tttcgtggag    3780
cagcacaagc attatctgga tgaaatcatc gaacaaatct ccgagttttc aaagcgcgtg    3840
atcctcgccg acgccaacct cgacaagtc tgtcggcct acaataagca tagagataag    3900
ccgatcagag aacaggccga aacattatc cactcgttca ccctgactaa cctgggagcc    3960
ccagccgcct tcaagtactt cgatactact atcgatcgca aaagatacac gtccaccaag    4020
gaagttctgg acgcgaccct gatccaccaa agcatcactg gactctacga aactaggatc    4080
gatctgtcgc agctgggtgg cgatggcggt ggatctccga aaaagaagag aaaggtgtaa    4140
tga                                                                  4143

SEQ ID NO: 206         moltype = AA  length = 1379
FEATURE                Location/Qualifiers
REGION                 1..1379
                       note = Synthetic: Cas9 nickase (D10A) amino acid sequence
source                 1..1379
                       mol_type = protein
                       organism = synthetic construct
SEQUENCE: 206
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGDGG GSPKKKRKV  1379

SEQ ID NO: 207         moltype = RNA  length = 4140
FEATURE                Location/Qualifiers
misc_feature           1..4140
                       note = Synthetic: Cas9 nickase (D10A) mRNA ORF
source                 1..4140
                       mol_type = other RNA
                       organism = synthetic construct
SEQUENCE: 207
atggacaaga agtacagcat cggactggca atcggaacaa acagcgtcgg atgggcagtc    60
atcacagacg aatacaaggt cccgagcaag aagttcaagg tcctgggaaa cacagacaga   120
cacagcatca agaagaacct gatcggagca ctgctgttcg acagcggaga aacagcagaa   180
gcaacaagac tgaagagaac agcaagaaga agatacagaa agaaaaagaa cagaatctgc   240
tacctgcagg aaatcttcag caacgaaatg gcaaaggtcg acgacagctt cttccacaga   300
ctggaagaaa gcttcctggt cgaagaagac aagaagcacg aagacaccc gatcttcgga   360
aacatcgtcg acgaagtcgc ataccacgaa aagtacccga caatctacca cctgagaaag   420
aagctggtcg acagcacaga caaggcagac ctgagactga tctacctggc actggcacac   480
atgatcaagt tcagaggaca cttcctgatc gaaggagacc tgaacccgga caacagcgac   540
gtcgacaagc tgttcatcca gctggtccag acatacaacc agctgttcga agaaaacccg   600
atcaacgcaa gcggagtcga cgcaaaggca atcctgagcg caagactgag caagagcaga   660
agactggaaa acctgatcgc acagctgccg ggagaaaaga gaacggact gttcggaaac   720
ctgatcgcac tgagcctggg actgacaccg aacttcaaga gcaactgga cctggcagaa   780
gacgcaaagc tgcagctgag caaggacaca tacgacgacg acctggacaa cctgctggca   840
cagatcggag accagtacgc agacctgttc ctggcagcaa agaacctgag cgacgcaatc   900
ctgctgagcg acatcctgag agtcaacaca gaaatcacaa aggcaccgct gagcgcaagc   960
atgatcaaga gatacgacga acaccaccag gacctgacac tgctgaaggc actggtcaga  1020
cagcagctgc cggaaaagta caaggaaatc ttcttcgacc agagcaagaa cggatacgca  1080
ggatacatcg acggaggagc aagccaggaa gaattctaca agttcatcaa gccgatcctg  1140
```

```
gaaaagatgg acggaacaga agaactgctg gtcaagctga acagagaaga cctgctgaga  1200
aagcagagaa cattcgacaa cggaagcatc ccgcaccaga tccacctggg agaactgcac  1260
gcaatcctga agagcagga agacttctac ccgttcctga aggacaacag agaaaagatc  1320
gaaaagatcc tgacattcag aatcccgtac tacgtcggac cgctggcaag aggaaacagc  1380
agattcgcat ggatgacaag aaagagcgaa gaaacaatca caccgtggac cttcgaagaa  1440
gtcgtcgaca agggagcaag cgcacagagc ttcatcgaaa gaatgacaaa cttcgacaag  1500
aacctgccga cgaaaaggt cctgccgaag cacagcctgc tgtacgaata cttcacagtc  1560
tacaacgaac tgacaaaggt caagtacgtc acagaaggaa tgagaaagcc ggcattcctg  1620
agcggagaac agaaaaggc aatcgtcgac ctgctgttca agacaaacag aaaggtcaca  1680
gtcaagcagc tgaaggaaga ctacttcaag aagatcgaat gcttcgacag cgtcgaaatc  1740
agcggagtcg aagacagatt caacgcaagc ctgggaacat accacgacct gctgaagatc  1800
atcaaggaca aggacttcct ggacaacgaa gaaaacgaag acatcctgga agacatcgtc  1860
ctgacactga cactgttcga agacagagaa atgatcgaag aaagactgaa gacatacgca  1920
cacctgttcg acgacaaggt catgaagcag ctgaagagaa gatacacgga ggatggggga  1980
agactgagca gaaagctgat caacggaatc agagacaagc agagcggaaa gacaatcctg  2040
gacttcctga gagcgacgg attcgcaaac agaaacttca tgcagctgat ccacgacgac  2100
agcctgacat tcaaggaaga catccagaag gcacaggtca gcggacaggg agacagcctg  2160
cacgaacaca tcgcaaacct ggcaggaagc ccggcaatca gaaagggaat cctgcagaca  2220
gtcaaggtcg tcgacgaact ggtcaaggtc atgggaagac acaagccgga aaacatcgtc  2280
atcgaaatgg caagagaaaa ccagacaaca cagaagggac agaagaacag cagagaaaga  2340
atgaagagaa tcgaagaagg aatcaaggaa ctgggaagcc agatcctgaa ggaacacccg  2400
gtcgaaacaa cacagctgca gaacgaaaag ctgtacctgt actacctgca gaacggaaga  2460
gacatgtacg tcgaccagga actggacatc aacagactga gcgactacga cgtcgaccac  2520
atcgtcccgc agagcttcct gaaggacgac agcatcgaca caaggtcctg gacaagaagc  2580
gacaagaaca gaggaaagag cgacaacgtc ccgagcgaag aagtcgtcaa gaagatgaag  2640
aactactgga gacagctgct gaacgcaaag ctgatcacaa ggaaaagtt cgacaacctg  2700
acaaaggcag agaggaggag actgagcgaa ctggacaagg caggattcat caagagacag  2760
ctggtcgaaa caagacagat cacaaagcac gtcgcacaga tcctggacag cagaatgaac  2820
acaaagtacg acgaaaacga caagctgatc agagaagtca aggtcatcac actgaagagc  2880
aagctggtca gcgacttcag aaaggacttc cagttctaca aggtcagaga aatcaacaac  2940
taccaccacg cacacgacgc atacctgaac gcagtcgtcg gaacagcact gatcaagaag  3000
tacccgaagc tggaaagcga attcgtctac ggagactaca aggtctacga cgtcagaaag  3060
atgatcgcaa agagcgaaca ggaaatcgga aaggcaacag caaagtactt cttctacagc  3120
aacatcatga acttcttcaa gacagaaatc acactggcaa acggagaaat cagaaagaga  3180
ccgctgatcg aaacaaacgg agaaacagga gaaatcgtct gggacaaggg aagagacttc  3240
gcaacagtca gaaaggtcct gagcatgccg caggtcaaca tcgtcaagaa gacagaagtc  3300
cagacaggag gattcagcaa ggaaagcatc ctgccgaaga aaacagcga caagctgatc  3360
gcaagaaaga aggactggga cccgaagaag tacgaggat tcgacagccc gacagtcgca  3420
tacagcgtcc tggtcgtcgc aaaggtcgaa aagggaaaga gcaagaagct gaagagcgtc  3480
aaggaactgc tgggaatcac aatcatggaa agaagcagct tcgaaaagaa cccgatcgac  3540
ttcctggaag caagggata caaggaagtc aagaaggacc tgatcatcaa gctgccgaag  3600
tacagcctgt cgaactgga aaacggaaga aagagaatgc tggcaagcgc aggagaactg  3660
cagaagggaa acgaactggc cctgccgagc aagtacgtca acttcctgta cctggcaagc  3720
cactacgaaa agctgaaggg aagcccggaa gacaacgaac agaagcagct gttcgtcgaa  3780
cagcacaagc actacctgga cgaaatcatc gaacagatca gcgaattcag caagagagtc  3840
atcctggcag acgcaaacct ggacaaggtc ctgagcgcat acaacaagca cagagacaag  3900
ccgatcagag aacaggcaga aaacatcatc cacctgttca cactgacaaa cctgggagca  3960
ccggcagcat tcaagtactt cgacacaaca atcgacagaa agagatacac aagcacaaag  4020
gaagtcctgg acgcaacact gatccaccag agcatcacag gactgtacga aacaagaatc  4080
gacctgagcc agctgggagg agacggagga ggaagcccga agaagaagag aaaggtctag  4140
```

SEQ ID NO: 208        moltype = AA  length = 1379
FEATURE                Location/Qualifiers
REGION                 1..1379
                        note = Synthetic: dCas9 (D10A H840A) amino acid sequence
source                 1..1379
                        mol_type = protein
                        organism = synthetic construct

```
SEQUENCE: 208
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
```

```
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDGG GSPKKKRKV    1379

SEQ ID NO: 209           moltype = RNA  length = 4140
FEATURE                  Location/Qualifiers
misc_feature             1..4140
                         note = Synthetic: dCas9 (D10A H840A) mRNA ORF
source                   1..4140
                         mol_type = other RNA
                         organism = synthetic construct
SEQUENCE: 209
atggacaaga agtacagcat cggactggca atcggaacaa acagcgtcgg atgggcagtc   60
atcacagacg aatacaaggt cccgagcaag aagttcaagg tcctgggaaa cacagacaga   120
cacagcatca agaagaacct gatcggagca ctgctgttcg acagcggaga aacagcagaa   180
gcaacaagac tgaagagaac agcaagaaga agatacacaa gaagaagaa  cagaatctgc   240
tacctgcagg aaatcttcag caacgaaatg gcaaggtcg  acgacagctt cttccacaga   300
ctggaagaaa gcttcctggt cgaagaagac aagaagcacg aaagacaccc gatcttcgga   360
aacatcgtcg acgaagtcgc ataccacgaa aagtacccga caatctacca cctgagaaag   420
aagctggtcg acagcacaga caaggcagac ctgagactga tctacctggc actggcacac   480
atgatcaagt tcagaggaca cttcctgatc gaaggagacc tgaacccgga caacagcgac   540
gtcgacaagc tgttcatcca gctgttccag acatacaacc agctgttcga agaaaacccg   600
atcaacgcaa gcggagtcga cgcaaaggca atcctgagcg caagactgag caagagccga   660
agactggaaa acctgatcgc acagctgccg ggagaaaaga gaacggact  gttcggaaac   720
ctgatcgcac tgagcctggg actgacaccg aacttcaaga caacttcga  cctggcagaa   780
gacgcaaagc tgcagctgag caaggacaca tacgacgagc acctggacaa cctgctggca   840
cagatcggag accagtacgc agacctgttc ctggcagcaa agaacctgag cgacgcaatc   900
ctgctgagcg acatcctgag agtcaacaca gaaatcacaa aggcaccgct gagcgcaagc   960
atgatcaaga gatacgacga acaccaccag gacctgacac tgctgaaggc actggtcaga   1020
cagcagctgc cggaaaagta caaggaaatc ttcttcgacc agagcaagaa cggatacgca   1080
ggatacatcg acggaggagc aagccaggaa gaattctaca gttcatcaa  gccgatcctg   1140
gaaaagatgg acggaacaga agaactgctg gtcaagctga cagagaaga  cctgctgaga   1200
aagcagagaa cattcgacaa cggaagcatc ccgcaccaga tccacctggg agaactgcac   1260
gcaatcctga gaagacagga agacttctac ccgttcctga aggacaacag agaaaagatc   1320
gaaaagatcc tgacattcag aatcccgtac tacgtcggac cgctggcaag aggaaacagc   1380
agattcgcat ggatgacaag aaagagcgaa gaaacaatca ccgtcgaa  cttcgaagaa   1440
gtcgtcgaca agggagcaag cgcacagagc ttcatcgaa  gaatgacaaa cttcgacaag   1500
aacctgccga acgaaaaggt cctgccgaag cacagcctgc tgtacgaata cttcacagtc   1560
tacaacgaac tgacaaaggt caagtacgtc acagaaggaa tgagaaagcc ggcattcctg   1620
agcggagaac agaagaaggc aatcgtcgac ctgctgttca gacaaacag  aaaggtcaca   1680
gtcaagcagc tgaaggaaga ctacttcaag aagatcgaat gcttcgacag cgtcgaaatc   1740
agcggagtcg aagacagatt caacgcaagc ctgggaacat accacgacct gctgaagatc   1800
atcaaggaca aggacttcct ggacaacgaa gaaaacgaag acatcctgga agacatcgtc   1860
ctgacactga cactgttcga agacagagaa atgatcgaaa aagactgaa  gacatacgca   1920
cacctgttcg acgacaaggt catgaagcag ctgaagagaa gaagatacac aggatgggga   1980
agactgagca gaaagctgat caacggaatc agagacaagc agagcggaaa gacaatcctg   2040
gacttcctga gagcgacgg  attcgcaaac agaaacttca tgcagctgat ccacgacgac   2100
agcctgacat tcaaggaaga catccagaag gcacaggtca gcggacaggg agacagcctg   2160
cacgaacaca tcgcaaacct ggcaggaagc ccggcaatca gaagggaat  cctgcagaca   2220
gtcaaggtc  tcgacgaact ggtcaaggtc atggaagac  acaagccgga aaacatcgtc   2280
atcgaaatgg caagagaaaa ccagacaaca cagaaggac  agaagaacag cagagaaaga   2340
atgaagagaa tcgaagaagg aatcaaggaa ctgggaagcc agatcctgaa ggaacacccg   2400
gtcgaaaaca cacagctgca gaacgaaaag ctgtacctgt actacctgca gaacggaaga   2460
gacatgtacg tcgaccagga actggacatc aacagactga gcgactacga cgtcgacgca   2520
atcgtcccgc agagcttcct gaaggacgac agcatcgaca caaggtcct  gacaaggaac   2580
gacaagaaca gaggaaagag cgacaacgtc ccgagcgaag aagtcgtcaa gaagatgaag   2640
aactactgga gacagctgct gaacgcaaag ctgatcacac agagaaagtt cgacaacctg   2700
acaaaggcag agagggagg  actgagcgaa ctggacaagg caggattcat caagagacag   2760
ctggtcgaaa cagacagat  cacaaagcac gtcgcacaga tcctggacag cagaatgaac   2820
acaaagtacg acgaaaacga caagctgatc agagaagtca aggtcatcac actgaagagc   2880
aagctggtca gcgacttcag aaaggacttc cagttctaca ggtcagaga  atcaacaac    2940
taccaccacg cacacgacgc ataccctgaac gcagtcgtcg aacagcact  gatcaagaag   3000
tacccgaagc tggaaagcga attcgtctac ggagactaca aggtctacga cgtcagaaag   3060
atgatcgcaa agagcgaaca ggaaatcgga aaggcaacag caaagtactt cttctacagc   3120
aacatcatga acttcttcaa gacagaaatc acactggcaa acggagaaat cagaaagaga   3180
ccgctgatcg aaacaaacgg agaaacagga gaaatcgtct gggacaaggg aagagacttc   3240
gcaacagtca gaaaggtcct gagcatgccg caggtcaaca tcgtcaagaa gacagaagtc   3300
cagacaggag gattcagcaa ggaaagcatc ctgccgaaga aaacagcca  aagctgatc    3360
gcaagaaaga agactggga  cccgaagaag tacggggat  tcgacagccc gacagtcgca   3420
tacagcgtcc tggtcgtcgc aaaggtcgaa aagggaaaga gcaagaagct gaagagcgtc   3480
aaggaactgc tgggaatcac aatcatggaa agaagcagct cgaaaagaa  cccgatcgac   3540
ttcctggaag caagggata  caaggaagtc aagaaggacc tgatcatcaa gctgccgaag   3600
tacagcctgt tcgaactgga aaacggaaga agagaatgt  ggcaagcgc  aggagaactg   3660
cagaagggaa acgaactggc acttgccagc aagtacgtca cttcctgta cctggcaga    3720
cactacgaaa agctgaaggg aagcccggaa gacaacgaac agaagcagct gttcgtcgaa   3780
cagcacaagc actacctgga cgaaatcatc gaacagatca gcgaattcag caagagagtc   3840
atcctggcag acgcaaacct ggacaaggtc ctgagcgcat acaacaagca cagagacaag   3900
ccgatcgag  aacaggcaga aaacatcatc cacctgttca cactgacaaa cctgggagca   3960
ccggcagcat tcaagtactt cgacacaaca atcgacagaa agagatacac aagcacaaag   4020
```

```
gaagtcctgg acgcaacact gatccaccag agcatcacag gactgtacga aacaagaatc  4080
gacctgagcc agctgggagg agacggagga ggaagcccga agaagaagag aaaggtctag  4140
```

| SEQ ID NO: 210 | moltype = RNA   length = 4134 |
|---|---|
| FEATURE | Location/Qualifiers |
| misc_feature | 1..4134 |
| | note = Synthetic: Cas9 mRNA coding sequence using minimal uridine codons (no start or stop codons; suitable for inclusion in fusion protein coding sequence) |
| source | 1..4134 |
| | mol_type = other RNA |
| | organism = synthetic construct |

SEQUENCE: 210

```
gacaagaagt acagcatcgg actggacatc ggaacaaaca gcgtcggatg ggcagtcatc   60
acagacgaat acaaggtccc gagcaagaag ttcaaggtcc tgggaaacac agacagacac  120
agcatcaaga agaacctgat cggagcactg ctgttcgaca gcgagaaac agcagaagca  180
acaagactga agagaacagc aagaagaaga tacacaagaa gaaagaacag aatctgctac  240
ctgcaggaaa tcttcagcaa cgaaatggca aaggtcgacg acagcttctt ccacagactg  300
gaagaaagct tcctggtcga agaagacaag aagcacgaaa gacacccgat cttcggaaac  360
atcgtcgacg aagtcgcata ccacgaaaag tacccgacaa tctaccacct gagaaagaag  420
ctggtcgaca gcacagacaa ggcagacctg agactgatct acctggcact ggcacacatg  480
atcaagttca gaggacactt cctgatcgaa ggagacctga acccggacaa cagcgacgtc  540
gacaagctgt tcatccagct ggtccagaca tacaaccagc tgttcgaaga aaacccgatc  600
aacgcaagcg gagtcgacgc aaaggcaatc ctgagcgcaa gactgagcaa gagcagaaga  660
ctggaaaacc tgatcgcaca gctgccggga gaaaagaaga acggactgtt cggaaacctg  720
atcgcactga gcctgggact gacaccgaac ttcaagagca acttcgacct ggcagaagac  780
gcaaagctgc agctgagcaa ggacacatac gacgacgacc tggacaacct gctggcacag  840
atcggagacc agtacgcaga cctgttcctg gcagcaaaga acctgagcga cgcaatcctg  900
ctgagcgaca tcctgagagt caacacagaa atcacaaagg caccgctgag cgcaagcatg  960
atcaagagat acgacgaaca ccaccaggac ctgacactgc tgaaggcact ggtcagacag 1020
cagctgccgg aaaagtacaa ggaaatcttc ttcgaccaga gcaagaacgg atacgcagga 1080
tacatcgacg gaggagcaag ccaggaagaa ttctacaagt tcatcaagcc gatcctggaa 1140
aagatggacg gaacagaaga actgctggtc aagctgaaca gagaagacct gctgagaaag 1200
cagagaacat tcgacaacgg aagcatcccg caccagatcc acctgggaga actgcacgca 1260
atcctgagaa gacaggaaga cttctaccc gttcctgaag gacaacagaa aaagatcgaa 1320
aagatcctga cattcagaat cccgtactac gtcggaccgc tggcaagagg aaacagcaga 1380
ttcgcatgga tgacaagaaa gagcgaagaa acaatcacac cgtggaactt cgaagaagtc 1440
gtcgacaagg gagcaagcgc acagagcttc atcgaaagaa tgacaaactt cgacaagaac 1500
ctgccgaacg aaaaggtcct gccgaagcac agcctgctgt acgaatactt cacagtctac 1560
aacgaactga caaaggtcaa gtacgtcaca gaaggaatga gaaagccggc attcctgagc 1620
ggagaacaga agaaggcaat cgtcgacctg ctgttcaaga aaacagaaa ggtcacagtc 1680
aagcagctga aggaagacta cttcaagaag atcgaatgct tcgacagcgt cgaaatcagc 1740
ggagtcgaag acagattcaa cgcaagcctg ggaacataca acgacctgct gaatcagatc 1800
aaggacaagg acttcctgga caacgaagaa aacgaagaca tcctggaaga catcgtcctg 1860
acactgacac tgttcgaaga cagagaaatg atcgaagaaa gactgaagac atacgcacac 1920
ctgttcgacg acaaggtcat gaagcagctg aagagaagaa gatacacagg atggggaaga 1980
ctgagcagaa agctgatcaa cggaatcaga gacaagcaga gcggaaagac aatcctggac 2040
ttcctgaaga gcgacggatt cgcaaacaga aacttcatgc agctgatcca cgacgacagc 2100
ctgacattca aggaagacat ccagaaggca caggtcagcg gacagggaga cagcctgcac 2160
gaacacatcg caaacctggc aggaagcccg gcaatcaaga gggaatcct gcagacagtc 2220
aaggtcgtcg acgaactggt caaggtcatg ggaagacaca agcoggaaaa catcgtcatc 2280
gaaatggcaa gagaaaacca gacaacacag aagggacaga gaacagcag agaaagaatg 2340
aagagaatcg aagaaggaat caaggaactg ggaagccaga tcctgaagga cacccggtc 2400
gaaaacacac agctgcagaa cgaaaagctg tacctgtact acctgcagaa cggaagagac 2460
atgtacgtcg accaggaact ggacatcaac agactgacgt actacgactg cgaccacatc 2520
gtcccgcaga gcttcctgaa ggacgacagc atcgacaaca aggtcctgac aagaagcgac 2580
aagaacagag aaagcgcaa cgtcccgagc aagaag tcgtcaagaa gatgaagaac 2640
tactggagac agctgctgaa cgcaaagctg atcacacaga aagttcga caacctgaca 2700
aaggcagaga gaggaggact gagcgaactg gacaaggcag gattcatcaa gagacagctg 2760
gtcgaaacaa gacagatcac aaagcacgtc gcacagatcc tggacagcag aatgaacaca 2820
aagtacgacg aaaacgacaa gctgatcaga gaagtcaagg tcatcacact gaagagcaag 2880
ctggtcagcg acttcagaaa ggacttccag ttctacaagg tcagagaaat caacaactac 2940
caccacgcac acgacgcata cctgaacgca gtcgtcggaa cagcactgat caagaagtac 3000
ccgaagctgg aaagcgaatt cgtctacgga gactacaagg tctacgacgt cagaaagatg 3060
atcgcaaaga gcgaacagga aatcggaaag gcaacagcaa agtacttctt ctacagcaac 3120
atcatgaact tcttcaagac agaaatcaca ctggcaaacg gagaaatcag aaagagaccg 3180
ctgatcgaaa caacggaga acaggagaa atcgtctggg acaagggaag agacttcgca 3240
acagtcagaa aggtcctgag catgccgcag gtcaacatcg tcaagaagac agaagtccag 3300
acaggaggat tcagcaagga aagcatcctg ccgaagagaa acagcgacaa gctgatccga 3360
agaaagaagg actgggaccc gaagaagtac ggaggattcg acagccgac agtcgcatac 3420
agcgtcctgg tcgtcgcaaa ggtcgaaaag ggaaagagca gaagctgaa gagcgtcaag 3480
gaactgctgg gaatcacaat catggaaaga agcagcttcg aaaagaaccc gatcgacttc 3540
ctggaagcaa agggatacaa ggaagtcaag aaggacctga tcatcaagct gccgaagtac 3600
agcctgttcg aactggaaaa cggaagaaag agaatgctgg caagcgcagg agaactgcag 3660
aagggaaaca aactggcact gccgagcaag tacgtcaact tcctgtacct ggcaagccac 3720
tacgaaaagc tgaagggaag cccggaagac aacgaacaga gcagctgtt cgtcgaacag 3780
cacaagcact acctggacga aatcatcgaa cagatcagcg aattcagcaa gagagtcatc 3840
ctggcagacg caaacctgga caaggtcctg agcgcatcca acaagcacag agacaagccg 3900
atcagagaac aggcagaaaa catcatccac ctgttcacac tgacaaacct gggagcaccg 3960
```

```
gcagcattca agtacttcga cacaacaatc gacagaaaga gatacacaag cacaaaggaa   4020
gtcctggacg caacactgat ccaccagagc atcacaggac tgtacgaaac aagaatcgac   4080
ctgagccagc tgggaggaga cggaggagga agcccgaaga agaagagaaa ggtc         4134

SEQ ID NO: 211          moltype = RNA   length = 4134
FEATURE                 Location/Qualifiers
misc_feature            1..4134
                        note = Synthetic: Cas9 nickase bare coding sequence
source                  1..4134
                        mol_type = other RNA
                        organism = synthetic construct
SEQUENCE: 211
gacaagaagt acagcatcgg actggcaatc ggaacaaaca gcgtcggatg ggcagtcatc   60
acagacgaat acaaggtccc gagcaagaag ttcaaggtcc tgggaaacac agacagacac   120
agcatcaaga agaacctgat cggagcactg ctgttcgaca gcggagaaac agcagaagca   180
acaagactga gagaacagca agaagaagaa tacacaagaa gaaagaacag aatctgctac   240
ctgcaggaaa tcttcagcaa cgaaatggca aaggtcgacg acagcttctt ccacagactg   300
gaagaaagct tcctggtcga agaagacaag aagcacgaaa gacacccgat cttcggaaac   360
atcgtcgacg aagtcgcata ccacgaaaag taccccgaca tctaccaccc tgagaaagaa   420
ctggtcgaca gcacagacaa ggcagacctg agactgatct acctggcact ggcacacatg   480
atcaagttca gaggacactt cctgatcgaa ggagacctga cccggacaa cagcgacgtc   540
gacaagctgt tcatccagct ggtccagaca tacaaccagc tgttcgaaga aaacccgatc   600
aacgcaagcg gagtcgacgc aaaggcaatc ctgagcgcaa gactgagcaa gagcagaaga   660
ctggaaaacc tgatcgcaca gctgccggga gaaaagaaga acggactgtt cggaaacctg   720
atcgcactga gcctgggact gacaccgaac ttcaagagca cttcgacct ggcagaagac   780
gcaaagctga gctgagcaa ggacacatac gacgacgacc tggacaacct gctggcactg   840
atcggagacc agtacgcaga cctgttcctg gcagcaaaga acctgagcga cgcaatcctg   900
ctgagcgaca tcctgagagt caacacagaa atcacaaagg caccgctgag cgcaagcatg   960
atcaagagat acgacgaaca ccaccaggac ctgacactgc tgaaggcact ggtcagacag   1020
cagctgccgg aaaagtacaa ggaaatcttc ttcgaccaga gcaagaacgg atacgcagga   1080
tacatcgacg gaggagcaag ccaggaagaa ttctacaagt tcatcaagcc gatcctggaa   1140
aagatggacg gaacagaaga actgctggtc aagctgaaca gagaagacct gctgagaaag   1200
cagagaacat tcgacaacgg aagcatcccg caccagatcc acctgggaga actgcacgca   1260
atcctgagaa gacagggaag cttctaccog ttcctgaaga caaacagaga aagatgcaa   1320
aagatcctga cattcagaat cccgtactac gtcggaccgc tggcagagg aaacagcaga   1380
ttcgcatgga tgacaagaaa gagcgaagaa acaatcacac cgtggaactt cgaagaagtc   1440
gtcgacaagg gagcaagcgc acagagcttc atcgaaagaa tgacaaactt cgacaagaac   1500
ctgccgaacg aaaaggtcct gccgaagcac agcctgctgt acgaatactt cacagtctac   1560
aacgaactga caaaggtcaa gtacgtcaca gaaggaatga gaaagccgc attcctgagc   1620
ggagaacaga agaaggcaat cgtcgacctg ctgttcaaga caaacagaaa ggtcacagtc   1680
aagcagctga aggaagacta cttcaagaag atcgaatgct cgacagcgt cgaaatcagc   1740
ggagtcgaag acagattcaa cgcaagcctg ggaacatacc acgacctgct gaagatcatc   1800
aaggacaagg acttcctgga caacgaagaa aacgaagaca tcctgaagga catcgtcctg   1860
acactgacac tgttcgaaga cagagaaatg atcgaagaaa gactgaagac atacgcacac   1920
ctgttcgacg acaaggtcat gaagcagctg aagagaagaa gatacacagg atgggggaaga   1980
ctgagcagaa agctgatcaa cggaatcaga gacaagcaga gcggaaaga caatcctggac   2040
ttcctgaaga gcgacggatt cgcaaacaga aacttcatgc agctgatcca cgacgacagc   2100
ctgacattca aggaagacat ccagaaggca caggtcagcg gacagggaca gcctgcac    2160
gaacacatcg caaacctggc aggaagcccg gcaatcaaga agggaatcct gcagacagtc   2220
aaggtcgtcg acgaactggt caaggtcatg ggaagacaca gccgaaaa catcgtcatc   2280
gaaatggcaa gagaaaacca gacaacacag aagggacaga gaacagcag aagaagaatg   2340
aagagaatcg aagaaggaat caaggaactg ggaagccaga tcctgaagga cacccggtc   2400
gaaacacaca gctgcagaa cgaaaagctg taccotgtact acctgcagaa cggaagagac   2460
atgtacgtcg accaggaact ggacatcaac agactgagcg actacgacgt cgaccacatc   2520
gtcccgcaga gcttcctgaa ggacgacagc atcgacaaca aggtcctgac aagaagcgac   2580
aagaacagag gaaagagcga caacgtcccg agcgaagaag tcgtcaagaa gatgaagaac   2640
tactggagac agctgctgaa cgcaaagctg atcacacaga aagttcga caacctgaca   2700
aaggcagaga aggaggact gagcgaactg gacaaggcag gattcatcaa gagacagctg   2760
gtcgaaacaa gacagatcac aaagcacgtc gcacagatcc tggacagcag aatgaacaca   2820
aagtacgacg aaaacgacaa gctgatcaga gaagtcaagg tcatcacact gaagagcaag   2880
ctggtcagcg acttcagaaa ggacttccag ttctacaagg tcagagaaat caacaactac   2940
caccacgcac acgacgcata cctgaacgca gtcgtcggaa cagcactgat caagaagtac   3000
ccgaagctga aagcgaatt cgtctacgga gactacaagg tctacgacgt cagaaagatg   3060
atcgcaaaga gcgaacagga aatcggaaag gcaacagcaa agtacttctt ctacagcaa   3120
atcatgaact tcttcaagac agaaatcaca ctggcaaacg agaaatcag aaagagacco   3180
ctgatcgaaa caaacggaga aacaggagaa atcgtctggg acaagggaag agacttcgca   3240
acagtcagaa aggtcctgag catgccgcag gtcaacatcg tcaagaagac agaagtccag   3300
acaggaggat tcagcaagga aagcatcctg ccgaagagaa actcgacgaca gctgatcgca   3360
agaaaggagg actgggaccc gaagaagtac ggaggattcg acagccgaca agtcgcatac   3420
agcgtcctgg tcgtcgcaaa ggtcgaaaag ggaaagagca gaagctgaa gagcgtcaag   3480
gaactgctgg aatcacaat catggaaaga agcagcttcg aaaagaaccc gatcgacttc   3540
ctggaagcaa agggatacaa ggaagtcaag aaggacctga tcatcaagct gccgaagtac   3600
agcctgttcg aactggaaaa cggaagaaag agaatgctgg caagcgcagg agaactgcag   3660
aagggaaacg aactggcact gccgagcaag tacgtcaact tcctgtacct cgaagccac   3720
tacgaaaagc tgaagggaag cccggaagac aacgaacaga gcagctgtt cgtcgaacag   3780
cacaagcact acctggacga aatcatcgaa cagatcagcg aattcagcaa gagagtcatc   3840
ctggcagacg caaacctgga caaggtcctg agcgcataca acaagcacag agacaagcog   3900
atcagagaac aggcagaaaa catcatccac ctgttcacac tgcaaacct gggagcaccg   3960
gcagcattca agtacttcga cacaacaatc gacagaaaga gatacacaag cacaaaggaa   4020
```

```
gtcctggacg caacactgat ccaccagagc atcacaggac tgtacgaaac aagaatcgac   4080
ctgagccagc tgggaggaga cggaggagga agcccgaaga agaagagaaa ggtc         4134

SEQ ID NO: 212         moltype = RNA  length = 4134
FEATURE                Location/Qualifiers
misc_feature           1..4134
                       note = Synthetic: dCas9 bare coding sequence
source                 1..4134
                       mol_type = other RNA
                       organism = synthetic construct
SEQUENCE: 212
gacaagaagt acagcatcgg actggcaatc ggaacaaaca gcgtcggatg ggcagtcatc     60
acagacgaat acaaggtccc gagcaagaag ttcaaggtcc tgggaaacac agacagacac    120
agcatcaaga agaacctgat cggagcactg ctgttcgaca gcagagaaga agcagaagca    180
acaagactga agagaacagc aagaagaaga tacacaagag gaaagaacag aatctgctac    240
ctgcaggaaa tcttcagcaa cgaaatggca aaggtcgacg acagcttctt ccacagactg    300
gaagaaagct tcctggtcga agaagacaag aagcacgaaa gacacccgat cttcggaaac    360
atcgtcgacg aagtcgcata ccacgaaaag tacccgacaa tctaccacct gagaaagaag    420
ctggtcgaca gcacagacaa ggcagacctg agactgatct acctggcact ggcacacatg    480
atcaagttca gaggacactt cctgatcgaa ggagacctga cccgacaa cagcgacgtc      540
gacaagctgt tcatccagct ggtccagaca tacaaccagc tgttcgaaga aaacccgatc    600
aacgcaagcg gagtcgacgc aaaggcaatc ctgagcgcaa gactgagcaa gagcagaaga    660
ctggaaaacc tgatcgcaca gctgccggga gaaaagaaga acggactgtt cggaaacctg    720
atcgcactga gcctgggact gacaccgaac ttcaagagca acttcgacct ggcagaagac    780
gcaaagctgc agctgagcaa ggacatatac gacgacgacc tggacaacct gctggcacag    840
atcggagacc agtacgcaga cctgttcctg gcagcaaaga acctgagcga cgcaatcctg    900
ctgagcgaca tcctgagagt caacacagaa atcacaaagg caccgctgag cgcaagcatg    960
atcaagagat acgacgaaca ccaccaggac ctgacactgc tgaaggcact ggtcagacag   1020
cagctgccgg aaaagtacaa ggaaatcttc ttcgaccaga gcaagaacgg atacgcagga   1080
tacatcgacg gaggagcaag ccaggaagaa ttctacaagt tcatcaagcc gatcctggaa   1140
aagatggacg gaacagaaga actgctggtc aagctgaaca gagaagacct gctgagaaag   1200
cagagaacat tcgacaacgg aagcatcccg caccagatcc acctgggaga actgcacgca   1260
atcctgagaa gacaggaaga cttctaccg ttcctgaagg acaacagaga aaagatcgaa    1320
aagatcctga cattcagaat cccgtactac gtcggaccgc tggcaagagg aaacagcaga   1380
ttcgcatgga tgacaagaaa gagcgaagaa acaatcacac cgtggaactt cgaagaagtc   1440
gtcgacaagg gagcaagcgc acagagcttc atcgaaagaa tgacaaactt cgacaagaac   1500
ctgccgaacg aaaaggtcct gccgaagcac agcctgctgt acgaatactt cacagtctac   1560
aacgaactga caaaggtcaa gtacgtcaca gaaggaatga aaagccggc attcctgagc   1620
ggagaacaga agaaggcaat cgtcgacctg ctgttcaaaa caaacagaaa ggtcacagtc   1680
aagcagctga aggaagacta cttcaagaag atcgaatgct tcgacagcgt cgaaatcagc   1740
ggagtcgaag acagattcaa cgcaagcctg ggaacatacc acgacctgct gaagatcatc   1800
aaggacaagg acttcctgga caacgaagaa aacgaagaca tcctggaaga catcgtcctg   1860
acactgacac tgttcgaaga cagagaaatg atcgaagaac gactgaagac atacgcacac   1920
ctgttcgacg acaaggtcat gaagcagctg aagagaagaa gatacacagg atggggaaga   1980
ctgagcagaa agctgatcaa cggaatcaga gacaagcaga gcggaaagac aatcctggac   2040
ttcctgaaga gcgacggatt cgcaaacaga aacttcatgc agctgatcca cgacgacagc   2100
ctgacattca aggaagacat ccagaaggca caggtcagcg gacagggaga cagcctgcac   2160
gaacacatcg caaacctggc aggaagcccc gcaatcaaga agggaatcct gcagacagtc   2220
aaggtcgtcg acgaactggt caaggtcatg ggaagacaca gccggaaaaa catcgtcatc   2280
gaaatggcaa gagaaaacca gacaacacag aaggacagag aacagcag agaaagaatg   2340
aagagaatcg aagaggaat caaggaactg ggaagccaaa tcctgaagga acacccggtg   2400
gaaaacacac agctgcagaa cgaaaagctg tacctgtact acctgcagaa cggaagagac   2460
atgtacgtcg accaggaact ggacatcaac agactgagcg actacgacgt cgacgcaatc   2520
gtcccgcaga gcttcctgaa ggacgacagc atcgacaaca aggtcctgac aagaagcgac   2580
aagaacagag gaaagagcga caacgtcccg agcgaagaag tcgtcaagaa gatgaagaac   2640
tactggagac agctgctgaa cgcaaagctg atcacacaga gaaagttcga caacctgaca   2700
aaggcagaga gaggaggact gagcgaactg gacaaggcag gattcatcaa gagacagctg   2760
gtcgaaacaa gacagatcac aaagcacgtc gcacagatcc tggacagcag aatgaacaca   2820
aagtacgacg aaaacgacaa gctgatcaga gaagtcaagg tcatcacact gaagagcaag   2880
ctggtcagcg acttcagaaa ggacttccag ttctacaagg tcagagaaat caacaactac   2940
caccacgcac acgacgcata cctgaacgca gtcgtcggaa cagcactgat caagaagtac   3000
ccgaagctgg aaagcgaatt cgtctacgga gactacaagg tctacgacgt cagaaagatg   3060
atcgcaaaga gcgaacagga aatcggaaag gcaacagcaa agtacttctt ctacagcaac   3120
atcatgaact tcttcaagac agaaatcaca ctggcaaatg gagaaatcag aaagagaccg   3180
ctgatcgaaa caaacggaga aacaggagaa atcgtctggg acaagggaag agacttcgca   3240
acagtcagaa aggtcctgag catgccgcag gtcaacatcg tcaagaagac agaagtccag   3300
acaggaggat tcagcaagga aagcatcctg ccgaagagaa acagcgacaa gctgatcgca   3360
agaaagaagg actgggaccc gaagaagtac ggaggattcg acagcccgac agtcgcatac   3420
agcgtcctgg tcgtcgcaaa ggtcgaaaag ggaaagagca agaagctgaa gagcgtcaag   3480
gaactgctgg gaatcacaat catggaaaga agcagcttcg aaaagaaccc gatcgacttc   3540
ctggaagcaa agggatacaa ggaagtcaag aaggacctga tcatcaagct gccgaagtac   3600
agcctgttcg aactggaaaa cggaagaaag agaatgctgg caagcgcagg agaactgcag   3660
aagggaaacg aactggcact gccgagcaag tacgtcaact tcctgtacct ggcaagccac   3720
tacgaaaagc tgaagggaag cccggaagac aacgaacaga agcagctgtt cgtcgaacag   3780
cacaagcact acctggacga aatcatcgaa cagatcagcg aattcagcaa gagagtcatc   3840
ctggcagacg caaacctgga caaggtcctg agcgcataca acaagcacag agacaagccg   3900
atcagagaac aggcagaaaa catcatccac ctgttcacac tgacaaacct gggagcaccg   3960
gcagcattca agtacttcga cacaacaatc gacagaaaga gatacacaag cacaaaggaa   4020
gtcctggacg caacactgat ccaccagagc atcacaggac tgtacgaaac aagaatcgac   4080
```

```
ctgagccagc tgggaggaga cggaggagga agcccgaaga agaagagaaa ggtc         4134

SEQ ID NO: 213          moltype = AA   length = 1368
FEATURE                 Location/Qualifiers
REGION                  1..1368
                        note = Synthetic: Amino acid sequence of Cas9 (without NLS)
source                  1..1368
                        mol_type = protein
                        organism = synthetic construct
SEQUENCE: 213
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD              1368

SEQ ID NO: 214          moltype = RNA   length = 4107
FEATURE                 Location/Qualifiers
misc_feature            1..4107
                        note = Synthetic: Cas9 mRNA ORF encoding SEQ ID NO: 213
                         using minimal uridine codons, with start and stop codons
source                  1..4107
                        mol_type = other RNA
                        organism = synthetic construct
SEQUENCE: 214
atggacaaga agtacagcat cggactggac atcggaacaa acagcgtcgg atgggcagtc   60
atcacagacg aatacaaggt cccgagcaag aagttcaagg tcctgggaaa cacagacaga  120
cacagcatca agaagaacct gatcggagca ctgctgttcg acagcggaga aacagcagaa  180
gcaacaagac tgaagagaac agcaagaaga agatacagaa gaaagaagaa cagaatctgc  240
tacctgcagg aaatcttcag caacgaaatg gcaaaggtcg acgacagctt cttccacaga  300
ctggaagaaa gcttcctggt cgaagaagac aagaagcacg aaagacaccc gatcttcgga  360
aacatcgtcg acgaagtcgc ataccacgaa aagtacccga caatctacca cctgagaaag  420
aagctggtcg acagcacaga caaggcagac ctgagactga tctacctggc actggcacac  480
atgatcaagt tcagaggaca cttcctgatc gaaggagacc tgaacccgga caacagcgac  540
gtcgacaagc tgttcatcca gctggtccag acatacaacc agctgttcga agaaaacccg  600
atcaacgcaa gcggagtcga cgcaaaggca atcctgagcg caagactgag caagagcaga  660
agactggaaa acctgatcgc acagctgccg ggagaaaaga agaacggact gttcggaaac  720
ctgatcgcac tgagcctggg actgacaccg aacttcaaga gcaacttcga cctgcagaa   780
gacgcaaagc tgcagctgag caaggacaca tacgacgacg acctggacaa cctgctggca  840
cagatcggag accagtacgc agacctgttc ctggcagcaa agaacctgag cgacgcaatc  900
ctgctgagcg acatcctgag agtcaacaca gaaatcacaa aggcaccgct gagcgcaagc  960
atgatcaaga gatacgacga acaccaccag gacctgacac tgctgaaggc actggtcaga 1020
cagcagctgc cggaaaagta caaggaaatc ttcttcgacc agagcaagaa cggatacgca 1080
ggatacatcg acggaggagc aagccaggaa gaattctaca agttcatcaa gccgatcctg 1140
gaaaagatgg acggaacaga agaactgctg gtcaagctga acagagaaga cctgctgaga 1200
aagcagaga cattcgacaa cggaagcatc ccgcaccaga tccacctggg agaactgcac 1260
gcaatcctga agagacagga agacttctac ccgttcctga aggacaacag agaaaagatc 1320
gaaaagatcc tgacattcag aatcccgtac tacgtcggac cgctggcaag aggaaacagc 1380
agattcgcat ggatgacaag aaagagcgaa gaaacaatca caccgtggaa cttcgaagaa 1440
gtcgtcgaca agggagcaag cgcacagagc ttcatcgaaa gaatgacaaa cttcgacaag 1500
aacctgccga acgcaaaagt cctgccgaag cacagcctgc tgtacgaata cttcacagtc 1560
tacaacgaac tgacaaaggt caagtacgtc acagaaggaa tgagaaagcc ggcattcctg 1620
agcggagaac agaagaaggc aatcgtcgac ctgctgttca gacaaacag aaaggtcaca 1680
gtcaagcagc tgaaggaaga ctacttcaag aagatcgaat gcttcgacag cgtcgaaatc 1740
agcggagtcg aagacagatt caacgcaagc tgggaacat accgaccct gctgaagatc 1800
atcaaggaca aggacttcct ggacaacgaa gaaaacgaag acatcctgga agacatcgtc 1860
ctgacactga cactgttcga agacagagaa atgatcgaaa aagactgaa gacatacgca 1920
cacctgttcg acgacaaggt catgaagcag ctgaagagaa gaagatacac aggatgggga 1980
agactgagca gaaagctgat caacggaatc agagacaagc agagcggaaa gacaatcctg 2040
gacttcctga gagcgacgg attcgcaaac agaaacttca tgcagctgat ccacgacgac 2100
agcctgacat tcaaggaaga catccagaag gcacaggtca gcggacaggg agacagcctg 2160
```

```
cacgaacaca tcgcaaacct ggcaggaagc ccggcaatca agaagggaat cctgcagaca    2220
gtcaaggtcg tcgacgaact ggtcaaggtc atgggaagac acaagccgga aaacatcgtc    2280
atcgaaatgg caagagaaaa ccagacaaca cagaagggac agaagaacag cagagaaaga    2340
atgaagagaa tcgaagaagg aatcaaggaa ctgggaagcc agatcctgaa ggaacacccg    2400
gtcgaaaaca cacagctgca gaacgaaaag ctgtacctgt actacctgca gaacggaaga    2460
gacatgtacg tcgaccagga actggacatc aacagactga gcgactacga cgtcgaccac    2520
atcgtcccgc agagcttcct gaaggacgac agcatcgaca caaggtcct gacaagaagc     2580
gacaagaaca gaggaaagag cgacaacgtc ccgagcgaag aagtcgtcaa gaagatgaag    2640
aactactgga gacagctgct gaacgcaaag ctgatcacac agagaaagtt cgacaacctg    2700
acaaaggcag agagaggagg actgagcgaa ctggacaagg caggattcat caagagacag    2760
ctggtcgaaa caagacagat cacaaagcac gtcgcacaga tcctggacag cagaatgaac    2820
acaaagtacg acgaaaacga caagctgatc agagaagtca aggtcatcac actgaagagc    2880
aagctggtca gcgacttcag aaaggacttc cagttctaca aggtcagaga atcaacaac    2940
taccaccacg cacacgacgc atacctgaac gcagtcgtcg gaacagcact gatcaagaag    3000
tacccgaagc tggaaagcga attcgtctac ggagactaca aggtctacga cgtcagaaag    3060
atgatcgcaa agagcgaaca ggaaatcgga aaggcaacag caagtacttc cttctacagc    3120
aacatcatga acttcttcaa gacagaaatc acactggcaa acggagaaat cagaaagaga    3180
ccgctgatcg aaacaaacgg agaaacagga gaaatcgtct gggcaaaggg aagagacttc    3240
gcaacagtca gaaaggtcct gagcatgccg caggtcaaca tcgtcaagaa gacagaagtc    3300
cagacaggag gattcagcaa ggaaagcatc ctgccgaaga aaacagcga caagctgatc    3360
gcaagaagaa aggactggga cccgaagaag tacgaggat cgacagccc gacagtcgca     3420
tacagcgtcc tggtcgtcgc aaaggtcgaa aagggaaaga gcaagaagct gaagagcgtc    3480
aaggaactgc tgggaatcac aatcatggaa agaagcagct cgaaaagaa cccgatcgac    3540
ttcctgaagg caaagggata caggaagtc aagaaggacc tgatcatcaa gctgccgaag    3600
tacagcctgt tcgaactgga aaacggaaga agagaatgc tggcaagcgc aggagaactg    3660
cagaaggaaa acgaactggc actgccgagc aagtacgtca acttcctgta cctggcaagc    3720
cactacgaaa agctgaaggg aagcccggaa gacaacgaac agaagcagct gttcgtcgaa    3780
cagcacaagc actacctgga cgaaatcatc gaacagatca gcgaattcag caagagagtc    3840
atcctggcag acgcaaacct ggacaaggtc ctgagcgcat acaacaagca cagagacaag    3900
ccgatcagag aacaggcaga aaacatcatc cacctgttca cactgacaaa cctgggacgc    3960
ccggcagcat tcaagtactt cgacacaaca atcgacagaa agagatacac aagcacaaag    4020
gaagtcctgg acgcaacact gatccaccag agcatcacag gactgtacga aacaagaatc    4080
gacctgagcc agctgggagg agactag                                        4107
```

SEQ ID NO: 215       moltype = RNA  length = 4101
FEATURE             Location/Qualifiers
misc_feature       1..4101
                     note = Synthetic: Cas9 coding sequence encoding SEQ ID NO:
                     213 using minimal uridine codons (no start or stop codons;
                     suitable for inclusion in fusion protein coding sequence)
source               1..4101
                     mol_type = other RNA
                     organism = synthetic construct
SEQUENCE: 215

```
gacaagaagt acagcatcgg actggacatc ggaacaaaca gcgtcggatg ggcagtcatc      60
acagacgaat caaggtcccc gagcaagaag ttcaaggtcc tgggaaacac agacagacac     120
agcatcaaga agaacctgat cggagcactg cgttcgcaga gcgcagaaca agcagaagca     180
acaagactga gagaacagc aagaagaaga tacacaagaa gaaagaacag aatcctgtac      240
ctgcaggaaa tcttcagcaa cgaaatggca aaggtcgacg acagcttctt ccacagactg     300
gaagaaagct tcctggtcga agaagacaag aagcacgaaa gacacccgat cttcggaaac     360
atcgtcgacg aagtcgcata ccacgaaaag taccccgaca tctaccacct gagaaagaaa     420
ctggtcgaca gcacagacaa ggcagacctg agactgatct acctggcact ggcacacatg     480
atcaagttca gaggacactt cctgatcgaa ggagacctga accgacaa cagcgacgtc       540
gacaagctgt tcatccagct ggtccagaca tacaaccagc tgttcgaaga aaacccgatc     600
aacgcaagcg gagtcgacgc aaaggcaatc ctgagcgcaa gactgagcaa gagcagaaga    660
ctggaaaacc tgatcgcaca gctgccggga gaaaagaaga acggactgtt cggaaacctg    720
atcgcactga gcctgggact gacaccgaac ttcaagagca acttcgacct ggcagaagac    780
gcaaagctgc agctgagcaa ggacacatac gacgacgacc tggacaacct gctggcacag    840
atcggagacc agtacgcaga cctgttcctg gcagcaaaga acctgagcga cgcaatcctg    900
ctgagcgaca tcctgagagt caacacagaa atcacaaagg cacgctgag cgcaagcatg     960
atcaagagat acgacgaaca ccaccaggac ctgacactgc tgaaggcact ggtcagacag   1020
cagctgccgg aaaagtacaa ggaaatcttc ttcgaccaga gcaagaacgg atacgcagga   1080
tacatcgacg gaggagcaag ccaggaagaa ttctacaagt tcatcaagcc gatcctggaa   1140
aagatggacg gaacagaaga actgctggtc aagctgaaca gagaagacct gctgagaaag   1200
cagagaacat tcgacaacgg aagcatcccg caccagatcc acctgggaga actgcacgca   1260
atcctgagaa gacaggaaga cttctacccg ttcctgaagg acaacagaga aaagatcgaa   1320
aagatcctga cattcagaat cccgtactac gtcggaccgc tggcaagagg aaacagcaga   1380
ttcgcatgga tgacaagaaa gagcgaagaa acaatcacac cgtggaactt cgaagaagtc   1440
gtcgacaagg gagcaagcgc acagagcttc atcgaaagaa tgcaaacttc cgacaagaac   1500
ctgccgaacg aaaaggtcct gccgaagcac agcctgctgt acgaatactt cacagtctac   1560
aacgaactga caaaggtcaa gtacgtcaca gaaggaatga gaaagccggc attcctgagc   1620
ggagaacaga gaaggcaat cgtcgacctg ctgttcaaga aaacagaaa ggtcacagtc    1680
aagcagctga aggaagacta cttcaagaag atcgaatgct tcgacagcgt cgaaatcagc   1740
ggagtcgaag acagattcaa cgcaagcctg ggaacataccg acgtcgaca gatcatc     1800
aaggacaagg acttcctgga caacgaagaa aacgaagaca tcctggaaga catcgtcctg   1860
acactgacac tgttcgaaga cagagaaatg atcgaagaaa gactgaagac atacgcacac   1920
ctgttcgacg acaaggtcat gaagcagctg aagagaagaa gatacacagg atgggggaaga   1980
ctgagcagaa agctgatcaa cggaatcaga gacaagcaga gcggaaagac aatcctggac   2040
ttcctgaaga gcgacggatt cgcaaacaga aacttcatgc agctgatcca cgacgacagc   2100
```

```
ctgacattca aggaagacat ccagaaggca caggtcagcg gacagggaga cagcctgcac  2160
gaacacatcg caaacctggc aggaagcccg gcaatcaaga agggaatcct gcagacagtc  2220
aaggtcgtcg acgaactggt caaggtcatg ggaagacaca agccggaaaa catcgtcatc  2280
gaaatggcaa gagaaaacca gacaacacag aagggacaga gaacagcag agaaagaatg  2340
agagaacga aagaaggaat caaggaactg ggaagccaga tcctgaagga acacccggtc  2400
gaaaacacac agctgcgaaa cgaaaagctg tacctgtact acctgcagaa cggaagagac  2460
atgtacgtcg accaggaact ggacatcaac agactgagcg actacgacgt cgaccacatc  2520
gtcccgcaga gcttcctgaa ggacgacagc atcgacaaca aggtcctgac aagaagcgac  2580
aagaacagag gaaagagcga caacgtcccg agcgaagaag tcgtcaagga tgtgaagaac  2640
tactggagac agctgctgaa cgcaaagctg atcacacaga gaaagttcga caacctgaca  2700
aaggcagaga gaggaggact gagcgaactg gacaaggcag gattcatcaa gagacagctg  2760
gtcgaaacaa gacagatcac aaagcacgtc gcacagatcc tggacagcag aatgaacaca  2820
aagtacgacg aaaacgacaa gctgatcaga gaagtcaagg tcatcacact gaagagcaag  2880
ctggtcagcg acttcagaaa ggacttccaa ttctacaagg tcagagaaat caacaactac  2940
caccacgcac acgacgcata cctgaacgca gtcgtcggaa cagcactgat caagaagtac  3000
ccgaagctgg aaagcgaatt cgtctacgga gactacaagg tctacgacgt cagaaagatg  3060
atcgcaaaga gcgaacagga aatcggaaag gcaacagcaa agtacttctt ctacagcaac  3120
atcatgaact tcttcaagac agaaatcaca ctggcaaacg agaaatcaga aagagaccg  3180
ctgatcgaaa caaacggaga aacaggagaa atcgtctggg acaagggaag agacttcgca  3240
acagtcagaa aggtcctgag catgccgcag gtcaacatcg tcaagaagac agaagtccag  3300
acaggaggat tcagcaagga agcatcctg ccgaagagaa acagcgacaa gctgatcgca  3360
agaaagaagg actgggaccc gaagaagtac ggaggattcg acccccgcac agtcgcatac  3420
agcgtcctgg tcgtcgcaaa ggtcgaaaag ggaagagca agaagctgaa gagcgtcaag  3480
gaactgctgg aatcacaat catggaaaga agcagcttcg aaaagaaccc gatcgacttc  3540
ctggaagcaa agggatacaa ggaagtcaag aaggacctga tcatcaagct gccgaagtac  3600
agcctgttcg aactggaaaa cggaagaaag aagatgctgg caagcgcagg agaactgcag  3660
aagggaaacg aactggcact gccgagcaag tacgtcaact tcctgtacct ggcaagccac  3720
tacgaaaagc tgaagggaag cccggaagac aacgaacaga agcagctgtt cgtcgaacag  3780
cacaagcact acctggacga aatcatcgaa cagatcagcg aattcagcaa gagagtcatc  3840
ctggcagacg caaacctgga caaggtcctg agcgcataca acaagcacag agacaagccg  3900
atcagagaac aggcagaaaa catcatccac ctgttcacac tgacaaacct gggagcaccg  3960
gcagcattca gtacttcga cacaacaatc gacagaaaga gatacacaag cacaaaggaa  4020
gtcctggacg caacactgat ccaccagagc atcacaggac tgtacgaaac aagaatcgac  4080
ctgagccagc tgggaggaga c                                            4101

SEQ ID NO: 216          moltype = AA  length = 1368
FEATURE                 Location/Qualifiers
REGION                  1..1368
                        note = Synthetic: Amino acid sequence of Cas9 nickase
                        (without NLS)
source                  1..1368
                        mol_type = protein
                        organism = synthetic construct
SEQUENCE: 216
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD             1368

SEQ ID NO: 217          moltype = RNA  length = 4107
FEATURE                 Location/Qualifiers
misc_feature            1..4107
                        note = Synthetic: Cas9 nickase mRNA ORF encoding SEQ ID NO:
                        216 using minimal uridine codons as listed in Table 3,
                        with start and stop codons
source                  1..4107
                        mol_type = other RNA
                        organism = synthetic construct
SEQUENCE: 217
atggacaaga agtacagcat cggactggca atcggaacaa acagcgtcgg atgggcagtc   60
```

```
atcacagacg aatacaaggt cccgagcaag aagttcaagg tcctgggaaa cacagacaga  120
cacagcatca agaagaacct gatcggagca ctgctgttcg acagcggaga aacagcagaa  180
gcaacaagac tgaagagaac agcaagaaga agatacacaa gaagaaagaa cagaatctgc  240
tacctgcagg aaatcttcag caacgaaatg gcaaaggtcg acgacagctt cttccacaga  300
ctggaagaaa gcttcctggt cgaagaagac aagaagcacg aagacaccc gatcttcgga  360
aacatcgtcg acgaagtcgc ataccacgaa aagtacccga caatctacca cctgagaaag  420
aagctggtcg acagcacaga caaggcagac ctgagactga tctacctggc actggcacac  480
atgatcaagt tcagaggaca cttcctgatc gaaggagacc tgaacccgga caacagcgac  540
gtcgacaagc tgttcatcca gctggtccag acatacaacc agctgttcga agaaaacccg  600
atcaacgcaa gcggagtcga cgcaaaggca atcctgagcg caagactgag caagagcaga  660
agactggaaa acctgatcgc acagctgccg ggagaaaaga gaacggact gttcggaaac  720
ctgatcgcac tgagcctggg actgacaccg aacttcaaga gcaacttcga cctggcagaa  780
gacgcaaagc tgcagctgag caaggacaca tacgacgacg acctggacaa cctgctggca  840
cagatcggag accagtacgc agacctgttc ctggcagcaa agaacctgag cgacgcaatc  900
ctgctgagcg acatcctgag agtcaacaca gaaatcacaa aggcaccgct gagcgcaagc  960
atgatcaaga gatacgacga acaccaccag gacctgacac tgctgaaggc actggtcaga 1020
cagcagctgc cggaaaagta caaggaaatc ttcttcgacc agagcaagaa cggatacgca 1080
ggatacatcg acggaggagc aagccaggaa gaattctaca agttcatcaa gccgatcctg 1140
gaaaagatgg acgaacaga gaactgctg gtcaagctga acagagaaga cctgctgaga 1200
aagcagagaa cattcgacaa cggaagcatc ccgcaccaga tccacctggg agaactgcac 1260
gcaatcctga gaagacagga agacttctac ccgttcctga aggacaacag agaaaagatc 1320
gaaaagatcc tgacattcag aatcccgtac tacgtcggac cgctggcaag aggaaacagc 1380
agattcgcat ggatgacaag aaagagcgaa gaaacaatca caccgtggaa cttcgaagaa 1440
gtcgtcgaca agggagcaag cgcacagagc ttcatcgaaa gaatgacaaa cttcgacaag 1500
aacctgccga acgaaaaggt cctgccgaag cacagcctgc tgtacgaata cttcacagtc 1560
tacaacgaac tgacaaaggt caagtacgtc acagaaggaa tgagaaagcc ggcattcctg 1620
agcggagaac agaagaaggc aatcgtcgac ctgctgttca gacaaaacag aaaggtcaca 1680
gtcaagcagc tgaaggaaga ctacttcaag aagatcgaat gcttcgacag cgtcgaaatc 1740
agcggagtcg aagacagatt caacgcaagc ctgggaacat accacgacct gctgaagatc 1800
atcaaggaca aggacttcct ggacaacgaa gaaaacgaag acatcctgga agacatcgtc 1860
ctgacactga cactgttcga agacagagaa atgatcgaag aaagactgaa gacatacgca 1920
cacctgttcg acgacaaggt catgaagcag ctgaagagaa gaagatacac aggatgggga 1980
agactgagca gaaagctgat caacggaatc agagacaagc agagcggaaa gacaatcctg 2040
gacttcctga agagcgacgg attcgcaaac agaaacttca tgcagctgat ccacgacgac 2100
agcctgacat tcaaggaaga catccagaag gcacaggtca gcgacagggg agacagcctg 2160
cacgaacaca tcgcaaacct ggcaggaagc ccggcaatca gaagggaat cctgcagaca 2220
gtcaaggtcg tcgacgaact ggtcaaggtc atgggaagac acaagccgga aaacatcgtc 2280
atcgaaatgg caagagaaaa ccagacaaca cagaagggac agaaaaacag cagagaaaga 2340
atgaagagaa tcgaagaagg aatcaaggaa ctgggaagcc agatcctgaa ggaacaccc 2400
gtcgaaaaca cacagctgca gaacgaaaag ctgtacctgt actacctgca gaacggaaga 2460
gacatgtacg tcgaccagga actggacatc aacagactga gcgactacga cgtcgaccac 2520
atcgtcccgc agagcttcct gaaggacgac agcatcgaca caaggtcct gacaagaagc 2580
gacaagaaca gaggaaagag cgacaacgtc ccgagcgaag aagtcgtcaa gaagatgaag 2640
aactactgga gacagctgct gaacgcaaag ctgatcacac agagaaagtt cgacaacctg 2700
acaaaggcag agagaggagg actgagcgaa ctggacaagg caggattcat caagagacag 2760
ctggtcgaaa aagacagat cacaaagcac gtcgcacaga tcctggacag cagaatgaac 2820
acaaagtacg acgaaaacga caagtgatc agagaagtca ctgaagagc 2880
aagctggtca gcgacttcag aaaggacttc cagttctaca aggtcagaga aatcaacaac 2940
taccaccacg cacacgacgc atacctgaac gcagtcgtcg gaacagcact gatcaagaag 3000
tacccgaagc tggaaagcga attcgtctac ggagactaca aggtctacga cgtcagaaag 3060
atgatcgcaa agagcgaaca ggaaatcgga aaggcaacag caaagtactt cttctactgc 3120
aacatcatga acttcttcaa gacagaaatc acactggcaa acggagaaat cagaaagaga 3180
ccgctgatcg aaacaaacgg agaaacagga gaaatcgtct gggacaaggg aagagacttc 3240
gcaacagtca gaaaggtcct gagcatgccg caggtcaaca tcgtcaagaa gacagaagtc 3300
cagacaggag gattcagcaa ggaaagcatc ctgccgaaga gaaacagcga caagctgatc 3360
gcaagaaaga aggactggga cccgaagaag tacggaggat tcgacagccc gacagtcgca 3420
tacagcgtcc tggtcgtcgc aaaggtcgaa aagggaaaga gcaagaagct gaagagcgtc 3480
aaggaactgc tgggaatcac aatcatggaa agaagcagct tcgaaaagaa cccgatcgac 3540
ttcctggaag caaagggata caaggaagtc aagaaggacc tgatcatcaa gctgccgaag 3600
tacagcctgt tcgaactgga aaacggaaga agagaatgc tggcaagcgc aggagaactg 3660
cagagggaa acgaactggc actgccgagc aagtacgtca acttcctgta cctggcaagc 3720
cactacgaaa agctgaaggg aagcccgaa gacaacgaac agaagcagct gttcgtcgaa 3780
cagcacaagc actacctgga cgaaatcatc gaacagatca gcgaattcag caagagagtc 3840
atcctggcag acgcaaacct ggacaaggtc tgagcgcat acaacaagca cagagacaag 3900
ccgatcagag aacaggcaga aaacatcatc cacctgttca cactgacaaa cctgggagca 3960
ccggcagcat tcaagtactt cgacacaaca atcgacagaa agagatacac aagcacaaag 4020
gaagtcctgg acgcaacact gatccaccag agcatcacag gactgtacga aacaagaatc 4080
gacctgagcc agctgggagg agactag                                     4107
```

SEQ ID NO: 218    moltype = RNA   length = 4101
FEATURE           Location/Qualifiers
misc_feature      1..4101
                  note = Synthetic: Cas9 nickase coding sequence encoding SEQ
                  ID NO: 216 using minimal uridine codons as listed in Table
                  3 (no start or stop codons; suitable for inclusion in
                  fusion protein coding sequence)
source            1..4101
                  mol_type = other RNA
                  organism = synthetic construct

```
SEQUENCE: 218
gacaagaagt acagcatcgg actggcaatc ggaacaaaca gcgtcggatg ggcagtcatc    60
acagacgaat acaaggtccc gagcaagaag ttcaaggtcc tgggaaacac agacagacac   120
agcatcaaga agaacctgat cggagcactg ctgttcgaca gcggagaaac agcagaagca   180
acaagactga agagaacagc aagaagaaga tacacaagaa gaaagaacag aatctgctac   240
ctgcaggaaa tcttcagcaa cgaaatggca aaggtcgacg acagcttctt ccacagactg   300
gaagaaagct tcctggtcga agaagacaag aagcacgaaa gacacccgat cttcggaaac   360
atcgtcgacg aagtcgcata ccacgaaaag tacccgacaa tctaccacct gagaaagaag   420
ctggtcgaca gcacagacaa ggcagacctg agactgatct acctggcact ggcacacatg   480
atcaagttca gaggacactt cctgatcgaa ggagacctga acccggacaa cagcgacgtc   540
gacaagctgt tcatccagct ggtccagaca tacaaccagc tgttcgaaga aaacccgatc   600
aacgcaagcg gagtcgacgc aaaggcaatc ctgagcgcaa gactgagcaa gagcagaaga   660
ctggaaaaacc tgatcgcaca gctgccggga gaaaagaaga acggactgtt cggaaacctg   720
atcgcactga gcctgggact gacaccgaac ttcaagagca acttcgacct ggcagaagac   780
gcaaagctgc agctgagcaa ggacacatac gacgacgacc tggacaacct gctggcacag   840
atcggagacc agtacgcaga cctgttcctg gcagcaaaga acctgagcga cgcaatcctg   900
ctgagcgaca tcctgagagt caacacagaa atcacaaagg caccgctgag cgcaagcatg   960
atcaagagat acgacgaaca ccaccaggac ctgacactgc tgaaggcact ggtcagacag  1020
cagctgccgg aaaagtacaa ggaaatcttc ttcgaccaga gcaagaacgg atacgcagga  1080
tacatcgacg gaggagcaag ccaggaagaa ttctacaagt tcatcaagcc gatcctggaa  1140
aagatggacg gaacagaaga actgctggtc aagctgaaca gagaagacct gctgagaaag  1200
cagagaacat tcgacaacgg aagcatcccg caccagatcc acctgggaga actgcacgca  1260
atcctgagaa gacaggaaga cttctaccccg ttcctgaagg acaacagaga aaagatcgaa  1320
aagatcctga cattcagaat cccgtactac gtcggaccgc tgcaagagg aaacagcaga  1380
```
(OCR partial — sequence data page)

```
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVDVRK  1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD           1368
```

SEQ ID NO: 220        moltype = RNA   length = 4107
FEATURE               Location/Qualifiers
misc_feature          1..4107
                      note = Synthetic: dCas9 mRNA ORF encoding SEQ ID NO: 219
                      using minimal uridine codons as listed in Table 3, with
                      start and stop codons
source                1..4107
                      mol_type = other RNA
                      organism = synthetic construct
SEQUENCE: 220

```
atggacaaga agtacagcat cggactggca atcggaacaa acagcgtcgg atgggcagtc   60
atcacagacg aatacaaggt cccgagcaag aagttcaagg tcctgggaaa cacagacaga  120
cacagcatca agaagaacct gatcggagca ctgctgttcg acagcggaga acagcagaa  180
gcaacaagac tgaagagaac agcaagaaga agatacacaa gaagaagca cagaatctgc  240
tacctgcagg aaatcttcag caacgaaatg caaagcgtca gcagcagctt cttccacaga  300
ctggaagaaa gcttcctggt cgaagaagac aagaagcacg aagacaccc gatcttcgga  360
aacatcgtcg acgaagtcgc ataccacgaa agtacccga caatctacca cctgagaaag  420
aagctggtcg acagcacaga caaggcagac ctgagactga tctacctggc actggcacac  480
atgatcaagt tcagaggaca cttcctgatc gaaggagacc tgaacccgga caacagcgac  540
gtcgacaagc tgttcatcca gctggtccga acatacaacc agctgttcga agaaaacccg  600
atcaacgcaa gcggagtcga cgcaaaggca atcctgagcg caagactgag caagagcaga  660
agactggaaa acctgatcgc acagctgccg ggagaaaaga gaacggact gttcggaaac  720
ctgatcgcac tgagcctggg actgacaccg aacttcaaga gcaacttcga cctggcagaa  780
gacgcaaagc tgcagctgag caaggacaca tacgacgacg acctggacaa cctgctggca  840
cagatcggag accagtacgc agacctgttc ctggcagcaa agaacctgag cgacgcaatc  900
ctgctgagcg acatcctgag agtcaacaca gaaatcacaa aggcaccgct gagcgcaagc  960
atgatcaaga gatacgacga acaccaccag gacctgacac tgctgaaggc actggtcaga 1020
cagcagctgc cggaaaagta caaggaaatc ttcttcgacc agagcaagaa cggatacgca 1080
ggatacatcg acggaggagc aagccaggaa gaattctaca gttcatcaa gccgatcctg 1140
gaaaagatgg acggaacaga agaactgctg gtcaagctga cagagaaga cctgctgaga 1200
aagcagagaa cattcgacaa cggaagcatc ccgcaccaca tccacctggg agaactgcac 1260
gcaatcctga gaagacagga agacttctac ccgttcctga aggacaacag agaaaagatc 1320
gaaaagatcc tgacattcag aatcccgtac tacgtcggac cgctggcaag aggaaacagc 1380
agattcgcat ggatgacaag aaagagcgaa gaaacaatca ccgtgaa cttcgaagaa 1440
gtcgtcgaca agggagcaag cgcacagagc ttcatcgaaa gaatgacaaa cttcgacaag 1500
aacctgccga acgaaaaggt cctgccgaag cacagcctgc tgtacgaata cttcacagtc 1560
tacaacgaac tgacaaaggt caagtacgtc acagaaggaa tgagaaagcc ggcattcctg 1620
agcggagaac agaagaaggc aatcgtcgac ctgctgttca gacaaacag aaaggtcaca 1680
gtcaagcagc tgaaggaaga ctacttcaag aagatcgaat gcttcgacag cgtcgaaatc 1740
agcggagtcg aagacagatt caacgcaagc ctgggaacat accacgacct gctgaagatc 1800
atcaaggaca aggacttcct ggacaacgaa gaaaacgaag acatcctgga agacatcgtc 1860
ctgacactga cactgttcga agacagaaga atgatcgaaa gaaagactaa gacatacgca 1920
cacctgttcg acgacaaggt catgaagcag ctgaagagaa agagatacac aggatgggga 1980
agactgagca gaaaactgat caacggaatc agagacaagc agagcggaaa gacaatcctg 2040
gacttcctga gagcgacgg attcgcaaac agaaacttca tgcagctgat ccacgacgac 2100
agcctgacat caaggaaga catccagaag gcacaggtca gcggacaggg agacagcctg 2160
cacgaacaca tcgcaaacct ggcaggaagc ccggcaatca agagggaat cctgcagaca 2220
gtcaaggtcg tcgacgaact ggtcaaggtc atggaagac acaagccgga aaacatcgtc 2280
atcgaaatgg caagagaaaa ccagacaaca cagaaggac agaagaacag cagagaaaga 2340
atgaagagaa tcgaagaagg aatcaaggaa ctggaagcgt cgcaactgat caaggaacac 2400
gtcgaaaaca cacagctgca gaacgaaaag ctgtacctgt actacctgca gaacggaaga 2460
gacatgtacg tcgaccagga actggacatc aacagactga gcgactacga cgtcgacgca 2520
atcgtcccgc agagcttcct gaaggacgac agcatcgaca acaaggtcct gacaagaagc 2580
gacaagaaca gaggaaagag cgacaacgtc ccgagcgaag aagtcgtcaa gaagatgaag 2640
aactactgga gacagctgct gaacgcaaag ctgatcacag agagaaagtt cgacaacctg 2700
```

```
acaaaggcag agagaggagg actgagcgaa ctggacaagg caggattcat caagagacag  2760
ctggtcgaaa caagacagat cacaaagcac gtcgcacaga tcctggacag cagaatgaac  2820
acaaagtacg acgaaaacga caagctgatc agagaagtca aggtcatcac actgaagagc  2880
aagctggtca gcgacttcag aaaggacttc cagttctaca aggtcagaga atcaacaac   2940
taccaccacg cacacgacgc atacctgaac gcagtcgtcg gaacagcact gatcaagaag  3000
tacccgaagc tggaaagcga attcgtctac ggagactaca aggtctacga cgtcagaaag  3060
atgatcgcaa agagcgaaca ggaaatcgga aaggcaacag caaagtactt cttctacagc  3120
aacatcatga acttcttcaa gacagaaatc acactggcaa acggagaaat cagaaagaga  3180
ccgctgatcg aaacaaacgg agaaacagga gaaatcgtct gggacaaggg aagagacttc  3240
gcaacagtca gaaggtcct gagcatgccg caggtcaaca tcgtcaagaa gacagaagtc  3300
cagacaggag gattcagcaa ggaaagcatc ctgccgaaga gaaacagcga caagctgatc  3360
gcaagaaaga aggactggga cccgaagaag tacggaggat cgacagccc gacagtcgca  3420
tacagcgtcc tggtcgtcgc aaaggtcgaa aagggaaaga gcaagaagct gaagagcgtc  3480
aaggaactgc tgggaatcac aatcatgaa agaagcagct tcgaaaagaa cccgatcgac  3540
ttcctggaag caaagggata caaggaagtc aagaaggacc tgatcatcaa gctgccgaag  3600
tacagcctgt tcgaactgga aaacggaaga aagagaatgc tggcaagcgc aggagaactg  3660
cagaagggaa acgaactggc actgccgagc aagtacgtca acttcctgta cctggcaagc  3720
cactacgaaa agctgaaggg aagcccggaa gacaacgaac ggaagcagct gttcgtcgaa  3780
cagcacaagc actacctgga cgaaatcatc gaacagatca gcgaattcag caagagagtc  3840
atcctggcag acgcaaacct ggacaaggtc ctgagcgcat acaacaagca cagagacaag  3900
ccgatcagag aacaggcaga aaacatcatc cacctgttca cactgacaaa cctgggagca  3960
ccggcagcat tcaagtactt cgacacaaca atcgacagaa agagatacac aagcacaaag  4020
gaagtcctgg acgcaacact gatccaccag agcatcacag gactgtacga aacaagaatc  4080
gacctgagcc agctgggagg agactag                                       4107

SEQ ID NO: 221        moltype = RNA  length = 4113
FEATURE               Location/Qualifiers
misc_feature          1..4113
                      note = Synthetic: dCas9 coding sequence encoding SEQ ID NO:
                      219 using minimal uridine codons as listed in Table 3 (no
                      start or stop codons; suitable for inclusion in fusion
                      protein coding sequence)
source                1..4113
                      mol_type = other RNA
                      organism = synthetic construct
SEQUENCE: 221
gacaagaagt acagcatcgg actggcaatc ggaacaaaca cgtcggatg ggcagtcatc    60
acagacgaat caaggtccc gagcaagaag ttcaaggtcc tgggaaacac agacagacac   120
agcatcaaga agaacctgat cggagcactg tgttcgaca gcggagaaac agcagaagca   180
acaagactga agaacagc aagaagaaga tacacaagaa gaaagaacag aatctgctac   240
ctgcaggaaa tcttcagcaa cgaaatggca aaggtcgacg cacagcttctt ccacagactg   300
gaagaaagct tcctggtcga agaagacaag aagcacgaaa gacacccgat cttcggaaac   360
atcgtcgaca aagtcgcata ccacgaaaag tacccgacaa tctaccacct gagaaagaag   420
ctggtcgaca gcacagacaa ggcagacctg agactgatct acctggcact ggcacacatg   480
atcaagttca gaggacactt cctgatcgaa ggagacctga accgcgacaa cagcgacgtc   540
gacaagctgt tcatccagct ggtccagaca tacaaccagc tgttcgaaga aaacccgatc   600
aacgcaagcg gagtcgacgc aaaggcaatc ctgagcgcaa gactgagcaa gagcagaaga   660
ctggaaaacc tgatcgcaca gctgccggga gaaaagaaga acggactgtt cggaaacctg   720
atcgcactga gcctgggact gacaccgaac ttcaagagca acttcgacct ggcagaagac   780
gcaaagctgc agctgagcaa ggacacatac gacgacgacc tggacaacct gctggcacag   840
atcggagacc agtacgcaga cctgttcctg gcagcaaaga acctgagcga cgcaatcctg   900
ctgagcgaca tcctgagagt caacacagaa atcacaaagg caccgctgag cgcaagcatg   960
atcaagagat acgacgaaca ccaccaggac ctgacactgc tgaaggcact ggtcagacag  1020
cagctgccgg aaaagtacaa ggaaatcttc ttcgaccaga gcaagaacgg atacgcagga  1080
tacatcgacg gaggagcaag ccaggaagaa ttctacaagt tcatcaagcc gatcctggaa  1140
aagatggacg gaacagaaga actgctggtc aagctgaaca gagaagacct gctgagaaag  1200
cagagaacat tcgacaacgg aagcatcccg caccagatcc acctgggaga actgcacgca  1260
atcctgagaa gacaggaaga cttctaccc g ttcctgaagg acaacagaga aaagatcgaa  1320
aagatcctga cattcagaat cccgtactac gtcggaccgc tggcaagagg aaacagcaga  1380
ttcgcatgga tgacaagaaa gagcgaagaa acaatcacac gtggaactt cgaagaagtc  1440
gtcgacaagg gagcaagcgc acagagcttc atcgaaagaa tgacaaactt cgacaagaac  1500
ctgccgaacg aaaaggtcct gccgaagcac agcctgctgt acgaatactt cacagtctac  1560
aacgaactga caaaggtcaa gtacgtcaca gaaggaatga gaaagccggc attcctgagc  1620
ggagaacaga agaaggcaat cgtcgacctg gtgttcaaga caaacagaaa ggtcacagtc  1680
aagcagctga aggaagacta cttcaagaag atcgaatgct tcgacagcgt cgaaatcagc  1740
ggagtcgaag acagattcaa cgcaagcctg ggaacatacc acgacctgct gaagatcatc  1800
aaggacaagg acttcctgga caacgaagaa acgaagaca tcctggaaga catcgtcctg  1860
acactgacac tgttcgaaga cagagaaatg atcgaagaga gactgaagac atacgcacac  1920
ctgttcgacg acaaggtcat gaagcagctg aagagaagaa gatacacagg atgggggaaga  1980
ctgagcagaa agctgatcaa cggaatcaga gacaagcaga gcggaaagac aatcctggac  2040
ttcctgaaga gcgacggatt cgcaaacaga aacttcatgc agctgatcca cgacgacagc  2100
ctgacattca aggaagacat ccagaaggca caggtcagcg gacagggaga cagcctgcac  2160
gaacacatcg caaacctggc aggaagcccg gcaatcaaga agggaatcct gcagacagtc  2220
aaggtcgtcg acgaactggt caaggtcatg ggaagacaca agccggaaaa catcgtcatc  2280
gaaatggcaa gagaaaacca gacaacacag aagggacaga agaacagcag agaaagaatg  2340
aagagaatcg aagaggaat caaggaactg ggaagccaga tcctgaagga acaccgggtc  2400
gaaaacacac agctgcagaa cgaaaagctg tacctgtact acctgcagaa cggaagagac  2460
atgtacgtcg accaggaact ggacatcaac agactgagcg actacgacgt cgacgcaatc  2520
gtcccgcaga gcttcctgaa ggacgacagc atcgacaaca aggtcctgac aagaagcgac  2580
```

```
aagaacagag gaaagagcga caacgtcccg agcgaagaag tcgtcaagaa gatgaagaac    2640
tactggagac agctgctgaa cgcaaagctg atcacacaga gaaagttcga caacctgaca    2700
aaggcagaga gaggaggact gagcgaactg gacaaggcag gattcatcaa gagacagctg    2760
gtcgaaacaa gacagatcac aaagcacgtc gcacagatcc tggacagcag aatgaacaca    2820
aagtacgacg aaaacgacaa gctgatcaga gaagtcaaga tcatcacact gaagagcaag    2880
ctggtcagcg acttcagaaa ggacttccag ttctacaagg tcagagaaat caacaactac    2940
caccacgcac acgacgcata cctgaacgca gtcgtcggaa cagcactgat caagaagtac    3000
ccgaagctgg aaagcgaatt cgtctacgga gactacaagg tctacgacgt cagaaagatg    3060
atcgcaaaga gcgaacagga aatcggaaag agcgaacaga agtacttctt ctacagcaac    3120
atcatgaact tcttcaagac agaaatcaca ctggcaaacg tgaaatcag aaagagaccg     3180
ctgatcgaaa caaacggaga aacaggagaa atcgtctggg acaagggaag agacttcgca    3240
acagtcagaa aggtcctgag catgccgcag gtcaacatcg tcaagaagac agaagtccag    3300
acaggaggat tcagcaagga aagcatcctg ccgaagagaa cacgcgacaa gctgatcgca    3360
agaaagaagg actgggaccc gaagaagtac ggaggattcg gacccgac agtcgcatac      3420
agcgtcctgg tcgtcgcaaa ggtcgaaaag ggaaagagca gaagctgaa gagcgtcaag     3480
gaactgctgg gaatcacaat catggaagag agcagcttcg aaaagaaccc gatcgacttc    3540
ctggaagcaa agggatacaa ggaagtcaag aaggacctga tcatcaagct gccgaagtac    3600
agcctgttcg aactggaaaa cggaagaaag gaatgcgag caagcgcagg agaactgcag     3660
aagggaaacg aactggcact gccgagcaag tacgtcaact tcctgtacct ggcaagccac    3720
tacgaaaagc tgaagggaag cccggaagac aacgaacaga agcagcagtt cgtcgaacag    3780
cacaagcact acctggacga aatcatcgaa cagatcagcg aattcagcaa gagagtcatc    3840
ctggcagacg caaacctgga caaggtcctg agcgcataca acaagcacag agacaagccg    3900
atcagagaac aggcagaaaa catcatccac ctgttcacac tgacaaacct gggagcaccg    3960
gcagcattca gtacttcga cacaacaatc gacagaaaga gatacacaag cacaaaggaa     4020
gtcctggacg caacactgat ccaccagagc atcacaggac tgtacgaaac aagaatcgac    4080
ctgagccagc tgggaggaga cggaggagga agc                                 4113
```

SEQ ID NO: 222         moltype = AA  length = 1392
FEATURE                Location/Qualifiers
REGION                 1..1392
                         note = Synthetic: Amino acid sequence of Cas9 with two
                         nuclear localization signals (2xNLS) as the C-terminal
                         amino acids
source                 1..1392
                         mol_type = protein
                         organism = synthetic construct

```
SEQUENCE: 222
MDKKYSIGLD IGTNSVGWAV ITDEYKVPSK KFKVLGNTDR HSIKKNLIGA LLFDSGETAE      60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDGS GSPKKKRKVD   1380
GSPKKKRKVD SG                                                      1392
```

SEQ ID NO: 223         moltype = RNA  length = 4233
FEATURE                Location/Qualifiers
misc_feature        1..4233
                         note = Synthetic: Cas9 mRNA ORF encoding SEQ ID NO: 222
                         using minimal uridine codons, with start and stop codons
source                 1..4233
                         mol_type = other RNA
                         organism = synthetic construct

```
SEQUENCE: 223
atggacaaga agtacagcat cggactggac atcggaacaa cagcgtcgg atgggcagtc       60
atcacagacg aatacaaggt cccgagcaag aagttcaagg tcctgggaaa cacagacaga    120
cacagcatca agaagaacct gatcggagca ctgctgttcg acagcggaga aacagcagaa    180
gcaacaagac tgaagagaac agcaagaaga agatacacaa gaagaaagaa cagaatctgc    240
tacctgcagg aaatcttcag caacgaaatg gcaaaggtcg acgacagctt cttccacaga    300
ctgaaggaaa gcttcctggt cgaagaagac aagaagcacg aaagacaccc gatcttcgga    360
aacatcgtcg acgaagtcgc ataccacgaa aagtacccga caatctacca cctgagaaag    420
aagctggtcg acagcacaga caaggcagac ctgagactga tctacctggc actggcacac    480
```

```
atgatcaagt tcagaggaca cttcctgatc gaaggagacc tgaacccgga caacagcgac    540
gtcgacaagc tgttcatcca gctggtccag acatacaacc agctgttcga agaaaacccg    600
atcaacgcaa gcggagtcga cgcaaaggca atcctgagcg caagactgag caagagcaga    660
agactggaaa acctgatcgc acagctgccg ggagaaaaga gaacggact gttcggaaac     720
ctgatcgcac tgagcctggg actgacaccg aacttcaaga gcaacttcga cctggcagaa    780
gacgcaaagc tgcagctgag caaggacaca tacgacgacg acctggacaa cctgctggca    840
cagatcggag accagtacgc agacctgttc ctggcagcaa agaacctgag cgacgcaatc    900
ctgctgagcg acatcctgag agtcaacaca gaaatcacaa aggcaccgct gagcgcaagc    960
atgatcaaga gatacgacga acaccaccag gacctgacac tgctgaaggc actggtcaga   1020
cagcagctgc cggaaaagta caaggaaatc ttcttcgacc agagcaagaa cggatacgca   1080
ggatacatcg acggaggagc aagccaggaa gaattctaca agttcatcaa gccgatcctg   1140
gaaaagatgg acgaacagag agaactgctg gtcaagctga acagagaaga cctgctgaga   1200
aagcagagaa cattcgacaa cggaagcatc ccgcaccaga tccacctggg agaactgcac   1260
gcaatcctga gaagacagga agacttctac ccgttcctga aggacaacag agaaaagatc   1320
gaaaagatcc tgacattcag aatcccgtac tacgtcggac cgctggcaag aggaaacagc   1380
agattcgcat ggatgacaag aaagagcgaa gaaacaatca caccgtggaa cttcgaagaa   1440
gtcgtcgaca agggagcaag cgcacagagc ttcatcgaaa gaatgacaaa cttcgacaag   1500
aacctgccga acgaaaaggt cctgccgaag cacagcctgc tgtacgaata cttcacagtc   1560
tacaacgaac tgacaaaggt caagtacgtc acagaaggaa tgagaaagcc ggcattcctg   1620
agcggagaac agaagaaggc aatcgtcgac ctgctgttca agacaaacag aaaggtcaca   1680
gtcaagcagc tgaaggaaga ctacttcaag aagatcgaat gcttcgacag cgtcgaaatc   1740
agcggagtcg aagacagatt caacgcaagc ctggaacaat accacgacct gctgaagatc   1800
atcaaggaca aggacttcct ggacaacgaa gaaaacgaag acatcctgga agacatcgtc   1860
ctgacactga cactgttcga agacagagaa atgatcgaaa aagactgaa gacatacgca    1920
cacctgttcg acgacaaggt catgaagcag ctgaagagaa gagatacac aggatgggga    1980
agactggaca gaaagctgat caacggaatc agagacaagc agcgcgaaa gacaatcctg    2040
gacttcctga gagcgacgg attcgcaaac agaaacttca tgcagctgat ccacgacgac    2100
agcctgacat tcaaggaaga catccagaag gcacaggtca gcggacaggg agacagcctg    2160
cacgaacaca tcgcaaacct ggcaggaagc ccggcaatca gaagggaat cctgcagaca    2220
gtcaaggtcg tcgacgaact ggtcaaggtc atgggaagac aaagccggga aaacatcgtc    2280
atcgaaatgg caagagaaaa ccagacaaca cagaagggac agaagaacag cagagaaaga    2340
atgaagagaa tcgaagaagg aatcaaggaa ctgggaagcc agatcctgaa ggaacacccg    2400
gtcgaaaaca cacagctgca gaacgaaaag ctgtacctgt actacctgca gaacggaaga    2460
gacatgtacg tcgaccagga actggacatc aacagactga gcgactacga cgtcgaccac    2520
atcgtcccgc agagcttcct gaaggacgac agcatcgaca caaggtcct gacaagaagc    2580
gacaagaaca gaggaaagag cgacaacgtc ccgagcgaag aagtcgtcaa gaagatgaag    2640
aactactgga gacagctgct gaacgcaaag ctgatcacac agaagaagt cgacaacctg    2700
acaaaggcag agagaggagg actgagcgaa ctggacaagg caggattcat caagagacag    2760
ctggtcgaaa cagacagat cacaaagcac gtcgcacaga tcctggacag cagaatgaac    2820
acaaagtacg acgaaaacga caagctgatc agagaagtca aggtcatcac actgaagagc    2880
aagctggtca gcgacttcag aaaggacttc cagttctaca aggtcagaga aatcaacaac    2940
taccaccacg cacacgacgc ataccctgaac gcagtcgtcg aacagcact gatcaagaag    3000
tacccgaagc tggaaagcga attcgtctac ggagactaca aggtctacga cgtcagaaag    3060
atgatcgcaa agagcgaaca ggaaatcgga aaggcaacag caaagtactt cttcctacag    3120
aacatcatga acttcttcaa gacagaaatc acactggcaa acggagaaat cagaaagaga    3180
ccgctgatcg aaacaaacgg agaaacagga gaaatcgtct gggacaaggg aagagacttc    3240
gcaacagtca gaaaggtcct gagcatgccg caggtcaaca tcgtcaagaa gacagaagtc    3300
cagacaggag gattcagcaa ggaaagcatc ctgccgaaga gaaacagcga caagctgatc    3360
gcaagaaaga aggactggga cccgaagaag tacggaggat cgacagccc gacagtcgca    3420
tacagcgtcc tggtcgtcgc aaaggtcgaa aagggaaaga gcaagaagct gaagagcgtc    3480
aaggaactgc tgggaatcac aatcatgaag agaagcagct tcgaaaagaa cccgatcgac    3540
ttcctggaag caaagggata caaggaagtc aagaaggacc tgatcatcaa gctgccgaag    3600
tacagcctgt tcgaactgga aaacggaaga agagaatgc tggcaagcgc aggagaactg    3660
cagaagggaa acgaactggc actgccgagc aagtacgtca acttcctgta cctggcaagc    3720
cactacgaaa agctgaaggg aagcccggaa gacaacgaac agaaacagct gttcgtcgaa    3780
cagcacaagc actacctgga cgaaatcatc gaacagatca gcgaattcag caagagagtc    3840
atcctggcag acgcaaacct ggacaaggtc ctgagcgcat acaacaagca cagagacaag    3900
ccgatcagaa acaggcaga aaacatcatc cacctgttca cactgacaaa cctgggagca    3960
ccggcagcat tcaagtactt cgacacaaca atcgacagaa agagatacga agcacaaag    4020
gaagtcctgg acgcaacact gatccaccag agcatcacag gactgtacga aacaagaatc    4080
gacctgagcc agctgggagg agacggagga ggaagcccga gaagaagag aaaggtcccg    4140
aagaagaaga gaaaggtcgg aagcggaagc ccgaagaaga agagaaaggt cgacggaagc    4200
ccgaagaaga agagaaaggt cgacagcgga tag                                4233
```

| | |
|---|---|
| SEQ ID NO: 224 | moltype = RNA length = 4227 |
| FEATURE | Location/Qualifiers |
| misc_feature | 1..4227 |
| | note = Synthetic: Cas9 coding sequence encoding SEQ ID NO: 222 using minimal uridine codons (no start or stop codons; suitable for inclusion in fusion protein coding sequence) |
| source | 1..4227 |
| | mol_type = other RNA |
| | organism = synthetic construct |
| SEQUENCE: 224 | |

```
gacaagaagt acagcatcgg actggacatc ggaacaaaca gcgtcggatg ggcagtcatc     60
acagacgaat acaaggtccc gagcaagaag ttcaaggtcc tgggaaacac agacagacac    120
agcatcaaga gaacctgat cggagcactg ctgttcgaca cggagaaac agcagaagca     180
acaagactga agagaacagc aagaagaaga tacacaagaa gaaagaacag aatctgctac    240
ctgcaggaaa tcttcagcaa cgaaatggca aaggtcgacg acagcttctt ccacagactg    300
```

```
gaagaaagct tcctggtcga agaagacaag aagcacgaaa gacacccgat cttcggaaac    360
atcgtcgacg aagtcgcata ccacgaaaag tacccgacaa tctaccacct gagaaagaag    420
ctggtcgaca gcacagacaa ggcagacctg agactgatct acctggcact ggcacacatg    480
atcaagttca gaggacactt cctgatcgaa ggagacctga acccgacaa cagcgacgtc     540
gacaagctgt tcatccagct ggtccagaca tacaaccagc tgttcgaaga aaacccgatc    600
aacgcaagcg gagtcgacgc aaaggcaatc ctgagcgcaa gactgagcaa gagcagaaga    660
ctggaaaacc tgatcgcaca gctgccggga gaaaagaaga acggactgtt cggaaacctg    720
atcgcactga gcctgggact gacaccgaac ttcaagagca acttcgacct ggcagaagac    780
gcaaagctgc agctgagcaa ggacacatac gacgacgacc tggacaacct gctggcacag    840
atcggagacc agtacgcaga cctgttcctg gcagcaaaga acctgagcga cgcaatcctg    900
ctgagcgaca tcctgagagt caacacagaa atcacaaagg caccgctgag cgcaagcatg    960
atcaagagat acgacgaaca ccaccaggac ctgacactgc tgaaggcact ggtcagacag   1020
cagctgccgg aaaagtacaa ggaaatcttc ttcgaccaga gcaagaacgg atacgcagga   1080
tacatcgacg gaggagcaag ccaggaagaa ttctacaagt tcatcaagcc gatcctggaa   1140
aagatggacg gaacagaaga actgctggtc aagctgaaca gagaagacct gctgagaaag   1200
cagagaacat tcgacaacgg aagcatcccg caccagatcc acctgggaga actgcacgca   1260
atcctgagaa gacaggaaga cttctacccg ttcctgaagg acaacagaga aaagatcgaa   1320
aagatcctga cattcagaat cccgtactac gtcggaccgc tggcaagagg aaacagcaga   1380
ttcgcatgga tgacaagaaa gagcgaagaa acaatcacac cgtggaactt cgaagaagtc   1440
gtcgacaagg gagcaagcgc acagagcttc atcgaaagaa tgacaaactt cgacaagaac   1500
ctgccgaacg aaaaggtcct gccgaagcac agcctgctgt acgaatactt cacagtctac   1560
aacgaactga caaaggtcca gtacgtcaca gaaggaatga aaagccggc attcctgagc   1620
ggagaacaga agaaggcaat cgtcgacctg ctgttcaaga caaacagaaa ggtcacagtc   1680
aagcagctga aggaagacta cttcaagaag atcgaatgct cgacagcgt cgaaatcagc   1740
ggagtcgaag acagattcaa cgcaagcctg ggaacatacc acgacctgct gaagatcatc   1800
aaggacaagg acttcctgga caacgaagaa aacgaagaca tcctggaaga catcgtcctg   1860
acactgacac tgttcgaaga cagagaaatg atcgaagaaa gactgaagac atacgcacac   1920
ctgttcgacg acaaggtcat gaagcagctg aagagaagaa gatacacagg atggggaaga   1980
ctgagcagaa agctgatcaa cggaatcaga gacaagcaga gcgaaaagac aatcctggac   2040
ttcctgaaga gcgacggatt cgcaaacaga aacttcatgc agctgatcca cgacgacagc   2100
ctgacattca aggaagacat ccagaaggca caggtcagcg gacagggaga cagcctgcac   2160
gaacacatcg caaacctggc aggaagcccg gcaatcaaga gggaatcct gcagacagtc   2220
aaggtcgtcg acgaactggt caaggtcatg ggaagacaca gccggaaaa catcgtcatc   2280
gaaatggcaa gagaaaacca gacaacacag aagggcagaa agaacagcag agaaagaatg   2340
aagagaatcg aagaggaat caaggaactg ggaagccaga tcctgaagga acacccgagtc   2400
gaaaacacac agctgcagaa cgaaaagctg tacctgtact acctgcagaa cggaagagac   2460
atgtacgtcg accaggaact ggacatcaac agactgagcg actacgacgt cgaccacatc   2520
gtcccgcaga gcttcctgaa ggacgacagc atcgacaaca aggtcctgac aagaagcgac   2580
aagaacagag gaaagagcga caacgtcccg agcgaagaag tcgtcaagaa gatgaagaac   2640
tactggagac agctgctgaa cgcaaagctg atcacacaga gaagttcga aacctgaca   2700
aaggcagaga gaggaggact gagcgaactg gacaaggcag gattcatcaa gagacagctg   2760
gtcgaaacaa gacagatcac aaagcacgtc gcacagatcc tggacagcag aatgaacaca   2820
aagtacgacg aaaacgacaa gctgatcaga gaagtcaagg tcatccact gaagagcaag   2880
ctggtcagcg acttcagaaa ggacttccag ttctacaagg tcagagaaat caacaactac   2940
caccacgcac acgacgcata cctgaacgca gtcgtcggaa cagcactgat caagaagtac   3000
ccgaagctgg aaagcgaatt cgtctacgga gactacaagg tctacgacgt cagaaagatg   3060
atcgcaaaga gcgaacagga aatcggaaag gcaacagcaa agtactttctt ctacagcaac   3120
atcatgaact tcttcaagac agaaatcaca ctggcaaacg gagaaatcag aaagagaccg   3180
ctgatcgaaa caaacggaga aacaggagaa atcgtctggg acaagggaag agacttcgca   3240
acagtcagaa aggtcctgag catgccgcag gtcaacatcg tcaagaagac agaagtccag   3300
acaggaggat tcagcaagga aagcatcctg ccgaagagaa acagcgacaa gctgatcgca   3360
agaaagaagg actgggaccc gaagaagtac ggaggattcg acagcccgac agtcgcgtac   3420
agcgtcctgg tcgtcgcaaa ggtcgaaaag ggaagagca agaagctgaa gagcgtcaag   3480
gaactgctgg gaatcacaat catggaaaga agcagcttcg aaaagaaccc gatcgacttc   3540
ctggaagcaa agggatacaa ggaagtcaag aaggacctga tcatcaagct gccgaagtac   3600
agcctgttcg aactgaaaa cggaagaaag agaatgctgg caagcgcagg agaactgcag   3660
aagggaaacg aactggcact gccgagcaag tacgtcaact tcctgtacct ggcaagccac   3720
tacgaaaagc tgaagggaag cccggaagac aacgaacaga agcagctgtt cgtcgaacag   3780
cacaagcact acctggacga aatcatcgaa cagatcagc aattcagcaa gagagtcatc   3840
ctggcagacg caaacctgga caaggtcctg agcgcataca acaagcacag agacaagccg   3900
atcagagaac aggcagaaaa catcatccac ctgttcacac tgacaaacct gggagcaccg   3960
gcagcattca agtacttcga cacaacaatc gacagaaaga gatacacaag cacaaaggaa   4020
gtcctggacg caacactgat ccaccagagc atcacggact gtacgaaac aagaatcgac   4080
ctgagccagc tgggaggaga cggaggagga agcccgaaga agaagagaaa ggtcccgaag   4140
aagaagagaa aggtcggaag cggaagcccg aagaagaaga aaggtcga cggaagcccg   4200
aagaagaaga gaaaggtcga cagcgga                                       4227

SEQ ID NO: 225       moltype = AA   length = 1392
FEATURE              Location/Qualifiers
REGION               1..1392
                     note = Synthetic: Amino acid sequence of Cas9 nickase with
                     two nuclear localization signals as the C-terminal amino
                     acids
source               1..1392
                     mol_type = protein
                     organism = synthetic construct
SEQUENCE: 225
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
```

```
NIVDEVAYHE  KYPTIYHLRK  KLVDSTDKAD  LRLIYLALAH  MIKFRGHFLI  EGDLNPDNSD   180
VDKLFIQLVQ  TYNQLFEENP  INASGVDAKA  ILSARLSKSR  RLENLIAQLP  GEKKNGLFGN   240
LIALSLGLTP  NFKSNFDLAE  DAKLQLSKDT  YDDDLDNLLA  QIGDQYADLF  LAAKNLSDAI   300
LLSDILRVNT  EITKAPLSAS  MIKRYDEHHQ  DLTLLKALVR  QQLPEKYKEI  FFDQSKNGYA   360
GYIDGGASQE  EFYKFIKPIL  EKMDGTEELL  VKLNREDLLR  KQRTFDNGSI  PHQIHLGELH   420
AILRRQEDFY  PFLKDNREKI  EKILTFRIPY  YVGPLARGNS  RFAWMTRKSE  ETITPWNFEE   480
VVDKGASAQS  FIERMTNFDK  NLPNEKVLPK  HSLLYEYFTV  YNELTKVKYV  TEGMRKPAFL   540
SGEQKKAIVD  LLFKTNRKVT  VKQLKEDYFK  KIECFDSVEI  SGVEDRFNAS  LGTYHDLLKI   600
IKDKDFLDNE  ENEDILEDIV  LTLTLFEDRE  MIEERLKTYA  HLFDDKVMKQ  LKRRRYTGWG   660
RLSRKLINGI  RDKQSGKTIL  DFLKSDGFAN  RNFMQLIHDD  SLTFKEDIQK  AQVSGQGDSL   720
HEHIANLAGS  PAIKKGILQT  VKVVDELVKV  MGRHKPENIV  IEMARENQTT  QKGQKNSRER   780
MKRIEEGIKE  LGSQILKEHP  VENTQLQNEK  LYLYYLQNGR  DMYVDQELDI  NRLSDYDVDH   840
IVPQSFLKDD  SIDNKVLTRS  DKNRGKSDNV  PSEEVVKKMK  NYWRQLLNAK  LITQRKFDNL   900
TKAERGGLSE  LDKAGFIKRQ  LVETRQITKH  VAQILDSRMN  TKYDENDKLI  REVKVITLKS   960
KLVSDFRKDF  QFYKVREINN  YHHAHDAYLN  AVVGTALIKK  YPKLESEFVY  GDYKVYDVRK  1020
MIAKSEQEIG  KATAKYFFYS  NIMNFFKTEI  TLANGEIRKR  PLIETNGETG  EIVWDKGRDF  1080
ATVRKVLSMP  QVNIVKKTEV  QTGGFSKESI  LPKRNSDKLI  ARKKDWDPKK  YGGFDSPTVA  1140
YSVLVVAKVE  KGKSKKLKSV  KELLGITIME  RSSFEKNPID  FLEAKGYKEV  KKDLIIKLPK  1200
YSLFELENGR  KRMLASAGEL  QKGNELALPS  KYVNFLYLAS  HYEKLKGSPE  DNEQKQLFVE  1260
QHKHYLDEII  EQISEFSKRV  ILADANLDKV  LSAYNKHRDK  PIREQAENII  HLFTLTNLGA  1320
PAAFKYFDTT  IDRKRYTSTK  EVLDATLIHQ  SITGLYETRI  DLSQLGGDGS  GSPKKKRKVD  1380
GSPKKKRKVD  SG                                                         1392

SEQ ID NO: 226          moltype = RNA   length = 4179
FEATURE                 Location/Qualifiers
misc_feature            1..4179
                        note = Synthetic: Cas9 nickase mRNA ORF encoding SEQ ID NO:
                        25 using minimal uridine codons as listed in Table 3, with
                        start and stop codons
source                  1..4179
                        mol_type = other RNA
                        organism = synthetic construct
SEQUENCE: 226
atggacaaga agtacagcat cggactggca atcggaacaa acagcgtcgg atgggcagtc    60
atcacagacg aatacaaggt cccgagcaag aagttcaagg tcctgggaaa cacagacaga   120
cacagcatca agaagaacct gatcggagca ctgctgttcg acagcggaga aacagcagaa   180
gcaacaagac tgaagagaac agcaagaaga agatacacaa gaagaaagaa cagaatctgc   240
tacctgcagg aaatcttcag caacgaaatg gcaaggtcg acgacagctt cttccacaga   300
ctggaagaaa gcttcctggt cgaagaagac aagaagcacg gatcttcgga   360
aacatcgtcg acgaagtcgc ataccacgaa agtacccga caatctacca cctgagaaag   420
aagctggtcg acagcacaga caaggcagac ctgagactga tctacctggc actggcacac   480
atgatcaagt tcagaggaca cttcctgatc gaaggagacc tgaacccgga caacagcgac   540
gtcgacaagc tgttcatcca gctggtccag acatacaagc agctgttcga agaaaacccg   600
atcaacgcaa gcggagtcga cgcaaaggca atcctgagcg caagactgag caagagcaga   660
agactggaaa acctgatcgc acagctgccg ggagaaaaga gaacggact gttcggaaac   720
ctgatcgcac tgagcctggg actgacaccg aacttcaaga gcaacttcga cctggcagaa   780
gacgcaaagc tgcagctgag caaggacaca tacgacgagc cctgctggca   840
cagatcggag accagtacgc agacctgttc ctggcagcaa agaacctgag cgacgcaatc   900
ctgctgagcg acatcctgag agtcaacaca gaaatcacaa aggcaccgct gagcgcaagc   960
atgatcaaga gatacgacga acaccaccag gacctgacac tgctgaaggc actggtcaga  1020
cagcagctgc cggaaaagta caaggaaatc ttcttcgacc agagcaagaa cggatacgca  1080
ggatacatcg acggaggagc aagccaggaa gaattctaca agttcatcaa gccgatcctg  1140
gaaaagatgg acggaacaga agaactgctg gtcaagctga cagagaaga cctgctgaga  1200
aagcagagaa cattcgacaa cggaagcatc ccgcaccaga tccacctggg agaactgcac  1260
gcaatcctga gaagacagga agacttctac ccgttcctga aggacaacag agaaaagatc  1320
gaaaagatcc tgacattcag aatcccgtac tacgtcggac cgctggcaag aggaaacagc  1380
agattcgcat ggatgacaag aaagagcgaa gaaacaatca ccgtggaa cttcgaagaa  1440
gtcgtcgaca agggagcaag cgcacagagc ttcatcgaaa gaatgacaaa cttcgacaag  1500
aacctgccga cgaaaaggt cctgccgaag cacagcctgc tgtacgaata cttcacagtc  1560
tacaacgaac tgacaaaggt caagtacgtc acagaaggag tgagaagcc ggcattcctg  1620
agcggagaac agaagaaggc aatcgtcgac ctgctgttca gacaaacag aaaggtcaca  1680
gtcaagcagc tgaaggaaga ctacttcaag aagatcgaat gcttcgacag cgtcgaaatc  1740
agcggagtcg aagacagatt caacgcaagc ctgggaacat accgacct gctgaagatc  1800
atcaaggaca aggacttcct ggacaacgaa gaaaacgaag acatcctgga agacatcgtc  1860
ctgacactga cactgttcga agacagaaga atgatcgaag aaagactgaa gacatacgca  1920
cacctgttcg acgacaaggt catgaagcag ctgaagagaa gaagatacac aggatgggga  1980
agactgagca gaaagctgat caacggaatc agagacaagc agagcggaaa gacaatcctg  2040
gacttcctga gagcgacgg attccgcaaac agaaacttca tgcagctgat ccacgacgac  2100
agcctgacat tcaaggaaga catccagaag cacaggtcg gcgacaaggg agacagcctg  2160
cacgaacaca tcgcaaacct ggcaggaagc ccggcaatca gaagggaat cctgcagaca  2220
gtcaaggtcg tcgacgaact ggtcaaggtc atgggaagac acaagccgga aaacatcgtc  2280
atcgaaatgg caagagaaaa ccagacaaca cagaagggac agaagaacag cagagaaaga  2340
atgaagagaa tcgaagaagg aatcaaggaa ctgggaagcc agatcctgaa ggaacacccg  2400
gtcgaaacac agctgcaaaa cgaaaagctg tacctgt actacctgca aaacggaaga  2460
gacatgtacg tcgaccagga actgacatc aacagactga gcgactacga cgtcgaccac  2520
atcgtcccgc agagcttcct gaaggacgac agcatcgaca caaggtcct gacaagaagc  2580
gacaagaaca gaggaaagag cgacaacgtc ccgagcgaag aagtcgtcaa gaagatgaag  2640
aactactgga gacagctgct gaacgcaaag ctgatcacac agagaaagtt cgacaacctg  2700
acaaaggcag agaggagg actgagcgaa ctggacaagg caggattcat caagagacag  2760
```

```
ctggtcgaaa caagacagat cacaaagcac gtcgcacaga tcctggacag cagaatgaac    2820
acaaagtacg acgaaaacga caagctgatc agagaagtca aggtcatcac actgaagagc    2880
aagctggtca gcgacttcag aaaggacttc cagttctaca aggtcagaga atcaacaac     2940
taccaccacg cacacgacgc atacctgaac gcagtcgtcg aacagcact gatcaagaag     3000
tacccgaagc tggaaagcga attcgtctac ggagactaca aggtctacga cgtcagaaag    3060
atgatcgcaa agagcgaaca ggaaatcgga aaggcaacag caaagtactt cttctacagc    3120
aacatcatga acttcttcaa gacagaaatc acactggcaa acggagaaat cagaaagaga    3180
ccgctgatcg aaacaaacgg agaaacagga gaaatcgtct gggacaaggg aagagacttc    3240
gcaacagtca gaaaggtcct gagcatgccg caggtcaaca tcgtcaagaa gacagaagtc    3300
cagacaggag gattcagcaa ggaaagcatc ctgccgaaga gaaacagcga caagctgatc    3360
gcaagaaaga aggactggga cccgaagaag tacggaggat tcgacagccc gacagtcgca    3420
tacagcgtcc tggtcgtcgc aaaggtcgaa aagggaaaga gcaagaagct gaagagcgtc    3480
aaggaactgc tgggaatcac aatcatggaa agaagcagct tcgaaaagaa cccgatcgaa    3540
ttcctggaag caaagggata caaggaagtc aagaaggacc tgatcatcaa gctgccgaag    3600
tacagcctgt tcgaactgga aaacggaaga aagagaatgc tggcaagcgc aggagaactg    3660
cagaagggaa acgaactggc actgccgagc aagtacgtca acttcctgta cctggcaagc    3720
cactacgaaa agctgaaggg aagcccggaa gacaacgaac agaagcagct gttcgtcgaa    3780
cagcacaagc actacctgga cgaaatcatc gaacagatca gcgaattcag caagagagtc    3840
atcctggcag acgcaaacct ggacaaggtc ctgagcgcat acaacaagca cagagacaag    3900
ccgatcagaa acaggcaga aaacatcatc cacctgttca cactgacaaa cctgggagca     3960
ccggcagcat tcaagtactt cgacacaaca atcgacagaa agagatacac aagcacaaag    4020
gaagtcctgg acgcaaacac tgatccaccag agcatcacag agctgacga aacaagaatc    4080
gacctgagcc agctgggagg agacggaagc ggaagcccga agaagaagag aaaggtcgac    4140
ggaagcccga agaagaagag aaaggtcgac agcggatag                           4179
```

SEQ ID NO: 227          moltype = RNA   length = 4173
FEATURE                Location/Qualifiers
misc_feature       1..4173
                      note = Synthetic: Cas9 nickase coding sequence encoding SEQ
                      ID NO: 25 using minimal uridine codons (no start or stop
                      codons; suitable for inclusion in fusion protein coding
                      sequence)
source                  1..4173
                      mol_type = other RNA
                      organism = synthetic construct
SEQUENCE: 227

```
gacaagaagt acagcatcgg actggcaatc ggaacaaaca gcgtcggatg ggcagtcatc      60
acagacgaat caaggtccc gagcaagaag ttcaaggtcc tgggaaacac agacagacac      120
agcatcaaga agaacctgat cggagcactg ctgttcgaca gcggagaaac agcagaagca     180
acaagactga agagaacagc aagaagaaga tacacaagaa gaagaacag atctgctac       240
ctgcaggaaa tcttcagcaa cgaaatggca aaggtcgacg acagcttctt ccacagactg     300
gaagaaagct tcctggtcga agaagacaag aagcacgaaa gacacccgat cttcggaaac     360
atcgtcgacg aagtcgcata ccacgaaaag tacccgacca tctaccacct ggagaaagaa     420
ctggtcgaca gcacagacaa ggcagacctg agactgatct acctggcact ggcacacatg    480
atcaagttca gaggacactt cctgatcgaa ggagacctga accgacaa cagcgacgtc       540
gacaagctgt tcatccagct ggtccagaca tacaaccagc tgttcgaaga aaacccgatc    600
aacgcaagcg gagtcgacgc aaaggcaatc ctgagcgcaa gactgagcaa gagcagaaga    660
ctggaaaacc tgatcgcaca gctgccggga gaaaagaaga acggactgtt cggaaacctg    720
atcgcactga gcctgggact gacaccgaac ttcaagcaa acttcgacct ggcagaagac    780
gcaaagctgc agctgagcaa ggacacatac gacgacgacc tggacaacct gctggcacag    840
atcggagacc agtacgcaga cctgttcctg gcagcaaaga acctgagcga cgcaatcctg    900
ctgagcgaca tcctgagagt caacacagaa atcacaaagg caccgctgag cgcaagcatg    960
atcaagagat acgacgaaca ccaccaggac ctgacactgc tgaaggcact ggtcagacag   1020
cagctgccgg aaaagtacaa ggaaatcttc ttcgaccaga gcaagaacgg atacgcagga   1080
tacatcgacg gaggagcaag ccaggaagaa ttctacaagt tcatcaagcc gatcctggaa   1140
aagatggacg gaacagaaga actgctggtc aagctgaaca gagaagacct gctgagaaag   1200
cagagaacat tcgacaacgg aagcatcccg caccagatcc acctgggaga actgcacgca   1260
atcctgagaa gacaggaaga cttctacccg ttcctgaagg acaacagaga aaagatcgaa   1320
aagatcctga cattcagaat cccgtactac gtcggacccc tggcaagagg aaacagcaga   1380
ttcgcatgga tgacaagaaa gagcgaagaa acaatcacac cgtggaactt cgaagaagtc   1440
gtcgacaagg gagcaagcgc acagagcttc atcgaaagaa tgacaaactt cgacaagaac   1500
ctgccgaacg aaaaggtcct gccgaagcac agcctgctgt acgaatactt cacagtctac   1560
aacgaactga caaaggtcaa gtacgtcaca gaaggaatga gaaagccggc attcctgagc   1620
ggagaacaga aaggcaat cgtcgacctg ctgttcaaa caaacagga ggtcacagtc       1680
aagcagctga aggaagacta cttcaagaag atcgaatgct tcgacagcgt cgaaatcagc   1740
ggagtcgaag acagattcaa cgcaagcctg ggaacatacc acgacctgct gaagatcatc   1800
aaggacaagg acttcctgga caacgaagaa acgaagaca tcctggaaga catcgtcctg   1860
acactgacac tgttcgaaga cagagaaatg atcgaagaga gactgaagac atacgcacac   1920
ctgttcgacg acaaggtcat gaagcagctg aagagaagaa gatacacagg atgggaaga  1980
ctgagcagaa agctgatcaa cggaatcaga gacaagcaga gcggaaagac aatcctggac   2040
ttcctgaaga gcgacggatt cgcaaacaga aacttcatgc agctgatcca cgacgacagc   2100
ctgacattca aggaagacat ccagaaggca caggtcagcg gacagggaga cagcctgcac   2160
gaacacatcg caaacctggc aggaagcccg gcaatcaaga agggaatcct gcagacagtc   2220
aaggtcgtcg acgaactggt caaggtcatg ggaagacaca agccggaaaa catcgtcatc   2280
gaaatggcaa gagaaaacca gacaacacag aagggacaga agaacagcag agaaagaatg   2340
aagagaatcg aagaggaat caaggaactg ggaagccaga tcctgaagga acacccggtc   2400
gaaaacacac agctgcagaa cgaaaagctg tacctgtact acctgcagaa cggaagagac   2460
atgtacgtcg accaggaact ggacatcaac agactgagcg actacgacgt cgaccacatc   2520
gtcccgcaga gcttcctgaa ggacgacagc atcgacaaca aggtcctgac aagaagcgac   2580
```

```
aagaacagag gaaagagcga caacgtcccg agcgaagaag tcgtcaagaa gatgaagaac   2640
tactggagac agctgctgaa cgcaaagctg atcacacaga gaaagttcga caacctgaca   2700
aaggcagaga gaggaggact gagcgaactg gacaaggcag gattcatcaa gagacagctg   2760
gtcgaaacaa gacagatcac aaagcacgtc gcacagatcc tggacagcag aatgaacaca   2820
aagtacgacg aaaacgacaa gctgatcaga gaagtcaaga tcatcacact gaagagcaag   2880
ctggtcagcg acttcagaaa ggacttccag ttctacaagg tcagagaaat caacaactac   2940
caccacgcac acgacgcata cctgaacgca gtcgtcggaa cagcactgat caagaagtac   3000
ccgaagctgg aaagcgaatt cgtctacgga gactacaagg tctacgacgt cagaaagatg   3060
atcgcaaaga gcgaacagga aatcggaaag agcaagacag agtacttctt ctacagcaac   3120
atcatgaact tcttcaagac agaaatcaca ctggcaaacg agaaatcag aaagagaccg    3180
ctgatcgaaa caaacggaga aacaggagaa atcgtctggg acaagggaag agacttcgca   3240
acagtcagaa aggtcctgag catgccgcag gtcaacatcg tcaagaagac agaagtccag   3300
acaggaggat tcagcaagga agcatcctg ccgaagagaa acgcgacaa gctgatcgca    3360
agaaagaagg actgggaccc gaagaagtac ggaggattcg acagcccgac agtcgcatac   3420
agcgtcctgg tcgtcgcaaa ggtcgaaaag ggaaagagca gaagctgaa gagcgtcaag    3480
gaactgctgg gaatcacaat catggaagaa gcagcttcg aaaagaaccc gatcgacttc     3540
ctggaagcaa agggatacaa ggaagtcaag aaggacctga tcatcaagct gccgaagtac   3600
agcctgttcg aactggaaaa cggaagaaaa gaatgcctgg caagcgcagg agaactgcag   3660
aagggaaacg aactggcact gccgagcaag tacgtcaact tcctgtacct ggcaagccac   3720
tacgaaaagc tgaagggaag cccggaagac aacgaacaga gcagcagtt cgtcgaacag    3780
cacaagcact acctggacga aatcatcgaa cagatcagcg aattcagcaa gagagtcatc   3840
ctggcagacg caaacctgga caaggtcctg agcgcataca acaagcacag agacaagcg    3900
atcagagaac aggcagaaaa catcatccac ctgttcacac tgacaaacct gggagcaccg   3960
gcagcattca gtacttcga cacaacaatc gacagaaaga gatacacaag cacaaaggaa    4020
gtcctggacg caacactgat ccaccagagc atcacggact gtacgaaac aagaatcgac    4080
ctgagccagc tgggaggaga cggaagcgga agcccgaaga gaagagaaa ggtcgacgga    4140
agcccgaaga gaagagaaa ggtcgacagc gga                                  4173

SEQ ID NO: 228        moltype = AA  length = 1392
FEATURE               Location/Qualifiers
REGION                1..1392
                      note = Synthetic: Amino acid sequence of dCas9 with two
                      nuclear localization signals as the C-terminal amino acids
source                1..1392
                      mol_type = protein
                      organism = synthetic construct
SEQUENCE: 228
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGS GSPKKKRKVD  1380
GSPKKKRKVD SG                                                     1392

SEQ ID NO: 229        moltype = RNA  length = 4179
FEATURE               Location/Qualifiers
misc_feature          1..4179
                      note = Synthetic: dCas9 mRNA ORF encoding SEQ ID NO: 228
                      using minimal uridine codons, with start and stop codons
source                1..4179
                      mol_type = other RNA
                      organism = synthetic construct
SEQUENCE: 229
atggacaaga agtacagcat cggactggca atcggaacaa cagcgtcgg atgggcagtc     60
atcacagacg aatacaaggt cccgagcaag aagttcaagg tcctgggaaa cacagacaga   120
cacagcatca agaagaacct gatcggagca ctgctgttcg acagcggaga aacagcagaa   180
gcaacaagac tgaagagaac agcaaggaga agatacacaa gaagaaagaa cagaatctgc   240
tacctgcagg aaatcttcag caacgaaatg gcaaaggtcg acgacagctt cttccacaga   300
ctgaaggaaa gcttcctggt cgaagaagac aagaagcacg aaagacaccc gatcttcgga   360
aacatcgtcg acgaagtcgc ataccacgaa aagtacccga caatctacca cctgagaaag   420
aagctggtcg acagcacaga caaggcagac ctgagactga tctacctggc actggcacac   480
```

```
atgatcaagt tcagaggaca cttcctgatc gaaggagacc tgaacccgga caacagcgac    540
gtcgacaagc tgttcatcca gctggtccag acatacaacc agctgttcga agaaaacccg    600
atcaacgcaa gcggagtcga cgcaaaggca atcctgagcg caagactgag caagagcaga    660
agactggaaa acctgatcgc acagctgccg ggagaaaaga agaacggact gttcggaaac    720
ctgatcgcac tgagcctggg actgacaccg aacttcaaga gcaacttcga cctggcagaa    780
gacgcaaagc tgcagctgag caaggacaca tacgacgacg acctggacaa cctgctggca    840
cagatcggag accagtacgc agacctgttc ctggcagcaa agaacctgag cgacgcaatc    900
ctgctgagcg acatcctgag agtcaacaca gaaatcacaa aggcaccgct gagcgcaagc    960
atgatcaaga gatacgacga acaccaccag gacctgacac tgctgaaggc actggtcaga   1020
cagcagctgc cggaaaagta caaggaaatc ttcttcgacc agagcaagaa cggatacgca   1080
ggatacatcg acgaggagc aagccaggaa gaattctaca agttcatcaa gccgatcctg   1140
gaaaagatgg acgaacaga agaactgctg gtcaagctga acagagaaga cctgctgaga   1200
aagcagagaa cattcgacaa cggaagcatc ccgcaccaga tccacctggg agaactgcac   1260
gcaatcctga gaagacagga agacttctac ccgttcctga aggacaacag agaaaagatc   1320
gaaaagatcc tgacattcag aatcccgtac tacgtcggac cgctggcaag aggaaacagc   1380
agattcgcat ggatgacaag aaagagcgaa gaaacaatca caccgtggaa cttcgaagaa   1440
gtcgtcgaca agggagcaag cgcacagagc ttcatcgaaa gaatgacaaa cttcgacaag   1500
aacctgccga acgaaaaggt cctgccgaag cacagcctgc tgtacgaata cttcacagtc   1560
tacaacgaac tgacaaaggt caagtacgtc acagaaggaa tgagaaagcc ggcattcctg   1620
agcggagaac agaagaaggc aatcgtcgac ctgctgttca agacaaacag aaaggtcaca   1680
gtcaagcagc tgaaggaaga ctacttcaag aagatcgaat gcttcgacag cgtcgaaatc   1740
agcggagtcg aagacagatt caacgcaagc ctgggaacat accacgacct gctgaagatc   1800
atcaaggaca aggacttcct ggacaacgaa gaaaacgaag acatcctgga agacatcgtc   1860
ctgacactga cactgttcga agacagagaa atgatcgaaa aagactgaa gacatacgca   1920
cacctgttcg acgacaaggt catgaagcag ctgaagagaa aagatacac aggatgggga   1980
agactgagca gaaagctgat caacggaatc agagacaagc agcggaaa gacaatcctg   2040
gacttcctga gagcgacgg attcgcaaac agaaacttca tgcagctgat ccacgacgac   2100
agcctgacat tcaaggaaga catccagaag gcacaggtca gcggacaggg agacagcctg   2160
cacgaacaca tcgcaaacct ggcaggaagc ccggcaatca gaagggaat cctgcagaca   2220
gtcaaggtcg tcgacgaact ggtcaaggtc atgggaagac aaagccgga aaacatcgtc   2280
atcgaaatgg caagagaaaa ccagacaaca cagaagggac agaagaacag cagagaaaga   2340
atgaagagaa tcgaagaagg aatcaaggaa ctgggaagcc agatcctgaa ggaacacccg   2400
gtcgaaaaca cacagctgca gaacgaaaag ctgtacctgt actacctgca gaacggaaga   2460
gacatgtacg tcgaccagga actggacatc aacagactga gcgactacga cgtcgaccga   2520
atcgtcccgc agagcttcct gaaggacgac agcatcgaca caaggtcct gacaagaagc   2580
gacaagaaca gaggaaagag cgacaacgtc ccgagcgaag aagtcgtcaa gaagatgaag   2640
aactactgga gacagctgct gaacgcaaag ctgatcacac agaaagtt cgacaacctg   2700
acaaaggcag agagaggagg actgagcgaa ctggacaagg caggattcat caagagacag   2760
ctggtcgaaa caagacagat cacaaagcac gtcgcacaga tcctggacag cagaatgaac   2820
acaaagtacg acgaaaacga caagctgatc agagaagtca aggtcatcac actgaagagc   2880
aagctggtca gcgacttcag aaaggacttc cagttctaca aggtcagaga atcaacaac   2940
taccaccacg cacacgacgc ataccctgaac gcagtcgtcg gaacagcact gatcaagaag   3000
tacccgaagc tggaaagcga attcgtctac ggagactaca aggtctacga cgtcagaaag   3060
atgatcgcaa agagcgaaca ggaaatcgga aaggcaacag caaagtactt cttctacagc   3120
aacatcatga acttcttcaa gacagaaatc acactggcaa acggagaaat cagaaagaga   3180
ccgctgatcg aaacaaacgg agaaacagga gaaatcgtct gggacaaggg aagagacttc   3240
gcaacagtca gaaaggtcct gagcatgccg caggtcaaca tcgtcaagaa gacagaagtc   3300
cagacaggag gattcagcaa ggaaagcatc ctgccgaaga gaaacagcga caagctgatc   3360
gcaagaaaga aggactggga cccgaagaag tacggaggat tcgacagccc gacagtcgca   3420
tacagcgtcc tggtcgtcgc aaaggtcgaa aagggaaaga gcaagaagct gaagagcgtc   3480
aaggaactgc tgggaatcac aatcatgaga gaagcagct tcgaaaagaa cccgatcgac   3540
ttcctggaag caaagggata caaggaagtc aagaaggacc tgatcatcaa gctgccgaag   3600
tacagcctgt tcgaactgga aaacggaaga agagaatgc tggcaagcgc aggagaactg   3660
cagaagggaa acgaactggc actgccgagc aagtacgtca acttcctgta cctggcaagc   3720
cactcgaaa agctgaaggg aagcccggaa gacaacgaac agaagcagct gttcgtcgaa   3780
cagcacaagc actacctgga cgaaatcatc gaacagatca gcgaattcag caagagagtc   3840
atcctggcag acgcaaacct ggacaaggtc ctgagcgcat acaacaagca cagagacaag   3900
ccgatcagga acaggcaga aacatcatc cacctgttca cactgacaaa cctgggagca   3960
ccggcagcat tcaagtactt cgacacaaca atcgacagaa agagtacac aagcacaaag   4020
gaagtcctgg acgcaacact gatccaccag agcatcacag gactgtacga aacaagaatc   4080
gacctgagcc agctgggagg agacggaagc ggaagcccga agaagaagag aaaggtcgac   4140
ggaagcccga agaagaagag aaaggtcgac agcggatag                          4179

SEQ ID NO: 230           moltype = RNA   length = 4173
FEATURE                  Location/Qualifiers
misc_feature             1..4173
                         note = Synthetic: dCas9 coding sequence encoding SEQ ID NO:
                         228 using minimal uridine codons (no start or stop codons;
                         suitable for inclusion in fusion protein coding sequence)
source                   1..4173
                         mol_type = other RNA
                         organism = synthetic construct
SEQUENCE: 230
gacaagaagt acagcatcgg actggcaatc ggaacaaaca gcgtcggatg ggcagtcatc     60
acagacgaat acaaggtccc gagcaagaag ttcaaggtcc tgggaaacac agacagacac    120
agcatcaaga gaacctgat cggagcactg ctgttcgaca gcgagaaac agcagaagca    180
acaagactga gagaacagc aagaagaaga tacacaagaa gaagaacag atctgctac     240
ctgcaggaaa tcttcagcaa cgaaatgca aaggtcgacg acagcttctt ccacagactg    300
gaagaaagct tcctggtcga agaagacaag aagcacgaaa gacacccgat cttcggaaac    360
```

```
atcgtcgacg aagtcgcata ccacgaaaag tacccgacaa tctaccacct gagaaagaag   420
ctggtcgaca gcacagacaa ggcagacctg agactgatct acctggcact ggcacacatg   480
atcaagttca gaggacactt cctgatcgaa ggagacctga acccggacaa cagcgacgtc   540
gacaagctgt tcatccagct ggtccagaca taaccagc tgttcgaaga aaacccgatc    600
aacgcaagcg gagtcgacgc aaaggcaatc ctgagcgcaa gactgagcaa gagcagaaga   660
ctggaaaacc tgatcgcaca gctgccggga gaaaagaaga acggactgtt cggaaacctg   720
atcgcactga gcctgggact gacaccgaac ttcaagagca acttcgacct ggcagaagac   780
gcaaagctgc agctgagcaa ggacacatac gacgacgacc tggacaacct gctggcacag   840
atcggagacc agtacgcaga cctgttcctg gcagcaaaga acctgagcga cgcaatcctg   900
ctgagcgaca tcctgagagt caacacagaa atcacaaagg caccgctgag cgcaagcatg   960
atcaagagat acgacgaaca ccaccaggac ctgacactgc tgaaggcact ggtcagacag  1020
cagctgccgg aaaagtacaa ggaaatcttc ttcgaccaga gcaagaacgg atacgcagga  1080
tacatcgacg gaggagcaag ccaggaagaa ttctacaagt tcatccagcc gatcctggaa  1140
aagatggacg gaacagagaa actgctggtc aagctgacaa gagaagacct gctgagaaag  1200
cagagaacat tcgacaacgg aagcatcccg caccagatcc acctgggaga actgcacgca  1260
atcctgagaa gacaggaaga cttctacccg ttcctgaagg acaacagaga aaagatcgaa  1320
aagatcctga cattcagaat cccgtactac gtcggaccgc tggcaagagg aaacagcaga  1380
ttcgcatgga tgacaagaaa gagcgaagaa acaatccacc cgtggaactt cgaagaagtc  1440
gtcgacaagg gagcaagcgc acagagcttc atcgaaagaa tgacaaactt cgacaagaac  1500
ctgccgaacg aaaaggtcct gccgaagcac agcctgctgt acgaatactt cacagtctac  1560
aacgaactga caaaggtcaa gtacgtcaca gaaggaatga gaaagccggc attcctgagc  1620
ggagaacaga agaaggcaat cgtcgacctg ctgttcaaga caacagaaag gctcacagtc  1680
aagcagctga aggaagacta cttcaagaag atcgaatgct cgacagcgt cgaaatcagc  1740
ggagtcgaag acagattcaa cgcaagcctg ggaacatacc acgacctgct gaagatcatc  1800
aaggacaagg acttcctgga caacgaagaa acgaagaca tcctggaaga catcgtcctg  1860
acactgacac tgttcgaaga cagagaaatg atcgaagaaa gactgaagac atacgcacac  1920
ctgttcgacg acaaggtcat gaagcagctg aagagaagaa gatacacagg atggggaaga  1980
ctgagcagaa agctgatcaa cggaatcaga gacaagcaga gcggaaagac aatcctggac  2040
ttcctgaaga gcgacggatt cgcaaacaga aacttcatgc agctgatcca cgacgacagc  2100
ctgacattca aggaagacat ccagaaggca caggtcagcg gacaggggaa cagcctgcac  2160
gaacacatcg caaacctggc aggaagcccg gcaatcaaga agggaatcct gcagacagtc  2220
aaggtcgtcg acgaactggt caaggtcatg ggaagacaca agccggaaaa catcgtcatc  2280
gaaatggcaa gagaaaacca gacaacacag aagggacaga gaacagcag agaaagaatg  2340
aagagaacgg aagaaggaat caaggaactg ggaagccaga tcctgaagga cacccggtc  2400
gaaaacacac agctgcagaa cgaaaagctg tacctgtact acctgcagaa cggaagagac  2460
atgtacgtcg accaggaact ggacatcaac agactgagcg actacgacgt cgacgcaatc  2520
gtcccgcaga gcttcctgaa ggacgacagc atcgacaaca aggtcctgac aagaagcgac  2580
aagaacagag aaagagcga caacgtcccg agcgaagaag tcgtcaagaa gatgaagaac  2640
tactgcgaca gctgctgaa cgcaaagctg atcacacaga gaaagttcga caacctgaca  2700
aaggcagaga gaggaggact gagcgaactg gacaaggcag gattcatcaa gagacagctg  2760
gtcgaaacaa gacagatcac aaagcacgtc gcacagatcc tggacagcag aatgaacaca  2820
aagtacgacg aaaacgacaa gctgatcaga gaagtcaagg tcatcacact gaagagcaag  2880
ctggtcagcg acttcagaaa ggacttccag ttctacaagg tcagagaaat caacaactac  2940
caccacgcac acgacgcata cctgaacgca gtcgtcggaa cagcactgat caagaagtac  3000
ccgaagctgg aaagcgaatt cgtctacgga gactacaagg tctacgacgt cagaaagatg  3060
atcgcaaaga gcgaacagga atcggaaag gcaacagcaa agtacttctt ctacagcaac  3120
atcatgaact tcttcaagac agaaatcaca ctggcaaacg gagaaatcag aaagagaccg  3180
ctgatcgaaa caaacggaga aacaggagaa atcgtctggg acaagggaag agacttcgca  3240
acagtcagaa aggtcctgag catgccgcag gtcaacatcg tcaagaagac agaagtccag  3300
acaggaggat tcagcaagga aagcatcctg ccgaagagaa acagcgacaa gctgatcgca  3360
agaaagaagg actgggaccc gaagaagtac ggaggattgc agacccgac agtcgcatac  3420
agcgtcctgg tcgtcgcaaa ggtcgaaaag ggaagagca agaagctgaa gagcgtcaag  3480
gaactgctgg gaatcacaat catggaaaga agcagcttcg aaaagaaccc gatcgacttc  3540
ctggaagcaa agggatacaa ggaagtcaag aaggacctga tcatcaagct gccgaagtac  3600
agcctgttcg aactggaaaa cggaagaaag agaatgctgg caagcgcagg agaactgcag  3660
aagggaaacg aactggcact gccgagcaag tacgtcaact tcctgtacct ggcaagccac  3720
tacgaaaagc tgaagggaag cccggaagac aacgaacaga gcagctgtt cgtcgaacag  3780
cacaagcact acctggacga aatcatcgaa cagatcagcg aattcagcaa gagagtcatc  3840
ctggcagacg caaacctgga caaggtcctg agcgcataca acaagcacag agcaagccag  3900
atcagagaac aggcagaaaa catcatccac ctgttcacac tgacaaacct gggagcaccg  3960
gcagcattca gtacttcga cacaacatc gacagaaaga gatacacaag cacaaaggaa  4020
gtcctggacg caacactgat ccaccagagc atcacaggac tgtacgaaac aagaatcgac  4080
ctgagccagc tgggaggaga cggaagcgga agcccgaaga gaagagaaa ggtcgacgga  4140
agcccgaaga agaagagaa ggtcgacagc gga                                4173

SEQ ID NO: 231          moltype = DNA  length = 17
FEATURE                 Location/Qualifiers
misc_feature            1..17
                        note = Synthetic: T7 Promoter
source                  1..17
                        mol_type = other DNA
                        organism = synthetic construct
SEQUENCE: 231
taatacgact cactata                                                   17

SEQ ID NO: 232          moltype = DNA  length = 50
FEATURE                 Location/Qualifiers
misc_feature            1..50
                        note = Human beta-globin 5 UTR
```

```
source                  1..50
                        mol_type = genomic DNA
                        organism = Homo sapiens
SEQUENCE: 232
acatttgctt ctgacacaac tgtgttcact agcaacctca aacagacacc          50

SEQ ID NO: 233          moltype = DNA   length = 132
FEATURE                 Location/Qualifiers
misc_feature            1..132
                        note = Human beta-globin 3 UTR
source                  1..132
                        mol_type = genomic DNA
                        organism = Homo sapiens
SEQUENCE: 233
gctcgctttc ttgctgtcca atttctatta aggttccttt gttcccctaa gtccaactac    60
taaactgggg gatattatga agggccttga gcatctggat tctgcctaat aaaaaacatt  120
tattttcatt gc                                                      132

SEQ ID NO: 234          moltype = DNA   length = 66
FEATURE                 Location/Qualifiers
misc_feature            1..66
                        note = Human alpha-globin 5 UTR
source                  1..66
                        mol_type = genomic DNA
                        organism = Homo sapiens
SEQUENCE: 234
cataaaccct ggcgcgctcg cggcccggca ctcttctggt ccccacagac tcagagagaa   60
cccacc                                                             66

SEQ ID NO: 235          moltype = DNA   length = 110
FEATURE                 Location/Qualifiers
misc_feature            1..110
                        note = Human alpha-globin 3 UTR
source                  1..110
                        mol_type = genomic DNA
                        organism = Homo sapiens
SEQUENCE: 235
gctggagcct cggtggccat gcttcttgcc ccttgggcct ccccccagcc cctcctcccc   60
ttcctgcacc cgtaccccccg tggtctttga ataaagtctg agtgggcggc            110

SEQ ID NO: 236          moltype = DNA   length = 29
FEATURE                 Location/Qualifiers
misc_feature            1..29
                        note = Xenopus laevis beta-globin 5 UTR
source                  1..29
                        mol_type = genomic DNA
                        organism = Xenopus laevis
SEQUENCE: 236
aagctcagaa taaacgctca actttggcc                                    29

SEQ ID NO: 237          moltype = DNA   length = 130
FEATURE                 Location/Qualifiers
misc_feature            1..130
                        note = Xenopus laevis beta-globin 3 UTR
source                  1..130
                        mol_type = genomic DNA
                        organism = Xenopus laevis
SEQUENCE: 237
accagcctca agaacacccg aatggagtct ctaagctaca taataccaac ttcactttta   60
caaaatgttg tcccccaaaa tgtagccatt cgtatctgct cctaataaaa agaaagtttc  120
ttcacattct                                                         130

SEQ ID NO: 238          moltype = DNA   length = 27
FEATURE                 Location/Qualifiers
misc_feature            1..27
                        note = Bovine Growth Hormone 5 UTR
source                  1..27
                        mol_type = genomic DNA
                        organism = Bos taurus
SEQUENCE: 238
cagggtcctg tggacagctc accagct                                      27

SEQ ID NO: 239          moltype = DNA   length = 102
FEATURE                 Location/Qualifiers
misc_feature            1..102
                        note = Bovine Growth Hormone 3 UTR
source                  1..102
                        mol_type = genomic DNA
                        organism = Bos taurus
```

-continued

```
SEQUENCE: 239
ttgccagcca tctgttgttt gcccctcccc cgtgccttcc ttgaccctgg aaggtgccac    60
tcccactgtc ctttcctaat aaaatgagga aattgcatcg ca                      102

SEQ ID NO: 240          moltype = DNA   length = 93
FEATURE                 Location/Qualifiers
misc_feature            1..93
                        note = Mus musculus hemoglobin alpha, adult chain 1
                           (Hba-a1), 3UTR
source                  1..93
                        mol_type = genomic DNA
                        organism = Mus musculus
SEQUENCE: 240
gctgccttct gcggggcttg ccttctggcc atgcccttct tctctcccct gcacctgtac    60
ctcttggtct ttgaataaag cctgagtagg aag                                93

SEQ ID NO: 241          moltype = DNA   length = 61
FEATURE                 Location/Qualifiers
misc_feature            1..61
                        note = Synthetic: HSD17B4 5 UTR
source                  1..61
                        mol_type = other DNA
                        organism = synthetic construct
SEQUENCE: 241
tcccgcagtc ggcgtccagc ggctctgctt gttcgtgtgt gtgtcgttgc aggccttatt    60
c                                                                    61

SEQ ID NO: 242          moltype = RNA   length = 100
FEATURE                 Location/Qualifiers
misc_feature            1..100
                        note = Synthetic: G282 single guide RNA targeting the mouse
                           TTR gene
modified_base           1..3
                        mod_base = OTHER
                        note = PS linkage, 2'-O-Me nucleotide
modified_base           29..40
                        mod_base = OTHER
                        note = 2'-O-Me nucleotide
modified_base           69..96
                        mod_base = OTHER
                        note = 2'-O-Me nucleotide
modified_base           97..100
                        mod_base = OTHER
                        note = PS linkage, 2'-O-Me nucleotide
source                  1..100
                        mol_type = other RNA
                        organism = synthetic construct
SEQUENCE: 242
ttacagccac gtctacagca gttttagagc tagaaatagc aagttaaaat aaggctagtc    60
cgttatcaac ttgaaaaagt ggcaccgagt cggtgctttt                         100

SEQ ID NO: 243          moltype =    length =
SEQUENCE: 243
000

SEQ ID NO: 244          moltype = DNA   length = 4405
FEATURE                 Location/Qualifiers
misc_feature            1..4405
                        note = Synthetic: Cas9 transcript with 5 UTR of HSD, ORF
                           corresponding to SEQ ID NO: 204, and 3 UTR of ALB
source                  1..4405
                        mol_type = other DNA
                        organism = synthetic construct
SEQUENCE: 244
gggtcccgca gtcggcgtcc agcggctctg cttgttcgtg tgtgtgtcgt tgcaggcctt    60
attcggatcc atggacaaga agtacagcat cggactggac atcggaacaa acagcgtcgg   120
atgggcagtg atcacagacg aatacaaggt cccgagcaag aagttcaagg tcctgggaaa   180
cacagacaga cacagcatca agaagaacct gatcggagca ctgctgttcg acagcggaga   240
aacagcagaa gcaacaagac tgaagagaac agcaagaaga agatacacaa gaagaaagaa   300
cagaatctgc tacctgcagg aaatcttcag caacgaaatg gcaaaggtcg acgacagctt   360
cttccacaga ctggaagaaa gcttcctggt cgaagaagac aagaagcacg aaagacaccc   420
gatcttcgga aacatcgtcg acgaagtcgc ataccacgaa agtacccga caatctacca   480
cctgagaaag aagctggtcg acagcacaga caaggcagac tgagactga tctacctggc   540
actggcacac atgatcaagt tcagaggaca cttcctgatc gaaggagacc tgaacccgga   600
caacagcgac gtcgacaagc tgttcatcca gctggtccag acatacaacc agctgttcga   660
agaaaacccg atcaacgcaa gcggagtcga cgcaaaggca atcctgagcg caagactgag   720
caagagcaga agactggaaa acctgatcgc acagctgccg ggagaaaaga gaacggact   780
gttcggaaac ctgatcgcac tgagcctggg actgacaccg aacttcaaga gcaacttcga   840
cctggcagaa gacgcaaagc tgcagctgag caaggacaca tacgacgacg acctggacaa   900
```

```
cctgctggca cagatcggag accagtacgc agacctgttc ctggcagcaa agaacctgag    960
cgacgcaatc ctgctgagcg acatcctgag agtcaacaca gaaatcacaa aggcaccgct   1020
gagcgcaagc atgatcaaga gatacgacga acaccaccag gacctgacac tgctgaaggc   1080
actggtcaga cagcagctgc cggaaaagta caaggaaatc ttcttcgacc agagcaagaa   1140
cggatacgca ggatacatcg acggaggagc aagccaggaa gaattctaca agttcatcaa   1200
gccgatcctg gaaagatgg acggaacaga agaactgctg gtcaagctga acagagaaga    1260
cctgctgaga aagcagagaa cattcgacaa cggaagcatc ccgcaccaga tccacctggg   1320
agaactgcac gcaatcctga agacagga agacttctac ccgttcctga aggacaacag     1380
agaaaagatc gaaaagatcc tgacattcag aatcccgtac tacgtcggac cgctggcaag   1440
aggaaacagc agattcgcat ggatgacaag aaagagcgaa gaaacaatca caccgtggaa   1500
cttcgaagaa gtcgtcgaca agggagcaag cgcacagagc ttcatcgaaa gaatgacaaa   1560
cttcgacaag aacctgccga cgaaaaggt cctgccgaag cacagcctgc tgtacgaata    1620
cttcacagtc tacaacgaac tgacaaaggt caagtacgtc acagaaggaa tgagaaagcc   1680
ggcattcctg agcggagaac agaagaaggc aatcgtcgac ctgctgttca agacaaacag   1740
aaaggtcaca gtcaagcagc tgaaggaaga ctacttcaag aagatcgaat gcttcgacag   1800
cgtcgaaatc agcggagtcg aagacagatt caacgcaagc ctgggaacat accacgacct   1860
gctgaagatc atcaaggaca aggacttcct ggacaacgaa gaaaacgaag acatcctgga   1920
agacatcgtc ctgacactga cactgttcga agacagagaa atgatcgaag aaagactgaa   1980
gacatacgca caccctgttcg acgacaaggt catgaagcag ctgaagagaa gaagatacac   2040
aggatgggga agactgagca gaaagctgat caacggaatc agagacaagc agagcggaaa   2100
gacaatcctg gacttcctga agagcgacgg attcgcaaac agaaacttca tgcagctgat   2160
ccacgacgac agcctgacat tcaaggaaga catccagaag gcacaggtca gcggacaggg   2220
agacagcctg cacgaacaca tcgcaaacct ggcaggaagc ccggcaatca gaagggaat    2280
cctgcagaca gtcaaggtcg tcgacgaact ggtcaaggtc atgggaagac acaagccgga   2340
aaacatcgtc atcgaaatgg caagagaaaa ccagacaaca cagaagggac agaagaacag   2400
cagagaaaga atgaagagaa tcgaagaagg aatcaaggaa ctgggaagcc agatcctgaa   2460
ggaacacccg gtcgaaaaca cacagctgca gaacgaaaag ctgtacctgt actacctgca   2520
gaacggaaga gacatgtacg tcgaccagga actggacatc aacagactga gcgactacga   2580
cgtcgaccac atcgtcccgc agagcttcct gaaggacgac agcatcgaca caaggtcct    2640
gacaagaagc gacaagaaca gaggaaagag cgacaacgtc ccgagcgaag aagtcgtcaa   2700
gaagatgaag aactactgga gacagctgct gaacgcaaag ctgatcacac agagaaagtt   2760
cgacaacctg acaaaggcag agaggaggag actgagcgaa ctggacaagg caggattcat   2820
caagagacag ctggtcgaaa caagacagat cacaaagcac gtcgcacaga tcctggacag   2880
cagaatgaac acaaagtacg acgaaaacga caagctgatc agagaagtca aggtcatcac   2940
actgaagagc aagctggtca gcgacttcag aaaggacttc cagttctaca aggtcagaga   3000
aatcaacaac taccaccacg cacacgacgc atacctgaac gcagtcgtcg gaacagcact   3060
gatcaagaag taccccgaagc tggaaagcga attcgtctac ggagactaca aggtctacga   3120
cgtcagaaag atgatcgcaa agagcgaaca ggaaatcgga aaggcaacag caaagtactt   3180
cttctacagc aacatcatga acttcttcaa gacagaaatc acactggcaa acggagaaat   3240
cagaaagaga ccgctgatcg aaacaaacgg agaaacagga gaaatcgtct gggacaaggg   3300
aagagacttc gcaacagtca gaaaggtcct gagcatgccg caggtcaaca tcgtcaagaa   3360
gacagaagtc cagacaggag gattcagcaa ggaaagcatc ctgccgaaga gaaacagcga   3420
caagctgatc gcaagaaaga aggactggga cccgaagaag tcgacagccc   3480
gacagtcgca tacagcgtcc tggtcgtcgc aaaggtcgaa aagggaaaga gcaagaagct   3540
gaagagcgtc aaggaactgc tgggaatcac aatcatggaa agaagcagct cgaaaagaa    3600
cccgatcgac ttcctggaag caagggata caaggaagtc agaaggacc tgatcatcaa     3660
gctgccgaag tacagcctgt tcgaactgga aaacggaaga aaggaatgc tggcaagcgc    3720
aggagaactg cagaagggaa acgaactggc actgccgagc aagtacgtca acttcctgta   3780
cctggcaagc cactacgaaa agctgaaggg aagcccggaa gacaacgaac agaagcagct   3840
gttcgtcgaa cagcacaagc actacctgga cgaaatcatc gaacagatca gcgaattcag   3900
caagagagtc atcctggcag acgcaaacct ggacaaggtc ctgagcgcat acaacaagca   3960
cagagacaag ccgatcagag aacaggcaga aaacatcatc caccctgttca cactgacaaa   4020
cctgggagca ccggcagcat tcaagtactt cgacacaaca atcgacagaa agagatacac   4080
aagcacaaag gaagtcctgg acgcaacact gatccaccag agcatcacag gactgtacga   4140
aacaagaatc gacctgagcc agctgggagg agacgggaga ggaagcccga cgaagaagag   4200
aaaggtctag ctagccatca catttaaaag catctcagcc taccatgaga ataagaaaa    4260
gaaaatgaag atcaatagct tattcatctc ttttctttt cgttggtgt aaagccaaca     4320
ccctgtctaa aaaacataaa ttttctttaat cattttgcct cttttctctg tgcttcaatt   4380
aataaaaaat ggaagaacc tcgag                                          4405

SEQ ID NO: 245       moltype = DNA   length = 4188
FEATURE              Location/Qualifiers
misc_feature         1..4188
                     note = Synthetic: Alternative Cas9 ORF with 19.36% U content
source               1..4188
                     mol_type = other DNA
                     organism = synthetic construct
SEQUENCE: 245
atggataaga agtactcgat cgggctggat atcggaacta attccgtggg ttgggcagtg    60
atcacggatg aatacaaagt gccgtccaag aagttcaagg tcctggggaa caccgataga   120
cacagcatca gaagaatct catcggagcc ctgctgtttg actccggcga aaccgcagaa    180
gcgacccggc tcaaacgtac cgcgaggcga cgctacaccc ggcggaagaa tcgcatctgc   240
tatctgcaag aaatcttttc gaacgaaatg gcaaggtgg acgacagctt cttccaccgc   300
ctggaagaat ctttcctggt ggaggaggac aagaagcatg aacggcatcc tatctttga    360
aacatcgtgg acgaagtggc gtaccacgaa aagtacccga ccatctacca tctgcgaaag   420
aagttggttg actcaactga aaggccgac ctcagattga tctacttggc cctgcccat     480
atgatcaaat tccgcggaca cttcctgatc gaaggcgatc tgaaccctga taactccgac   540
gtggataagc tgttcattca actggtgcag acctacaacc aactgttcga agaaaaccca   600
atcaatgcca gcggcgtcga tgccaaggcc atcctgtccg ccggctgtc gaagtcgcgg   660
```

```
cgcctcgaaa acctgatcgc acagctgccg ggagagaaga agaacggact tttcggcaac   720
ttgatcgctc tctcactggg actcactccc aatttcaagt ccaattttga cctggccgag   780
gacgcgaagc tgcaactctc aaaggacacc tacgacgacg acttggacaa tttgctggca   840
caaattggcg atcagtacgc ggatctgttc cttgccgcta agaacctttc ggacgcaatc   900
ttgctgtccg atatcctgcg cgtgaacacc gaaataacca aagcgccgct tagcgcctcg   960
atgattaagc ggtacgacga gcatcaccag gatctcacgc tgctcaaagc gctcgtgaga  1020
cagcaactgc ctgaaaagta caaggagatt ttcttcgacc agtccaagaa tgggtacgca  1080
gggtacatcg atggaggcgc cagccaggaa gagttctata agttcatcaa gccaatcctg  1140
gaaaagatgg acggaaccga agaactgctg gtcaagctga acagggagga tctgctccgc  1200
aaacagagaa cctttgacaa cggaagcatt ccacaccaga tccatctggg tgagctgcac  1260
gccatcttgc ggcgccagga ggacttttac ccattcctca aggacaaccg ggaaaagatc  1320
gagaaaattc tgacgttccg catcccgtat tacgtgggcc cactggcgcg cggcaattcg  1380
cgcttcgcgt ggatgactag aaaatcgagg gaaaccatca ctccttggaa tttcgaggag  1440
gttgtggata agggagcttc ggcacaatcc ttcatcgaag atgaccaa cttcgacaag  1500
aatctcccaa acgagaaggt gcttcctaag cacagcctcc tttacgaata cttcactgtc  1560
tacaacgaac tgactaaagt gaaatacgtt actgaaggaa tgaggaagcc ggcctttctg  1620
agcggagaac agaagaaagc gattgtcgat ctgctgttca agaccaaccg caaggtgacc  1680
gtcaagcagc ttaaagagga ctacttcaag aagatcgagt gtttcgactc agtggaaatc  1740
agcggagtgg aggacagatt caacgcttcg ctgggaacct atcatgatct cctgaagatc  1800
atcaaggaca aggacttcct tgacaacgag gagaacgagg acatcctgga agatatcgtc  1860
ctgaccttga cccttttcga ggatcgcgag atgatcgagg agaggcttaa gacctacgct  1920
catctcttcg acgataaggt catgaaacaa ctcaagcgcc gccggtacac tggttgggc  1980
cgcctctccc gcaagctgat caacggtatt cgcgataaac agagcggtaa aactatcctg  2040
gatttcctca aatcggatgg cttcgctaat cgtaacttca tgcagttgat ccacgacgac  2100
agcctgacct ttaaggagga catccagaaa gcacaagtga gcgacaggg agactcactc  2160
catgaacaca tcgcgaatct ggccggttcg ccggcgatta agaagggaat cctgcaaact  2220
gtgaaggtgg tggacgagct ggtgaaggtc atgggacgag acaaaccgga gaatatcgtg  2280
attgaaatgg cccgagaaaa ccagactacc cagaagggcc agaagaactc ccgcgaaagg  2340
atgaagcgga tcgaagaagg aatcaaggag ctgggcagcc agatcctgaa agagcacccg  2400
gtggaaaaca cgcagctgca gaacgagaag tctctacctgt actatttgca aaatggacgg  2460
gacatgtacg tggaccaaga gctggacatc aatcgttgt ctgattacga cgtggaccac  2520
atcgttccac agtcctttct gaaggatgac tccatcgata caaggtgtt gactcgcagc  2580
gacaagaaca gagggaagtc agataatgtg ccatcggagg aggtcgtgaa gaagatgaag  2640
aattactggc ggcagctcct gaatgcgaag ctgattaccc agagaaagtt tgacaatctg  2700
actaaagccg agcgcggcgg actctcagag ctggataagg ctggattcat caaacggcag  2760
ctggtcgaga ctcggcagat taccaagcac gtgcgcaga tcctggactc ccgcatgaac  2820
actaaatacg acgagaacga taagctcatc cgggaagtga aggtgattac cctgaaaagc  2880
aaacttgtgt cggactttcg gaaggacttt cagttttaca aagtgagaga atcaacaac  2940
taccatcacg cgcatgacgc atacctcacg gctgtgtcg gcacgcccct gatcaagaag  3000
tacctaaac ttgaatcgga gtttgtgtac ggagactaca aggtctacga cgtgaggaag  3060
atgatagcca agtccgaaca ggaaatcggg aaagcaactg cgaaatactt cttttactca  3120
aacatcatga acttcttcaa gactgaaatt acgctggcca atggagaaat caggaagagg  3180
ccactgatcg aaactaacgg agaaacgggc gaaatcgtgt gggacaaggg cagggacttc  3240
gcaactgttc gcaaagtgct ctctatgccg caagtcaata ttgtgaagaa accgaagtg  3300
caaaccggcg gattttcaaa ggaatcgatc ctcccaaaga gaaatagcga caagctcatt  3360
gcacgcaaga aagactggga cccgaagaag tacgaggat tcgattcgcc gactgtcgca  3420
tactccgtcc tcgtgtgc caggtgag aagggaaga acaagaagct caaatccgtc  3480
aaagagctgc tggggattac catcatgaa cgatcctcgt tcgagaagaa cccgattgat  3540
ttcctggagg cgaagggtta caaggaggtg aagaaggatc tgatcatcaa actgcccaag  3600
tactcactgt tcgaactgga aaatggtcgg aagcgcatgc tggcttcggc cggagaactc  3660
cagaaaggaa atgagctggc cttgcctagc aagtacgtca acttcctcta tcttgcttcg  3720
cactacgaga aactcaaagg gtcaccggaa gataacgaac agaagcagct tttcgtggag  3780
cagcacaagc attatctgga tgaaatcatc gaacaaatct ccgagttttc aaagcgcgtg  3840
atcctcgccg acgccaacct cgacaaagtc ctgtcggcct acaataagca tagagataag  3900
ccgatcagag aacaggccga gaacattac cacttgttca ccctgactaa cctgggagct  3960
ccagccgcct tcaagtactt cgatactact atcgaccgca aaagatacac gtccaccaag  4020
gaagttctgg acgcgaccct gatccaccaa agcatcactg gactctacga aactaggatc  4080
gatctgtcgc agctgggtgg cgatggtggc ggtggatcct acccatacga cgtgcctgac  4140
tacgcctccg gaggtggtgg ccccaagaag aaacggaagg tgtgataag          4188

SEQ ID NO: 246     moltype = DNA   length = 4459
FEATURE            Location/Qualifiers
misc_feature       1..4459
                   note = Synthetic: Cas9 transcript with 5 UTR of HSD, ORF
                     corresponding to SEQ ID NO: 245, Kozak sequence, and 3 UTR
                     of ALB
source             1..4459
                   mol_type = other DNA
                   organism = synthetic construct
SEQUENCE: 246
gggtcccgca gtcggcgtcc agcggctctg cttgttcgtg tgtgtgtcgt tgcaggcctt    60
attcggatct gccaccatgg ataagaagta ctcgatcggg ctggatatcg aactaattc   120
cgtgggttgg gcagtgatca cggatgaata caaagtgccg tccaagaagt tcaaggtcct   180
ggggaacacc gatagacaca gcatcaagaa gaatctcatc ggagccctgc tgtttgactc   240
cggcgaaacc gcagaagcga cccgctcaa acgtaccgcg aggcgacgct acacccggg   300
gaagaatcgc atctgctatc tgcaagaaat cttttcgaac gaaatggcaa aggtggacga   360
cagcttcttc caccgcctgg aagaatcttt cctggtggag gaggacaaga agcatgaacg   420
gcatcctatc tttggaaaca tcgtggacga agtggcgtac cacgaaaagt acccgaccat   480
ctaccatctg cggaagaagt tggttgactc aactgacaag gccgacctca gattgatcta   540
```

```
cttggccctc gcccatatga tcaaattccg cggacacttc ctgatcgaag gcgatctgaa    600
ccctgataac tccgacgtgg ataagctgtt cattcaactg gtgcagacct acaaccaact    660
gttcgaagaa aacccaatca atgccagcgg cgtcgatgcc aaggccatcc tgtccgcccg    720
gctgtcgaag tcgcggcgcc tcgaaaacct gatcgcacag ctgccgggag agaagaagaa    780
cggactttc ggcaacttga tcgctctctc actgggact actcccaatt tcaagtccaa     840
ttttgacctg gccgaggacg cgaagctgca actctcaaag gacacctacg acgacgactt    900
ggacaatttg ctggcacaaa ttggcgatca gtacgcggat ctgttccttg ccgctaagaa    960
cctttcggac gcaatcttgc tgtccgatat cctgcgcgtg aacaccgaaa taaccaaagc   1020
gccgcttagc gcctcgatga ttaagcggta cgacgacgat caccaggatc tcacgctgct   1080
caaagcgctc gtgagacagc aactgcctga aaagtacaag gagattttct tcgaccagtc   1140
caagaatggg tacgcagggt acatcgatgg aggcgccagc caggaagagt tctataagtt   1200
catcaagcca atcctggaaa agatggacgg aaccgaagaa ctgctggtca agctgaacag   1260
ggaggatctg ctccgcaaac agagaacctt tgacaacgga agcattccac accagatcca   1320
tctgggtgag ctgcacgcca tcttcggcg ccaggaggac ttttacccat tcctcaagga    1380
caaccgggaa aagatcgaga aaattctgac gttccgcatc ccgtattacg tgggcccact   1440
ggcgcgcggc aattcgcgct tcgcgtggat gactagaaaa tcagaggaaa ccatcactcc   1500
ttggaatttc gaggaagttg tggataaggg agcttcggca caatccttca tcgaacgaat   1560
gaccaacttc gacaagaatc tcccaaacga gaaggtgctt cctaagcaca gcctcctta    1620
cgaatacttc actgtctaca acgaactgac taaagtgaaa tacgttactg aaggaatgag   1680
gaagccggcc tttctgagcg gagaacagaa gaaagcgatt gtcgatctgc tgttcaagac   1740
caaccgcaag gtgaccgtca gcagcttaa agaggactac ttcaagaaga tcgagtgttt    1800
cgactcagtg gaaatcaagc ggatggagga cagattcaac gcttcgctgg gaacctatca   1860
tgatctcctg aagatcatca aggacaagga cttccttgac aacgaggaga acgaggacat   1920
cctggaagat atcgtcctga ccttgacct tttcgaggat cgcgagatga tcgaggagag    1980
gcttaagacc tacgctcatc tcttcgacga taaggtcatg aaacaactca agcgccgccg   2040
gtacactggt tggggccgcc tctcccgcaa gctgatcaac ggtattcgcg ataaacagag   2100
cggtaaaact atcctggatt tcctcaaatc ggatggcttc gctaatcgta acttcatgca   2160
gttgatccac gacgacagcc tgaccttaa ggaggcatc cagaaagcac aagtgagcgg    2220
acagggagac tcactccatg aacacatcgc gaatctggcc ggttcgccgg cgattaagaa   2280
gggaatcctg caaactgtga aggtggtgga cgagctggta aggtcatgg gacggcacaa    2340
accggagaat atcgtgattg aaatggcccg agaaaaccag actcccagaa agggccagaa   2400
gaactcccgc gaaaggatga gcggatcga agaaggaatc aaggagctgg gcagccagat   2460
cctgaaagag caccccggtg gaaaacacgca gctgcagaac gagaagctct acctgtacta   2520
tttgcaaaat ggacgggaca tgtacgtgga ccaagagctg gacatcaatc ggttgtcgga   2580
ttacgacgtg gaccacatcg ttccacagtc ctttctgaag gatgactcca tcgataacaa   2640
ggtgttgact cgcagcgaca agaacagagg gaagtcagat aatgtgccat cggaggaggt   2700
cgtgaagaag atgaagaatt actggcggca gctcctgaat gcgaagctga ttacccagag   2760
aaagtttgac aatctcacta agccgagcg cggcggactc tcagagctgg ataaggctgg   2820
attcatcaaa cggcagctgg tcgagactcg gcagattacc aagcacgtgg cgcagatcct   2880
ggactcccgc atgaacacta aatacgacga gaacgataag ctcatccggg aagtgaaggt   2940
gattaccctg aaaagcaaac ttgtgtcgga ctttcggaag gactttcagt tttacaaagt   3000
gagagaaatc aacaactacc atcacgcgca tgacgcatac ctcaacgctg tggtcggcac   3060
cgccctgatc aagaagtacc ctaaacttga atcggagttt gtgtacggag actacaaggt   3120
ctacgacgtg aggaagatga tagccaagtc cgaacaggaa atcggaaag caactgcgaa    3180
atacttcttt tactcaaaca tcatgaactt cttcaagact gaaattacgc tggccaatgg   3240
agaaatcagg aagaggccac tgatcgaaac taacggagaa acgggcgaaa tcgtgtggga   3300
caagggcagg gacttcgcaa ctgttcgcaa agtgctctct atgccgcaag tcaatattgt   3360
gaagaaaacc gaagtgcaaa ccggcggatt ttcaaaggaa tcgatcctcc caaagagaaa   3420
tagcgacaag ctcattgcac gcaagaaaga ctgggacccg aagaagtacg gaggattcga   3480
ttcgccgact gtcgcatact ccgtcctcgt ggtggccaag gtgagaagg gaaagagcaa    3540
gaagctcaaa tccgtcaaag agctgctggg gattaccatg atggaacgat cctcgttcga   3600
gaagaacccg attgatttcc tggaggcgaa gggttacaag gaggtgaaga aggatctgat   3660
catcaaactg cccaagtact cactgttcga actggaaaat ggtcggaagc gcatgctggc   3720
ttcggccgga gaactccaga aaggaaatga gctggccttg cctagcaagt acgtcaactt   3780
cctctatctt gcttcgcact acgagaaact caaagggtca ccggaagata acgaacagaa   3840
gcagcttttc gtggagcagc acaagcatta tctggatgaa atcatcgaac aaatctccga   3900
gttttcaaag cgcgtgatcc tcgccgacgc caacctcgac aaagtcctgt cggcctacaa   3960
taagcataga gataagccga tcagagaaca ggccgagaac attatccact tgttcacct   4020
gactaacctg ggagctccag ccgccttcaa gtacttcgat actactatcg accgcaaaag   4080
atacacgtcc accaaggaag ttctggacgc gaccctgatc caccaaagca tcactggact   4140
ctacgaaact aggatcgatc tgtcgcagct gggtggcgat ggtggcggtg atcctaccc    4200
atacgacgtg cctgactacg cctccggagg tggtggcccc aagaagaaac ggaaggtgtg   4260
atagctagcc atcacattta aaagcatctc agcctaccat gagaataaga gaaagaaat    4320
gaagatcaat agcttattca tctctttttc ttttcgtttg gtgtaaagcc aacaccctgt   4380
ctaaaaaca taaattcctt taatcatttt gcctcttttc tctgtgcttc aattaataaa   4440
aaatggaaag aacctcgag                                               4459
```

SEQ ID NO: 247         moltype = DNA   length = 4453
FEATURE                Location/Qualifiers
misc_feature           1..4453
                       note = Synthetic: Cas9 transcript with 5 UTR of HSD, ORF
                        corresponding to SEQ ID NO: 245, and 3 UTR of ALB
source                 1..4453
                       mol_type = other DNA
                       organism = synthetic construct
SEQUENCE: 247
gggtcccgca gtcggcgtcc agcggctctg cttgttcgtg tgtgtgtcgt tgcaggcctt     60
attcggatct atggataaga agtactcgat cgggctggat atcggaacta attccgtggg   120
ttgggcagtg atcacggatg aatacaaagt gccgtccaag aagttcaagg tcctggggaa   180

```
caccgataga cacagcatca agaagaatct catcggagcc ctgctgtttg actccggcga    240
aaccgcagaa gcgacccggc tcaaacgtac cgcgaggcga cgctacaccc ggcggaagaa    300
tcgcatctgc tatctgcaag aaatctttc gaacgaaatg gcaaaggtgg acgacagctt    360
cttccaccgc ctggaagaat ctttcctggt ggaggaggac aagaagcatg aacggcatcc    420
tatctttgga aacatcgtgg acgaagtggc gtaccaccga aagtacccga ccatctacca    480
tctgcggaag aagttggttg actcaactga caaggccgac ctcagattga tctacttggc    540
cctgcccat atgatcaaat tccgcggaca cttcctgatc gaaggcgatc tgaaccctga    600
taactccgac gtggataagc tgttcattca actggtgcag acctacaacc aactgttcga    660
agaaaccca atcaatgcca gcggcgtcga tgccaaggcc atcctgtccg cccggctgtc    720
gaagtcgcgg cgcctcgaaa acctgatcgc acagctgccg ggagagaaga agaaccggact  780
tttcggcaac ttgatcgctc tctcactggg actcactccc aatttcaagt ccaattttga    840
cctgccgag gacgcgaagc tgcaactctc aaaggacacc tacgacgacg acttggacaa    900
tttgctggca caaattggcg atcagtacgc ggatctgttc cttgccgcta agaaccttc    960
ggacgcaatc ttgctgtccg atatcctgcg cgtgaaccac gaaataacca aagcgccgct  1020
tagcgcctcg atgattaagc ggtacgacga gcatccacag gatctcacgc tgctcaaagc  1080
gctcgtgaga cagcaactgc ctgaaaagta caagggagat tcttcgacc agtccaagaa  1140
tgggtacgca gggtacatcg atggaggcgc cagccaggaa gagttctata agttcatcaa  1200
gccaatcctg gaaaagatgg acggaaccga agaactgctg gtcaagctga acagggagga  1260
tctgctccgc aaacagagaa cctttgacaa cggaagcatt ccacaccaga tccatctggg  1320
tgagctgcac gccatcttgc ggcgccagga ggacttttac ccattcctca aggacaaccg  1380
ggaaaagatc gagaaaattc tgacgttccg catcccgtat tacgtgggcc cactggcgcg  1440
cggcaattcg cgcttcgcgt ggatgactag aaaatcagag gaaaccatca ctccttggaa  1500
tttcgaggaa gttgtggata agggagcttc ggcacaatcc ttcatcgaac gaatgaccaa  1560
cttcgacaag aatctcccaa acgagaaggt gcttcctaag cacagcctcc tttacgaata  1620
cttcactgtc tacaacgaac tgactaaagt gaaatacgtt actgaaggaa tgaggaagcc  1680
ggcctttctg agcggagaac agaagaaagc gattgtcgat ctgctgttca agaccaaccg  1740
caaggtgacc gtcaagcagc ttaaagagga ctacttcaag aagatcgagt gtttcgactc  1800
agtggaaatc agcggagtgg aggacagatt caacgcttcg ctgggaacct atcatgatct  1860
cctgaagatc atcaaggaca aggacttcct tgacaacgag gagaacgagg acatcctgga  1920
agatatcgtc ctgaccttga ccctttcga ggatcgcgag atgatcgagg agaggcttaa  1980
gacctacgct catctcttcg acgataaggt catgaaacaa ctcaagcgcc gccggtacac  2040
tggttgggc cgcctctccc gcaagctgat aacggtatt cgcgataaac agagcggtaa  2100
aactatcctg gatttcctca aatcggatgg cttcgctaat cgtaacttca tgcagttgat  2160
ccacgacgac agcctgacct ttaaggagga catccagaaa gcacaagtga gcggacaggg  2220
agactcactc catgaacaca tcgcgaatct ggccggttcg ccggcgatta agaaggaat  2280
cctgcaaact gtgaaggtgg tggacgagct ggtgaaggtc atgggacggc acaaaccgga  2340
gaatatcgtg attgaaatgg cccgagaaaa ccagactacc cagaagggcc agaagaactc  2400
ccgcgaaagg atgaagcgga tcgaagaagg aatcaaggag ctgggcagcc agatcctgaa  2460
agagcacccg gtggaaaaca cgcagctgca gaacgagaag ctctcacctgt actatttgca  2520
aaatggacgg gacatgtacg tggaccaaga gctggacatc aatcggttgt ctgattacga  2580
cgtgaccac atcgttccac agtcctttct gaaggatgac tccatcgata caaggtgtt  2640
gactcgcagc gacaagaaca gagggaagtc agataatgtg ccatcggagg aggtcgtgaa  2700
gaagatgaag aattactggc ggcagctcct gaatgcgaag ctgattaccc agagaaagtt  2760
tgacaatctc actaaagccg agcgcggcg actctcagag ctggataagg ctggattcat  2820
caaacggcag ctggtcgaga ctcggcagat taccaagcac gtggcgcaga tcctggactc  2880
ccgcatgaac actaaatacg acgagaacga taagctcatc cgggaagtga aggtgattac  2940
cctgaaaagc aaacttgtgt cggactttcg gaaggactt cagttttaca aagtgagaga  3000
aatcaacaac taccatcacg cgcatgacgc atacctcaac gctgtggtcg gcaccgccct  3060
gatcaagaag tacccaaac ttgaatcgga gttgtgtac ggagactaca aggtctacga  3120
cgtgaggaag atgatagcca agtccgaaca ggaaatcggg aaagcaactg cgaaatactt  3180
cttttactca aacatcatga acttcttcaa gactgaaatt acgctggcca atggagaaat  3240
caggaagagg ccactgatcg aaactaacgg agaaacgggc gaaatcgtgt gggacaaggg  3300
cagggacttc gcaactgttc gcaaagtgct ctctatgccg caagtcaata ttgtgaagaa  3360
aaccgaagtg caaaccggcg gattttcaaa ggaatcgatc ctcccaaaga gaatagcga  3420
caagctcatt gcacgcaaga aagactgga cccgaagaag tacggaggat tcgattcgcc  3480
gactgtcgca tactccgtcc tcgtggtggc caaggtggag aagggaaaga gcaagaagct  3540
caaatccgtc aaagagctgc tggggattac catcatggaa cgatcctcgt tcgagaagaa  3600
cccgattgat ttcctggagg cgaagggtta caaggaggtg aagaaggatc tgatcatcaa  3660
actgcccaag tactcactgt tcgaactgga aaatggtcgg aagcgcatgc tggcttcggc  3720
cggagaactc cagaaaggaa atgagctggc cttgcctagc aagtacgtca acttcctcta  3780
tcttgcttcg cactacgaga aactcaaagg gtcaccggaa gataacgaac agaagcagct  3840
tttcgtggag cagcacaagc attatctgga tgaaatcatc gaacaaatct ccgagttttc  3900
aaagcgcgtg atcctcgccg acgccaacct cgacaaagtc ctgtcggcct acaataagca  3960
tagagataag ccgatcagag aacaggccga gaacttatc cacttgttca ccctgactaa  4020
cctgggagct ccagccgcct tcaagtactc cgatactact atcgaccgca aaagatacac  4080
gtccaccaag gaagttctgg acgcgaccct gatccaccaa agcatcactg gactctacga  4140
aactaggatc gatctgtcgc agctgggtgg cgatggtggc ggtggatcct acccatcga  4200
cgtgcctgac tacgcctccg gaggtggtgg ccccaagaag aaacggaagg tgtgatagct  4260
agccatcaca tttaaaagca tctcagccta ccatgagaat aagagaaaga aaatgaagat  4320
caatagctta ttcatctctt ttcttttc gttggtgtaa agccaacacc ctgtctaaaa  4380
aacataaatt tctttaatca ttttgcctct tttctctgtg cttcaattaa taaaaaatgg  4440
aaagaacctc gag                                                     4453

SEQ ID NO: 248        moltype =    length =
SEQUENCE: 248
000

SEQ ID NO: 249        moltype = DNA    length = 4409
FEATURE               Location/Qualifiers
```

| misc_feature | 1..4409 |
| --- | --- |
| | note = Synthetic: Cas9 transcript comprising Kozak sequence with Cas9 ORF using codons with generally high expression in humans |
| source | 1..4409 |
| | mol_type = other DNA |
| | organism = synthetic construct |

SEQUENCE: 249

```
gggtcccgca gtcggcgtcc agcggctctg cttgttcgtg tgtgtgtcgt tgcaggcctt    60
attcggatcc gccaccatgc ctaagaaaaa gcggaaggtc gacggggata agaagtactc   120
aatcgggctg gatatcggaa ctaattccgt ggggttgggca gtgatcacgg atgaatacaa   180
agtgccgtcc aagaagttca aggtcctggg gaacaccgat agacacagca tcaagaaaaa   240
tctcatcgga gccctgctgt ttgactccgg cgaaaccgca gaagcgaccc ggctcaaacg   300
taccgcgagg cgacgctaca cccggcggaa gaatcgcatc tgctatctgc aagagatctt   360
ttcgaacgaa atggcaaagg tcgacgcacg cttcttccac cgcctggaag aatctttcct   420
ggtgagcag gacaagaagc atgaacggca tcctatcttt ggaaacatcg tcgacgaagt   480
ggcgtaccac gaaaagtacc cgaccatcta ccatctgcgg aagaagttgg ttgactcaac   540
tgacaaggcc gacctcagat tgatctactt ggccctcgcc catatgatca aattccgcgg   600
acacttcctg atcgaaggcg atctgaaccc tgataactcc gacgtggata agcttttcat   660
tcaactggtg cagacctaca accaactgtt cgaagaaaac ccaatcaatg ctagcggcgt   720
cgatgccaag gccatcctgt ccgccggct gtcgaagtcg cggcgcctcg aaaacctgat   780
cgcacagctc ccgggagaga aaaagaacgg acttttcgcg aacttgatcg ctctctcact   840
gggactcact cccaatttca agtccaattt tgacctggcc gaggacgcga agctgcaact   900
ctcaaaggac acctacgacg acgacttgga caatttgctg gcacaaattg gcgatcagta   960
cgcggatctg ttccttgccg ctaagaacct ttcggacgca atcttgctgt ccgatatcct  1020
gcgcgtgaac accgaaataa ccaaagcgcg cttagcgcc tcgatgatta gcggtacga  1080
cgagcatcac caggatctca cgctgctcaa agcgctcgtg agacagcaac tgcctgaaaa  1140
gtacaaggag atcttcttcg accagtccaa gaatgggtac gcagggtaca tcgatggagg  1200
cgctagccaa gaagagttct ataagttcat caagccaatc ctggaaaaga tggacggaac  1260
cgaagaactg ctggtcaagc tgaacaggga ggatctgctc cggaaacaga gaacctttga  1320
caacggatcc attccccacc agatccatct gggtgagctg cacgccatct tgcgcgcca  1380
ggaggacttt tacccattcc tcaaggacaa ccgggaaaag atcgagaaaa ttctgacgtt  1440
ccgcatcccg tattacgtgg gcccactggc gcgcggcaat tcgcgcttcg cgtggatgac  1500
tagaaaatca gaggaaacca tcactccttg gaatttcgag gaagttgtgg ataagggag  1560
ttcggcacaa agcttcatcg aacgaatgac caacttcgac aagaatctcc caacgagaa  1620
ggtgcttcct aagcacagcc tcctttacga atacttcact gtctacaacg aactgactaa  1680
agtgaaatac gttactgaag aatgaggaa gccggccttt ctgtccggag aacagaagaa  1740
agcaattgtc gatctgctgt tcaagaccaa ccgcaaggtg accgtcaagc agcttaaaga  1800
ggactacttc aagaagatcg agtgtttcga ctcagtggaa atcagcgggg tggaggacag  1860
attcaacgct tcgctgggaa cctatcatga tctcctgaag atcatcaagg acaaggactt  1920
ccttgacaac gaggagaacg aggacatcct ggaagatatc gtcctgaccc tgaccctttt  1980
cgaggatcgc gagatgatcg aggagaggct taagacctac gctcatcct cgacgataa  2040
ggtcatgaaa caactcaagc gccgccgta cactggttgg gccgccctct cccgcaagct  2100
gatcaacggt attcgcgata acagagcgg taaaactatc ctggatttcc tcaaatcgga  2160
tggcttcgct aatcgtaact tcatgcaatt gatccacgac gacagcctga cctttaagga  2220
ggacatccaa aaagcacaag tgtccggaca gggagactca ctccatgaac acatcgcgaa  2280
tctggccggt tcgccggcga ttaagaaggg aattctgcaa actgtggacg tggtcgacga  2340
gctggtgaag gtcatgggac ggcacaaacc ggagaatatc gtgattgaaa tggcccgaga  2400
aaaccagact acccagaagg gccagaaaaa ctcccgcgaa aggtgaagc ggatcgaaga  2460
aggaatcaag gagctgggca gccagatcct gaaagagcac ccggtggaaa acacgcagct  2520
gcagaacgag aagctctacc tgtactattt gcaaaatgga cgggacatgt actggaccca  2580
agagctggac atcaatcggt tgtctgatta cgacgtggac cacatcgttc cacagtcctt  2640
tctgaaggat gactcgatcg ataacaaggt gttgactcgc agcgcaaga acagagggaa  2700
gtcagataat gtgccatcgg aggaggtcgt gaagaagatg aagaattact ggcggcagct  2760
cctgaatgcg aagctgatta cccagagaaa gtttgacaat ctcactaaag ccgagcgcgg  2820
cggactctca gagctggata aggctggatt catcaaacgg cagctggtcg agactcggca  2880
gattaccaag cacgtggcgc agatcttgga ctcccgcatg aacactaaat acgacgagaa  2940
cgataagctc atccgggaag tgaaggtgat taccctgaaa agcaaacttg tgtcggactt  3000
tcggaaggac tttcagtttt acaaagtgag agaaatcaac aactaccatc acgcgcatga  3060
cgcatacctc aacgctgtgg tcggtaccgc cctgatcaaa aagtacccta acttgaatc  3120
ggagtttgtg tacggagact acaaggtcta cgacgtgagg aagatgatag ccaagtccga  3180
acaggaaatc gggaaagcaa ctgcgaaata cttcttttac tcaaacatca tgaacttttt  3240
caagactgaa attacgctgg ccaatggaga aatcaggaag aggccactga tcgaaactaa  3300
cggagaaacg ggcgaaatcg tgtgggacaa gggcagggac ttcgcaactg ttcgcaaagt  3360
gctctctatg ccgcaagtca atattgtgaa gaaaaccgaa gtgcaaaccg gcggattttc  3420
aaaggaatcg atcctcccaa agagaaatag cgacaagctc attgcacgca agaaagactg  3480
ggaccccgaa agtacggag gattcgattc gccgactgtc gcatactccg tcctcgtggt  3540
ggccaaggtg gagaagggaa agagcaaaaa gctcaaatcc gtcaaagagc tgctggggat  3600
taccatcatg gaacgatcct cgttcgtgaa gaacccgatt gatttcctcg aggcgaaggg  3660
ttacaaggag gtgaagaagg atctgatcat caaactcccc aagtactcac tgttcgaact  3720
ggaaaatggt cggaagcgca tgctggcttc ggccggagaa ctccaaaaag gaatgagct  3780
ggccttgcct agcaagtacg tcaacttcct ctatcttgct tcgcactacg aaaaactcaa  3840
agggtcaccg gaagataacg aacagaagca gcttttcgtg gagcagcaca gcattatct  3900
ggatgaaatc atcgaacaaa tctccgagtt ttcaaagcgc gtgatcctcg ccgacgcaa  3960
cctcgacaaa gtcctgtcgg cctacaataa gcatagagat aagccgatca gagaacaggc  4020
cgagaacatt atccacttgt tcaccctgac taacctggga gccccagccg ccttcaagta  4080
cttcgatact actatcgatc gcaaaagata cacgtccacc aaggaagttc tggacgcgac  4140
cctgatccac caaagcatca ctggactcta cgaaactagg atcgatctgt cgcagctggg  4200
tggcgattga tagtctagcc atcacatttta aaagcatctc agcctaccat gagaataaga  4260
```

```
gaaagaaaat gaagatcaat agcttattca tctcttttc tttttcgttg gtgtaaagcc   4320
aacaccctgt ctaaaaaaca taaatttctt taatcatttt gcctctttc tctgtgcttc   4380
aattaataaa aaatggaaag aacctcgag                                    4409

SEQ ID NO: 250          moltype = DNA   length = 4140
FEATURE                 Location/Qualifiers
misc_feature            1..4140
                        note = Synthetic: Cas9 ORF with splice junctions removed;
                        12.75% U content
source                  1..4140
                        mol_type = other DNA
                        organism = synthetic construct
SEQUENCE: 250
atggacaaga agtacagcat cggactggac atcggaacaa acagcgtcgg atgggcagtc    60
atcacagacg aatacaaggt cccgagcaag aagttcaagg tcctgggaaa cacagacaga   120
cacagcatca agaagaacct gatcggagca ctgctgttcg acagcggaga aacagcagaa   180
gcaacaagac tgaagagaac agcaagaaga agatacacaa gaagaaagaa cagaatctgc   240
tacctgcagg aaatcttcag caacgaaatg gcaaaggtcg acgcagctt cttccaccgg    300
ctggaagaaa gcttcctggt cgaagaagac aagaagcacg aaagacaccc gatcttcgga   360
aacatcgtcg acgaagtcgc ataccacgaa aagtacccga caatcctacc cctgagaaag   420
aagctggtca cagcacagaa caaggcagac ctgagactga tctacctggc actggcacac   480
atgatcaagt tcagaggaca cttcctgatc gaaggaagc tgaacccgga caacagcgac   540
gtcgacaagc tgttcatcca gctggtccaa acatacaacc agctgttcga agaaaacccg   600
atcaacgcaa gcggagtcga cgcaaaggca atcctgagcg caagactgag caagagcaga   660
agactggaaa acctgatcgc acagctgccg ggagaaaaga gaacggact gttcggaaac    720
ctgatcgcac tgagcctggg actgacaccg aacttcaaga caacttgca cctggcagaa   780
gacgcaaagc tgcagctgag caaggacaca tacgacgacg acctggacaa cctgctggca   840
cagatcggag accagtacgc agacctgttc ctggcagcaa agaacctgag cgacgcaatc   900
ctgctgagcg acatcctgag agtcaacaca gaaatcacaa aggcaccgct gagcgcaagc   960
atgatcaaga gatacgacga acaccaccag gacctgacac tgctgaaggc actggtcaga  1020
cagcagctgc cggaaaagta caaggaaatc ttcttcgacc agagcaagaa cggatacgca  1080
ggatacatcg acgaggagc aagccaggaa gaattctaca agttcatcaa gccgatcctg  1140
gaaagatgg acgaacaga gaactgctg gtcaagctga acagaagga cctgctgaga  1200
aagcagaaa cattcgacaa cggaagcatc ccgcaccaga tccacctggg agaactgcac  1260
gcaatcctga aagacaggca agacttctac ccgttcctga aggacaacag agaaaagatc  1320
gaaaagatcc tgacattcag aatcccgtac tacgtcggac cgctggcaag aggaaacagc  1380
agattcgcat ggatgacaag aaagagcgaa gaaacaatca ccgtggaa cttcgaagaa  1440
gtcgtcgaca agggagcaag cgcacagagc ttcatcgaaa gaatgacaaa cttcgacaag  1500
aacctgccga cgaaaaggt cctgccgaag cacagcctgc tgtacgaata cttcacagtc  1560
tacaacgaac tgacaaaggt caagtacgtc acagaaggaa tgagaaagcc ggcattcctg  1620
agcggagaac agaagaaggc aatcgtcgac ctgctgttca gacaaacag aaaggtcaca  1680
gtcaagcagc tgaaggaaga ctacttcaag aagatcgaat gcttcgacag cgtcgaaatc  1740
agcggagtcg aagacagatt caacgcaagc ctgggaacat accacgacct gctgaagatc  1800
atcaaggaca aggacttcct ggacaacgaa gaaaacgaag acatcctgga agacatcgtc  1860
ctgacactga cactgttcga agacagaaa atgatcgaaa aagactgaa gacatacgca  1920
cacctgttcg acgacaaggt catgaagcag ctgaagagaa aagatacac aggatgggga  1980
agactgagca gaaagctgat caacggaatc agagacaagc agcgggaaa gacaatcctg  2040
gacttcctga agagcgacgg attcgcaaac agaaacttca tgcagctgat ccacgacgac  2100
agcctgacat caaggaaga catccagaag gcacaggtca gcggacaggg agacagcctg  2160
cacgaacaca tcgcaaacct ggcaggaagc ccggcaatca gaagggaat cctgcagaca  2220
gtcaaggtcg tcgacgaact ggtcaaggtc atgggaagac acaagccgga aaacatcgtc  2280
atcgaaatgg caagagaaaa ccagacaaca cagaagggac agaagaacag cagagaaaga  2340
atgaagagaa tcgaagaagg aatcaaggaa ctgggaagcc agatcctgaa ggaacacccg  2400
gtcgaaaaca cacagctgca gaacgaaaag ctgtacctgt actacctgca aaacggaaga  2460
gacatgtacg tcgaccagga actggacatc aacagactga gcgactacga cgtcgaccac  2520
atcgtcccgc agagcttcct gaaggacgac agcatcgaca caaggtcct gacaagaagc  2580
gacaagaaca gaggaaagag cgacaacgtc ccgagcgaag aagtcgtcaa gaagatgaag  2640
aactactgga gacagctgct gaacgcaaag ctgatcacac agagaagtt cgacaacctg  2700
acaaaggcag agaggagg actgagcgaa ctggacaagg caggatcat caagagacag  2760
ctggtcgaaa caagacgat cacaaagcac gtcgcacaga tcctggacag cagaatgaac  2820
acaaagtacg acgaaaacga caagctgatc agagaagtca aggtcatcac actgaagagc  2880
aagctggtca cgcacttcag aaaggacttc cagttctaca aggtcagaga atcaacaac  2940
taccaccacg cacacgacgc ataccctgaac gcagtcgtcg aacagcact gatcaagaag  3000
tacccgaagc tggaaagcga attcgtctac ggagactaca aggtctacga cgtcagaaa  3060
atgatcgcaa agagcgaaca ggaaatcgga aaggcaacag caagtactt cttctacagc  3120
aacatcatga acttcttcaa gacagaaatc acactggcaa acggagaaat cagaaagaga  3180
ccgctgatca aaacaacgg agaaacagga gaaatcgtct gggacaaggg aagagacttc  3240
gcaacagtca gaaaggtcct gagcatgccg caggtcaaca tcgtcaagaa gacagaagtc  3300
cagacaggag gattcagcaa ggaaagcatc ctgccgaaga gaaacagcga caagctgatc  3360
gcaagaaaga aggactggga cccgaagaag tacggaggat cgacagccc gacagtcgca  3420
tacagcgtcc tggtcgtcgc aaaggtcgaa aagggaaaga caagaagct gaagagcgtc  3480
aaggaactgc tgggaatcac aatcatggaa agaagcagct cgaaaagaa cccgatcgac  3540
ttcctggaag caaagggata caaggaagtc aagaaggacc tgatcatcaa gctgccgaag  3600
tacagcctgt tcgaactgga aaacggaaga agagaatgc tggcaagcgc aggagaactg  3660
cagaagggaa acgaactggc actgccgagc aagtacgtca acttcctgta cctggcaagc  3720
cactacgaaa agctgaaggg aagcccggaa gacaacgaaa gaagcagct gttcgtcgaa  3780
cagcacaagc actacctgga cgaaatcatc gaacagatca gcgaattcag caagagagtc  3840
atcctggcag acgcaaacct ggacaaggtc ctgagcgcat acaacaagca cagagacaag  3900
ccgatcagag aacaggcaga aaacatcatc caccctgttca cactgacaaa cctgggagca  3960
```

```
ccggcagcat tcaagtactt cgacacaaca atcgacagaa agagatacac aagcacaaag    4020
gaagtcctgg acgcaacact gatccaccag agcatcacag gactgtacga aacaagaatc    4080
gacctgagcc agctgggagg agacggagga ggaagcccga agaagaagag aaaggtctag    4140
```

| | |
|---|---|
| SEQ ID NO: 251 | moltype = DNA length = 4411 |
| FEATURE | Location/Qualifiers |
| misc_feature | 1..4411 |
| | note = Synthetic: Cas9 transcript with 5 UTR of HSD, ORF |
| | corresponding to SEQ ID NO: 250, Kozak sequence, and 3 UTR |
| | of ALB |
| source | 1..4411 |
| | mol_type = other DNA |
| | organism = synthetic construct |

SEQUENCE: 251
```
gggtcccgca gtcggcgtcc agcggctctg cttgttcgtg tgtgtgtcgt tgcaggcctt      60
attcggatcc gccaccatgg acaagaagta cagcatcgga ctggacatcg gaacaaacag     120
cgtcggatgg gcagtcatca cagacgaata caaggtcccg agcaagaagt tcaaggtcct     180
gggaaacaca gacagacaca gcatcaagaa gaacctgatc ggagcactgc tgttcgacag     240
cggagaaaca gcagaagcaa caagactgaa gagaacagca agaagaagat acacaagaag     300
aaagaaccaga atctgctacc tgcaggaaat cttcagcaac gaaatggcaa aggtcgacga     360
cagcttcttc caccggctgg aagaaagctt cctggtcgaa gaagacaaga gcacgaaag     420
acaccgatc ttcggaaaca tcgtcgacga agtcgcatac cacgaaaagt acccgacaat     480
ctaccacctg agaagaagc tggtcgacag cacagacagg gcagacctga gactgatcta     540
cctggcactg gcacacatga tcaagttcag aggacacttc ctgatcgaag agacctgaa     600
cccggacaac agcgacgtcg acaagctgtt catccagctg gtccagacat caaccagct     660
gttcgaagaa aacccgatca acgcaagcgg agtcgacgca aaggcaatcc tgagcgcaag     720
actgagcaag agcagaagac tggaaaacct gatcgcacag ctgccgggag aaaagaagaa     780
cggactgttc ggaaacctga tcgcactgag cctgggactg acaccgaact tcaagagcaa     840
cttcgacctg gcagaagacg caaagctgca gctgagcaag gacacatacg acgacgacct     900
ggacaacctg ctggcacaga tcggagacca gtacgcagac ctgttcctgg cagcaaagaa     960
cctgagcgac gcaatcctgc tgagcgacat cctgagagtc aacacagaaa tcacaaaggc    1020
accgctgagc gcaagcatga tcaagagata cgacgaacac caccaggacc tgacactgct    1080
gaaggcactg gtcagacagc agctgccgga aaagtacaag gaaatcttct tcgaccagag    1140
caagaacgga tacgcaggat acatcgacgg aggagcaaac caggaagaat tctacaagtt    1200
catcaagccg atcctggaaa agatggacgg aacagaagaa ctgctggtca agctgaacag    1260
agaagacctg ctgagaaagc agaacattc gacaacgga agcatcccgc accagatcca    1320
cctgggagaa ctgcacgcaa tcctgagaag acaggaagac ttctaccgt tcctgaagga    1380
caacagagaa aagatcgaaa agatcctgac attcagaatc ccgtactacg tcggaccgct    1440
ggcaagagga aacagcagat tcgcatggat gacaagaaag agcgaagaaa caatcacacc    1500
gtggaacttc gaagaagtcg tcgacaaggg agcaagcgca cagagcttca tcgaaagaat    1560
gacaaacttc gacaagaacc tgccgaacga aaaggtcctg ccgaagcaca gcctgctgta    1620
cgaatacttc acagtctaca acgaactgac aaaggtcaag tacgtcacag aaggaatgag    1680
aaagccggca ttcctgagcg gagaacagaa gaaggcaatc gtcgacctgc tgttcaagac    1740
aaacagaaag gtcacagtca gcagctgaa ggaagactac ttcaagaaga tcgaatgctt    1800
cgacagcgtc gaaatcagcg gagtcgaaga cagattcaac gcaagcctgg gaacatacca    1860
cgacctgctg aagatcatca aggacaagga cttcctggac aacgaagaaa acgaagacat    1920
cctggaagac atcgtcctga cactgacact gttcgaagac agagaaatga tcgaagaaag    1980
actgaagaca tacgcacacc tgttcgacga caaggtcatg aagcagctga agagaagaag    2040
atacacagga tggggaagac tgagcagaaa gctgatcaac ggaatcagag acaagcagag    2100
cggaaagaca atcctggact tcctgaagag cgacggattc gcaaacagaa acttcatgca    2160
gctgatccac gacgacagcc tgacattcaa ggaagacatc cagaaggcac aggtcagcgg    2220
acagggagac agcctgcacg aacacatcgc aaacctggca ggaagcccgg caatcaagaa    2280
gggaatcctg cagacagtca aggtcgtcga cgaactggtc aaggtcatgg gaagacacaa    2340
gccggaaaac atcgtcatcg aaatggcaag agaaaaccag acaacacaga agggacagaa    2400
gaacagcaga gaaagaatga agagaatcga agaaggaatc aaggaactgg gaagccagat    2460
cctgaaggaa cacccggtcg aaaacacaca gctgcagaac gaaaagctgt acctgtacta    2520
cctgcaaaac ggaagagaca tgtacgtcga ccaggaactg gacatcaaca gactgagcga    2580
ctacgacgtc gaccacatcg tcccgcagag cttcctgaag gacgacagca tcgacaacaa    2640
ggtcctgaca agaagcgaca agaacagagg aaagagcgac aacgtcccga gcgaagaagt    2700
cgtcaagaag atgaagaact actggagaca gctgctgaac gcaaagctga tcacacagag    2760
aaagttcgac aacctgacaa aggcagagag gaggactg agcgaactgg acaaggcagg    2820
attcatcaag agacagctgg tcgaaacaag acagatcaca aagcacgtcg cacagatcct    2880
ggacagcaga atgaacacaa agtacgacga aaacgacaag ctgatcagag aagtcaaggt    2940
catcacactg aagagcaagc tggtcagcga cttcagaaag gacttccagt tctacaaggt    3000
cagagaaatc aacaactacc accacgcaca cgacgcatac ctgaacgcag tcgtcggaac    3060
agcactgatc aagaagtacc cgaagctgga aagcgaattc gtctacggag actacaaggt    3120
ctacgacgtc agaagatga tcgcaaagag cgaacaggaa atcggaaagg caacagcaaa    3180
gtacttcttc tacagcaaca tcatgaactt cttcaagaca gaaatcacac tggcaaacgg    3240
agaaatcaga aagagaccgc tgatcgaaac aaacggagaa acaggagaaa tcgtctgcag    3300
caagggaaga gacttcgcaa cagtcagaaa ggtcctgagc atgccgcagg tcaacatcgt    3360
caagaagaca gaagtccaga caggaggatt cagcaaggaa agcatcctgc cgaagagaaa    3420
cagcgacaag ctgatcgcaa gaaagaagga ctgggacccg aagaagtacg gaggattcga    3480
cagcccgaca gtcgcataca gcgtcctggt cgtcgcaaag gtcgaaaagg gaaagagcaa    3540
gaagctgaag agcgtcaagg aactgctggg aatcacaatc atggaaagag cagcttcga    3600
aaagaacccg atcgacttcc tggaagcaaa gggatacaag gaagtcaaga aggacctgat    3660
catcaagctg ccgaagtaca gcctgttcga actggaaaac ggaagaaaga gaatgctggc    3720
aagcgcagga gaactgcaga agggaaacga actggcactg ccgagcaagt acgtcaactt    3780
cctgtacctg gcaagccact acgaaaagct gaagggaagc ccggaagaca acgaacagaa    3840
gcagctgttc gtcgaacagc acaagcacta cctggacgaa atcatcgaac agatcagcga    3900
```

```
attcagcaag agagtcatcc tggcagacgc aaacctggac aaggtcctga gcgcatacaa  3960
caagcacaga gacaagccga tcagagaaca ggcagaaaac atcatccacc tgttcacact  4020
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
gaagagaaag gtctagctag ccatcacatt taaaagcatc tcagcctacc atgagaataa  4260
gagaaagaaa atgaagatca atagcttatt catctctttt tcttttttcgt tggtgtaaag  4320
ccaacacccct gtctaaaaaaa cataaatttc tttaatcatt ttgcctcttt tctctgtgct  4380
tcaattaata aaaatggaa agaacctcga g                                   4411
```

```
SEQ ID NO: 252          moltype = DNA   length = 4140
FEATURE                 Location/Qualifiers
misc_feature            1..4140
                        note = Synthetic: Cas9 ORF with minimal uridine codons
                         frequently used in humans in general; 12.75% U content
source                  1..4140
                        mol_type = other DNA
                        organism = synthetic construct
SEQUENCE: 252
atggacaaga agtacagcat cggcctggac atcggcacca cagcgtgggg ctgggccgtg   60
atcaccgacg agtacaaggt gcccagcaag aagttcaagg tgctgggcaa caccgacaga  120
cacagcatca agaagaacct gatcggcgcc ctgctgttcg acagcggcga gaccgccgag  180
gccaccagac tgaagagaac cgccagaaga agatacacca gaagaaagaa cagaatctgc  240
tacctgcagg agatcttcag caacgagatg gccaaggtgg acgacagctt cttccacaga  300
ctggaggaga gcttcctggt ggaggaggac aagaagcacg agagacaccc catcttcggc  360
aacatcgtgg acgaggtggc ctaccacgag aagtaccca ccatctacca cctgagaaag  420
aagctggtgg acagcaccga caaggccgac ctgagactga tctacctggc cctggcccac  480
atgatcaagt tcagaggcca cttcctgatc gagggcgacc tgaaccccga caacagcgac  540
gtggacaagc tgttcatcca gctggtgcag acctacaacc agctgttcga ggagaacccc  600
atcaacgccag gcgcgtgga cgccaaggcc atcctgagcg ccagactgag caagagcagg  660
agactggaga acctgatcgc ccagctgccc ggcgagaaga gaacggcct gttcggcaac  720
ctgatcgccc tgagcctggg cctgaccccc aacttcaaga gcaacttcga cctggccgag  780
gacgccaagc tgcagctgag caaggacacc tacgacgacg acctggacaa cctgctggcc  840
cagatcggcg accagtacgc cgacctgttc ctggccgcca agaacctgag cgacgccatc  900
ctgctgagcg acatcctgag agtgaacacc gagatccaca aggcccccct gagcgccag  960
atgatcaaga gatacgacga gcaccaccag gacctgaccc tgctgaaggc cctggtgaga  1020
cagcagctgc ccgagaagta caaggagatc ttcttcgacc agagcaagaa cggctacgcc  1080
ggctacatcg acggcggcgc cagccaggag gagttctaca agttcatcaa gcccatcctg  1140
gagaagatgg acggcaccga ggagctgctg gtgaagctga acagagagga cctgctgaga  1200
aagcagagaa cctcgacaa cggcagcatc ccccaccaga tccacctggg cgagctgcac  1260
gccatcctga agacagga ggacttctac cccttcctga aggacaacag agaagaagatc  1320
gagaagatcc tgaccttcag aatccccct ctacgtgggcc cctggccag aggcaacagc  1380
agattcgcct ggatgaccag aaagagcgag gagaccatca ccccgaggag cttcgaggag  1440
gtggtggaca agggcgccag cgcccagagc ttcatcgaga gaatgaccaa cttcgacaag  1500
aacctgccca cgagaaggt gctgcccaag cacagcctgc tgtacgagta cttcaccgtg  1560
tacaacgagc tgaccaaggt gaagtacgtg accgagggca tgagaaagcc cgccttcctg  1620
agcggcgagc agaagaaggc catcgtggac ctgctgttca agaccaacag aaaggtgacc  1680
gtgaagcagc tgaaggagga ctacttcaag aagatcgagt gcttcgacag cgtggagatc  1740
agcggcgtgg aggacagatt caacgccagc ctgggcacct accacgacct gctgaagatc  1800
atcaaggaca aggacttcct ggacaacgag gagaacgagg acatcctgga ggacatcgtg  1860
ctgacctga cccctgttcga ggacagagag atgatcgagg agagactgaa gacctacgcc  1920
cacctgttcg acgacaaggt gatgaagcag ctgaagagaa gaagatacac cggctggggg  1980
agactgagca gaaagctgat caacggcatc agagacaagc agagcggcaa gaccatcctg  2040
gacttcctga gagcgacgg cttcgccaac agaaacttca tgcagctgat ccacgacgac  2100
agcctgacct tcaaggaga catccagaag gcccaggtga gcggccaggg cgacagcctg  2160
cacgagcaca tcgccaacct ggccggcagc cccgccatca agaagggat cctgcagacc  2220
gtgaaggtgg tggacgagct ggtgaaggtg atgggcagac acaagcccga aacatcgtg  2280
atcgagatgg ccagagagaa ccagaccacc cagaagggcc agaagaacag cagagagaga  2340
atgaagagaa tcgaggaggg catcaaggag ctgggcagcc agatcctgaa ggagcaccc  2400
gtggagaaca cccagctgca gaacgagaag ctgtacctgt actacctgca gaacggcaga  2460
gacatgtacg tggaccagga gctggacatc aacagactga gcgactacga cgtgaccac  2520
atcgtgcccc agagcttcct gaaggacgac agcatcgaca caaggtgct gaccagaagc  2580
gacaagaaca gaggcaagag cgacaacgtg cccagcgagg aggtggtgaa gaagatgaag  2640
aactactgga gacagctgct gaacgccaag ctgatcacca gagaaagtt cgacaacctg  2700
accaaggccg agagaggcgg cctgagcgag ctgacaagg ccggcttcat caagagacag  2760
ctggtggaga ccagacagat caccaagcac gtgcccaga tcctggacag cagaatgaac  2820
accaagtacg acgagaacga caagctgatc agagaggtga aggtgatcac cctgaagagc  2880
aagctggtga gcgacttcag aaaggacttc cagttctaca aggtgagaga gatcaacaac  2940
taccaccacg cccacgacgc ctacctgaac gccgtgtgg gcaccgccct gatcaagaag  3000
tacccccaagc tggagagcga gttcgtgtac ggcgactaca aggtgtacga cgtgagaaag  3060
atgatcgcca gagcgagca ggagatcggc aaggccaccg ccaagtactt cttctacagc  3120
aacatcatga acttcttcaa gaccgagatc accctggcca cggcgagat cagaaagaga  3180
cccctgatcg agaccaacgg cgagaccggc gagatcgtgt gggacaaggg cagagacttc  3240
gccaccgtga aaggtgct gagcatgcc caggtgaaca tcgtgaagaa gaccgaggtg  3300
cagaccggcg gcttcagcaa ggagagcatc ctgcccaaga gaaacagcga caagctgatc  3360
gccagaaaga aggactggga ccccaagaag tacggcggct cgacagccc caccgtggcc  3420
tacagcgtgc tggtggtggc caggtggag agggcaaga gcaagaagct gaagagcgtg  3480
aaggagctgc tgggcatcac catcatggag agaagcagct cgagaagaa ccccatcgac  3540
ttcctggagg ccaagggcta caaggaggtg aagaaggacc tgatcatcaa gctgcccaag  3600
```

```
tacagcctgt tcgagctgga gaacggcaga aagagaatgc tggccagcgc cggcgagctg   3660
cagaagggca acgagctggc cctgcccagc aagtacgtga acttcctgta cctggccagc   3720
cactacgaga agctgaaggg cagccccgag gacaacgagc agaagcagct gttcgtggag   3780
cagcacaagc actacctgga cgagatcatc gagcagatca cgagttcag caagagagtg   3840
atcctggccg acgccaacct ggacaaggtg ctgagcgcct acaacaagca cagagacaag   3900
cccatcagag agcaggccga gaacatcatc cacctgttca ccctgaccaa cctgggcgcc   3960
cccgccgcct tcaagtactt cgacaccacc atcgacagaa agatacac cagcaccaag   4020
gaggtgctgg acgccaccct gatccaccag agcatcaccg gcctgtacga gaccagaatc   4080
gacctgagcc agctgggcgg cgacggcggc ggcagcccca agaagaagag aaaggtgtga   4140

SEQ ID NO: 253         moltype = DNA  length = 4411
FEATURE                Location/Qualifiers
misc_feature           1..4411
                       note = Synthetic: Cas9 transcript with 5 UTR of HSD, ORF
                        corresponding to SEQ ID NO: 252, Kozak sequence, and 3 UTR
                        of ALB
source                 1..4411
                       mol_type = other DNA
                       organism = synthetic construct
SEQUENCE: 253
gggtcccgca gtcggcgtcc agcggctctg cttgttcgtg tgtgtgtcgt tgcaggcctt   60
attcggatcc gccaccatgg acaagaagta cagcatcggc ctggacatcg gcaccaacag   120
cgtgggctgg gccgtgatca ccgacgagta caaggtgccc agcaagaagt tcaaggtgct   180
gggcaacacc gacagacaca gcatcaagaa gaacctgatc ggcgccctgc tgttcgacag   240
cggcgagacc gccgaggcca ccagactgaa gagaaccgcc agaagaagat accagaag   300
aaagaacaga atctgctacc tgcaggagat cttcagcaac gagatggcca aggtggacga   360
cagcttcttc cacagactgg aggagagctt cctggtggag gaggacaaga agcacgagag   420
acaccccatc ttcggcaaca tcgtggacga ggtggcctac cacgaagagt accccaccat   480
ctaccacctg agaaagaagc tggtggacag caccgacaag gccgacctga gactgatcta   540
cctggccctg gcccacatga tcaagttcag aggccactc ctgatcgagg gcgacctgaa   600
ccccgacaac agcgacgtgg acaagctgtt catccagctg gtgcagacct acaaccagct   660
gttcgaggag aacccatca acgcagcgg cgtggacgcc aaggccatcc tgagcgccag   720
actgagcaag agcagaagac tggagaacct gatcgcccag ctgcccggcg agaagaagaa   780
cggcctgttc ggcaacctga tcgccctgag cctgggcctg acccccaact tcaagagcaa   840
cttcgacctg gccgaggacg ccaagctgca gctgagcaag gacacctacg acgacgacct   900
ggacaacctg ctggcccaga tcggcgacca gtacgccgac ctgttcctgg ccgccaagaa   960
cctgagcgac gccatcctgc tgagcgacat cctgagagtg aacaccgaga tcaccaaggc   1020
ccccctgagc gccagcatga tcaagagata cgacgagcac caccaggacc tgaccctgct   1080
gaaggccctg gtgagacagc agctgcccga gaagtacaag gagatcttct tcgaccagag   1140
caagaacggc tacgccggct acatcgacgg cggcgccagc caggaggagt tctacaagtt   1200
catcaagccc atcctggaga gatggaacgg caccgaggag ctgctggtga agctgaacag   1260
agaggacctg ctgagaaagc agagaacctt cgacaacggc agcatccccc accagatcca   1320
cctgggcgag ctgcacgcca tcctgagaag acaggaggac ttctacccct tcctgaagga   1380
caacagagag aagatcgaga gatcctgac cttcagaatc ccctactacg tgggcccct   1440
ggccagaggc aacagcagat cgcctggat gaccagaaag agcgaggaga ccatcacccc   1500
ctggaacttc gaggaggtgg tggacaaggg cgccagcgcc cagagcttca tcgagagaat   1560
gaccaacttc gacaagaacc tgcccaacga aaggtgctg cccaagcaga gctgctgta   1620
cgagtacttc accgtgtaca acgagctgac caaggtgaag tacgtgaccg agggcatgag   1680
aaagcccgcc ttcctgagcg gcgagcagaa gaaggccatc gtggacctgc tgttcaagac   1740
caacagaaag gtgaccgtga agcagctgaa ggaggactac ttcaagaaga tcgagtgctt   1800
cgacagcgtg gagatcagcg gcgtggagga cagattcaac gccagcctgg gcacctacca   1860
cgacctgctg aagatcatca aggacaagga cttcctggac aacgaggaga acgaggacat   1920
cctggaggac atcgtgctga ccctgaccct gttcgaggac agagagatga tcgaggagag   1980
actgaagacc tacgcccacc tgttcgacga caaggtgatg aagcagctga gagaagaag   2040
atacaccggc tggggcagac tgagcagaaa gctgatcaac ggcatcagag acaagcagag   2100
cggcaagacc atcctggact tcctgaagag cgacggcttc gccaacagaa acttcatgca   2160
gctgatccac gacgacagcc tgaccttcaa ggagacatc cagaaggccc aggtgagcgg   2220
ccagggcgac agcctgcacg agcacatcgc caacctggcc ggcagcccg ccatcaagaa   2280
gggcatcctg cagaccgtga aggtggtgga cgagctggtg aaggtgatgg gcagacacaa   2340
gcccgagaac atcgtgatcg agatggccag agagaaccag accacccgag agggccagaa   2400
gaacagcaga gagagaatga agagaatcga ggagggcatc aaggagctgg gcagccagat   2460
cctgaaggag caccccgtgg agaacaccca gctgcagaac gagaagctgt acctgtacta   2520
cctgcagaac ggcagagaca tgtacgtgga ccaggagctg gacatcaaca actgagcga   2580
ctacgacgtg gaccacatcg tgccccagag cttcctgaag gacagagca tcgacaacaa   2640
ggtgctgacc agaagcgaca agaacagagg caagagcgac aacgtgccca gcgaggaggt   2700
ggtgaagaag atgaagaact actggagaca gctgctgaac gccaagctga tcacccagag   2760
aaagttcgac aacctgacca aggccgagag aggcggcctg agcgagctgg acaaggccgg   2820
cttcatcaag agacagctgg tggagacag acagtacacc aagcacgtgg cccagatcct   2880
ggacagcaga atgaacacca gtatgacga gaacgacaag ctgatcagag aggtgaaggt   2940
gatcaccctg aagagcaagc tggtgagcga cttcagaaag gacttccagt tctacaaggt   3000
gagagagatc aacaactacc accacgccca cgacgcctac ctgaacgccg tggtgggcac   3060
cgccctgatc aagaagtacc ccaagctgga gagcgagttc gtgtacgggg actacaaggt   3120
gtacgacgtg agaaagatga tcgccaagag cgagcaggag atcggcaagg ccaccgccaa   3180
gtacttcttc tacagcaaca tcatgaactt cttcaagacc gagatcacc tggccaaccg   3240
cgagatcaga aagagacccc tgatcgagac caacggcgag accggcgaga tcgtgtggga   3300
caagggcaga gacttcgcca ccgtgagaaa ggtgctgagc atgccccagg tgaacatcgt   3360
gaagaagacc gaggtgcaga ccggcggctt cagcaaggag agcatcctgc ccaagagaaa   3420
cagcgacaag ctgatcgcca gaagaaggga ctgggacccc aagaagtacg gcggcttcga   3480
cagccccacc gtggcctaca gcgtgctggt ggtggccaag gtggagaagg gcaagagcaa   3540
```

```
gaagctgaag agcgtgaagg agctgctggg catcaccatc atggagagaa gcagcttcga   3600
gaagaacccc atcgacttcc tggaggccaa gggctacaag gaggtgaaga aggacctgat   3660
catcaagctg cccaagtaca gcctgttcga gctggagaac ggcagaaaga gaatgctggc   3720
cagcgccggc gagctgcaga agggcaacga gctggccctg cccagcaagt acgtgaactt   3780
cctgtacctg gccagccact acgagaagct gaagggcagc cccgaggaca agagcagaa   3840
gcagctgttc gtggagcagc acaagcacta cctggacgag atcatcgagc agatcagcga   3900
gttcagcaag agagtgatcc tggccgacgc caacctggac aaggtgctga gcgcctacaa   3960
caagcacaga gacaagccca tcagagagca ggccgagaac atcatccacc tgttcaccct   4020
gaccaacctg ggcgcccccg ccgccttcaa gtacttcgac accaccatcg acagaaagag   4080
atacaccagc accaaggagg tgctggacgc caccctgatc caccagagca tcaccggcct   4140
gtacgagacc agaatcgacc tgagccagct gggcggcgac ggcggcggca gcccaagaa   4200
gaagagaaag gtgtgactag ccatcacatt taaagcatc tcagcctacc atgagaataa   4260
gagaaagaaa atgaagatca atagcttatt catctctttt tcttttcgt tggtgtaag   4320
ccaacaccct gtctaaaaa cataaatttc tttaatcatt ttgcctcttt tctctgtgct   4380
tcaattaata aaaatggaa agaacctcga g                                   4411

SEQ ID NO: 254          moltype = DNA   length = 4140
FEATURE                 Location/Qualifiers
misc_feature            1..4140
                        note = Synthetic: Cas9 ORF with minimal uridine codons
                        infrequently used in humans in general; 12.75% U content
source                  1..4140
                        mol_type = other DNA
                        organism = synthetic construct
SEQUENCE: 254
atggacaaaa aatacagcat agggctagac atagggacga acagcgtagg gtgggcggta    60
ataacggacg aatacaaagt accgagcaaa aaattcaaag tactagggaa cacggaccga   120
cacagcataa aaaaaaacct aatagggcg ctactattcg acagcgggga aacggcggaa   180
gcgacgcgac taaaacgaac ggcgcgacga cgatacacgc gacgaaaaaa ccgaatatgc   240
tacctacaag aaatattcag caacgaaatg cgaaagtag acgacagctt cttccaccga   300
ctagaagaaa gcttcctagt agaagaagac aaaaaaacacg aacgacaccc gatattcgg   360
aacatagtag acgaagtagc gtaccacgaa aaatacccga cgatatacca cctacgaaaa   420
aaactagtag acagcacgga caaagcggac ctacgactaa tatacctagc gctagcgcac   480
atgataaaat tccgagggca cttcctaata gaaggggacg taaacccgga caacagcgaa   540
gtagacaaac tattcataca actagtacaa acgtacaacc aactattcga agaaaacccg   600
ataaacgcga gcggggtaga cgcgaaagcg atactaagcg cgcgactaag caaaagccga   660
cgactagaaa acctaatagc gcaactaccg ggggaaaaaa aaacgggct attcgggaac   720
ctaatagcgc taagcctagg gctaacgccg aacttcaaaa gcaacttcga cctagcggaa   780
gacgcgaaac tacaactaag caaagacacg tacgacacg cctagacaa cctactagcg   840
caaatagggg accaatacgc ggacctattc ctagcggcga aaaacctaag cgacgcgata   900
ctactaagcg acatactacg agtaaacacg gaaatacga agcgccgct aagcgcgagc   960
atgataaaac gatacgacga acaccaccaa gacctaacgc tactaaaagc gctagtacga  1020
caacaactac cggaaaaata caagaaata ttcttcgacc aaagcaaaa cgggtacgcg  1080
gggtacatag acggggggc gagccaagaa gaattctaca aattcataaa accgatacta  1140
gaaaaaatgg acggggacgga agaactacta gtaaaactaa accgagaaga cctactacga  1200
aaacaacgaa cgttcgacaa cgggagcata ccgcaccaaa tacaccagg ggaactacac  1260
gcgatactac gacgacaaga agacttctac ccgttcctaa aagacaaccg aaaaaaata  1320
gaaaaaata taacgttccg aataccgta tacgtagggc cgctagcgcg agggaacagc  1380
cgattcgcgt ggatgacgcg aaaaagcgaa gaaacgataa cgccgtggaa cttcgaagaa  1440
gtagtagaca aaggggcgag cgcgcaaagc ttcatagaac gaatgacgaa cttcgacaaa  1500
aacctaccga acgaaaaagt actaccgaaa cacagcctac tatacgaata ttcacgta  1560
tacaacgaac taacgaaagt aaaatacgta acggaaggga tgcgaaaacc ggcgttccta  1620
agcgggaac aaaaaaaagc gatagtagac ctactattca aaacgaaccg aaaagtaacg  1680
gtaaaacaac taaagaaga ctacttcaaa aaaatagaat gcttcgacag cgtagaaata  1740
agcggggtag aagaccgatt caacgcgagc taggggacgt accacgacct actaaaaata  1800
ataaaagaca aagacttcct agacaacgaa gaaacgaag acatactaga agacatagta  1860
ctaacgctaa cgctattcga agaccgaga atgatagaag aacgactaaa aacgtacgcg  1920
cacctattcg acgacaaagt aatgaaacaa ctaaaacgac gacgatacac ggggtggggg  1980
cgactaagcc gaaaactaat aaacggggata gagacaaac gagacgggaa aacgatacta  2040
gacttcctaa aaagcgacgg gttcgcgaac cgaaacttca tgcaactaat acacgacgac  2100
agcctaacgt tcaaagaaga catacaaaaa gcgcaagtaa gcgggcaagg ggacagccta  2160
cacgaacaca tagcgaacct agcggggagc ccggcgataa aaaagggat actacaaacg  2220
gtaaaagtag tagacgaact agtaaagta atggggcgac acaaaccgga aaacatagta  2280
atagaaatgg cgcgagaaaa ccaaacgacg caaaagggc aaaaaacag ccgagaacga  2340
atgaaacgaa tagaagaagg gataaaagaa ctagggagcc aaatactaaa agaacacccg  2400
gtagaaaaca cgcaactaca aaacgaaaaa ctataccat actacctaca aaacgggcga  2460
gacatgtacg tagaccaaga actagacata aaccgactaa gcgactacga cgtagaccac  2520
atagtaccgc aaagcttcct aaaaagacgac agcatagaca caaagtact aacgcgaagc  2580
gacaaaaacc gagggaaag cgacaacgta ccgagcgaag aagtagtaaa aaaaatgaag  2640
aactactggc gacaactact aaacgcgaaa ctaataacgc aacgaaaatt cgacaaccta  2700
acgaaagcgg aacgagggg gctaagcgaa ctagacaaag cggggttcat aaaacgacaa  2760
ctagtagaaa cgcgacaaat aacgaaacac gtagcgcaaa tactagacag ccgaatgaac  2820
acgaaatacg acgaaaacga caaactaata cgagaagtaa agtaataac gctaaaaagc  2880
aaactagtaa gcgacttccg aaaagacttc caattctaca agtacgaga aataaacaac  2940
taccaccacg cgcacgacgc gtacctaaac gcggtagtag gacggcgct aataaaaaaa  3000
tacccgaaac tagaaagcga attcgtatac ggggactaca agtatacga cgtacgaaaa  3060
atgatagcga aaagcgaaca agaaataggg aagcgacgg cgaaatactt cttctacagc  3120
aacataatga acttcttcaa aacgaaata acgctagcga acggggaaat acgaaaacga  3180
ccgctaatag aaacgaacgg ggaaacgggg gaaatagtat gggacaaagg gcgagacttc  3240
```

```
gcgacggtac gaaaagtact aagcatgccg caagtaaaca tagtaaaaaa aacggaagta  3300
caaacggggg ggttcagcaa agaaagcata ctaccgaaac gaaacagcga caaactaata  3360
gcgcgaaaaa aagactggga cccgaaaaaa tacgggggt tcgacagccc gacggtagcg   3420
tacagcgtac tagtagtagc gaaagtagaa aaagggaaaa gcaaaaaact aaaaagcgta  3480
aaagaactac tagggataac gataatgaaa cgaagcagct tcgaaaaaaa cccgatagac  3540
ttcctagaag cgaaagggta caaagaagta aaaaaagacc taataataaa actaccgaaa  3600
tacagcctat tcgaactaga aaacgggcga aaacgaatgc tagcgagcgc ggggaacta   3660
caaaagggga acgaactagc gctaccgagc aaatacgtaa acttcctata cctagcgagc  3720
cactacgaaa aactaaaagg gagcccggaa gacaacgaaa aaaaacaact attcgtagaa  3780
caacacaaac actacctaga cgaaataata gaacaaataa gcgaattcag caaacgagta  3840
atactagcgg acgcgaacct agacaaagta ctaagcgcgt acaacaaaca ccgagacaaa  3900
ccgatacgag aacaagcgga aaacataata caccctattca cgctaacgaa cctaggggcg  3960
ccggcggcgt tcaaatactt cgacacgacg atagaccgaa aacgtacac gagcacgaaa   4020
gaagtactag acgcgacgct aatacaccaa agcataacgg ggctatacga aacgcgaata  4080
gacctaagcc aactaggggg ggacgggggg gggagcccga aaaaaaaacg aaaagtatga  4140

SEQ ID NO: 255        moltype = DNA   length = 4411
FEATURE               Location/Qualifiers
misc_feature          1..4411
                      note = Synthetic: Cas9 transcript with 5 UTR of HSD, ORF
                       corresponding to SEQ ID NO: 254, Kozak sequence, and 3 UTR
                       of ALB
source                1..4411
                      mol_type = other DNA
                      organism = synthetic construct
SEQUENCE: 255
gggtcccgca gtcggcgtcc agcggctctg cttgttcgtg tgtgtgtcgt tgcaggcctt   60
attcggatcc gccaccatgg acaaaaaata cagcataggg ctagacatag ggacgaacag   120
cgtagggtgg gcggtaataa cggacgaata caaagtaccg agcaaaaaat tcaaagtact   180
agggaacacg gaccgacaca gcataaaaaa aaacctaata ggggcgctac tattcgacag   240
cggggaaacg gcggaagcga cgcgactaaa acgaacggcg cgacgacgat acacgcgacg   300
aaaaaaccga atatgctacc tacaagaaat attcagcaac gaaatggcga agtagacga   360
cagcttcttc caccgactag aagaaagctt cctagtagaa gaagacaaaa aacacgaacg   420
acacccgata ttcgggaaca tagtagacga agtagcgtac cacgaaaaat acccgacgat   480
ataccaccta cgaaaaaaac tagtagacag cacggacaaa gcggacctac gactaatata   540
cctagcgcta cgcgcacatga taaaattccg agggcacttc ctaatagaag gggacctaaa   600
cccggacaac agcgacgtag acaaactatt catacaacta gtacaaacgt caaccaact   660
attcgaagaa aacccgataa acgcgagcgg ggtagacgcg aaagcgatac taagcgcgcg   720
actaagcaaa agcgacgac tagaaaacct aatagccgta ctaccgggg aaaaaaaaa    780
cgggctattc gggaacctaa tagcgctaag cctagggcta acgccgaact tcaaaagcaa   840
cttcgaccta gcgaaagacg cgaaactaca actaagcaaa gacacgtacg acgacgcct   900
agacaaccta ctagcgcaaa tagggaccaa atacgcggac ctattcctag cggcgaaaaa  960
cctaagcgac gcgatactac taagcgcat actacgagta aacacggaaa taacgaaagc  1020
gccgctaagc gcgagcatga taaaacgata cgacgaacac caccaagacc taacgctact  1080
aaaagcgcta gtacgacaac aactaccgga aaaatacaaa gaaatattct tcgaccaaag  1140
caaaaacggg tacgcggggt acatagacgg ggggcgagc caagaagaat tctacaaatt  1200
cataaaaccg atactagaaa aaatggacgg gacggaagaa ctactagtaa aactaaaccg  1260
agaagaccta ctacgaaaac aacgaacgtt cgacaacggg agcataccgc accaaatacc  1320
cctagggga ctacacgcga tactacgacg acaagaagac ttctaccgt tcctaaaaga   1380
caaccgagaa aaaatagaaa aaatactaac gttccgaata ccgtactacg tagggccgct  1440
agcgcgaggg aacagccgat tcgcgtggat gacgcgaaaa agcgaagaaa cgataacgcc  1500
gtggaacttc gaagaagtag tagacaaagg ggcgagcgcg caaagcttca tagaacgaat  1560
gacgaacttc gacaaaaacc taccgaacga aaaagtacta ccgaaacaca gcctactata  1620
cgaatacttc acgtataca acgaactaac gaaagtaaaa tacgtaacgg aagggatgcg  1680
aaaaccggcg ttcctaagcg gggaacaaaa aaaagcgta gtagacctac tattcaaaac  1740
gaaccgaaaa gtaacggtaa aacaactaaa agaagactac ttcaaaaaaa tagaatgctt  1800
cgacagcgta gaaataagcg gggtagaaga ccgattcaac gcgagcctag gacgtacca   1860
cgacctacta aaaataataa aagacaaaga cttcctagac aacgaagaaa acgaagacat  1920
actagaagac atagtactaa cgctaacgct attcgaagac gagaaatga tagaagaacg  1980
actaaaaacg tacgcgcacc tattcgacga caaagtaatg aaacaactaa aacgacgacg  2040
atacacgggg tgggggcgac taagccgaaa actaataaac gggatacgag acaaacaaag  2100
cgggaaaacg atactagact tcctaaaaag cgacgggttc gcgaaccgaa acttcatgca  2160
actaatacac gacgacagcc taacgttcaa agaagcata caaaaagcgc aagtaagcgg  2220
gcaaggggac agcctacacg aacacatagc gaactagta gggagcccgg cgataaaaaa  2280
agggatacta caaacggtaa agtagtagaa cgaactagta aaagtaatgg ggcgacacaa  2340
accgaaaac atagtaatag aaatggcgcg agaaaaccaa acgacgcaaa aagggcaaaa  2400
aaacagccga gaacgaatga acgaataga agaagggata aagaactag ggagccaaat   2460
actaaaagaa caccoggtag aaaacacgca actacaaaac gaaaaactaa acctatacta  2520
cctacaaaac gggcgagaca tgtacgtaga ccaagaacta gacataaacc gactaagcga  2580
ctacgacgta gaccacatag taccgcaaag cttcctaaaa gacgacagca tagacaacaa  2640
agtactaacg cgaagcgaca aaaaccgagg gaaaagcgac aacgtaccga gcgaagaagt  2700
agtaaaaaaa atgaaaaact actggcgaca actactaaac gcgaaactaa taacgcaacg  2760
aaaattcgac aacctaacga aagcggaacg aggggggcta agcgaactag acaaagcggg  2820
gttcataaaa cgacaactag tagaaacgcg acaaataacg cgtagcgtag cgcaaatact  2880
agacagccga atgaacacga aatacgacga aaacgacaaa ctaatacgag aagtaaaagt  2940
aataacgcta aaagcaaac tagtaagcga cttccgaaaa gacttccaat tctacaaagt  3000
acgagaaata aacaactacc accacgcgca cgacgcgtac ctaaacgcgg tagtagggac  3060
ggcgctaata aaaaaatacc cgaaactaga aagcgaattc gtatacgggg actacaaagt  3120
atacgacgta cgaaaaatga tagcgaaaag cgaacaagaa ataggggaaag cgacggcgaa  3180
```

```
atacttcttc tacagcaaca taatgaactt cttcaaaacg gaaataacgc tagcgaacgg    3240
ggaaatacga aaacgaccgc taatagaaac gaacgggaa acgggggaaa tagtatggga     3300
caaagggcga gacttcgcga cggtacgaaa agtactaagc atgccgcaag taaacatagt    3360
aaaaaaaacg gaagtacaaa cggggggtt cagcaaagaa agcatactac cgaaacgaaa     3420
cagcgacaaa ctaatagcgc gaaaaaaaga ctgggacccg aaaaaatacg ggggttcga    3480
cagcccgacg gtagcgtaca gcgtactagt agtagcgaaa gtagaaaaag ggaaaagcaa    3540
aaaactaaaa agcgtaaaag aactactagg gataacgata atggaacgaa gcagcttcga    3600
aaaaaacccg atagacttcc tagaagcgaa agggtacaaa gaagtaaaaa aagacctaat    3660
aataaaacta ccgaaatact gcctattcga actagaaaac gggcgaaaac gaatgctagc    3720
gagcgcgggg gaactacaaa aagggaacga actagcgcta ccgagcaat acgtaaactt     3780
cctataccta gcgagccact acgaaaaact aaaagggagc ccggaagaca acgaacaaaa    3840
acaactattc gtagaacaac acaaacacta cctagacgaa ataatagaac aaataagcga    3900
attcagcaaa cgagtaatac tagcggacgc gaacctagac aaagtactaa gcgcgtacaa    3960
caaacaccga gacaaaccga tacgagaaca agcggaaaac ataatacacc tattcacgct    4020
aacgaaccta ggggcgccgg cggcgttcaa atacttcgac acgacgatag accgaaaacg    4080
atacacgagc acgaaagaag tactagacgc gacgctaata caccaaagca taacggggct    4140
atacgaaacg cgaatagacc taagccaact agggggggac gggggggga gcccgaaaaa     4200
aaaacgaaaa gtatgactag ccatcacatt taaaagcatc tcagcctacc atgagaataa    4260
gagaaagaaa atgaagatca atagcttatt catctcttt tctttttcgt tggtgtaaag     4320
ccaacaccct gtctaaaaaa cataaatttc tttaatcatt ttgcctcttt tctctgtgct    4380
tcaattaata aaaatggaa agaacctcga g                                     4411

SEQ ID NO: 256          moltype = DNA   length = 4411
FEATURE                 Location/Qualifiers
misc_feature            1..4411
                        note = Synthetic: Cas9 transcript with AGG as first three
                         nucleotides for use with CleanCapTM, 5 UTR of HSD, ORF
                         corresponding to SEQ ID NO: 204, Kozak sequence, and 3 UTR
                         of ALB
source                  1..4411
                        mol_type = other DNA
                        organism = synthetic construct
SEQUENCE: 256
aggtcccgca gtcggcgtcc agcggctctg cttgttcgtg tgtgtgtcgt tgcaggcctt    60
attcggatcc gccaccatgg acaagaagta cagcatcgga ctggacatcg gaacaaacag    120
cgtcggatgg gcagtcatca cagacgaata caaggtcccg agcaagaagt tcaaggtcct    180
gggaaacaca gacagacaca gcatcaagaa gaacctgatc ggagcactgc tgttcgacag    240
cggagaaaca gcagaagcaa caagactgaa gagaacagca agaagaagat acacaagaag    300
aagaacagaa atctgctacc tgcaggaaat cttcagcaac gaaatggcaa agtcgacga     360
cagcttcttc cacagactgg aagaaagctt cctggtcgaa gaagacaaga agcacgaaag    420
acacccgatc ttcggaaaca tcgtcgacga agtcgcatac cacgaaagt cccgacaat    480
ctaccaccty agaaagaagc tggtcgacag cacagacaag gcagacctga gactgatcta    540
cctggcactg gcacacatga tcaagttcag aggacacttc ctgatcgaag gagcctgaa    600
cccggacaac agcgacgtcg acaagctgtt catccagctg gtccagacat acaaccagct    660
gttcgaagaa aacccgatca acgcaagcgg agtcgacgca aagcaatcc tgagcgcaag    720
actgagcaag agcagaagac tggaaaaacct gatcgcacag ctgccggag aaaagaagaa    780
cggactgttc ggaaaacctga tcgcactgag cctgggactg acaccagact tcaagagcaa    840
cttcgacctg gcagaagacg caaagctgca gctgagcaag gacacatacg acgacgacct    900
ggacaacctg ctggcacaga tcggagacca gtacgcagac ctgttcctgg cagcaaagaa    960
cctgagcgac gcaatcctgc tgagcgacat cctgagagtc aacacagaaa tcacaaaggc    1020
accgctgagc gcaagcatga tcaagagata cgacgaacac caccaggacc tgacactgct    1080
gaaggcactg gtcagacagc agctgccgga aaagtacaag gaaatcttct tcgaccagag    1140
caagaacgga tacgcaggat acatcgacgg aggagcaagc caggaagaat ctacaagtt    1200
catcaagccg atcctggaaa agatggacgg aacagaagaa ctgctggtca gctgaacag    1260
agaagacctg ctgagaaagc agagaacatt cgacaacgga agcatcccgc accagatcca    1320
cctgggagaa ctgcacgcaa tcctgagaag acaggaagac ttctacccgt tcctgaagga    1380
caacagagaa aagatcgaaa agatcctgac attcagaatc ccgtactacg tcggaccgct    1440
ggcaagagga aacagcagat tcgcatggat gacaagaaag agcgaagaa caatcacacc    1500
gtggaacttc gaagaagtcg tcgacaaggg agcaagcgca cagagcttca tcgaaagaat    1560
gacaaacttc gacaagaacc tgccgaacga aaaggtcctg ccgaagcaca gcctgctgta    1620
cgaatacttc acagtctaca acgaactgac aaaggtcaag tacgtcacag aaggaatgag    1680
aaagccggca ttcctgagcg gagaacgaaa gaaggcaatc gtcgacctgc tgttcaagac    1740
aaacagaaag gtcacagtca agcagctgaa ggaagactac ttcaagaaga tcgaatgctt    1800
cgacagcgtc gaaattcagc gagtcgaaga cagattcaac gcaagcctgg gaacatacca    1860
cgacctgctg aagatcatca ggacaagga cttcctggac aacgaagaaa acgaagacat    1920
cctggaagac atcgtcctga cactgacact gttcgaagac agaaatga tcgaagaaag    1980
actgaagaca tacgcacacc tgttcgacga caaggtcatg aagcagctga gagaagaag    2040
atacacagga tggggaagac tgagcagaaa gctgatcaac ggaatcagaa caagcagag    2100
cggaaaagca atcctggact tcctgaagag cgacggattc gcaaacagaa acttcatgca    2160
gctgatccac gacgacagcc tgacattcaa ggaagacatc cagaaggcac aggtcagcgg    2220
acagggagac agcctgcacg aacacatcgc aaacctggca ggaagccggg caatcaagaa    2280
gggaatcctg cagacagtca aggtcgtcga cgaactggtc aaggtcatgg aagacacaa    2340
gccggaaaac atcgtcatcg aaatggcaag agaaaaccag acaacacaga agggacagaa    2400
gacagcaga gaaaagaatga agagatcga agaaactggg aagccagat                2460
cctgaaggaa cacccggtcg aaaacacaca gctgcagaac gaaaagctgt acctgtacta    2520
cctgcagaac ggaagagaca tgtacgtcga ccaggaactg gacatcaaca gactgagcga    2580
ctacgacgtc gaccacatcg tcccgcagag cttcctgaag gacgacagca tcgacaacaa    2640
ggtcctgaca agagcgaca agaacagagg aaagagcgac aacgtcccga gcgaagaagt    2700
cgtcaagaag atgaagaact actggagaca gctgctgaac gcaaagctga tcacacagag    2760
```

```
aaagttcgac aacctgacaa aggcagagag aggaggactg agcgaactgg acaaggcagg    2820
attcatcaag agacagctgg tcgaaacaag acagatcaca aagcacgtcg cacagatcct    2880
ggacagcaga atgaacacaa agtacgacga aaacgacaag ctgatcagag aagtcaaggt    2940
catcacactg aagagcaagc tggtcagcga cttcagaaag gacttccagt tctacaaggt    3000
cagagaaatc aacaactacc accacgcaca cgacgcatac ctgaacgcag tcgtcggaac    3060
agcactgatc aagaagtacc cgaagctgga agcgaattc gtctacggag actacaaggt    3120
ctacgacgtc agaaagatga tcgcaaagag cgaacaggaa atcggaaagg caacagcaaa    3180
gtacttcttc tacagcaaca tcatgaactt cttcaagaca gaaatcacac tggcaaacgg    3240
agaaatcaga aagagaccgc tgatcgaaac aaacgagaaa acaggagaaa tcgtctggga    3300
caagggaaga gacttcgcaa cagtcagaaa ggtcctgagc atgccgcagg tcaacatcgt    3360
caagaagaca gaagtccaga caggaggatt cagcaaggaa agcatcctgc cgaagagaaa    3420
cagcgacaag ctgatcgcaa gaaagaagga ctgggacccg aagaagtacg gaggattcga    3480
cagcccgaca gtcgcataca gcgtcctggt cgtcgcaaag gtcgaaaagg gaaagagcaa    3540
gaagctgaag agcgtcaagg aactgctggg aatcacaatc atggaaagaa gcagcttcga    3600
aaagaacccg atcgacttcc tggaagcaaa gggatacaga gaagtcaaga aggacctgat    3660
catcaagctg ccgaagtaca gcctgttcga actggaaaac ggaagaaaga gaatgctggc    3720
aagcgcagga gaactgcaga agggaaacga actggcactg ccgagcaagt acgtcaactt    3780
cctgtacctg gcaagccact acgaaaagct gaagggaagc ccggaagaca gcgaacagaa    3840
gcagctgttc gtcgaacagc acaagcacta cctggacgaa atcatcgaac agatcagcga    3900
attcagcaag agagtcatcc tggcagacgc aaacctggac aaggtcctga gcgcatacaa    3960
caagcacaga gacaagccga tcagagaaca ggcagaaaac atcatccacc tgttcacact    4020
gacaaacctg ggagcaccgg cagcattcaa gtacttcgac acaacaatcg acagaaagag    4080
atacacaagc acaaaggaag tcctggacgc aacactgatc caccagagca tcacaggact    4140
gtacgaaaca agaatcgacc tgagccagct gggaggagac ggaggaggaa gcccgaagaa    4200
gaagagaaag gtctagctag ccatcacatt taaaagcatc tcagcctacc atgagaataa    4260
gagaaagaaa atgaagatca atagcttatt catctctttt tcttttttcgt tggtgtaaag    4320
ccaacaccct gtctaaaaaa cataaatttc tttaatcatt ttgcctcttt tctctgtgct    4380
tcaattaata aaaaatggaa agaacctcga g                                   4411

SEQ ID NO: 257           moltype = DNA  length = 4481
FEATURE                  Location/Qualifiers
misc_feature             1..4481
                         note = Synthetic: Cas9 transcript with 5 UTR from CMV, ORF
                          corresponding to SEQ ID NO: 204, Kozak sequence, and 3 UTR
                          of ALB
source                   1..4481
                         mol_type = other DNA
                         organism = synthetic construct
SEQUENCE: 257
gggcagatcg cctggagacg ccatccacgc tgttttgacc tccatagaag acaccgggac      60
cgatccagcc tccgcggccg ggaacggtgc attggaacgc ggattccccg tgccaagagt     120
gactcaccgt ccttgacacg gccaccatgg acaagaagta cagcatcgga ctggacatcg     180
gaacaaacag cgtcggatgg gcagtcatca cagacgaata caaggtcccg agcaagaagt     240
tcaaggtcct gggaaacaca gacagacaca gcatcaagaa gaacctgatc ggagcactgc     300
tgttcgacag cggagaaaca gcagaagcaa caagactgaa gagaacagca agaagaagat     360
acacaagaag aaagaacaga atctgctacc tgcaggaaat cttcagcaac gaaatggcaa     420
aggtcgacga cagcttcttc cacagactgg aagaaagctt cctggtcgaa gaagacaaga     480
agcacgaaag acacccgatc ttcggaaaca tcgtcgacga agtcgcatac cacgaaaagt     540
acccgacaat ctaccacctg agaaagaagc tggtcgacag cacagacaag gcagacctga     600
gactgatcta cctggcactg gcacacatga tcaagttcag aggacacttc ctgatcgaag     660
gagacctgaa cccggacaac agcgacgtcg acaagctgtt catccagctg gtccagacat     720
acaaccagct gttcgaagaa aacccgatca acgcaagcgg agtcgacgca aaggcaatcc     780
tgagcgcaag actgagcaag agcagaagac tggaaaacct gatcgcacag ctgccgggag     840
aaaagaagaa cggactgttc ggaaacctga tcgcactgag cctgggactg acaccgaact     900
tcaagagcaa cttcgacctg gcagaagacg caaagctgca gctgagcaag gacacatacg     960
acgacgacct ggacaacctg ctggcacaga tcggagacca gtacgcagac ctgttcctgg    1020
cagcaaagaa cctgagcgac gcaatcctgc tgagcgacat cctgagagtc aacacagaaa    1080
tcacaaaggc accgctgagc gcaagcatga tcaagagata cgacgaacac caccaggacc    1140
tgacactgct gaaggcactg gtcagacagc agctgccgga aaagtacaag gaaatcttct    1200
tcgaccagag caagaacgga tacgcaggat acatcgacgg aggagcaagc caggaagaat    1260
tctacaagtt catcaagccg atcctggaaa agatggacgg aacagaagaa ctgctggtca    1320
agctgaacag agaagacctg ctgagaaagc agagaacatt cgacaacgga agcatcccgc    1380
accagatcca cctgggagaa ctgcacgcaa tcctgagaag acaggaagac ttctaccctcg    1440
tcctgaagga caacagagaa aagatcgaaa agatcctgac attcagaatc ccgtactacg    1500
tcggaccgct ggcaagagga aacagcagat tcgcatggat gacaagaaag agcgaagaaa    1560
caatcacacc gtggaacttc gaagaagtcg tcgacaaggg agcaagcgca cagagcttca    1620
tcgaaagaat gacaaacttc gacaagaacc tgccgaacga aaaggtcctg ccgaagcaca    1680
gcctgctgta cgaatacttc acagtctaca acgaactgac aaaggtcaag tacgtcacag    1740
aaggaatgag aaagccggca ttcctgagcg gagaacagaa gaaggcaatc gtcgacctgc    1800
tgttcaagac aaacagaaag gtcacagtca gcagctgaa ggaagactac ttcaagaaga    1860
tcgaatgctt cgacagcgtc gaaatcagcg gagtcgaaga cagattcaac gcaagcctgg    1920
gaacatacca cgacctgctg aagatcatca aggacaagga cttcctggac aacgaagaaa    1980
acgaagacat cctggaagac atcgtcctga cactgacact gttcgaagac agaaatga    2040
tcgaagaaag actgaagaca tacgcacacc tgttcgacga caaggtcatg aagcagctga    2100
agagaagaag atacacagga tggggaagac tgagcagaaa gctgatcaac ggaatcagag    2160
acaagcagag cggaaagaca atcctggact tcctgaagag cgacggattc gcaaacagaa    2220
acttcatgca gctgatccac gacgacagcc tgacattcaa ggaagacatc cagaaggcac    2280
aggtcagcgg acagggagac agcctgcacg aacacatcgc aaacctggca ggaagcccgg    2340
caatcaagaa gggaatcctg cagacagtca aggtcgtcga cgaactggtc aaggtcatgg    2400
```

```
gaagacacaa gccggaaaac atcgtcatcg aaatggcaag agaaaaccag acaacacaga 2460
agggacagaa gaacagcaga gaaagaatga agagaatcga agaaggaatc aaggaactgg 2520
gaagccagat cctgaaggaa cacccggtcg aaaacacaca gctgcagaac gaaaagctgt 2580
acctgtacta cctgcagaac ggaagagaca tgtacgtcga ccaggaactg gacatcaaca 2640
gactgagcga ctacgacgtc gaccacatcg tcccgcagag cttcctgaag gacgacagca 2700
tcgacaacaa ggtcctgaca agaagcgaca agaacagaga aaagagcgac aacgtcccga 2760
gcgaagaagt cgtcaagaag atgaagaact actggagaca gctgctgaac gcaaagctga 2820
tcacacagag aaagttcgac aacctgacaa aggcagagag aggaggactg agcgaactgg 2880
acaaggcagg attcatcaag agacagctgg tcgaaacaag acagatcaca aagcacgtcg 2940
cacagatcct ggacagcaga atgaacacaa agtacgacga aaacgacaag ctgatcagag 3000
aagtcaaggt catcacactg aagagcaagc tggtcagcga cttcagaaag gacttccagt 3060
tctacaaggt cagagaaatc aacaactacc accacgcaca cgacgcatac ctgaacgcag 3120
tcgtcggaac agcactgatc aagaagtacc cgaagctgga aagcgaattc gtctacggag 3180
actacaaggt ctacgacgtc gaaaagatga tcgcaaagag cgaacaggaa atcggaaagg 3240
caacagcaaa gtacttcttc tacagcaaca tcatgaactt cttcaagaca gaaatcacac 3300
tggcaaacgg agaaatcaga aagagaccgc tgatcgaaac aaacggagaa acaggagaaa 3360
tcgtctggga caagggaaga gacttcgcaa cagtcagaaa ggtcctgagc atgccgcagg 3420
tcaacatcgt caagaagaca gaagtccaga caggaggatt cagcaaggaa agcatcctgc 3480
cgaagagaaa cagcgacaag ctgatcgcaa gaaagaagga ctgggacccg aagaagtacg 3540
gaggattcga cagcccgaca gtcgcataca gcgtcctggt cgtcgcaaag gtcgaaaagg 3600
gaaagagcaa gaagctgaag agcgtcaagg aactgctggg aatcacaatc atggaaagaa 3660
gcagcttcga aaagaacccg atcgacttcc tggaagcaaa gggatacaag gaagtcaaga 3720
aggacctgat catcaagctg ccgaagtaca gcctgttcga actggaaaac ggaagaaaga 3780
gaatgctggc aagcgcagga gaactgcaga agggaaacga actggcactg ccgagcaagt 3840
acgtcaactt cctgtacctg gcaagccact acgaaaagct gaagggaagc ccggaagaca 3900
acgaacagaa gcagctgttc gtcgaacaga caagcacta cctggacgaa atcatcgaac 3960
agatcagcga attcagcaag agagtcatcc tggcagacgc aaacctggac aaggtcctga 4020
gcgcatacaa caagcacaga gacaagccga tcagagaaca ggcagaaaac atcatccacc 4080
tgttcacact gacaaacctg ggagcaccgg cagcattcaa gtacttcgac acaacaatcg 4140
acagaaagag atacacaagc acaaaggaag tcctgacgag aacactgatc caccagagca 4200
tcacaggact gtacgaaaca agaatcgacc tgagccagct gggaggagac ggaggaggaa 4260
gcccgaagaa gaagagaaag gtctagctag ccatcacatt taaaagcatc tcagcctacc 4320
atgagaataa gagaaagaaa atgaagatca atagcttatt catctctttt tcttttttcgt 4380
tggtgtaaag ccaacaccct gtctaaaaaa cataaatttc tttaatcatt ttgcctcttt 4440
tctctgtgct tcaattaata aaaaatggaa agaacctcga g 4481

SEQ ID NO: 258        moltype = DNA   length = 4348
FEATURE               Location/Qualifiers
misc_feature          1..4348
                      note = Synthetic: Cas9 transcript with 5 UTR from HBB, ORF
                       corresponding to SEQ ID NO: 204, Kozak sequence, and 3 UTR
                       of HBB
source                1..4348
                      mol_type = other DNA
                      organism = synthetic construct
SEQUENCE: 258
gggacatttg cttctgacac aactgtgttc actagcaacc tcaaacagac accggatctg 60
ccaccatgga caagaagtac agcatcggac tggacatcgg aacaaacagc gtcggatggg 120
cagtcatcac agacgaatac aaggtcccga gcaagaagtt caaggtcctg ggaaacacag 180
acagacacag catcaagaag aacctgatcg gagcactgct gttcgacagc ggagaaaacag 240
cagaagcaac aagactgaag agaacagcaa gaagaagata cacaagaaga aagaacagaa 300
tctgctacct gcaggaaatc ttcagcaacg aaatggcaaa ggtcgacgac agcttcttcc 360
acagactgga agaaagcttc ctggtcgaag aagcaagaa gcacgaaaga cacccgatct 420
tcggaaacat cgtcgacgaa gtcgcatacc acgaaaagta cccgacaatc taccacctga 480
gaaagaagct ggtcgacagc acagacaagg cagacctgag actgatctac ctggcactgg 540
cacacatgat caagttcaga ggacactttc tgatcgaagg agacctgaac ccggacaaca 600
gcgacgtcga caagctgttc atccagctgg tccagacata caaccagctg ttcgaagaaa 660
acccgatcaa cgcaagcgga gtcgacgcaa aggcaatcct gagcgcaaga ctgagcaaga 720
gcagaagact ggaaaacctg atcgcacagc tgccgggaga aaagaagaac ggactgttcg 780
gaaacctgat cgcactgagc ctgggactga caccgaactt caagagcaac ttcgacctgg 840
cagaagacgc aaagctgcag ctgagcaagg acacatacga cgacgacctg gacaacctgc 900
tggcacagat cggagaccag tacgcagacc tgttcctggc agcaaagaac ctgagcgacg 960
caatcctgct gagcgacatc ctgagagtca acacagaaat cacaaaggca ccgctgagcg 1020
caagcatgat caagagatac gacgaacacc accggacct gcactgtg aaggcactgg 1080
tcagacagca gctgccggaa aagtacaagg aaatcttctt cgaccagagc aagaacggat 1140
acgcaggata catcgacgga ggagcaagcc aggaagaatt ctacaagttc atcaagccga 1200
tcctggaaaa gatggacgga acagaagaac tgctggtcaa gctgaacaga gaagacctgc 1260
tgagaaagca gagaacattc gacaacggaa gcatcccgca ccagatccac ctgggagaac 1320
tgcacgcaat cctgagacga caggaagact ctacccgtt cctgaaggac aacagagaaa 1380
agatcgaaaa gatcctgaca ttcagaatcc cgtactacgt cggaccgctg gcaagaggaa 1440
acagcagatt cgcatggatg acaagaaaga gcgaagaaac aatcacaccg tggaacttcg 1500
aagaagtcgt cgacaaggga gcaagcgcac agagcttcat cgaaagaatg acaaacttcg 1560
acaagaacct gccgaacgaa aaggtcctgc cgaagcacag cctgctgtac gaatacttca 1620
cagtctcaca cgaactgaca aaggtcaagt acgtcacaga aggaatgcgc aagcggcat 1680
tcctgagcgg agaacagaag aaggcaatcg tcgacctgct gttcaagaca aacagaaagg 1740
tcacagtcaa gcagctgaag gaagactact tcaagaagat cgaatgcttc gacagcgtcg 1800
aaatcagcgg agtcgaagac agattcaacg caagcctggg aacataccac gacctgctga 1860
agatcatcaa ggacaaggac ttcctggaca cgaagaaaa cgaagacatc ctggaagaca 1920
tcgtcctgac actgacactg ttcgaagaca gagaaatgat cgaagaaga ctgaagacat 1980
```

```
acgcacacct gttcgacgac aaggtcatga agcagctgaa gagaagaaga tacacaggat 2040
ggggaagact gagcagaaag ctgatcaacg gaatcagaga caagcagagc ggaaagacaa 2100
tcctggactt cctgaagagc gacggattcg caaacagaaa cttcatgcag ctgatccacg 2160
acgacagcct gacattcaag gaagacatcc agaaggcaca ggtcagcgga cagggagaca 2220
gcctgcacga acacatcgca aacctggcag gaagcccggc aatcaagaag ggaatcctgc 2280
agacagtcaa ggtcgtcgac gaactggtca aggtcatggg aagacacaag ccggaaaaca 2340
tcgtcatcga aatggcaaga gaaaaccaga caacacagaa gggacagaag aacagcagag 2400
aaagaatgaa gagaatcgaa gaaggaatca aggaactggg aagccagatc ctgaaggaac 2460
acccggtcga aaacacacag ctgcagaacg aaaagctgta cctgtactac ctgcagaacg 2520
gaagagacat gtacgtcgac caggaactgg acatcaacag actgagcgac tacgacgtcg 2580
accacatcgt cccgcagagc ttcctgaagg acgacagcat cgacaacaag gtcctgacaa 2640
gaagcgacaa gaacagagga agagcgacaa acgtcccgag cgaagaagtc gtcaagaaga 2700
tgaagaacta ctggagacag ctgctgaacg caaagctgat cacacagaga aagttcgaca 2760
acctgacaaa ggcagagaga ggaggactga gcgaactgga caaggcagga ttcatcaaga 2820
gacagctggt cgaaacaaga cagatccaca agcacgtcgc acagatcctg gacagcagaa 2880
tgaacacaaa gtacgacgaa aacgacaagc tgatcagaga agtcaaggtc atcacactga 2940
agagcaagct ggtcagcgac ttcagaaagg acttccagtt ctacaaggtc agagaaatca 3000
acaactacca ccacgcacac gacgcatacc tgaacgcagt cgtcggaaca gcactgatca 3060
agaagtaccc gaagctggaa agcgaattcg tctacggaga ctacaaggtc tacgacgtca 3120
gaaagatgat cgcaaagagc gaacaggaaa tcggaaaggc aacagcaaag tacttcttct 3180
acagcaacat catgaacttc ttcaagacag aaatcacact ggcaaacgga gaaatcgaaa 3240
agagaccgct gatcgaaaca aacggagaaa caggagaaac cgtctggacc aagggaagag 3300
acttcgcaac agtcagaaag gtcctgagca tgccgcaggt caacatcgtc aagaagacag 3360
aagtccagac aggaggattc agcaaggaaa gcatcctgcc gaagagaaac agcgacaagc 3420
tgatcgcaag aaagaaggac tgggacccga gaagtacgg aggattcgac agcccgcag 3480
tcgcatacag cgtcctggtc gtcgcaaagg tcgaaaaggg aaagagcaag aagctgaaga 3540
gcgtcaagga actgctggga atcacaatca tggaaagag cagcttcgaa aagaacccga 3600
tcgacttcct ggaagcaaag ggatacaagg aagtcaagaa ggacctgatc atcaagctgc 3660
cgaagtacag cctgttcgaa ctggaaaacg gaagaaagag aatgctggca agcgcaggag 3720
aactgcagaa gggaaacgaa ctggcactgc cgagcaagta cgtcaacttc ctgtacctgg 3780
caagccacta cgaaaagctg aagggaagcc cggaagacaa cgaacagaag cagctgttcg 3840
tcgaacagca caagcactac ctggacgaaa tcatcgaaca gatcagcgaa ttcagcaaga 3900
gagtcatcct ggcagacgca aacctggaca aggtcctgag cgcatacaac aagcacagag 3960
acaagccgat cagagaacag gcagaaaaca tcatccacct gttcacactg caaaacctgg 4020
gagcaccggc agcattcaag tacttcgaca caacaatcga cagaaagaga tacacaagca 4080
caaaggaagt cctggacgca acactgatcc accagagcat cacaggactg tacgaaacaa 4140
gaatcgacct gagccagctg ggaggagacg gaggaggaag cccgaagaag aagagaaagg 4200
tctagctagc gctcgctttc ttgctgtcca atttctatta aaggttcctt tgttccctaa 4260
gtccaactac taaactgggg gatattatga agggccttga gcatctggat tctgcctaat 4320
aaaaaacatt tattttcatt gcctcgag                                   4348
```

| SEQ ID NO: 259 | moltype = DNA  length = 4325 |
| --- | --- |
| FEATURE | Location/Qualifiers |
| misc_feature | 1..4325 |
|  | note = Synthetic: Cas9 transcript with 5 UTR from XBG, ORF corresponding to SEQ ID NO: 204, Kozak sequence, and 3 UTR of XBG |
| source | 1..4325 |
|  | mol_type = other DNA |
|  | organism = synthetic construct |

SEQUENCE: 259
```
gggaagctca gaataaacgc tcaactttgg ccggatctgc caccatggac aagaagtaca 60
gcatcggact ggacatcgga acaaacagcg tcggatgggc agtcatcaca gacgaataca 120
aggtcccgag caagaagttc aaggtcctgg gaaacacaga cagacacagc atcaagaaga 180
acctgatcgg agcactgctg ttcgacagcg gagaaacagc agaagcaaca agactgaaga 240
gaacagcaag aagaagatac acaagaagaa agaacagaat ctgctacctg caggaaatct 300
tcagcaacga aatggcaaag gtcgacgaca gcttcttcca cagactggaa gaaagcttcc 360
tggtcgaaga agacaagaag cacgaaagac ccgatcttc ggaaacatc gtcgacgaag 420
tcgcatacca cgaaaagtac ccgacaatct accacctgag aaagaagctg gtcgacagca 480
cagacaaggc agacctgaga ctgatctacc tggcactgac acacatgatc aagttcagag 540
gacacttcct gatcgaagga gacctgaacc cggacaacag cgacgtcgac aagctgttca 600
tccagctggt ccagacatac aaccagctgt tcgaagaaaa cccgatcaac gcaagcggag 660
tcgacgcaaa ggcaatcctg agcgcaagac tgagcaagag cagaagactg gaaaacctga 720
tcgcacagct gccgggagaa aagaagaacg gactgttcga aaacctgatc gcactgagcc 780
tgggactgac accgaacttc aagagcaact tcgacctggc agaagacgca aagctgcagc 840
tgagcaagga cacatacgac gacgacctgg acaacctgct ggcacagatc ggagaccagt 900
acgcagacct gttcctggca gcaaagaacc tgagcgacgc aatcctgctg agcgacatcc 960
tgagagtcaa cacagagaat acaaaggcac cgctgagcgc aagcatgatc aagagatacg 1020
acgaacacca ccaggaccgt acactgctga aggcactggt cagacagcag ctgccggaaa 1080
agtacaagga aatcttcttc gaccagagca aagaacggata cgcaggatac atcgacggag 1140
gagcaagcca ggaagaattc tacaagttca tcaagccgat cctggaaaag atggacggaa 1200
cagaagaact gctggtcaag ctgaacagag aagacctgct gagaaagcag agaacattcg 1260
acaacggaag catcccgcac cagatccacc tgggagaact gcacgcaatc ctgagaagac 1320
aggaagactt ctacccgttc ctgaaggaca gcagagaaga aatcgagaag atcctgacat 1380
tcagaatccc gtactacgtc ggaccgctgc aagaggaaa cagcagattc gcatggatga 1440
caagaaagag cgaagaaaca atcacaccgt ggaacttcga agaagtcgtc gacaaggagg 1500
caagcgcaca gagcttcatc gaagaatgaa caaacttcga caagaacctg ccgaacgaaa 1560
aggtcctgcc gaagcacagc ctgctgtacg aatacttcac agtctacaac gaactgacaa 1620
aggtcaagta cgtcacagaa ggaatgagaa agccggcatt cctgagcgga gaacagaaga 1680
```

```
aggcaatcgt cgacctgctg ttcaagacaa acagaaaggt cacagtcaag cagctgaagg  1740
aagactactt caagaagatc gaatgcttcg acagcgtcga aatcagcgga gtcgaagaca  1800
gattcaacgc aagcctggga acataccacg acctgctgaa gatcatcaag acaaggact  1860
tcctggacaa cgaagaaaac gaagacatcc tggaagacat cgtcctgaca ctgacactgt  1920
tcgaagacag agaaatgatc gaagaaagac tgaagacata cgcacacctg ttcgacgaca  1980
aggtcatgaa gcagctgaag agaagaagat acacaggatg gggaagactg agcagaaagc  2040
tgatcaacga aatcagagac aagcagagcg aaagacaat cctggacttc ctgaagagcg  2100
acggattcgc aaacagaaac ttcatgcagc tgatccacga cgacagcctg acattcaagg  2160
aagacatcca gaaggcacag gtcagcgacc agggagacag cctgcacgaa cacatcgcaa  2220
acctggcagg aagcccggca atcaagaagg gaatcctgca gacagtcaag gtcgtcgacg  2280
aactggtcaa ggtcatggga agacacaagc cggaaaacat cgtcatcgaa atggcaagag  2340
aaaaccagac aacacagaag ggacagaaga acagcagaga aagaatgaag agaatcgaag  2400
aaggaatcaa ggaactggga agccagatcc tgaaggaaca cccggtcgaa aacacacagc  2460
tgcagaacga aaagctgtac ctgtactacc tgcagaacgg aagagacatg tacgtcgacc  2520
aggaactgga catcaacaga ctgagcgact acgacgtcga ccacatcgtc ccgcagagct  2580
tcctgaagga cgacagcatc gacaacaagg tcctgacaag aagcgacaag aacagaggaa  2640
agagcgacaa cgtcccgagc gaagaagtcg tcaagaagat gaagaactac tggagacagc  2700
tgctgaacgc aaagctgatc acacagagaa agttcgacaa cctgacaaag gcagagagag  2760
gaggactgag cgaactggac aaggcaggat tcatcaagag acagctggtc gaaacaagac  2820
agatcacaaa gcacgtcgca cagatcctgg acagcagaat gaacacaaag tacgacgaaa  2880
acgacaagct gatcagagaa gtcaaggtca tcacactgaa gagcaagctg gtcagcgact  2940
tcagaaagga cttccagttc tacaaggtca gagaaatcaa caactaccac cacgcacacg  3000
acgcatacct gaacgcagtc gtcggaacag cactgatcaa gaagtacccg aagctggaaa  3060
gcgaattcgt ctacggagac tacaaggtct acgacgtcag aaagatgatc gcaaagagcg  3120
aacaggaaat cggaaaggca acagcaaagt acttcttcta cagcaacatc atgaacttct  3180
tcaagacaga aatcacactg gcaaacgagg aaatcagaaa gagaccgctg atcgaaacaa  3240
acggagaaac aggagaaatc gtctgggaca agggaagaga cttcgcaaca gtcagaaagg  3300
tcctgagcat gccgcaggtc aacatcgtca agaagacaga agtccagaca ggaggattca  3360
gcaaggaaag catcctgccg aagagaaaca gcgacaagct gatcgcaaga aagaaggact  3420
gggacccgaa gaagtacgga ggattcgaca gcccgacagt cgcatacagc gtcctggtcg  3480
tcgcaaaggt cgaaaaggga aagagcaaga agctgaagag cgtcaaggaa ctgctgggaa  3540
tcacaatcat ggaagaagc agcttcgaaa agaacccgat cgacttcctg aagcaaagg  3600
gatacaagga agtcaagaag gacctgatca tcaagctgcc gaagtacagc ctgttcgaac  3660
tggaaaacgg aagaaagaga atgctggcaa gcgcaggaga actgcagaag ggaaacgaac  3720
tggcactgcc gagcaagtac gtcaacttcc tgtacctggc aagccactac gaaaagctga  3780
agggaagccc ggaagacaac gaacagaagc agctgttcgt cgaacagcac aagcactacc  3840
tggacgaaat catcgaacag atcagcgaat tcagcaagag agtcatcctg gcagacgcaa  3900
acctggacaa ggtcctgagc gcatacaaca agcacagaga caagccgatc agaaacagg  3960
cagaaaacat catccacctg ttcacactga aaacctggg agcaccggca gcattcaagt  4020
acttcgacac aacaatcgac agaaagagat acaaagcac aaaggaagtc ctggacgcaa  4080
cactgatcca ccagagcatc acaggactgt acgaaacaag aatcgacctg agccagctgg  4140
gaggagacgg aggaggaagc ccgaagaaga agagaaaggt ctagctagca ccagcctcaa  4200
gaacacccga atggagtctc taagctacat aataccaact tacactttac aaaatgttgt  4260
ccccaaaat gtagccattc gtatctgctc ctaataaaaa gaaagtttct tcacattctc  4320
tcgag                                                             4325
```

| SEQ ID NO: 260 | moltype = DNA   length = 4325 |
|---|---|
| FEATURE | Location/Qualifiers |
| misc_feature | 1..4325 |
| | note = Synthetic: Cas9 transcript with AGG as first three nucleotides for use with CleanCapTM, 5 UTR from XBG, ORF corresponding to SEQ ID NO: 204, Kozak sequence, and 3 UTR of XBG |
| source | 1..4325 |
| | mol_type = other DNA |
| | organism = synthetic construct |

SEQUENCE: 260

```
aggaagctca gaataaacgc tcaactttgg ccggatctgc caccatggac aagaagtaca  60
gcatcggact ggacatcgga acaaacagcg tcggatgggc agtcatcaca gacgaataca  120
aggtcccgag caagaagttc aaggtcctgg gaaacacaga cagacacagc atcaagaaga  180
acctgatcgg agcactgctg ttcgacagcg gagaaacagc agaagcaaca agactgaaga  240
gaacagcaag aagaagatac acaagaagaa agaacgaat ctgctacctg caggaaatct  300
tcagcaacga aatggcaaag gtcgacgaca gcttcttcca cagactggaa gaaagcttcc  360
tggtcgaaga agacaagaag cacgaaagac acccgatctt cggaaacatc gtcgacgaag  420
tcgcatacca cgaaaagtac ccgacaatct accacctgcg aaagaagctg gtcgacagca  480
cagacaaggc agacctgaga ctgatctacc tggcactggc acacatgatc aagttcagag  540
gacacttcct gatcgaagga gacctgaacc cggacaacag cgacgtcgac aagctgttca  600
tccagctggt ccagacatac aaccagctgt tcgaagaaaa cccgatcaac gcaagcggag  660
tcgacgcaaa ggcaatcctg agcgcaagac tgagcaagag cagaagactg gaaaacctga  720
tcgcacagct gccgggagaa aagaagaacg gactgttcgg aaacctgatc gcactgagcc  780
tgggactgac accgaacttc aagagcaact tcgacctggc agaagacgca aagctgcagc  840
tgagcaagga cacatacgac gacgacctgg acaacctgct ggcacagatc ggagaccagt  900
acgcagacct gttcctggca gcaaagaacc tgagcgacgc aatcctgctg agcgacatcc  960
tgagagtcaa cacagaaatc acaaaggcac cgctgagcgc aagcatgatc aagagatacg 1020
acgaacacca ccaggacctg acactgctga aggcactggt cagacagcag ctgccgaaa  1080
agtacaagga aatcttcttc gaccagagca agaacggata cgcaggatac atcgacgag  1140
gagcaagcca ggaagaattc tacaagttca tcaagccgat cctggaaaag atggacggaa  1200
cagaagaact gctggtcaag ctgaacagag aagacctgct gagaaagcag agaacattcg  1260
acaacggaag catcccgcac cagatccacc tgggagaact gcacgcaatc ctgagaagac  1320
```

```
aggaagactt ctacccgttc ctgaaggaca acagagaaaa gatcgaaaag atcctgacat   1380
tcagaatccc gtactacgtc ggaccgctgg caagagaaaa cagcagattc gcatggatga   1440
caagaaagag cgaagaaaca atcacaccgt ggaacttcga agaagtcgtc gacaagggag   1500
caagcgcaca gagcttcatc gaaagaatga caaacttcga caagaacctg ccgaacgaaa   1560
aggtcctgcc gaagcacagc ctgctgtacg aatacttcac agtctacaac gaactgacaa   1620
aggtcaagta cgtcacagaa ggaatgagaa agccggcatt cctgagcgga aacagaagaa   1680
aggcaatcgt cgacctgctg ttcaagacaa acagaaaggt cacagtcaag cagctgaagg   1740
aagactactt caagaagatc gaatgcttcg acagcgtcga aatcagcgga gtcgaagaca   1800
gattcaacgc aagcctggga acataccacg acctgctgaa gatcatcaag gacaaggact   1860
tcctggacaa cgaagaaaac gaagacatcc tggaagacat cgtcctgaca ctgacactgt   1920
tcgaagacag agaaatgatc gaagaaagac tgaagacata cgcacacctg ttcgacgaca   1980
aggtcatgaa gcagctgaag agaagaagat acacaggatg gggaagactg agcagaaagc   2040
tgatcaacgg aatcagagac aagcagagcg gaaagacaat cctggacttc ctgaagagcg   2100
acggattcgc aaacagaaac ttcatgcagc tgatccacga cgacagcctg acattcaagg   2160
aagacatcca gaaggcacag gtcagcggac agggacacag cctgcacgaa cacatcgcaa   2220
acctggcagg aagcccggca atcaagaagg gaatcctgca gacagtcaag gtcgtcgacg   2280
aactggtcaa ggtcatggga agacacaagc cggaaaacat cgtcatcgaa atggcaagag   2340
aaaaccagac aacacagaag ggacaagaaa acagcagaga aagaatgaag agaatcgaag   2400
aaggaatcaa ggaactggga agccagatcc tgaaggaaca cccggtcgaa aacacacagc   2460
tgcagaacga aaaagctgtac ctgtactacc tgcagaacgg aagagacatg tacgtcgacc   2520
aggaactgga catcaacaga ctgagcgact acgacgtcga ccacatcgtc ccgcagagct   2580
tcctgaagga cgacagcatc gacaacaagg tcctgacaag aagcgacaag aacagaggaa   2640
agagcgacaa cgtcccgagc gaagaagtcg tcaagaagat gaagaactac tggagacagc   2700
tgctgaacgc aaagctgatc acacagagaa agttcgacaa cctgacaaag gcagagagag   2760
gaggactgag cgaactggac aaggcaggat tcatcaagag acagctggtc gaaacaagac   2820
agatcacaaa gcacgtcgca cagatcctgg acagcagaat gaacacaaag tacgacgaaa   2880
acgacaagct gatcagagaa gtcaaggtca tcacactgaa gagcaagctg gtcagcgact   2940
tcagaaagga cttccagttc tacaaggtca gagaaatcaa caactaccac cacgcacacg   3000
acgcatacct gaacgcagtc gtcggaacag cactgatcaa gaagtacccg aagctggaaa   3060
gcgaattcgt ctacggagac tacaaggtct acgacgtcga aaagatgatc gcaaagagcg   3120
aacaggaaat cggaaaggca acagcaaagt acttcttcta cagcaacatc atgaacttct   3180
tcaagacaga aatcacactg gcaaacggag aaatcagaaa gagaccgctg atcgaaacaa   3240
acggagaaac aggagaaatc gtctgggaca agggaagaga cttcgcaaca gtcagaaagg   3300
tcctgagcat gccgcaggtc aacatcgtca agaagacaga agtccagaca ggaggattca   3360
gcaaggaaag catcctgccg aagagaaaca gcgacaagct gatcgcaaga aagaaggact   3420
gggacccgaa gaagtacgga ggattcgaca gcccgacagt cgcatacagc gtcctggtcg   3480
tcgcaaaggt cgaaaaggga aagagcaaga gctgaagagc gtcaaggaa ctgctgggaa   3540
tcacaatcat ggaaagaagc agcttcgaaa agaacccgat cgacttcctg gaagcaaagg   3600
gatacaagga agtcaagaag gacctgatca tcaagctgcc gaagtacgac ctgttcgaac   3660
tggaaaacgg aagaaagaga atgctggcaa gcgcaggaga actgcagaag ggaaacgaac   3720
tggcactgcc gagcaagtac gtcaacttcc tgtacctggc aagccactac gaaaagctga   3780
agggaagccc ggaagacaac gaacagaagc agctgttcgt cgaacagcac aagcactacc   3840
tggacgaaat catcgaacag atcagcgaat tcagcaagag agtcatcctg gcagacgcaa   3900
acctggacaa ggtcctgagc gcatacaaca gcacagaga caagccgatc agaaacagg   3960
cagaaaacat catccacctg ttcacactga caaacctggg agcaccggca gcattcaagt   4020
acttcgacac aacaatcgac agaaagagat acacaagcac aaaggaagtc ctggacgcaa   4080
cactgatcca ccagagcatc acaggactgt acgaaacaag aatcgacctg agccagctgg   4140
gaggagacgg aggaggaagc ccgaagaaga gagaaaaggt ctagctagca ccagcctcaa   4200
gaacacccga atggagtctc taagctacat aataccaact tacactttac aaaatgttgt   4260
cccccaaaat gtagccattc gtatctgctc ctaataaaaa gaaagtttct tcacattctc   4320
tcgag                                                              4325

SEQ ID NO: 261         moltype = DNA  length = 4411
FEATURE                Location/Qualifiers
misc_feature           1..4411
                       note = Synthetic: Cas9 transcript with AGG as first three
                         nucleotides for use with CleanCapTM, 5 UTR from HSD, ORF
                         corresponding to SEQ ID NO: 204, Kozak sequence, and 3 UTR
                         of ALB
source                 1..4411
                       mol_type = other DNA
                       organism = synthetic construct
SEQUENCE: 261
aggtcccgca gtcggcgtcc agcggctctg cttgttcgtg tgtgtgtcgt tgcaggcctt    60
attcggatcc gccaccatgg acaagaagta cagcatcgga ctggacatcg aacaaacag    120
cgtcggatgg gcagtcatca cagacgaata caaggtcccg agcaagaagt tcaaggtcct   180
gggaaacaca gacagacaca gcatcaagaa gaacctgatc ggagcactgc tgttcgacag   240
cggagaaaca gcaagactga agcaggaaca gaacagcaac agaagaagat acacaagaag   300
aaagaacaga atctgctacc tgcaggaaat cttcagcaac gaaatggcaa aggtcgacga   360
cagcttcttc cacagactgg aagaaagctt cctggtcgaa gaagacaaga gcacgaaag   420
acacccgatc ttcggaaaca tcgtcgacga agtcgcatac cacgaaaagt acccgacaat   480
ctaccacctg agaaagaagc tggtcgacag cacagacaag gcagacctga gactgatcta   540
cctggcactg gcacacatga tcaagttcag aggacacttc ctgatcgaag agacctgaa   600
cccggacaac agcgacgtcg acaagctgtt catccagctg gtccagacat acaaccagct   660
gttcgaagaa aacccgatca cgcaagcgg agtcgacgca aagcaatcc tgagcgcaag   720
actgagcaag agcagaagac tggaaaacct gatcgcacag ctgccgggag aaaagaagaa   780
cggactgttc ggaaacctga tcgcactgag cctgggactg acaccgaact tcaagagcaa   840
cttcgacctg gcagaagacg caaagctgca gctgagcaag acacatacg acgacgcct   900
ggacaacctg ctggcacaga tcggagacca gtacgcgac ctgttcctgg cagcaaagaa   960
```

```
cctgagcgac gcaatcctgc tgagcgacat cctgagagtc aacacagaaa tcacaaaggc 1020
accgctgagc gcaagcatga tcaagagata cgacgaacac caccaggacc tgacactgct 1080
gaaggcactg gtcagacagc agctgccgga aaagtacaag gaaatcttct tcgaccagag 1140
caagaacgga tacgcaggat acatcgacgg aggagcaagc caggaagaat tctacaagtt 1200
catcaagccg atcctggaaa agatgctgcg aacagaagaa ctgctggtca agctgaacag 1260
agaagacctg ctgagaaagc agagaacatt cgacaacgga agcatcccgc accagatcca 1320
cctgggagaa ctgcacgcaa tcctgagaag acaggaagac ttctacccgt tcctgaagga 1380
caacagagaa aagatcgaaa agatcctgac attcagaatc ccgtactacg tcggaccgct 1440
ggcaagagga aacagcagat tcgcatggat gacaagaaga agcgaagaaa caatcacacc 1500
gtggaacttc gaagaagtcg tcgacaaggg agcaagcgca cagagcttca tcgaaagaat 1560
gacaaacttc gacaagaacc tgccgaacga aaaggtcctg ccgaagcaca gcctgctgta 1620
cgaatacttc acagtctaca acgaactgac aaaggtcaag tacgtcacag aaggaatgag 1680
aaagccggca ttcctgagcg gagaacagaa gaaggcaatc gtcgacctgc tgttcaagac 1740
aaacagaaag gtcacagtca agcagctgaa ggaagactac ttcaagaaga tcgaatgctt 1800
cgacagcgtc gaaatcagcg gagtcgaaga cagattcaac gcaagcctgg gaacatacca 1860
cgacctgctg aagatcatca aggacaagga cttcctggac aacgaagaaa cgaagacat 1920
cctggaagac atcgtcctga cactgacact gttcgaagac agagaaatga tcgaagaaag 1980
actgaagaca tacgcacacc tgttcgacga caaggtcatg aagcagctga agagaagag 2040
atacacagga tggggaagac tgagcagaaa gctgatcaac ggaatcagag acaagcagag 2100
cggaaagaca atcctggact tcctgaagag cgacggattc gcaaacagaa acttcatgca 2160
gctgatccac gacgacagcc tgacattcaa ggaagacatc cagaaggcac aggtcagcgg 2220
acagggagac agcctgcacg aacacatcgc aaacctgccg gaagcccgg caatcaagaa 2280
gggaatcctg cagacagtca aggtcgtcga cgaactggtc aaggtcatgg gaagacacaa 2340
gccggaaaac atcgtcatcg aaatggcaag agaaaaccag acaacacaga agggacagaa 2400
gaacagcaga gaaagaatga gagaatcga agaaggaatc aaggaactgg gaagccagat 2460
cctgaaggaa caccccggtcg aaaacacaca gctgcagaaa agaaagctgt acctgtacta 2520
cctgcagaac ggaagagaca tgtacgtcga ccaggaactg gacatcaaca gactgagcga 2580
ctacgacgtc gaccacatcg tcccgcagag cttcctgaag gacgacagca tcgacaacaa 2640
ggtcctgaca gaagcgaca gaacagagg aaagagcgac aacgtcccga gcgaagaagt 2700
cgtcaagaag atgaagaact actggaagca gctgctgaac gcaaagctga tcacacagag 2760
aaagttcgac aacctgacaa aggcagagag aggaggactg agcgaactgg acaaggcagg 2820
attcatcaag acagctggc tcgaaacaag acagatcaca aagcacgtcg cacagatcct 2880
ggacagcaga atgaacacaa agtacgacga aaacgcaag ctgatcagag aagtcaaggt 2940
catcacactg aagagcaagc tggtcagcga cttcagaaag gacttccagt tctacaaggt 3000
cagagaaatc aacaactacc accacgcaca cgacgcatac ctgaacgcac tgtcggaac 3060
agcactgatc aagaagtacc cgaagctgga aagcgaattc gtctacgag actacaaggt 3120
ctacgacgtc agaagatga tcgcaaagag cgaacaggaa atcggaaagg caacagcaaa 3180
gtacttcttc tacagcaaca tcatgaactt cttcaagaca gaaatcacac tggcaaacgg 3240
agaaatcaga aagagaccgc tgatcgaaac aaacggaag acagagaaa tcgtctgggg 3300
caagggaaga gacttcgcaa cagtcagaaa ggtcctgagc atgccgcagg tcaacatcgt 3360
caagaagaca gaagtccaga caggaggatt cagcaaggaa agcatcctgc cgaagagaaa 3420
cagcgacaag ctgatcgcaa gaaagaagga ctgggaccg aagaagtacg gaggattcga 3480
cagcccgaca gtcgcataca gcgtcctggt cgtcgcaaag gtcgaaaagg gaaagagcaa 3540
gaagctgaag agcgtcaagg aactgctggg aatcacaatc atggaaagaa gcagcttcga 3600
aaagaacccg atcgacttcc tggaagcaaa gggatacaag gaagtcaaga aggacctgat 3660
catcaagctg ccgaagtaca gcctgttcga actgaaaac ggaagaaaga gaatgctggc 3720
aagcgcagga gaactgcaga agggaaacga actggccactg ccgagcaagt acgtcaactt 3780
cctgtacctg gcaagccact acgaaaagct gaagggaagc ccggaagaca cgaacagaa 3840
gcagctgttc gtcgaacagc acaagcacta cctggacgaa atcatcgaac agatcagcga 3900
attcagcaag agagtcatcc tggcagacgc aaacctggac aaggtcctga gcgcataaa 3960
caagcacaga gacaagccga tcagagaaca ggcagaaaac atcatccacc tgttcacact 4020
gacaaacctg ggagcaccgg cagcattcaa gtacttcgac acaacaatcg acagaaagag 4080
atacacaagc acaaaggaag tcctggacga acactgatc caccagagca tcacaggact 4140
gtacgaaaca agaatcgacc tgagccagct gggaggagac ggaggaggaa gcccgaagaa 4200
gaagagaaag gtctagctag ccatcacatt taaaagcatc tcagcctacc atgagaataa 4260
gagaaagaaa atgaagatca atagcttatt catctctttt tctttttcgt tggtgtaaag 4320
ccaacacct gtctaaaaa cataaatttc tttaatcatt ttgcctctt tctctgtgct 4380
tcaattaata aaaatggaa agaacctcga g 4411
```

SEQ ID NO: 262     moltype =    length =
SEQUENCE: 262
000

SEQ ID NO: 263     moltype = DNA  length = 93
FEATURE            Location/Qualifiers
misc_feature       1..93
                   note = Synthetic: poly-A 100 sequence
source             1..93
                   mol_type = other DNA
                   organism = synthetic construct
SEQUENCE: 263
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaa                             93

SEQ ID NO: 264     moltype = DNA  length = 44
FEATURE            Location/Qualifiers
misc_feature       1..44
                   note = Synthetic: G209 single guide RNA targeting the mouse
                   TTR gene

```
source                 1..44
                       mol_type = other DNA
                       organism = synthetic construct
SEQUENCE: 264
aaataagaga gaaaagaaga gtaagaagaa atataagagc cacc                   44

SEQ ID NO: 265         moltype = DNA  length = 3312
FEATURE                Location/Qualifiers
misc_feature           1..3312
                       note = Synthetic: ORF encoding Neisseria meningitidis Cas9
                        using minimal uridine codons, with start and stop codons
source                 1..3312
                       mol_type = other DNA
                       organism = synthetic construct
SEQUENCE: 265
atggcagcat tcaagccgaa ctcgatcaac tacatcctgg gactggacat cggaatcgca   60
tcggtcggat gggcaatggt cgaaatcgac gaagaagaaa acccgatcag actgatcgac  120
ctgggagtca gagtcttcga aagagcagaa gtcccgaaga caggagactc gctggcaatg  180
gcaagaagac tggcaagatc ggtcagaaga ctgacaagaa gaagagcaca cagactgctg  240
agaacaagaa gactgctgaa gagagaagga gtcctgcagg cagcaaactt cgacgaaaac  300
ggactgatca agtcgctgcc gaacacaccg tggcagctga gcagcagc actggacaga  360
aagctgacac cgctggaatg gtcggcagtc tgctgcagac tgatcaagca cagaggatac  420
ctgtcgcaga gaagaacga aggagaaaca gcagacaagg aactgggagc actgctgaag  480
ggagtcgcag gaaacgcaca cgcactgcag acaggagact tcagaacacc ggcagaactg  540
gcactgaaca agttcgaaaa ggaatcggga cacatcagaa accagagatc ggactactcg  600
cacacattct cgagaaagga cctgcaggca gaactgctcc tgcgttcga aaagcagaag  660
gaattcggaa accgcacgt ctcgggagga ctgaaggaag gaatcgaaac actgctgatg  720
acacagagac cggcactgtc gggagacgca gtccagaaga tgctgggaca ctgcacattc  780
gaaccggcag aaccgaaggc agcaaagaac acatacacag cagaaagatt catctggctg  840
acaaagctga caacctgag aatcctggaa cagggatcga aagaccgct gacagacaca  900
gaaagagcaa cactgatgga cgaaccgtac agaaagtcga agctgacata cgcacaggca  960
agaaagctgc tgggactgga agacacagca ttcttcaagg gactgagata cggaaaggac 1020
aacgcagaag catcgacact gatggaaatg aaggcatacc acgcaatctc gagagcactg 1080
gaaaaggaga gactgaagga caagaagtcg ccgctgaacc tgtcgccgca actgcaggac 1140
gaaatcggaa cagcattctc gctgttcaag acagaccgaa acatcacagg aagactgaag 1200
gacagaatcc agccgaaat cctggaagca ctgctgaagc acatctcgtt cgacaagttc 1260
gtccagatct cgctgaaggc actggagaaga atcgtcccgc tgatggaaca gggaaagaga 1320
tacgacgaag catgcgcaga aatctacgga gaccactacg gaaagaagaa cacagaagaa 1380
aagatctacc tgccgccgat cccggcagac gaaatcgaaa acccggtcgt cctgagagca 1440
ctgtcgcagg caagaaaggt catcaacgga gtcgtcagaa gatacggatc gccggcaaga 1500
atccacatcg aaacagcaag agaagtcgga aagtcgttca aggacagaaa ggaaatcgaa 1560
aagagacagg aagaaacag aaaggacaga gaaaaggcag cagcaaagtt cagagaatac 1620
ttcccgaact tcgtcggaga accgaagtcg aaggacatcc tgaagctgac actgtacgaa 1680
cagcagcacg gaaagtgcct gtactcggga aaggaaatca acctgggaag actgaacgaa 1740
aagggatacg tcgaaatcga ccacgcactg ccgttctcga acatgggaac gactcgttc 1800
aacaacaagg tcctggtcct gggatcggaa accagaaca agggaaacca gacaccgtac 1860
gaatacttca acggaaagga caactcgaga gaatggcaag aattcaaggc aagagtcgaa 1920
acatcgagat tcccgagatc gaagaagcag agaatcctgc tgcagaagtt cgacgaagac 1980
ggattcaagg aaagaaacct gaacgacaca agatacgtca cagattcct gtgccagttc 2040
gtcgcagaca gaatgagact gacaggaaag ggaagaagaa gagtcttcgc atcgaacgga 2100
cagatcacaa acctgctgag aggattctgg ggactggaca aggtcagagc agaaaacgac 2160
agacaccacg cactggacgc agtcgtcgtc gcatgctcga cagtcgcaat gcagcagaag 2220
atcacaagat tcgtcagata caaggaaatg aacgcattcg acggaaagac aatcgacaag 2280
gaaacaggag aagtcctgca ccagaagaca cacttcccgc agccgtggga attcttcgca 2340
caggaagtca tgatcagagt cttcggaaag ccggacggaa agccggaatt cgaagaagca 2400
gacacactgg aaaagctgag aacactgctg gcagaaaagc tgtcgtcgag accggaagca 2460
gtccacgaat acgtcacacc gctgttcgtc tcgagagcac cgaacagaaa gatgtcggga 2520
cagggacaca tggaaacagt caagtcgcca agagactgg acgaaggagt ctcggtcctg 2580
agagtcccgc tgacacagct gaagctgaag gacctggaaa agatggtcaa cagagaaaga 2640
gaaccgaagc tgtacagagc actgaaggca agactgaagc acacaaggga cgcaccggca 2700
aaggcattcg cagaaccgtt ctacaagtac gacaaggcag aaacagaac acagcaggtc 2760
aaggcagtca gagtcgaaca ggtccagaag acaggagtct gggtcagaaa ccacaacgga 2820
atcgcagaca acgcaacaat ggtcagagta gacgtcttcg aaaagggaga caagtactac 2880
ctggtcccga tctactcgtg gcaggtccca aaggaatcc tgccggacag acgcagtcgtc 2940
cagggaaagg acgaagaaga ctggcagctg atcgacgact cgttcaactt caagttctcg 3000
ctgcacccga cgacctggt cgaagtcatc acaaagaagg caagaatgtt cggatacttc 3060
gcatcgtgcc acagaggaac aggaaacatc aacatcagaa tccacgacct ggaccacaag 3120
atcggaaaga acggaatcct ggaaggaatc ggagtcaaga cagcactgtc gttccagaag 3180
taccagatcg acgaactggg aaaggaaatc agaccgtgca gactgaagaa gagaccgccg 3240
gtcagatccg gaaagtgaac agcagacgga tcggaattcg aatcgccgaa gaagaagaga 3300
aaggtcgaat ga                                                      3312

SEQ ID NO: 266         moltype = DNA  length = 3306
FEATURE                Location/Qualifiers
misc_feature           1..3306
                       note = Synthetic: ORF encoding Neisseria meningitidis Cas9
                        using minimal uridine codons (no start or stop codons;
                        suitable for inclusion in fusion protein coding sequence)
source                 1..3306
```

```
                        mol_type = other DNA
                        organism = synthetic construct
SEQUENCE: 266
gcagcattca agccgaactc gatcaactac atcctgggac tggacatcgg aatcgcatcg    60
gtcggatggg caatggtcga aatcgacgaa gaagaaaacc cgatcagact gatcgacctg   120
ggagtcagag tcttcgaaag agcagaagtc ccgaagacag gagactcgct ggcaatggca   180
agaagactgg caagatcggt cagaagactg caagaagaa gagcacacag actgctgaga    240
acaagaagac tgctgaagag agaaggagtc ctgcaggcag caaacttcga cgaaaacgga   300
ctgatcaagt cgctgccgaa cacaccgtgg cagctgagag cagcagcact ggacagaaag   360
ctgacaccgc tggaatggtc ggcagtcctg ctgcacctga tcaagcacag aggatacctg   420
tcgcagagaa agaacgaagg agaaacagca gacaaggaac tgggagcact gctgaaggga   480
gtcgcaggaa acgcacacgc actgcagaca ggagacttca gaacaccggc agaactggca   540
ctgaacaagt tcgaaaagga atcgggacac atcagaaacc agatccggaa ctactcgcac   600
acattctcga gaaaggacct gcaggcagaa ctgatcctgc tgttcgaaaa gcagaaggaa   660
ttcggaaacc cgcacgtctc gggaggactg aaggaaggaa tcgaaacact gctgatgaca   720
cagagaccgg cactgtcggg agacgcagtc cagaagatgc tgggacactg cacattcgaa   780
ccggcagaac cgaaggcagc aaagaacaca tacacgcag aaagattcat ctggctgaca    840
aagctgaaca acctggaact cctggaacag ggatcggaaa gaccgctgac agacacagaa   900
agagcaaacac tgatggacga accgtacaga aagtcgaagc tgacatacgc acaggcaaga   960
aagctgctgg gactggaaga cacagcattc ttcaagggac tgagatacgg aaaggacaac  1020
gcagaagcat cgacactgat ggaaatgaag gcataccacg caatctcgag agcactggaa  1080
aaggaaggac tgaaggacaa gaagtcgccg ctgaacctgt cgccggaacc tgcaggacgaa  1140
atcggaacag cattctcgct gttcaagaca gacgaagaca tcacaggaag actgaaggac  1200
agaatccagc cggaaatcct ggaagcactg ctgaagcaca tctcgttcga caagttcgtc  1260
cagatctcgc tgaaggcact gagaagaatc gtcccgctga tggaacaggg aaagagatac  1320
gacgaagcat cgcagaaat ctacggagac cactacggaa agaacaacac agagaaaag  1380
atctacctgc cgccgatccc ggcagacgaa atcagaaacc cggtcgtcct gagagcactg  1440
tcgcaggcaa gaaaggtcat caacggagtc gtcagaagat acgatcgcc ggcaagaatc   1500
cacatcgaaa cagcaagaga agtcggaaag tcgttcaagg acagaaagga aatcgaaaag  1560
agacaggaag aaaacagaaa ggacagaaa aaggcagcaca caaagttcag agaatacttc  1620
ccgaacttcg tcggagaacc gaagtcgaag gacatcctga agctgagact gtacgacaag  1680
cagcacggaa agtgcctgta ctcgggaaag gaaatcaacc tgggaagact gaacgaaaag  1740
ggatacgtcg aaatcgacca cgcactgccg ttctcgagaa catgggacga ctcgttcaac  1800
aacaaggtcc tggtcctggg atcggaaaac cagaacagga gaaaccagac accgtacgaa  1860
tacttcaacg gaaaggacaa ctcgcaggaa tggcaggaat tcaaggcaag agtcgaaaca  1920
tcgagattcc cgagatcgaa gaagcagaga atcctgctgc agaagttcga cgaagacgga  1980
ttcaaggaaa gaaacctgaa cgacacaaga tacgtcaaca gattcctgtg ccagttcgtc  2040
gcagacagaa tgagactgac aggaaaggga agaagagag tcttcgcatc gaacggacag  2100
atcacaaacc tgctgagagg attctgggga ctgagaaagg tcagagcaga aaacgacaga  2160
caccacgcac tggacgcagt cgtcgtcgca tgctcgacaa tcgcaatgca gcagaagatc  2220
acaagattcg tcagatacaa ggaaatgaac gcattcgacg gaaagacaat cgacaaggaa  2280
acaggagaag tcctgcacca agagacacac ttccgcagc cgtgggaatt cttcgcacag   2340
gaagtcatga tcagagtctt cggaaagccg gacggaaagc ctgaattga agaagcagac   2400
acactggaaa agctgagaac actgctggca gaaaagctgt cgtcgagacc ggaagcagtc   2460
cacgaatacg tcacaccgct gttcgtctcg agacaccga acagaaagat gtcgggacag   2520
ggacacatgg aaacagtcaa gtcggcaaag agactggacg aaggagtctc ggtcctgaga   2580
gtcccgctga cacagctgaa gctgaaggac ctggaaaacag tggtcaacag agaaagagaa   2640
ccgaagctgt acgaagcact gaaggcaaga ctggaagcac acaaggacga cccggcaaag   2700
gcattcgcag aaccgttcta caagtacgac aaggcaggaa acagaacaca gcaggtcaag   2760
gcagtcagag tcgaacaggt ccagaagaca ggagtctggg tcagaaacca caacggaatc   2820
gcagacaacg caacaatggt cagagtagac gtcttcgaaa agggagacaa tgtactacctg   2880
gtcccgatct actcgtggca ggtcgcaaag ggaatcctgc cggacagagc agtcgtccga   2940
ggaaaggacg aagaagactg gcagctgatc gacgactcgt tcaacttcaa gttctcgctg   3000
cacccgaacg acctggtcga agtcatcaca aagaaggcaa gaatgttcgg atacttcgca   3060
tcgtgccaca gaggaacagg aaacatcaac atcgacctga cacacaagatc              3120
ggaaagaacg gaatcctgga aggaatcgga gtcaagacag cactgtcgtt ccagaagtac   3180
cagatcgacg aactgggaaa ggaaatcaga ccgtgcagac tgaagaagag accgccggtc   3240
agatccggaa agaacagc agacggatcg gaattcgaat cgccgaagaa gaagagaaag   3300
gtcgaa                                                              3306

SEQ ID NO: 267         moltype = DNA  length = 3636
FEATURE                Location/Qualifiers
misc_feature           1..3636
                        note = Synthetic: Transcript comprising SEQ ID NO: 265
                        (encoding Neisseria meningitidis Cas9)
source                 1..3636
                        mol_type = other DNA
                        organism = synthetic construct
SEQUENCE: 267
gggagaccca agctggctag cgtttaaact taagcttgga tccgccacca tggcagcatt    60
caagccgaac tcgatcaact acatcctggg actggacatc ggaatcgcat cggtcggatg   120
ggcaatggtc gaaatcgacg aagaagaaaa cccgatcaga ctgatcgacc tgggagtcag   180
agtcttcgaa agagcagaag tcccgaagac aggagactcg ctggcaatgg caagaagact   240
ggcaagatcg gtcagaagac tgcaagaaga agagcacaca gactgctgaa gaacaagaag   300
actgctgaag agagaaggag tcctgcaggc agcaaacttc gacgaaaacg gactgatcaa   360
gtcgctgccg aacacaccgt ggcagctgag agcagcagca ctggacagaa agctgacacc   420
gctggaatgg tcggcagtcc tgctgcacct gatcaagcac agaggatacc tgtcgcagag   480
aaagaacgaa ggagaaacag cagacaagga actgggagca ctgctgaagg gagtcgcagg   540
aaacgcacac gcactgcaga caggagactt cagaacaccg gcagaactgg cactgaacaa   600
```

-continued

```
gttcgaaaag gaatcgggac acatcagaaa ccagagatcg gactactcgc acacattctc    660
gagaaaggac ctgcaggcag aactgatcct gctgttcgaa aagcagaagg aattcggaaa    720
cccgcacgtc tcgggaggac tgaaggaagg aatcgaaaca ctgctgatga cacagagacc    780
ggcactgtcg ggagacgcag tccagaagat gctgggacac tgcacattcg aaccggcaga    840
accgaaggca gcaaagaaca catacacagc agaaagattc atctggctga caaagctgaa    900
caacctgaga atcctggaac agggatcgga agaccgctg acagacacag aaagagcaac     960
actgatggac gaaccgtaca gaaagtcgaa gctgacatac gcacaggcaa gaaagctgct   1020
gggactggaa gacacagcat tcttcaaggg actgagatac ggaaaggaca acgcagaagc   1080
atcgacactg atggaaatga aggcatacca cgcaatctcg agagcactgg aaaaggaagg   1140
actgaaggac aagaagtcgc cgctgaacct gtcgccggaa ctgcaggacg aaatcggaac   1200
agcattctcg ctgttcaaga cagacgaaga catcacagga agactgaagg acagaatcca   1260
gccggaaatc ctgaagcac tgctgaagca catctcgttc gacaagttcg tccagatctc    1320
gctgaaggca ctgagaagaa tcgtcccgct gatggaacag ggaaagagat acgacgaagc   1380
atgcgcagaa atctacggag accactacgg aaagaagaac acagaagaaa agatctacct   1440
gccgccgatc ccggcagacg aaatcagaaa cccggtcgtc ctgagagcac tgtcgcaggc   1500
aagaaaggtc atcaacggag tcgtcagaag atacggatcg ccggcaagaa tccacatcga   1560
aacagcaaga gaagtcggaa agtcgttcaa ggacagaaag gaaatcgaaa agagacagga   1620
agaaaacaga aaggacagag aaaaggcagc agcaaagttc agagaatact ccccgaactt   1680
cgtcggagaa ccgaagtcga aggacatcct gaagctgaga ctgtacgaac agcagcacgg   1740
aaagtgcctg tactcgggaa aggaaatcaa cctgggaaga ctgaacgaaa agggatacgt   1800
cgaaatcgac cacgcactgc cgttctcgag aacatgggac gactcgttca caacaaggt    1860
cctggtcctg ggatcggaaa accagaacaa gggaaaccag acaccgtaca aatacttcaa   1920
cggaaaggac aactcgagag aatggcagga attcaaggca agagtcgaaa catcgagatt   1980
cccgagatcg aagaagcaga gaatcctgct gcagaagttc gacgaagacg gattcaagga   2040
aagaaacctg aacgacacaa gatacgtcaa cagattcctg tgccagttcg tcgcagacag   2100
aatgagactg acaggaaagg aaaagaagag agtcttcgca tcgaacggac agatcacaaa   2160
cctgctgaga ggattctggg gactgagaaa ggtcagagca gaaaacgaca gacaccacgc   2220
actggacgca gtcgtcgtcg catgctcgac agtcgcaatg cagcagaaga tcacaagatt   2280
cgtcagatac aaggaaatga acgcattcga cggaaagaca atcgacaagg aaacaggaga   2340
agtcctgcac cagaagacac acttcccgca gccgtgggaa ttcttcgcac aggaagtcat   2400
gatcagagtc ttcggaaagc cggacgaaaa gccggaattc gaagaagcag acacactgga   2460
aaagctgaga acactgctgg cagaaaagct gtcgtcgaga ccggaagcag tccacgaata   2520
cgtcacaccg ctgttcgtct cgagagcacc gaacagaaaa atgtcgggac agggacacat   2580
ggaaacagtc aagtcggcaa agagactgga cgaaggagtc tcggtcctga gagtcccgct   2640
gacacagctg aagctgaagg acctggaaaa gatggtcaac agagaaagag aaccgaagct   2700
gtacgaagca ctgaaggcaa gactggaagc acacaaggca gacccggcaa aggcattcgc   2760
agaaccgttc tacaagtacg acaaggcagg aaacagaaca cagcaggtca aggcagtcag   2820
agtcgaacag gtccagaaga caggagtctg ggtcagagca cacaacggaa tcgcagacaa   2880
cgcaacaatg cgtcagagtag acgtcttcga aaagggagca aagtactacc tggtcccgat   2940
ctactcgtgg caggtcgcaa agggaatcct gccggacaga gcagtcgtcc agggaaagga   3000
cgaagagagc tggcagctga tcgacgactc gttcaacttc aagttctcgc tgcacccgaa   3060
cgacctggtc gaagtcatca caagaaggc aagaatgttc ggatacttcg catcgtgcca    3120
cagaggaaca ggaaacatca acatcagaat ccacgacctg gaccacaaga tcggaaagaa   3180
cggaatcctg gaaggaatcg agtcaagac agcactgtcg ttccagaagt accagatcga   3240
cgaactggga aaggaaatca accgtcag actgaagaac agaccgccgg tcagatccgg    3300
aaagagaaca gcagacggat cggaattcga atcgccgaag aagaagagaa aggtcgaatg   3360
atagctagct cgagtctaga gggcccgttt aaacccgctc agcctccg actgtgcctt    3420
ctagttgcca gccatctgtt gtttgcccct cccccgtgcc ttccttgacc ctggaaggtg   3480
ccactcccac tgtcctttcc taataaaatg aggaaattgc atcgcattgt ctgagtaggt   3540
gtcattctat tctgggggggt ggggtggggc aggacagcaa gggggaggat tgggaagaca   3600
atagcaggca tgctgggat gcggtgggct ctatgg                              3636
```

| SEQ ID NO: 268 | moltype = AA length = 1103 |
|---|---|
| FEATURE | Location/Qualifiers |
| REGION | 1..1103 |
| | note = Synthetic: Amino acid sequence of Neisseria meningitidis Cas9 |
| source | 1..1103 |
| | mol_type = protein |
| | organism = synthetic construct |

SEQUENCE: 268

```
MAAFKPNSIN YILGLDIGIA SVGWAMVEID EEENPIRLID LGVRVFERAE VPKTGDSLAM    60
ARRLARSVRR LTRRRAHRLL RTRRLLKREG VLQAANFDEN GLIKSLPNTP WQLRAAALDR   120
KLTPLEWSAV LLHLIKHRGY LSQRKNEGET ADKELGALLK GVAGNAHALQ TGDFRTPAEL   180
ALNKFEKESG HIRNQRSDYS HTFSRKDLQA ELILLFEKQK EFGNPHVSGG LKEGIETLLM   240
TQRPALSGDA VQKMLGHCTF EPAEPKAAKN TYTAERFIWL TKLNNLRILE QGSERPLTDT   300
ERATLMDEPY RKSKLTYAQA RKLLGLEDTA FFKGLRYGKD NAEASTLMEM KAYHAISRAL   360
EKEGLKDKKS PLNLSPELQD EIGTAFSLFK TDEDITGRLK DRIQPEILEA LLKHISFDKF   420
VQISLKALRR IVPLMEQGKR YDEACAEIYG DHYGKKNTEE KIYLPPIPAD EIRNPVVLRA   480
LSQARKVING VVRRYGSPAR IHIETAREVG KSFKDRKEIE KRQEENRKDR EKAAAKFREY   540
FPNFVGEPKS KDILKLRLYE QQHGKCLYSG KEINLGRLNE KGYVEIDHAL PFSRTWDDSF   600
NNKVLVLGSE NQNKGNQTPY EYFNGKDNSR EWQEFKARVE TSRFPRSKKQ RILLQKFDED   660
GFKERNLNDT RYVNRFLCQF VADRMRLTGK GKKRVFASNG QITNLLRGFW GLRKVRAEND   720
RHHALDAVVV ACSTVAMQQK ITRFVRYKEM NAFDGKTIDK ETGEVLHQKT HFPQPWEFFA   780
QEVMIRVFGK PDGKPEFEEA DTLEKLRTLL AEKLSSRPEA VHEYVTPLFV SRAPNRKMSG   840
QGHMETVKSA KRLDEGVSVL RVPLTQLKLK DLEKMVNRER EPKLYEALKA RLEAHKDDPA   900
KAFAEPFYKY DKAGNRTQQV KAVREQVQK TGVWVRNHNG IADNATMVRV DVFEKGDKYY    960
LVPIYSWQVA KGILPDRAVV QGKDEEDWQL IDDSFNFKFS LHPNDLVEVI TKKARMFGYF  1020
ASCHRGTGNI NIRIHDLDHK IGKNGILEGI GVKTALSFQK YQIDELGKEI RPCRLKKRPP  1080
```

| SEQ ID NO: 269 | moltype = RNA  length = 100 |
| --- | --- |
| FEATURE | Location/Qualifiers |
| misc_feature | 1..100 |
| | note = Synthetic: G390 single guide RNA targeting the rat TTR gene |
| modified_base | 1..3 |
| | mod_base = OTHER |
| | note = PS linkage, 2'-O-Me nucleotide |
| modified_base | 29..40 |
| | mod_base = OTHER |
| | note = 2'-O-Me nucleotide |
| modified_base | 69..96 |
| | mod_base = OTHER |
| | note = 2'-O-Me nucleotide |
| modified_base | 97..100 |
| | mod_base = OTHER |
| | note = PS linkage, 2'-O-Me nucleotide |
| source | 1..100 |
| | mol_type = other RNA |
| | organism = synthetic construct |

SEQUENCE: 269
gccgagtctg gagagctgca gttttagagc tagaaatagc aagttaaaat aaggctagtc  60
cgttatcaac ttgaaaaagt ggcaccgagt cggtgctttt                        100

| SEQ ID NO: 270 | moltype = RNA  length = 74 |
| --- | --- |
| FEATURE | Location/Qualifiers |
| misc_feature | 1..74 |
| | note = Synthetic: trRNA |
| source | 1..74 |
| | mol_type = other RNA |
| | organism = synthetic construct |

SEQUENCE: 270
aacagcatag caagtttaaa taaggctagt ccgttatcaa cttgaaaaag tggcaccgag  60
tcggtgcttt tttt                                                    74

| SEQ ID NO: 271 | moltype =   length = |
| --- | --- |

SEQUENCE: 271
000

| SEQ ID NO: 272 | moltype = RNA  length = 100 |
| --- | --- |
| FEATURE | Location/Qualifiers |
| misc_feature | 1..100 |
| | note = Synthetic: G534 single guide RNA targeting the rat TTR gene |
| modified_base | 1..3 |
| | mod_base = OTHER |
| | note = PS linkage, 2'-O-Me nucleotide |
| modified_base | 29..40 |
| | mod_base = OTHER |
| | note = 2'-O-Me nucleotide |
| modified_base | 69..96 |
| | mod_base = OTHER |
| | note = 2'-O-Me nucleotide |
| modified_base | 97..100 |
| | mod_base = OTHER |
| | note = PS linkage, 2'-O-Me nucleotide |
| source | 1..100 |
| | mol_type = other RNA |
| | organism = synthetic construct |

SEQUENCE: 272
acgcaaatat cagtccagcg gttttagagc tagaaatagc aagttaaaat aaggctagtc  60
cgttatcaac ttgaaaaagt ggcaccgagt cggtgctttt                        100

| SEQ ID NO: 273 | moltype = RNA  length = 95 |
| --- | --- |
| FEATURE | Location/Qualifiers |
| misc_feature | 1..95 |
| | note = Synthetic: G000395 5 truncated inactive sgRNA modified sequence |
| modified_base | 1..3 |
| | mod_base = OTHER |
| | note = PS linkage, 2'-O-Me nucleotide |

```
modified_base     24..35
                  mod_base = OTHER
                  note = 2'-O-Me nucleotide
modified_base     64..91
                  mod_base = OTHER
                  note = 2'-O-Me nucleotide
modified_base     92..95
                  mod_base = OTHER
                  note = PS linkage, 2'-O-Me nucleotide
source            1..95
                  mol_type = other RNA
                  organism = synthetic construct
SEQUENCE: 273
gcaatggtgt agcgggtttt agagctagaa atagcaagtt aaaataaggc tagtccgtta    60
tcaacttgaa aaagtggcac cgagtcggtg ctttt                               95

SEQ ID NO: 274    moltype = AA  length = 7
FEATURE           Location/Qualifiers
REGION            1..7
                  note = Synthetic: SV40 NLS
source            1..7
                  mol_type = protein
                  organism = synthetic construct
SEQUENCE: 274
PKKKRKV                                                              7

SEQ ID NO: 275    moltype = AA  length = 7
FEATURE           Location/Qualifiers
REGION            1..7
                  note = Synthetic: Alternate SV40 NLS
source            1..7
                  mol_type = protein
                  organism = synthetic construct
SEQUENCE: 275
PKKKRRV                                                              7

SEQ ID NO: 276    moltype = AA  length = 16
FEATURE           Location/Qualifiers
REGION            1..16
                  note = Synthetic: Nucleoplasmin NLS
source            1..16
                  mol_type = protein
                  organism = synthetic construct
SEQUENCE: 276
KRPAATKKAG QAKKKK                                                    16

SEQ ID NO: 277    moltype = RNA  length = 10
FEATURE           Location/Qualifiers
misc_feature      1..10
                  note = Synthetic: Exemplary Kozak sequence
source            1..10
                  mol_type = other RNA
                  organism = synthetic construct
SEQUENCE: 277
gccrccatgg                                                           10

SEQ ID NO: 278    moltype = RNA  length = 13
FEATURE           Location/Qualifiers
misc_feature      1..13
                  note = Synthetic: Exemplary Kozak sequence
source            1..13
                  mol_type = other RNA
                  organism = synthetic construct
SEQUENCE: 278
gccgccrcca tgg                                                       13
```